United States Patent
Villemure et al.

(10) Patent No.: US 12,428,419 B2
(45) Date of Patent: *Sep. 30, 2025

(54) THERAPEUTIC COMPOUNDS

(71) Applicant: Genentech, Inc., South San Francisco, CA (US)

(72) Inventors: Elisia Villemure, South San Francisco, CA (US); Joachim Rudolph, South San Francisco, CA (US); Mingshuo Zeng, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/604,314

(22) Filed: Mar. 13, 2024

(65) Prior Publication Data

US 2024/0383897 A1 Nov. 21, 2024

Related U.S. Application Data

(63) Continuation of application No. 17/883,004, filed on Aug. 8, 2022, now Pat. No. 11,993,599.

(60) Provisional application No. 63/231,219, filed on Aug. 9, 2021, provisional application No. 63/231,220, filed on Aug. 9, 2021.

(51) Int. Cl.
| | | |
|---|---|---|
| *C07D 487/14* | (2006.01) | |
| *A61K 31/4985* | (2006.01) | |
| *C07D 471/08* | (2006.01) | |
| *C07D 471/10* | (2006.01) | |

(52) U.S. Cl.
CPC ......... *C07D 471/08* (2013.01); *C07D 471/10* (2013.01); *C07D 487/14* (2013.01)

(58) Field of Classification Search
CPC ................ C07D 487/14; C07D 401/14; A61K 31/4985; A61K 31/501; A61P 35/00
USPC .......................................... 544/234; 514/250
See application file for complete search history.

(56) References Cited

U.S. PATENT DOCUMENTS

| | | | | |
|---|---|---|---|---|
| 11,702,423 | B2 * | 7/2023 | Lin | .......... A61P 35/00 514/210.16 |
| 11,993,559 | B2 | 5/2024 | Aribert | |
| 2023/0112485 | A1 | 4/2023 | Villemure | |

FOREIGN PATENT DOCUMENTS

| | | |
|---|---|---|
| WO | 2016138114 A1 | 9/2016 |
| WO | 2019207538 A1 | 10/2019 |
| WO | 2019213005 A1 | 11/2019 |
| WO | 2020010227 A1 | 1/2020 |
| WO | 2020078933 A1 | 4/2020 |
| WO | 2020172655 A1 | 8/2020 |
| WO | 2020251969 A1 | 12/2020 |
| WO | 2020251971 A1 | 12/2020 |
| WO | 2021048799 A1 | 3/2021 |
| WO | 2021067606 A1 | 4/2021 |
| WO | 2021083949 A1 | 5/2021 |
| WO | 2021086785 A1 | 5/2021 |
| WO | 2021142247 A1 | 7/2021 |
| WO | 2021207291 A1 | 10/2021 |
| WO | 2022109396 A1 | 5/2022 |
| WO | 2022125804 A1 | 6/2022 |
| WO | 2022183056 A1 | 9/2022 |

OTHER PUBLICATIONS

Cantley, J. et al. (2022, e-pub. Nov. 10, 2022). "Selective PROTAC-Mediated Degradation of SMARCA2 is Efficacious in SMARCA4 Mutant Cancers," Nature Communications 13:6814, 14 pages.
Ehrenhöfer-Wölfer, K et al. (2019, e-pub. Aug. 12, 2019). "SMARCA2-Deficiency Confers Sensitivity to Targeted Inhibition of SMARCA4 in Esophageal Squamous Cell Carcinoma Cell Lines," Scientific Reports 9:11661, 12 pages.
Farnaby, W. et al. (Jul. 2019). "BAF Complex Vulnerabilities in Cancer Demonstrated via Structure-Based PROTAC Design," Nat. Chem. Biol. 15(7):672-680, 29 pages.
Hodis, E. et al. (Jul. 20, 2012). "A Landscape of Driver Mutations in Melanoma," Cell 150(2):251-263, 24 pages.
International Search Report and Written Opinion mailed Oct. 31, 2022, for PCT Application No. PCT/US2022/039696, filed on Aug. 8, 2022, 16 pages.
Kofink, C. et al. (2022, e-pub. Oct. 10, 2022). "A Selective and Orally Bioavailable VHL-Recruiting PROTAC Achieves SMARCA2 Degradation in vivo," Nature Communications 13:5969, 15 pages.
Mélin, L. et al. (Aug. 9, 2021). "Design and Synthesis of LM146, A Potent Inhibitor of PB1 with an Improved Selectivity Profiled Over SMARCA2," ACS Omega 6(33):21327-21338.
Non-Final Office Action, mailed Aug. 18, 2023, for U.S. Appl. No. 17/883,004, filed Aug. 8, 2022, 8 pages.
Wanior, M. et al. (Dec. 10, 2020, e-pub. Nov. 20, 2020). "Pan-SMARCA/PB1 Bromodomain Inhibitors and their Role in Regulating Adipogenesis," Journal of Medicinal Chemistry 63(23):14680-14699.
Xiao, L. et al. (Jan. 20, 2022, e-pub. Dec. 22, 2021). "Targeting SWI/SNF ATPases in Enhancer-Addicted Prostate Cancer," Nature 601:434-439 and Supplemental, 40 pages total.
Yang, L. et al. (2023). "Discovery of SMD-3040 as a Potent and Selective SMARCA2 PROTAC Degrader with Strong in vivo Antitumor Activity," Journal of Medicinal Chemistry, 21 pages.

* cited by examiner

*Primary Examiner* — Charanjit Aulakh
(74) *Attorney, Agent, or Firm* — Morrison & Foerster LLP

(57) ABSTRACT

The present disclosure relates to compounds and salts thereof that are useful for modulating target polypeptides and proteins, in particular BRM. Also disclosed are pharmaceutical compositions comprising the compounds, or a salt (e.g., a pharmaceutically acceptable salt) thereof, and methods of using such compounds and salts in the treatment of various BRM-mediated and/or BRG1-mediated diseases or disorders.

14 Claims, No Drawings

THERAPEUTIC COMPOUNDS

CROSS REFERENCE TO RELATED APPLICATIONS

This application is a continuation of U.S. application Ser. No. 17/883,004, filed Aug. 8, 2022, which claims priority to U.S. Provisional Application Nos. 63/231,219, filed Aug. 9, 2021, and 63/231,220, filed Aug. 9, 2021, the content of each of which is herein incorporated by reference in its entirety.

BACKGROUND OF THE DISCLOSURE

The description provides compounds that demonstrate an ability to modulate BRM, and methods of use thereof.

SWI/SNF-Related, Matrix-Associated, Actin-Dependent Regulator of Chromatin, Subfamily A is a multi-subunit complex that modulates chromatic structure through the activity of two mutually exclusive helicase/ATPase catalytic subunits: (1) SWI/SNF-Related, Matrix-Associated, Actin-Dependent Regulator of Chromatin, Subfamily A Member 2 (SMARCA2) (i.e., BRAHMA or BRM); and (2) SWI/SNF-Related, Matrix-Associated, Actin-Dependent Regulator of Chromatin, Subfamily A, Member 4 (SMARCA4) (i.e., BRG1). The core and the regulatory subunits couple ATP hydrolysis to the perturbation of histone-DNA contacts, thereby providing access points to transcription factors and cognate DNA elements that facilitate gene activation and repression.

Mutations in the genes encoding the twenty canonical SWI/SNF subunits are observed in nearly 20% of all cancers. Despite having a high degree of homology, and their presumed overlapping functions, BRM and BRG1 have been reported as having different roles in cancer. For example, BRG1 is frequently mutated in primary tumors, while BRM inactivation is infrequent in tumor development. In fact, numerous types of cancer have been shown to be BRG1-related (e.g., cancers having a BRG1-mutation or a BRG1-deficiency, such as lack of expression), including, e.g., lung cancer (such as non-small cell lung cancer).

BRM has been demonstrated as one of the top essential genes in BRG1-related or BRG1-mutant cancer cell lines. This is because BRG1-deficient patient populations or cells depend exclusively on BRM activity—i.e., there is a greater incorporation of BRM into the complex to compensate for the BRG1 deficiency. Thus, BRM may be targeted for inhibition or degradation in BRG1-related/deficient cancers. The co-occurrence of the deficiency of the expression of two (or more) genes that leads to cell death is known as synthetic lethality. Accordingly, synthetic lethality can be leveraged in the treatment of certain BRM/BRG1-related cancers.

There is an ongoing need for effective treatment for disorders, diseases, and conditions that are treatable by modulating, inhibiting, or degrading BRM. As such, small-molecule therapeutic agents that target BRM would prove useful.

SUMMARY

The present disclosure is directed to compounds effective in the treatment of cancer, immunological disorders, and other BRM-mediated disorders. The present disclosure is further directed to methods of using an effective amount of the compounds described herein for the treatment or amelioration of a disease or conditions such as cancer and in particular BRG1-related/deficient cancers such as lung cancer or non-small cell lung cancer.

In one aspect, provided herein is a compound of formula (IV'):

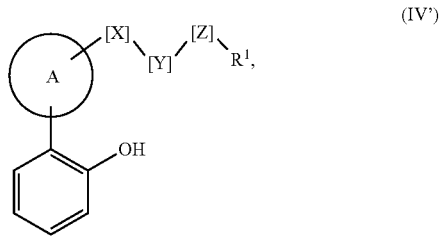

or a stereoisomer or tautomer thereof, or a pharmaceutically acceptable salt of any of the foregoing, wherein:

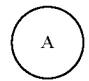

is 3-15 membered heterocyclyl or 5-20 membered heteroaryl, each of which is independently optionally substituted with one or more $R''$, wherein $R''$ is selected from the group consisting of —N($R^x$)($R^y$), —OH, CN, halo, $C_{1-4}$alkyl, and $C_{1-4}$haloalkyl;

[X] is absent, or 3-15 membered heterocyclyl or 5-20 membered heteroaryl, each of which is independently optionally substituted with one or more —OH or $C_{1-6}$alkyl;

[Y] is absent, or $C_{3-6}$cycloalkyl, $C_{1-6}$alkylene, $C_{2-6}$alkenylene, or $C_{2-6}$-alkynylene, each of which is independently optionally substituted with one or more substitutents selected from the group consisting of $C_{1-6}$alkyl, and halo;

[Z] is absent, or 3-15 membered heterocyclyl or 5-20 membered heteroaryl; and $R^1$ is:
(a) —C≡C—$R^a$, wherein
  (i) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
  the 3-15 membered heterocyclyl of $R^b$ is optionally substituted with one or more $R^c$, and the $C_{1-6}$alkoxy of $R^b$ is optionally substituted with one or more —OH, or
  (ii) $R^a$ is $C_{3-10}$cycloalkyl, wherein the $C_{3-10}$cycloalkyl of $R^a$ is optionally substituted with one or more $R^c$, or
  (iii) $R^a$ is 3-15 membered heterocyclyl, wherein the 3-15 membered heterocyclyl of $R^a$ is optionally substituted with one or more $R^c$, or
  (iv) $R^a$ is 5-20 membered heteroaryl, wherein the 5-20 membered heteroaryl of $R^a$ is optionally substituted with one or more $R^c$,
  wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein the C$_{1-6}$alkyl of R$^c$ is optionally substituted with one or more —OH, —CN, halo, C$_{1-6}$alkoxy, or 3-15 membered heterocyclyl,
the C$_{3-10}$ cycloalkyl of R$^c$ is optionally substituted with one or more halo,
the C$_{6-10}$aryl of R$^c$ is optionally substituted with one or more —CN,
the 3-15 membered heterocyclyl of R$^c$ is optionally substituted with one or more C$_{1-6}$alkyl or —C(O)—C$_{1-6}$alkyl, or
(b) —(CH$_2$)$_n$—R$^g$, wherein
n is an integer from 1-6, and
R$^g$ is —N(R$^x$)(R$^y$) or —OH;
wherein
the R$^x$ and R$^y$ of —C(O)N(R$^x$)(R$^y$) and —N(R$^x$)(R$^y$) are, independently of each other and independently at each occurrence, H, —C(O)—(CH$_2$)$_p$—N(R$^p$)(R$^q$), —C(O)—R$^s$, 5-20 membered heterocycle, 5-20 membered heteroaryl, or C$_{1-6}$alkyl, wherein
p is an integer from 1-6,
R$^p$ and R$^q$ are, independently of each other and independently at each occurrence H, or C$_{1-6}$alkyl,
R$^s$ is 5-20 membered heterocycle optionally substituted with one or more substituents selected from the group consisting of C$_{1-4}$alkyl, C$_{3-8}$cycloalkyl, and —C(O)—C$_{1-6}$alkyl,
the C$_{1-6}$alkyl of R$^x$ or R$^y$ is optionally substituted with one or more —OH, 3-15 membered heterocyclyl, or —C(O)-(3-15 membered heterocyclyl), and
the 5-20 membered heterocycle of R$^x$ or R$^y$ is optionally substituted with one or more oxo, or
(c) —C≡C—R$^d$, wherein R$^d$ is C$_{1-6}$alkyl, wherein the C$_{1-6}$alkyl of R$^d$ is optionally substituted with one or more R$^e$, wherein each R$^e$ is independently 3-15 membered heterocyclyl, wherein the 3-15 membered heterocyclyl of R$^e$ is optionally substituted with one or more R$^f$, wherein each R$^f$ is independently —OH, —CN, halo, oxo, C$_{1-6}$alkyl, C$_{1-6}$alkoxy, or —C(O)—C$_{1-6}$alkoxy.

In one aspect, provided herein is a compound of formula (IV'-L):

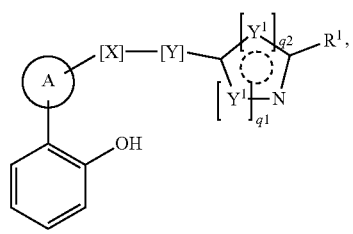

(IV'- L)

or a stereoisomer or tautomer thereof, or a pharmaceutically acceptable salt of any of the foregoing, wherein each Y$^1$ is independently N or CH, and q$_1$ and q$_2$ are each integers and the sum of q$_1$ and q$_2$ is 2 or 3, and

[X], [Y], and R$^1$ are as defined above or elsewhere herein for a compound of formula (IV').

In one aspect, provided herein is a compound of formula (I'):

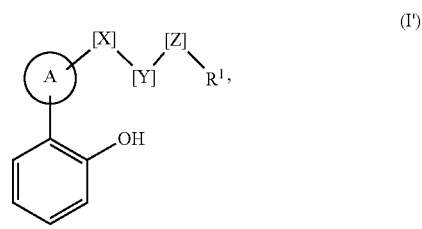

(I')

or a stereoisomer or tautomer thereof, or a pharmaceutically acceptable salt of any of the foregoing, wherein:

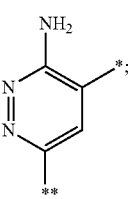

is selected from the group consisting of:

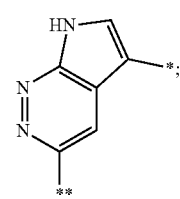

(a)

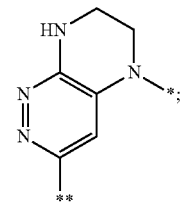

(b)

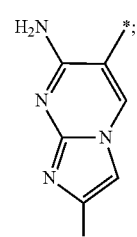

(c)

(d)

-continued

(e) ; and

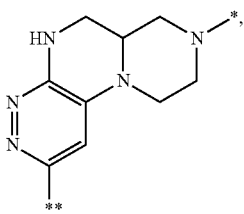
(f)

wherein, for (a)-(f), * denotes the point of attachment to [X], or, if [X] is absent, * denotes the point of attachment to [Y], or, if [X] and [Y] are absent, * denotes the point of attachment to [Z], and ** denotes the point of attachment to the remainder of the molecule;

and wherein:

(i) [X] is 3-15 membered heterocyclyl or 5-20 membered heteroaryl, provided that, when

is (a), then [X] is not

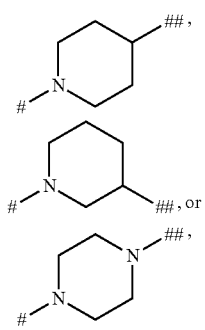

wherein # denotes the point of attachment to

and ## denotes the point of attachment to $R^1$, and provided that, when

is (f), and [X] is

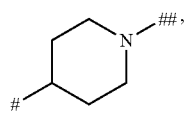

wherein # denotes the point of attachment to

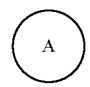

and ## denotes the point of attachment to $R^1$, then when $R^1$ is $-(CH_2)_n-R^g$, $R^g$ is not OH, or

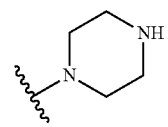

[Y] is absent, and
[Z] is absent; or (ii) [X] is 3-15 membered heterocyclyl or 5-20 membered heteroaryl, wherein the 3-15 membered heterocyclyl of [X] is optionally substituted with one or more —OH or $C_{1-6}$alkyl,
[Y] is absent, and
[Z] is 3-15 membered heterocyclyl or 5-20 membered heteroaryl, provided that, when

is (a), [X] is

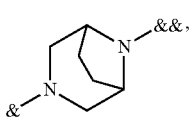

wherein & denotes the point of attachment to

and && denotes the point of attachment to [Z], and [Z] is

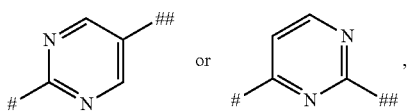

wherein # denotes the point of attachment to [X] and ## denotes the point of attachment to R¹, then:

(a-i) when R¹ is —C≡C—R$^a$ and R$^a$ is C$_{1-6}$ alkyl substituted with N(R$^x$)(R$^y$), R$^x$ and R$^y$ are not H or C$_{1-6}$ alkyl, and (a-ii) when R¹ is —(CH$_2$)$_n$—R$^g$ and R$^g$ is N(R$^x$)(R$^y$), then R$^x$ and R$^y$ are not H or C$_{1-6}$ alkyl, and provided that, when

is (b), [X] is

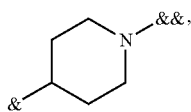

wherein & denotes the point of attachment to

and && denotes the point of attachment to [Z], and [Z] is

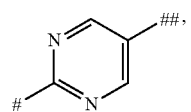

wherein # denotes the point of attachment to [X] and ## denotes the point of attachment to R¹, then:

(a-i) when R¹ is —C≡C—R$^a$ and R$^a$ is C$_{1-6}$ alkyl substituted with N(R$^x$)(R$^y$), R$^x$ and R$^y$ are not H or C$_{1-6}$ alkyl, and (a-ii) when R¹ is —(CH$_2$)$_n$—R$^g$ and R$^g$ is N(R$^x$)(R$^y$), then R$^x$ and R$^y$ are not H or C$_{1-6}$ alkyl; or (iii) [X] is 3-15 membered heterocyclyl or 5-20 membered heteroaryl,

[Y] is methylene, wherein the methylene of [Y] is optionally substituted with one or more methyl group, and

[Z] is 3-15 membered heterocyclyl; or (iv) [X] is absent,

[Y] is ethenylene, wherein the ethenylene of [Y] is optionally substituted with one or more halo, and

[Z] is 5-20 membered heteroaryl, provided that

is (a), (b), (d), or (e); or (v) [X] is absent,

[Y] is ethynylene, and

[Z] is 5-20 membered heteroaryl, provided that

is (a), (b), (d), or (e); or (vi) [X] is absent,

[Y] is cyclopropyl or cyclobutyl, and

[Z] is 5-20 membered heteroaryl, provided that

is (a), (b), (d), or (e); or (vii) [X] is absent,

[Y] is absent, and

[Z] is 5-20 membered heteroaryl; and

R¹ is:

(a) —C≡C—R$^a$, wherein (i) R$^a$ is C$_{1-6}$alkyl, wherein the C$_{1-6}$alkyl of R$^a$ is optionally substituted with one or more R$^b$, wherein each R$^b$ is independently 3-15 membered heterocyclyl, —O-(3-15 membered heterocyclyl), C$_{1-6}$alkoxy, —OH, —CN, halo, or —N(R$^x$)(R$^y$), wherein the 3-15 membered heterocyclyl of R$^b$ is optionally substituted with one or more R$^c$, wherein each R$^c$ is independently —OH, —CN, halo, oxo, C$_{1-6}$alkyl, C$_{1-6}$alkoxy, —S(O)$_2$—(C$_{1-6}$alkyl), C$_{3-10}$cycloalkyl, C$_{6-10}$aryl, 3-15 membered heterocyclyl, 5-20 membered heteroaryl, —O—(C$_{6-10}$aryl), —C(O)-(3-15 membered heterocyclyl), —C(O)—C$_{1-6}$alkoxy, —C(O)—N(R$^x$)(R$^y$), or —N(R$^x$)(R$^y$), wherein the C$_{1-6}$alkyl of R$^c$ is optionally substituted with one or more —OH, —CN, halo, C$_{1-6}$alkoxy, or 3-15 membered heterocyclyl, the C$_{3-10}$ cycloalkyl of R$^c$ is optionally substituted with one or more halo, the C$_{6-10}$aryl of R$^c$ is optionally substituted with one or more —CN, the 3-15 membered heterocyclyl of R$^c$ is optionally substituted with one or more C$_{1-6}$ alkyl or —C(O)—C$_{1-6}$alkyl, and the C$_{1-6}$alkoxy of R$^b$ is optionally substituted with one or more —OH, or (ii) R$^a$ is C$_{3-10}$ cycloalkyl, wherein the C$_{3-10}$ cycloalkyl of R$^a$ is optionally substituted with one or more R$^z$, or (iii) R$^a$ is 3-15 membered heterocyclyl, wherein the 3-15 membered heterocyclyl of R$^a$ is optionally substituted with one or more R$^z$, or (iv) R$^a$ is 5-20 membered heteroaryl, wherein the 5-20 membered heteroaryl of R$^a$ is optionally substituted with one or more R$^z$, or (b) —(CH$_2$)$_n$—R$^g$, wherein
n is an integer from 1-6, and
R$^g$ is —N(R$^x$)(R$^y$) or —OH;
wherein
R$^z$ is, independently at each occurrence, —OH, —CN, halo, C$_{1-6}$alkyl, C$_{1-6}$alkoxy, —N(R$^x$)(R$^y$), or —C(O)—N(R$^x$)(R$^y$); and
the R$^x$ and R$^y$ of —C(O)N(R$^x$)(R$^y$) and —N(R$^x$)(R$^y$) are, independently of each other and independently at each occurrence, H, —C(O)—(CH$_2$)$_p$—N(R$^p$)(R$^q$), —C(O)—R$^s$, 5-20 membered heterocycle, 5-20 membered heteroaryl, or C$_{1-6}$alkyl, wherein
p is an integer from 1-6,
R$^p$ and R$^q$ are, independently of each other and independently at each occurrence H, or C$_{1-6}$alkyl,
R$^s$ is 5-20 membered heterocycle optionally substituted with one or more substituents selected from the group consisting of C$_{1-4}$alkyl, C$_{3-8}$cycloalkyl, and —C(O)—C$_{1-6}$alkyl,
the C$_{1-6}$alkyl of R$^x$ or R$^y$ is optionally substituted with one or more —OH, 3-15 membered heterocyclyl, or —C(O)-(3-15 membered heterocyclyl), and
the 5-20 membered heterocycle of R$^x$ or R$^y$ is optionally substituted with one or more oxo, or
(c) —C≡C—R$^d$, wherein R$^d$ is C$_{1-6}$alkyl, wherein the C$_{1-6}$alkyl of R$^d$ is optionally substituted with one or more R$^e$, wherein each R$^e$ is independently 3-15 membered heterocyclyl, wherein the 3-15 membered heterocyclyl of R$^e$ is optionally substituted with one or more R$^f$, wherein each R$^f$ is independently —OH, —CN, halo, oxo, C$_{1-6}$alkyl, C$_{1-6}$alkoxy, or —C(O)—C$_{1-6}$alkoxy.

In some embodiments, R$^c$ is selected from OH, —CN, halo, C$_{1-6}$alkyl, C$_{1-6}$alkoxy, —N(R$^x$)(R$^y$), or —C(O)—N(R$^x$)(R$^y$). In some embodiments, R$^a$ is C$_{1-6}$alkyl substituted with R$^b$, wherein R$^b$ is 3-15 membered heterocyclyl, or R$^a$ is 3-15 membered heterocyclyl, wherein each 3-15 membered heterocyclyl of R$^a$ is optionally substituted with one or more R$^c$. In some embodiments, the 3-15 membered heterocyclyl is —N(R$^j$)(R$^k$). In some embodiments, the 3-15 membered heterocyclyl is —N(R$^j$)(R$^k$), wherein the R$^j$ and R$^k$ of —N(R$^j$)(R$^k$), together with the N atom to which they are attached, form a 4- to 12-membered heterocycle.

In one aspect, provided herein is a compound of formula (I):

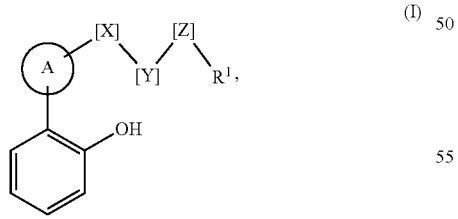

or a stereoisomer or tautomer thereof, or a pharmaceutically acceptable salt of any of the foregoing, wherein:

is selected from the group consisting of:

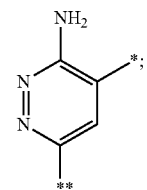
(a)

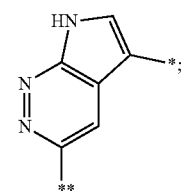
(b)

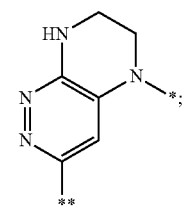
(c)

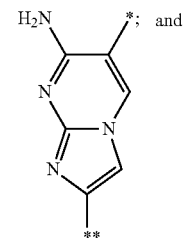
(d) ; and

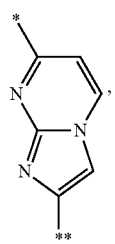
(e)

wherein, for (a)-(e), * denotes the point of attachment to [X], or, if [X] is absent, * denotes the point of attachment to [Y], and ** denotes the point of attachment to the remainder of the molecule;

and wherein:

(i) [X] is 3-15 membered heterocyclyl or 5-20 membered heteroaryl, provided that, when is (a), then [X] is not

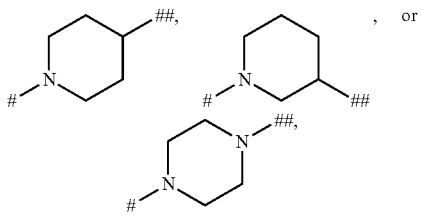

wherein # denotes the point of attachment to

and ## denotes the point of attachment to R¹,
[Y] is absent, and
[Z] is absent; or
(ii) [X] is 3-15 membered heterocyclyl or 5-20 membered heteroaryl, wherein the 3-15 membered heterocyclyl of [X] is optionally substituted with one or more —OH or $C_{1-6}$alkyl,
[Y] is absent, and
[Z] is 3-15 membered heterocyclyl or 5-20 membered heteroaryl,
provided that, when

is (a) and [X] is

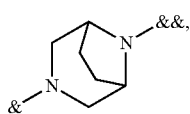

wherein & denotes the point of attachment to

and && denotes the point of attachment to [Z], then [Z] is not

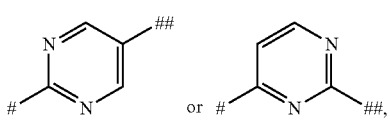

wherein # denotes the point of attachment to [X] and ## denotes the point of attachment to R¹; or
(iii) [X] is 3-15 membered heterocyclyl or 5-20 membered heteroaryl,

[Y] is methylene, wherein the methylene of [Y] is optionally substituted with one or more methyl group, and
[Z] is 3-15 membered heterocyclyl; or
(iv) [X] is absent,
[Y] is ethenylene, wherein the ethenylene of [Y] is optionally substituted with one or more halo, and
[Z] is 5-20 membered heteroaryl,
provided that

is (a), (b), (d), or (e); or
(v) [X] is absent,
[Y] is ethynylene, and
[Z] is 5-20 membered heteroaryl,
provided that

is (a), (b), (d), or (e); or
(vi) [X] is absent,
[Y] is cyclopropyl or cyclobutyl, and
[Z] is 5-20 membered heteroaryl,
provided that

is (a), (b), (d), or (e); and
R¹ is:
(a) —C≡C—$R^a$, wherein
(i) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$ cycloalkyl of $R^c$ is optionally substituted with one or more halo, and
the 3-15 membered heterocyclyl of $R^c$ is optionally substituted with one or more $C_{1-6}$ alkyl or —C(O)—$C_{1-6}$alkyl, and
the $C_{1-6}$alkoxy of $R^b$ is optionally substituted with one or more —OH, or
(ii) $R^a$ is $C_{3-10}$ cycloalkyl, wherein the $C_{3-10}$ cycloalkyl of $R^a$ is optionally substituted with one or more $R^z$, or
(iii) $R^a$ is 3-15 membered heterocyclyl, wherein the 3-15 membered heterocyclyl of $R^a$ is optionally substituted with one or more $R^z$, or (iv) R$^a$ is 5-20 membered heteroaryl, wherein the 5-20 membered heteroaryl of R$^a$ is optionally substituted with one or more R$^z$, or (b) —(CH$_2$)$_n$—R$^g$, wherein n is an integer from 1-6, and R$^g$ is —N(R$^x$)(R$^y$) or —OH;

wherein

R$^z$ is, independently at each occurrence, —OH, —CN, halo, C$_{1-6}$alkyl, C$_{1-6}$alkoxy, —N(R$^x$)(R$^y$), or —C(O)—N(R$^x$)(R$^y$); and the R$^x$ and R$^y$ of —C(O)N(R$^x$)(R$^y$) and —N(R$^x$)(R$^y$) are, independently of each other and independently at each occurrence, H, —C(O)—(CH$_2$)$_p$—N(R$^p$)(R$^q$), 5-20 membered heteroaryl, or C$_{1-6}$alkyl, wherein p is an integer from 1-6, R$^p$ and R$^q$ are, independently of each other and independently at each occurrence H, or C$_{1-6}$alkyl, and the C$_{1-6}$alkyl of R$^x$ or R$^y$ is optionally substituted with one or more —OH, 3-15 membered heterocyclyl, or —C(O)-(3-15 membered heterocyclyl).

In one aspect, provided herein is a compound of formula (I-A):

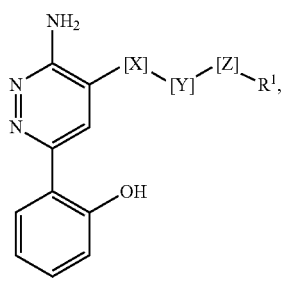

(I-A)

or a stereoisomer or tautomer thereof, or a pharmaceutically acceptable salt of any of the foregoing, wherein [X], [Y], [Z], and R$^1$ are as defined above or elsewhere herein for a compound of formula (I). In another variation, [X], [Y], [Z], and R$^1$ of formula I-A are as defined for a compound of formula (I'), or a stereoisomer or tautomer thereof, or a pharmaceutically acceptable salt of any of the foregoing, or any variation or embodiment thereof.

Any embodiments provided herein of a compound of formula (I), or a stereoisomer or tautomer thereof, or a pharmaceutically acceptable salt of any of the foregoing, or any variation or embodiment thereof, are also embodiments of a compound of formula (I') or formula (III') or a stereoisomer or tautomer thereof, or a pharmaceutically acceptable salt of any of the foregoing, or any variation or embodiment thereof.

Any embodiments provided herein of a compound of formula (I), (I'), (II), (II'), or (III'), or a stereoisomer or tautomer thereof, or a pharmaceutically acceptable salt of any of the foregoing, or any variation or embodiment thereof, are also embodiments of a compound of formula (IV'), or a stereoisomer or tautomer thereof, or a pharmaceutically acceptable salt of any of the foregoing, or any variation or embodiment thereof.

In one aspect, provided herein is a compound of formula (I-B):

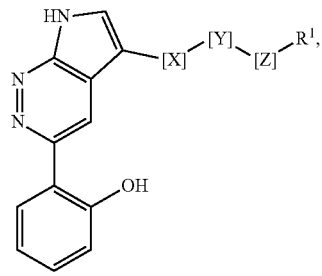

(I-B)

or a stereoisomer or tautomer thereof, or a pharmaceutically acceptable salt of any of the foregoing, wherein [X], [Y], [Z], and R$^1$ are as defined above or elsewhere herein for a compound of formula (I). In another variation, [X], [Y], [Z], and R$^1$ of formula I-B are as defined for a compound of formula (I'), or a stereoisomer or tautomer thereof, or a pharmaceutically acceptable salt of any of the foregoing, or any variation or embodiment thereof.

In one aspect, provided herein is a compound of formula (I-C):

(I-C)

or a stereoisomer or tautomer thereof, or a pharmaceutically acceptable salt of any of the foregoing, wherein [X], [Y], [Z], and R$^1$ are as defined above or elsewhere herein for a compound of formula (I). In another variation, [X], [Y], [Z], and R$^1$ of formula (I-C) are as defined for a compound of formula (I'), or a stereoisomer or tautomer thereof, or a pharmaceutically acceptable salt of any of the foregoing, or any variation or embodiment thereof.

In one aspect, provided herein is a compound of formula (I-D):

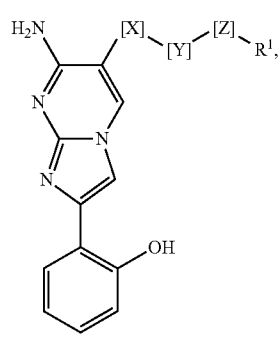

(I-D)

or a stereoisomer or tautomer thereof, or a pharmaceutically acceptable salt of any of the foregoing, wherein [X], [Y],

[Z], and R¹ are as defined above or elsewhere herein for a compound of formula (I). In another variation, [X], [Y], [Z], and R¹ of formula (I-D) are as defined for a compound of formula (I'), or a stereoisomer or tautomer thereof, or a pharmaceutically acceptable salt of any of the foregoing, or any variation or embodiment thereof.

In one aspect, provided herein is a compound of formula (I-E):

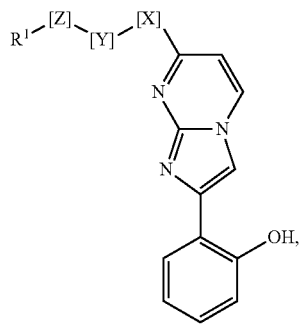

(I-E)

or a stereoisomer or tautomer thereof, or a pharmaceutically acceptable salt of any of the foregoing, wherein [X], [Y], [Z], and R¹ are as defined above or elsewhere herein for a compound of formula (I). In another variation, [X], [Y], [Z], and R¹ of formula (I-E) are as defined for a compound of formula (I'), or a stereoisomer or tautomer thereof, or a pharmaceutically acceptable salt of any of the foregoing, or any variation or embodiment thereof.

In one aspect, provided herein is a compound of formula (I-F):

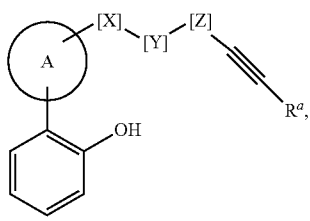

(I-F)

or a stereoisomer or tautomer thereof, or a pharmaceutically acceptable salt of any of the foregoing, wherein [X], [Y], [Z], and

A are as defined above or elsewhere herein for a compound of formula (I). In another variation, [X], [Y], [Z], and $R^a$ of formula (I-F) are as defined for a compound of formula (I'), or a stereoisomer or tautomer thereof, or a pharmaceutically acceptable salt of any of the foregoing, or any variation or embodiment thereof.

In one aspect, provided herein is a compound of formula (I-G):

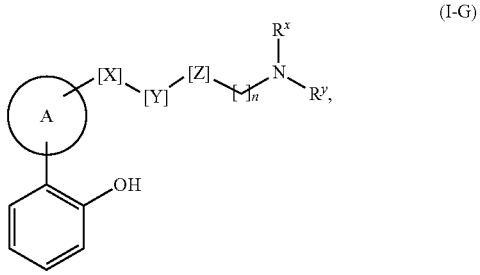

(I-G)

or a stereoisomer or tautomer thereof, or a pharmaceutically acceptable salt of any of the foregoing, wherein [X], [Y], [Z],

A n, $R^x$, and $R^y$ are as defined above or elsewhere herein for a compound of formula (I). In another variation, [X], [Y], [Z], $R^x$ and $R^y$ of formula (I-G) are as defined for a compound of formula (I'), or a stereoisomer or tautomer thereof, or a pharmaceutically acceptable salt of any of the foregoing, or any variation or embodiment thereof.

In one aspect, provided herein is a compound of formula (I-H):

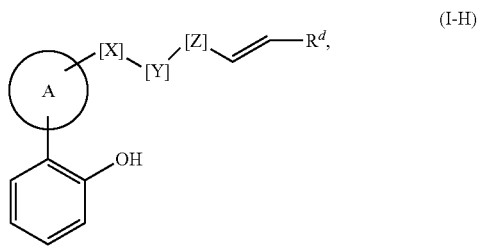

(I-H)

or a stereoisomer or tautomer thereof, or a pharmaceutically acceptable salt of any of the foregoing, wherein [X], [Y], [Z] and $R^d$ are as defined above or elsewhere herein for a compound of formula (I). In another variation, [X], [Y], [Z], and $R^d$ of formula (I-H) are as defined for a compound of formula (I'), or a stereoisomer or tautomer thereof, or a pharmaceutically acceptable salt of any of the foregoing, or any variation or embodiment thereof.

In one aspect, provided herein is a compound of formula (I-I):

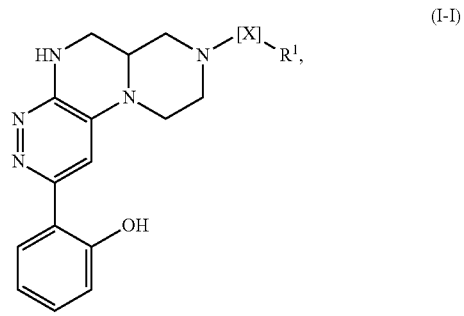

(I-I)

or a stereoisomer or tautomer thereof, or a pharmaceutically acceptable salt of any of the foregoing, wherein [X], and $R^1$ are as defined above or elsewhere herein for a compound of formula (I').

In one aspect, provided herein is a compound of formula (I-I1):

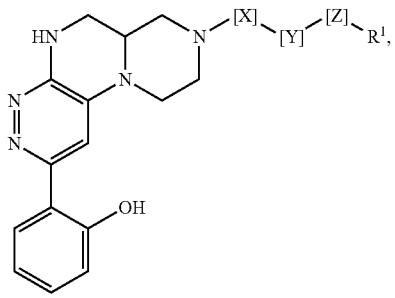
(I-I1)

or a stereoisomer or tautomer thereof, or a pharmaceutically acceptable salt of any of the foregoing, wherein [X], [Y], [Z], and $R^1$ are as defined above or elsewhere herein for a compound of formula (I').

In one aspect, provided herein is a pharmaceutical composition, comprising (i) a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a pharmaceutical composition, comprising (i) a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is a pharmaceutical composition, comprising (i) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a pharmaceutical composition, comprising (i) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is a method of modulating BRM in a cell, comprising exposing the cell to (1) an effective amount of a compound of formula (III'),

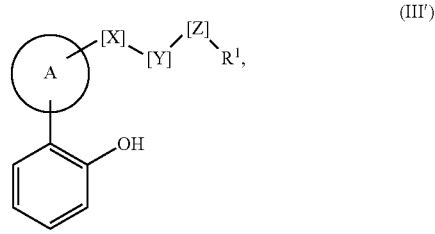
(III')

or a stereoisomer or tautomer thereof, or a pharmaceutically acceptable salt of any of the foregoing, or (2) a pharmaceutical composition, comprising (i) a compound of formula (III'), or a stereoisomer or tautomer thereof, or a pharmaceutically acceptable salt of any of the foregoing, and (ii) one or more pharmaceutically acceptable excipients, wherein:

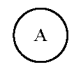

is selected from the group consisting of:

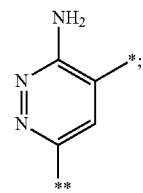
(a)

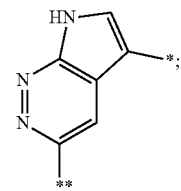
(b)

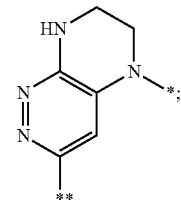
(c)

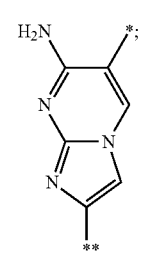
(d)

-continued

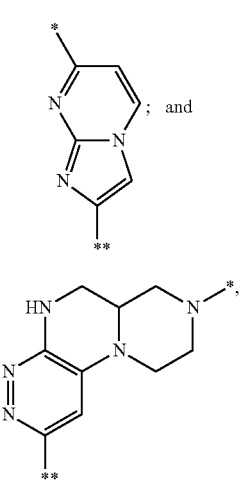

(e)

(f)

wherein, for (a)-(f), * denotes the point of attachment to [X], or, if [X] is absent, * denotes the point of attachment to [Y], or, if [X] and [Y] are absent, * denotes the point of attachment to [Z], and ** denotes the point of attachment to the remainder of the molecule;
and wherein:
(i) [X] is 3-15 membered heterocyclyl or 5-20 membered heteroaryl,
  [Y] is absent, and
  [Z] is absent; or
(ii) [X] is 3-15 membered heterocyclyl or 5-20 membered heteroaryl, wherein the 3-15 membered heterocyclyl of [X] is optionally substituted with one or more —OH or $C_{1-6}$alkyl,
  [Y] is absent, and
  [Z] is 3-15 membered heterocyclyl or 5-20 membered heteroaryl; or
(iii) [X] is 3-15 membered heterocyclyl or 5-20 membered heteroaryl,
  [Y] is methylene, wherein the methylene of [Y] is optionally substituted with one or more methyl group, and
  [Z] is 3-15 membered heterocyclyl; or
(iv) [X] is absent,
  [Y] is ethenylene, wherein the ethenylene of [Y] is optionally substituted with one or more halo, and
  [Z] is 5-20 membered heteroaryl; or
(v) [X] is absent,
  [Y] is ethynylene, and
  [Z] is 5-20 membered heteroaryl; or
(vi) [X] is absent,
  [Y] is cyclopropyl or cyclobutyl, and
  [Z] is 5-20 membered heteroaryl; or
(v) [X] is absent,
  [Y] is absent, and
  [Z] is 5-20 membered heteroaryl; and
$R^1$ is:
(a) —C≡C—$R^a$, wherein
(i) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$ alkyl), $C_{3-10}$cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$ cycloalkyl of $R^c$ is optionally substituted with one or more halo,
the $C_{6-10}$aryl of $R^c$ is optionally substituted with one or more —CN,
the 3-15 membered heterocyclyl of $R^c$ is optionally substituted with one or more $C_{1-6}$ alkyl or —C(O)—$C_{1-6}$alkyl, and
the $C_{1-6}$alkoxy of $R^b$ is optionally substituted with one or more —OH, or
(ii) $R^a$ is $C_{3-10}$ cycloalkyl, wherein the $C_{3-10}$ cycloalkyl of $R^a$ is optionally substituted with one or more $R^z$, or
(iii) $R^a$ is 3-15 membered heterocyclyl, wherein the 3-15 membered heterocyclyl of $R^a$ is optionally substituted with one or more $R^z$, or
(iv) $R^a$ is 5-20 membered heteroaryl, wherein the 5-20 membered heteroaryl of $R^a$ is optionally substituted with one or more $R^z$, or
(b) —(CH$_2$)$_n$—$R^g$, wherein
n is an integer from 1-6, and
$R^g$ is —N($R^x$)($R^y$) or —OH;
wherein
$R^z$ is, independently at each occurrence, —OH, —CN, halo, $C_{1-6}$alkyl, $C_{1-6}$alkoxy, —N($R^x$)($R^y$), or —C(O)—N($R^x$)($R^y$); and
the $R^x$ and $R^y$ of —C(O)N($R^x$)($R^y$) and —N($R^x$)($R^y$) are, independently of each other and independently at each occurrence, H, —C(O)—(CH$_2$)$_p$—N($R^p$)($R^q$), —C(O)—$R^s$, 5-20 membered heterocycle, 5-20 membered heteroaryl, or $C_{1-6}$alkyl, wherein
p is an integer from 1-6,
$R^p$ and $R^q$ are, independently of each other and independently at each occurrence H, or $C_{1-6}$alkyl,
$R^s$ is 5-20 membered heterocycle optionally substituted with one or more substituents selected from the group consisting of $C_{1-4}$alkyl, $C_{3-8}$cycloalkyl, and —C(O)—$C_{1-6}$alkyl,
the $C_{1-6}$alkyl of $R^x$ or $R^y$ is optionally substituted with one or more —OH, 3-15 membered heterocyclyl, or —C(O)-(3-15 membered heterocyclyl), and
the 5-20 membered heterocycle of $R^x$ or $R^y$ is optionally substituted with one or more oxo, or
(c) —C≡C—$R^d$, wherein $R^d$ is $C_{1-6}$alkyl, wherein the $C_{1-6}$alkyl of $R^d$ is optionally substituted with one or more $R^e$, wherein each $R^e$ is independently 3-15 membered heterocyclyl, wherein the 3-15 membered heterocyclyl of $R^c$ is optionally substituted with one or more $R^f$, wherein each $R^f$ is independently —OH, —CN, halo, oxo, $C_{1-6}$alkyl, $C_{1-6}$alkoxy, or —C(O)—$C_{1-6}$alkoxy.

In one aspect, provided herein is a method of modulating BRM in a cell, comprising exposing the cell to (1) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, or (2) a pharmaceutical composition, comprising (i) a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a method of modulating BRM in a cell, comprising exposing the cell to (1) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, or (2) a pharmaceutical composition, comprising (i) a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is a method of inhibiting BRM in a cell, comprising exposing the cell to (1) an effective amount of a compound of formula (III'), or a stereoisomer or tautomer thereof, or a pharmaceutically acceptable salt of any of the foregoing, or (2) a pharmaceutical composition, comprising (i) a compound of formula (III'), or a stereoisomer or tautomer thereof, or a pharmaceutically acceptable salt of any of the foregoing, and (ii) one or more pharmaceutically acceptable excipients. In one aspect, provided herein is a method of inhibiting BRM in a cell, comprising exposing the cell to (1) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, or (2) a pharmaceutical composition, comprising (i) a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a method of inhibiting BRM in a cell, comprising exposing the cell to (1) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, or (2) a pharmaceutical composition, comprising (i) a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is a method of degrading BRM in a cell, comprising exposing the cell to (1) an effective amount of a compound of formula (III'), or a stereoisomer or tautomer thereof, or a pharmaceutically acceptable salt of any of the foregoing, or (2) a pharmaceutical composition, comprising (i) a compound of formula (III'), or a stereoisomer or tautomer thereof, or a pharmaceutically acceptable salt of any of the foregoing, and (ii) one or more pharmaceutically acceptable excipients. In one aspect, provided herein is a method of degrading BRM in a cell, comprising exposing the cell to (1) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, or (2) a pharmaceutical composition, comprising (i) a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a method of degrading BRM in a cell, comprising exposing the cell to (1) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, or (2) a pharmaceutical composition, comprising (i) a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is a method of treating a BRM- or BRG1-mediated disease, disorder, or condition in an individual in need thereof, comprising administering to the individual (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In one aspect, provided herein is a method of treating a BRM- or BRG1-mediated disease, disorder, or condition in an individual in need thereof, comprising administering to the individual (1) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, or (2) a pharmaceutical composition, comprising (i) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a method of treating a BRM- or BRG1-mediated disease, disorder, or condition in an individual in need thereof, comprising administering to the individual (1) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is a method of treating a BRM-mediated disease, disorder, or condition in an individual in need thereof, comprising administering to the individual (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In one aspect, provided herein is a method of treating a BRM-mediated disease, disorder, or condition in an individual in need thereof, comprising administering to the individual (1) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, or (2) a pharmaceutical composition, comprising (i) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a method of treating a BRM-mediated disease, disorder, or condition in an individual in need thereof, comprising administering to the individual (1) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is a method of increasing the efficacy of cancer treatment in an individual in need thereof, comprising administering to the individual (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In one aspect, provided herein is a method of increasing the efficacy of cancer treatment in an individual in need thereof, comprising administering to the individual (1) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, or (2) a pharmaceutical composition, comprising (i) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a method of increasing the efficacy of cancer treatment in an individual in need thereof, comprising administering to the individual (1) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is a method of preventing or delaying development of cancer resistance to a cytotoxic agent in a human, comprising administering to the individual (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In one aspect, provided herein is a method of preventing or delaying development of cancer resistance to a cytotoxic agent in a human, comprising administering to the individual (1) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, or (2) a pharmaceutical composition, comprising (i) an effective amount of a compound of formula (I'), such as a compound of formula (I-A), (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a method of preventing or delaying development of cancer resistance to a cytotoxic agent in a human, comprising administering to the individual (1) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is a method of extending the duration of response to a cancer therapy in a human, comprising administering to the individual (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In one aspect, provided herein is a method of extending the duration of response to a cancer therapy in a human, comprising administering to the individual (1) an effective amount of a compound of formula (I'), such as a compound of formula (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, or (2) a pharmaceutical composition, comprising (i) an effective amount of a compound of formula (I'), such as a compound of formula (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, and (ii) one or more pharmaceutically acceptable excipients. In one aspect, provided herein is a method of extending the duration of response to a cancer therapy in a human, comprising administering to the individual (1) an effective amount of a compound of formula (I), such as a compound of formula (I-B), (I-C), (I-D) (I-E), (I-F), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-B), (I-C), (I-D) (I-E), (I-F), or (I-G), or a stereoisomer or tautomer thereof, or a pharmaceutically acceptable salt of any of the foregoing, and (ii) one or more pharmaceutically acceptable excipients.

In one aspect, provided herein is the use of a compound of formula (III'), or a stereoisomer or tautomer thereof, or a pharmaceutically acceptable salt of any of the foregoing, in the manufacture of a medicament for use in the treatment of a disease, disorder, or condition mediated by BRM or BRG1. In one aspect, provided herein is the use of a compound of formula (I'), such as a compound of formula (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, in the manufacture of a medicament for use in the treatment of a disease, disorder, or condition mediated by BRM or BRG1. In one aspect, provided herein is the use of a compound of formula (I'), such as a compound of formula (I-B), (I-C), (I-D) (I-E), (I-F), or (I-G), or a stereoisomer or tautomer thereof, or a pharmaceutically acceptable salt of any of the foregoing, in the manufacture of a medicament for use in the treatment of a disease, disorder, or condition mediated by BRM or BRG1.

In one aspect, provided herein is the use of a compound of formula (III'), or a stereoisomer or tautomer thereof, or a pharmaceutically acceptable salt of any of the foregoing, in the manufacture of a medicament for use in the treatment of a disease, disorder, or condition mediated by BRM. In one aspect, provided herein is the use of a compound of formula (I'), such as a compound of formula (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, in the manufacture of a medicament for use in the treatment of a disease, disorder, or condition mediated by BRM. In one aspect, provided herein is the use of a compound of formula (I'), such as a compound of formula (I-B), (I-C), (I-D) (I-E), (I-F), or (I-G), or a stereoisomer or tautomer thereof, or a pharmaceutically acceptable salt of any of the foregoing, in the manufacture of a medicament for use in the treatment of a disease, disorder, or condition mediated by BRM.

In one aspect, provided herein is the use of a compound of formula (III'), or a stereoisomer or tautomer thereof, or a pharmaceutically acceptable salt of any of the foregoing, in the manufacture of a medicament for use in the treatment of cancer. In one aspect, provided herein is the use of a compound of formula (I'), such as a compound of formula (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, in the manufacture of a medicament for use in the treatment of cancer. In one aspect, provided herein is the use of a compound of formula (I), such as a compound of formula (I-B), (I-C), (I-D) (I-E), (I-F), or (I-G), or a stereoisomer or tautomer thereof, or a pharmaceutically acceptable salt of any of the foregoing, in the manufacture of a medicament for use in the treatment of cancer.

In one aspect, provided herein is a compound of formula (III'), or a stereoisomer or tautomer thereof, or a pharmaceutically acceptable salt of any of the foregoing, for use in the treatment of a disease, disorder, or condition mediated by BRM or BRG1. In one aspect, provided herein is a compound of formula (I'), such as a compound of formula (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, for use in the treatment of a disease, disorder, or condition mediated by BRM or BRG1. In one aspect, provided herein is a compound of formula (I), such as a compound of formula (I-B), (I-C), (I-D) (I-E), (I-F), or (I-G), or a stereoisomer or tautomer thereof, or a pharmaceutically acceptable salt of any of the foregoing, for use in the treatment of a disease, disorder, or condition mediated by BRM or BRG1.

In one aspect, provided herein is a compound of formula (III'), or a stereoisomer or tautomer thereof, or a pharmaceutically acceptable salt of any of the foregoing, for use in the treatment of a disease, disorder, or condition mediated by BRM. In one aspect, provided herein is a compound of formula (I'), such as a compound of formula (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, for use in the treatment of a disease, disorder, or condition mediated by BRM. In one aspect, provided herein is a compound of formula (I), such as a compound of formula (I-B), (I-C), (I-D) (I-E), (I-F), or (I-G), or a stereoisomer or tautomer thereof, or a pharmaceutically acceptable salt of any of the foregoing, for use in the treatment of a disease, disorder, or condition mediated by BRM.

In one aspect, provided herein is a compound of formula (I'), such as a compound of formula (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, for use in the treatment of cancer. In one aspect, provided herein is a compound of formula (III'), or a stereoisomer or tautomer thereof, or a pharmaceutically acceptable salt of any of the foregoing, for use in the treatment of cancer. In one aspect, provided herein is a compound of formula (I), such as a compound of formula (I-B), (I-C), (I-D) (I-E), (I-F), or (I-G), or a stereoisomer or tautomer thereof, or a pharmaceutically acceptable salt of any of the foregoing, for use in the treatment of cancer.

In one aspect, provided herein is a process for preparing a compound of formula (III'), or a stereoisomer or tautomer thereof, or a pharmaceutically acceptable salt of any of the foregoing. In one aspect, provided herein is a process for preparing a compound of formula (I'), such as a compound of formula (I-B), (I-C), (I-D) (I-E), (I-F), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing. In one aspect, provided herein is a process for preparing a compound of formula (I), such as a compound of formula (I-B), (I-C), (I-D) (I-E), (I-F), or (I-G), or a stereoisomer or tautomer thereof, or a pharmaceutically acceptable salt of any of the foregoing.

In one aspect, provided herein is a compound of formula (II'):

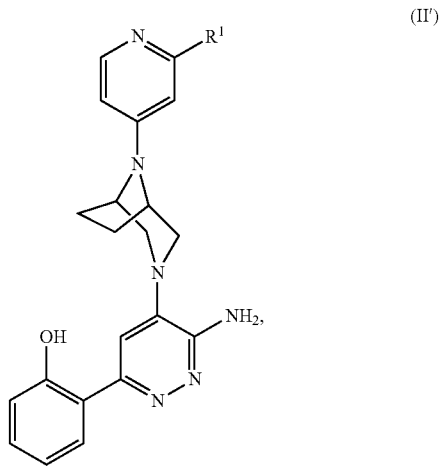

or a stereoisomer or tautomer thereof, or a pharmaceutically acceptable salt of any of the foregoing, wherein:
(i) $R^1$ is —C≡C—$R^a$, wherein
(a) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$ alkyl), $C_{3-10}$cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$ cycloalkyl of $R^c$ is optionally substituted with one or more halo,
the $C_{6-10}$aryl of $R^c$ is optionally substituted with one or more —CN,
the 3-15 membered heterocyclyl of $R^c$ is optionally substituted with one or more $C_{1-6}$ alkyl or —C(O)—$C_{1-6}$alkyl, and
the $C_{1-6}$alkoxy of $R^b$ is optionally substituted with one or more —OH, or
(b) $R^a$ is $C_{3-10}$ cycloalkyl, wherein the $C_{3-10}$ cycloalkyl of $R^a$ is optionally substituted with one or more $R^z$, or (c) $R^a$ is 3-15 membered heterocyclyl, wherein the 3-15 membered heterocyclyl of $R^a$ is optionally substituted with one or more $R^z$, or
(d) $R^a$ is 5-20 membered heteroaryl, wherein the 5-20 membered heteroaryl of $R^a$ is optionally substituted with one or more $R^z$, or (ii) $R^1$ is —(CH$_2$)$_n$—$R^g$, wherein
$R^g$ is —N(R$^x$)(R$^y$) or —OH, and
n is an integer from 1-6;
wherein
$R^z$ is, independently at each occurrence, —OH, —CN, halo, C$_{1-6}$alkyl, C$_{1-6}$alkoxy, —N(R$^x$)(R$^y$), or —C(O)—N(R$^x$)(R$^y$); and
the R$^x$ and R$^y$ of —C(O)N(R$^x$)(R$^y$) and —N(R$^x$)(R$^y$) are, independently of each other and independently at each occurrence, H, —C(O)—(CH$_2$)$_p$—N(R$^p$)(R$^q$), —C(O)—R$^s$, 5-20 membered heterocycle, 5-20 membered heteroaryl, or C$_{1-6}$alkyl, wherein
p is an integer from 1-6,
$R^p$ and $R^q$ are, independently of each other and independently at each occurrence H, or C$_{1-6}$alkyl,
$R^s$ is 5-20 membered heterocycle optionally substituted with one or more substituents selected from the group consisting of C$_{1-4}$alkyl, C$_{3-8}$cycloalkyl, and —C(O)—C$_{1-6}$alkyl,
the C$_{1-6}$alkyl of R$^x$ or R$^y$ is optionally substituted with one or more —OH, 3-15 membered heterocyclyl, or —C(O)-(3-15 membered heterocyclyl), and
the 5-20 membered heterocycle of R$^x$ or R$^y$ is optionally substituted with one or more oxo.

In one aspect, provided herein is a compound of formula (II):

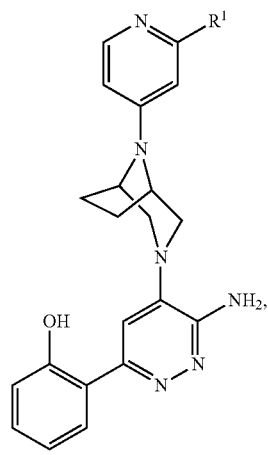

(II)

or a stereoisomer or tautomer thereof, or a pharmaceutically acceptable salt of any of the foregoing, wherein:
(i) $R^1$ is —C≡C—R$^a$, wherein
(a) $R^a$ is C$_{1-6}$alkyl, wherein the C$_{1-6}$alkyl of $R^a$ is optionally substituted with one or more $R^b$, wherein each $R^b$ is independently 3-15 membered heterocyclyl, —O-(3-15 membered heterocyclyl), C$_{1-6}$alkoxy, —OH, —CN, halo, or —N(R$^x$)(R$^y$), wherein
the 3-15 membered heterocyclyl of $R^b$ is optionally substituted with one or more $R^c$, wherein each $R^c$ is independently —OH, —CN, halo, oxo, C$_{1-6}$alkyl, C$_{1-6}$alkoxy, C$_{3-10}$ cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein
the C$_{1-6}$alkyl of R$^c$ is optionally substituted with one or more —OH, —CN, halo, C$_{1-6}$alkoxy, or 3-15 membered heterocyclyl,
the C$_{3-10}$ cycloalkyl of R$^c$ is optionally substituted with one or more halo, and
the 3-15 membered heterocyclyl of R$^c$ is optionally substituted with one or more C$_{1-6}$ alkyl or —C(O)—C$_{1-6}$alkyl, and
the C$_{1-6}$alkoxy of R$^b$ is optionally substituted with one or more OH, or
(b) $R^a$ is C$_{3-10}$ cycloalkyl, wherein the C$_{3-10}$ cycloalkyl of $R^a$ is optionally substituted with one or more $R^z$, or
(c) $R^a$ is 3-15 membered heterocyclyl, wherein the 3-15 membered heterocyclyl of $R^a$ is optionally substituted with one or more $R^z$, or
(d) $R^a$ is 5-20 membered heteroaryl, wherein the 5-20 membered heteroaryl of $R^a$ is optionally substituted with one or more $R^z$, or (ii) $R^1$ is —(CH$_2$)$_n$—$R^g$, wherein
n is an integer from 1-6, and
$R^g$ is —N(R$^x$)(R$^y$) or —OH,
wherein
$R^z$ is, independently at each occurrence, —OH, —CN, halo, C$_{1-6}$alkyl, C$_{1-6}$alkoxy, —N(R$^x$)(R$^y$), or —C(O)—N(R$^x$)(R$^y$); and
the R$^x$ and R$^y$ of —C(O)N(R$^x$)(R$^y$) and —N(R$^x$)(R$^y$) are, independently of each other and independently at each occurrence, H, —C(O)—(CH$_2$)$_p$—N(R$^p$)(R$^q$), 5-20 membered heteroaryl, or C$_{1-6}$alkyl, wherein
p is an integer from 1-6,
$R^p$ and $R^q$ are, independently of each other and independently at each occurrence H, or C$_{1-6}$alkyl, and
the C$_{1-6}$alkyl of R$^x$ or R$^y$ is optionally substituted with one or more —OH, 3-15 membered heterocyclyl, or —C(O)-(3-15 membered heterocyclyl).

Any embodiments provided herein of a compound of formula (II), or a stereoisomer or tautomer thereof, or a pharmaceutically acceptable salt of any of the foregoing, or any variation or embodiment thereof, are also embodiments of a compound of formula (II'), or a stereoisomer or tautomer thereof, or a pharmaceutically acceptable salt of any of the foregoing, or any variation or embodiment thereof.

In one aspect, provided herein is a compound of formula (II-A):

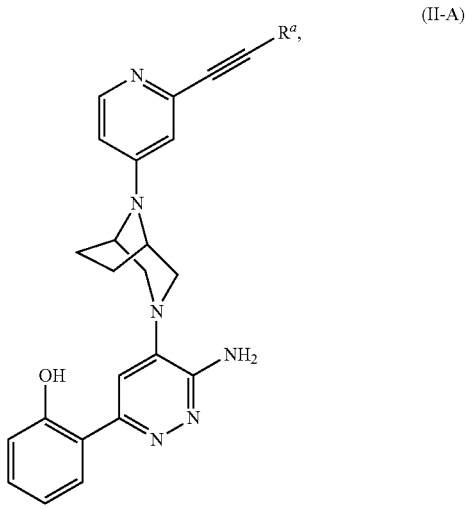

(II-A)

or a stereoisomer or tautomer thereof, or a pharmaceutically acceptable salt of any of the foregoing, wherein $R^a$ is as defined above or elsewhere herein for a compound of formula (II). In another variation, $R^a$ of formula (II-A) are as defined for a compound of formula (II'), or a stereoisomer or tautomer thereof, or a pharmaceutically acceptable salt of any of the foregoing, or any variation or embodiment thereof.

In one aspect, provided herein is a compound of formula (II-A1):

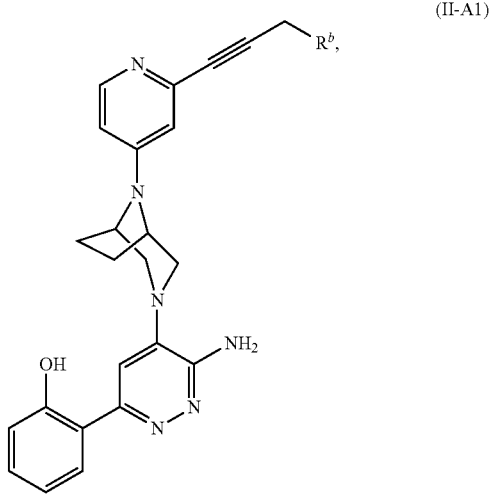

(II-A1)

or a stereoisomer or tautomer thereof, or a pharmaceutically acceptable salt of any of the foregoing, wherein $R^b$ is as defined above or elsewhere herein for a compound of formula (II). In another variation, $R^b$ of formula (II-A1) are as defined for a compound of formula (II'), or a stereoisomer or tautomer thereof, or a pharmaceutically acceptable salt of any of the foregoing, or any variation or embodiment thereof.

In one aspect, provided herein is a compound of formula (I-B):

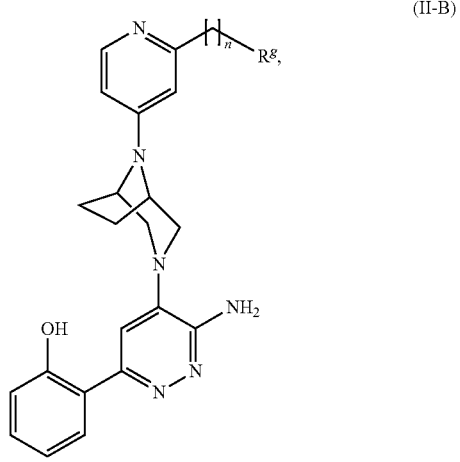

(II-B)

or a stereoisomer or tautomer thereof, or a pharmaceutically acceptable salt of any of the foregoing, wherein $R^g$ is as defined above or elsewhere herein for a compound of formula (II). In another variation, $R^g$ of formula (II-B) are as defined for a compound of formula (II'), or a stereoisomer or tautomer thereof, or a pharmaceutically acceptable salt of any of the foregoing, or any variation or embodiment thereof.

In one aspect, provided herein is a compound of formula (II-B1):

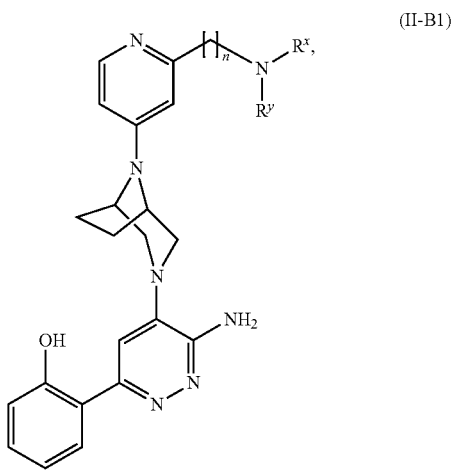

(II-B1)

or a stereoisomer or tautomer thereof, or a pharmaceutically acceptable salt of any of the foregoing, wherein $R^x$, $R^y$, and n are as defined above or elsewhere herein for a compound of formula (II). In another variation, $R^x$, $R^y$, and n of formula (II-B1) are as defined for a compound of formula (II'), or a stereoisomer or tautomer thereof, or a pharmaceutically acceptable salt of any of the foregoing, or any variation or embodiment thereof.

In one aspect, provided herein is a pharmaceutical composition, comprising (i) a compound of formula (II'), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients. In one aspect, provided herein is a pharmaceutical composition, comprising (i) a compound of formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In one aspect, provided herein is a method of modulating BRM in a cell, comprising exposing the cell to (1) an effective amount of a compound of formula (II'), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) a compound of formula (II'), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients. In one aspect, provided herein is a method of modulating BRM in a cell, comprising exposing the cell to (1) an effective amount of a compound of formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) a compound of formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In one aspect, provided herein is a method of inhibiting BRM in a cell, comprising exposing the cell to (1) an effective amount of a compound of formula (II'), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) a compound of formula (II'), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients. In one aspect, provided herein is a method of inhibiting BRM in a cell, comprising exposing the cell to (1) an effective amount of a compound of formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) a compound of formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In one aspect, provided herein is a method of degrading BRM in a cell, comprising exposing the cell to (1) an effective amount of a compound of formula (II'), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) a compound of formula (II'), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients. In one aspect, provided herein is a method of degrading BRM in a cell, comprising exposing the cell to (1) an effective amount of a compound of formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) a compound of formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In one aspect, provided herein is a method of treating a BRM- or BRG1-mediated disease, disorder, or condition in an individual in need thereof, comprising administering to the individual (1) an effective amount of a compound of formula (II'), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II'), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients. In one aspect, provided herein is a method of treating a BRM- or BRG1-mediated disease, disorder, or condition in an individual in need thereof, comprising administering to the individual (1) an effective amount of a compound of formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In one aspect, provided herein is a method of treating a BRM-mediated disease, disorder, or condition in an individual in need thereof, comprising administering to the individual (1) an effective amount of a compound of formula (II'), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II'), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients. In one aspect, provided herein is a method of treating a BRM-mediated disease, disorder, or condition in an individual in need thereof, comprising administering to the individual (1) an effective amount of a compound of formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In one aspect, provided herein is a method of increasing the efficacy of cancer treatment in an individual in need thereof, comprising administering to the individual (1) an effective amount of a compound of formula (II'), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II'), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients. In one aspect, provided herein is a method of increasing the efficacy of cancer treatment in an individual in need thereof, comprising administering to the individual (1) an effective amount of a compound of formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In one aspect, provided herein is a method of preventing or delaying development of cancer resistance to a cytotoxic agent in a human, comprising administering to the individual (1) an effective amount of a compound of formula (II'), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II'), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients. In one aspect, provided herein is a method of preventing or delaying development of cancer resistance to a cytotoxic agent in a human, comprising administering to the individual (1) an effective amount of a compound of formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In one aspect, provided herein is a method of extending the duration of response to a cancer therapy in a human, comprising administering to the individual (1) an effective amount of a compound of formula (II'), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II'), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients. In one aspect, provided herein is a method of extending the duration of response to a cancer therapy in a human, comprising administering to the individual (1) an effective amount of a compound of formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In one aspect, provided herein is the use of a compound of formula (II'), such as a compound of formula (II-A), (II-A1), (II-B), or (II-B1), or a stereoisomer or tautomer thereof, or a pharmaceutically acceptable salt of any of the foregoing, in the manufacture of a medicament for use in the treatment of a disease, disorder, or condition mediated by BRM or BRG1. In one aspect, provided herein is the use of a compound of formula (II), such as a compound of formula (II-A), (II-A1), (II-B), or (II-B1), or a stereoisomer or tautomer thereof, or a pharmaceutically acceptable salt of any of the foregoing, in the manufacture of a medicament for use in the treatment of a disease, disorder, or condition mediated by BRM or BRG1.

In one aspect, provided herein is the use of a compound of formula (II'), such as a compound of formula (II-A), (II-A1), (II-B), or (II-B1), or a stereoisomer or tautomer thereof, or a pharmaceutically acceptable salt of any of the foregoing, in the manufacture of a medicament for use in the treatment of a disease, disorder, or condition mediated by BRM. In one aspect, provided herein is the use of a compound of formula (II), such as a compound of formula (II-A), (II-A1), (II-B), or (II-B1), or a stereoisomer or tautomer thereof, or a pharmaceutically acceptable salt of any of the foregoing, in the manufacture of a medicament for use in the treatment of a disease, disorder, or condition mediated by BRM.

In one aspect, provided herein is the use of a compound of formula (II'), such as a compound of formula (II-A), (II-A1), (II-B), or (II-B1), or a stereoisomer or tautomer thereof, or a pharmaceutically acceptable salt of any of the foregoing, in the manufacture of a medicament for use in the treatment of cancer. In one aspect, provided herein is the use of a compound of formula (II), such as a compound of formula (II-A), (II-A1), (II-B), or (II-B1), or a stereoisomer or tautomer thereof, or a pharmaceutically acceptable salt of any of the foregoing, in the manufacture of a medicament for use in the treatment of cancer.

In one aspect, provided herein is a compound of formula (II'), such as a compound of formula (II-A), (II-A1), (II-B), or (II-B1), or a stereoisomer or tautomer thereof, or a pharmaceutically acceptable salt of any of the foregoing, for use in the treatment of a disease, disorder, or condition mediated by BRM or BRG1. In one aspect, provided herein is a compound of formula (II), such as a compound of formula (II-A), (II-A1), (II-B), or (II-B1), or a stereoisomer or tautomer thereof, or a pharmaceutically acceptable salt of any of the foregoing, for use in the treatment of a disease, disorder, or condition mediated by BRM or BRG1.

In one aspect, provided herein is a compound of formula (II'), such as a compound of formula (II-A), (II-A1), (II-B), or (II-B1), or a stereoisomer or tautomer thereof, or a pharmaceutically acceptable salt of any of the foregoing, for use in the treatment of a disease, disorder, or condition mediated by BRM. In one aspect, provided herein is a compound of formula (II), such as a compound of formula (II-A), (II-A1), (II-B), or (II-B1), or a stereoisomer or tautomer thereof, or a pharmaceutically acceptable salt of any of the foregoing, for use in the treatment of a disease, disorder, or condition mediated by BRM.

In one aspect, provided herein is a compound of formula (II'), such as a compound of formula (II-A), (II-A1), (II-B), or (II-B1), or a stereoisomer or tautomer thereof, or a pharmaceutically acceptable salt of any of the foregoing, for use in the treatment of cancer. In one aspect, provided herein is a compound of formula (II), such as a compound of formula (II-A), (II-A1), (II-B), or (II-B1), or a stereoisomer or tautomer thereof, or a pharmaceutically acceptable salt of any of the foregoing, for use in the treatment of cancer.

In one aspect, provided herein is a process for preparing a compound of formula (II'), such as a compound of formula (II-A), (II-A1), (II-B), or (II-B1), or a stereoisomer or tautomer thereof, or a pharmaceutically acceptable salt of any of the foregoing. In one aspect, provided herein is a process for preparing a compound of formula (II), such as a compound of formula (II-A), (II-A1), (II-B), or (II-B1), or a stereoisomer or tautomer thereof, or a pharmaceutically acceptable salt of any of the foregoing.

DETAILED DESCRIPTION

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers alternatives, modifications, and equivalents. In the event that one or more of the incorporated literature, patents, and similar materials differs from or contradicts this application, including, but not limited to, defined terms, term usage, described techniques, or the like, this application controls. Unless otherwise defined, technical and scientific terms used herein have the same meaning as commonly understood by one of ordinary skill in the art to which this disclosure belongs, applying that term in context to its use in describing the present disclosure. The terminology used in the description is for describing particular embodiments only and is not intended to be limiting of the disclosure. All publications, patent applications, patents, and other references mentioned herein are incorporated herein by reference in their entirety.

I. Definitions

The terms "moiety" or "group" refers to a component that is covalently bound or linked to another component.

A "patient" or an "individual" or a "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human. In embodiments, the patient may be a "cancer patient," i.e. one who is suffering or at risk for suffering from one or more symptoms of cancer.

The term "cancer" refers to or describes the physiological condition in mammals that is typically characterized by unregulated cell growth/proliferation. In particular, the term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. A "tumor" comprises one or more cancerous cells. Examples of cancer are provided elsewhere herein.

As used herein, "treatment" (and grammatical variations thereof, such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In embodiments, the compounds and compositions of the subject matter described herein are used to delay development of a disease or to slow the progression of a disease. In embodiments, treatment is performed for prophylaxis only. In an embodiment, treatment is performed during the course of clinical pathology only (i.e., not for prophylaxis). In an embodiment, treatment is performed both during the course of clinical pathology and for prophylaxis.

As used herein, the term "modulate" (and grammatical variations thereof, such as "modulation" or "modulating") means to directly or indirectly modify, vary, control, alter, increase, or decrease the rate, extent, or size of a given action, activity, process, event, or characteristic. For example, in non-limiting embodiments, modulating the BRM activity in a cell means to increase the activity of BRM in the cell. In other non-limiting embodiments, modulating the BRM activity in a cell means to decrease the activity of BRM in the cell. The term "modulate" encompasses the term "inhibit", as defined below.

As used herein, the term "inhibit" (and grammatical variations thereof, such as "inhibition" and "inhibiting") means to directly or indirectly hinder, reduce, or prevent a given action, activity, process, event, or characteristic. The inhibition may be total or partial. For example, in non-limiting embodiments, inhibiting the BRM activity in a cell means to hinder, reduce, or prevent the activity of BRM in the cell.

As used herein, the term "degrade" (and grammatical variations thereof, such as "degradation" and "degrading") means to break down a target entity or cause a target entity to be broken down (either directly or directly). In embodiments, the degradation of the target entity results in the inhibition of a given action, activity, process, event, or characteristic. For example, in non-limiting embodiments, degradation of BRM in a cell means to break down the BRM in the cell or cause the BRM in the cell to be broken down (either directly or indirectly) such that there is a reduction in or prevention of activity of the BRM in the cell.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

The term "effective", when used to describe an amount of a compound, composition, or component which, when used within the context of its intended use, achieves the desired therapeutic or prophylactic result. The term effective subsumes other effective amount or effective concentration terms, which are otherwise described or used in the present application. As used herein, the term "therapeutically effective amount" means the minimum amount which, as compared to a corresponding subject who has not received such amount, results in treatment of a disease, disorder, condition, or side effect, or a decrease in the rate of advancement of a disease, disorder, condition, or side effect. The term also includes within its scope amounts effective to enhance normal physiological function. For use in therapy, therapeutically effective amounts of a compound of the present disclosure, as well as pharmaceutically acceptable salts thereof, may be administered as the raw chemical. Additionally, the active ingredient may be presented as a pharmaceutical composition.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted", "further optionally substituted" or variations thereof denote an optional substitution, including multiple degrees of substitution, with one or more substituent group, for example, one, two, three, four or five. The phrase should not be interpreted as duplicative of the substitutions herein described and depicted.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19, herein incorporated by reference in its entirety). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115, herein incorporated by reference in its entirety. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10, herein incorporated by reference in its entirety. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$ alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

The term "alkyl" as used herein refers to a saturated linear or branched-chain monovalent hydrocarbon radical of any length from one to twelve carbon atoms ($C_1$-$e_{12}$), wherein the alkyl radical may be optionally substituted independently with one or more substituents described herein. In an embodiment, an alkyl radical is one to eight carbon atoms ($C_{1-8}$), or one to six carbon atoms ($C_{1-6}$), or one to four carbon atoms ($C_{1-4}$), or one to three carbon atoms ($C_{1-3}$). Examples of alkyl groups include, but are not limited to: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, isopropyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, tert-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The terms "carbocycle", "carbocyclyl", "carbocyclic ring", and "cycloalkyl" refer to a monovalent non-aromatic, saturated or partially unsaturated ring having 3 to 12 carbon atoms ($C_{3-12}$) as a monocyclic ring or 7 to 12 carbon atoms as a bicyclic ring. In some non-limiting embodiments, the cycloalkyl has 3 to 10 carbon atoms, 3 to 8 carbon atoms, 3 to 6 carbon atoms, 3 to 5 carbon atoms, 4 to 6 carbon atoms, or 4 to 5 carbon atoms. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Spiro moieties are also included within the scope of this definition. As defined herein, cabocyclyl groups include any polycylic ring systems wherein one or more of the ring moieties within the polycyclic ring system is non-aromatic, even if one or more of the other ring moieites within the polycyclic ring system is aromatic, regardless of the point of attachment of the polycyclic ring system to the remainder of the molecule. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, indanyl, 1,2,3,4,-tetrahydronaphthyl, and the like. Carbocyclyl groups are optionally substituted independently with one or more substituents described herein.

"Aryl" means a monovalent aromatic hydrocarbon radical of 6-20 carbon atoms ($C_{6-20}$) derived by the removal of one hydrogen atom from a single carbon atom of a parent aromatic ring system. Some aryl groups are represented in the exemplary structures as "Ar". Typical aryl groups include, but are not limited to, radicals derived from benzene (phenyl), substituted benzenes, naphthalene, anthracene, biphenyl, indenyl, and the like. Aryl groups are optionally substituted independently with one or more substituents described herein.

The terms "heterocycle," "heterocyclyl," and "heterocyclic ring" are used interchangeably herein and refer to a non-aromatic, saturated or partially unsaturated carbocyclic radical of about 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described herein. As defined herein, heterocyclyl groups include any polycylic ring systems wherein one or more of the ring moieties within the polycyclic ring system is non-aromatic, even if one or more of the other ring moieites within the polycyclic ring system is aromatic, regardless of the point of attachment of the polycyclic ring system to the remainder of the molecule. In some non-limiting embodiments, the heterocyclyl has 3 to 15 ring atoms, 3 to 12 ring atoms, 3 to 10 ring atoms, 3 to 8 ring atoms, 3 to 6 ring atoms, 4 to 6 ring atoms, or 5 to 6 ring atoms. A heterocycle may be a monocycle or a polycylic ring system wherein at least two rings share two single atoms (bicyclic) or a single atom (spirocyclic or spiro). The monocyclic heterocycle may have 3 to 8 ring members (2 to 7 carbon atoms and 1 to 4 heteroatoms selected from N, O, P, and S) A polycyclic heterocycle such as a bicycle or spiro moiety may have 7 to 12 ring members (4 to 9 carbon atoms and 1 to 6 heteroatoms selected from N, O, P, and S). Bicyclic heterocycles having 7 to 12 atoms can be arranged, for example, as a bicyclo [4,5], [5,5], [5,6] or [6,6] system, and bicyclic heterocycles having 9 or 10 ring atoms can be arranged as a bicyclo [5,6] or [6,6] system, or as bridged systems such as azabicyclo [2.2.1]heptane, azabicyclo[2.2.2]octane and azabicyclo [3.2.2]nonane. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566, each incorporated herein by reference in their entirety.

Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems of 5-20 atoms, containing one or more heteroatoms independently selected from nitrogen, oxygen, and sulfur. In some non-limiting embodiments, the heteroaryl has 5 to 18 ring atoms, 5 to 12 ring atoms, 5 to 10 ring atoms, 5 to 8 ring atoms, or 5 to 6 ring atoms. Examples of heteroaryl groups are pyridinyl (including, for example, 2-hydroxypyridinyl), imidazolyl, imidazopyridinyl, 1-methyl-1H-benzo[d]imidazole, [1,2,4]triazolo[1,5-a]pyridine, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiazolyl, benzoxazolyl, quinazolinyl, quinoxalinyl, and the like. Heteroaryl groups are optionally substituted independently with one or more substituents described herein.

The heterocycle or heteroaryl groups may be carbon (carbon-linked) or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to —O-alkyl. In one variation, "methoxy" refers to —O—CH$_3$.

The term "hydroxy" refers to —OH.

The term "cyano" refers to —CN.

The term "oxo" refers to =O.

The term "halo" refers to atoms occupying group VIIA of The Periodic Table and includes fluorine (fluoro), chlorine (chloro), bromine (bromo), and iodine (iodo).

The term "t-butyl" or "tBu" refers to tert-butyl.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York, each herein incorporated by reference in their entirety. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond ⫽ is shown, both a double bond and single bond are represented within the context of the compound shown.

As used herein a wavy line ⟿ that intersects a bond in a chemical structure indicate the point of attachment of the atom to which the wavy bond is connected in the chemical structure to the remainder of a molecule, or to the remainder of a fragment of a molecule.

In certain embodiments disclosed herein, certain groups (e.g., phenyl or heteroaryl) are described as "substituted". In some such embodiments, the "substituted" group may be substituted with 1, 2, 3, 4, 5, or more substituents, as indicated herein. In certain embodiments, certain groups may be substituted with one or more substituents independently selected from, but not limited to, alkyl, alkenyl, alkynyl, cycloalkyl, heterocyclyl, aryl, heteroaryl, halo (i.e., halogen), haloalkyl, oxo, —OH, CN, —O-alkyl, S-alkyl, NH-alkyl, N(alkyl)$_2$, O-cycloalkyl, S-cycloalkyl, NH-cycloalkyl, N(cycloalkyl)$_2$, N(cycloalkyl)(alkyl), NH$_2$, SH, SO$_2$-alkyl, P(O)(O-alkyl)(alkyl), P(O)(O-alkyl)$_2$, Si(OH)$_3$, Si(alkyl)$_3$, Si(OH)(alkyl)$_2$, CO-alkyl, CO$_2$H, NO$_2$, SF$_5$, SO$_2$NH-alkyl, SO$_2$N(alkyl)$_2$, SONH-alkyl, SON(alkyl)$_2$, CONH-alkyl, CON(alkyl)$_2$, N(alkyl)CONH(alkyl), N(alkyl)CON(alkyl)$_2$, NHCONH(alkyl), NHCON(alkyl)$_2$, NHCONH$_2$, N(alkyl)SO$_2$NH(alkyl), N(alkyl)SO$_2$N(alkyl)$_2$, NHSO$_2$NH(alkyl), NHSO$_2$N(alkyl)$_2$, and NHSO$_2$NH$_2$.

Still additional definitions and abbreviations are provided elsewhere herein.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The articles "a" and "an" as used herein and in the appended claims are used to refer to one or to more than one (i.e., to at least one) of the grammatical object of the article unless the context clearly indicates otherwise. By way of example, "an element" means one element or more than one element.

In the claims, as well as in the specification above, transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, In embodiments, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

II. Compounds

In one aspect, the present disclosure is directed to a compound of formula (IV'):

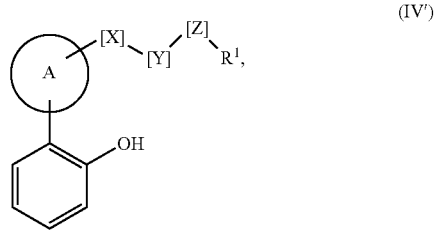

or a stereoisomer or tautomer thereof, or a pharmaceutically acceptable salt of any of the foregoing, wherein:

is 3-15 membered heterocyclyl or 5-20 membered heteroaryl, each of which is independently optionally substituted with one or more $R^n$, wherein $R^n$ is selected from the group consisting of —N($R^x$)($R^y$), —OH, CN, halo, $C_{1-4}$alkyl, and $C_{1-4}$haloalkyl;

[X] is absent, or 3-15 membered heterocyclyl or 5-20 membered heteroaryl, each of which is independently optionally substituted with one or more —OH or $C_{1-6}$alkyl;

[Y] is absent, or $C_{3-6}$cycloalkyl, $C_{1-6}$alkylene, $C_{2-6}$alkenylene, or $C_{2-6}$-alkynylene, each of which is independently optionally substituted with one or more substitutents selected from the group consisting of $C_{1-6}$alkyl, and halo;

[Z] is absent, or 3-15 membered heterocyclyl or 5-20 membered heteroaryl; and $R^1$ is:

(a) —C≡C—$R^a$, wherein (i) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, and the $C_{1-6}$alkoxy of $R^b$ is optionally substituted with one or more —OH, or (ii) $R^a$ is $C_{3-10}$ cycloalkyl, wherein the $C_{3-10}$ cycloalkyl of $R^a$ is optionally substituted with one or more $R^c$, or (iii) $R^a$ is 3-15 membered heterocyclyl, wherein the 3-15 membered heterocyclyl of $R^a$ is optionally substituted with one or more $R^c$, or (iv) $R^a$ is 5-20 membered heteroaryl, wherein the 5-20 membered heteroaryl of $R^a$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, or (b) —(CH$_2$)$_n$—$R^g$, wherein n is an integer from 1-6, and $R^g$ is —N($R^x$)($R^y$) or —OH;

wherein the $R^x$ and $R^y$ of —C(O)N($R^x$)($R^y$) and —N($R^x$)($R^y$) are, independently of each other and independently at each occurrence, H, —C(O)—(CH$_2$)$_p$—N($R^p$)($R^q$), —C(O)—$R^s$, 5-20 membered heterocycle, 5-20 membered heteroaryl, or $C_{1-6}$alkyl, wherein p is an integer from 1-6, $R^p$ and $R^q$ are, independently of each other and independently at each occurrence H, or $C_{1-6}$alkyl, $R^s$ is 5-20 membered heterocycle optionally substituted with one or more substituents selected from the group consisting of $C_{1-4}$alkyl, $C_{3-8}$cycloalkyl, and —C(O)—$C_{1-6}$ alkyl, the $C_{1-6}$alkyl of $R^x$ or $R^y$ is optionally substituted with one or more —OH, 3-15 membered heterocyclyl, or —C(O)-(3-15 membered heterocyclyl), and the 5-20 membered heterocycle of $R^x$ or $R^y$ is optionally substituted with one or more oxo, or (c) —C≡C—$R^d$, wherein $R^d$ is $C_{1-6}$alkyl, wherein the $C_{1-6}$alkyl of $R^d$ is optionally substituted with one or more $R^e$, wherein each $R^e$ is independently 3-15 membered heterocyclyl, wherein the 3-15 membered heterocyclyl of $R^c$ is optionally substituted with one or more $R^f$, wherein each $R^f$ is independently —OH, —CN, halo, oxo, $C_{1-6}$alkyl, $C_{1-6}$alkoxy, or —C(O)—$C_{1-6}$alkoxy.

In one aspect, provided herein is a compound of formula (IV'-L):

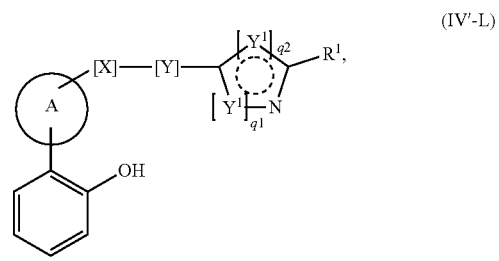

(IV'-L)

or a stereoisomer or tautomer thereof, or a pharmaceutically acceptable salt of any of the foregoing, wherein:

each $Y^1$ is independently N or CH;

$q_1$ and $q_2$ are each integers and the sum of $q_1$ and $q_2$ is 2 or 3;

is 3-15 membered heterocyclyl or 5-20 membered heteroaryl, each of which is independently optionally substituted with one or more $R^n$, wherein $R^n$ is selected from the group consisting of —N($R^x$)($R^y$), —OH, CN, halo, $C_{1-4}$alkyl, and $C_{1-4}$haloalkyl;

[X] is absent, or 3-15 membered heterocyclyl or 5-20 membered heteroaryl, each of which is independently optionally substituted with one or more —OH or $C_{1-6}$alkyl;

[Y] is absent, or $C_{3-6}$cycloalkyl, $C_{1-6}$alkylene, $C_{2-6}$alkenylene, or $C_{2-6}$-alkynylene, each of which is independently optionally substituted with one or more substitutents selected from the group consisting of $C_{1-6}$alkyl, and halo;

[Z] is absent, or 3-15 membered heterocyclyl or 5-20 membered heteroaryl; and $R^1$ is:

(a) —C≡C—$R^a$, wherein (i) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, and the $C_{1-6}$alkoxy of $R^b$ is optionally substituted with one or more —OH, or (ii) $R^a$ is $C_{3-10}$ cycloalkyl, wherein the $C_{3-10}$ cycloalkyl of $R^a$ is optionally substituted with one or more $R^c$, or (iii) $R^a$ is 3-15 membered heterocyclyl, wherein the 3-15 membered heterocyclyl of $R^a$ is optionally substituted with one or more $R^c$, or
(iv) $R^a$ is 5-20 membered heteroaryl, wherein the 5-20 membered heteroaryl of $R^a$ is optionally substituted with one or more $R^c$,
wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$ cycloalkyl of $R^c$ is optionally substituted with one or more halo,
the $C_{6-10}$aryl of $R^c$ is optionally substituted with one or more —CN,
the 3-15 membered heterocyclyl of $R^c$ is optionally substituted with one or more $C_{1-6}$alkyl or —C(O)—$C_{1-6}$alkyl, or
(b) —(CH$_2$)$_n$—$R^g$, wherein
n is an integer from 1-6, and
$R^g$ is —N($R^x$)($R^y$) or —OH;
wherein
the $R^x$ and $R^y$ of —C(O)N($R^x$)($R^y$) and —N($R^x$)($R^y$) are, independently of each other and independently at each occurrence, H, —C(O)—(CH$_2$)$_p$—N($R^p$)($R^q$), —C(O)—$R^s$, 5-20 membered heterocycle, 5-20 membered heteroaryl, or $C_{1-6}$alkyl, wherein
p is an integer from 1-6,
$R^p$ and $R^q$ are, independently of each other and independently at each occurrence H, or $C_{1-6}$alkyl,
$R^s$ is 5-20 membered heterocycle optionally substituted with one or more substituents selected from the group consisting of $C_{1-4}$alkyl, $C_{3-8}$cycloalkyl, and —C(O)—$C_{1-6}$alkyl,
the $C_{1-6}$alkyl of $R^x$ or $R^y$ is optionally substituted with one or more —OH, 3-15 membered heterocyclyl, or —C(O)-(3-15 membered heterocyclyl), and
the 5-20 membered heterocycle of $R^x$ or $R^y$ is optionally substituted with one or more oxo, or
(c) —C≡C—$R^d$, wherein $R^d$ is $C_{1-6}$alkyl, wherein the $C_{1-6}$alkyl of $R^d$ is optionally substituted with one or more $R^e$, wherein each $R^e$ is independently 3-15 membered heterocyclyl, wherein the 3-15 membered heterocyclyl of $R^e$ is optionally substituted with one or more $R^f$, wherein each $R^f$ is independently —OH, —CN, halo, oxo, $C_{1-6}$alkyl, $C_{1-6}$alkoxy, or —C(O)—$C_{1-6}$alkoxy.

In some embodiments of formula (IV'-L), [Y] is absent. In some embodiments of formula (IV'-L), [X] is absent. In some embodiments of formula (IV'-L), [X] is selected from the group consisting

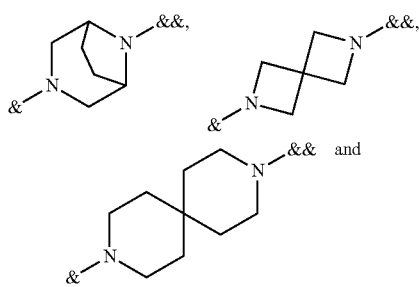

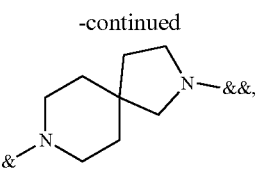

wherein & denotes the point of attachment to

and && denotes the point of attachment to the remainder of the molecule. In some embodiments of formula (IV'-L), [X] is

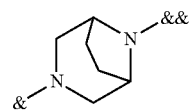

wherein & denotes the point of attachment to

and && denotes the point of attachment to the remainder of the molecule. In some embodiments of formula (IV'-L), [X] is

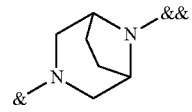

wherein & denotes the point of attachment to

and && denotes the point of attachment to the remainder of the molecule, and [Y] is absent. In some embodiments of formula (IV'-L), $q_1$ is 0 and $q_2$ is 2. In some embodiments of formula (IV'-L), $q_1$ is 2 and $q_2$ is 1. In some embodiments of formula (IV'-L), $q_1$ is 1 and $q_2$ is 1. In some embodiments of formula (IV'-L), $q_1$ is 1 and $q_2$ is 2. In some embodiments of formula (IV'-L), $q_1$ is 2 and $q_2$ is 1. In some embodiments of formula (IV'-L), $q_1$ is 0 and $q_2$ is 3. In some embodiments of formula (IV'-L), $q_1$ is 3 and $q_2$ is 0.

In embodiments, provided herein is a compound of formula (IV'), wherein the compound is of formula (IV'-L1):

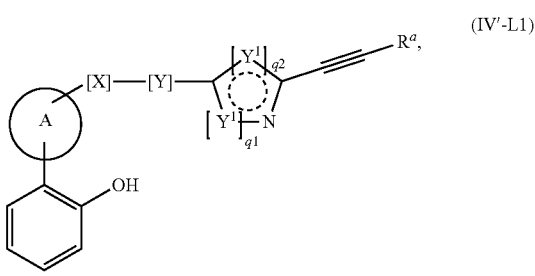

or a stereoisomer or tautomer thereof, or a pharmaceutically acceptable salt of any of the foregoing, wherein each each $Y^1$ is independently N or CH, $q_1$ and $q_2$ are each integers and the sum of $q_1$ and $q_2$ is 2 or 3, and

[X], [Y], and $R^a$ are as defined above or elsewhere herein for a compound of formula (IV'). In some embodiments of formula (IV'-L1), $R^a$ is a 3- to 15-membered heterocycle optionally substituted with one or more $R^c$. In some embodiments of formula (IV'-L1), $R^a$ is a monocyclic 3- to 15-membered heterocycle. In some embodiments of formula (IV'-L1), $R^a$ is a fused bicyclic 3- to 15-membered heterocycle. In some embodiments of formula (IV'-L1), $R^a$ is a bridged bicyclic 3- to 15-membered heterocycle. In some embodiments of formula (IV'-L1), $R^a$ is a spiro 3- to 15-membered heterocycle. In some embodiments of formula (IV'-L1), $R^a$ is a 4- to 12-membered heterocycle optionally substituted with one or more $R^c$. In some embodiments of formula (IV'-L1), $R^a$ is a monocyclic 4- to 12-membered heterocycle. In some embodiments of formula (IV'-L1), $R^a$ is a fused bicyclic 4- to 12-membered heterocycle. In some embodiments of formula (IV'-L1), $R^a$ is a bridged bicyclic 4- to 12-membered heterocycle. In some embodiments of formula (IV'-L1), $R^a$ is a spiro 4- to 12-membered heterocycle.

In embodiments, provided herein is a compound of formula (IV'), wherein the compound is of formula (IV'-L2):

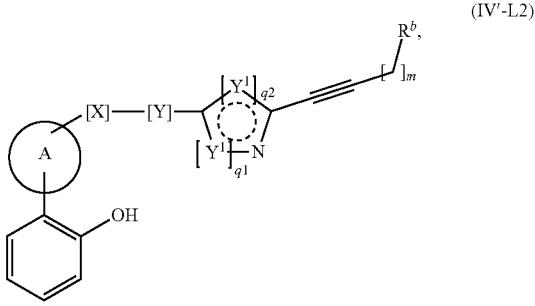

or a stereoisomer or tautomer thereof, or a pharmaceutically acceptable salt of any of the foregoing, wherein each $Y^1$ is independently N or CH, $q_1$ and $q_2$ are each integers and the sum of $q_1$ and $q_2$ is 2 or 3, m is 1 or 2, and

[X], [Y], and $R^b$ are as defined above or elsewhere herein for a compound of formula (IV'). In some embodiments of formula (IV'-L2), m is 1. In some embodiments of formula (IV'-L2), m is 2. In some embodiments of formula (IV'-L2), $R^b$ is a 3- to 15-membered heterocycle optionally substituted with one or more $R^c$. In some embodiments of formula (IV'-L2), $R^b$ is a monocyclic 3- to 15-membered heterocycle. In some embodiments of formula (IV'-L2), $R^b$ is a fused bicyclic 3- to 15-membered heterocycle. In some embodiments of formula (IV'-L2), $R^b$ is a bridged bicyclic 3- to 15-membered heterocycle. In some embodiments of formula (IV'-L2), $R^b$ is a spiro 3- to 15-membered heterocycle. In some embodiments of formula (IV'-L2), $R^b$ is a 4- to 12-membered heterocycle optionally substituted with one or more $R^c$. In some embodiments of formula (IV'-L2), $R^b$ is a monocyclic 4- to 12-membered heterocycle. In some embodiments of formula (IV'-L2), $R^b$ is a fused bicyclic 4- to 12-membered heterocycle. In some embodiments of formula (IV'-L2), $R^b$ is a bridged bicyclic 4- to 12-membered heterocycle. In some embodiments of formula (IV'-L2), $R^b$ is a spiro 4- to 12-membered heterocycle.

In embodiments, provided herein is a compound of formula (IV'), wherein the compound is of formula (IV'-L3):

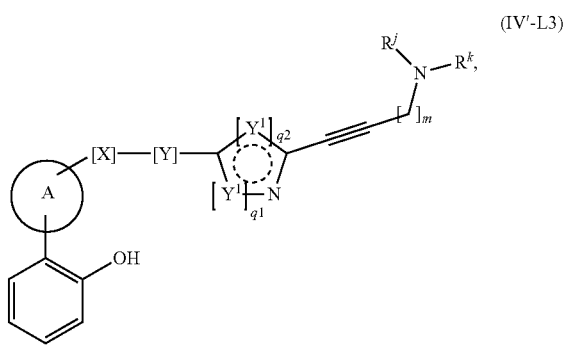

or a stereoisomer or tautomer thereof, or a pharmaceutically acceptable salt of any of the foregoing, wherein each $Y^1$ is independently N or CH, $q_1$ and $q_2$ are each integers and the sum of $q_1$ and $q_2$ is 2 or 3, m is 0, 1, or 2, $R^j$ and $R^k$, taken together with the N atom to which they are attached, form a 3- to 15-membered heterocycle optionally substituted with one or more $R^c$, and

[X], and [Y] are as defined above or elsewhere herein for a compound of formula (IV'). In some embodiments of formula (IV'-L3), m is 0. In some embodiments of formula (IV'-L3), m is 1. In some embodiments of formula (IV'-L3), m is 2. In some embodiments of a formula of (IV'-L3), $R^j$ and $R^k$, taken together with the N atom to which they are attached, form a 4- to 12-membered heterocycle optionally substituted with one or more $R^c$ In embodiments, provided herein is a compound of formula (IV'), wherein the compound is of formula (IV'-L4):

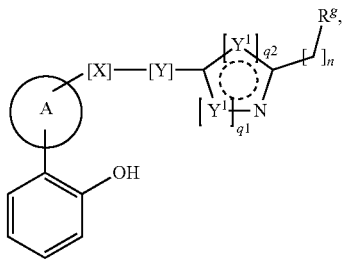
(IV'-L4)

or a stereoisomer or tautomer thereof, or a pharmaceutically acceptable salt of any of the foregoing, wherein each $Y^1$ is independently N or CH, $q_1$ and $q_2$ are each integers and the sum of $q_1$ and $q_2$ is 2 or 3, and

,

[X], [Y], n, and $R^g$ are as defined above or elsewhere herein for a compound of formula (IV'). In some embodiments of formula (IV'-L4), n is 1, 2, 3, 4, 5, or 6. In some embodiments of formula (IV'-L4), $R^g$ is —N(R$^x$)(R$^y$). In some embodiments of formula (IV'-L4), $R^g$ is —OH.

In embodiments, provided herein is a compound of formula (IV'), wherein the compound is of formula (IV'-L5):

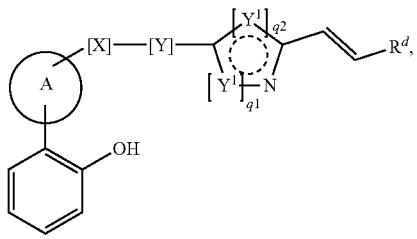
(IV'-L5)

or a stereoisomer or tautomer thereof, or a pharmaceutically acceptable salt of any of the foregoing, wherein each each $Y^1$ is independently N or CH, $q_1$ and $q_2$ are each integers and the sum of $q_1$ and $q_2$ is 2 or 3, and

,

[X], [Y], and $R^d$ are as defined above or elsewhere herein for a compound of formula (IV').

In embodiments, provided herein is a compound of formula (IV'), wherein the compound is of formula (IV'-M):

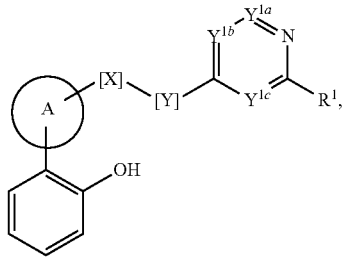
(IV'-M)

or a stereoisomer or tautomer thereof, or a pharmaceutically acceptable salt of any of the foregoing, wherein each of $Y^{1a}$ $Y^{1b}$ and $Y^{1c}$ is independently N or CH, and

,

[X], [Y], and $R^1$ are as defined above or elsewhere herein for a compound of formula (IV'). In some embodiments of formula (IV'-M), [Y] is absent. In some embodiments of formula (IV'-M), [X] is absent. In some embodiments of formula (IV'-M), [X] is selected from the group consisting

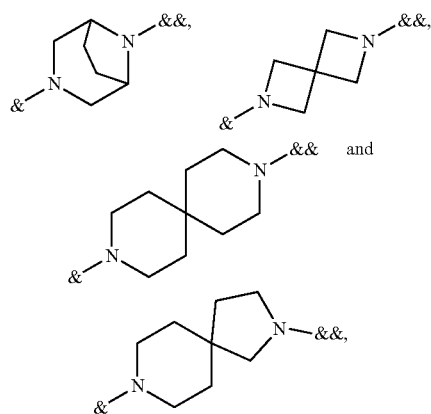

and wherein & denotes the point of attachment to

and && denotes the point of attachment to the remainder of the molecule. In some embodiments of formula (IV'-m), [X] is

a wherein & denotes the point of attachment to

and && denotes the point of attachment to the remainder of the molecule. In some embodiments of formula (IV'-M), [X] is

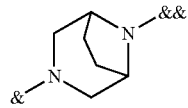

wherein & denotes the point of attachment to

and && denotes the point of attachment to the remainder of the molecule, and [Y] is absent. In some embodiments of formula (IV'-M), $Y^{1a}$ and $Y^{1b}$ are each CH. In some embodiments of formula (IV'-M), $Y^{1a}$ is N, $Y^{1b}$ is CH, and $Y^{1c}$ is CH. In some embodiments of formula (IV'-M), $Y^{1a}$ is CH, $Y^{1b}$ is N, and $Y^{1c}$ is CH. In some embodiments of formula (IV'-M), $Y^{1a}$ is CH, $Y^{1b}$ is CH, and $Y^{1c}$ is N. In some embodiments of formula (IV'-M), $Y^{1a}$ $Y^{1b}$ and $Y^{1c}$ are CH.

In embodiments, provided herein is a compound of formula (IV'), wherein the compound is of formula (IV'-M1):

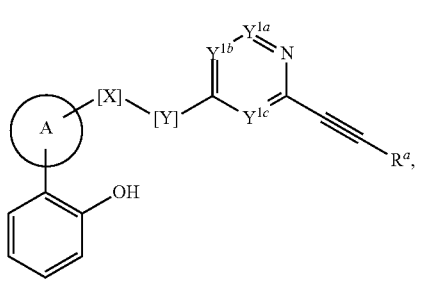

(IV'-M1)

or a stereoisomer or tautomer thereof, or a pharmaceutically acceptable salt of any of the foregoing, wherein each of $Y^{1a}$ $Y^{1b}$ and $Y^{1c}$ is independently N or CH, and

[X], [Y], and $R^a$ are as defined above or elsewhere herein for a compound of formula (IV'). In some embodiments of formula (IV'-M1), $R^a$ is a 3- to 15-membered heterocycle optionally substituted with one or more $R^c$. In some embodiments of formula (IV'-M1), $R^a$ is a 4- to 12-membered heterocycle optionally substituted with one or more $R^c$. In some embodiments of formula (IV'-M1), $R^a$ is a monocyclic 3- to 15-membered heterocycle. In some embodiments of formula (IV'-M1), $R^a$ is a fused bicyclic 3- to 15-membered heterocycle. In some embodiments of formula (IV'-M1), $R^a$ is a bridged bicyclic 3- to 15-membered heterocycle. In some embodiments of formula (IV'-M1), $R^a$ is a spiro 3- to 15-membered heterocycle.

In embodiments, provided herein is a compound of formula (IV'), wherein the compound is of formula (IV'-M2):

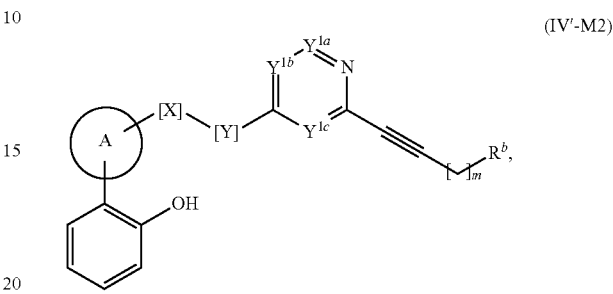

(IV'-M2)

or a stereoisomer or tautomer thereof, or a pharmaceutically acceptable salt of any of the foregoing, wherein each of $Y^{1a}$ $Y^{1b}$ and $Y^{1c}$ is independently N or CH, m is 1 or 2, and

[X], [Y], and $R^b$ are as defined above or elsewhere herein for a compound of formula (IV'). In some embodiments of formula (IV'-M2), m is 1. In some embodiments of formula (IV'-M2), m is 2. In some embodiments of formula (IV'-M2), $R^b$ is a 3- to 15-membered heterocycle. In some embodiments of formula (IV'-M2), $R^b$ is a 4- to 12-membered heterocycle. In some embodiments of formula (IV'-M2), $R^b$ is a monocyclic 3- to 15-membered heterocycle. In some embodiments of formula (IV'-M2), $R^b$ is a fused bicyclic 3- to 15-membered heterocycle. In some embodiments of formula (IV'-M2), $R^b$ is a bridged bicyclic 3- to 15-membered heterocycle. In some embodiments of formula (IV'-M2), $R^b$ is a spiro 3- to 15-membered heterocycle.

In embodiments, provided herein is a compound of formula (IV'), wherein the compound is of formula (IV'-M3):

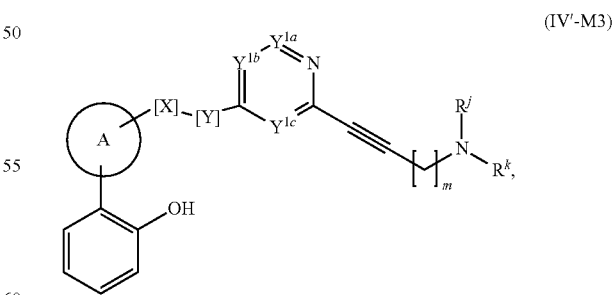

(IV'-M3)

or a stereoisomer or tautomer thereof, or a pharmaceutically acceptable salt of any of the foregoing, wherein each of $Y^{1a}$ $Y^{1b}$ and $Y^{1c}$ is independently N or CH, m is 0, 1, or 2, $R^j$ and $R^k$, taken together with the N atom to which they are attached, form a 3- to 15-membered heterocycle optionally substituted with one or more $R^c$, and

[X], and [Y] are as defined above or elsewhere herein for a compound of formula (IV'). In some embodiments of formula (IV'-M3), m is 0. In some embodiments of formula (IV'-M3), m is 1. In some embodiments of formula (IV'-M3), m is 2. In some embodiments of formula (IV'-M3) $R^j$ and $R^k$, taken together with the N atom to which they are attached, form a 4- to 12-membered heterocycle optionally substituted with one or more $R^c$.

In embodiments, provided herein is a compound of formula (IV'), wherein the compound is of formula (IV'-M4):

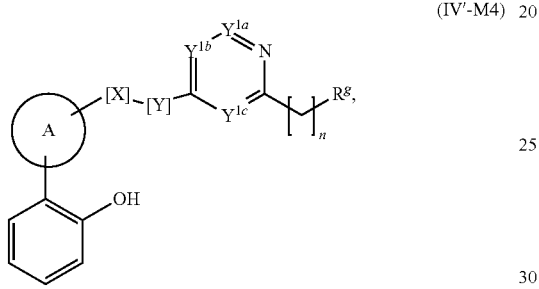

(IV'-M4)

or a stereoisomer or tautomer thereof, or a pharmaceutically acceptable salt of any of the foregoing, wherein each of $Y^{1a}$ $Y^{1b}$ and $Y^{1c}$ is independently N or CH, and

[X], [Y], n, and $R^g$ are as defined above or elsewhere herein for a compound of formula (IV'). In some embodiments of formula (IV'-M4), n is 1, 2, 3, 4, 5, or 6. In some embodiments of formula (IV'-M4), $R^g$ is —N($R^x$)($R^y$). In some embodiments of formula (IV'-M4), $R^g$ is —OH.

In embodiments, provided herein is a compound of formula (IV'), wherein the compound is of formula (IV'-M5):

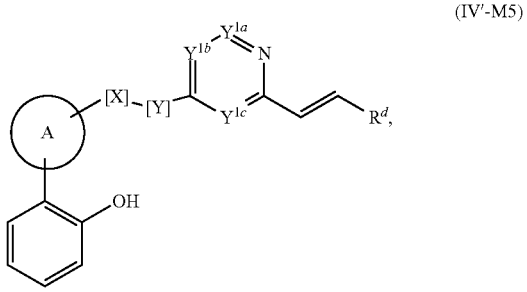

(IV'-M5)

or a stereoisomer or tautomer thereof, or a pharmaceutically acceptable salt of any of the foregoing, wherein each of $Y^{1a}$ $Y^{1b}$ and $Y^{1c}$ is independently N or CH, and

[X], [Y], and $R^d$ are as defined above or elsewhere herein for a compound of formula (IV').

In embodiments, provided herein is a compound of formula (IV'), wherein the compound is of formula (IV'-N):

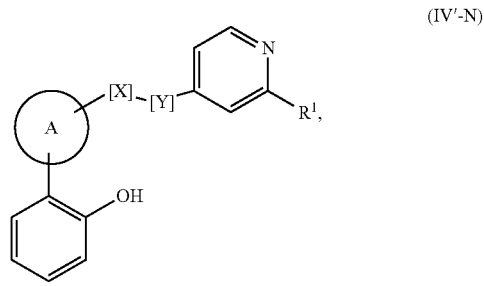

(IV'-N)

or a stereoisomer or tautomer thereof, or a pharmaceutically acceptable salt of any of the foregoing, wherein

[X], [Y], and $R^1$ are as defined above or elsewhere herein for a compound of formula (IV'). In some embodiments of formula (IV'-N), [Y] is absent. In some embodiments of formula (IV'-N), [X] is absent. In some embodiments of formula (IV'-N), [X] is selected from the group consisting

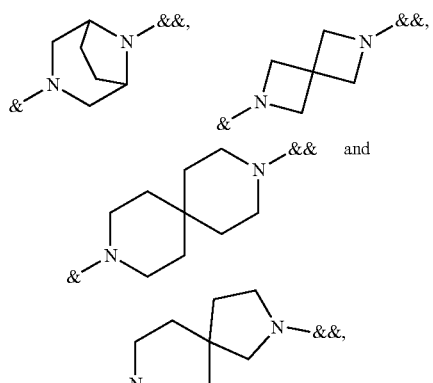

wherein & denotes the point of attachment to

and && denotes the point of attachment to the remainder of the molecule. In some embodiments of formula (IV'-N), [X] is

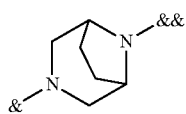

wherein & denotes the point of attachment to

and && denotes the point of attachment to the remainder of the molecule. In some embodiments of formula (IV'-N), [X] is

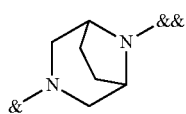

wherein & denotes the point of attachment to

and && denotes the point of attachment to the remainder of the molecule, and [Y] is absent.

In embodiments, provided herein is a compound of formula (IV'), wherein the compound is of formula (IV'-N1):

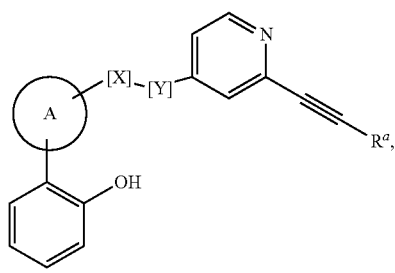

(IV'-N1)

or a stereoisomer or tautomer thereof, or a pharmaceutically acceptable salt of any of the foregoing, wherein

[X], [Y], and $R^a$ are as defined above or elsewhere herein for a compound of formula (IV'). In some embodiments of formula (IV'-N1), $R^a$ is a 3- to 15-membered heterocycle optionally substituted with one or more $R^c$. In some embodiments of formula (IV'-N1), $R^a$ is a monocyclic 3- to 15-membered heterocycle. In some embodiments of formula (IV'-N1), $R^a$ is a fused bicyclic 3- to 15-membered heterocycle. In some embodiments of formula (IV'-N1), $R^a$ is a bridged bicyclic 3- to 15-membered heterocycle. In some embodiments of formula (IV'-N1), $R^a$ is a spiro 3- to 15-membered heterocycle. In some embodiments of formula (IV'-N1), $R^a$ is a 4- to 12-membered heterocycle optionally substituted with one or more $R^c$. In some embodiments of formula (IV'-N1), $R^a$ is a monocyclic 4- to 12-membered heterocycle. In some embodiments of formula (IV'-N1), $R^a$ is a fused bicyclic 4- to 12-membered heterocycle. In some embodiments of formula (IV'-N1), $R^a$ is a bridged bicyclic 4- to 12-membered heterocycle. In some embodiments of formula (IV'-N1), $R^a$ is a spiro 4- to 12-membered heterocycle.

In embodiments, provided herein is a compound of formula (IV'), wherein the compound is of formula (IV'-N2):

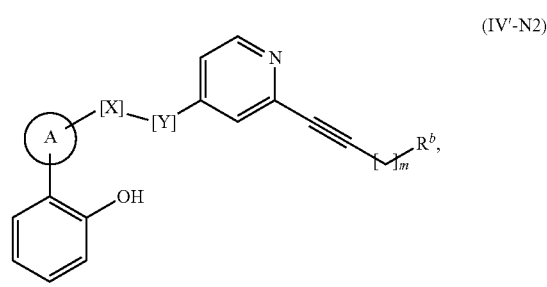

(IV'-N2)

or a stereoisomer or tautomer thereof, or a pharmaceutically acceptable salt of any of the foregoing, wherein m is 1 or 2, and

[X], [Y], and $R^b$ are as defined above or elsewhere herein for a compound of formula (IV'). In some embodiments of formula (IV'-N2), m is 1. In some embodiments of formula (IV'-N2), m is 2. In some embodiments of formula (IV'-N2), $R^b$ is a 3- to 15-membered heterocycle. In some embodiments of formula (IV'-N2), $R^b$ is a monocyclic 3- to 15-membered heterocycle. In some embodiments of formula (IV'-N2), $R^b$ is a fused bicyclic 3- to 15-membered heterocycle. In some embodiments of formula (IV'-N2), $R^b$ is a bridged bicyclic 3- to 15-membered heterocycle. In some embodiments of formula (IV'-N2), $R^b$ is a spiro 3- to 15-membered heterocycle. In some embodiments of formula (IV'-N2), $R^b$ is a 4- to 12-membered heterocycle. In some embodiments of formula (IV'-N2), $R^b$ is a monocyclic 4- to 12-membered heterocycle. In some embodiments of formula (IV'-N2), $R^b$ is a fused bicyclic 4- to 12-membered heterocycle. In some embodiments of formula (IV'-N2), $R^b$ is a bridged bicyclic 4- to 12-membered heterocycle. In some embodiments of formula (IV'-N2), $R^b$ is a spiro 4- to 12-membered heterocycle.

In embodiments, provided herein is a compound of formula (IV'), wherein the compound is of formula (IV'-N3):

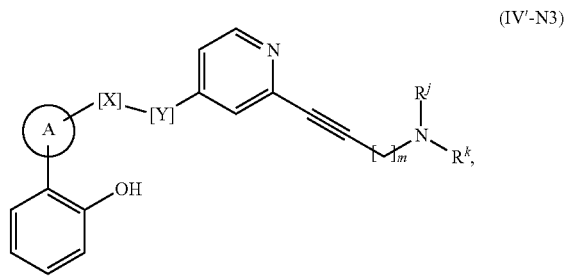 (IV'-N3)

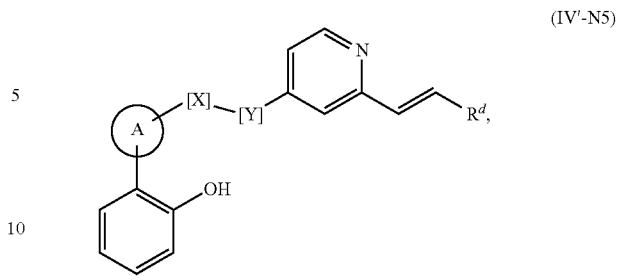 (IV'-N5)

or a stereoisomer or tautomer thereof, or a pharmaceutically acceptable salt of any of the foregoing, wherein m is 0, 1, or 2, $R^j$ and $R^k$, taken together with the N atom to which they are attached, form a 3- to 15-membered heterocycle optionally substituted with one or more $R^c$, and

,

[X], and [Y] are as defined above or elsewhere herein for a compound of formula (IV'). In some embodiments of formula (IV'-N3), m is 0. In some embodiments of formula (IV'-N3), m is 1. In some embodiments of formula (IV'-N3), m is 2. In some embodiments of formula (IV'-N3), $R^j$ and $R^k$, taken together with the N atom to which they are attached, form a 4- to 12-membered heterocycle optionally substituted with one or more $R^c$.

In embodiments, provided herein is a compound of formula (IV'), wherein the compound is of formula (IV'-N4):

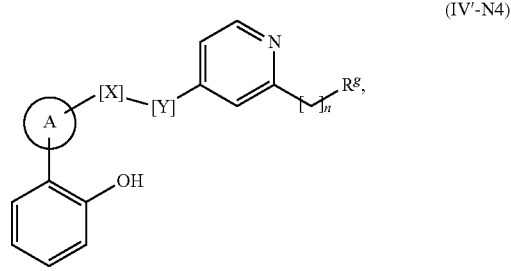 (IV'-N4)

or a stereoisomer or tautomer thereof, or a pharmaceutically acceptable salt of any of the foregoing, wherein each of

,

[X], [Y], n, and $R^g$ are as defined above or elsewhere herein for a compound of formula (IV'). In some embodiments of formula (IV'-N4), n is 1, 2, 3, 4, 5, or 6. In some embodiments of formula (IV'-N4), $R^g$ is —N($R^x$)($R^y$). In some embodiments of formula (IV'-N4), $R^g$ is —OH.

In embodiments, provided herein is a compound of formula (IV'), wherein the compound is of formula (IV'-N5):

or a stereoisomer or tautomer thereof, or a pharmaceutically acceptable salt of any of the foregoing, wherein each of

,

[X], [Y], and $R^d$ are as defined above or elsewhere herein for a compound of formula (IV').

In some embodiments of a compound of formula (IV'), (IV'-L), (IV'-L1), (IV'-L2), (IV'-M), (IV'-M1), (IV'-M2), (IV'-N), (IV'-N1), or (IV'-N2), or any applicable subformulae thereof, $R^b$ is a monocyclic heterocycle. In some embodiments, the monocyclic heterocycle is selected from the group consisting of

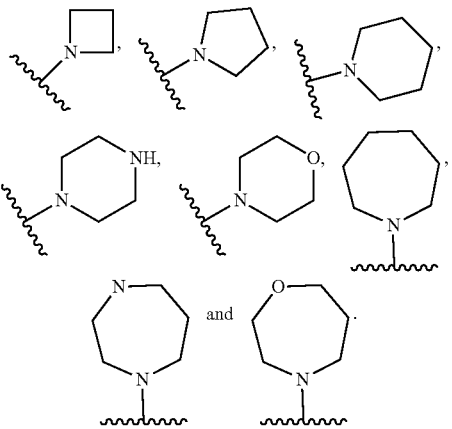

In some embodiments, $R^b$ is a fused bicyclic heterocycle. In some embodiments, $R^b$ is a fused bicyclic 4- to 12-membered heterocycle. In some embodiments, the fused bicyclic heterocycle is selected from the group consisting of

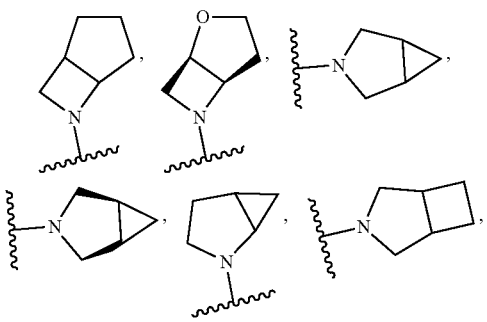

-continued

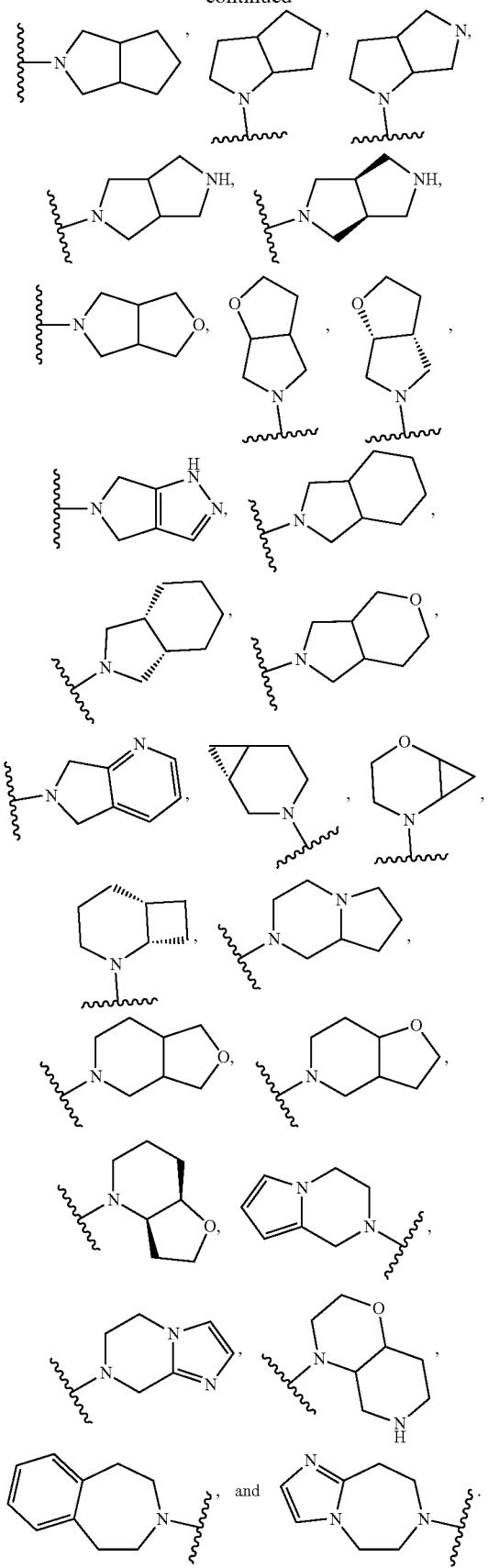

In some embodiments, $R^b$ is a bridged heterocycle. In some embodiments, $R^b$ is a bridged 4- to 12-membered heterocycle. In some embodiments the bridged heterocycle is selected from the group consisting of

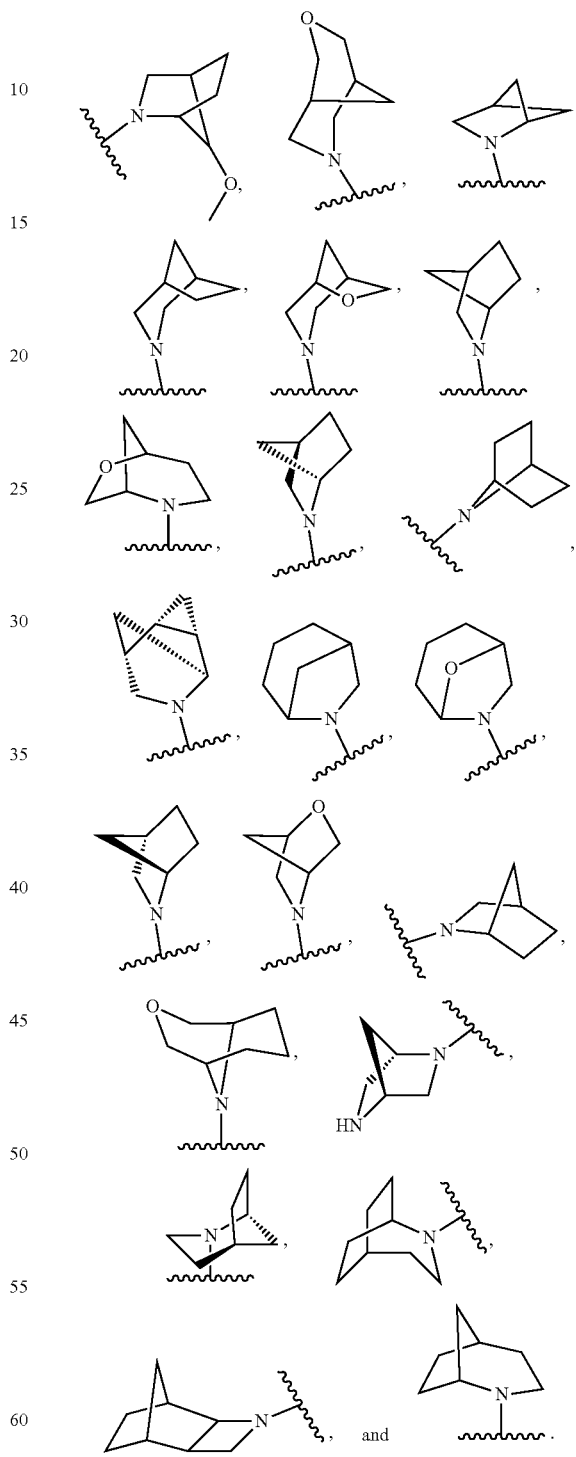

In some embodiments, $R^b$ is a spiro heterocycle. In some embodiments, $R^b$ is a spiro 4- to 12-membered heterocycle. In some embodiments, the spiro heterocycle is selected from the group consisting of

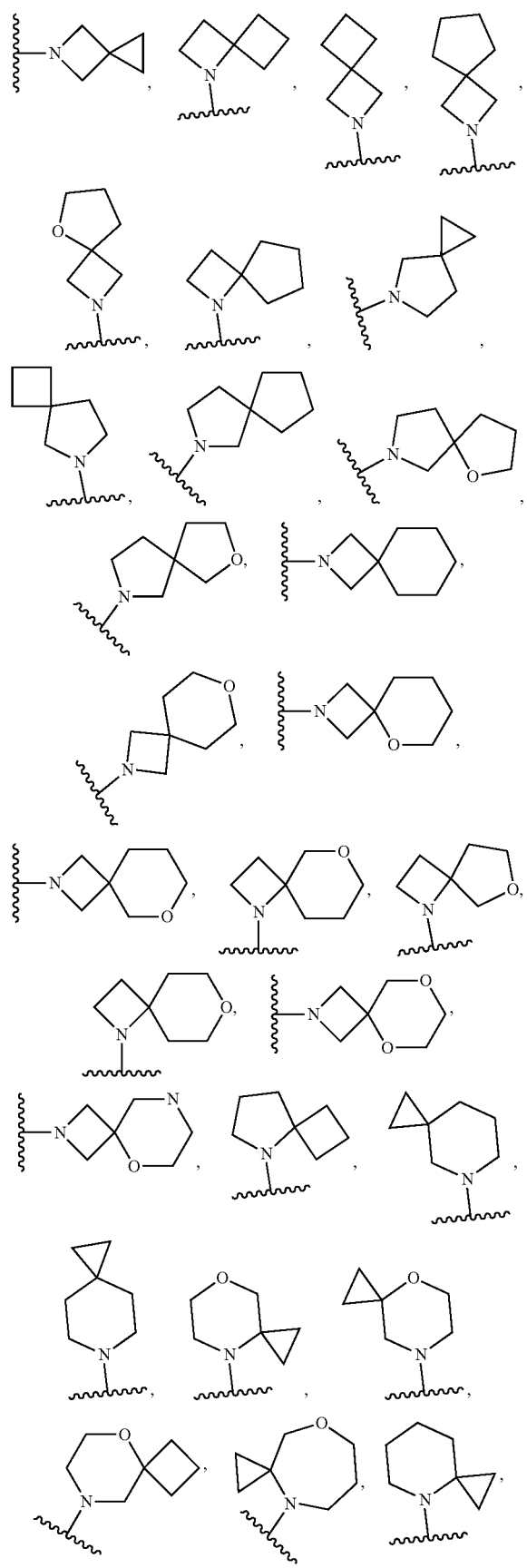

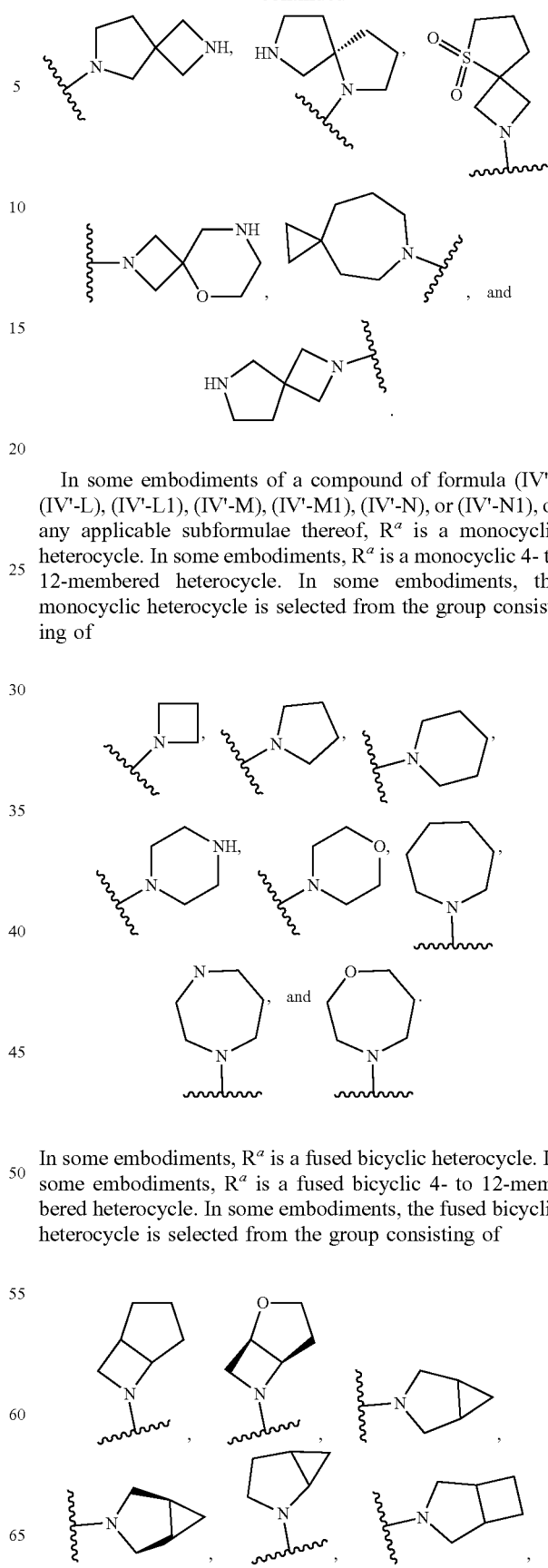

In some embodiments of a compound of formula (IV'), (IV'-L), (IV'-L1), (IV'-M), (IV'-M1), (IV'-N), or (IV'-N1), or any applicable subformulae thereof, $R^a$ is a monocyclic heterocycle. In some embodiments, $R^a$ is a monocyclic 4- to 12-membered heterocycle. In some embodiments, the monocyclic heterocycle is selected from the group consisting of In some embodiments, $R^a$ is a fused bicyclic heterocycle. In some embodiments, $R^a$ is a fused bicyclic 4- to 12-membered heterocycle. In some embodiments, the fused bicyclic heterocycle is selected from the group consisting of -continued

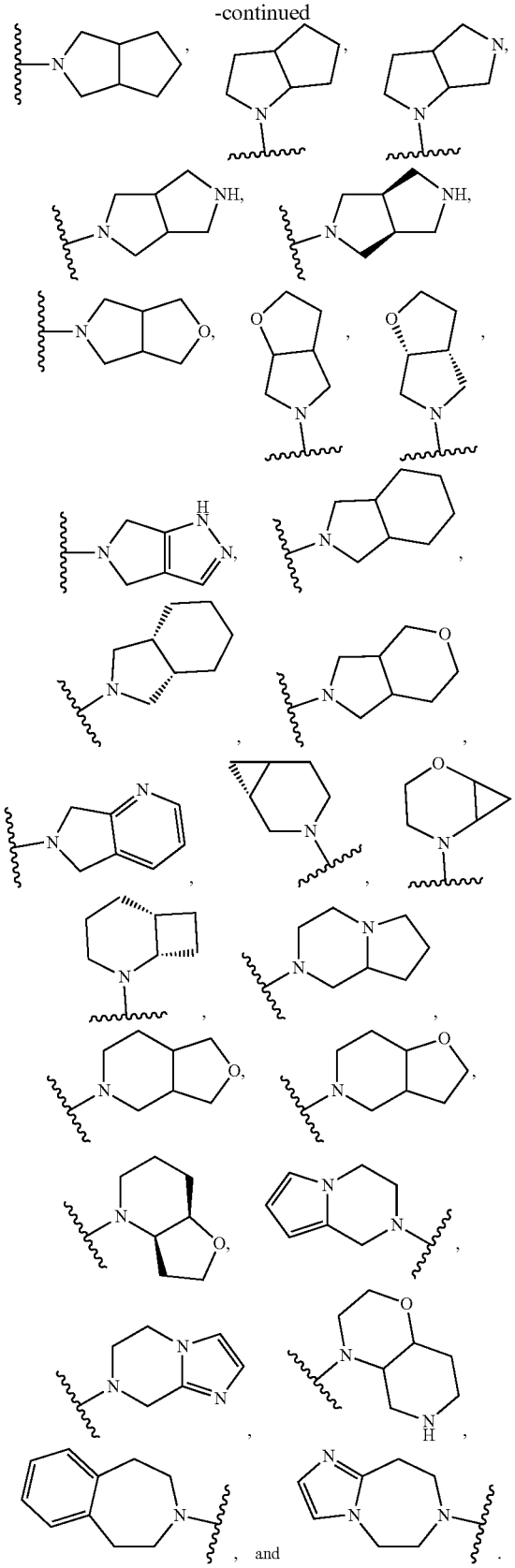

In some embodiments, $R^a$ is a bridged heterocycle. In some embodiments, $R^a$ is a bridged 4- to 12-membered heterocycle. In some embodiments the bridged heterocycle is selected from the group consisting of

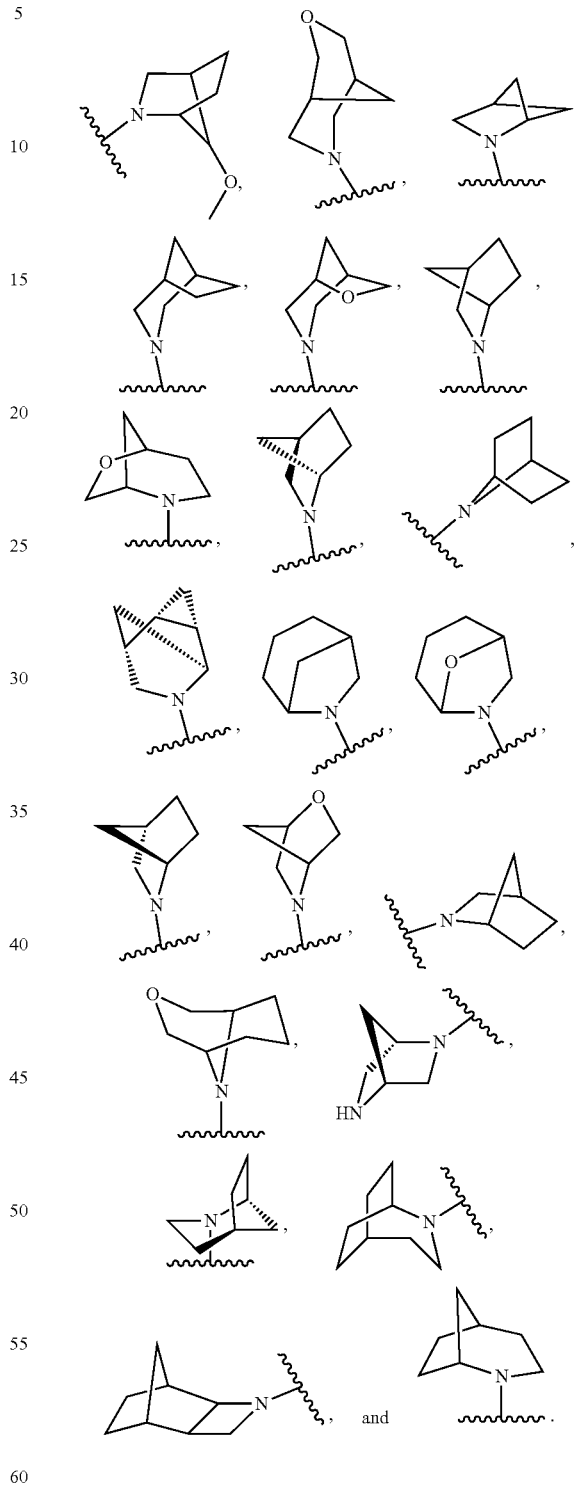

In some embodiments $R^a$ is a spiro heterocycle. In some embodiments, $R^a$ is a spiro 4- to 12-membered heterocycle. In some embodiments, the spiro heterocycle is selected from the group consisting of

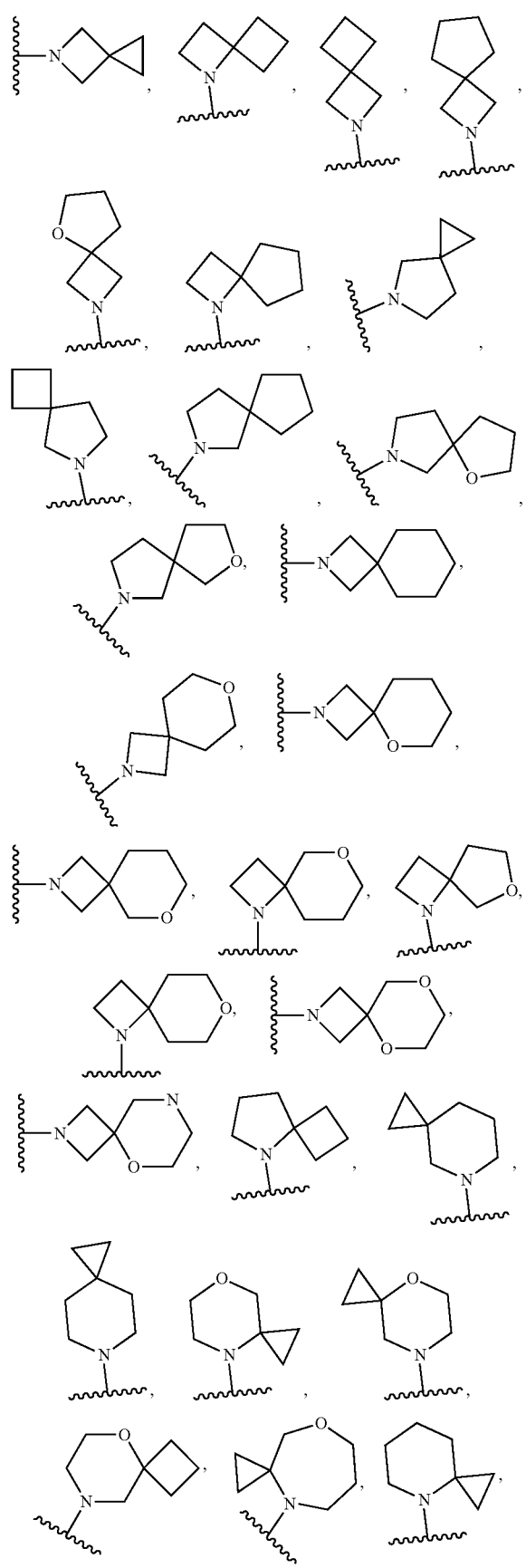

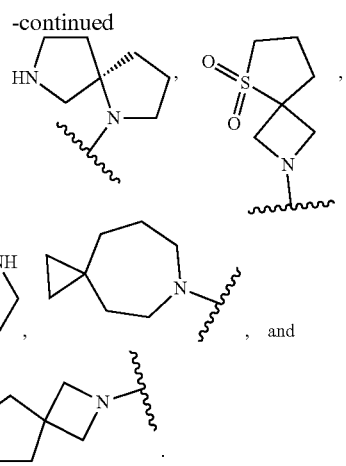

In some embodiments of a compound of formula (IV'), (IV'-L), (IV'-L1), (IV'-L2), (IV'-L3), (IV'-M), (IV'-M1), (IV'-M2), (IV'-M3), (IV'-N), or (IV'-N1), (IV'-N2), (IV'-N3), or any applicable subformulae thereof, $R^j$ and $R^k$ of —N($R^j$)($R^k$), together with the N atom to which they are attached, form a 4- to 12-membered monocyclic heterocycle, optionally substituted with one or more $R^c$. In some embodiments, the monocyclic heterocycle is selected from the group consisting of

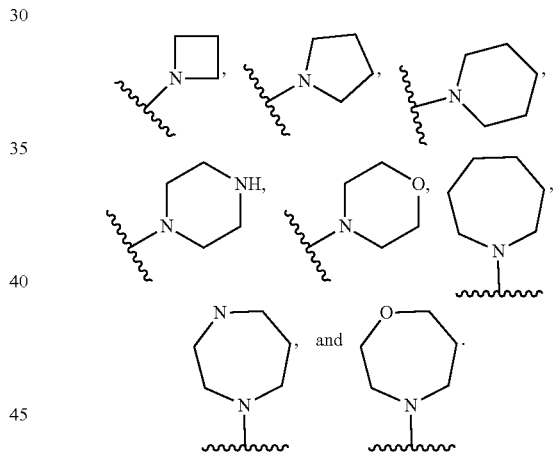

In some embodiments, $R^j$ and $R^k$ of —N($R^j$)($R^k$), together with the N atom to which they are attached, form a 4- to 12-membered fused bicyclic heterocycle, optionally substituted with one or more $R^c$. In some embodiments, the fused bicyclic heterocycle is selected from the group consisting of

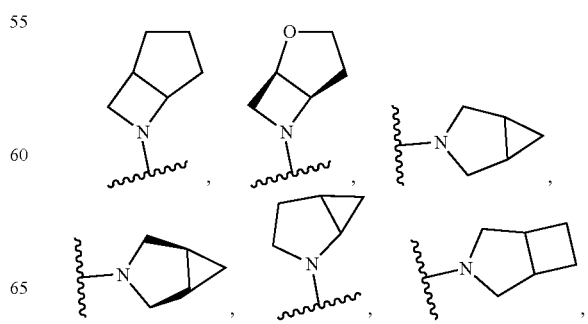

-continued

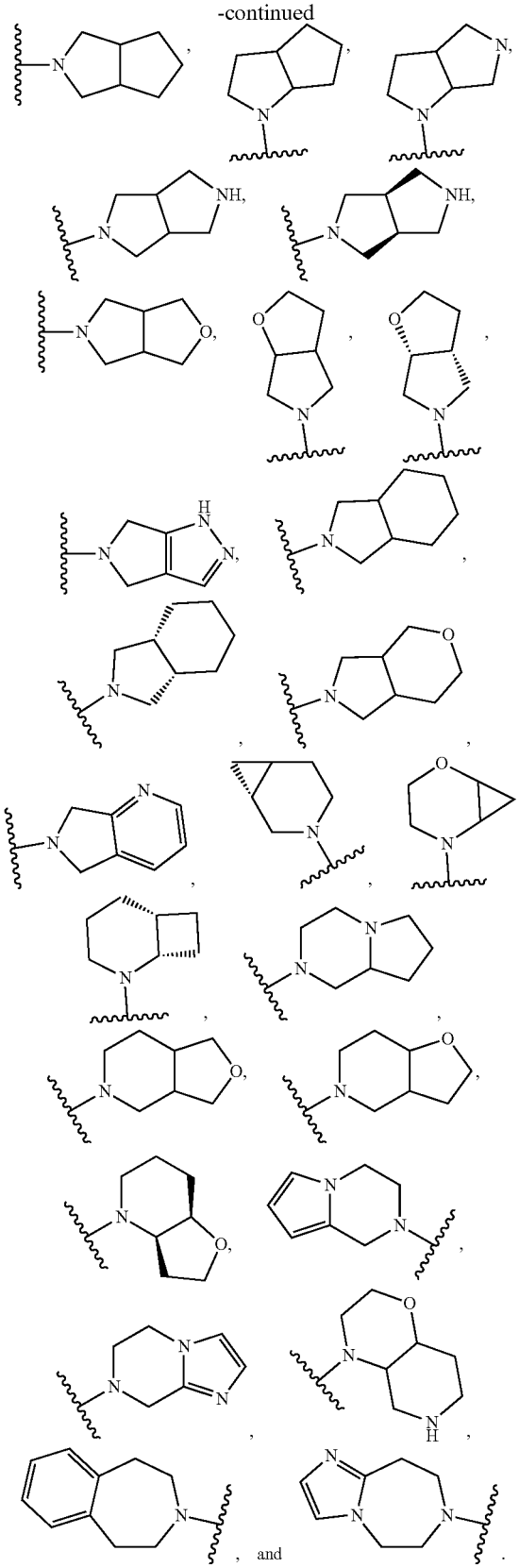

In some embodiments, $R^j$ and $R^k$ of —N($R^j$)($R^k$), together with the N atom to which they are attached, form a 4- to 12-membered bridged bicyclic heterocycle, optionally substituted with one or more $R^c$. In some embodiments the bridged heterocycle is selected from the group consisting of

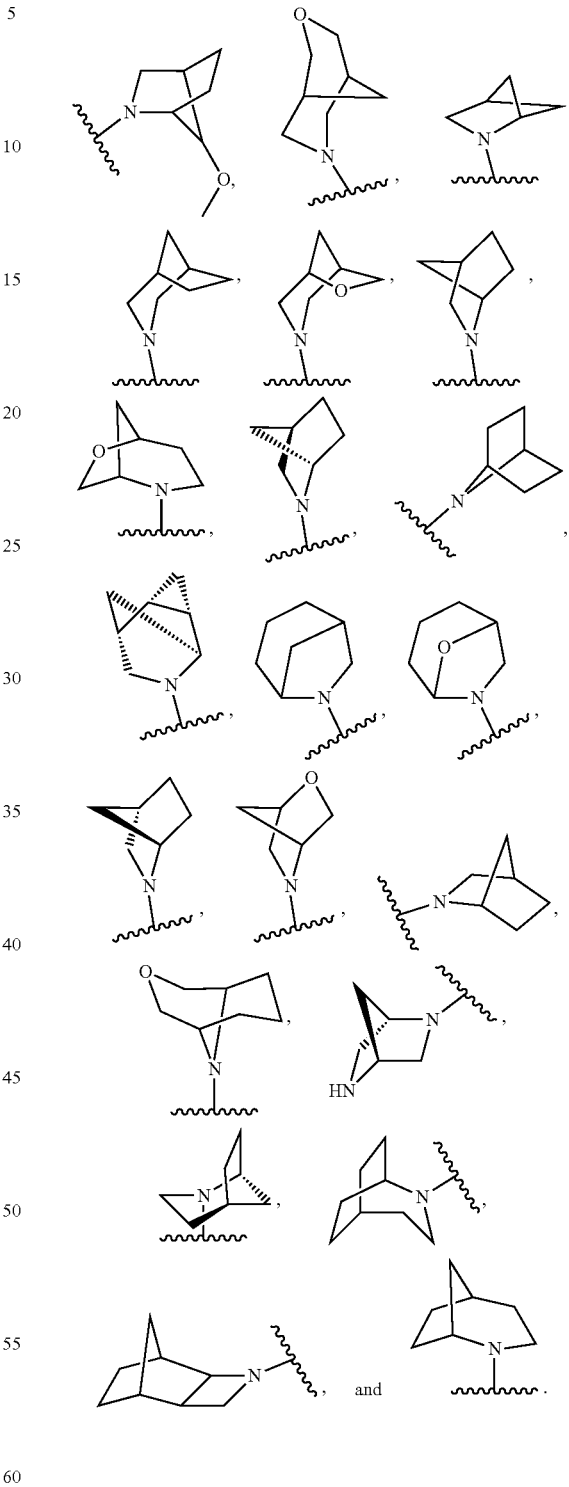

In some embodiments, $R^j$ and $R^k$ of —N($R^j$)($R^k$), together with the N atom to which they are attached, form a 4- to 12-membered spiro heterocycle, optionally substituted with one or more $R^c$. In some embodiments, the spiro heterocycle is selected from the group consisting of

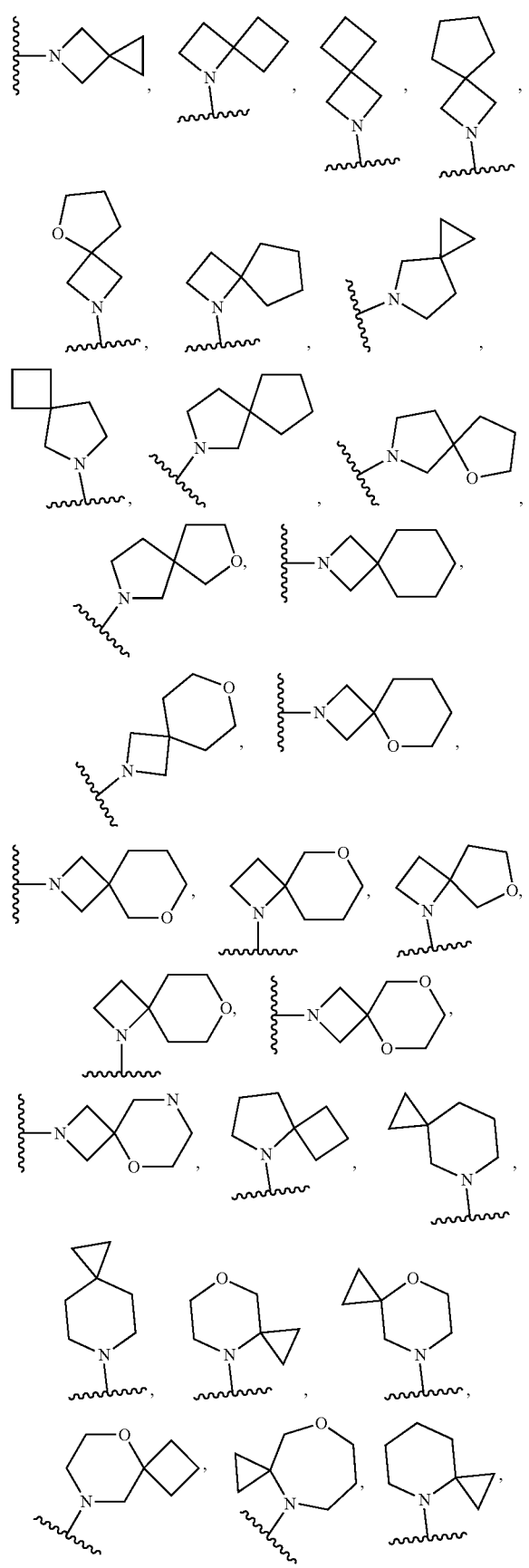

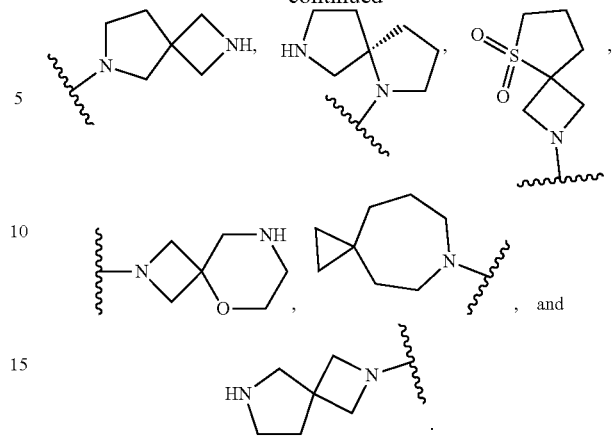

In embodiments, $R^a$ is 3- to 15-membered heterocycle optionally substituted with one or more $R^c$. In embodiments, $R^a$ is 3- to 15-membered heterocycle optionally substituted with one or more substituents selected from the group consisting of —OH, —CN, —F, -oxo, —CH$_3$, —CH$_2$CH$_3$, —CH$_2$CN, —CH$_2$OH, —CH$_2$F, —CHF$_2$, —CF$_3$, —O—CH$_3$, —CH$_2$—O—CH$_3$, —C(O)—O—CH$_3$, —C(O)—NH(CH$_3$), S(O)$_2$—(CH$_3$), —NH$_2$, cyclopropyl, morpholino, furan, and phenyl, wherein the phenyl is optionally further substituted with CN. In embodiments, $R^a$ is 4- to 12-membered heterocycle optionally substituted with one or more substituents selected from the group consisting of —OH, —CN, —F, -oxo, —CH$_3$, —CH$_2$CH$_3$, —CH$_2$CN, —CH$_2$OH, —CH$_2$F, —CHF$_2$, —CF$_3$, —O—CH$_3$, —CH$_2$—O—CH$_3$, —C(O)—O—CH$_3$, —C(O)—NH(CH$_3$), S(O)$_2$—(CH$_3$), —NH$_2$, cyclopropyl, morpholino, furan, and phenyl, wherein the phenyl is optionally further substituted with CN.

In embodiments, $R^b$ is 3- to 15-membered heterocycle optionally substituted with one or more $R^c$. In embodiments, $R^b$ is 3- to 15-membered heterocycle optionally substituted with one or more substituents selected from the group consisting of —OH, —CN, —F, -oxo, —CH$_3$, —CH$_2$CH$_3$, —CH$_2$CN, —CH$_2$OH, —CH$_2$F, —CHF$_2$, —CF$_3$, —O—CH$_3$, —CH$_2$—O—CH$_3$, —C(O)—O—CH$_3$, —C(O)—NH(CH$_3$), S(O)$_2$—(CH$_3$), —NH$_2$, cyclopropyl, morpholino, furan, and phenyl, wherein the phenyl is optionally further substituted with CN. In embodiments, $R^b$ is 4- to 12-membered heterocycle optionally substituted with one or more substituents selected from the group consisting of —OH, —CN, —F, -oxo, —CH$_3$, —CH$_2$CH$_3$, —CH$_2$CN, —CH$_2$OH, —CH$_2$F, —CHF$_2$, —CF$_3$, —O—CH$_3$, —CH$_2$—O—CH$_3$, —C(O)—O—CH$_3$, —C(O)—NH(CH$_3$), S(O)$_2$—(CH$_3$), —NH$_2$, cyclopropyl, morpholino, furan, and phenyl, wherein the phenyl is optionally further substituted with CN.

In some embodiments, $R^a$ is 3- to 15-membered heterocycle optionally substituted with at least one $R^c$. In some embodiments, $R^a$ is $C_{1-6}$alkyl substituted with one $R^b$, wherein $R^b$ is 3- to 15-membered heterocycle optionally substituted with at least one $R^c$. In some embodiments, the 3- to 15-membered heterocycle of $R^a$ or $R^b$ is —N(R$^j$)(R$^k$), wherein the R$^j$ and R$^k$ of —N(R$^j$)(R$^k$), together with the N atom to which they are attached, form a 4- to 12-membered heterocycle.

In embodiments, $R^b$ is —N(R$^j$)(R$^k$). In embodiments, $R^a$ is —N(R$^j$)(R$^k$). In embodiments, R$^j$ and R$^k$ of —N(R$^j$)(R$^k$) together with the N atom to which they are attached, form a 3- to 15-membered heterocycle optionally substituted with one or more R$^c$. In embodiments, R$^j$ and R$^k$ of —N(R$^j$)(R$^k$)

together with the N atom to which they are attached, form a 4- to 12-membered heterocycle optionally substituted with one or more R$^c$. In embodiments, R$^j$ and R$^k$ of —N(R$^j$)(R$^k$) together with the N atom to which they are attached, form a 4- to 12-membered unsubstituted heterocycle. In embodiments, R$^j$ and R$^k$ of —N(R$^j$)(R$^k$) together with the N atom to which they are attached, form a 4- to 12-membered heterocycle substituted with 1, 2, 3, 4, 5, or 6 R$^c$. In embodiments, R$^j$ and R$^k$ of —N(R$^j$)(R$^k$) together with the N atom to which they are attached, form a 4- to 12-membered heterocycle substituted with 1, 2, or 3 R$^c$.

In embodiments, R$^j$ and R$^k$ of —N(R$^j$)(R$^k$) together with the N atom to which they are attached, form a 3- to 15-membered heterocycle optionally substituted with R$^c$, wherein each R$^c$ is independently —OH, —CN, halo, oxo, C$_{1-6}$alkyl, C$_{1-6}$alkoxy, C$_{3-10}$ cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein the C$_{1-6}$alkyl of R$^c$ is optionally substituted with one or more —OH, —CN, halo, C$_{1-6}$alkoxy, or 3-15 membered heterocyclyl, the C$_{3-10}$ cycloalkyl of R$^c$ is optionally substituted with one or more halo, and the 3-15 membered heterocyclyl of R$^c$ is optionally substituted with one or more C$_{1-6}$alkyl or —C(O)—C$_{1-6}$alkyl. In embodiments, R$^j$ and R$^k$ of —N(R$^j$)(R$^k$) together with the N atom to which they are attached, form a 3- to 15-membered heterocycle optionally substituted with —OH, —CN, —F, -oxo, —CH$_3$, —CH$_2$CH$_3$, —CH$_2$CN, —CH$_2$OH, —CH$_2$F, —CHF$_2$, —CF$_3$, —O—CH$_3$, —CH$_2$—O—CH$_3$, —C(O)—O—CH$_3$, —C(O)—NH(CH$_3$), S(O)$_2$—(CH$_3$), —NH$_2$, cyclopropyl, morpholino, furan, or phenyl, wherein the phenyl is optionally further substituted with CN. In embodiments, R$^j$ and R$^k$ of —N(R$^j$)(R$^k$) together with the N atom to which they are attached, form a 4- to 12-membered heterocycle optionally substituted with —OH, —CN, —F, -oxo, —CH$_3$, —CH$_2$CH$_3$, —CH$_2$CN, —CH$_2$OH, —CH$_2$F, —CHF$_2$, —CF$_3$, —O—CH$_3$, —CH$_2$—O—CH$_3$, —C(O)—O—CH$_3$, —C(O)—NH(CH$_3$), S(O)$_2$—(CH$_3$), —NH$_2$, cyclopropyl, morpholino, furan, or phenyl, wherein the phenyl is optionally further substituted with CN.

In some embodiments, provided is a compound of formula (IV'), or a stereoisomer or tautomer thereof, or a pharmaceutically acceptable salt thereof, wherein [Z] is

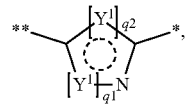

wherein each Y$^1$ is independently N or CH, and q$_1$ and q$_2$ are each integers and the sum of q$_1$ and q$_2$ is 2 or 3, and wherein * denotes the attachment point to R$^1$, and  denotes the point of attachment to [Y], or, if [Y] is absent,  denotes the point of attachment to [X], or, if [X] and [Y] are absent, ** denotes the point of attachment to

In some embodiments, provided is a compound of formula (IV') or (IV'-L), or a stereoisomer or tautomer thereof, or a pharmaceutically acceptable salt thereof, wherein each Y$^1$ is CH, and the sum of q$_1$ and q$_2$ is 3.

In some embodiments, provided is a compound of formula (IV') or (IV'-L), or a stereoisomer or tautomer thereof, or a pharmaceutically acceptable salt thereof, wherein [Z] is

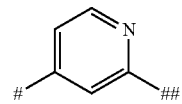

wherein ## denotes the attachment point to R$^1$, and # denotes the point of attachment to [Y], or, if [Y] is absent, # denotes the point of attachment to [X], or, if [X] and [Y] are absent, # denotes the point of attachment to

In some embodiments, provided is a compound of formula (IV') or (IV'-L), or a stereoisomer or tautomer thereof, or a pharmaceutically acceptable salt thereof, wherein [Y] is absent.

In some embodiments, provided is a compound of formula (IV') or (IV'-L), or a stereoisomer or tautomer thereof, or a pharmaceutically acceptable salt thereof, wherein R$^1$ is —C≡C—R$^a$. In some embodiments, provided is a compound of formula (IV') (IV'-L1), (IV'-M1), or (IV'-N1), wherein the C$_{1-6}$alkyl of R$^a$ is substituted with —N(R$^j$)(R$^k$), wherein the R$^j$ and R$^k$ of —N(R$^j$)(R$^k$), together with the N atom to which they are attached, form a 4- to 12-membered heterocycle, wherein the 4- to 12-membered heterocycle is optionally substituted with at least one R$^c$.

In some embodiments, provided is a compound of formula (IV') (IV'-L2), (IV'-M2), or (IV'-N2), wherein R$^b$ is a monocyclic 4- to 12-membered heterocycle. In some embodiments, the 4- to 12-membered heterocycle is selected from the group consisting of

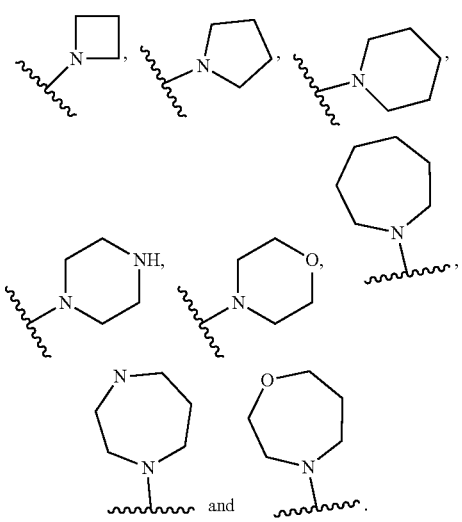

In some embodiments, provided is a compound of formula (IV') (IV'-L2), (IV'-M2), or (IV'-N2), wherein R$^b$ is a fused bicyclic 4- to 12-membered heterocycle. In some embodiments, the fused bicyclic 4- to 12-membered heterocycle is selected from the group consisting of

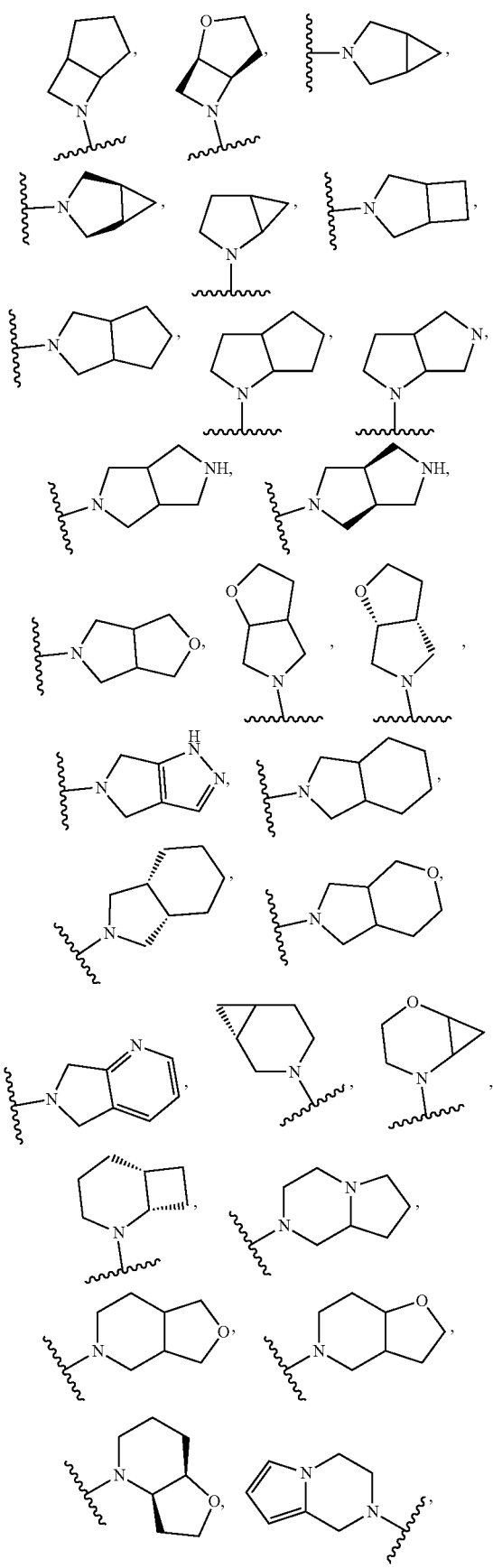
-continued
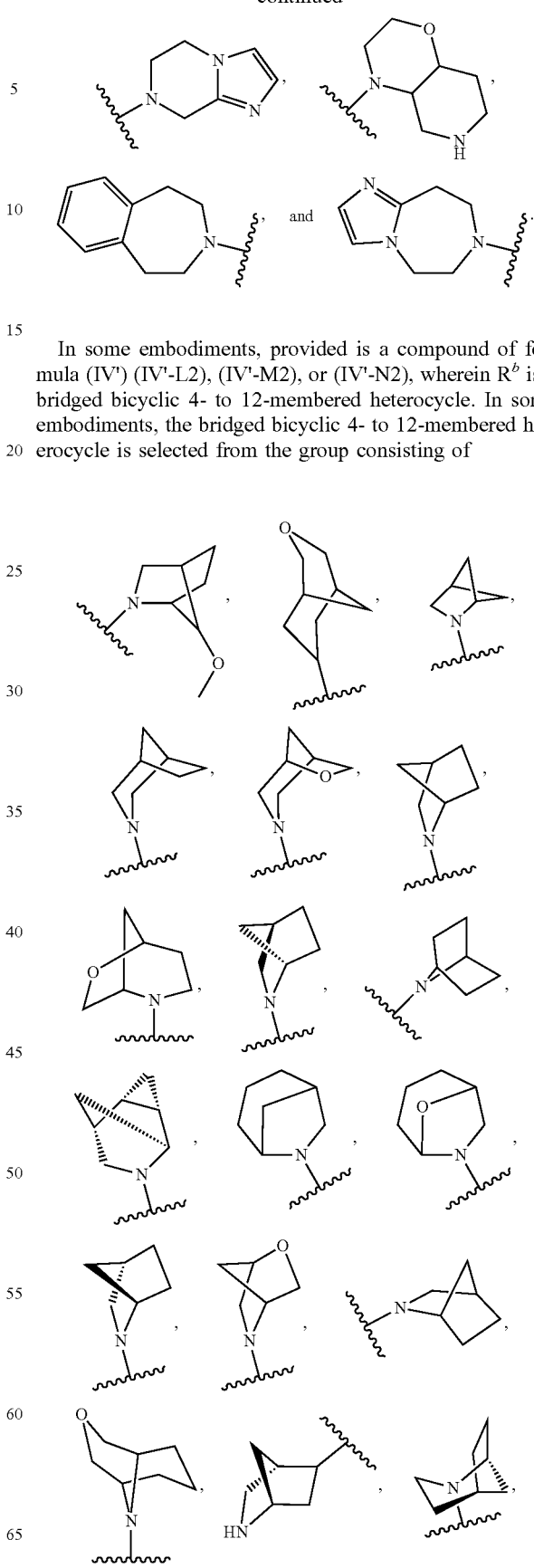
In some embodiments, provided is a compound of formula (IV') (IV'-L2), (IV'-M2), or (IV'-N2), wherein $R^b$ is a bridged bicyclic 4- to 12-membered heterocycle. In some embodiments, the bridged bicyclic 4- to 12-membered heterocycle is selected from the group consisting of

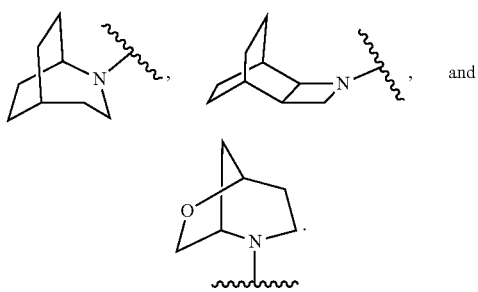

In some embodiments, provided is a compound of formula (IV') (IV'-L2), (IV'-M2), or (IV'-N2), wherein $R^b$ is a spiro 4- to 12-membered heterocycle. In some embodiments, the spiro 4- to 12-membered heterocycle is selected from the group consisting of N

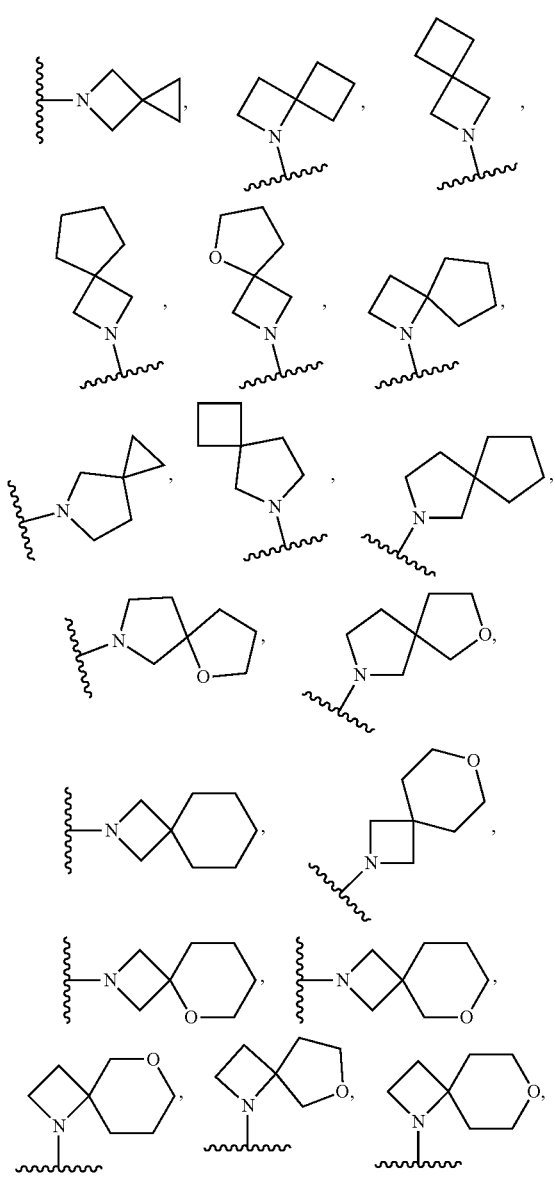

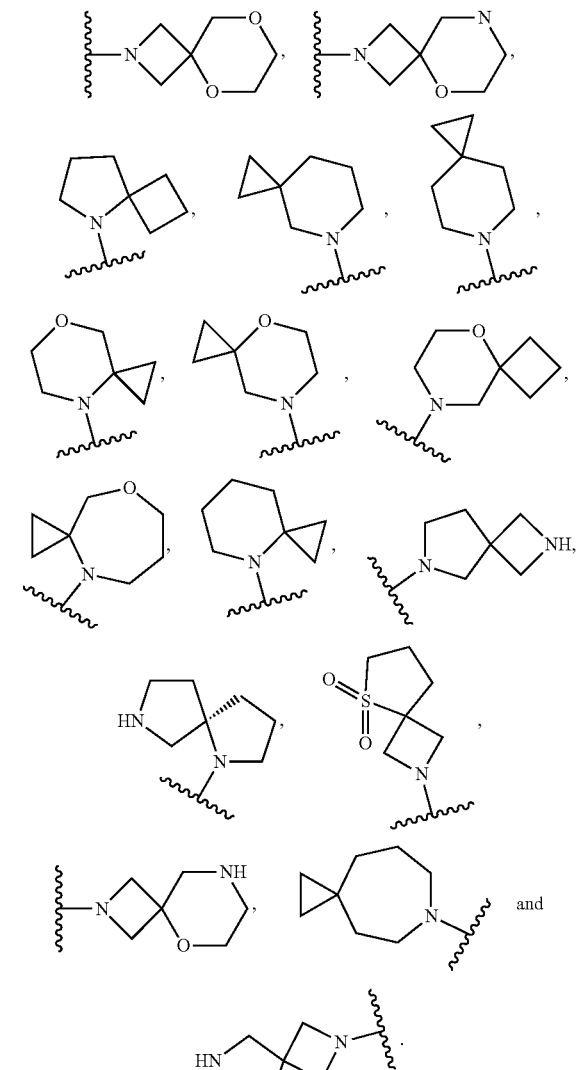

In some embodiments, the 4- to 12-membered heterocycle of $R^b$ is substituted one, two, three or four $R^c$. In some embodiments, the 4- to 12-membered heterocycle of $R^b$ is substituted one, two, three or four substituents selected from the group consisting of fluorine, —OH, oxo, methyl, methanol, cyclopropyl, methoxy, ethoxy and —CF$_3$.

In some embodiments, provided is a compound of formula (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt thereof, wherein is selected from the group consisting of

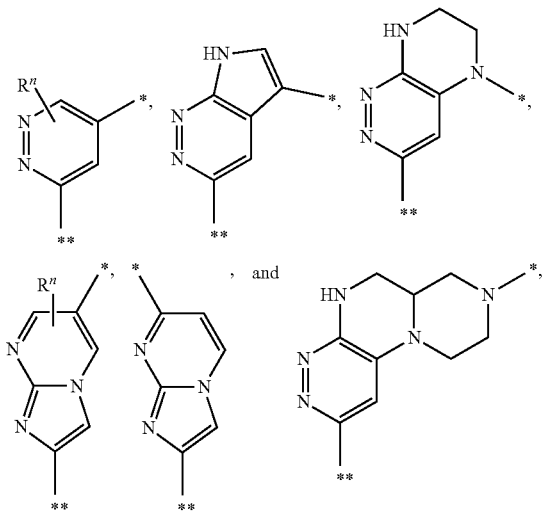

wherein R″ is —NH₂, and wherein * denotes the point of attachment to [X], or, if [X] is absent, * denotes the point of attachment to [Y], or, if [X] and [Y] are absent, * denotes the point of attachment to [Z], and ** denotes the point of attachment to the remainder of the molecule. In some embodiments, provided is a compound of formula (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt thereof, wherein

Ⓐ is

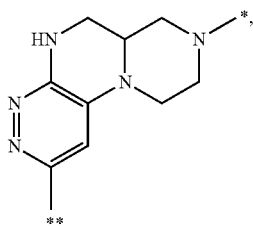

and R″ is —NH₂ wherein * denotes the point of attachment to [X], or, if [X] is absent, * denotes the point of attachment to [Y], or, if [X] and [Y] are absent, * denotes the point of attachment to [Z], and ** denotes the point of attachment to the remainder of the molecule. In some embodiments, provided is a compound of formula (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt thereof, wherein

Ⓐ is

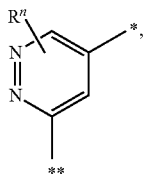

and [X] is absent, wherein * denotes the point of attachment to [Y], or, if [Y] is absent, * denotes the point of attachment to [Z], and ** denotes the point of attachment to the remainder of the molecule.

In some embodiments, provided is a compound of formula (IV'), or any applicable subformulae thereof, or a stereoisomer or tautomer thereof, or a pharmaceutically acceptable salt thereof, wherein

Ⓐ is

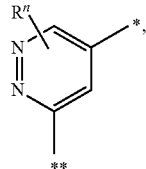

and R″ is NH₂ wherein * denotes the point of attachment to [X] and ** denotes the point of attachment to the remainder of the molecule, [X] is

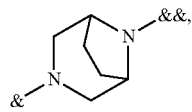

wherein & denotes the point of attachment to

Ⓐ and && denotes the point of attachment to the remainder of the molecule, [Y] is absent, [Z] is

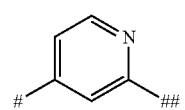

wherein ## denotes the attachment point to R¹, and # denotes the point of attachment to [X], and R¹ is —C≡C—Rᵃ, wherein the C₁₋₆alkyl of Rᵃ is substituted with one Rᵇ, wherein Rᵇ is —N(Rʲ)(Rᵏ), wherein the Rʲ and Rᵏ of —N(Rʲ)

($R^k$), together with the N atom to which they are attached, form a 4- to 12-membered heterocycle, wherein the 4- to 12-membered heterocycle is optionally substituted with at least one $R^c$.

In some embodiments, provided is a compound of formula (IV'), or any applicable subformulae thereof, or a stereoisomer or tautomer thereof, or a pharmaceutically acceptable salt thereof, wherein

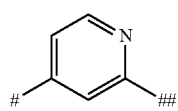

is

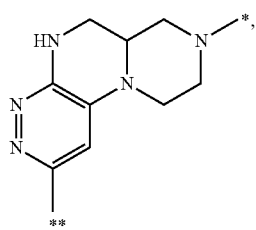

wherein * denotes the point of attachment to [Z] and ** denotes the point of attachment to the remainder of the molecule, [X] is absent, [Y] is absent, [Z] is

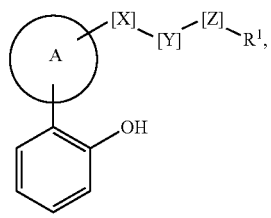

wherein ## denotes the attachment point to $R^1$, and # denotes the point of attachment to [X], and $R^1$ is —C≡C—$R^a$, wherein the $C_{1-6}$alkyl of $R^a$ is substituted with one $R^b$, wherein $R^b$ is —N($R^j$)($R^k$), wherein the $R^j$ and $R^k$ of —N($R^j$)($R^k$), together with the N atom to which they are attached, form a 4- to 12-membered heterocycle, wherein the 4- to 12-membered heterocycle is optionally substituted with at least one $R^c$.

In some embodiments of formula (IV'), or any applicable subformulae wherein $R^1$ is —C≡C—$R^a$ and $R^a$ is selected from the group consisting of $C_{3-10}$cycloalkyl optionally substituted with one or more $R^c$, 3-15 membered heterocyclyl, optionally substituted with one or more $R^c$, or 5-20 membered heteroaryl optionally substituted with one or more $R^c$, $R^c$ is $R^z$, wherein $R^z$ is, independently at each occurrence, —OH, —CN, halo, $C_{1-6}$alkyl, $C_{1-6}$alkoxy, —N($R^x$)($R^y$), or —C(O)—N($R^x$)($R^y$). In some embodiments, the compound of formula (IV') is a compound of formula (I').

In one aspect, the present disclosure is directed to a compound of formula (I'):

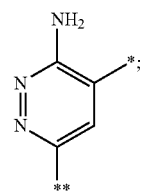

(I')

or a stereoisomer or tautomer thereof, or a pharmaceutically acceptable salt of any of the foregoing, wherein:

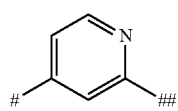

is selected from the group consisting of:

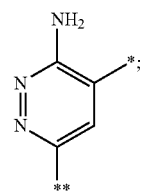

(a)

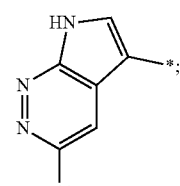

(b)

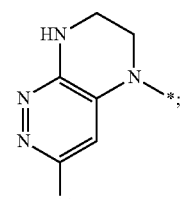

(c)

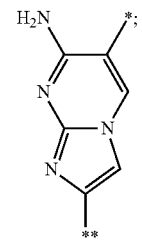

(d)

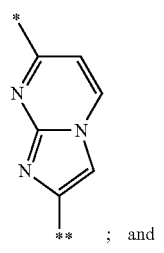

; and (e)

-continued

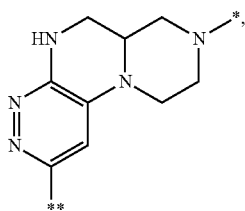
(f)

wherein, for (a)-(f), * denotes the point of attachment to [X], or, if [X] is absent, * denotes the point of attachment to [Y], or, if [X] and [Y] are absent, * denotes the point of attachment to [Z], and ** denotes the point of attachment to the remainder of the molecule;

and wherein:
(i) [X] is 3-15 membered heterocyclyl or 5-20 membered heteroaryl,
provided that, when

is (a), then [X] is not

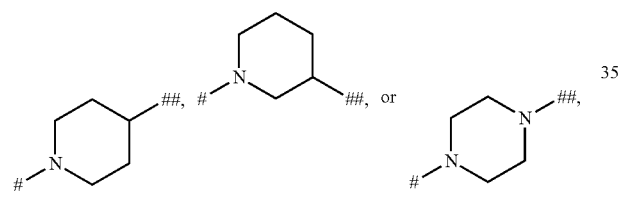

wherein # denotes the point of attachment to

and ## denotes the point of attachment to $R^1$, and provided that, when

is (f), and [X] is

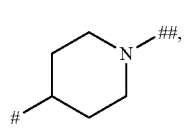

wherein # denotes the point of attachment to

and ## denotes the point of attachment to $R^1$, then when $R^1$ is —(CH$_2$)$_n$—R$^g$, R$^g$ is not OH or

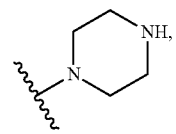

[Y] is absent, and
[Z] is absent; or
(ii) [X] is 3-15 membered heterocyclyl or 5-20 membered heteroaryl, wherein the 3-15 membered heterocyclyl of [X] is optionally substituted with one or more —OH or C$_{1-6}$alkyl,
[Y] is absent, and
[Z] is 3-15 membered heterocyclyl or 5-20 membered heteroaryl,
provided that, when

is (a), [X] is

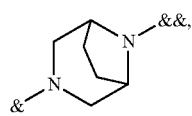

wherein & denotes the point of attachment to

and && denotes the point of attachment to [Z], and [Z] is

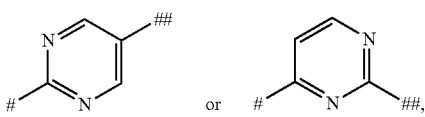

wherein # denotes the point of attachment to [X] and ## denotes the point of attachment to $R^1$, then:
(a-i) when $R^1$ is —C≡C—R$^α$ and R$^α$ is C$_{1-6}$ alkyl substituted with N(R$^x$)(R$^y$), R$^x$ and R$^y$ are not H or C$_{1-6}$ alkyl, and
(a-ii) when $R^1$ is —(CH$_2$)$_n$—R$^g$ and R$^g$ is N(R$^x$)(R$^y$), then R$^x$ and R$^y$ are not H or C$_{1-6}$ alkyl, and provided that, when

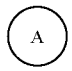

is (b), [X] is

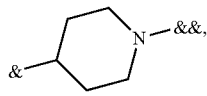

wherein & denotes the point of attachment to

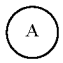

and && denotes the point of attachment to [Z], and [Z] is

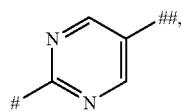

wherein # denotes the point of attachment to [X] and ## denotes the point of attachment to $R^1$, then:

(a-i) when $R^1$ is —C≡C—$R^a$ and $R^a$ is $C_{1-6}$ alkyl substituted with $N(R^x)(R^y)$, $R^x$ and $R^y$ are not H or $C_{1-6}$ alkyl, and (a-ii) when $R^1$ is —$(CH_2)_n$—$R^g$ and $R^g$ is $N(R^x)(R^y)$, then $R^x$ and $R^y$ are not H or $C_{1-6}$ alkyl; or (iii) [X] is 3-15 membered heterocyclyl or 5-20 membered heteroaryl,
[Y] is methylene, wherein the methylene of [Y] is optionally substituted with one or more methyl group, and
[Z] is 3-15 membered heterocyclyl; or (iv) [X] is absent,
[Y] is ethenylene, wherein the ethenylene of [Y] is optionally substituted with one or more halo, and
[Z] is 5-20 membered heteroaryl,
provided that

is (a), (b), (d), or (e); or (v) [X] is absent,
[Y] is ethynylene, and
[Z] is 5-20 membered heteroaryl,
provided that

is (a), (b), (d), or (e); or (vi) [X] is absent,
[Y] is cyclopropyl or cyclobutyl, and
[Z] is 5-20 membered heteroaryl,
provided that

is (a), (b), (d), or (e); or (vii) [X] is absent,
[Y] is absent, and
[Z] is 5-20 membered heteroaryl; and $R^1$ is:
(a) —C≡C—$R^a$, wherein
(i) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —$N(R^x)(R^y)$, wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —$S(O)_2$—($C_{1-6}$ alkyl), $C_{3-10}$cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—$N(R^x)(R^y)$, or —$N(R^x)(R^y)$, wherein
the $C_{1-6}$alkyl of $R^c$ is optionally substituted with one or more —OH, —CN, halo, $C_{1-6}$alkoxy, or 3-15 membered heterocyclyl,
the $C_{3-10}$ cycloalkyl of $R^c$ is optionally substituted with one or more halo,
the $C_{6-10}$aryl of $R^c$ is optionally substituted with one or more —CN,
the 3-15 membered heterocyclyl of $R^c$ is optionally substituted with one or more $C_{1-6}$ alkyl or —C(O)—$C_{1-6}$alkyl, and
the $C_{1-6}$alkoxy of $R^b$ is optionally substituted with one or more —OH, or (ii) $R^a$ is $C_{3-10}$ cycloalkyl, wherein the $C_{3-10}$ cycloalkyl of $R^a$ is optionally substituted with one or more $R^z$, or
(iii) $R^a$ is 3-15 membered heterocyclyl, wherein the 3-15 membered heterocyclyl of $R^a$ is optionally substituted with one or more $R^z$, or
(iv) $R^a$ is 5-20 membered heteroaryl, wherein the 5-20 membered heteroaryl of $R^a$ is optionally substituted with one or more $R^z$, or (b) —$(CH_2)_n$—$R^g$, wherein
n is an integer from 1-6, and
$R^g$ is —$N(R^x)(R^y)$ or —OH;

$R^z$ is, independently at each occurrence, —OH, —CN, halo, $C_{1-6}$alkyl, $C_{1-6}$alkoxy, —$N(R^x)(R^y)$, or —C(O)—$N(R^x)(R^y)$; and the $R^x$ and $R^y$ of —$C(O)N(R^x)(R^y)$ and —$N(R^x)(R^y)$ are, independently of each other and independently at each occurrence, H, —C(O)—$(CH_2)_p$—$N(R^p)(R^q)$, —C(O)—$R^s$, 5-20 membered heterocycle, 5-20 membered heteroaryl, or $C_{1-6}$alkyl, wherein
p is an integer from 1-6,
$R^p$ and $R^q$ are, independently of each other and independently at each occurrence H, or $C_{1-6}$alkyl,
$R^s$ is 5-20 membered heterocycle optionally substituted with one or more substituents selected from the group consisting of $C_{1-4}$alkyl, $C_{3-8}$cycloalkyl, and —C(O)—$C_{1-6}$alkyl, the C$_{1-6}$alkyl of R$^x$ or R$^y$ is optionally substituted with one or more —OH, 3-15 membered heterocyclyl, or —C(O)-(3-15 membered heterocyclyl), and the 5-20 membered heterocycle of R$^x$ or R$^y$ is optionally substituted with one or more oxo, or (c) —C≡C—R$^d$, wherein R$^d$ is C$_{1-6}$alkyl, wherein the C$_{1-6}$alkyl of R$^d$ is optionally substituted with one or more R$^e$, wherein each R$^e$ is independently 3-15 membered heterocyclyl, wherein the 3-15 membered heterocyclyl of R$^e$ is optionally substituted with one or more R$^f$, wherein each R$^f$ is independently —OH, —CN, halo, oxo, C$_{1-6}$alkyl, C$_{1-6}$alkoxy, or —C(O)—C$_{1-6}$alkoxy.

In one aspect, the present disclosure is directed to a compound of formula (I):

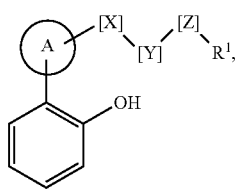
(I)

or a stereoisomer or tautomer thereof, or a pharmaceutically acceptable salt of any of the foregoing, wherein:

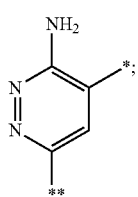

is selected from the group consisting of:

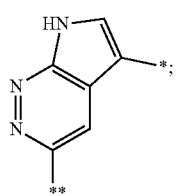
(a)

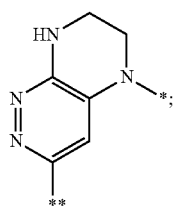
(b)

(c)

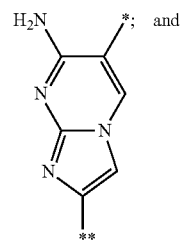
(d)

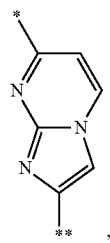
(e)

wherein, for (a)-(e), * denotes the point of attachment to [X], or, if [X] is absent, * denotes the point of attachment to [Y], and ** denotes the point of attachment to the remainder of the molecule;

and wherein:

(i) [X] is 3-15 membered heterocyclyl or 5-20 membered heteroaryl, provided that, when

is (a), then [X] is not #

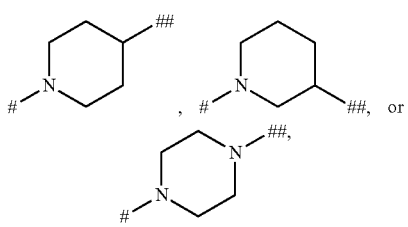

wherein # denotes the point of attachment to

and ## denotes the point of attachment to R$^1$,

[Y] is absent, and

[Z] is absent; or (ii) [X] is 3-15 membered heterocyclyl or 5-20 membered heteroaryl, wherein the 3-15 membered heterocyclyl of [X] is optionally substituted with one or more —OH or C$_{1-6}$alkyl,

[Y] is absent, and

[Z] is 3-15 membered heterocyclyl or 5-20 membered heteroaryl, provided that, when is

(a) and [X] is

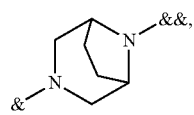

wherein & denotes the point of attachment to

and && denotes the point of attachment to [Z], then [Z] is not

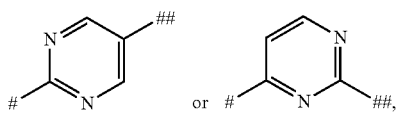

wherein # denotes the point of attachment to [X] and ## denotes the point of attachment to $R^1$; or
(iii) [X] is 3-15 membered heterocyclyl or 5-20 membered heteroaryl,
[Y] is methylene, wherein the methylene of [Y] is optionally substituted with one or more methyl group, and
[Z] is 3-15 membered heterocyclyl; or
(iv) [X] is absent,
[Y] is ethenylene, wherein the ethenylene of [Y] is optionally substituted with one or more halo, and
[Z] is 5-20 membered heteroaryl,
provided that

is (a), (b), (d), or (e); or
(v) [X] is absent,
[Y] is ethynylene, and
[Z] is 5-20 membered heteroaryl,
provided that is

(a), (b), (d), or (e); or
(vi) [X] is absent,
[Y] is cyclopropyl or cyclobutyl, and
[Z] is 5-20 membered heteroaryl, provided that

is (a), (b), (d), or (e); and
$R^1$ is:
(a) —C≡C—$R^a$, wherein
(i) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$ cycloalkyl of $R^c$ is optionally substituted with one or more halo, and
the 3-15 membered heterocyclyl of $R^c$ is optionally substituted with one or more $C_{1-6}$ alkyl or —C(O)—$C_{1-6}$alkyl, and
the $C_{1-6}$alkoxy of $R^b$ is optionally substituted with one or more —OH, or
(ii) $R^a$ is $C_{3-10}$ cycloalkyl, wherein the $C_{3-10}$ cycloalkyl of $R^a$ is optionally substituted with one or more $R^z$, or
(iii) $R^a$ is 3-15 membered heterocyclyl, wherein the 3-15 membered heterocyclyl of $R^a$ is optionally substituted with one or more $R^z$, or
(iv) $R^a$ is 5-20 membered heteroaryl, wherein the 5-20 membered heteroaryl of $R^a$ is optionally substituted with one or more $R^z$, or
(b) —(CH$_2$)$_n$—$R^g$, wherein
n is an integer from 1-6, and
$R^g$ is —N($R^x$)($R^y$) or —OH;
wherein
$R^z$ is, independently at each occurrence, —OH, —CN, halo, $C_{1-6}$alkyl, $C_{1-6}$alkoxy, —N($R^x$)($R^y$), or —C(O)—N($R^x$)($R^y$); and
the $R^x$ and $R^y$ of —C(O)N($R^x$)($R^y$) and —N($R^x$)($R^y$) are, independently of each other and independently at each occurrence, H, —C(O)—(CH$_2$)$_p$—N($R^p$)($R^q$), 5-20 membered heteroaryl, or $C_{1-6}$alkyl, wherein
p is an integer from 1-6,
$R^p$ and $R^q$ are, independently of each other and independently at each occurrence H, or $C_{1-6}$alkyl, and
the $C_{1-6}$alkyl of $R^x$ or $R^y$ is optionally substituted with one or more —OH, 3-15 membered heterocyclyl, or —C(O)-(3-15 membered heterocyclyl).
In some embodiments, provided herein is a compound of formula (I), or a stereoisomer or tautomer thereof, or a pharmaceutically acceptable salt of any of the foregoing, wherein

is

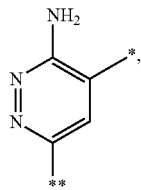

such that the compound is of formula (I-A):

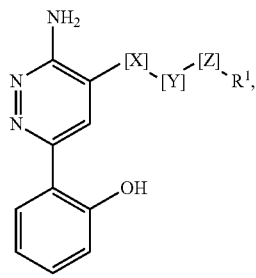

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof.

In some embodiments of formula (I-A), [X] is 3-15 membered heterocyclyl or 5-20 membered heteroaryl, provided that [X] is not

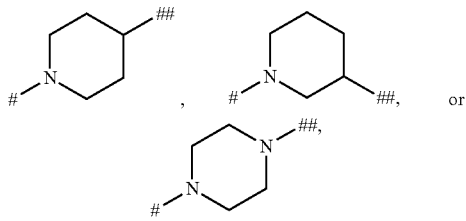

wherein # denotes the point of attachment to (A)

and ## denotes the point of attachment to $R^1$; [Y] is absent; and [Z] is absent. In some variations, the embodiments provided herein also apply to a compound of formula (I'), or a stereoisomer or tautomer thereof, or a pharmaceutically acceptable salt of any of the foregoing, or any variation or embodiment thereof.

In some embodiments, provided herein is a compound of formula (I), or a stereoisomer or tautomer thereof, or a pharmaceutically acceptable salt of any of the foregoing, wherein the compound is of formula (I-A1):

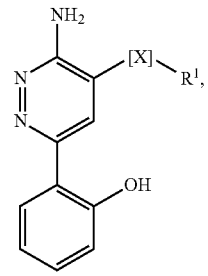

or a stereoisomer or tautomer thereof, or a pharmaceutically acceptable salt of any of the foregoing, wherein [X] is 3-15 membered heterocyclyl or 5-20 membered heteroaryl, provided that [X] is not

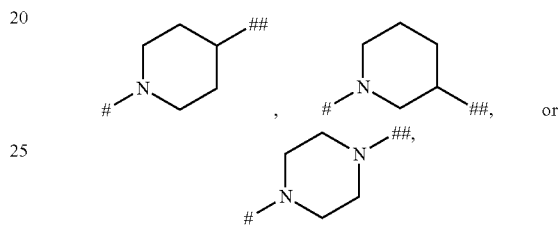

wherein # denotes the point of attachment to (A)

and ## denotes the point of attachment to $R^1$. In some embodiments of the foregoing, [X] is 3-15 membered heterocyclyl. In some embodiments, [X] is 3-12 membered heterocyclyl. In some embodiments, [X] is a bicyclic heterocyclyl. In some embodiments, [X] is spiro. In some embodiments, [X] is a 5-20 membered heteroaryl. In some embodiments, [X] is a 5-10 membered heteroaryl. In some embodiments, [X] is a 5-6 membered heteroaryl. In some embodiments, [X] is a 5-membered heteroaryl. In some embodiments, [X] is a monocyclic heteroaryl. In some embodiments, [X] is not a monocyclic heterocyclyl. In some embodiments, [X] is a bridged heterocyclyl. In some embodiments, [X] comprises at least two annular heteroatoms. In some embodiments, [X] comprises at least one annular N atom. In some embodiments, [X] comprises at least two annular N atoms. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Y], [Z], and $R^1$ are as defined above or elsewhere herein for a compound of formula (I). In another variation, [X], [Y], [Z], and $R^1$ of formula (I-A1) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I), (I-A), or (I-A1), or a stereoisomer or tautomer thereof, or a pharmaceutically acceptable salt of any of the foregoing, wherein the compound is selected from the group consisting of

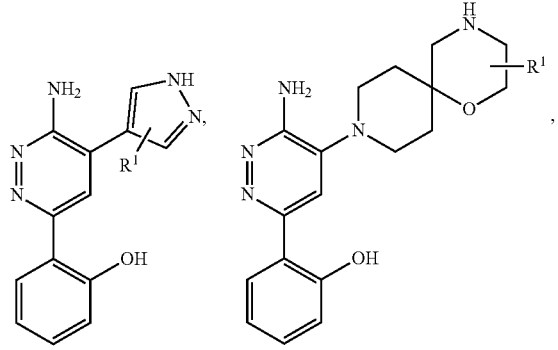
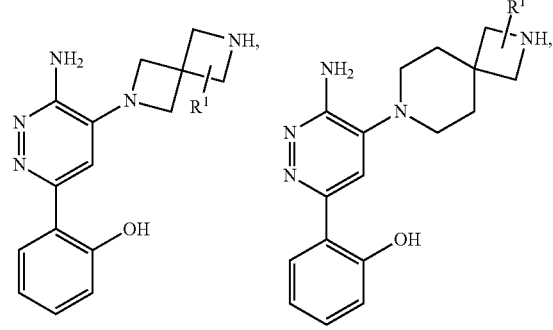
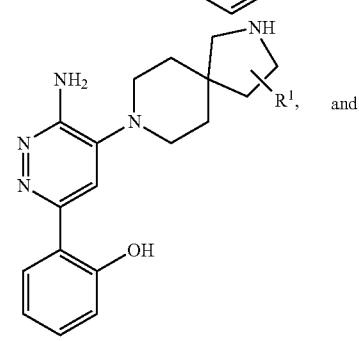
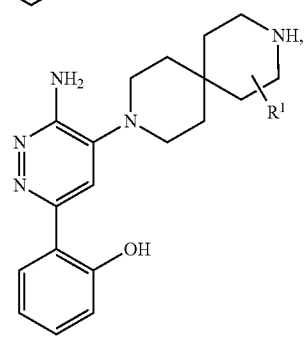

or a stereoisomer or tautomer thereof, or a pharmaceutically acceptable salt of any of the foregoing. In some variations, $R^1$ is as defined above or elsewhere herein for a compound of formula (I), (I-A), or (I-A1). In another variation, $R^1$ of formula (I), (I-A), or (I-A1), are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I-A), or a stereoisomer or tautomer thereof, or a pharmaceutically acceptable salt of any of the foregoing, wherein [X] is 3-15 membered heterocyclyl or 5-20 membered heteroaryl, wherein the 3-15 membered heterocyclyl of [X] is optionally substituted with one or more —OH or $C_{1-6}$alkyl; [Y] is absent; and [Z] is 3-15 membered heterocyclyl or 5-20 membered heteroaryl, provided that, when [X] is

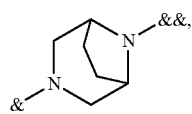

wherein & denotes the point of attachment to

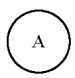

and && denotes the point of attachment to [Z], and [Z]

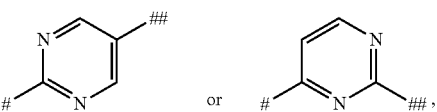

wherein # denotes the point of attachment to [X] and ## denotes the point of attachment to $R^1$, then when $R^1$ is —C≡C—$R^a$ and $R^a$ is $C_{1-6}$ alkyl substituted with $N(R^x)(R^y)$, $R^x$ and $R^y$ are not H or $C_{1-6}$ alkyl, and when $R^1$ is —$(CH_2)_n$—$R^g$ and $R^g$ is $N(R^x)(R^y)$, then $R^x$ and $R^y$ are not H or $C_{1-6}$ alkyl. In some variations, the embodiments provided herein also apply to a compound of formula (I'), or a stereoisomer or tautomer thereof, or a pharmaceutically acceptable salt of any of the foregoing, or any variation or embodiment thereof.

In some embodiments, provided herein is a compound of formula (I-A), or a stereoisomer or tautomer thereof, or a pharmaceutically acceptable salt of any of the foregoing, wherein [X] is 3-15 membered heterocyclyl or 5-20 membered heteroaryl, wherein the 3-15 membered heterocyclyl of [X] is optionally substituted with one or more —OH or $C_{1-6}$alkyl; [Y] is absent; and [Z] is 3-15 membered heterocyclyl or 5-20 membered heteroaryl, provided that, when

is (a) and [X] is

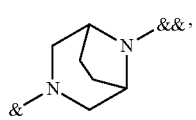

wherein & denotes the point of attachment to

and && denotes the point of attachment to [Z], then [Z] is not

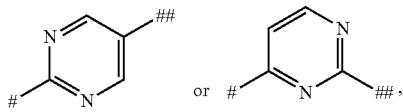

wherein # denotes the point of attachment to [X] and ## denotes the point of attachment to $R^1$; In some variations, the embodiments provided herein also apply to a compound of formula (I'), or a stereoisomer or tautomer thereof, or a pharmaceutically acceptable salt of any of the foregoing, or any variation or embodiment thereof.

In some embodiments, provided herein is a compound of formula (I'), or a stereoisomer or tautomer thereof, or a pharmaceutically acceptable salt of any of the foregoing, wherein the compound is of formula (I-A2):

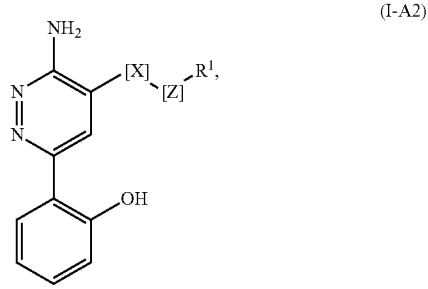

(I-A2)

or a stereoisomer or tautomer thereof, or a pharmaceutically acceptable salt of any of the foregoing, wherein [X] is 3-15 membered heterocyclyl or 5-20 membered heteroaryl, wherein the 3-15 membered heterocyclyl of [X] is optionally substituted with one or more —OH or $C_{1-6}$alkyl; and [Z] is 3-15 membered heterocyclyl or 5-20 membered heteroaryl, provided that, when [X] is

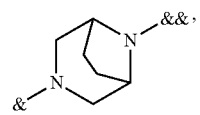

wherein & denotes the point of attachment to

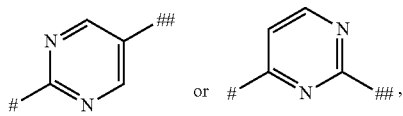

and && denotes the point of attachment to [Z], and [Z] is

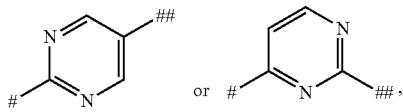

wherein # denotes the point of attachment to [X] and ## denotes the point of attachment to $R^1$, then when $R^1$ is —C≡C—$R^a$ and $R^a$ is $C_{1-6}$ alkyl substituted with N($R^x$)($R^y$), $R^x$ and $R^y$ are not H or $C_{1-6}$ alkyl, and when $R^1$ is —(CH$_2$)$_n$—$R^g$ and $R^g$ is N($R^x$)($R^y$), then $R^x$ and $R^y$ are not H or $C_{1-6}$ alkyl. In some embodiments, [X] is 3-15 membered heterocyclyl, wherein the 3-15 membered heterocyclyl of [X] is optionally substituted with one or more —OH or $C_{1-6}$alkyl. In some embodiments, [X] is 3-10 membered heterocyclyl, wherein the 3-10 membered heterocyclyl of [X] is optionally substituted with one or more —OH or $C_{1-6}$ alkyl. In some embodiments, [X] is 3-8 membered heterocyclyl, wherein the 3-8 membered heterocyclyl of [X] is optionally substituted with one or more —OH or $C_{1-6}$ alkyl. In some embodiments, [X] is 6-8 membered heterocyclyl, wherein the 6-8 membered heterocyclyl of [X] is optionally substituted with one or more —OH or $C_{1-6}$ alkyl. In some embodiments, [X] is 6-8 membered heterocyclyl, wherein the 6-8 membered heterocyclyl of [X] is optionally substituted with one or more —OH. In some embodiments, the 6-8 membered heterocyclyl of [X] is unsubstituted. In some embodiments, [X] is a monocyclic heterocyclyl. In some embodiments, [X] is a bridged heterocyclyl. In some embodiments, [X] is 5-20 membered heteroaryl. In some embodiments, [X] is 5-10 membered heteroaryl. In some embodiments, [X] is 5-6 membered heteroaryl. In some embodiments, [X] is 5-membered heteroaryl. In some embodiments, [Z] is 3-15 membered heterocyclyl. In some embodiments, [Z] is 3-10 membered heterocyclyl. In some embodiments, [Z] is 5-6 membered heterocyclyl. In some embodiments, [Z] is 6-membered heterocyclyl. In some embodiments, [Z] is a monocyclic heterocyclyl. In some embodiments, [Z] is 5-20 membered heteroaryl. In some embodiments, [Z] is 5-10 membered heteroaryl. In some embodiments, [Z] is 5-6 membered heteroaryl. In some embodiments, [Z] is 6-membered heteroaryl. In some embodiments, [X] is 3-15 membered heterocyclyl, wherein the 3-15 membered heterocyclyl of [X] is optionally substituted with one or more —OH or $C_{1-6}$alkyl and [Z] is 5-20 membered heteroaryl. In some embodiments, [X] is 5-20 membered heteroaryl and [Z] is 3-15 membered heterocyclyl. In some embodiments, [X] is 5-20 membered heteroaryl and [Z] is 5-20 membered heteroaryl. In some embodiments, [X] comprises at least one annular N atom. In some embodiments, [Z] is a 3-15 membered heterocyclyl that comprises only one heteroatom. In some embodiments, [Z] is comprises at least one annular N atom. In some embodiments, [Z] comprises only one annular N atom.

In some embodiments, provided herein is a compound of formula (I), or a stereoisomer or tautomer thereof, or a pharmaceutically acceptable salt of any of the foregoing, wherein the compound is of formula (I-A2):

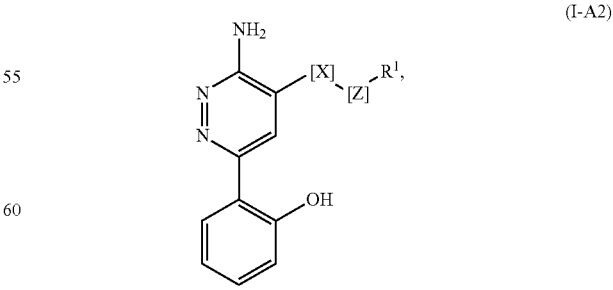

(I-A2)

or a stereoisomer or tautomer thereof, or a pharmaceutically acceptable salt of any of the foregoing, wherein [X] is 3-15 membered heterocyclyl or 5-20 membered heteroaryl, wherein the 3-15 membered heterocyclyl of [X] is optionally substituted with one or more —OH or $C_{1-6}$alkyl; and [Z] is 3-15 membered heterocyclyl or 5-20 membered heteroaryl, provided that, when [X] is

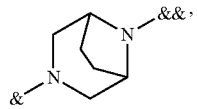

wherein & denotes the point of attachment to

and && denotes the point of attachment to [Z], then [Z] is not

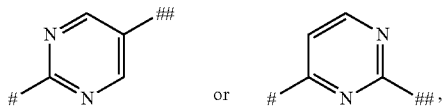

wherein # denotes the point of attachment to [X] and ## denotes the point of attachment to $R^1$. In some embodiments of the foregoing, [X] is 3-15 membered heterocyclyl, wherein the 3-15 membered heterocyclyl of [X] is optionally substituted with one or more —OH or $C_{1-6}$alkyl. In some embodiments, [X] is 3-10 membered heterocyclyl, wherein the 3-10 membered heterocyclyl of [X] is optionally substituted with one or more —OH or $C_{1-6}$alkyl. In some embodiments, [X] is 3-8 membered heterocyclyl, wherein the 3-8 membered heterocyclyl of [X] is optionally substituted with one or more —OH or $C_{1-6}$alkyl. In some embodiments, [X] is 6-8 membered heterocyclyl, wherein the 6-8 membered heterocyclyl of [X] is optionally substituted with one or more —OH or $C_{1-6}$alkyl. In some embodiments, [X] is 6-8 membered heterocyclyl, wherein the 6-8 membered heterocyclyl of [X] is optionally substituted with one or more —OH. In some embodiments, the 6-8 membered heterocyclyl of [X] is unsubstituted. In some embodiments of the foregoing, [X] is a monocyclic heterocyclyl. In some embodiments of the foregoing, [X] is a bridged heterocyclyl. In some embodiments of the foregoing, [X] is 5-20 membered heteroaryl. In some embodiments, [X] is 5-10 membered heteroaryl. In some embodiments, [X] is 5-6 membered heteroaryl. In some embodiments, [X] is 5-membered heteroaryl. In some embodiments of the foregoing, [Z] is 3-15 membered heterocyclyl. In some embodiments, [Z] is 3-10 membered heterocyclyl. In some embodiments, [Z] is 5-6 membered heterocyclyl. In some embodiments, [Z] is 6-membered heterocyclyl. In some embodiments of the foregoing, [Z] is a monocyclic heterocyclyl. In some embodiments, [Z] is 5-20 membered heteroaryl. In some embodiments, [Z] is 5-10 membered heteroaryl. In some embodiments, [Z] is 5-6 membered heteroaryl. In some embodiments, [Z] is 6-membered heteroaryl. In some embodiments of the foregoing, [X] is 3-15 membered heterocyclyl, wherein the 3-15 membered heterocyclyl of [X] is optionally substituted with one or more —OH or $C_{1-6}$alkyl and [Z] is 5-20 membered heteroaryl. In some embodiments, [X] is 5-20 membered heteroaryl and [Z] is 3-15 membered heterocyclyl. In some embodiments, [X] is 5-20 membered heteroaryl and [Z] is 5-20 membered heteroaryl.

In some embodiments, provided herein is a compound of formula (I), (I-A), or (I-A2), or a stereoisomer or tautomer thereof, or a pharmaceutically acceptable salt of any of the foregoing, wherein the compound is selected from the group consisting of

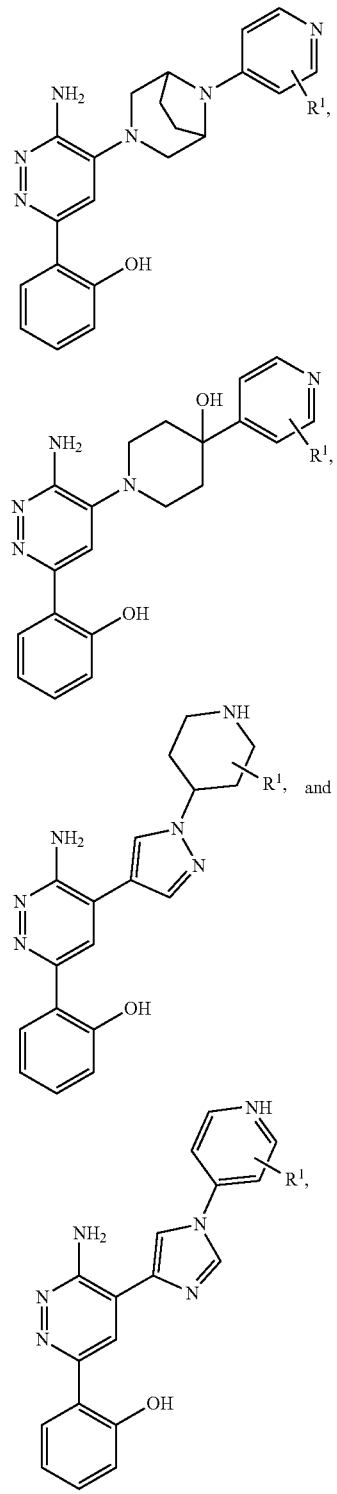

or a stereoisomer or tautomer thereof, or a pharmaceutically acceptable salt of any of the foregoing. In one embodiment, the compound of formula (I), (I-A), or (I-A2), or a stereoisomer or tautomer thereof, or a pharmaceutically acceptable salt of any of the foregoing, is

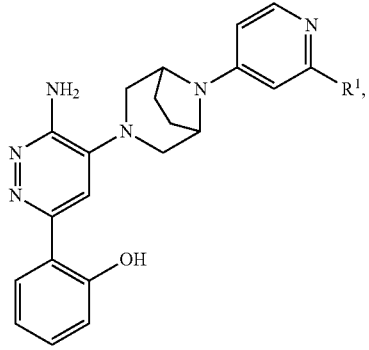

or a stereoisomer or tautomer thereof, or a pharmaceutically acceptable salt of any of the foregoing. In some variations, R¹ is as defined above or elsewhere herein for a compound of formula (I), (I-A), or (I-A2). In another variation, R¹ of formula (I), (I-A), or (I-A2), are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I), (I-A), or (I-A2), or a stereoisomer or tautomer thereof, or a pharmaceutically acceptable salt of any of the foregoing, wherein the 3-15 membered heterocyclyl or 5-20 membered heteroaryl of [X] and [Z] each comprise at least one annular N atom. In some embodiments, [X] is a 3-15 membered heterocyclyl containing at least one annular N atom, and [Z] is a 5-20 membered heteroaryl containing only one annular N atom. In some embodiments, [X] is

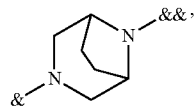

& wherein & denotes the point of attachment to

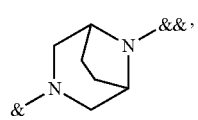

and && denotes the point of attachment to [Z], and [Z] is a 5-20 membered heteroaryl comprising only one annular N atom. In some embodiments, [X] is

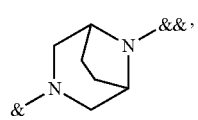

wherein & denotes the point of attachment to

Ⓐ and && denotes the point of attachment to [Z], and [Z] is a 5-6 membered heretoaryl containing only one annular N atom. In some variations, R¹ is as defined above or elsewhere herein for a compound of formula (I), (I-A), or (I-A2). In another variation, R¹ of formula (I), (I-A), or (I-A2), are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I'), or a stereoisomer or tautomer thereof, or a pharmaceutically acceptable salt of any of the foregoing, wherein [X] is 3-15 membered heterocyclyl or 5-20 membered heteroaryl, [Y] is methylene, wherein the methylene of [Y] is optionally substituted with one or more methyl group, and [Z] is 3-15 membered heterocyclyl. In some embodiments, provided herein is a compound of formula (I), or a stereoisomer or tautomer thereof, or a pharmaceutically acceptable salt of any of the foregoing, wherein [X] is 3-15 membered heterocyclyl or 5-20 membered heteroaryl, [Y] is methylene, wherein the methylene of [Y] is optionally substituted with one or more methyl group, and [Z] is 3-15 membered heterocyclyl.

In some embodiments of the foregoing, provided herein is a compound of formula (I) or (I-A), or a stereoisomer or tautomer thereof, or a pharmaceutically acceptable salt of any of the foregoing, wherein the compound is of formula (I-A3):

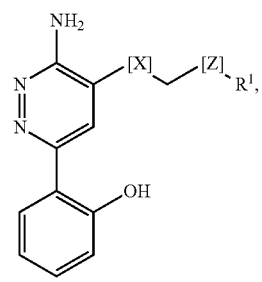

(I-A3)

or a stereoisomer or tautomer thereof, or a pharmaceutically acceptable salt of any of the foregoing, wherein [X] is 3-15 membered heterocyclyl or 5-20 membered heteroaryl and [Z] is 3-15 membered heterocyclyl. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Z], and R¹ are as defined above or elsewhere herein for a compound of formula (I). In another variation, [X], [Z], and R¹ of formula (I-A3) are as defined for a compound of formula (I'), or a stereoisomer or tautomer thereof, or a pharmaceutically acceptable salt of any of the foregoing, or any variation or embodiment thereof.

In some embodiments of the foregoing, provided herein is a compound of formula (I) or (I-A), or a stereoisomer or tautomer thereof, or a pharmaceutically acceptable salt of any of the foregoing, wherein the compound is of formula (I-A4):

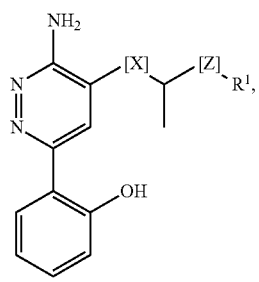

(I-A4)

or a stereoisomer or tautomer thereof, or a pharmaceutically acceptable salt of any of the foregoing, wherein [X] is 3-15 membered heterocyclyl or 5-20 membered heteroaryl and [Z] is 3-15 membered heterocyclyl. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Z], and $R^1$ are as defined above or elsewhere herein for a compound of formula (I). In another variation, [X], [Z], and $R^1$ of formula (I-A4) are as defined for a compound of formula (I'), or a stereoisomer or tautomer thereof, or a pharmaceutically acceptable salt of any of the foregoing, or any variation or embodiment thereof.

In some embodiments of the foregoing, provided herein is a compound of formula (I-A3) or (I-A4), or a stereoisomer or tautomer thereof, or a pharmaceutically acceptable salt of any of the foregoing, wherein [X] is 3-15 membered heterocyclyl. In some embodiments, [X] is 3-12 membered heterocyclyl. In some embodiments, [X] is 6-12 membered heterocyclyl. In some embodiments, [X] is 8-12 membered heterocyclyl. In some embodiments of the foregoing, [Z] is 3-10 membered heterocyclyl. In some embodiments, [Z] is 5-6 membered heterocyclyl. In some embodiments, [Z] is 6-membered heterocyclyl. In some embodiments of the foregoing, provided herein is a compound of formula (I-A3) or (I-A4), or a stereoisomer or tautomer thereof, or a pharmaceutically acceptable salt of any of the foregoing, wherein [X] is 3-15 membered heterocyclyl and [Z] is 3-15 membered heterocyclyl. In some embodiments, [X] is 5-20 membered heteroaryl and [Z] is 3-15 membered heterocyclyl. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Z], and $R^1$ are as defined above or elsewhere herein for a compound of formula (I). In another variation, [X], [Z], and $R^1$ of formula (I-A4) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I) or (I-A), or a stereoisomer or tautomer thereof, or a pharmaceutically acceptable salt of any of the foregoing, wherein the compound is selected from the group consisting of

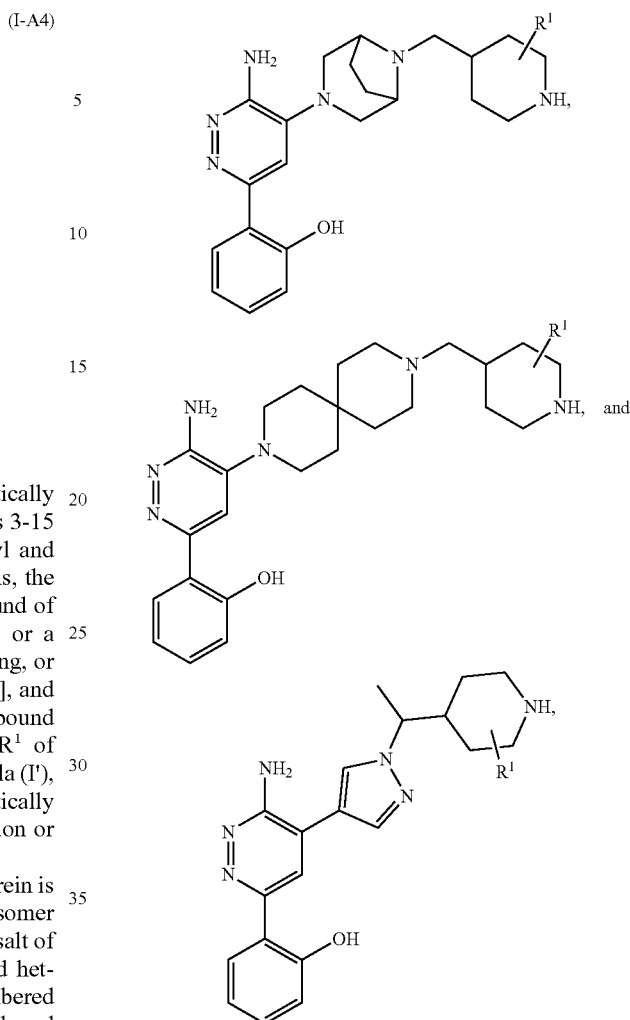

or a stereoisomer or tautomer thereof, or a pharmaceutically acceptable salt of any of the foregoing. In some variations, $R^1$ is as defined above or elsewhere herein for a compound of formula (I), or (I-A). In another variation, $R^1$ of formula (I), or (I-A), are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I'), or a stereoisomer or tautomer thereof, or a pharmaceutically acceptable salt of any of the foregoing, wherein [X] is absent, [Y] is ethenylene, wherein the ethenylene of [Y] is optionally substituted with one or more halo, and [Z] is 5-20 membered heteroaryl. In some embodiments, provided herein is a compound of formula (I), or a stereoisomer or tautomer thereof, or a pharmaceutically acceptable salt of any of the foregoing, wherein [X] is absent, [Y] is ethenylene, wherein the ethenylene of [Y] is optionally substituted with one or more halo, and [Z] is 5-20 membered heteroaryl.

In some embodiments, provided herein is a compound of formula (I) or (I-A), or a stereoisomer or tautomer thereof, or a pharmaceutically acceptable salt of any of the foregoing, wherein the compound is of formula (I-A5):

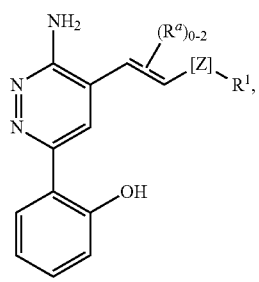

(I-A5)

or a stereoisomer or tautomer thereof, or a pharmaceutically acceptable salt of any of the foregoing, wherein [Y] is ethenylene, wherein the ethenylene of [Y] is optionally substituted with one or two $R^a$, wherein each $R^a$ is halo, and [Z] is 5-20 membered heteroaryl. In some embodiments of the foregoing, [Y] is unsubstituted ethylene. In some embodiments, [Y] is ethylene substituted with two halo. In some embodiments, [Y] is ethylene substituted with one halo. In some embodiments of the foregoing, the halo is fluoro. In some embodiments of the foregoing, [Z] is 5-10 membered heteroaryl. In some embodiments, [Z] is 5-6 membered heteroaryl. In some embodiments, [Z] is 5-membered heteroaryl. In some embodiments, [Z] is 6-membered heteroaryl. In some variations, the embodiments provided herein also apply to a compound of formula (I'), or a stereoisomer or tautomer thereof, or a pharmaceutically acceptable salt of any of the foregoing, or any variation or embodiment thereof, wherein [Z], $R^a$ and $R^1$ are as defined above or elsewhere herein for a compound of formula (I). In another variation, [Z], $R^a$ and $R^1$ of formula (I-A5) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I), (I-A), or (I-A5), or a stereoisomer or tautomer thereof, or a pharmaceutically acceptable salt of any of the foregoing, wherein the compound is selected from the group consisting of

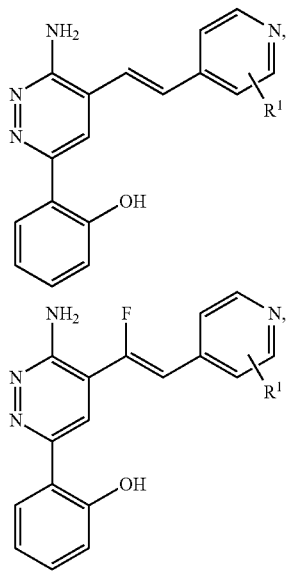

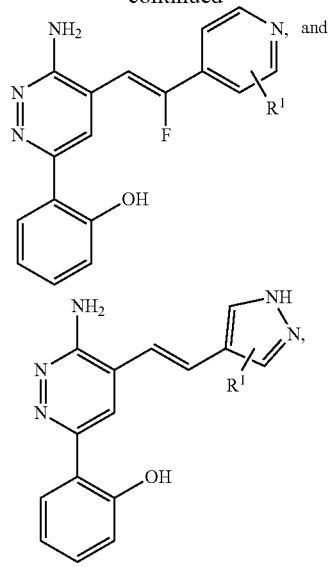

or a stereoisomer or tautomer thereof, or a pharmaceutically acceptable salt of any of the foregoing. In some variations, the embodiments provided herein also apply to a compound of formula (I-A5), or a stereoisomer or tautomer thereof, or a pharmaceutically acceptable salt of any of the foregoing, or any variation or embodiment thereof, wherein $R^1$ is as defined above or elsewhere herein for a compound of formula (I'), or formula (I). In some variations, $R^1$ is as defined above or elsewhere herein for a compound of formula (I), (I-A), or (I-A3). In another variation, $R^1$ of formula (I), (I-A), or (I-A3), are as defined for a compound of formula (I'), or a stereoisomer or tautomer thereof, or a pharmaceutically acceptable salt of any of the foregoing, or any variation or embodiment thereof.

In one embodiment, provided herein is a compound of formula (I') or (I-A), or a stereoisomer or tautomer thereof, or a pharmaceutically acceptable salt of any of the foregoing, wherein [X] is absent, [Y] is ethynylene, and [Z] is 5-20 membered heteroaryl. In one embodiment, provided herein is a compound of formula (I) or (I-A), or a stereoisomer or tautomer thereof, or a pharmaceutically acceptable salt of any of the foregoing, wherein [X] is absent, [Y] is ethynylene, and [Z] is 5-20 membered heteroaryl.

In some embodiments, provided herein is a compound of formula (I) or (I-A), or a stereoisomer or tautomer thereof, or a pharmaceutically acceptable salt of any of the foregoing, wherein the compound is of formula:

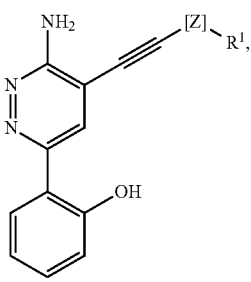

(I-A6)

or a stereoisomer or tautomer thereof, or a pharmaceutically acceptable salt of any of the foregoing, wherein [Z] is 5-20 membered heteroaryl. In some embodiments of the foregoing, [Z] is 5-10 membered heteroaryl. In some embodiments, [Z] is 5-6 membered heteroaryl. In some embodiments, [Z] is 5-membered heteroaryl. In some embodiments, [Z] is 6-membered heteroaryl. In some variations, the embodiments provided herein also apply to a compound of formula (I'), or a stereoisomer or tautomer thereof, or a pharmaceutically acceptable salt of any of the foregoing, or any variation or embodiment thereof, wherein [Z], and R¹ are as defined above or elsewhere herein for a compound of formula (I). In another variation, [Z], and R¹ of formula (I-A6) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I), (I-A), or (I-A6), or a stereoisomer or tautomer thereof, or a pharmaceutically acceptable salt of any of the foregoing, wherein the compound is selected from the group consisting of

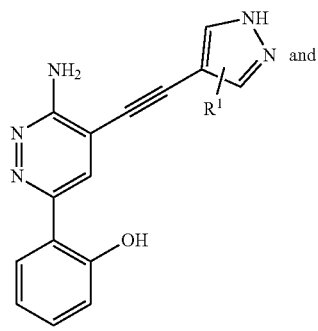

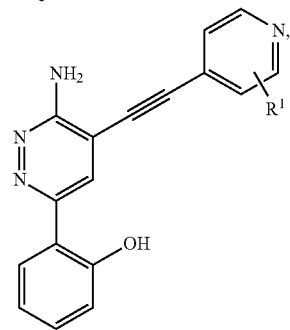

and or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof. In some variations, R¹ is as defined above or elsewhere herein for a compound of formula (I), (I-A), or (I-A6). In another variation, R¹ of formula (I), (I-A), or (I-A6), are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I'), or a stereoisomer or tautomer thereof, or a pharmaceutically acceptable salt of any of the foregoing, wherein [X] is absent, [Y] is cyclopropyl or cyclobutyl, and [Z] is 5-20 membered heteroaryl. In some embodiments, provided herein is a compound of formula (I), or a stereoisomer or tautomer thereof, or a pharmaceutically acceptable salt of any of the foregoing, wherein [X] is absent, [Y] is cyclopropyl or cyclobutyl, and [Z] is 5-20 membered heteroaryl.

In some embodiments, provided herein is a compound of formula (I) or (I-A), or a stereoisomer or tautomer thereof, or a pharmaceutically acceptable salt of any of the foregoing, wherein the compound is of formula (I-A7):

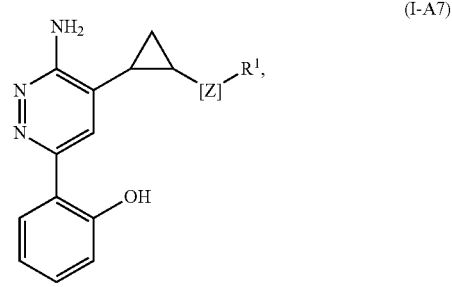

(I-A7)

or a stereoisomer or tautomer thereof, or a pharmaceutically acceptable salt of any of the foregoing, wherein [Z] is 5-20 membered heteroaryl. In some variations, the embodiments provided herein also apply to a compound of formula (I'), or a stereoisomer or tautomer thereof, or a pharmaceutically acceptable salt of any of the foregoing, or any variation or embodiment thereof, wherein [Z], and R¹ are as defined above or elsewhere herein for a compound of formula (I). In another variation, [Z], and R¹ of formula (I-A7) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I) or (I-A), or a stereoisomer or tautomer thereof, or a pharmaceutically acceptable salt of any of the foregoing, wherein the compound is of formula (I-A8):

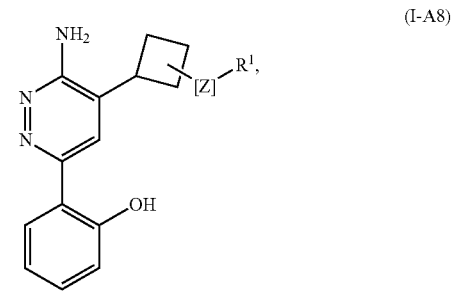

(I-A8)

or a stereoisomer or tautomer thereof, or a pharmaceutically acceptable salt of any of the foregoing, wherein [Z] is 5-20 membered heteroaryl. In some variations, the embodiments provided herein also apply to a compound of formula (I'), or a stereoisomer or tautomer thereof, or a pharmaceutically acceptable salt of any of the foregoing, or any variation or embodiment thereof, wherein [Z], and R¹ are as defined above or elsewhere herein for a compound of formula (I). In another variation, [Z], and R¹ of formula (I-A8) are as defined for a compound of formula (I'), or a stereoisomer or tautomer thereof, or a pharmaceutically acceptable salt of any of the foregoing, or any variation or embodiment thereof.

In some embodiments of the foregoing, [Z] is 5-10 membered heteroaryl. In some embodiments, [Z] is 5-6 membered heteroaryl. In some embodiments, [Z] is 5-membered heteroaryl. In some embodiments, [Z] is 6-membered heteroaryl.

In some embodiments, provided herein is a compound of formula (I), (I-A), or (I-A7), or a stereoisomer or tautomer thereof, or a pharmaceutically acceptable salt of any of the foregoing, wherein the compound is

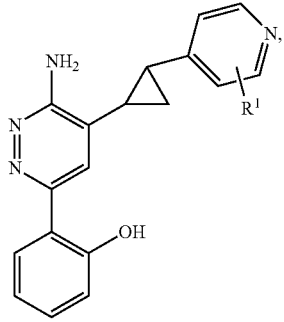

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof. In some variations, $R^1$ is as defined above or elsewhere herein for a compound of formula (I), (I-A), or (I-A7). In another variation, $R^1$ of formula (I), (I-A), or (I-A7), are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I), or a stereoisomer or tautomer thereof, or a pharmaceutically acceptable salt of any of the foregoing, wherein

Ⓐ is

such that the compound is of formula (I-B):

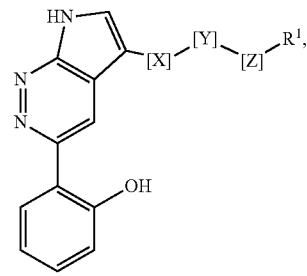

(I-B)

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Y], [Z], and $R^1$ are as defined above or elsewhere herein for a compound of formula (I). In another variation, [X], [Y], [Z], and $R^1$ of formula (I-B) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I-B), or a stereoisomer or tautomer thereof, or a pharmaceutically acceptable salt of any of the foregoing, wherein [X] is 3-15 membered heterocyclyl or 5-20 membered heteroaryl, wherein the 3-15 membered heterocyclyl of [X] is optionally substituted with one or more —OH or $C_{1-6}$alkyl; [Y] is absent; and [Z] is 3-15 membered heterocyclyl or 5-20 membered heteroaryl, provided that, when [X] is

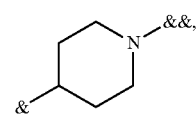

wherein & denotes the point of attachment to

Ⓐ and && denotes the point of attachment to [Z], and [Z] is

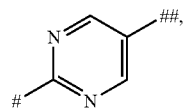

wherein # denotes the point of attachment to [X] and ## denotes the point of attachment to $R^1$, then when $R^1$ is —C≡C—$R^a$ and $R^a$ is $C_{1-6}$ alkyl substituted with $N(R^x)(R^y)$, $R^x$ and $R^y$ are not H or $C_{1-6}$ alkyl, and when $R^1$ is —$(CH_2)_n$—$R^g$ and $R^g$ is $N(R^x)(R^y)$, then $R^x$ and $R^y$ are not H or $C_{1-6}$ alkyl. In some variations, the embodiments provided herein also apply to a compound of formula (I'), or a stereoisomer or tautomer thereof, or a pharmaceutically acceptable salt of any of the foregoing, or any variation or embodiment thereof.

In some embodiments, provided herein is a compound of formula (I), or a stereoisomer or tautomer thereof, or a pharmaceutically acceptable salt of any of the foregoing, wherein

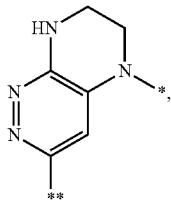

is

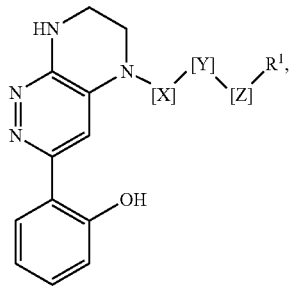

such that the compound is of formula (I-C):

(I-C)

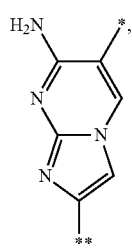

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Y], [Z], and $R^1$ are as defined above or elsewhere herein for a compound of formula (I). In another variation, [X], [Y], [Z], and $R^1$ of formula (I-C) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I), or a stereoisomer or tautomer thereof, or a pharmaceutically acceptable salt of any of the foregoing, wherein

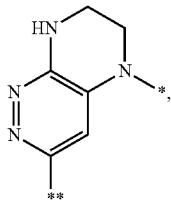

is

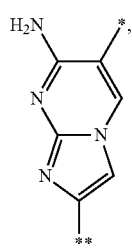

such that the compound of formula (I) is a compound of formula (I-D):

(I-D)

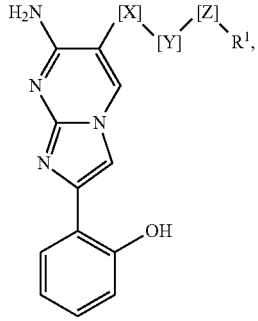

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Y], [Z], and $R^1$ are as defined above or elsewhere herein for a compound of formula (I). In another variation, [X], [Y], [Z], and $R^1$ of formula (I-D) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I), or a stereoisomer or tautomer thereof, or a pharmaceutically acceptable salt of any of the foregoing, wherein

is

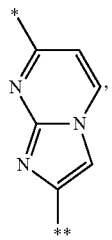

such that the compound of formula (I) is a compound of formula (I-E):

(I-E)

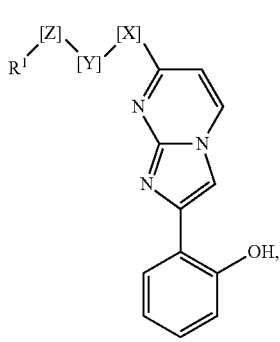

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Y], [Z], and $R^1$ are as defined above or elsewhere herein for a compound of formula (I). In another variation, [X], [Y], [Z], and $R^1$ of formula (I-E) are as defined for a compound of formula (I'), or a stereoisomer or tautomer thereof, or a pharmaceutically acceptable salt of any of the foregoing, or any variation or embodiment thereof.

In some embodiments of formula (I-E), [X] is 3-15 membered heterocyclyl; [Y] is absent; and [Z] is 5-20 membered heteroaryl. In some embodiments, provided herein is a compound of formula (I-E), or a stereoisomer or tautomer thereof, or a pharmaceutically acceptable salt of any of the foregoing, wherein the compound is of formula (I-E1):

(I-E1)

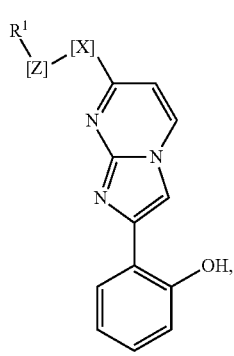

or a stereoisomer or tautomer thereof, or a pharmaceutically acceptable salt of any of the foregoing, wherein [X] is 3-15 membered heterocyclyl and [Z] is 5-20 membered heteroaryl. In some embodiments of the foregoing, [X] is 3-10 membered heterocyclyl. In some embodiments of the foregoing, [X] is 6-8 membered heterocyclyl. In some embodiments, [X] is 8-membered heterocyclyl. In some embodiments of the foregoing, [Z] is 5-10 membered heteroaryl. In some embodiments, [Z] is 5-6 membered heteroaryl. In some embodiments, [Z] is 6-membered heteroaryl. In some embodiments of the foregoing, provided herein is a compound of formula (I), (I-E), or (I-E1), or a stereoisomer or tautomer thereof, or a pharmaceutically acceptable salt of any of the foregoing, wherein the compound is

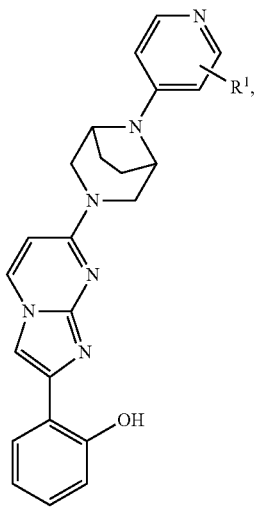

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Y], [Z], and $R^1$ are as defined above or elsewhere herein for a compound of formula (I). In another variation, [X], [Y], [Z], and $R^1$ of formula (I-E1) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I), (I-E), or (I-E1), or a stereoisomer or tautomer thereof, or a pharmaceutically acceptable salt of any of the foregoing, wherein the 3-15 membered heterocyclyl or 5-20 membered heteroaryl of [X] and [Z] each comprise at least one annular N atom. In some embodiments, [X] is a heterocyclyl that comprises at least one annular N atom, and [Z] is a heteroaryl comprising only one annular N atom. In some embodiments, [X] is

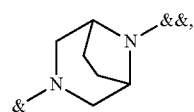

wherein & denotes the point of attachment to

and && denotes the point of attachment to [Z], and [Z] is a 5-20 membered heteroaryl containing only one annular N atom. In some embodiments, [X] is

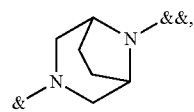

wherein & denotes the point of attachment to

and && denotes the point of attachment to [Z], and [Z] is a 5-6 membered heteroaryl containing only one annular N atom. In some variations, the embodiments provided herein also apply to a compound of formula (I'), or a stereoisomer or tautomer thereof, or a pharmaceutically acceptable salt of any of the foregoing, or any variation or embodiment thereof. In some variations, [X], [Z], and $R^1$ are as defined above or elsewhere herein for a compound of formula (I), (I-E), or (I-E1). In another variation, [X], [Z], and $R^1$ of formula (I), (I-E), or (I-E1), are as defined for a compound of formula (I'), or a stereoisomer or tautomer thereof, or a pharmaceutically acceptable salt of any of the foregoing, or any variation or embodiment thereof.

In embodiments, provided herein is a compound of formula (I'), (I), (I-A), (I-A1), (I-A2), (I-A3), (I-A4), (I-A5), (I-A6), (I-A7), (I-A8), (I-B), (I-C), (I-D), (I-E), (I-E1), or (I-I) or a stereoisomer or tautomer thereof, or a pharmaceutically acceptable salt of any of the foregoing, wherein $R^1$ is —C≡C—$R^a$, wherein
  (a) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, or —N($R^x$)($R^y$), wherein the 3-15 membered of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$ aryl), —C(O)-(3-15 membered heterocyclyl), —C(O)—$C_{1-6}$alkoxy, —C(O)—N($R^x$)($R^y$), or —N($R^x$)($R^y$), and wherein the $C_{1-6}$alkoxy of $R^b$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH, or
  (b) $R^a$ is $C_{3-10}$ cycloalkyl optionally substituted with one or more $R^z$, or
  (c) $R^a$ is 3-15 membered heterocyclyl optionally substituted with one or more $R^z$, or
  (d) $R^a$ is 5-20 membered heteroaryl optionally substituted with one or more $R^z$,
  wherein $R^z$ is, independently at each occurrence, $C_{1-6}$alkyl or —N($R^x$)($R^y$); and
  the $R^x$ and $R^y$ of —N($R^x$)($R^y$) are, independently of each other and independently at each occurrence, H, —C(O)—(CH$_2$)$_p$—N($R^p$)($R^q$), —C(O)—$R^s$, 5-20 membered heterocycle, 5-20 membered heteroaryl, or $C_{1-6}$alkyl, wherein p is an integer from 1-6, $R^p$ and $R^q$ are, independently of each other and independently at each occurrence H, or $C_{1-6}$alkyl, $R^s$ is 5-20 membered heterocycle optionally substituted with one or more substituents selected from the group consisting of $C_{1-4}$alkyl, $C_{3-8}$cycloalkyl, and —C(O)—$C_{1-6}$alkyl, the $C_{1-6}$alkyl of $R^x$ or $R^y$ is optionally substituted with one or more —OH, 3-15 membered heterocyclyl, or —C(O)-(3-15 membered heterocyclyl), and the 5-20 membered heterocycle of $R^x$ or $R^y$ is optionally substituted with one or more oxo.

In embodiments, provided herein is a compound of formula (I), (I-A), (I-A1), (I-A2), (I-A3), (I-A4), (I-A5), (I-A6), (I-A7), (I-A8), (I-B), (I-C), (I-D), (I-E), or (I-E1), or a stereoisomer or tautomer thereof, or a pharmaceutically acceptable salt of any of the foregoing, wherein $R^1$ is —C≡C—$R^a$, wherein
  (a) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, or —N($R^x$)($R^y$), wherein the 3-15 membered heterocyclyl of $R^b$ is optionally substituted with one or more $R^c$, wherein each $R^c$ is independently oxo or —N($R^x$)($R^y$), and wherein the $C_{1-6}$alkoxy of $R^b$ is optionally substituted with one or more —OH, or
  (b) $R^a$ is $C_{3-10}$cycloalkyl optionally substituted with one or more $R^z$, or
  (c) $R^a$ is 3-15 membered heterocyclyl optionally substituted with one or more $R^z$, or
  (d) $R^a$ is 5-20 membered heteroaryl optionally substituted with one or more $R^z$,
  wherein $R^z$ is, independently at each occurrence, $C_{1-6}$alkyl or —N($R^x$)($R^y$); and
  the $R^x$ and $R^y$ of —N($R^x$)($R^y$) are, independently of each other and independently at each occurrence, H or $C_{1-6}$alkyl, wherein the $C_{1-6}$alkyl of $R^x$ or $R^y$ is optionally substituted with one or more —OH. In some variations, the embodiments provided herein also apply to a compound of formula (I'), or a stereoisomer or tautomer thereof, or a pharmaceutically acceptable salt of any of the foregoing, or any variation or embodiment thereof. In embodiments, $R^1$ is —(CH$_2$)$_n$—$R^g$, wherein,
n is an integer from 1-6, and
$R^g$ is —N($R^x$)($R^y$) or —OH, wherein the $R^x$ and $R^y$ of —N($R^x$)($R^y$) are, independently of each other and independently at each occurrence —C(O)—$R^s$, 5-20 membered heterocycle, 5-20 membered heteroaryl, wherein $R^s$ is 5-20 membered heterocycle optionally substituted with one or more substituents selected from the group consisting of $C_{1-4}$alkyl, $C_{3-8}$ cycloalkyl, and —C(O)—$C_{1-6}$alkyl.

In embodiments, $R^1$ is —(CH$_2$)$_n$—$R^g$, wherein
n is an integer from 1-6, and
$R^g$ is —N($R^x$)($R^y$), wherein the $R^x$ and $R^y$ of —N($R^x$)($R^y$) are, independently of each other and independently at each occurrence, H, —C(O)—CH$_2$—NH$_2$, or $C_{1-6}$alkyl.

In embodiments, provided herein is a compound of formula (I'), (I), (I-A), (I-A1), (I-A2), (I-A3), (I-A4), (I-A5), (I-A6), (I-A7), (I-A8), (I-B), (I-C), (I-D), (I-E), or (I-E1), or a stereoisomer or tautomer thereof, or a pharmaceutically acceptable salt of any of the foregoing, wherein $R^1$ is —C≡C—$R^a$. In embodiments, provided herein is a compound of formula (I), (I-A), (I-A1), (I-A2), (I-A3), (I-A4), (I-A5), (I-A6), (I-A7), (I-A8), (I-B), (I-C), (I-D), (I-E), or (I-E1), or a stereoisomer or tautomer thereof, or a pharmaceutically acceptable salt of any of the foregoing, wherein $R^1$ is —C≡C—$R^a$.

In embodiments, provided herein is a compound of formula (I'), (I), (I-A), (I-A1), (I-A2), (I-A3), (I-A4), (I-A5), (I-A6), (I-A7), (I-A8), (I-B), (I-C), (I-D), (I-E), or (I-E1), or a stereoisomer or tautomer thereof, or a pharmaceutically acceptable salt of any of the foregoing, wherein R¹ is —(CH₂)ₙ—Rᵍ. In embodiments, provided herein is a compound of formula (I), (I-A), (I-A1), (I-A2), (I-A3), (I-A4), (I-A5), (I-A6), (I-A7), (I-A8), (I-B), (I-C), (I-D), (I-E), or (I-E1), or a stereoisomer or tautomer thereof, or a pharmaceutically acceptable salt of any of the foregoing, wherein R¹ is —(CH₂)ₙ—Rᵍ.

In embodiments, R¹ is —C═C—Rᵈ, wherein Rᵈ is $C_{1-6}$alkyl, wherein the $C_{1-6}$ alkyl of Rᵈ is optionally substituted with one or more Rᵉ, wherein each Rᵉ is independently 3-15 membered heterocyclyl, wherein the 3-15 membered heterocyclyl of Rᵉ is optionally substituted with one or more Rᶠ, wherein each Rᶠ is independently —OH, —CN, halo, oxo, $C_{1-6}$alkyl, $C_{1-6}$alkoxy, or —C(O)—$C_{1-6}$alkoxy.

In embodiments, provided herein is a compound of formula (I), or a stereoisomer or tautomer thereof, or a pharmaceutically acceptable salt of any of the foregoing, wherein R¹ is —C≡C—Rᵃ, such that the compound is of formula (I-F):

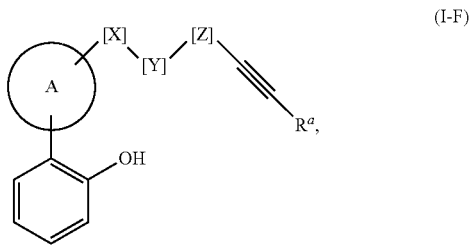

(I-F)

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Y], [Z], and R¹ are as defined above or elsewhere herein for a compound of formula (I). In another variation, [X], [Y], [Z], and R¹ of formula (I-F) are as defined for a compound of formula (I'), or a stereoisomer or tautomer thereof, or a pharmaceutically acceptable salt of any of the foregoing, or any variation or embodiment thereof.

In embodiments, provided herein is a compound of formula (I-F), or a stereoisomer or tautomer thereof, or a pharmaceutically acceptable salt of any of the foregoing, wherein Rᵃ is $C_{1-6}$alkyl, wherein the $C_{1-6}$alkyl of Rᵃ is optionally substituted with one or more Rᵇ. In embodiments of the foregoing, Rᵃ is $C_{1-4}$alkyl, wherein the $C_{1-4}$ alkyl of Rᵃ is optionally substituted with one or more Rᵇ. In embodiments, Rᵃ is $C_{1-3}$ alkyl, wherein the $C_{1-3}$alkyl of Rᵃ is optionally substituted with one or more Rᵇ. In embodiments, Rᵃ is ethyl, wherein the ethyl of Rᵃ is optionally substituted with one or more Rᵇ. In embodiments, Rᵃ is ethyl, wherein the ethyl of Rᵃ is optionally substituted with one Rᵇ. In embodiments, Rᵃ is methyl, wherein the methyl of Rᵃ is optionally substituted with one or more Rᵇ. In embodiments, Rᵃ is methyl, wherein the methyl of Rᵃ is optionally substituted with one Rᵇ. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, —Rᵃ—Rᵇ is —$C_{1-2}$alkyl-(4-6 membered heterocyclyl). In embodiments, —Rᵃ—Rᵇ is —$C_{1-2}$alkyl-[N(Rˣ)(Rʸ)], wherein Rˣ is H or $C_{1-2}$alkyl, and Rʸ is —$C_{1-2}$alkyl-OH. In embodiments, —Rᵃ—Rᵇ is —$C_{1-2}$alkyl-$C_{1-2}$alkoxy-OH.

In embodiments, —Rᵃ—Rᵇ is —$C_{1-2}$alkyl-(7 membered heterocyclyl). In embodiments, Rᵇ is

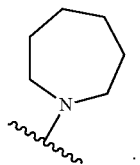 [SMILES: *N1CCCCCC1]

In embodiments, R¹ is

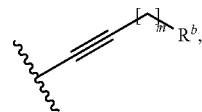

wherein m is an integer from 0-6 and Rᵇ is 3-15 membered heterocyclyl, —O-(3-15 membered heterocyclyl), $C_{1-6}$alkoxy, —OH, —CN, halo, or —N(Rˣ)(Rʸ), wherein
the 3-15 membered heterocyclyl of Rᵇ is optionally substituted with one or more Rᶜ, wherein each Rᶜ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N(Rˣ)(Rʸ), or —N(Rˣ)(Rʸ), wherein
the $C_{1-6}$alkyl of Rᶜ is optionally substituted with one or more —OH, —CN, halo, $C_{1-6}$alkoxy, or 3-15 membered heterocyclyl,
the $C_{3-10}$ cycloalkyl of Rᶜ is optionally substituted with one or more halo, and
the 3-15 membered heterocyclyl of Rᶜ is optionally substituted with one or more $C_{1-6}$ alkyl or —C(O)—$C_{1-6}$alkyl, and
the $C_{1-6}$alkoxy of Rᵇ is optionally substituted with one or more OH, wherein
the Rˣ and Rʸ of —C(O)N(Rˣ)(Rʸ) and —N(Rˣ)(Rʸ) are, independently of each other and independently at each occurrence, H, —C(O)—CH₂—NH₂, 5-20 membered heteroaryl, or $C_{1-6}$ alkyl, wherein the $C_{1-6}$alkyl of Rˣ or Rʸ is optionally substituted with one or more —OH, 3-15 membered heterocyclyl, or —C(O)-(3-15 membered heterocyclyl).

In embodiments, R¹ is

wherein m is an integer from 0-6 and Rᵇ is 3-15 membered heterocyclyl, —O-(3-15 membered heterocyclyl), $C_{1-6}$alkoxy, —OH, —CN, halo, or —N(Rˣ)(Rʸ), wherein the 3-15 membered heterocyclyl of Rᵇ is optionally substituted with one or more Rᶜ, wherein each Rᶜ is independently —OH, —CN, halo, oxo, $C_{1-6}$alkyl, $C_{1-6}$alkoxy, —S(O)₂—($C_{1-6}$alkyl), $C_{3-10}$ cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$ cycloalkyl of $R^c$ is optionally substituted with one or more halo,
the $C_{6-10}$aryl of $R^c$ is optionally substituted with one or more —CN,
the 3-15 membered heterocyclyl of $R^c$ is optionally substituted with one or more $C_{1-6}$ alkyl or —C(O)—$C_{1-6}$alkyl, and
the $C_{1-6}$alkoxy of $R^b$ is optionally substituted with one or more —OH, wherein
the $R^x$ and $R^y$ of —C(O)N($R^x$)($R^y$) and —N($R^x$)($R^y$) are, independently of each other and independently at each occurrence, H, —C(O)—$CH_2$—$NH_2$, 5-20 membered heteroaryl, or $C_{1-6}$ alkyl, wherein the $C_{1-6}$alkyl of $R^x$ or $R^y$ is optionally substituted with one or more —OH, 3-15 membered heterocyclyl, or —C(O)-(3-15 membered heterocyclyl).

In embodiments, m is 0 and $R^b$ is 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more OH, wherein the $R^x$ and $R^y$ of —C(O)N($R^x$)($R^y$) and —N($R^x$)($R^y$) are, independently of each other and independently at each occurrence, H, —C(O)—$CH_2$—$NH_2$, 5-20 membered heteroaryl, or $C_{1-6}$alkyl, wherein the $C_{1-6}$alkyl of $R^x$ or $R^y$ is optionally substituted with one or more —OH, 3-15 membered heterocyclyl, or —C(O)-(3-15 membered heterocyclyl).

In embodiments, m is 0 and $R^b$ is 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH, wherein the $R^x$ and $R^y$ of —C(O)N($R^x$)($R^y$) and —N($R^x$)($R^y$) are, independently of each other and independently at each occurrence, H, —C(O)—$CH_2$—$NH_2$, 5-20 membered heteroaryl, or $C_{1-6}$alkyl, wherein the $C_{1-6}$alkyl of $R^x$ or $R^y$ is optionally substituted with one or more —OH, 3-15 membered heterocyclyl, or —C(O)-(3-15 membered heterocyclyl).

In embodiments, m is an integer from 1-6 and $R^b$ is 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more OH, wherein the $R^x$ and $R^y$ of —C(O)N($R^x$)($R^y$) and —N($R^x$)($R^y$) are, independently of each other and independently at each occurrence, H, —C(O)—$CH_2$—$NH_2$, 5-20 membered heteroaryl, or $C_{1-6}$alkyl, wherein the $C_{1-6}$alkyl of $R^x$ or $R^y$ is optionally substituted with one or more —OH, 3-15 membered heterocyclyl, or —C(O)-(3-15 membered heterocyclyl). In embodiments, m is an integer from 1-6 and $R^b$ is 3-15 membered heterocyclyl, wherein the 3-15 membered heterocyclyl of $R^b$ is optionally substituted with one or more $R^c$.

In embodiments, m is an integer from 1-6 and $R^b$ is 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH, wherein the $R^x$ and $R^y$ of —C(O)N($R^x$)($R^y$) and —N($R^x$)($R^y$) are, independently of each other and independently at each occurrence, H, —C(O)—$CH_2$—$NH_2$, 5-20 membered heteroaryl, or $C_{1-6}$alkyl, wherein the $C_{1-6}$alkyl of $R^x$ or $R^y$ is optionally substituted with one or more —OH, 3-15 membered heterocyclyl, or —C(O)-(3-15 membered heterocyclyl). In embodiments, m is an integer from 1-6 and $R^b$ is 3-15 membered heterocyclyl, wherein the 3-15 membered heterocyclyl of $R^b$ is optionally substituted with one or more $R^c$.

In embodiments, m is 1 and $R^b$ is 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more OH, wherein the $R^x$ and $R^y$ of —C(O)N($R^x$)($R^y$) and —N($R^x$)($R^y$) are, independently of each other and independently at each occurrence, H, —C(O)—CH$_2$—NH$_2$, 5-20 membered heteroaryl, or $C_{1-6}$alkyl, wherein the $C_{1-6}$alkyl of $R^x$ or $R^y$ is optionally substituted with one or more —OH, 3-15 membered heterocyclyl, or —C(O)-(3-15 membered heterocyclyl). In embodiments, m is 1 and $R^b$ is 3-15 membered heterocyclyl, wherein the 3-15 membered heterocyclyl of $R^b$ is optionally substituted with one or more $R^c$.

In embodiments, m is 1 and $R^b$ is 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$ aryl), —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH, wherein the $R^x$ and $R^y$ of —C(O)N($R^x$)($R^y$) and —N($R^x$)($R^y$) are, independently of each other and independently at each occurrence, H, —C(O)—CH$_2$—NH$_2$, 5-20 membered heteroaryl, or $C_{1-6}$alkyl, wherein the $C_{1-6}$alkyl of $R^x$ or $R^y$ is optionally substituted with one or more —OH, 3-15 membered heterocyclyl, or —C(O)-(3-15 membered heterocyclyl), or the $R^x$ and $R^y$ of —C(O)N($R^x$)($R^y$) and —N($R^x$)($R^y$), together with the N atom to which they are attached, form a 4- to 12-membered heterocycle, wherein the 4- to 12-membered heterocycle is optionally substituted with at least one substituent selected from the group consisting of halo, —OH, oxo, $C_{1-4}$alkyl optionally substituted with one or more —OH, $C_{3-7}$cycloalkyl, $C_{1-4}$alkoxy, $C_{1-4}$haloalkyl, and —C(O)—N($R^h$)($R^i$), wherein $R^h$ and $R^i$ are each independently selected from the group consisting of H and $C_1$-$C_4$alkyl, wherein the $C_1$-$C_4$alkyl of $R^h$ or $R^i$ is independently optionally substituted with one or more —OH. In embodiments, m is 1 and $R^b$ is 3-15 membered heterocyclyl, wherein the 3-15 membered heterocyclyl of $R^b$ is optionally substituted with one or more $R^c$.

In embodiments, m is 2 and $R^b$ is 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more OH, wherein the $R^x$ and $R^y$ of —C(O)N($R^x$)($R^y$) and —N($R^x$)($R^y$) are, independently of each other and independently at each occurrence, H, —C(O)—CH$_2$—NH$_2$, 5-20 membered heteroaryl, or $C_{1-6}$alkyl, wherein the $C_{1-6}$alkyl of $R^x$ or $R^y$ is optionally substituted with one or more —OH, 3-15 membered heterocyclyl, or —C(O)-(3-15 membered heterocyclyl). In embodiments, m is 2 and $R^b$ is 3-15 membered heterocyclyl, wherein the 3-15 membered heterocyclyl of $R^b$ is optionally substituted with one or more $R^c$.

In embodiments, m is 2 and $R^b$ is 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$ aryl), —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH, wherein the $R^x$ and $R^y$ of —C(O)N($R^x$)($R^y$) and —N($R^x$)($R^y$) are, independently of each other and independently at each occurrence, H, —C(O)—CH$_2$—NH$_2$, 5-20 membered heteroaryl, or $C_{1-6}$alkyl, wherein the $C_{1-6}$alkyl of $R^x$ or $R^y$ is optionally substituted with one or more —OH, 3-15 membered heterocyclyl, or —C(O)-(3-15 membered heterocyclyl). In embodiments, m is 2 and $R^b$ is 3-15 membered heterocyclyl, wherein the 3-15 membered heterocyclyl of $R^b$ is optionally substituted with one or more $R^c$.

In embodiments, provided herein is a compound of formula (I-F), or a stereoisomer or tautomer thereof, or a pharmaceutically acceptable salt of any of the foregoing, wherein $R^a$ is methyl, wherein the methyl of $R^a$ is substituted with one $R^b$, such that the compound of formula (I-F) is a compound of formula (I-F1):

(I-F1)

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Y], [Z], and $R^b$ are as defined above or elsewhere herein for a compound of formula (I). In another variation, [X], [Y], [Z], and $R^b$ of formula (I-F1) are as defined for a compound of formula (I'), or a stereoisomer or tautomer thereof, or a pharmaceutically acceptable salt of any of the foregoing, or any variation or embodiment thereof.

In some embodiments, provided herein is a compound of formula (I), (I-A), or (I-A2), or a stereoisomer or tautomer thereof, or a pharmaceutically acceptable salt of any of the foregoing, wherein $R^a$ is methyl, wherein the methyl of $R^a$ is substituted with one $R^b$, such that the compound is of formula (I-A9):

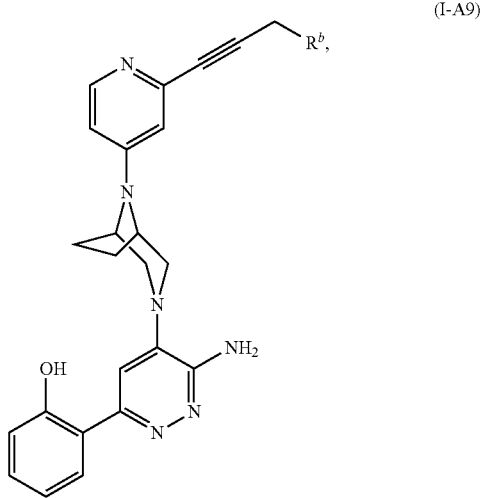

(I-A9)

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing. In some variations, $R^b$ is as defined above or elsewhere herein for a compound of formula (I), (I-A), (I-A2) or (I-A9). In another variation, $R^b$ of formula (I), (I-A), (I-A2) or (I-A9), are as defined for a compound of formula (I'), or a stereoisomer or tautomer thereof, or a pharmaceutically acceptable salt of any of the foregoing, or any variation or embodiment thereof.

In embodiments, provided herein is a compound of formula (I), such as a compound of formula (I), (I-F), (I-F1), or (I-A9), or a stereoisomer or tautomer thereof, or a pharmaceutically acceptable salt of any of the foregoing, wherein $R^b$ is 3-15 membered heterocyclyl, wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl. In embodiments, provided herein is a compound of formula (I), such as a compound of formula (I), (I-F), (I-F1), or (I-A9), or a stereoisomer or tautomer thereof, or a pharmaceutically acceptable salt of any of the foregoing, wherein $R^b$ is 3-15 membered heterocyclyl, wherein the 3-15 membered heterocyclyl of $R^b$ is optionally substituted with one or more $R^c$, wherein each $R^c$ is independently —OH, —CN, halo, oxo, $C_{1-6}$alkyl, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is 4-10 membered heterocyclyl, wherein the 4-10 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is 4-10 membered heterocyclyl, wherein the 4-10 membered heterocyclyl of $R^b$ is optionally substituted with one or more $R^c$, wherein each $R^c$ is independently —OH, —CN, halo, oxo, $C_{1-6}$alkyl, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH. In some variations, the embodiments provided herein also apply to a compound of formula (I'), or a stereoisomer or tautomer thereof, or a pharmaceutically acceptable salt of any of the foregoing. In some variations, $R^b$ and $R^c$ are as defined above or elsewhere herein for a compound of formula (I), (I-F), (I-F1), or (I-A9). In another variation, $R^b$ and $R^c$ of formula (I), (I-F), (I-F1), or (I-A9), are as defined for a compound of formula (I'), or a stereoisomer or tautomer thereof, or a pharmaceutically acceptable salt of any of the foregoing, or any variation or embodiment thereof.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is 5-6 membered heterocyclyl, wherein the 5-6 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is 5-6 membered heterocyclyl, wherein the 5-6 membered heterocyclyl of $R^b$ is optionally substituted with one or more $R^c$, wherein each $R^c$ is independently —OH, —CN, halo, oxo, $C_{1-6}$alkyl, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I'), (I-F), (I-F1), or (I-A9), or a stereoisomer or tautomer thereof, or a pharmaceutically acceptable salt of any of the foregoing, wherein $R^b$ is 5-6 membered heterocyclyl, wherein the 5-6 membered heterocyclyl of $R^b$ is optionally substituted with one or more $R^c$, wherein each $R^c$ is independently oxo or —N($R^x$)($R^y$). In embodiments, each $R^c$ is independently oxo or —NH$_2$. In embodiments, each $R^c$ is oxo. In embodiments, each $R^c$ is —NH$_2$. In embodiments, provided herein is a compound of formula (I), (I-F), (I-F1), or (I-A9), or a stereoisomer or tautomer thereof, or a pharmaceutically acceptable salt of any of the foregoing, wherein $R^b$ is 5-6 membered heterocyclyl, wherein the 5-6 membered heterocyclyl of $R^b$ is optionally substituted with one or more $R^c$, wherein each $R^c$ is independently oxo or —N($R^x$)($R^y$). In embodiments, each $R^c$ is independently oxo or —NH$_2$. In embodiments, each $R^c$ is oxo. In embodiments, each $R^c$ is —NH$_2$.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is a saturated 5-6 membered heterocyclyl, wherein the saturated 5-6 membered heterocyclyl of $R^b$ comprises at least one annular N atom, and is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is a saturated 5-6 membered heterocyclyl, wherein the saturated 5-6 membered heterocyclyl of $R^b$ comprises at least one annular N atom, and is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$cycloalkyl, $C_{6-10}$aryl, 3-15 membered heterocyclyl, 5-20 membered heteroaryl, —O—($C_{6-10}$aryl), C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I'), (I-F), (I-F1), or (I-A9), or a stereoisomer or tautomer thereof, or a pharmaceutically acceptable salt of any of the foregoing, wherein $R^b$ is a saturated 5-6 membered heterocyclyl, wherein the saturated 5-6 membered heterocyclyl of $R^b$ comprises at least one annular N atom and is optionally substituted with one or more $R^c$, wherein each $R^c$ is independently oxo or —N($R^x$)($R^y$). In embodiments, each $R^c$ is independently oxo or —NH$_2$. In embodiments, each $R^c$ is oxo. In embodiments, each $R^c$ is —NH$_2$. In embodiments, provided herein is a compound of formula (I), (I-F), (I-F1), or (I-A9), or a stereoisomer or tautomer thereof, or a pharmaceutically acceptable salt of any of the foregoing, wherein $R^b$ is a saturated 5-6 membered heterocyclyl, wherein the saturated 5-6 membered heterocyclyl of $R^b$ comprises at least one annular N atom and is optionally substituted with one or more $R^c$, wherein each $R^c$ is independently oxo or —N($R^x$)($R^y$). In embodiments, each $R^c$ is independently oxo or —NH$_2$. In embodiments, each $R^c$ is oxo. In embodiments, each $R^c$ is —NH$_2$.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is pyrrolidinyl, piperidinyl, piperazinyl, morpholinyl, or thiomorpholinyl, wherein the pyrrolidinyl, piperidinyl, piperazinyl, morpholinyl, or thiomorpholinyl of $R^b$ is independently optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is pyrrolidinyl, piperidinyl, piperazinyl, morpholinyl, or thiomorpholinyl, wherein the pyrrolidinyl, piperidinyl, piperazinyl, morpholinyl, or thiomorpholinyl of $R^b$ is independently optionally substituted with one or more $R^c$, wherein each $R^c$ is independently —OH, —CN, halo, oxo, $C_{1-6}$alkyl, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$ aryl), —C(O)-(3-15 membered heterocyclyl), —C(O)—$C_{1-6}$alkoxy, —C(O)—N(R$^x$)(R$^y$), or —N(R$^x$)(R$^y$), wherein the $C_{1-6}$alkyl of R$^c$ is optionally substituted with one or more —OH, —CN, halo, or $C_{1-6}$alkoxy, the $C_{3-10}$ cycloalkyl of R$^c$ is optionally substituted with one or more halo, the $C_{6-10}$aryl of R$^c$ is optionally substituted with one or more —CN, the 3-15 membered heterocyclyl of R$^c$ is optionally substituted with one or more $C_{1-6}$alkyl or —C(O)—$C_{1-6}$alkyl, and the $C_{1-6}$alkoxy of R$^b$ is optionally substituted with one or more —OH. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I), (I-F), (I-F1), or (I-A9), or a stereoisomer or tautomer thereof, or a pharmaceutically acceptable salt of any of the foregoing, wherein R$^b$ is pyrrolidinyl, piperidinyl, piperazinyl, morpholinyl, or thiomorpholinyl, wherein the pyrrolidinyl, piperidinyl, piperazinyl, morpholinyl, or thiomorpholinyl of R$^b$ is independently optionally substituted with one or more R$^c$, wherein each R$^c$ is independently oxo or —N(R$^x$)(R$^y$). In embodiments, each R$^c$ is independently oxo or —NH$_2$. In embodiments, each R$^c$ is oxo. In embodiments, each R$^c$ is —NH$_2$. In some variations, the embodiments provided herein also apply to a compound of formula (I'), or a stereoisomer or tautomer thereof, or a pharmaceutically acceptable salt of any of the foregoing, or any variation or embodiment thereof.

In embodiments of the foregoing, R$^b$ is selected from the group consisting of

In embodiments of the foregoing, R$^b$ is selected from the group consisting of

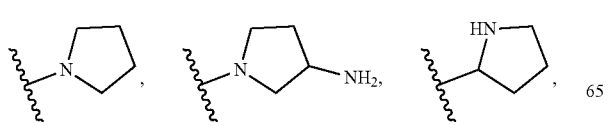

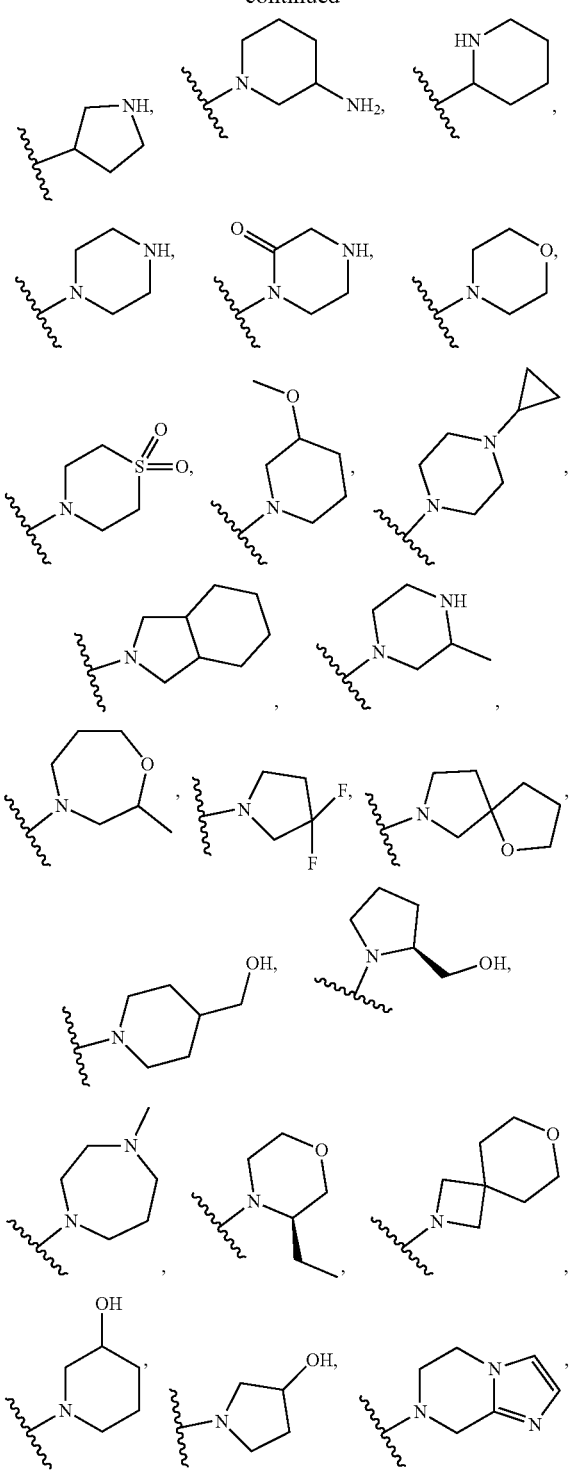

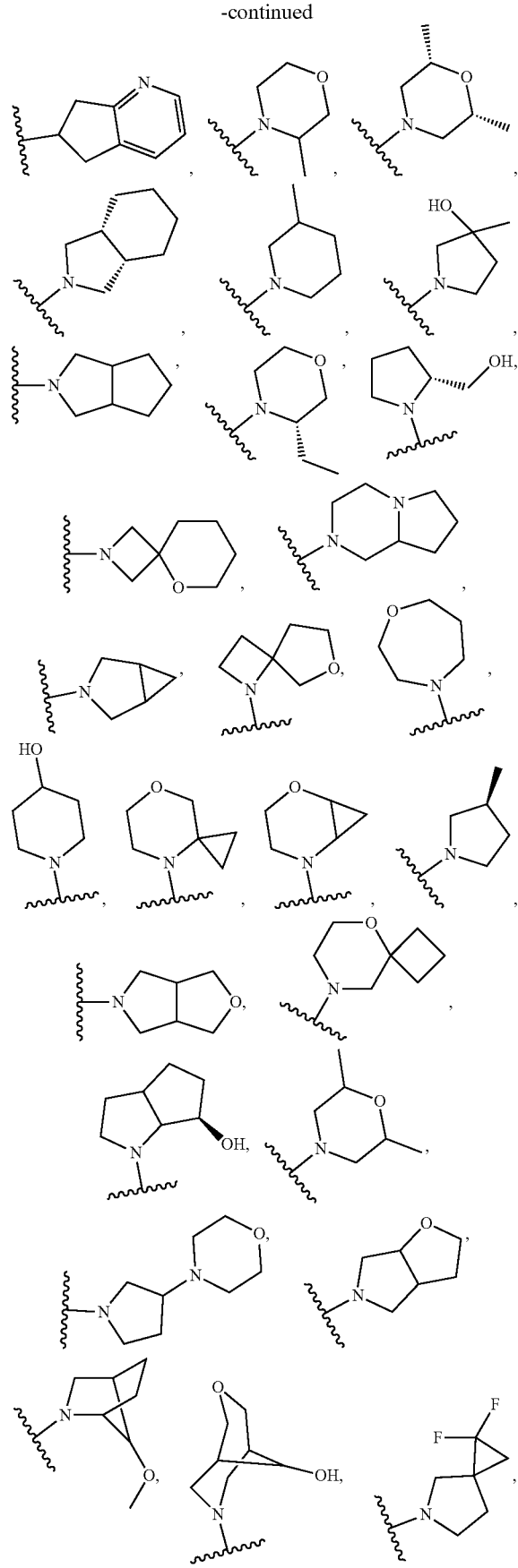
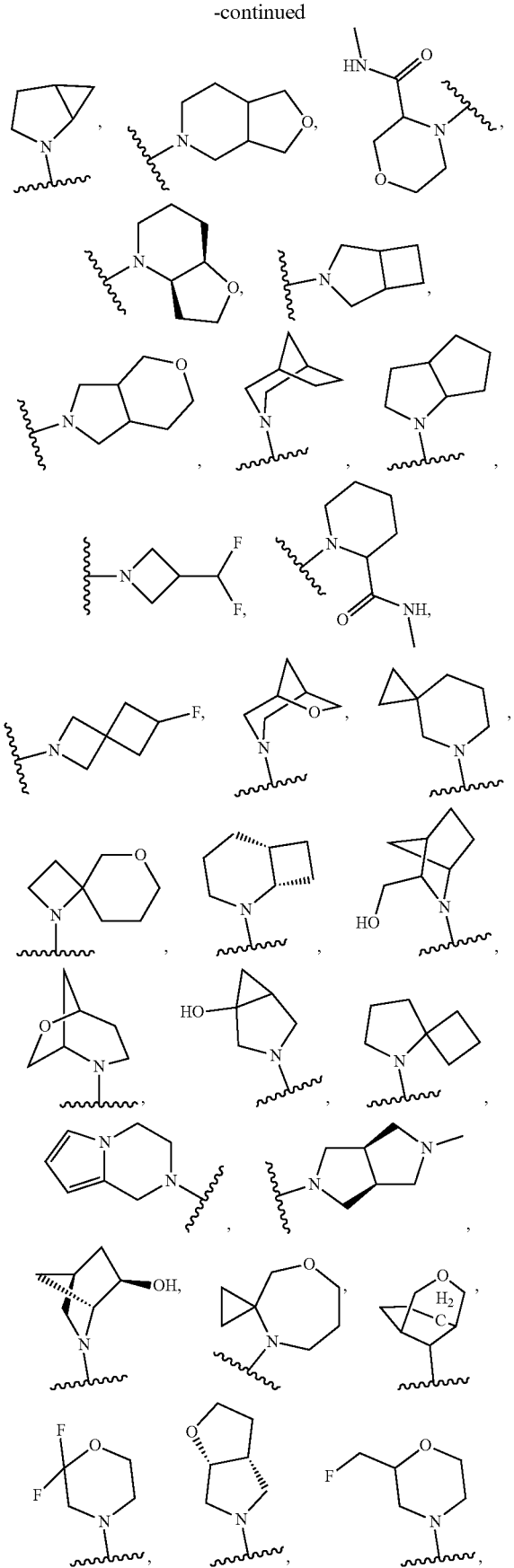

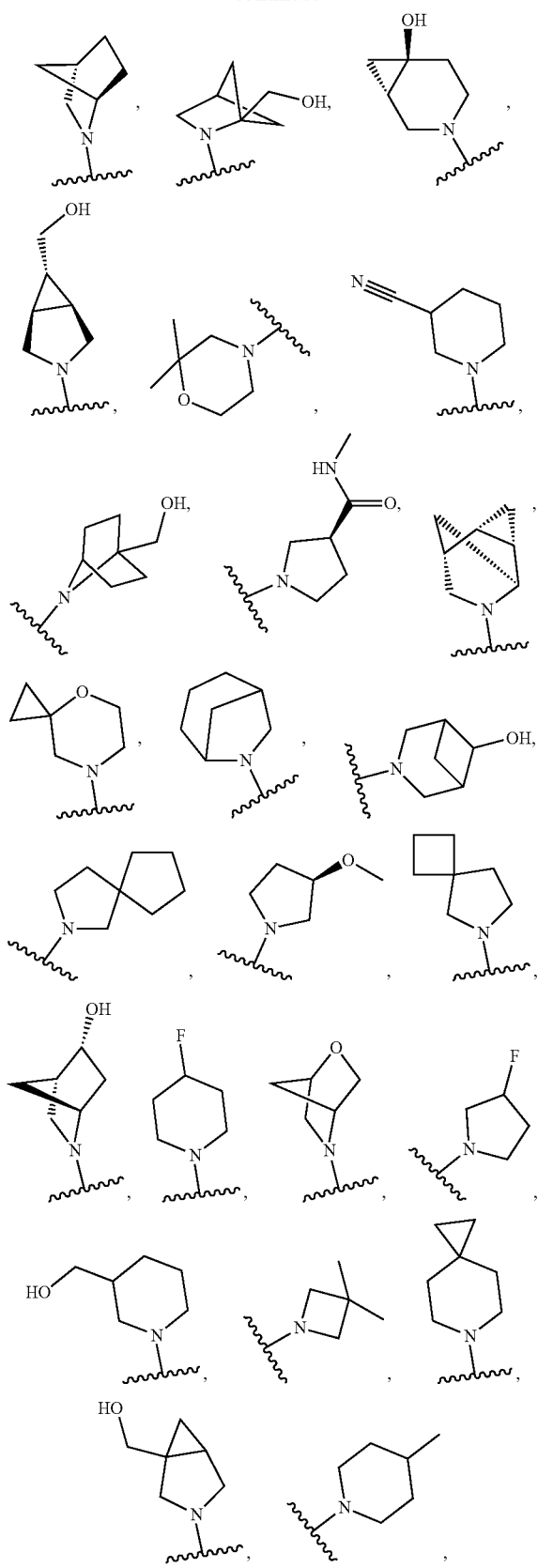
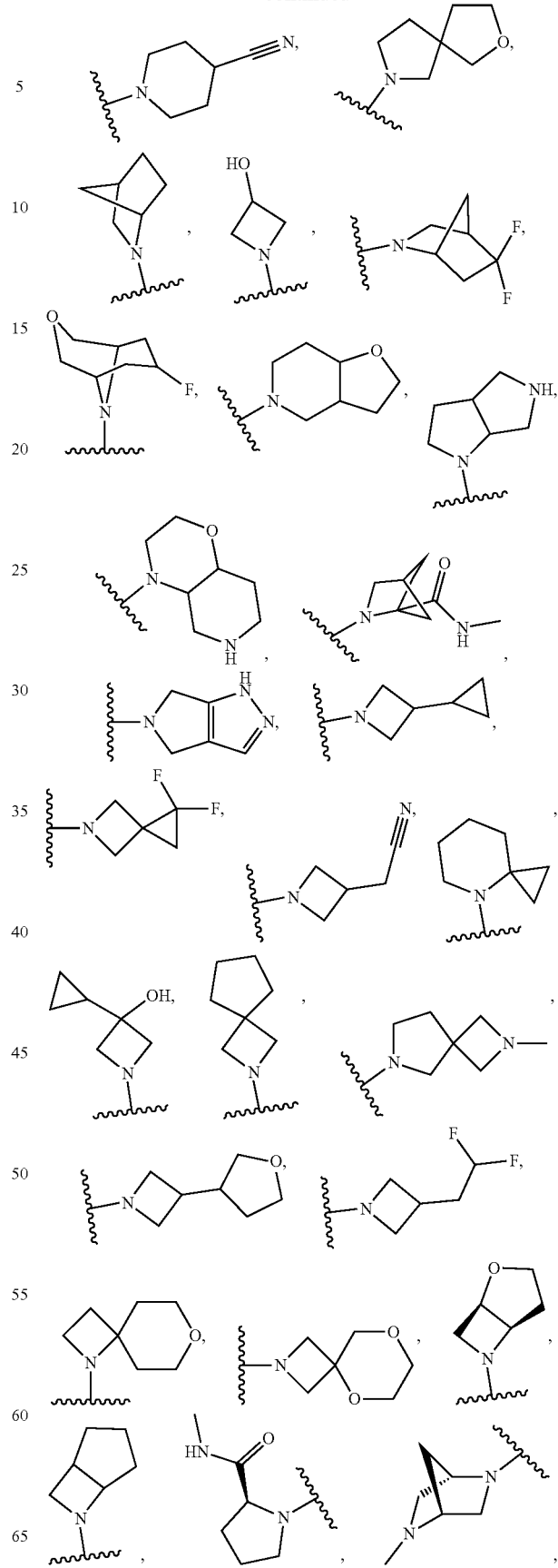

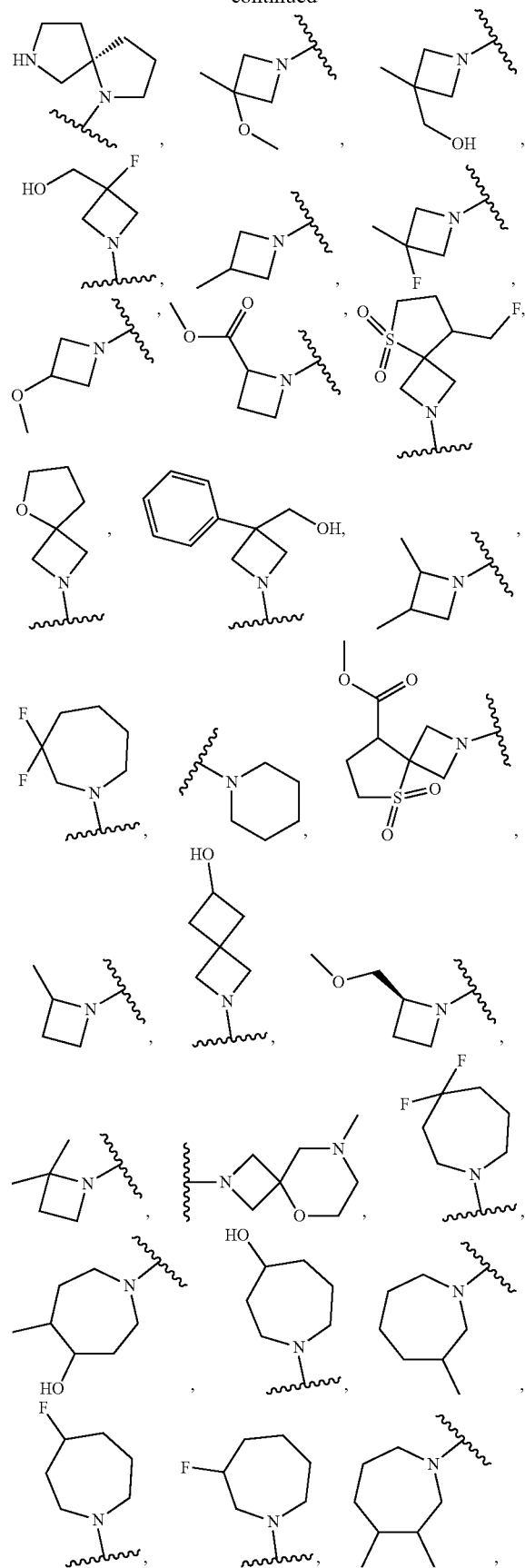
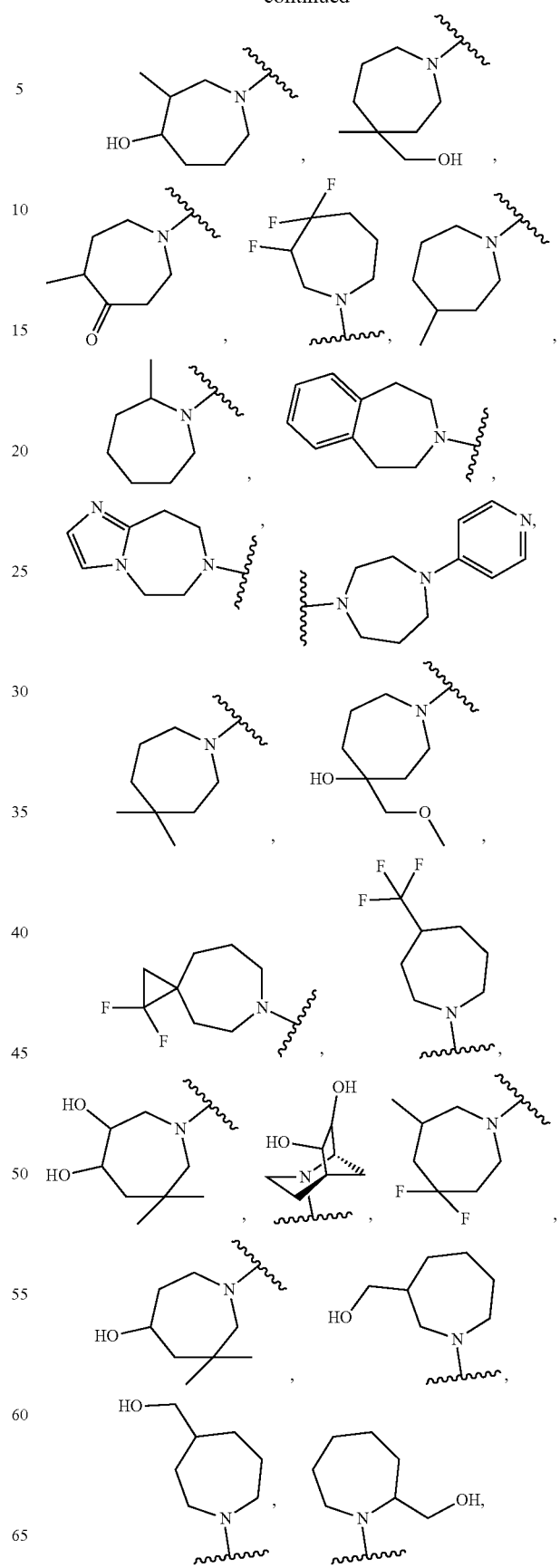

135

-continued

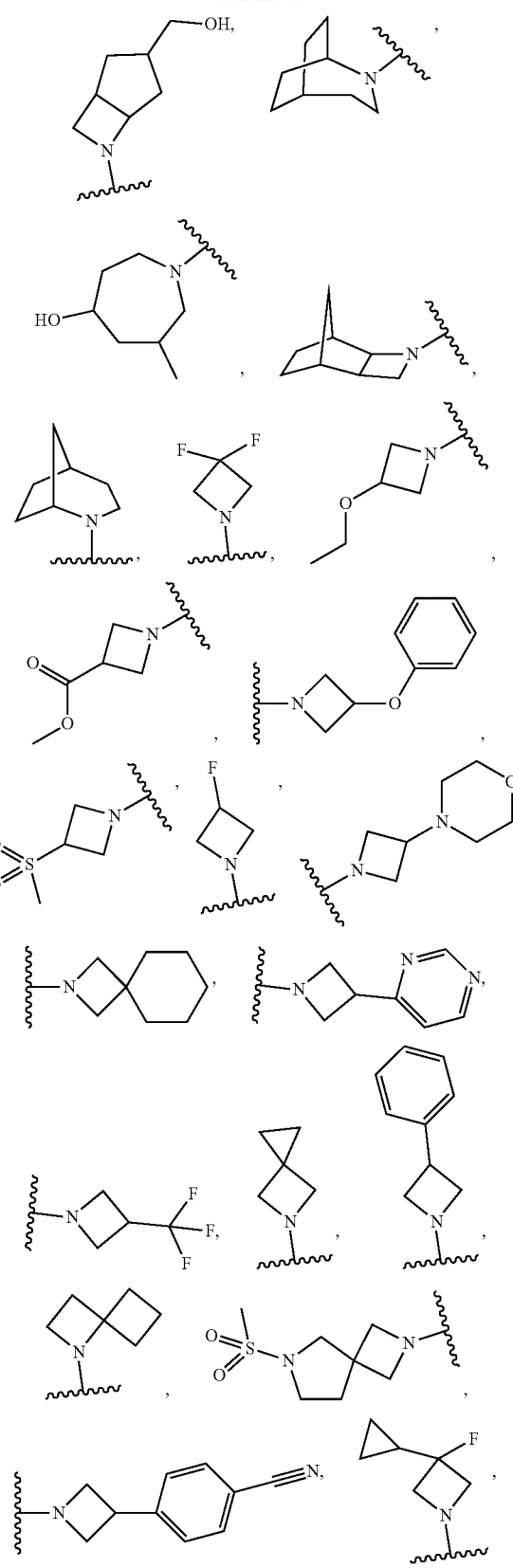

136

-continued

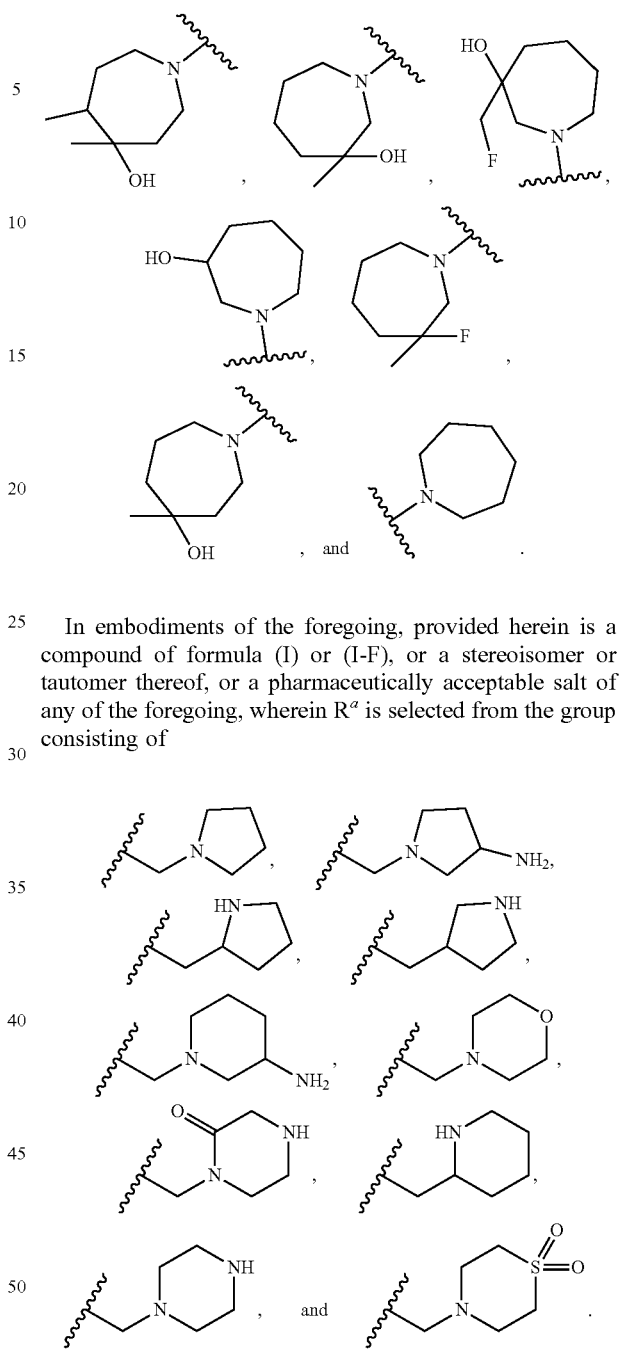

In embodiments of the foregoing, provided herein is a compound of formula (I) or (I-F), or a stereoisomer or tautomer thereof, or a pharmaceutically acceptable salt of any of the foregoing, wherein $R^a$ is selected from the group consisting of In some variations, the embodiments provided herein also apply to a compound of formula (I'), or a stereoisomer or tautomer thereof, or a pharmaceutically acceptable salt of any of the foregoing, or any variation or embodiment thereof.

In embodiments of the foregoing, provided herein is a compound of formula (I) or (I-F), or a stereoisomer or tautomer thereof, or a pharmaceutically acceptable salt of any of the foregoing, wherein $R^a$ is selected from the group consisting of

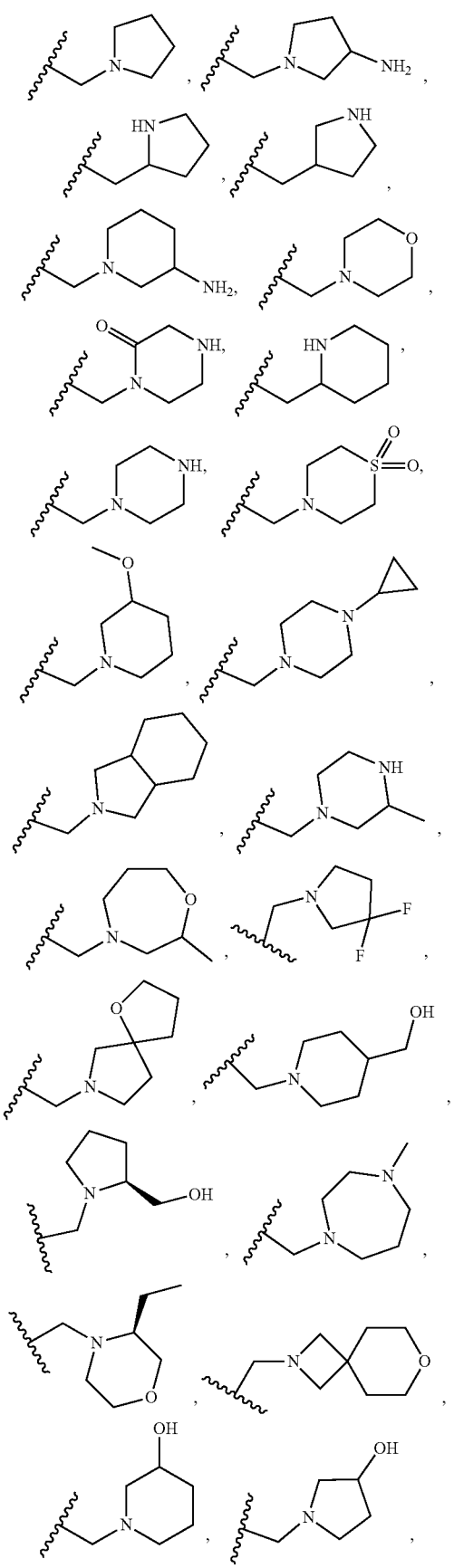

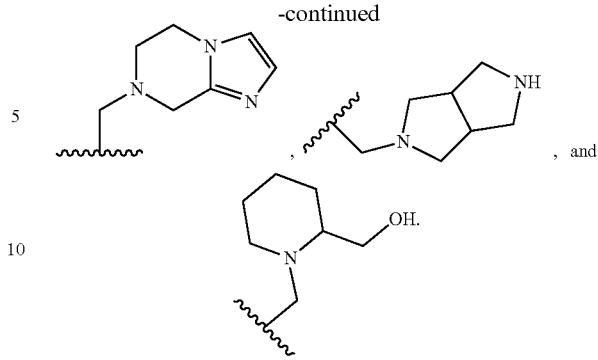

, and

In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I), (I-A), or (I-A1), or a stereoisomer or tautomer thereof, or a pharmaceutically acceptable salt of any of the foregoing, wherein $R^b$ is —N($R^x$)($R^y$). In embodiments, $R^b$ is —N($R^x$)($R^y$), wherein $R^x$ and $R^y$ are each independently H or $C_{1-6}$alkyl, wherein the $C_{1-6}$alkyl is optionally substituted with one or more —OH. In embodiments, $R^b$ is selected from the group consisting of

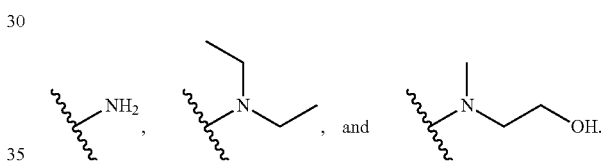

In embodiments of the foregoing, provided herein is a compound of formula (I) or (I-F), or a stereoisomer or tautomer thereof, or a pharmaceutically acceptable salt of any of the foregoing, wherein $R^a$ is selected from the group consisting of

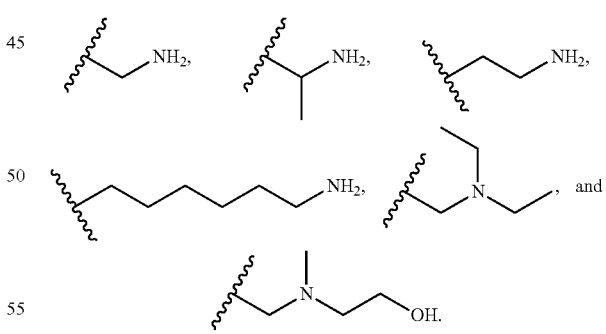

In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I), (I-A), or (I-A1), or a stereoisomer or tautomer thereof, or a pharmaceutically acceptable salt of any of the foregoing, wherein $R^b$ is —N($R^x$)($R^y$). In embodiments, $R^b$ is —N($R^x$)($R^y$), wherein $R^x$ and $R^y$ are each independently H or $C_{1-6}$alkyl, wherein the $C_{1-6}$alkyl is optionally substituted with one or more —OH. In embodiments, $R^b$ is selected from the group consisting of

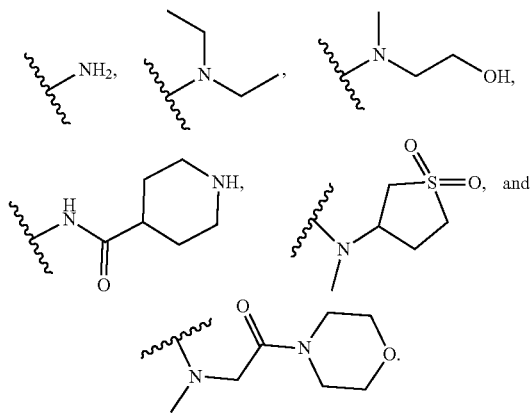

In embodiments of the foregoing, provided herein is a compound of formula (I) or (I-F), or a stereoisomer or tautomer thereof, or a pharmaceutically acceptable salt of any of the foregoing, wherein $R^a$ is selected from the group consisting of

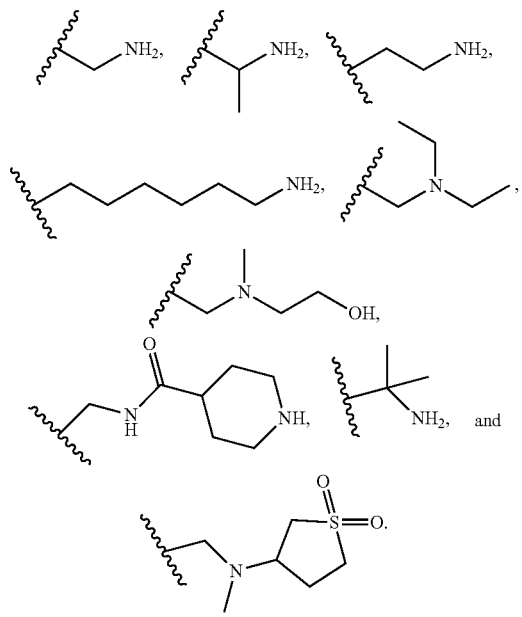

In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is —OH. In embodiments, provided herein is a compound of formula (I) or (I-F), or a stereoisomer or tautomer thereof, or a pharmaceutically acceptable salt of any of the foregoing, wherein $R^a$ is

In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is —O-(3-15 membered heterocyclyl). In embodiments, $R^b$ is —O-(4-10 membered heterocyclyl). In embodiments, $R^b$ is —O-(4-6 membered heterocyclyl). In embodiments, $R^b$ is —O-(5-6 membered heterocyclyl). In embodiments, $R^b$ is —O-(6 membered heterocyclyl). In embodiments, the 6-membered heterocyclyl of —O-(6 membered heterocyclyl) is saturated and comprises at least one annular N atom. In embodiments, $R^b$ is —O-(piperidinyl). In embodiments, In embodiments, $R^b$ is

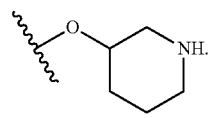 [SMILES: *OC1CCCNC1]

In embodiments, provided herein is a compound of formula (I) or (I-F), or a stereoisomer or tautomer thereof, or a pharmaceutically acceptable salt of any of the foregoing, wherein $R^a$ is

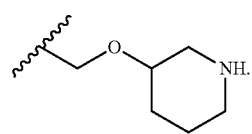 [SMILES: *COC1CCCNC1]

In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I), (I-F), (I-F1), or (I-A9), or a stereoisomer or tautomer thereof, or a pharmaceutically acceptable salt of any of the foregoing, wherein $R^b$ is $C_{1-6}$alkoxy, wherein the $C_{1-6}$alkoxy of $R^b$ is optionally substituted with one or more —OH. In embodiments, $R^b$ is $C_{1-4}$alkoxy, wherein the $C_{1-4}$alkoxy of $R^b$ is optionally substituted with one or more —OH. In embodiments, $R^b$ is $C_{1-3}$ alkoxy, wherein the $C_{1-3}$alkoxy of $R^b$ is optionally substituted with one or more —OH. In embodiments, In embodiments, $R^b$ is $C_{1-2}$alkoxy, wherein the $C_{1-2}$alkoxy of $R^b$ is optionally substituted with one or more —OH. In embodiments, $R^b$ is ethoxy, wherein the ethoxy of $R^b$ is optionally substituted with one or more —OH. In embodiments, $R^b$ is

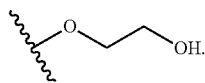 [SMILES: *OCCO]

In embodiments, provided herein is a compound of formula (I) or (I-F), or a stereoisomer or tautomer thereof, or a pharmaceutically acceptable salt of any of the foregoing, wherein $R^a$ is

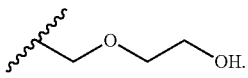 [SMILES: *COCCO]

In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I), (I-F), (I-F1), or (I-A9), or a stereoisomer or tautomer thereof, or a pharmaceutically acceptable salt of any of the foregoing, wherein $R^c$ is —S(O)$_2$—(C$_{1-6}$alkyl). In embodiments, provided herein is a compound of formula (I), (I-F), (I-F1), or (I-A9), or a stereoisomer or tautomer thereof, or a pharmaceutically acceptable salt of any of the foregoing, wherein $R^c$ is —C$_{6-10}$ aryl, wherein the C$_{6-10}$aryl of $R^c$ is optionally substituted with one or more —CN. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I) or (I-F), or a stereoisomer or tautomer thereof, or a pharmaceutically acceptable salt of any of the foregoing, wherein $R^a$ is C$_{3-10}$ cycloalkyl, wherein the C$_{3-10}$ cycloalkyl of $R^a$ is optionally substituted with one or more $R^z$, wherein $R^z$ is —OH, —CN, halo, C$_{1-6}$alkyl, C$_{1-6}$alkoxy, —N(R$^x$)(R$^y$), or —C(O)—N(R$^x$)(R$^y$). In embodiments, $R^a$ is C$_{3-6}$cycloalkyl, wherein the C$_{3-6}$cycloalkyl of $R^a$ is optionally substituted with one or more $R^z$. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I) or (I-F), or a stereoisomer or tautomer thereof, or a pharmaceutically acceptable salt of any of the foregoing, wherein $R^a$ is C$_{4-6}$cycloalkyl, wherein the C$_{4-6}$cycloalkyl of $R^a$ is optionally substituted with one or more $R^z$. In embodiments, $R^a$ is a saturated C$_{4-6}$cycloalkyl, wherein the saturated C$_{4-6}$cycloalkyl of $R^a$ is optionally substituted with one or more $R^z$. In embodiments, $R^a$ is cyclohexyl, wherein the cyclohexyl of $R^a$ is optionally substituted with one or more $R^z$. In embodiments, provided herein is a compound of formula (I) or (I-F), or a stereoisomer or tautomer thereof, or a pharmaceutically acceptable salt of any of the foregoing, wherein $R^a$ is C$_{4-6}$cycloalkyl, wherein the C$_{4-6}$cycloalkyl of $R^a$ is optionally substituted with one or more —NH$_2$. In embodiments, $R^a$ is C$_{4-6}$cycloalkyl, wherein the C$_{4-6}$cycloalkyl of $R^a$ is optionally substituted with one or more —NH$_2$. In embodiments, $R^a$ is cyclohexyl, wherein the cyclohexyl of $R^a$ is optionally substituted with one or more —NH$_2$. In embodiments, $R^a$ is

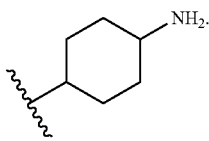 [SMILES: *C1CCC(N)CC1]

In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I) or (I-F), or a stereoisomer or tautomer thereof, or a pharmaceutically acceptable salt of any of the foregoing, wherein $R^a$ is 3-15 membered heterocyclyl, wherein the 3-15 membered heterocyclyl of $R^a$ is optionally substituted with one or more $R^z$, wherein $R^z$ is —OH, —CN, halo, C$_{1-6}$alkyl, C$_{1-6}$alkoxy, —N(R$^x$)(R$^y$), or —C(O)—N(R$^x$)(R$^y$). In embodiments, $R^a$ is 3-10 membered heterocyclyl, wherein the 3-10 membered heterocyclyl of $R^a$ is optionally substituted with one or more $R^z$. In embodiments, $R^a$ is 3-6 membered heterocyclyl, wherein the 3-6 membered heterocyclyl of $R^a$ is optionally substituted with one or more $R^z$. In embodiments, $R^a$ is 4-6 membered heterocyclyl, wherein the 4-6 membered heterocyclyl of $R^a$ is optionally substituted with one or more $R^z$. In embodiments, $R^a$ is 5-6 membered heterocyclyl, wherein the 5-6 membered heterocyclyl of $R^a$ is optionally substituted with one or more $R^z$. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, $R^a$ is 3-15 membered heterocyclyl, wherein the 3-15 membered heterocyclyl of $R^a$ is unsubstituted. In embodiments, $R^a$ is 4-6 membered heterocyclyl, wherein the 4-6 membered heterocyclyl of $R^a$ is unsubstituted. In embodiments, $R^a$ is a saturated 4-6 membered heterocyclyl, wherein the saturated 4-6 membered heterocyclyl of $R^a$ is unsubstituted. In embodiments, $R^a$ comprises at least one annular N atom or at least one annular O atom. In embodiments, $R^a$ is azetidinyl, pyrrolidinyl, piperidinyl, tetrahydro-2H-pyranyl, or morpholinyl, wherein the azetidinyl, pyrrolidinyl, piperidinyl, tetrahydro-2H-pyranyl, or morpholinyl of $R^a$ are independently optionally substituted with one or more $R^z$. In embodiments, the azetidinyl, pyrrolidinyl, piperidinyl, tetrahydro-2H-pyranyl, or morpholinyl of $R^a$ is unsubstituted. In embodiments, $R^a$ is selected from the group consisting of

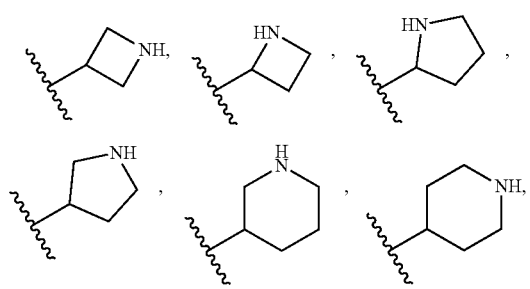

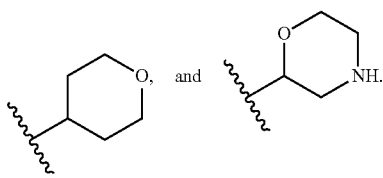 and 

In embodiments, provided herein is a compound of formula (I) or (I-F), or a stereoisomer or tautomer thereof, or a pharmaceutically acceptable salt of any of the foregoing, wherein $R^a$ is 5-20 membered heteroaryl, wherein the 5-20 membered heteroaryl of $R^a$ is optionally substituted with one or more $R^z$, wherein $R^z$ is —OH, —CN, halo, $C_{1-6}$alkyl, $C_{1-6}$alkoxy, —N($R^x$)($R^y$), or —C(O)—N($R^x$)($R^y$). In embodiments, $R^a$ is 5-10 membered heteroaryl, wherein the 5-10 membered heteroaryl of $R^a$ is optionally substituted with one or more $R^z$. In embodiments, $R^a$ is 5-6 membered heteroaryl, wherein the 5-6 membered heteroaryl of $R^a$ is optionally substituted with one or more $R^z$. In embodiments, $R^a$ is 5-membered heteroaryl, wherein the 5-membered heteroaryl of $R^a$ is optionally substituted with one or more $R^z$. In embodiments, $R^a$ is 5-6 membered heteroaryl, wherein the 5-6 membered heteroaryl of $R^a$ is optionally substituted with one or more $C_{1-6}$alkyl. In embodiments, $R^a$ is 5-membered heteroaryl, wherein the 5-membered heteroaryl of $R^a$ is optionally substituted with one or more $C_{1-6}$alkyl. In embodiments, $R^a$ is 5-membered heteroaryl, wherein the 5-membered heteroaryl of $R^a$ comprises at least one annular N atom and is optionally substituted with one or more $C_{1-6}$ alkyl. In embodiments, $R^a$ is 5-membered heteroaryl, wherein the 5-membered heteroaryl of $R^a$ is optionally substituted with one or more methyl. In embodiments, $R^a$ is pyrazolyl, wherein the pyrazolyl of $R^a$ is optionally substituted with one or more $C_{1-6}$alkyl. In embodiments, $R^a$ is pyrazolyl, wherein the pyrazolyl of $R^a$ is optionally substituted with one or more methyl. In embodiments, $R^a$ is

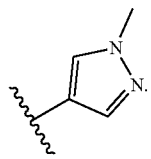 [SMILES: *c1cnn(C)c1]

In some variations, the embodiments provided herein also apply to a compound of formula (I'), or a stereoisomer or tautomer thereof, or a pharmaceutically acceptable salt of any of the foregoing, or any variation or embodiment thereof.

In some embodiments, $R^a$ is —(CH$_2$)$_n$—$R^g$ and $R^g$ is —OH. In some embodiments, provided herein is a compound of formula (I), (I-A), (I-A1), (I-A2), (I-A3), (I-A4), (I-A5), (I-A6), (I-A7), (I-A8), (I-B), (I-C), (I-D), (I-E), (I-E1), or (I-I), wherein $R^g$ is —OH. In some embodiments,

is (a) and $R^g$ is —OH. In some embodiments,

is (a), [X] is

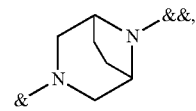

wherein & denotes the point of attachment to

and && denotes the point of attachment to [Z], and [Z] is

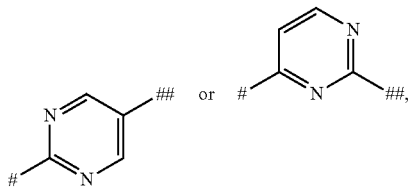

wherein # denotes the point of attachment to [X] and ## denotes the point of attachment to $R^1$, $R^g$ is —OH. In some embodiments,

is (b) and $R^g$ is —OH. In some embodiments,

is (b), [X] is

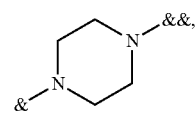

wherein & denotes the point of attachment to and && denotes the point of attachment to [Z], and [Z] is

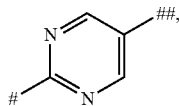

wherein # denotes the point of attachment to [X] and ##denotes the point of attachment to $R^1$, $R^g$ is —OH. In some embodiments,

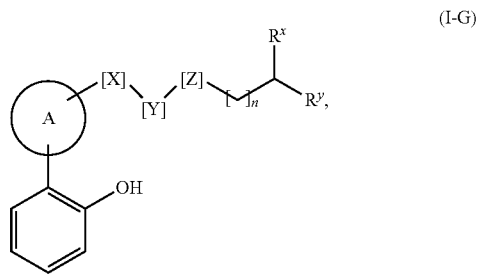

is selected from (c)-(f) and $R^g$ is —OH.

In embodiments, provided herein is a compound of formula (I), such as a compound of formula (I-A), (I-A1), (I-A2), (I-A3), (I-A4), (I-A5), (I-A6), (I-A7), (I-A8), (I-B), (I-C), (I-D), (I-E), or (I-E1), or a stereoisomer or tautomer thereof, or a pharmaceutically acceptable salt of any of the foregoing, wherein $R^1$ is —(CH$_2$)$_n$—$R^g$, wherein n is an integer from 1-6 and $R^g$ is —N($R^x$)($R^y$) or —OH. In embodiments of the foregoing, $R^g$ is —N($R^x$)($R^y$), such that the compound of formula (I) is a compound of formula (I-G):

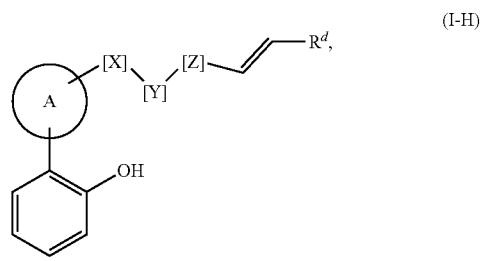

or a stereoisomer or tautomer thereof, or a pharmaceutically acceptable salt of any of the foregoing. In some variations, the embodiments provided herein also apply to a compound of formula (I'), or a stereoisomer or tautomer thereof, or a pharmaceutically acceptable salt of any of the foregoing, or any variation or embodiment thereof, wherein [X], [Y], [Z], $R^x$ and $R^y$ are as defined above or elsewhere herein for a compound of formula (I). In another variation, [X], [Y], [Z], $R^x$ and $R^y$ of formula (I-G) are as defined for a compound of formula (I'), or a stereoisomer or tautomer thereof, or a pharmaceutically acceptable salt of any of the foregoing, or any variation or embodiment thereof.

In embodiments, provided herein is a compound of formula (I) or (I-G), or a stereoisomer or tautomer thereof, or a pharmaceutically acceptable salt of any of the foregoing, wherein $R^x$ and $R^y$ are both H. In embodiments, one of $R^x$ and $R^y$ is H and the other of $R^x$ and $R^y$ is —C(O)—CH$_2$—NH$_2$. In embodiments of the foregoing, n is an integer from 1-5, from 1-4, from 1-3, or from 1-2. In embodiments, n is an integer from 2-6, from 3-6, from 4-6, or from 5-6. In embodiments, n is an integer from 2-4. In embodiments, n is 6. In embodiments, n is 5. In embodiments, n is 4. In embodiments, n is 3. In embodiments, n is 2. In embodiments, n is 1. In embodiments, $R^1$ is —(CH$_2$)$_3$—NH$_2$. In embodiments, $R^1$ is —(CH$_2$)$_3$—NH—C(O)—CH$_2$—NH$_2$. In embodiments, $R^1$ is —(CH$_2$)$_6$—NH$_2$. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I'), such as a compound of formula (I), (I-A), (I-A1), (I-A2), (I-A3), (I-A4), (I-A5), (I-A6), (I-A7), (I-A8), (I-B), (I-C), (I-D), (I-E), or (I-E1), or a stereoisomer or tautomer thereof, or a pharmaceutically acceptable salt of any of the foregoing, wherein $R^1$ is —C=C—$R^d$. In embodiments, $R^d$ is C$_{1-6}$alkyl, wherein the C$_{1-6}$alkyl of $R^d$ is optionally substituted with one or more $R^e$, such that the compound of formula (I) is a compound of formula (I-H):

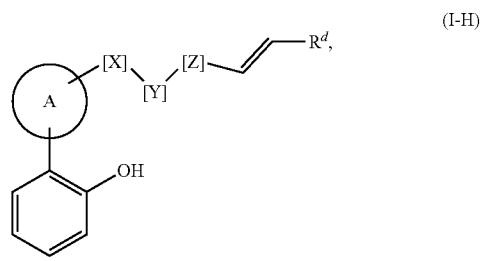

or a stereoisomer or tautomer thereof, or a pharmaceutically acceptable salt of any of the foregoing, wherein [X], [Y], [Z] and $R^d$ are as defined above or elsewhere herein for a compound of formula (I').

In embodiments provided herein, is a compound of formula (I'), such as a compound of formula (I), or (I-H), wherein $R^1$ is —C=C—$R^d$, wherein $R^d$ is C$_{1-6}$alkyl, wherein the C$_{1-6}$alkyl of $R^d$ is optionally substituted with one or more $R^e$, wherein each $R^e$ is independently 3-15 membered heterocyclyl, wherein the 3-15 membered heterocyclyl of $R^e$ is optionally substituted with one or more $R^f$, wherein each $R^f$ is independently —OH, —CN, halo, oxo, C$_{1-6}$alkyl, C$_{1-6}$alkoxy, or —C(O)—C$_{1-6}$alkoxy. In some variations, the embodiments provided herein also apply to a compound of formula (I'), or a stereoisomer or tautomer thereof, or a pharmaceutically acceptable salt of any of the foregoing, or any variation or embodiment thereof.

In embodiments, $R^1$ is —C≡C—$R^a$, wherein $R^a$ is C$_{1-6}$alkyl. In embodiments, $R^1$ is —C≡C—$R^a$, wherein $R^a$ is methylene substituted with one or more $R^b$. In embodiments, $R^1$ is —C≡C—$R^a$, wherein $R^a$ is ethylene substituted with one or more $R^b$. In embodiments, $R^1$ is —C≡C—$R^a$, wherein $R^a$ is C$_{1-6}$alkyl substituted with one $R^b$. In embodiments, $R^1$ is —C≡C—$R^a$, wherein $R^a$ is C$_{1-6}$alkyl substituted with one $R^b$, wherein $R^b$ is 3-15 membered heterocyclyl, wherein the 3-15 membered heterocyclyl of $R^b$ is optionally substituted with one or more $R^c$. In embodiments, $R^1$ is —C≡C—$R^a$, wherein $R^a$ is methylene substituted with one $R^b$, wherein $R^b$ is 3-15 membered heterocyclyl, wherein the 3-15 membered heterocyclyl of $R^b$ is optionally substituted with one or more $R^c$. In embodiments, $R^1$ is —C≡C—$R^a$, wherein $R^a$ is C$_{1-6}$alkyl substituted with $R^b$, wherein $R^b$ is 3-15 membered heterocyclyl, wherein the 3-15 membered heterocyclyl of $R^b$ is optionally substituted with one or more $R^c$, selected from the group consisting of

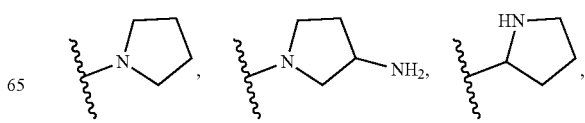

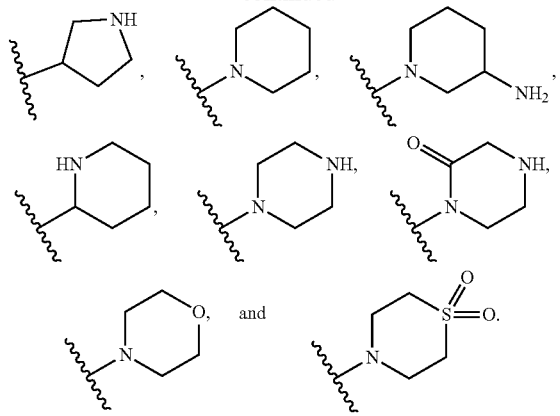

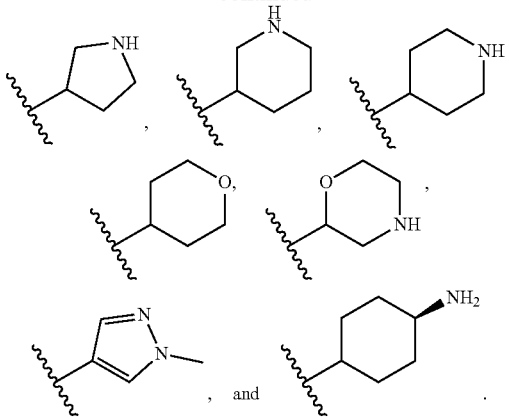

In embodiments, R¹ is —C≡C—Rᵃ, wherein Rᵃ is $C_{1-6}$alkyl substituted with one Rᵇ, wherein Rᵇ is —N(Rˣ)(Rʸ). In embodiments, R¹ is —C≡C—Rᵃ, wherein Rᵃ is $C_{1-6}$alkyl substituted with one Rᵇ, wherein Rᵇ is —N(Rˣ)(Rʸ), wherein the Rˣ and Rʸ of —N(Rˣ)(Rʸ) are, independently of each other and independently at each occurrence, hydrogen or $C_{1-6}$alkyl, wherein the $C_{1-6}$alkyl of Rˣ or Rʸ is optionally substituted with one or more —OH.

In embodiments, R¹ is —C≡C—Rᵃ, wherein Rᵃ is $C_{3-10}$ cycloalkyl, 3-15 membered heterocyclyl, or 5-20 membered heteroaryl, wherein the $C_{3-10}$ cycloalkyl, 3-15 membered heterocyclyl, or 5-20 membered heteroaryl of Rᵃ is independently optionally substituted with one or more Rᶻ.

In embodiments, R¹ is —C≡C—Rᵃ, wherein Rᵃ is 3-15 membered heterocyclyl. In embodiments, R¹ is —C≡C—Rᵃ, wherein Rᵃ is 3-15 membered heterocyclyl selected from the group consisting of

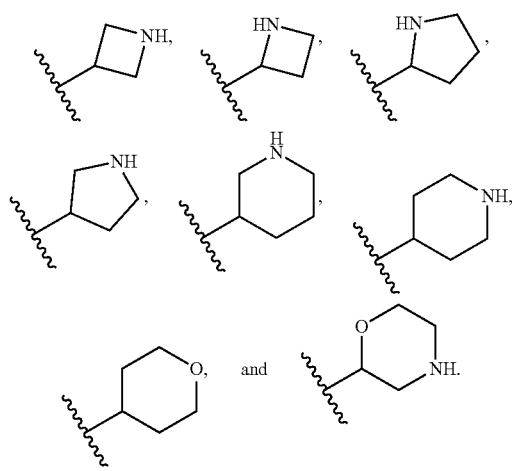

In embodiments, R¹ is —C≡C—Rᵃ, wherein Rᵃ is 3-15 membered heterocyclyl selected from the group consisting of

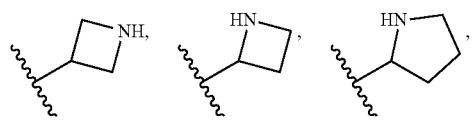

In embodiments, R¹ is —(CH₂)ₙ—Rᵍ, wherein n is an integer from 1-6, and Rᵍ is —N(Rˣ)(Rʸ), wherein the Rˣ and Rʸ of —N(Rˣ)(Rʸ) are each hydrogen.

In embodiments, (i) R¹ is —C≡C—Rᵃ, wherein (a) Rᵃ is $C_{1-6}$alkyl, wherein the $C_{1-6}$alkyl of Rᵃ is optionally substituted with one or more Rᵇ, wherein each Rᵇ is independently 3-15 membered heterocyclyl, —O-(3-15 membered heterocyclyl), $C_{1-6}$alkoxy, —OH or —N(Rˣ)(Rʸ), wherein the 3-15 membered heterocyclyl of Rᵇ is optionally substituted with one or more Rᶜ, wherein each Rᶜ is independently oxo, $C_{1-6}$alkyl or —N(Rˣ)(Rʸ), and wherein the $C_{1-6}$alkoxy of Rᵇ is optionally substituted with one or more —OH, or (b) Rᵃ is $C_{3-10}$cycloalkyl, wherein the $C_{3-10}$cycloalkyl of Rᵃ is optionally substituted with one or more Rᶻ, or (c) Rᵃ is 3-15 membered heterocyclyl, wherein the 3-15 membered heterocyclyl of Rᵃ is optionally substituted with one or more Rᶻ, or (d) Rᵃ is 5-20 membered heteroaryl, wherein the 5-20 membered heteroaryl of Rᵃ is optionally substituted with one or more Rᶻ, or (ii) R¹ is —(CH₂)ₙ—Rᵍ, wherein n is an integer from 1-6 and Rᵍ is —N(Rˣ)(Rʸ), wherein each Rᶻ is, independently at each occurrence, $C_{1-6}$alkyl or —N(Rˣ)(Rʸ), and the Rˣ and Rʸ of —C(O)N(Rˣ)(Rʸ) and —N(Rˣ)(Rʸ) are, independently of each other and independently at each occurrence, H, —C(O)—(CH₂)ₚ—N(Rᵖ)(Rᵍ), —C(O)—Rˢ, 5-20 membered heterocycle, 5-20 membered heteroaryl, or $C_{1-6}$alkyl, wherein p is an integer from 1-6, and Rᵖ and Rᵍ are, independently of each other and independently at each occurrence, H or $C_{1-6}$alkyl, and wherein Rˢ is 5-20 membered heterocycle optionally substituted with one or more substituents selected from the group consisting of $C_{1-4}$alkyl, $C_{3-8}$cycloalkyl, and —C(O)—$C_{1-6}$alkyl, the $C_{1-6}$alkyl of Rˣ or Rʸ is optionally substituted with one or more —OH, 3-15 membered heterocyclyl, or —C(O)-(3-15 membered heterocyclyl), and the 5-20 membered heterocycle of Rˣ or Rʸ is optionally substituted with one or more oxo (iii) —C═C—Rᵈ, wherein Rᵈ is $C_{1-6}$alkyl, wherein the $C_{1-6}$alkyl of Rᵈ is optionally substituted with one or more Rᵉ, wherein each Rᵉ is independently 3-15 membered heterocyclyl, wherein the 3-15 membered heterocyclyl of $R^c$ is optionally substituted with one or more $R^f$, wherein each $R^f$ is independently —OH, —CN, halo, oxo, $C_{1-6}$alkyl, $C_{1-6}$alkoxy, or —C(O)—$C_{1-6}$alkoxy.

In embodiments, provided herein is a compound of formula (I), or a stereoisomer or tautomer thereof, or a pharmaceutically acceptable salt of the foregoing, wherein $R^1$ is selected from the group consisting of

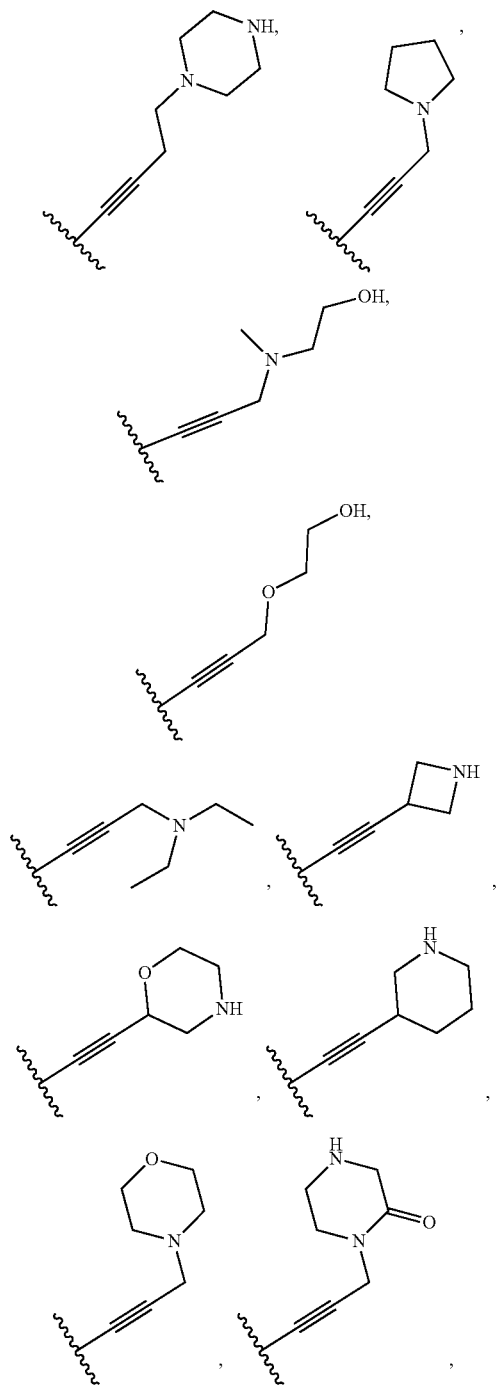

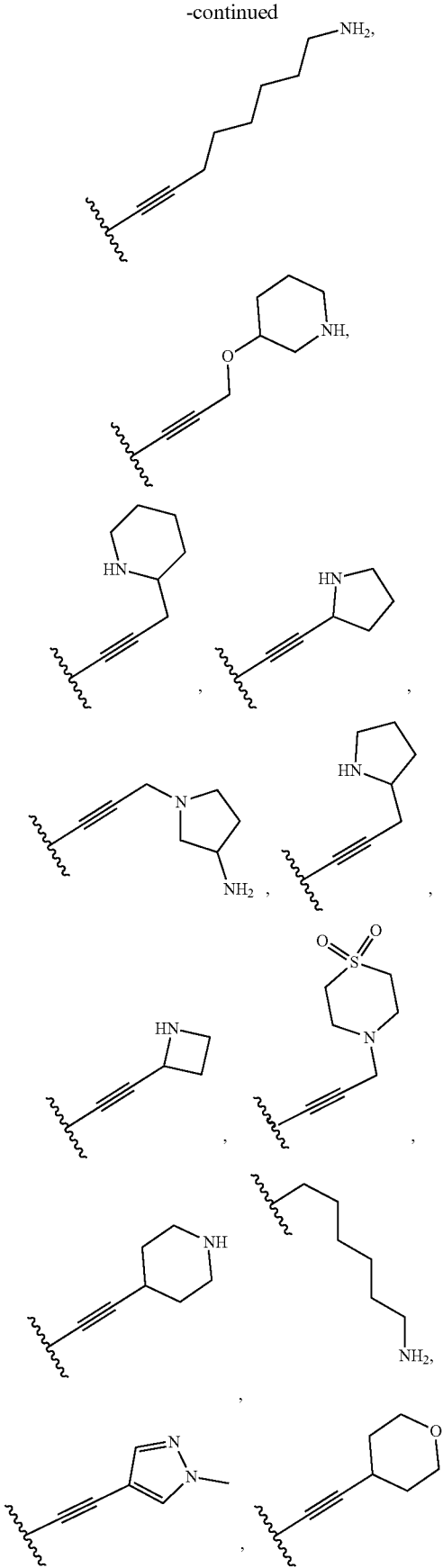

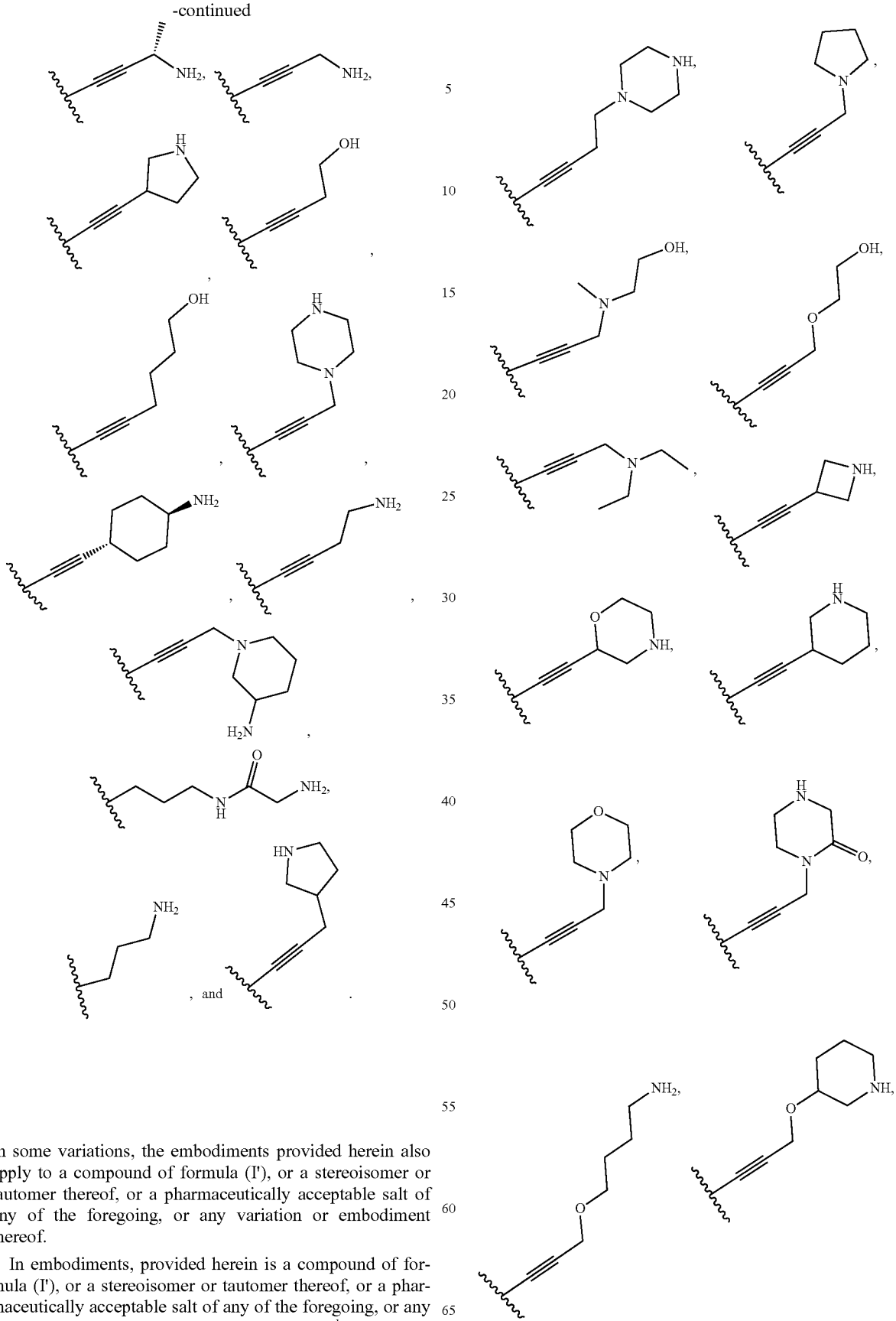

In some variations, the embodiments provided herein also apply to a compound of formula (I'), or a stereoisomer or tautomer thereof, or a pharmaceutically acceptable salt of any of the foregoing, or any variation or embodiment thereof.

In embodiments, provided herein is a compound of formula (I'), or a stereoisomer or tautomer thereof, or a pharmaceutically acceptable salt of any of the foregoing, or any variation or embodiment thereof, wherein $R^1$ is selected from the group consisting of

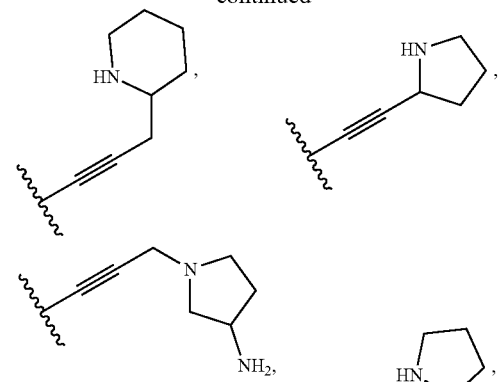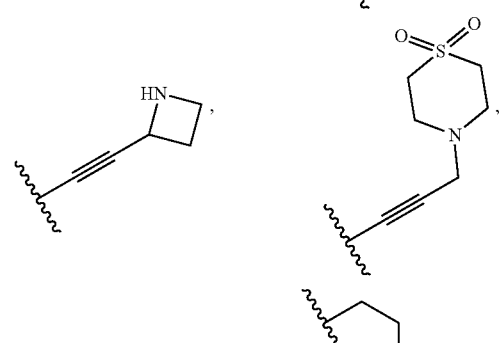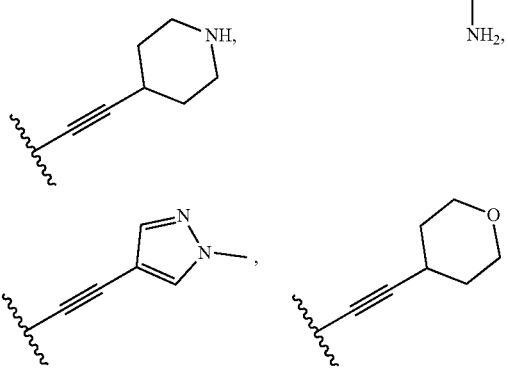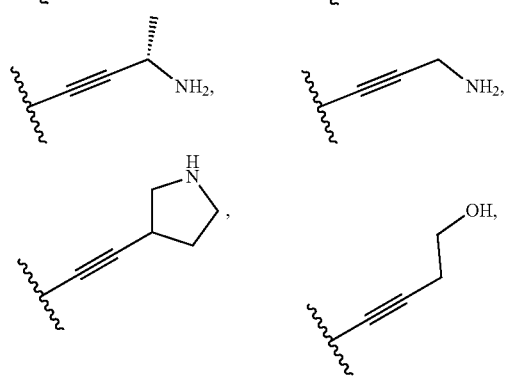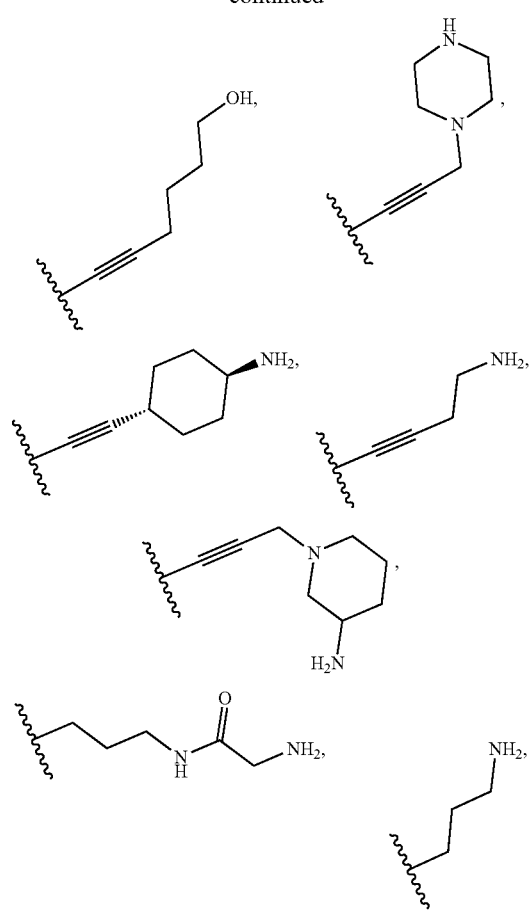

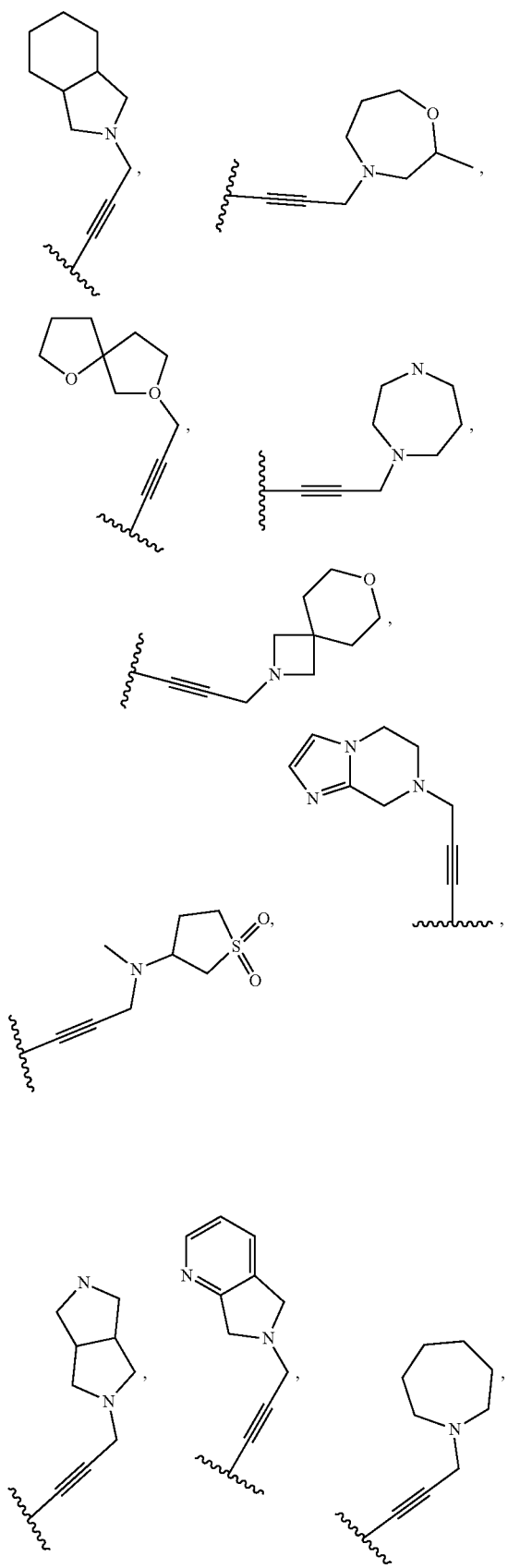
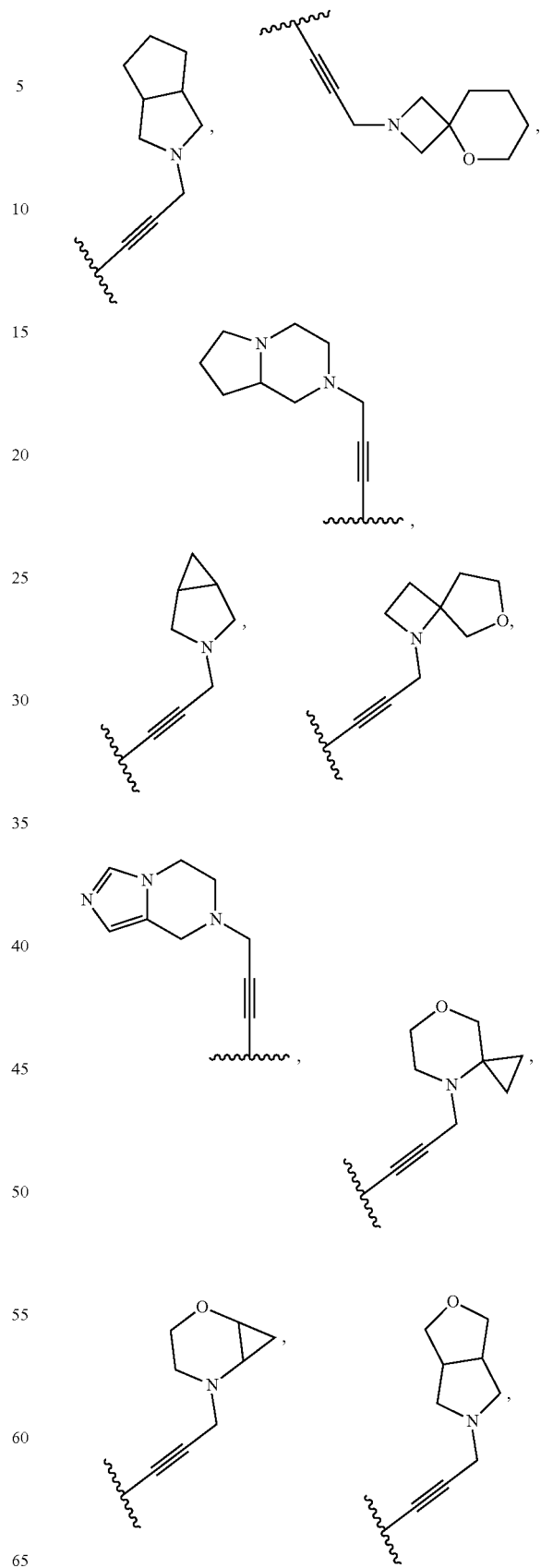

-continued
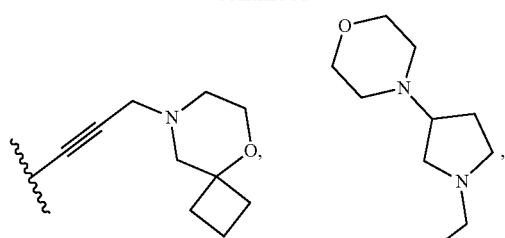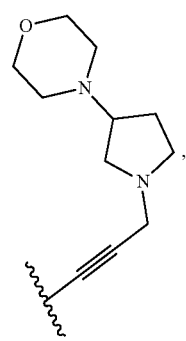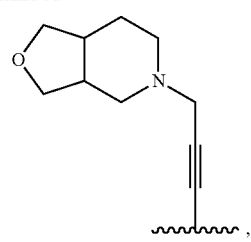
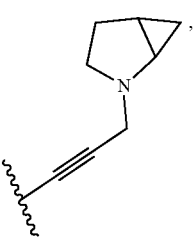
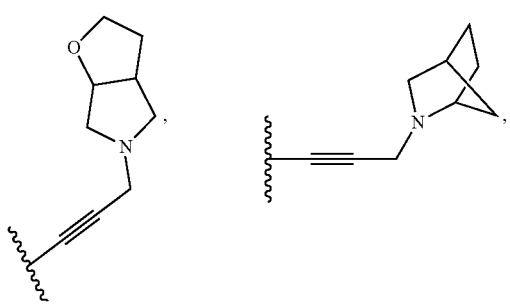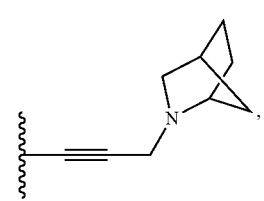
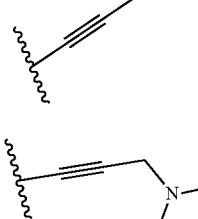
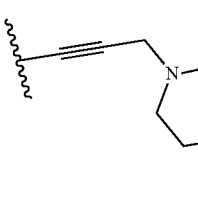
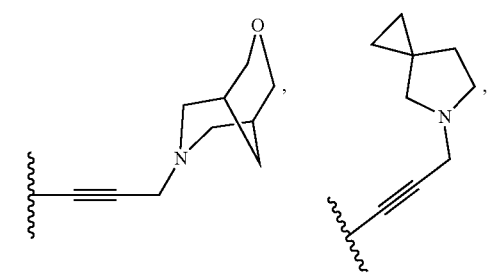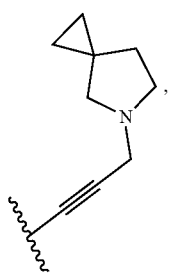
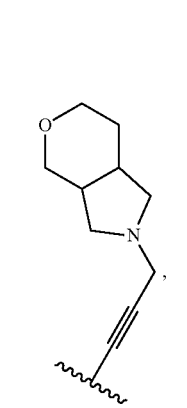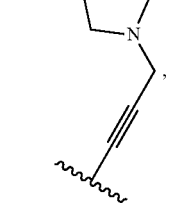
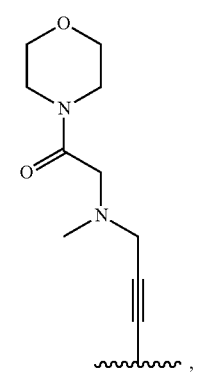
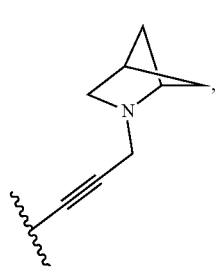
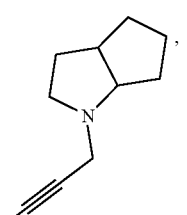

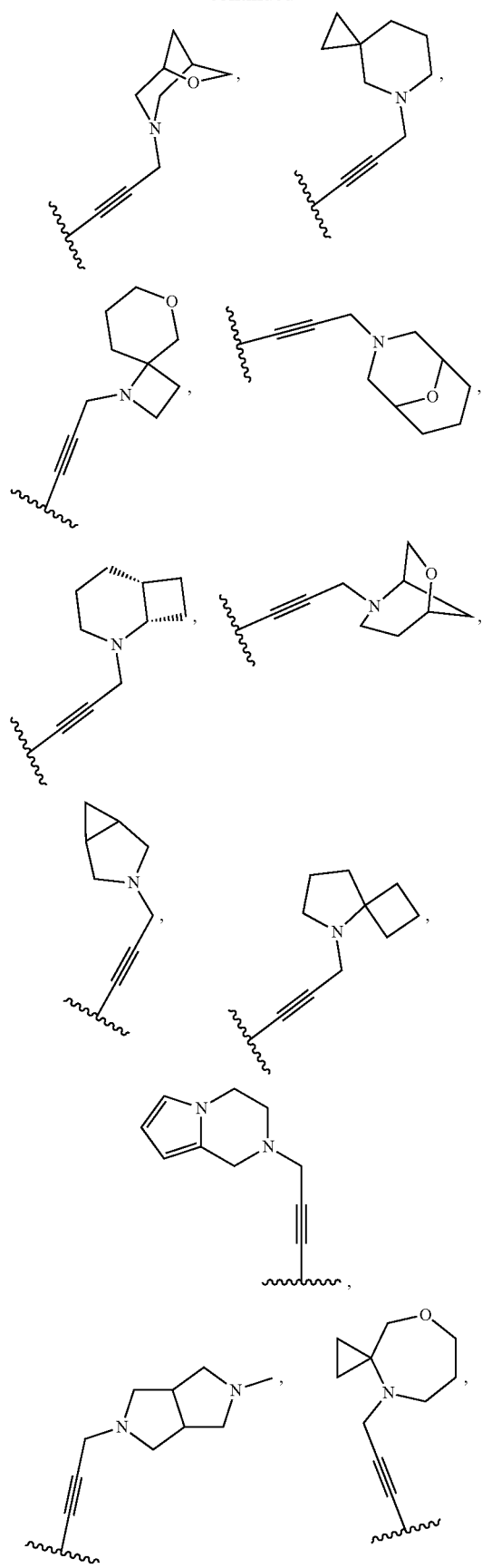
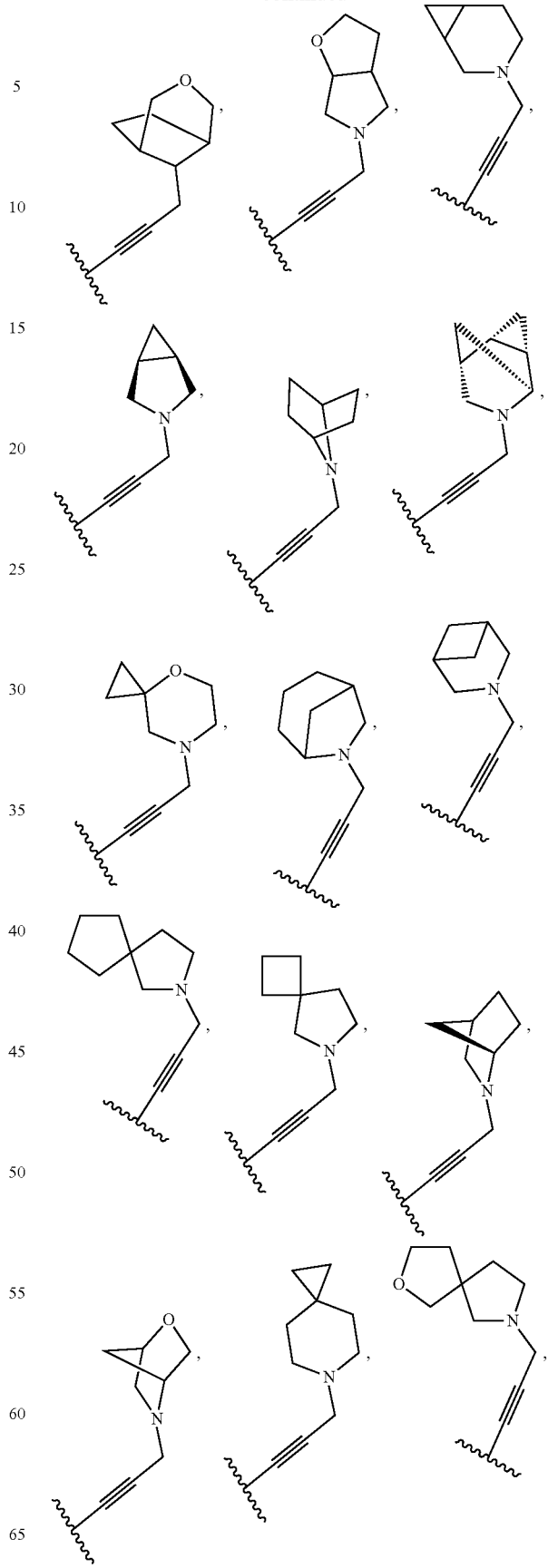

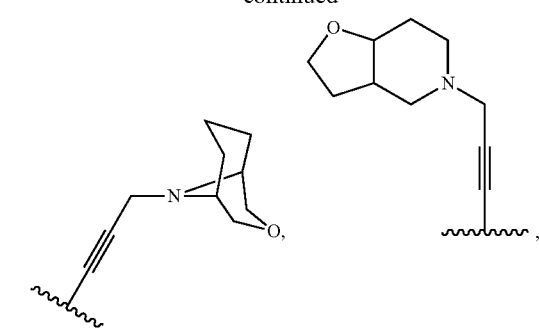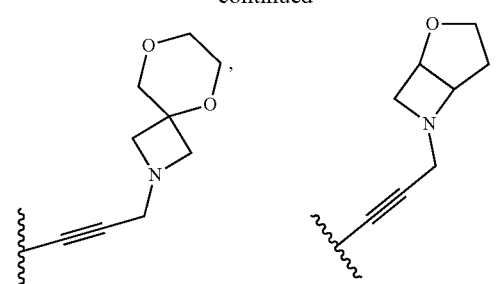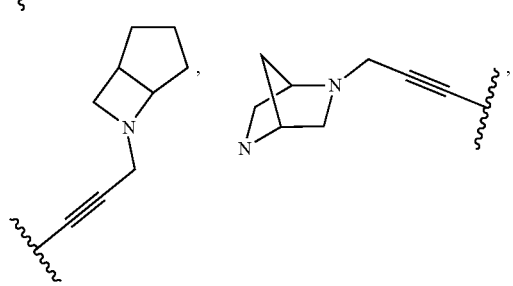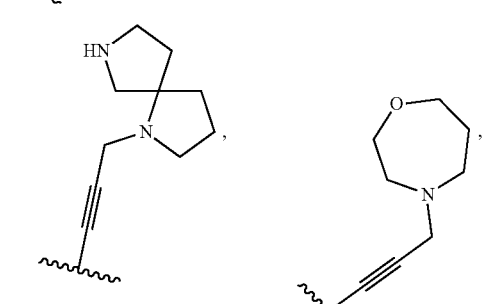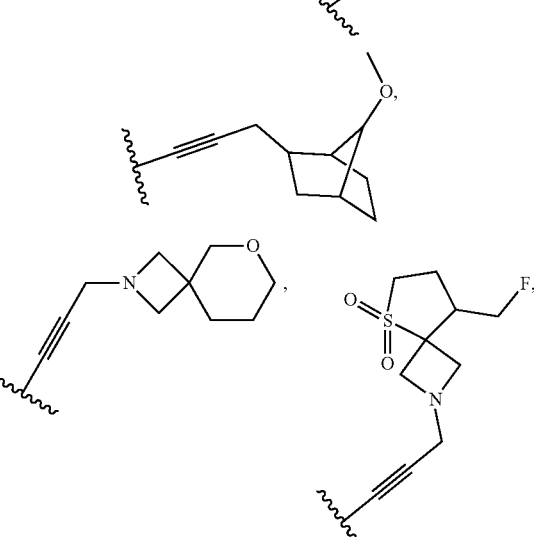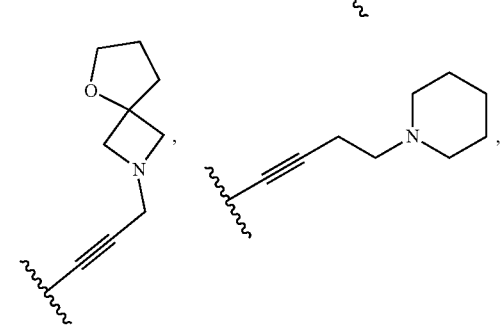

-continued

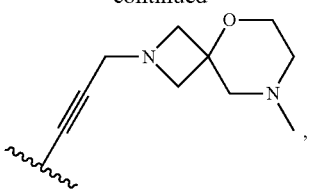

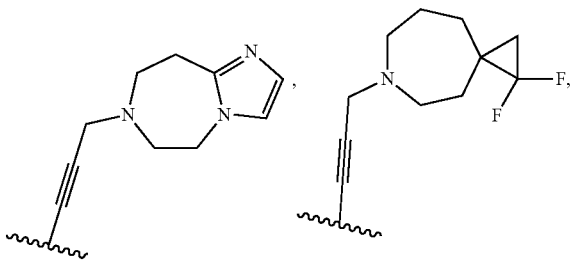

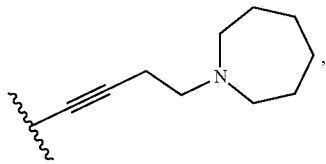

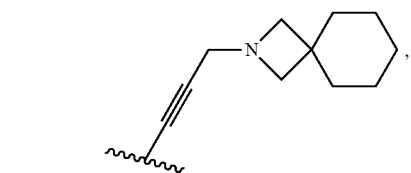

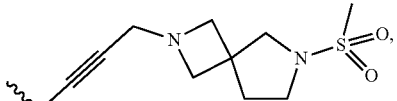

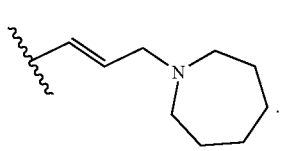

and

In embodiments, provided herein is a compound of formula (I'), or a stereoisomer or tautomer thereof, or a pharmaceutically acceptable salt of any of the foregoing, wherein (A)

is (f)

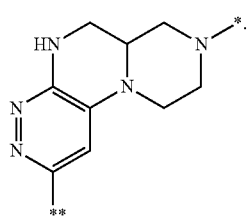

In embodiments, provided herein is a compound of formula (I'), or a stereoisomer or tautomer thereof, or a pharmaceutically acceptable salt of any of the foregoing, wherein (A)

is (f)

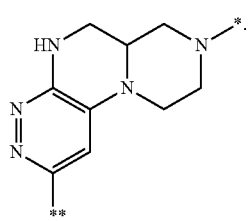

In embodiments, [X] is 3-15 membered heterocyclyl or 5-20 membered heteroaryl, [Y] is absent, [Z] is absent, such that a compound of formula (I') is a compound of formula (I-I):

(I-I)

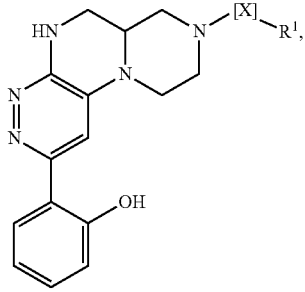

or a stereoisomer or tautomer thereof, or a pharmaceutically acceptable salt of any of the foregoing, wherein [X], and $R^1$ are as defined above or elsewhere herein for a compound of formula (I').

In some embodiments, provided herein is a compound of formula (I-I), provided that, when [X] is

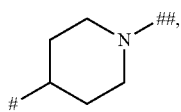

wherein # denotes the point of attachment to (A)

and ## denotes the point of attachment to $R^1$, then when $R^1$ is —$(CH_2)_n$—$R^g$, $R^g$ is not OH.

In embodiments herein, is a compound of formula (I'), such as a compound of formula (I'), or (I-I), wherein $R^1$ is:

(a) —C≡C—$R^a$, wherein
  (i) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
    the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$ alkyl), $C_{3-10}$cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein
    the $C_{1-6}$alkyl of $R^c$ is optionally substituted with one or more —OH, —CN, halo, $C_{1-6}$alkoxy, or 3-15 membered heterocyclyl,
    the $C_{3-10}$cycloalkyl of $R^c$ is optionally substituted with one or more halo,
    the $C_{6-10}$aryl of $R^c$ is optionally substituted with one or more —CN,
    the 3-15 membered heterocyclyl of $R^c$ is optionally substituted with one or more $C_{1-6}$ alkyl or —C(O)—$C_{1-6}$alkyl, and
    the $C_{1-6}$alkoxy of $R^b$ is optionally substituted with one or more —OH, or
  (ii) $R^a$ is $C_{3-10}$ cycloalkyl, wherein the $C_{3-10}$ cycloalkyl of $R^a$ is optionally substituted with one or more $R^z$, or
  (iii) $R^a$ is 3-15 membered heterocyclyl, wherein the 3-15 membered heterocyclyl of $R^a$ is optionally substituted with one or more $R^z$, or
  (iv) $R^a$ is 5-20 membered heteroaryl, wherein the 5-20 membered heteroaryl of $R^a$ is optionally substituted with one or more $R^z$, or
(b) —$(CH_2)_n$—$R^g$, wherein
  n is an integer from 1-6, and
  $R^g$ is —N($R^x$)($R^y$) or —OH;
$R^z$ is, independently at each occurrence, —OH, —CN, halo, $C_{1-6}$alkyl, $C_{1-6}$alkoxy, —N($R^x$)($R^y$), or —C(O)—N($R^x$)($R^y$); and
the $R^x$ and $R^y$ of —C(O)N($R^x$)($R^y$) and —N($R^x$)($R^y$) are, independently of each other and independently at each occurrence, H, —C(O)—$(CH_2)_p$—N($R^p$)($R^q$), —C(O)—$R^s$, 5-20 membered heterocycle, 5-20 membered heteroaryl, or $C_{1-6}$alkyl, wherein
p is an integer from 1-6,
$R^p$ and $R^q$ are, independently of each other and independently at each occurrence H, or $C_{1-6}$alkyl, $R^s$ is 5-20 membered heterocycle optionally substituted with one or more substituents selected from the group consisting of $C_{1-4}$alkyl, $C_{3-8}$cycloalkyl, and —C(O)—$C_{1-6}$alkyl,
the $C_{1-6}$alkyl of $R^x$ or $R^y$ is optionally substituted with one or more —OH, 3-15 membered heterocyclyl, or —C(O)-(3-15 membered heterocyclyl), and
the 5-20 membered heterocycle of $R^x$ or $R^y$ is optionally substituted with one or more oxo or the $R^x$ and $R^y$ of —C(O)N($R^x$)($R^y$) and —N($R^x$)($R^y$), together with the N atom to which they are attached, form a 4- to 12-membered heterocycle, wherein the 4- to 12-membered heterocycle is optionally substituted with at least one substituent selected from the group consisting of halo, —OH, oxo, $C_{1-4}$alkyl optionally substituted with one or more —OH, $C_{3-7}$cycloalkyl, $C_{1-4}$alkoxy, $C_{1-4}$haloalkyl, and —C(O)—N($R^h$)($R^i$), wherein $R^h$ and $R^i$ are each independently selected from the group consisting of H and $C_1$-$C_4$alkyl, wherein the $C_1$-$C_4$alkyl of $R^h$ or $R^i$ is independently optionally substituted with one or more —OH (c) —C≡C—$R^d$, wherein $R^d$ is $C_{1-6}$alkyl, wherein the $C_{1-6}$alkyl of $R^d$ is optionally substituted with one or more $R^e$, wherein each $R^e$ is independently 3-15 membered heterocyclyl, wherein the 3-15 membered heterocyclyl of $R^e$ is optionally substituted with one or more $R^f$, wherein each $R^f$ is independently —OH, —CN, halo, oxo, $C_{1-6}$alkyl, $C_{1-6}$alkoxy, or —C(O)—$C_{1-6}$alkoxy.

In embodiments, herein is a compound of formula (I'), such as a compound of formula (I'), or (I-I), wherein, $R^1$ is: —C≡C—$R^a$, wherein $R^a$ is $C_{1-6}$alkyl, wherein the $C_{1-6}$ alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$alkyl), $C_{3-10}$ cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein, the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, the $C_{6-10}$aryl of $R^c$ is optionally substituted with one or more —CN, the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH.

In embodiments, the present disclosure is directed to a compound of formula (I'), such as a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), or a stereoisomer or tautomer thereof, or a pharmaceutically acceptable salt of any of the foregoing, wherein the compound, or a stereoisomer or tautomer thereof, or a pharmaceutically acceptable salt of any of the foregoing, is selected from the group consisting of the compounds in Table 1. In embodiments, the present disclosure is directed to a compound of formula (I), such as a compound of formula (I'), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, wherein the compound, or a stereoisomer or tautomer thereof, or a pharmaceutically acceptable salt of any of the foregoing, is selected from the group consisting of the compounds in Table 1.

In embodiments, provided is a compound of formula (II')

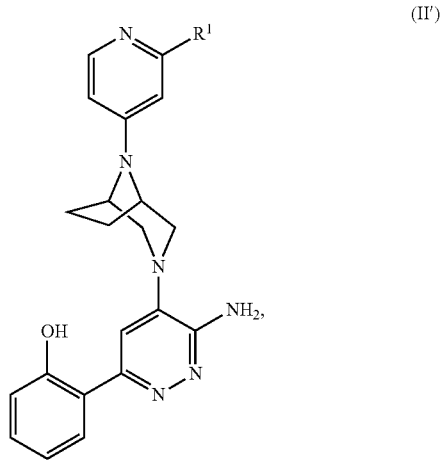

(II')

or a stereoisomer or tautomer thereof, or a pharmaceutically acceptable salt of any of the foregoing, wherein:
(i) $R^1$ is —C≡C—$R^a$, wherein
(a) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, —S(O)$_2$—($C_{1-6}$ alkyl), $C_{3-10}$cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$cycloalkyl of $R^c$ is optionally substituted with one or more halo,
the $C_{6-10}$aryl of $R^c$ is optionally substituted with one or more —CN,
the 3-15 membered heterocyclyl of $R^c$ is optionally substituted with one or more $C_{1-6}$alkyl or —C(O)—$C_{1-6}$alkyl, and
the $C_{1-6}$alkoxy of $R^b$ is optionally substituted with one or more —OH, or
(b) $R^a$ is $C_{3-10}$ cycloalkyl, wherein the $C_{3-10}$ cycloalkyl of $R^a$ is optionally substituted with one or more $R^z$, or
(c) $R^a$ is 3-15 membered heterocyclyl, wherein the 3-15 membered heterocyclyl of $R^a$ is optionally substituted with one or more $R^z$, or
(d) $R^a$ is 5-20 membered heteroaryl, wherein the 5-20 membered heteroaryl of $R^a$ is optionally substituted with one or more $R^z$, or
(ii) $R^1$ is —(CH$_2$)$_n$—$R^g$, wherein $R^g$ is —N($R^x$)($R^y$) or —OH, and
n is an integer from 1-6;
wherein
$R^z$ is, independently at each occurrence, —OH, —CN, halo, $C_{1-6}$alkyl, $C_{1-6}$alkoxy, —N($R^x$)($R^y$), or —C(O)—N($R^x$)($R^y$); and
the $R^x$ and $R^y$ of —C(O)N($R^x$)($R^y$) and —N($R^x$)($R^y$) are, independently of each other and independently at each occurrence, H, —C(O)—(CH$_2$)$_p$—N($R^p$)($R^q$), —C(O)—$R^s$, 5-20 membered heterocycle, 5-20 membered heteroaryl, or $C_{1-6}$alkyl, wherein
p is an integer from 1-6,
$R^p$ and $R^q$ are, independently of each other and independently at each occurrence H, or $C_{1-6}$alkyl,
$R^s$ is 5-20 membered heterocycle optionally substituted with one or more substituents selected from the group consisting of $C_{1-4}$alkyl, $C_{3-8}$cycloalkyl, and —C(O)—$C_{1-6}$alkyl,
the $C_{1-6}$alkyl of $R^x$ or $R^y$ is optionally substituted with one or more —OH, 3-15 membered heterocyclyl, or —C(O)-(3-15 membered heterocyclyl), and
the 5-20 membered heterocycle of $R^x$ or $R^y$ is optionally substituted with one or more oxo.

In embodiments, provided is a compound of formula (II):

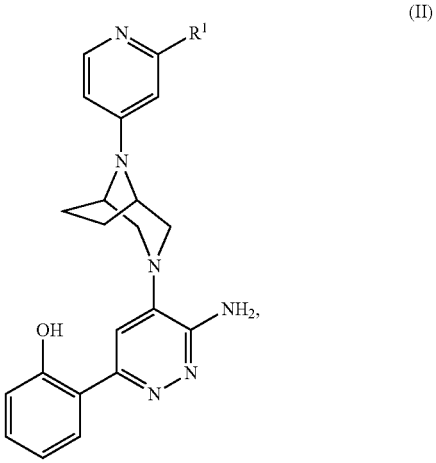

(II)

or a stereoisomer or tautomer thereof, or a pharmaceutically acceptable salt of any of the foregoing, wherein:
$R^1$ is —C≡C—$R^a$, wherein
(a) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more OH, or (b) $R^a$ is $C_{3-10}$cycloalkyl, wherein the $C_{3-10}$cycloalkyl of $R^a$ is optionally substituted with one or more $R^z$, or (c) $R^a$ is 3-15 membered heterocyclyl, wherein the 3-15 membered heterocyclyl of $R^a$ is optionally substituted with one or more $R^z$, or (d) $R^a$ is 5-20 membered heteroaryl, wherein the 5-20 membered heteroaryl of $R^a$ is optionally substituted with one or more $R^z$, or (ii) $R^1$ is —(CH$_2$)$_n$—$R^g$, wherein n is an integer from 1-6, and $R^g$ is —N($R^x$)($R^y$) or —OH, wherein $R^z$ is, independently at each occurrence, —OH, —CN, halo, $C_{1-6}$alkyl, $C_{1-6}$alkoxy, —N($R^x$)($R^y$), or —C(O)—N($R^x$)($R^y$); and the $R^x$ and $R^y$ of —C(O)N($R^x$)($R^y$) and —N($R^x$)($R^y$) are, independently of each other and independently at each occurrence, H, —C(O)—(CH$_2$)$_p$—N($R^p$)($R^q$), 5-20 membered heteroaryl, or $C_{1-6}$alkyl, wherein p is an integer from 1-6, $R^p$ and $R^q$ are, independently of each other and independently at each occurrence H, or $C_{1-6}$alkyl, and the $C_{1-6}$alkyl of $R^x$ or $R^y$ is optionally substituted with one or more —OH, 3-15 membered heterocyclyl, or —C(O)-(3-15 membered heterocyclyl).

In embodiments, $R^1$ is —C≡C—$R^a$, wherein (a) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, or —N($R^x$)($R^y$), wherein the 3-15 membered heterocyclyl of $R^b$ is optionally substituted with one or more $R^c$, wherein each $R^c$ is independently oxo or —N($R^x$)($R^y$), and wherein the $C_{1-6}$alkoxy of $R^b$ is optionally substituted with one or more —OH, or (b) $R^a$ is $C_{3-10}$cycloalkyl optionally substituted with one or more $R^z$, or (c) $R^a$ is 3-15 membered heterocyclyl optionally substituted with one or more $R^z$, or (d) $R^a$ is 5-20 membered heteroaryl optionally substituted with one or more $R^z$, wherein $R^z$ is, independently at each occurrence, $C_{1-6}$alkyl or —N($R^x$)($R^y$); and the $R^x$ and $R^y$ of —N($R^x$)($R^y$) are, independently of each other and independently at each occurrence, H or $C_{1-6}$alkyl, wherein the $C_{1-6}$alkyl of $R^x$ or $R^y$ is optionally substituted with one or more —OH. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, $R^1$ is —(CH$_2$)$_n$—$R^g$, wherein n is an integer from 1-6, and $R^g$ is —N($R^x$)($R^y$), wherein the $R^x$ and $R^y$ of —N($R^x$)($R^y$) are, independently of each other and independently at each occurrence, H, —C(O)—CH$_2$—NH$_2$, or $C_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), or a stereoisomer or tautomer thereof, or a pharmaceutically acceptable salt of any of the foregoing, wherein $R^1$ is —C≡C—$R^a$. In embodiments, provided herein is a compound of formula (II), or a stereoisomer or tautomer thereof, or a pharmaceutically acceptable salt of any of the foregoing, wherein $R^1$ is —C≡C—$R^a$, such that the compound of formula (II) is a compound of formula (II-A):

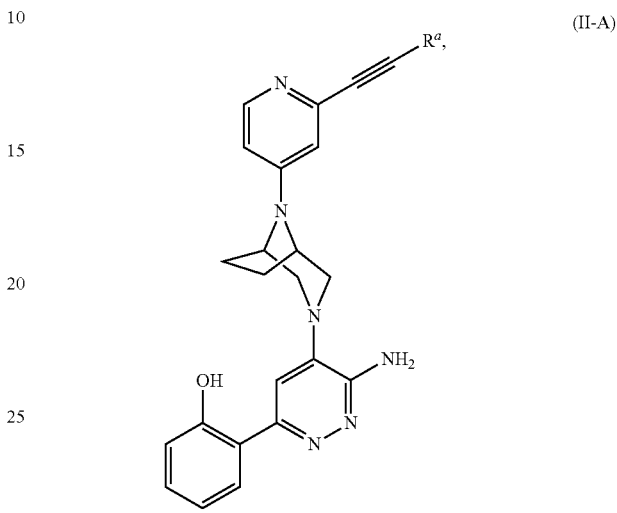

(II-A)

or a stereoisomer or tautomer thereof, or a pharmaceutically acceptable salt of any of the foregoing. In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^a$ is as defined above or elsewhere herein, for a compound of formula (II') or formula (II). In some variations, $R^a$ is as defined above or elsewhere herein for a compound of formula (II), or (II-A). In another variation, $R^a$ of formula (II), or (II-A), is as defined for a compound of formula (II'), or a stereoisomer or tautomer thereof, or a pharmaceutically acceptable salt of any of the foregoing, or any variation or embodiment thereof.

In embodiments, provided herein is a compound of formula (II) or formula (II-A), or a stereoisomer or tautomer thereof, or a pharmaceutically acceptable salt of any of the foregoing, wherein $R^a$ is $C_{1-6}$alkyl, wherein the $C_{1-6}$alkyl of $R^a$ is optionally substituted with one or more $R^b$. In embodiments, $R^a$ is $C_{1-4}$alkyl, wherein the $C_{1-4}$alkyl of $R^a$ is optionally substituted with one or more $R^b$. In embodiments, $R^a$ is $C_{1-3}$alkyl, wherein the $C_{1-3}$alkyl of $R^a$ is optionally substituted with one or more $R^b$. In embodiments, $R^a$ is ethyl, wherein the ethyl of $R^a$ is optionally substituted with one or more $R^b$. In embodiments, $R^a$ is ethyl, wherein the ethyl of $R^a$ is optionally substituted with one $R^b$. In embodiments, $R^a$ is methyl, wherein the methyl of $R^a$ is optionally substituted with one or more $R^b$. In embodiments, $R^a$ is methyl, wherein the methyl of $R^a$ is optionally substituted with one $R^b$. In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^a$ is as defined above or elsewhere herein, for a compound of formula (II') or formula (II).

In embodiments, —R$^a$—R$^b$ is —C$_{1-2}$alkyl-(4-6 membered heterocyclyl). In embodiments, —R$^a$—R$^b$ is —C$_{1-2}$alkyl-[N(R$^x$)(R$^y$)], wherein R$^x$ is H or C$_{1-2}$alkyl, and R$^y$ is —C$_{1-2}$alkyl-OH. In embodiments, —R$^a$—R$^b$ is —C$_{1-2}$alkyl-C$_{1-2}$alkoxy-OH. In some variations, the embodiments provided herein also apply to a compound of formula (II'), or a stereoisomer or tautomer thereof, or a pharmaceutically acceptable salt of any of the foregoing, or any variation or embodiment thereof. In embodiments, —R$^a$—R$^b$ is as defined above or elsewhere herein, for a compound of formula (II') or formula (II).

In embodiments, R$^1$ is

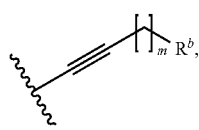

wherein m is an integer from 0-6 and R$^b$ is 3-15 membered heterocyclyl, —O-(3-15 membered heterocyclyl), C$_{1-6}$alkoxy, —OH, —CN, halo, or —N(R$^x$)(R$^y$), wherein
the 3-15 membered heterocyclyl of R$^b$ is optionally substituted with one or more R$^c$, wherein each R$^c$ is independently —OH, —CN, halo, oxo, C$_{1-6}$alkyl, C$_{1-6}$alkoxy, C$_{3-10}$ cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein
the C$_{1-6}$alkyl of R$^c$ is optionally substituted with one or more —OH, —CN, halo, C$_{1-6}$alkoxy, or 3-15 membered heterocyclyl,
the C$_{3-10}$ cycloalkyl of R$^c$ is optionally substituted with one or more halo,
the 3-15 membered heterocyclyl of R$^c$ is optionally substituted with one or more C$_{1-6}$ alkyl or —C(O)—C$_{1-6}$alkyl, and
the C$_{1-6}$alkoxy of R$^b$ is optionally substituted with one or more —OH, wherein
the R$^x$ and R$^y$ of —C(O)N(R$^x$)(R$^y$) and —N(R$^x$)(R$^y$) are, independently of each other and independently at each occurrence, H, —C(O)—CH$_2$—NH$_2$, 5-20 membered heteroaryl, or C$_{1-6}$ alkyl, wherein the C$_{1-6}$alkyl of R$^x$ or R$^y$ is optionally substituted with one or more —OH, 3-15 membered heterocyclyl, or —C(O)-(3-15 membered heterocyclyl). In some variations, the embodiments provided herein also apply to a compound of formula (II'), or a stereoisomer or tautomer thereof, or a pharmaceutically acceptable salt of any of the foregoing, or any variation or embodiment thereof. In embodiments, R$^1$ is as defined above or elsewhere herein, for a compound of formula (II') or formula (II).

In embodiments, m is 0 and R$^b$ is 3-15 membered heterocyclyl, —O-(3-15 membered heterocyclyl), C$_{1-6}$alkoxy, —OH, —CN, halo, or —N(R$^x$)(R$^y$), wherein the 3-15 membered heterocyclyl of R$^b$ is optionally substituted with one or more R$^c$, wherein each R$^c$ is independently —OH, —CN, halo, oxo, C$_{1-6}$alkyl, C$_{1-6}$alkoxy, C$_{3-10}$ cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein the C$_{1-6}$alkyl of R$^c$ is optionally substituted with one or more —OH, —CN, halo, C$_{1-6}$alkoxy, or 3-15 membered heterocyclyl, the C$_{3-10}$ cycloalkyl of R$^c$ is optionally substituted with one or more halo, and the 3-15 membered heterocyclyl of R$^c$ is optionally substituted with one or more C$_{1-6}$alkyl or —C(O)—C$_{1-6}$alkyl, and the C$_{1-6}$alkoxy of R$^b$ is optionally substituted with one or more —OH, wherein the R$^x$ and R$^y$ of —C(O)N(R$^x$)(R$^y$) and —N(R$^x$)(R$^y$) are, independently of each other and independently at each occurrence, H, —C(O)—CH$_2$—NH$_2$, 5-20 membered heteroaryl, or C$_{1-6}$alkyl, wherein the C$_{1-6}$alkyl of R$^x$ or R$^y$ is optionally substituted with one or more —OH, 3-15 membered heterocyclyl, or —C(O)-(3-15 membered heterocyclyl). In some variations, the embodiments provided herein also apply to a compound of formula (II'), or a stereoisomer or tautomer thereof, or a pharmaceutically acceptable salt of any of the foregoing, or any variation or embodiment thereof. In embodiments, m and R$^b$ are as defined above or elsewhere herein, for a compound of formula (II') or formula (II).

In embodiments, m is an integer from 1-6 and R$^b$ is 3-15 membered heterocyclyl, —O-(3-15 membered heterocyclyl), C$_{1-6}$alkoxy, —OH, —CN, halo, or —N(R$^x$)(R$^y$), wherein the 3-15 membered heterocyclyl of R$^b$ is optionally substituted with one or more R$^c$, wherein each R$^c$ is independently —OH, —CN, halo, oxo, C$_{1-6}$alkyl, C$_{1-6}$alkoxy, C$_{3-10}$cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein the C$_{1-6}$alkyl of R$^c$ is optionally substituted with one or more —OH, —CN, halo, C$_{1-6}$alkoxy, or 3-15 membered heterocyclyl, the C$_{3-10}$ cycloalkyl of R$^c$ is optionally substituted with one or more halo, and the 3-15 membered heterocyclyl of R$^c$ is optionally substituted with one or more C$_{1-6}$alkyl or —C(O)—C$_{1-6}$alkyl, and the C$_{1-6}$alkoxy of R$^b$ is optionally substituted with one or more —OH, wherein the R$^x$ and R$^y$ of —C(O)N(R$^x$)(R$^y$) and —N(R$^x$)(R$^y$) are, independently of each other and independently at each occurrence, H, —C(O)—CH$_2$—NH$_2$, 5-20 membered heteroaryl, or C$_{1-6}$alkyl, wherein the C$_{1-6}$alkyl of R$^x$ or R$^y$ is optionally substituted with one or more —OH, 3-15 membered heterocyclyl, or —C(O)-(3-15 membered heterocyclyl). In embodiments, m is an integer from 1-6 and R$^b$ is 3-15 membered heterocyclyl, wherein the 3-15 membered heterocyclyl of R$^b$ is optionally substituted with one or more R$^c$. In some variations, the embodiments provided herein also apply to a compound of formula (II'), or a stereoisomer or tautomer thereof, or a pharmaceutically acceptable salt of any of the foregoing, or any variation or embodiment thereof. In embodiments, m and R$^b$ are as defined above or elsewhere herein, for a compound of formula (II') or formula (II).

In embodiments, m is 1 and R$^b$ is 3-15 membered heterocyclyl, —O-(3-15 membered heterocyclyl), C$_{1-6}$alkoxy, —OH, —CN, halo, or —N(R$^x$)(R$^y$), wherein the 3-15 membered heterocyclyl of R$^b$ is optionally substituted with one or more R$^c$, wherein each R$^c$ is independently —OH, —CN, halo, oxo, C$_{1-6}$alkyl, C$_{1-6}$alkoxy, C$_{3-10}$ cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein the C$_{1-6}$alkyl of R$^c$ is optionally substituted with one or more —OH, —CN, halo, C$_{1-6}$alkoxy, or 3-15 membered heterocyclyl, the C$_{3-10}$ cycloalkyl of R$^c$ is optionally substituted with one or more halo, and the 3-15 membered heterocyclyl of R$^c$ is optionally substituted with one or more C$_{1-6}$alkyl or —C(O)—C$_{1-6}$alkyl, and the C$_{1-6}$alkoxy of R$^b$ is optionally substituted with one or more —OH, wherein the R$^x$ and R$^y$ of —C(O)N(R$^x$)(R$^y$) and —N(R$^x$)(R$^y$) are, independently of each other and independently at each occurrence, H, —C(O)—CH$_2$—NH$_2$, 5-20 membered heteroaryl, or C$_{1-6}$alkyl, wherein the C$_{1-6}$alkyl of R$^x$ or R$^y$ is optionally substituted with one or more —OH, 3-15 membered heterocyclyl, or —C(O)-(3-15 membered heterocyclyl). In embodiments, m is 1 and R$^b$ is 3-15 membered heterocyclyl, wherein the 3-15 membered heterocyclyl of R$^b$ is optionally substituted with one or more $R^c$. In some variations, the embodiments provided herein also apply to a compound of formula (II'), or a stereoisomer or tautomer thereof, or a pharmaceutically acceptable salt of any of the foregoing, or any variation or embodiment thereof. In embodiments, m and $R^b$ are as defined above or elsewhere herein, for a compound of formula (II') or formula (II).

In embodiments, m is 2 and $R^b$ is 3-15 membered heterocyclyl, —O-(3-15 membered heterocyclyl), $C_{1-6}$alkoxy, —OH, —CN, halo, or —N($R^x$)($R^y$), wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl, and the $C_{1-6}$alkoxy of $R^b$ is optionally substituted with one or more —OH, wherein the $R^x$ and $R^y$ of —C(O)N($R^x$)($R^y$) and —N($R^x$)($R^y$) are, independently of each other and independently at each occurrence, H, —C(O)—CH$_2$—NH$_2$, 5-20 membered heteroaryl, or $C_{1-6}$alkyl, wherein the $C_{1-6}$alkyl of $R^x$ or $R^y$ is optionally substituted with one or more —OH, 3-15 membered heterocyclyl, or —C(O)-(3-15 membered heterocyclyl). In embodiments, m is 2 and $R^b$ is 3-15 membered heterocyclyl, wherein the 3-15 membered heterocyclyl of $R^b$ is optionally substituted with one or more $R^c$. In some variations, the embodiments provided herein also apply to a compound of formula (II'), or a stereoisomer or tautomer thereof, or a pharmaceutically acceptable salt of any of the foregoing, or any variation or embodiment thereof. In embodiments, m and $R^b$ are as defined above or elsewhere herein, for a compound of formula (II') or formula (II).

In embodiments, provided herein is a compound of formula (II-A), or a stereoisomer or tautomer thereof, or a pharmaceutically acceptable salt of any of the foregoing, wherein $R^a$ is methyl, wherein the methyl of $R^a$ is substituted with one $R^b$, such that the compound of formula (II-A) is a compound of formula (II-A1):

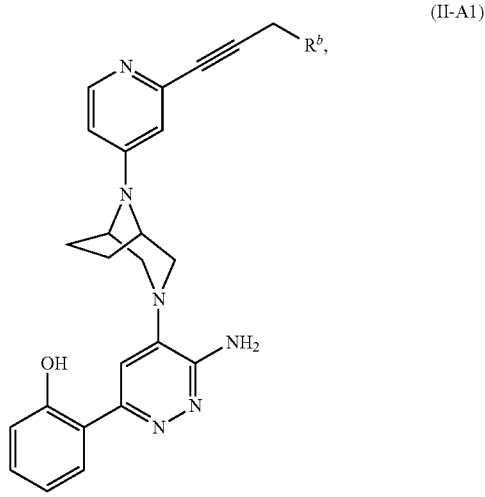

(II-A1)

or a stereoisomer or tautomer thereof, or a pharmaceutically acceptable salt of any of the foregoing. In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^b$ is as defined above or elsewhere herein, for a compound of formula (II') or formula (II). In some variations, $R^b$ is as defined above or elsewhere herein for a compound of formula (II-A), or (II-A1). In another variation, $R^b$ of formula (II-A), or (II-A1), is as defined for a compound of formula (II'), or a stereoisomer or tautomer thereof, or a pharmaceutically acceptable salt of any of the foregoing, or any variation or embodiment thereof.

In embodiments, provided herein is a compound of formula (II), such as a compound of formula (II-A) or (II-A1), or a stereoisomer or tautomer thereof, or a pharmaceutically acceptable salt of any of the foregoing, wherein $R^b$ is 3-15 membered heterocyclyl, wherein the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^b$ is as defined above or elsewhere herein, for a compound of formula (II') or formula (II).

In embodiments, provided herein is a compound of formula (II), (II-A), or (II-A1), or a stereoisomer or tautomer thereof, or a pharmaceutically acceptable salt of any of the foregoing, wherein $R^b$ is 4-10 membered heterocyclyl, wherein the 4-10 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^b$ is as defined above or elsewhere herein, for a compound of formula (II') or formula (II).

In embodiments, provided herein is a compound of formula (II), (II-A), or (II-A1), or a stereoisomer or tautomer thereof, or a pharmaceutically acceptable salt of any of the foregoing, wherein $R^b$ is 5-6 membered heterocyclyl, wherein the 5-6 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein the C$_{1-6}$alkyl of R$^c$ is optionally substituted with one or more —OH, —CN, halo, or C$_{1-6}$alkoxy, the C$_{3-10}$ cycloalkyl of R$^c$ is optionally substituted with one or more halo, and the 3-15 membered heterocyclyl of R$^c$ is optionally substituted with one or more C$_{1-6}$alkyl or —C(O)—C$_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof. In embodiments, R$^b$ is as defined above or elsewhere herein, for a compound of formula (II') or formula (II).

In embodiments, provided herein is a compound of formula (II), (II-A), or (II-A1), or a stereoisomer or tautomer thereof, or a pharmaceutically acceptable salt of any of the foregoing, wherein R$^b$ is 5-6 membered heterocyclyl, wherein the 5-6 membered heterocyclyl of R$^b$ is optionally substituted with one or more R$^c$, wherein each R$^c$ is independently oxo or —N(R$^x$)(R$^y$). In embodiments, each R$^c$ is independently oxo or —NH$_2$. In embodiments, each R$^c$ is oxo. In embodiments, each R$^c$ is —NH$_2$. In some variations, the embodiments provided herein also apply to a compound of formula (II'), or a stereoisomer or tautomer thereof, or a pharmaceutically acceptable salt of any of the foregoing, or any variation or embodiment thereof. In embodiments, R$^b$ is as defined above or elsewhere herein, for a compound of formula (II') or formula (II).

In embodiments, provided herein is a compound of formula (II), (II-A), or (II-A1), or a stereoisomer or tautomer thereof, or a pharmaceutically acceptable salt of any of the foregoing, wherein R$^b$ is a saturated 5-6 membered heterocyclyl, wherein the saturated 5-6 membered heterocyclyl of R$^b$ comprises at least one annular N atom, and is optionally substituted with one or more R$^c$, wherein each R$^c$ is independently —OH, —CN, halo, oxo, C$_{1-6}$alkyl, C$_{1-6}$alkoxy, C$_{3-10}$ cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein the C$_{1-6}$alkyl of R$^c$ is optionally substituted with one or more —OH, —CN, halo, or C$_{1-6}$alkoxy, the C$_{3-10}$ cycloalkyl of R$^c$ is optionally substituted with one or more halo, and the 3-15 membered heterocyclyl of R$^c$ is optionally substituted with one or more C$_{1-6}$alkyl or —C(O)—C$_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof. In embodiments, R$^b$ is as defined above or elsewhere herein, for a compound of formula (II') or formula (II).

In embodiments, provided herein is a compound of formula (II), (II-A), or (II-A1), or a stereoisomer or tautomer thereof, or a pharmaceutically acceptable salt of any of the foregoing, wherein R$^b$ is a saturated 5-6 membered heterocyclyl, wherein the saturated 5-6 membered heterocyclyl of R$^b$ comprises at least one annular N atom and is optionally substituted with one or more R$^c$, wherein each R$^c$ is independently oxo or —N(R$^x$)(R$^y$). In embodiments, each R$^c$ is independently oxo or —NH$_2$. In embodiments, each R$^c$ is oxo. In embodiments, each R$^c$ is —NH$_2$. In some variations, the embodiments provided herein also apply to a compound of formula (II'), or a stereoisomer or tautomer thereof, or a pharmaceutically acceptable salt of any of the foregoing, or any variation or embodiment thereof. In embodiments, R$^b$ is as defined above or elsewhere herein, for a compound of formula (II') or formula (II).

In embodiments, provided herein is a compound of formula (II), (II-A), or (II-A1), or a stereoisomer or tautomer thereof, or a pharmaceutically acceptable salt of any of the foregoing, wherein R$^b$ is pyrrolidinyl, piperidinyl, piperazinyl, morpholinyl, or thiomorpholinyl, wherein the pyrrolidinyl, piperidinyl, piperazinyl, morpholinyl, or thiomorpholinyl of R$^b$ is independently optionally substituted with one or more R$^c$, wherein each R$^c$ is independently —OH, —CN, halo, oxo, C$_{1-6}$alkyl, C$_{1-6}$alkoxy, C$_{3-10}$ cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein the C$_{1-6}$alkyl of R$^c$ is optionally substituted with one or more —OH, —CN, halo, or C$_{1-6}$alkoxy, the C$_{3-10}$ cycloalkyl of R$^c$ is optionally substituted with one or more halo, and the 3-15 membered heterocyclyl of R$^c$ is optionally substituted with one or more C$_{1-6}$alkyl or —C(O)—C$_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof, wherein R$^b$ and R$^c$ are as defined above or elsewhere herein for a compound of formula (II). In another variation, R$^b$ and R$^c$ of formula (II), (II-A), or (II-A1), are as defined for a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein R$^b$ is pyrrolidinyl, piperidinyl, piperazinyl, morpholinyl, or thiomorpholinyl, wherein the pyrrolidinyl, piperidinyl, piperazinyl, morpholinyl, or thiomorpholinyl of R$^b$ is independently optionally substituted with one or more R$^c$, wherein each R$^c$ is independently oxo or —N(R$^x$)(R$^y$). In embodiments, each R$^c$ is independently oxo or —NH$_2$. In embodiments, each R$^c$ is oxo. In embodiments, each R$^c$ is —NH$_2$. In some variations, the embodiments provided herein also apply to a compound of formula (II'), or a stereoisomer or tautomer thereof, or a pharmaceutically acceptable salt of any of the foregoing, or any variation or embodiment thereof, wherein R$^b$ and R$^c$ are as defined above or elsewhere herein for a compound of formula (II). In another variation, R$^b$ and R$^c$ of formula (II), (II-A), or (II-A1), are as defined for a compound of formula (II'), or a stereoisomer or tautomer thereof, or a pharmaceutically acceptable salt of any of the foregoing, or any variation or embodiment thereof.

In embodiments of the foregoing, R$^b$ is selected from the group consisting of

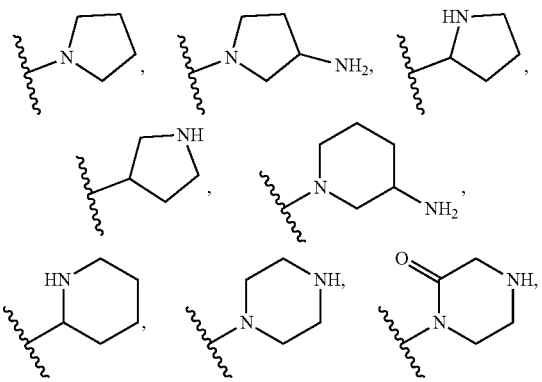

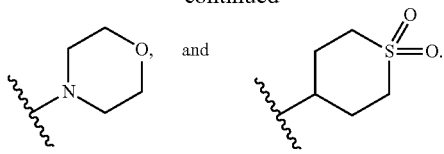

In embodiments of the foregoing, provided herein is a compound of formula (II) or (II-A), or a stereoisomer or tautomer thereof, or a pharmaceutically acceptable salt of any of the foregoing, wherein $R^a$ is selected from the group consisting of

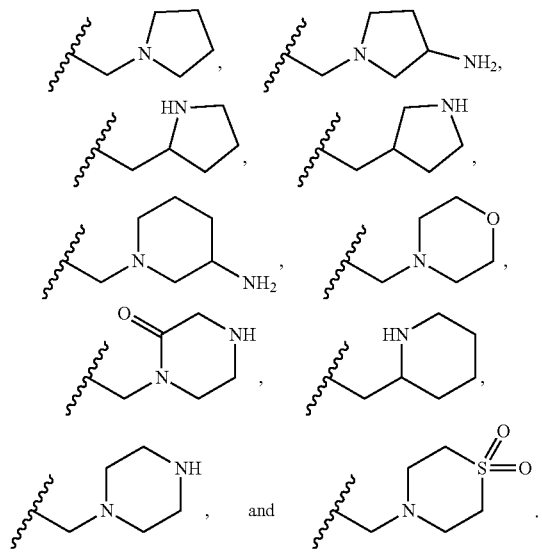

In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^a$ is as defined above or elsewhere herein, for a compound of formula (II') or formula (II).

In embodiments, provided herein is a compound of formula (II), (II-A), or (II-A1), or a stereoisomer or tautomer thereof, or a pharmaceutically acceptable salt of any of the foregoing, wherein $R^b$ is a 9-10 membered heterocycle, wherein the 9-10 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is a 9-10 membered heterocycle, wherein the 9-10 membered heterocyclyl of $R^b$ is optionally substituted with one or more $R^c$, wherein each $R^c$ is independently —OH, —$C_{1-2}$alkyl. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is a 9-10 membered heterocycle, wherein the 9-10 membered heterocyclyl of $R^b$ comprises at least one annular N atom and is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is a 9-10 membered heterocycle, wherein the 9-10 membered heterocyclyl of $R^b$ comprises at least one annular N atom and is optionally substituted with one or more $R^c$, wherein each $R^c$ is independently —OH, —$C_{1-2}$alkyl. In some variations, the embodiments provided herein also apply to a compound of formula (II'), or a stereoisomer or tautomer thereof, or a pharmaceutically acceptable salt of any of the foregoing, or any variation or embodiment thereof.

In embodiments of the foregoing, $R^b$ is a heterocycle selected from the group consisting of:

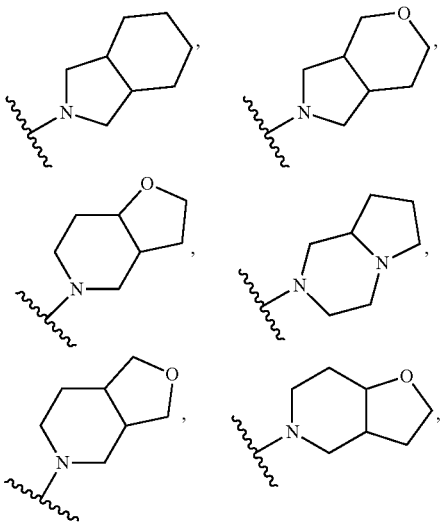

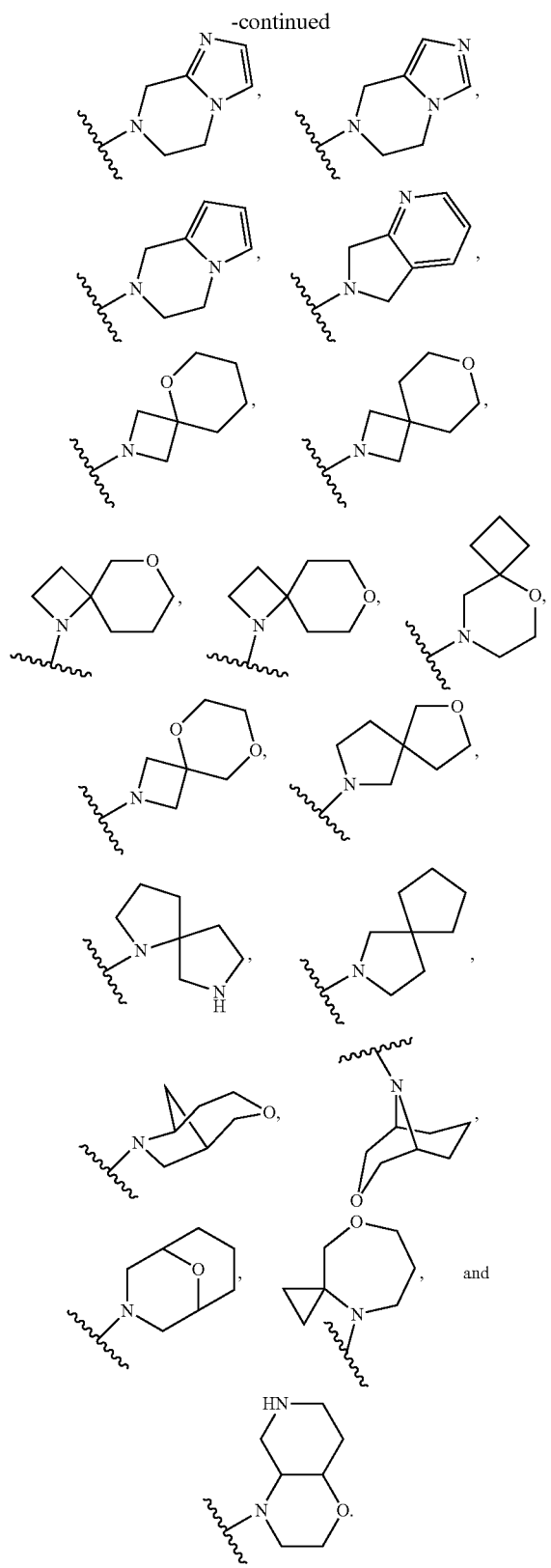

In embodiments, provided herein is a compound of formula (II), (II-A), or (II-A1), or a stereoisomer or tautomer thereof, or a pharmaceutically acceptable salt of any of the foregoing, wherein $R^b$ is a 7-8 membered heterocycle, wherein the 7-8 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is a 7-8 membered heterocycle, wherein the 7-8 membered heterocyclyl of $R^b$ is optionally substituted with one or more $R^c$, wherein each $R^c$ is independently —OH, -halo, —$C_{1-2}$alkyl, $C_{1-2}$ alkoxy, —$C_{1-5}$cycloalkyl, wherein the $C_{1-2}$alkyl is optionally substituted with one or more halo. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is a 7-8 membered heterocycle, wherein the 7-8 membered heterocyclyl of $R^b$ comprises at least one annular N atom and is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is a 7-8 membered heterocycle, wherein the 7-8 membered heterocyclyl of $R^b$ comprises at least one annular N atom and is optionally substituted with one or more $R^c$, wherein each $R^c$ is independently —OH, -halo, —$C_{1-2}$alkyl, $C_{1-2}$alkoxy, —$C_{1-5}$cycloalkyl, wherein the $C_{1-2}$alkyl is optionally substituted with one or more halo. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, $R^b$ is a heterocycle selected from the group consisting of:

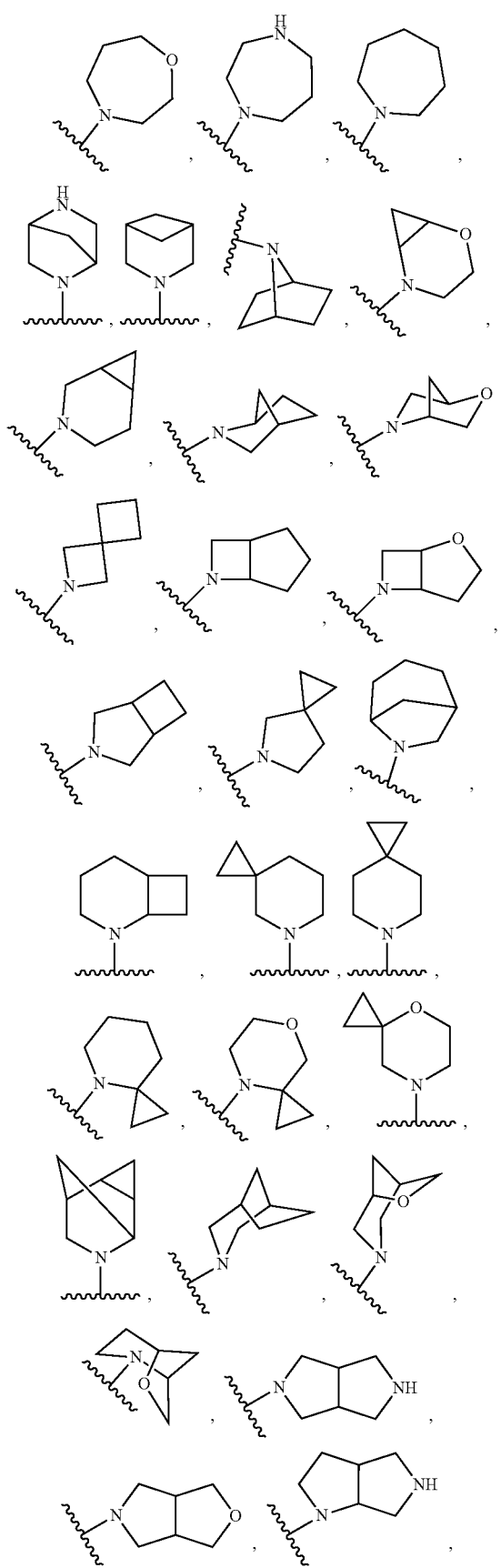

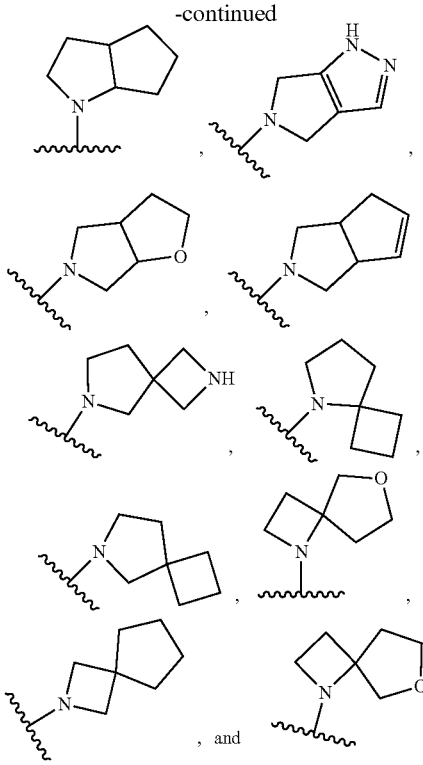

In embodiments, provided herein is a compound of formula (II), (II-A), or (II-A1), or a stereoisomer or tautomer thereof, or a pharmaceutically acceptable salt of any of the foregoing, wherein $R^b$ is a 4 membered heterocycle, wherein the 4 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is a 4 membered heterocycle, wherein the 4 membered heterocyclyl of $R^b$ is optionally substituted with one or more $R^c$, wherein each $R^c$ is independently —OH, —CN, $C_{1-2}$alkyl, $C_{3-5}$cycloalkyl, 3-5 membered heterocycle, wherein the $C_{1-2}$alkyl is optionally substituted with -halo, —CN. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is a 4 membered heterocycle, wherein the 4 membered heterocyclyl of $R^b$ comprises at least one annular N atom and is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, or $C_{1-6}$alkoxy, the $C_{3-10}$ cycloalkyl of $R^c$ is optionally substituted with one or more halo, and the 3-15 membered heterocyclyl of $R^c$ is optionally substituted with one or more $C_{1-6}$alkyl or —C(O)—$C_{1-6}$alkyl. In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is a 4 membered heterocycle, wherein the 4 membered heterocyclyl of $R^b$ comprises at least one annular N atom and is optionally substituted with one or more $R^c$, wherein each $R^c$ is independently —OH, —CN, $C_{1-2}$alkyl, $C_{3-5}$cycloalkyl, 3-5 membered heterocycle, wherein the $C_{1-2}$alkyl is optionally substituted with -halo, —CN. In some variations, the embodiments provided herein also apply to a compound of formula (II'), or a stereoisomer or tautomer thereof, or a pharmaceutically acceptable salt of any of the foregoing, or any variation or embodiment thereof.

In embodiments of the foregoing, $R^b$ is a heterocycle selected from the group consisting of:

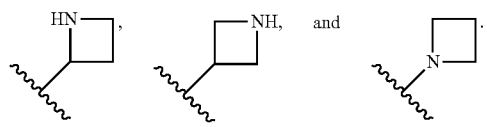 [SMILES: *C1CCN1 ; *C1CNC1 ; *N1CCC1]

In embodiments, provided herein is a compound of formula (II), (II-A), or (II-A1), or a stereoisomer or tautomer thereof, or a pharmaceutically acceptable salt of any of the foregoing, wherein $R^b$ is —N($R^x$)($R^y$). In embodiments, $R^b$ is —N($R^x$)($R^y$), wherein $R^x$ and $R^y$ are each independently H or $C_{1-6}$alkyl, wherein the $C_{1-6}$alkyl is optionally substituted with one or more —OH. In embodiments, $R^b$ is selected from the group consisting of

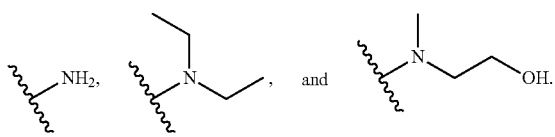

In embodiments of the foregoing, provided herein is a compound of formula (II) or (II-A), or a stereoisomer or tautomer thereof, or a pharmaceutically acceptable salt of any of the foregoing, wherein $R^a$ is selected from the group consisting of

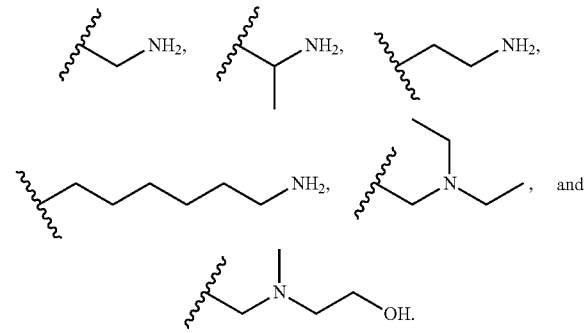

In embodiments, $R^b$ is as defined above for a compound of formula (II). In embodiments, $R^a$ as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^b$ and $R^a$ are as defined above or elsewhere herein, for a compound of formula (II').

In embodiments, $R^1$ is —C≡C—$R^a$, wherein $R^a$ is $C_{1-6}$alkyl, wherein the $C_{1-6}$alkyl of $R^a$ is optionally substituted with one or more $R^b$, wherein each $R^b$ is independently $C_{1-6}$alkyl, —NH$_2$. In embodiments, $R^a$ is

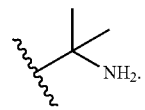 [SMILES: *C(C)(C)N]

In embodiments, provided herein is a compound of formula (II), formula (II), (II-A), or (II-A1), or a stereoisomer or tautomer thereof, or a pharmaceutically acceptable salt of any of the foregoing, wherein $R^b$ is —N($R^x$)($R^y$). In embodiments, $R^b$ is —N($R^x$)($R^y$), wherein $R^x$ and $R^y$ are each independently —H, $C_{1-6}$alkyl, or 3-6 membered heterocycle, wherein each $C_{1-6}$alkyl is optionally substituted with -oxo, 3-6 membered heterocycle. In embodiments, $R^b$ is selected from the group consisting of

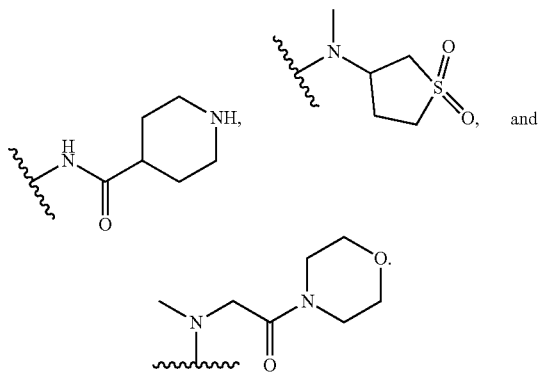

In some variations, the embodiments provided herein also apply to a compound of formula (II'), or a stereoisomer or tautomer thereof, or a pharmaceutically acceptable salt of any of the foregoing, or any variation or embodiment thereof.

In embodiments, provided herein is a compound of formula (II), (II-A), or (II-A1), or a stereoisomer or tautomer thereof, or a pharmaceutically acceptable salt of any of the foregoing, wherein $R^b$ is —OH. In embodiments, provided herein is a compound of formula (II) or (II-A), or a stereoisomer or tautomer thereof, or a pharmaceutically acceptable salt of any of the foregoing, wherein $R^a$ is

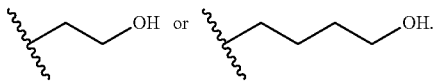

In embodiments, $R^b$ is as defined above for a compound of formula (II). In embodiments, $R^a$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^b$ and $R^a$ are as defined above or elsewhere herein, for a compound of formula (II').

In embodiments, provided herein is a compound of formula (II), (II-A), or (II-A1), or a stereoisomer or tautomer thereof, or a pharmaceutically acceptable salt of any of the foregoing, wherein $R^b$ is —O-(3-15 membered heterocyclyl). In embodiments, $R^b$ is —O-(4-10 membered heterocyclyl). In embodiments, $R^b$ is —O-(4-6 membered heterocyclyl). In embodiments, $R^b$ is —O-(5-6 membered heterocyclyl). In embodiments, $R^b$ is —O-(6 membered heterocyclyl). In embodiments, the 6-membered heterocyclyl of —O-(6 membered heterocyclyl) is saturated and comprises at least one annular N atom. In embodiments, $R^b$ is —O-(piperidinyl). In embodiments, In embodiments, $R^b$ is

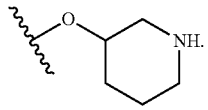

In embodiments, provided herein is a compound of formula (II) or (II-A), or a stereoisomer or tautomer thereof, or a pharmaceutically acceptable salt of any of the foregoing, wherein $R^a$ is

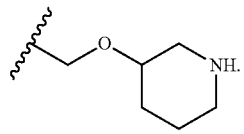 [SMILES: *COC1CCCNC1]

In embodiments, $R^b$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^b$ and $R^a$ are as defined above or elsewhere herein, for a compound of formula (II').

In embodiments, provided herein is a compound of formula (II), (II-A), or (II-A1), or a stereoisomer or tautomer thereof, or a pharmaceutically acceptable salt of any of the foregoing, wherein $R^b$ is $C_{1-6}$alkoxy, wherein the $C_{1-6}$alkoxy of $R^b$ is optionally substituted with one or more —OH. In embodiments, $R^b$ is $C_{1-4}$alkoxy, wherein the $C_{1-4}$alkoxy of $R^b$ is optionally substituted with one or more —OH. In embodiments, $R^b$ is $C_{1-3}$alkoxy, wherein the $C_{1-3}$alkoxy of $R^b$ is optionally substituted with one or more —OH. In embodiments, $R^b$ is $C_{1-2}$alkoxy, wherein the $C_{1-2}$alkoxy of $R^b$ is optionally substituted with one or more —OH. In embodiments, $R^b$ is ethoxy, wherein the ethoxy of $R^b$ is optionally substituted with one or more —OH. In embodiments, $R^b$ is

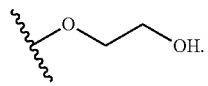 [SMILES: *OCCO]

In embodiments, provided herein is a compound of formula (II) or (II-A), or a stereoisomer or tautomer thereof, or a pharmaceutically acceptable salt of any of the foregoing, wherein $R^a$ is

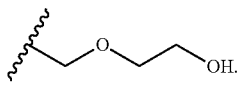 [SMILES: *COCCO]

In embodiments, $R^b$ is as defined above for a compound of formula (II). In embodiments, $R^a$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^b$ and $R^a$ are as defined above or elsewhere herein, for a compound of formula (II').

In embodiments, provided herein is a compound of formula (II) or (II-A), or a stereoisomer or tautomer thereof, or a pharmaceutically acceptable salt of any of the foregoing, wherein $R^a$ is $C_{3-10}$ cycloalkyl, wherein the $C_{3-10}$ cycloalkyl of $R^a$ is optionally substituted with one or more $R^z$, wherein $R^z$ is —OH, —CN, halo, $C_{1-6}$alkyl, $C_{1-6}$alkoxy, —N($R^x$)($R^y$), or —C(O)—N($R^x$)($R^y$). In embodiments, $R^a$ is $C_{3-6}$cycloalkyl, wherein the $C_{3-6}$ cycloalkyl of $R^a$ is optionally substituted with one or more $R^z$. In embodiments, $R^a$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^a$ is as defined above or elsewhere herein, for a compound of formula (II').

In embodiments, provided herein is a compound of formula (II) or (II-A), or a stereoisomer or tautomer thereof, or a pharmaceutically acceptable salt of any of the foregoing, wherein $R^a$ is $C_{4-6}$cycloalkyl, wherein the $C_{4-6}$cycloalkyl of $R^a$ is optionally substituted with one or more $R^z$. In embodiments, $R^a$ is a saturated $C_{4-6}$cycloalkyl, wherein the saturated $C_{4-6}$cycloalkyl of $R^a$ is optionally substituted with one or more $R^z$. In embodiments, $R^a$ is cyclohexyl, wherein the cyclohexyl of $R^a$ is optionally substituted with one or more $R^z$. In embodiments, provided herein is a compound of formula (II) or (II-A), or a stereoisomer or tautomer thereof, or a pharmaceutically acceptable salt of any of the foregoing, wherein $R^a$ is $C_{4-6}$cycloalkyl, wherein the $C_{4-6}$cycloalkyl of $R^a$ is optionally substituted with one or more —NH$_2$.

In embodiments, $R^a$ is $C_{4-6}$cycloalkyl, wherein the $C_{4-6}$cycloalkyl of $R^a$ is optionally substituted with one or more —$NH_2$. In embodiments, $R^a$ is cyclohexyl, wherein the cyclohexyl of $R^a$ is optionally substituted with one or more —$NH_2$. In embodiments, $R^a$ is

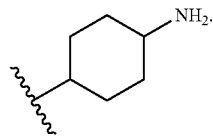 [SMILES: *C1CCC(N)CC1]

In embodiments, $R^a$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^a$ is as defined above or elsewhere herein, for a compound of formula (II').

In embodiments, provided herein is a compound of formula (II) or (II-A), or a stereoisomer or tautomer thereof, or a pharmaceutically acceptable salt of any of the foregoing, wherein $R^a$ is 3-15 membered heterocyclyl, wherein the 3-15 membered heterocyclyl of $R^a$ is optionally substituted with one or more $R^z$, wherein $R^z$ is —OH, —CN, halo, $C_{1-6}$alkyl, $C_{1-6}$alkoxy, —$N(R^x)(R^y)$, or —$C(O)$—$N(R^x)(R^y)$. In embodiments, $R^a$ is 3-10 membered heterocyclyl, wherein the 3-10 membered heterocyclyl of $R^a$ is optionally substituted with one or more $R^z$. In embodiments, $R^a$ is 3-6 membered heterocyclyl, wherein the 3-6 membered heterocyclyl of $R^a$ is optionally substituted with one or more $R^z$. In embodiments, $R^a$ is 4-6 membered heterocyclyl, wherein the 4-6 membered heterocyclyl of $R^a$ is optionally substituted with one or more $R^z$. In embodiments, $R^a$ is 5-6 membered heterocyclyl, wherein the 5-6 membered heterocyclyl of $R^a$ is optionally substituted with one or more $R^z$. In embodiments, $R^a$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^a$ is as defined above or elsewhere herein, for a compound of formula (II').

In embodiments, $R^a$ is 3-15 membered heterocyclyl, wherein the 3-15 membered heterocyclyl of $R^a$ is unsubstituted. In embodiments, $R^a$ is 4-6 membered heterocyclyl, wherein the 4-6 membered heterocyclyl of $R^a$ is unsubstituted. In embodiments, $R^a$ is a saturated 4-6 membered heterocyclyl, wherein the saturated 4-6 membered heterocyclyl of $R^a$ is unsubstituted. In embodiments, $R^a$ comprises at least one annular N atom or at least one annular O atom. In embodiments, $R^a$ is azetidinyl, pyrrolidinyl, piperidinyl, tetrahydro-2H-pyranyl, or morpholinyl, wherein the azetidinyl, pyrrolidinyl, piperidinyl, tetrahydro-2H-pyranyl, or morpholinyl of $R^a$ are independently optionally substituted with one or more $R^z$. In embodiments, the azetidinyl, pyrrolidinyl, piperidinyl, tetrahydro-2H-pyranyl, or morpholinyl of $R^a$ is unsubstituted. In embodiments, $R^a$ is selected from the group consisting of

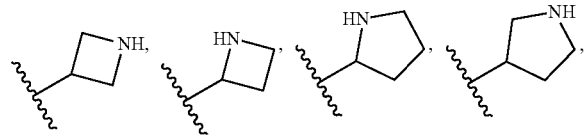

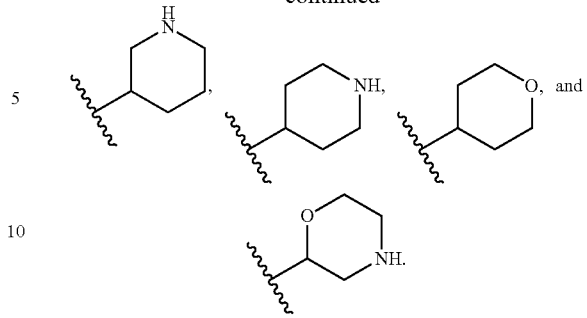

In embodiments, $R^a$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^a$ is as defined above or elsewhere herein, for a compound of formula (II').

In embodiments, provided herein is a compound of formula (II) or (II-A), or a stereoisomer or tautomer thereof, or a pharmaceutically acceptable salt of any of the foregoing, wherein $R^a$ is 5-20 membered heteroaryl, wherein the 5-20 membered heteroaryl of $R^a$ is optionally substituted with one or more $R^z$, wherein $R^z$ is —OH, —CN, halo, $C_{1-6}$alkyl, $C_{1-6}$alkoxy, —$N(R^x)(R^y)$, or —$C(O)$—$N(R^x)(R^y)$. In embodiments, $R^a$ is 5-10 membered heteroaryl, wherein the 5-10 membered heteroaryl of $R^a$ is optionally substituted with one or more $R^z$. In embodiments, $R^a$ is 5-6 membered heteroaryl, wherein the 5-6 membered heteroaryl of $R^a$ is optionally substituted with one or more $R^z$. In embodiments, $R^a$ is 5-membered heteroaryl, wherein the 5-membered heteroaryl of $R^a$ is optionally substituted with one or more $R^z$. In embodiments, $R^a$ is 5-6 membered heteroaryl, wherein the 5-6 membered heteroaryl of $R^a$ is optionally substituted with one or more $C_{1-6}$alkyl. In embodiments, $R^a$ is 5-membered heteroaryl, wherein the 5-membered heteroaryl of $R^a$ is optionally substituted with one or more $C_{1-6}$alkyl. In embodiments, $R^a$ is 5-membered heteroaryl, wherein the 5-membered heteroaryl of $R^a$ comprises at least one annular N atom and is optionally substituted with one or more $C_{1-6}$ alkyl. In embodiments, $R^a$ is 5-membered heteroaryl, wherein the 5-membered heteroaryl of $R^a$ is optionally substituted with one or more methyl. In embodiments, $R^a$ is pyrazolyl, wherein the pyrazolyl of $R^a$ is optionally substituted with one or more $C_{1-6}$alkyl. In embodiments, $R^a$ is pyrazolyl, wherein the pyrazolyl of $R^a$ is optionally substituted with one or more methyl. In embodiments, $R^a$ is

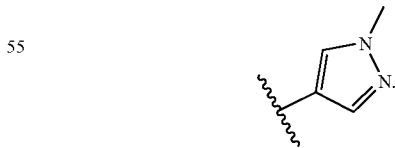

In embodiments, $R^a$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^a$ is as defined above or elsewhere herein, for a compound of formula (II').

In embodiments, provided herein is a compound of formula (II), or a stereoisomer or tautomer thereof, or a pharmaceutically acceptable salt of any of the foregoing, wherein $R^1$ is —$(CH_2)_n$—$R^g$, wherein n is an integer from 1-6 and $R^g$ is —$N(R^x)(R^y)$ or —OH. In embodiments of the foregoing, $R^g$ is —$N(R^x)(R^y)$, such that the compound of formula (II) is a compound of formula (II-B):

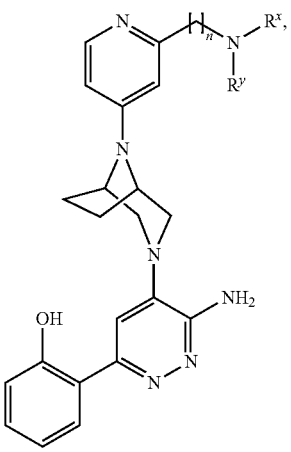

(II-B)

or a stereoisomer or tautomer thereof, or a pharmaceutically acceptable salt of any of the foregoing.

In embodiments, $R^1$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^1$ is as defined above or elsewhere herein, for a compound of formula (II').

In embodiments, provided herein is a compound of formula (II) or (II-B), or a stereoisomer or tautomer thereof, or a pharmaceutically acceptable salt of any of the foregoing, wherein $R^x$ and $R^y$ are both H. In embodiments, one of $R^x$ and $R^y$ is H and the other of $R^x$ and $R^y$ is —C(O)—$CH_2$—$NH_2$. In embodiments of the foregoing, n is an integer from 1-5, from 1-4, from 1-3, or from 1-2. In embodiments, n is an integer from 2-6, from 3-6, from 4-6, or from 5-6. In embodiments, n is an integer from 2-4. In embodiments, n is 6. In embodiments, n is 5. In embodiments, n is 4. In embodiments, n is 3. In embodiments, n is 2. In embodiments, n is 1. In embodiments, $R^x$ and $R^y$ are as defined above for a compound of formula (II). In embodiments, n is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, n, $R^x$ and $R^y$ are as defined above or elsewhere herein, for a compound of formula (II').

In embodiments, provided herein is a compound of formula (II), or a stereoisomer or tautomer thereof, or a pharmaceutically acceptable salt of any of the foregoing, wherein $R^1$ is —$(CH_2)_n$—$R^g$, wherein n is an integer from 1-3 and $R^g$ is —$N(R^x)(R^y)$, wherein the $R^x$ and $R^y$ of —$N(R^x)(R^y)$ are, independently of each other and independently at each occurrence, H, —C(O)—$(CH_2)_p$—$N(R^p)(R^q)$, 5-20 membered heteroaryl, or $C_{1-6}$alkyl, wherein p is an integer from 1-6, and $R^p$ and $R^q$ are, independently of each other and independently at each occurrence, H or $C_{1-6}$alkyl, and wherein the $C_{1-6}$alkyl of $R^x$ or $R^y$ is optionally substituted with one or more —OH. In embodiments, $R^1$ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, $R^1$ is as defined above or elsewhere herein, for a compound of formula (II').

In embodiments, $R^1$ is —$(CH_2)_n$—$R^g$, wherein n is 3 and $R^g$ is —$N(R^x)(R^y)$, wherein $R^x$ is H, and $R^y$ is —C(O)—$(CH_2)_p$—$N(R^p)(R^q)$, wherein p is 1, and $R^p$ and $R^q$ are, each H.

In embodiments, $R^1$ is —$(CH_2)_3$—$NH_2$. In embodiments, $R^1$ is —$(CH_2)_6$—$NH_2$. In embodiments, $R^1$ is —$(CH_2)_3$—NH—C(O)—$CH_2$—$NH_2$.

In embodiments, $R^1$ is —$(CH_2)_n$—$R^g$, wherein n is an integer from 1-6, and $R^g$ is —$N(R^x)(R^y)$, wherein the $R^x$ and $R^y$ of —$N(R^x)(R^y)$ are each hydrogen.

In embodiments, (i) $R^1$ is —C≡C—$R^a$, wherein
 (a) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH or —$N(R^x)(R^y)$, wherein
  the 3-15 membered heterocyclyl of $R^b$ is optionally substituted with one or more $R^c$, wherein each $R^c$ is independently oxo, $C_{1-6}$alkyl or —$N(R^x)(R^y)$, and wherein
  the $C_{1-6}$alkoxy of $R^b$ is optionally substituted with one or more —OH, or
 (b) $R^a$ is $C_{3-10}$cycloalkyl, wherein the $C_{3-10}$cycloalkyl of $R^a$ is optionally substituted with one or more $R^z$, or
 (c) $R^a$ is 3-15 membered heterocyclyl, wherein the 3-15 membered heterocyclyl of $R^a$ is optionally substituted with one or more $R^z$, or
 (d) $R^a$ is 5-20 membered heteroaryl, wherein the 5-20 membered heteroaryl of $R^a$ is optionally substituted with one or more $R^z$, or
(ii) $R^1$ is —$(CH_2)_n$—$R^g$, wherein n is an integer from 1-6 and $R^g$ is —$N(R^x)(R^y)$, wherein each $R^z$ is, independently at each occurrence, $C_{1-6}$alkyl or —$N(R^x)(R^y)$, and the $R^x$ and $R^y$ of —C(O)$N(R^x)(R^y)$ and —$N(R^x)(R^y)$ are, independently of each other and independently at each occurrence, H, —C(O)—$(CH_2)_p$—$N(R^p)(R^q)$, 5-20 membered heteroaryl, or $C_{1-6}$alkyl, wherein p is an integer from 1-6, and $R^p$ and $R^q$ are, independently of each other and independently at each occurrence, H or $C_{1-6}$alkyl, and wherein the $C_{1-6}$alkyl of $R^x$ or $R^y$ is optionally substituted with one or more —OH.

In embodiments, provided herein is a compound of formula (II), or a stereoisomer or tautomer thereof, or a pharmaceutically acceptable salt of the foregoing, wherein $R^1$ is selected from the group consisting of 191
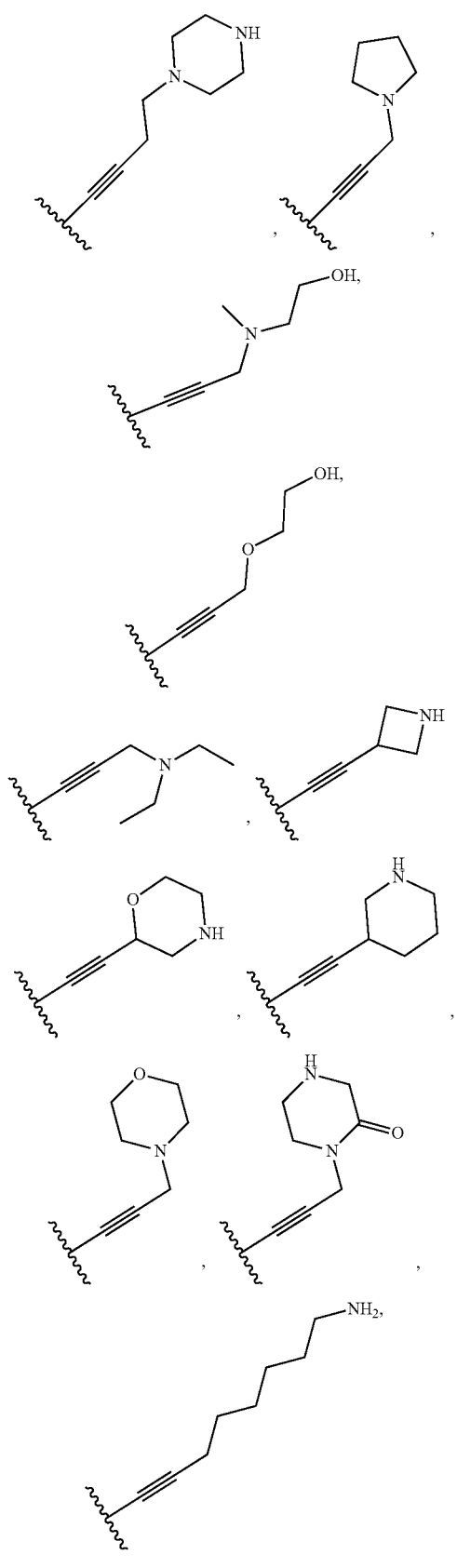
192
-continued
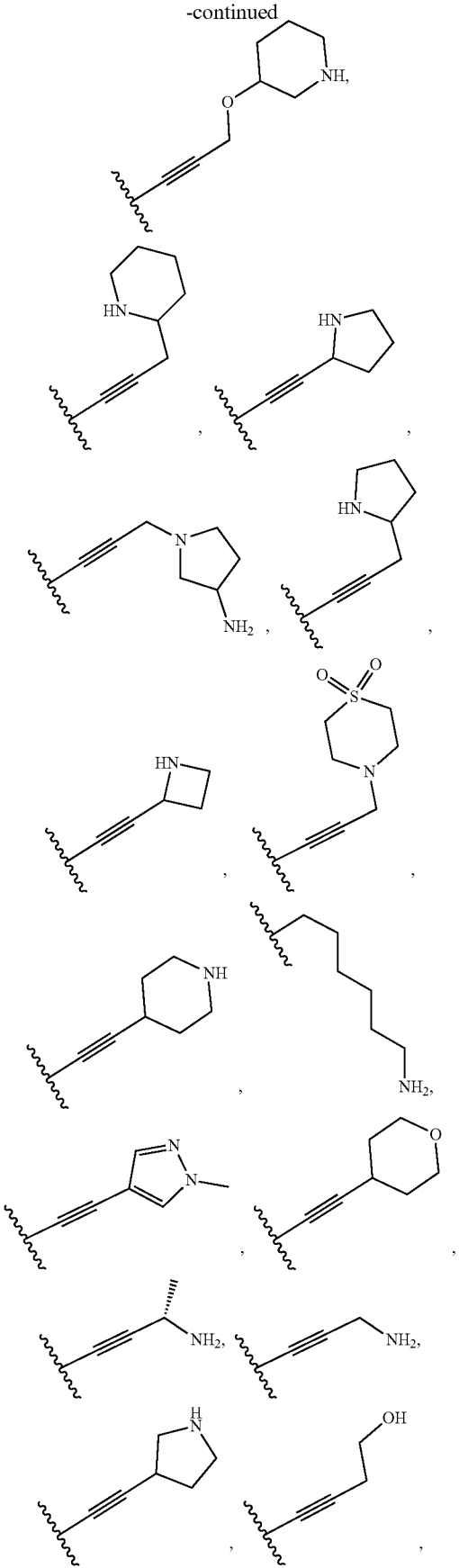

193

-continued

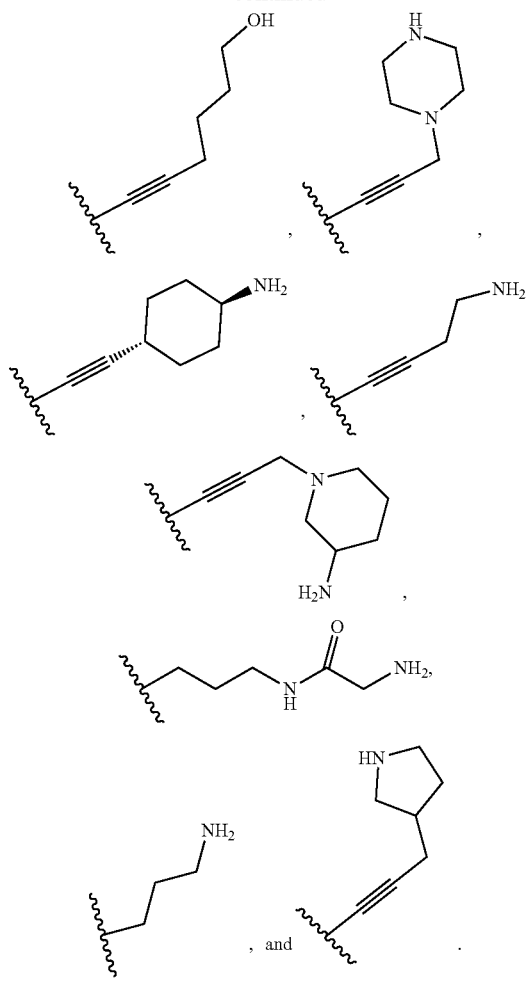

194

-continued

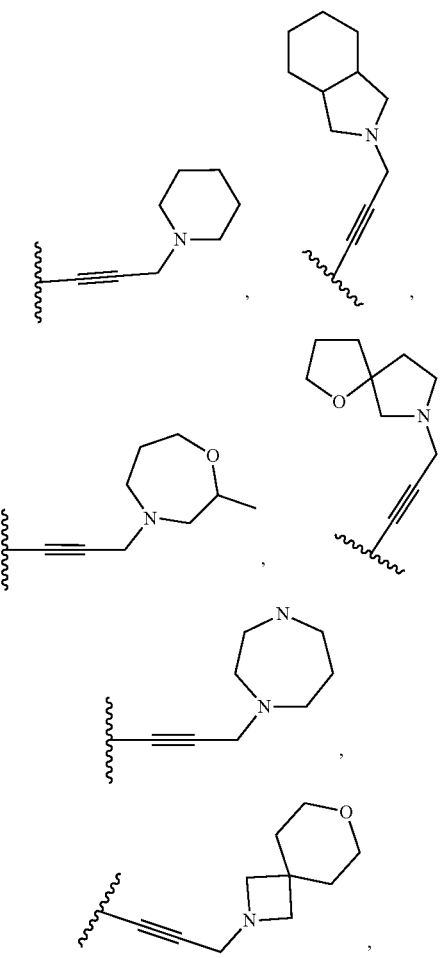

In embodiments, R¹ is as defined above for a compound of formula (II). In some variations, the embodiments provided herein also apply to a compound of formula (II'), or a stereoisomer or tautomer thereof, or a pharmaceutically acceptable salt of any of the foregoing, or any variation or embodiment thereof. In embodiments, R¹ is as defined above or elsewhere herein, for a compound of formula (II').

In embodiments, R¹ is selected from the group consisting of

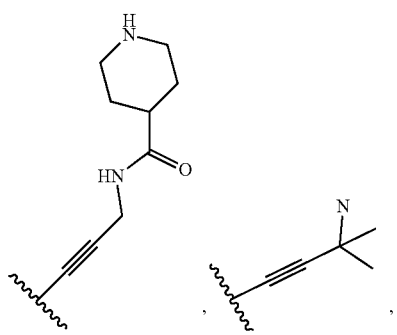

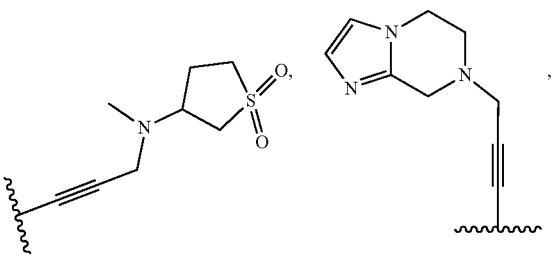

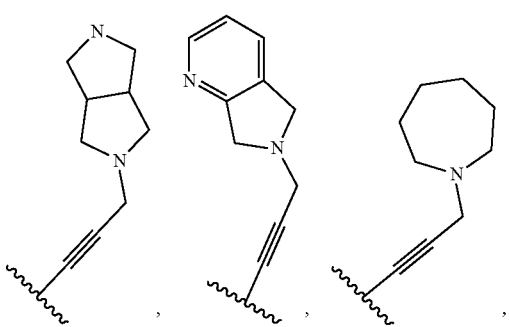

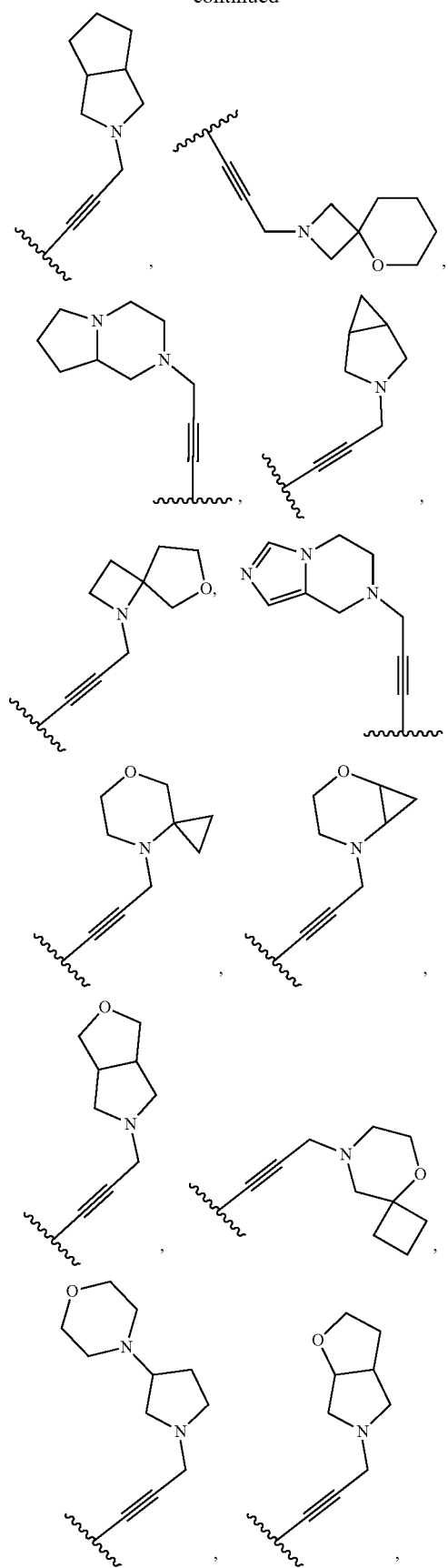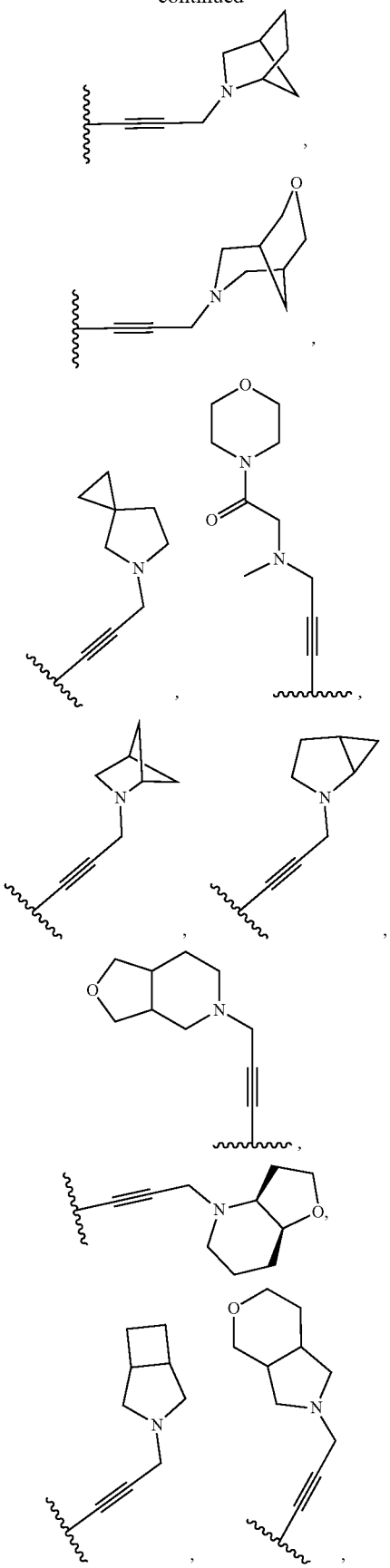

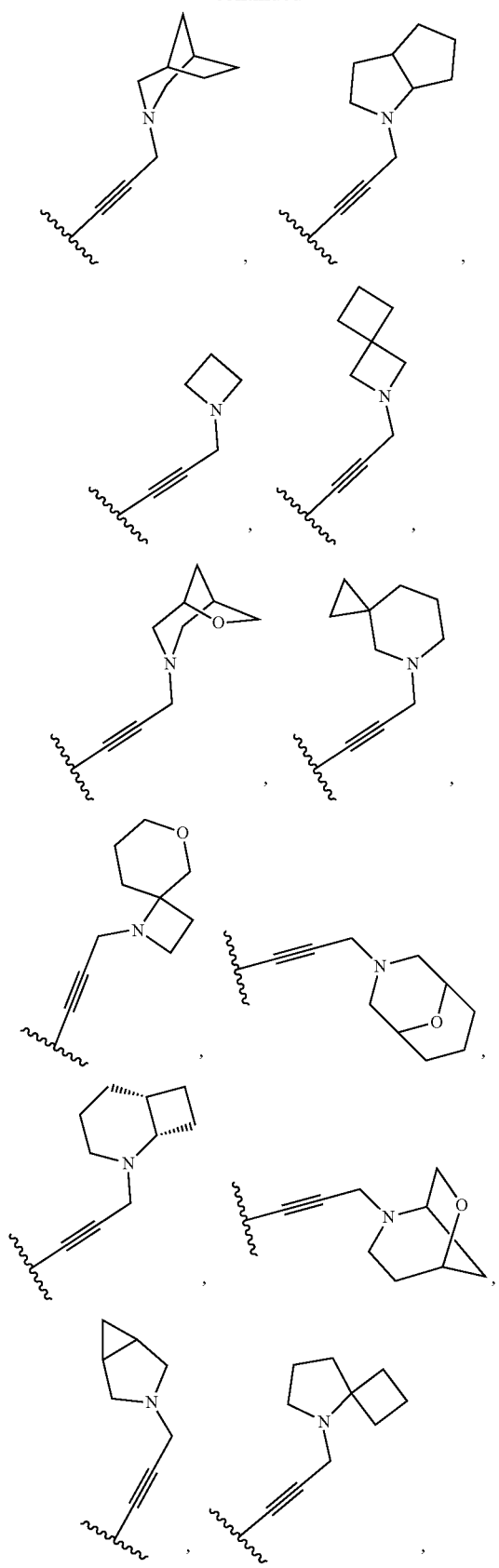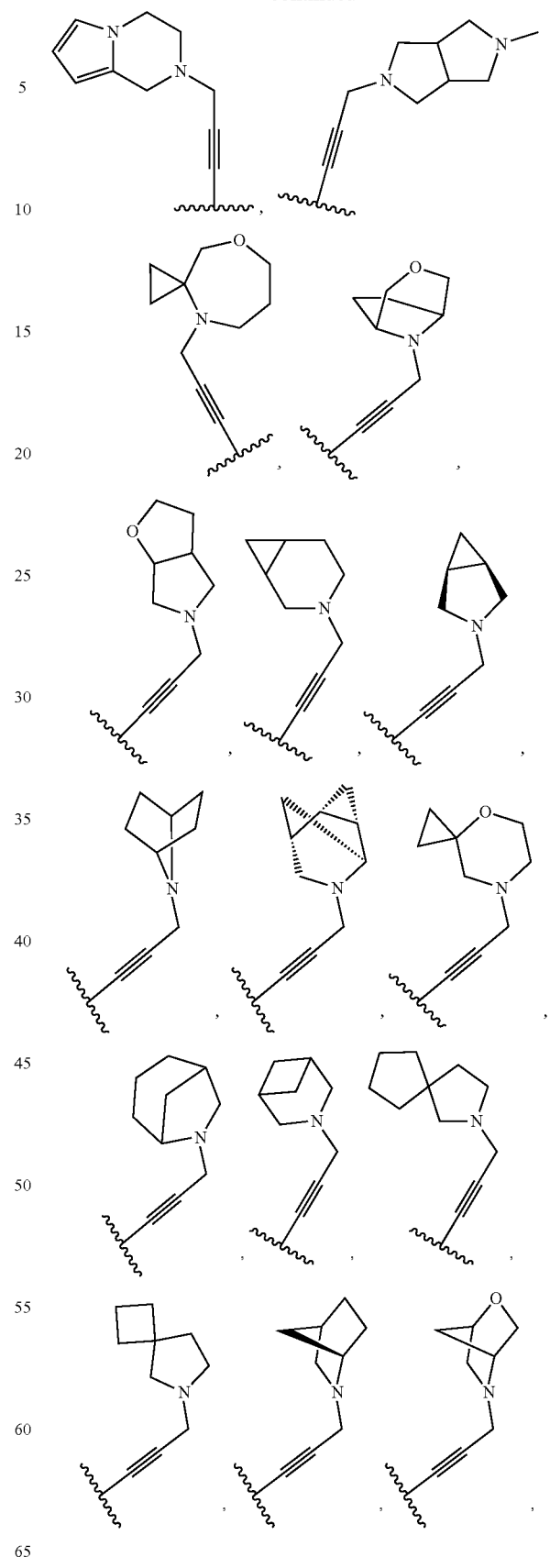

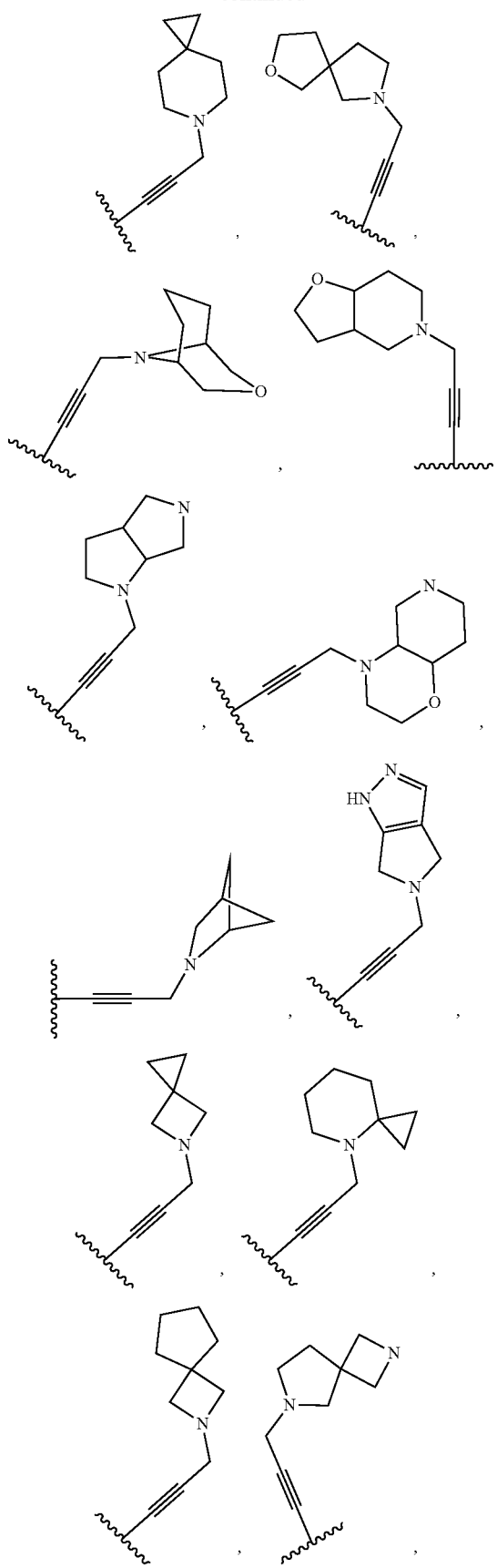

,

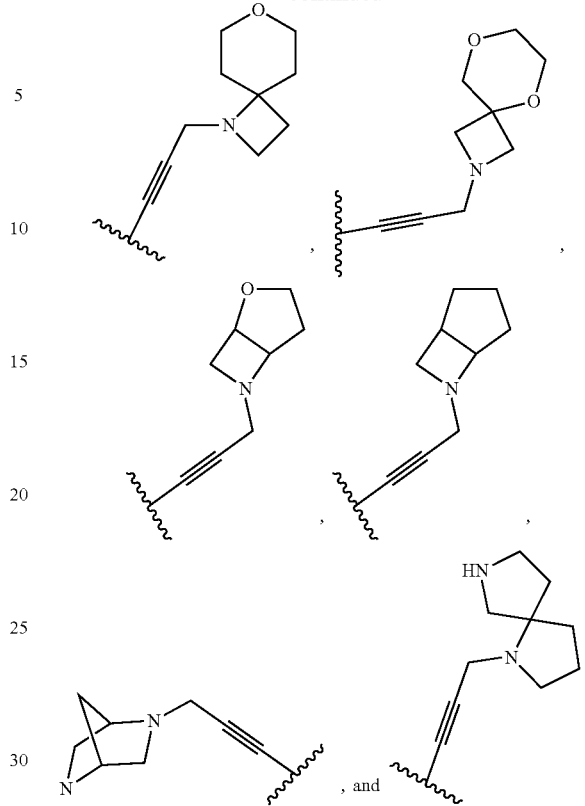

, and

In embodiments, provided is a a compound of formula (I') or (I), or any applicable subformulae thereof, or a stereoisomer or tautomer thereof, or a pharmaceutically acceptable salt of any of the foregoing, wherein [Z] is 5-20 membered heteroaryl. In embodiments, [Z] is 5-20 membered heteroaryl comprising at least one nitrogen heteroatom. In embodiments, [Z] is pyridinyl.

In some embodiments, provided herein is a compound of formula (I'), wherein the compound is of formula (I-J):

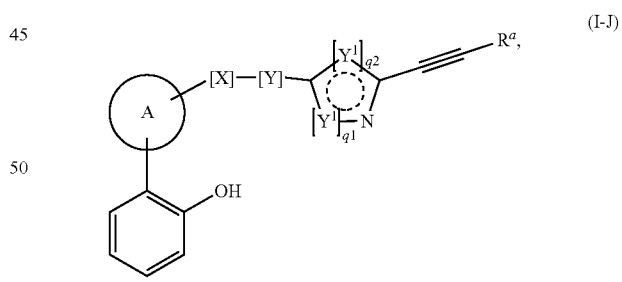

(I-J)

or a stereoisomer or tautomer thereof, or a pharmaceutically acceptable salt of any of the foregoing, wherein each $Y^1$ is independently N or CH, and $q_1$ and $q_2$ are each integers and the sum of $q_1$ and $q_2$ is 2 or 3, and

[X], [Y], and $R^a$ are as defined above or elsewhere herein for a compound of formula (I). In another variation,

[X], [Y], and $R^a$ of formula (I-J) are as defined for a compound of formula (I'), or a stereoisomer or tautomer thereof, or a pharmaceutically acceptable salt of any of the foregoing.

In some embodiments, provided herein is a compound of formula (I'), wherein the compound is of formula (I-J1):

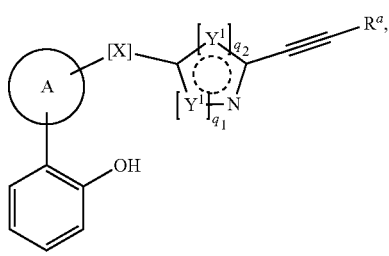

(I-J1)

or a stereoisomer or tautomer thereof, or a pharmaceutically acceptable salt of any of the foregoing, wherein each $Y^1$ is independently N or CH, and $q_1$ and $q_2$ are each integers and the sum of $q_1$ and $q_2$ is 2 or 3, and

[X], and $R^a$ are as defined above or elsewhere herein for a compound of formula (I). In another variation,

[X], and $R^a$ of formula (I-J1) are as defined for a compound of formula (I'), or a stereoisomer or tautomer thereof, or a pharmaceutically acceptable salt of any of the foregoing. In some embodiments of formula (I-J1), [X] is 3-15 membered heterocyclyl or 5-20 membered heteroaryl.

In some embodiments, provided herein is a compound of formula (I'), wherein the compound is of formula (I-J2):

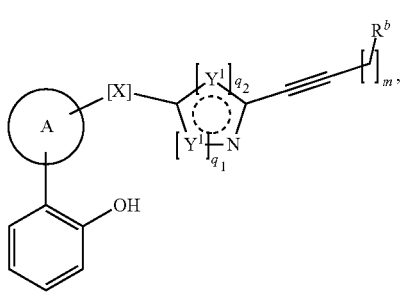

(I-J2)

or a stereoisomer or tautomer thereof, or a pharmaceutically acceptable salt of any of the foregoing, wherein each $Y^1$ is independently N or CH, $q_1$ and $q_2$ are each integers and the sum of $q_1$ and $q_2$ is 2 or 3, and m is 1 or 2, and

[X], and $R^b$ are as defined above or elsewhere herein for a compound of formula (I). In another variation,

[X], and $R^1$ of formula (I-J2) are as defined for a compound of formula (I'), or a stereoisomer or tautomer thereof, or a pharmaceutically acceptable salt of any of the foregoing. In some embodiments of formula (I-J2), [X] is 3-15 membered heterocyclyl or 5-20 membered heteroaryl.

In some embodiments, provided herein is a compound of formula (I'), wherein the compound is of formula (I-J3):

(I-J3)

[structure with $Y^{1a}$, $Y^{1b}$, $Y^{1c}$, [X], A, OH, $R^a$]

or a stereoisomer or tautomer thereof, or a pharmaceutically acceptable salt of any of the foregoing, wherein each of $Y^{1a}$ $Y^{1b}$ and $Y^{1c}$ is independently N or CH, and

[X], and $R^a$ are as defined above or elsewhere herein for a compound of formula (I). In another variation,

[X], and $R^a$ of formula (I-J3) are as defined for a compound of formula (I'), or a stereoisomer or tautomer thereof, or a pharmaceutically acceptable salt of any of the foregoing. In some embodiments of formula (I-J3), [X] is 3-15 membered heterocyclyl or 5-20 membered heteroaryl. In some embodiments of formula (I-J3), $Y^{1a}$ and $Y^{1b}$ are each CH. In some embodiments of formula (I-J3), $Y^{1a}$ is CH and $Y^{1b}$ is N. In some embodiments of formula (I-J3), at least one of $Y^{1a}$ $Y^{1b}$ and $Y^{1c}$ is CH. In some embodiments of formula (I-J3) [X] is

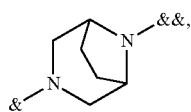

wherein & denotes the point of attachment to

and && denotes the point of attachment to the remainder of the molecule. In embodiments, $Y^{1a}$ and $Y^{1b}$ are each CH. In embodiments, $Y^{1a}$ is CH and $Y^{1b}$ is N.

In some embodiments, provided herein is a compound of formula (I'), wherein the compound is of formula (I-J4):

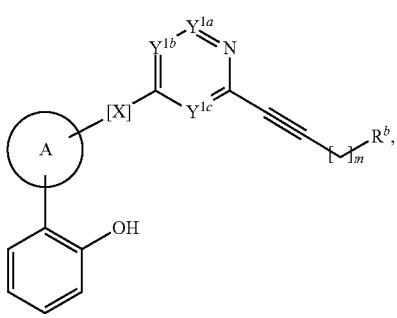

(I-J4)

or a stereoisomer or tautomer thereof, or a pharmaceutically acceptable salt of any of the foregoing, wherein each of $Y^{1a}$ $Y^{1b}$ and $Y^{1c}$ is independently N or CH, m is 1 or 2, and

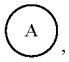

[X], and $R^b$ are as defined above or elsewhere herein for a compound of formula (I). In another variation,

[X], and $R^b$ of formula (I-J4) are as defined for a compound of formula (I'), or a stereoisomer or tautomer thereof, or a pharmaceutically acceptable salt of any of the foregoing. In some embodiments of formula (I-J4), [X] is 3-15 membered heterocyclyl or 5-20 membered heteroaryl. In some embodiments of formula (I-J4), $Y^{1a}$ and $Y^{1b}$ are each CH. In some embodiments of formula (I-J4), $Y^{1a}$ is CH and $Y^{1b}$ is N. In some embodiments of formula (I-J4), at least one of $Y^{1a}$ $Y^{1b}$ and $Y^{1c}$ is CH. In some embodiments of formula (I-J4) [X]

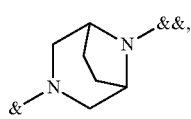

wherein & denotes the point of attachment to

and && denotes the point of attachment to the remainder of the molecule.

In some embodiments, provided herein is a compound of formula (I'), wherein the compound is of formula (I-J5):

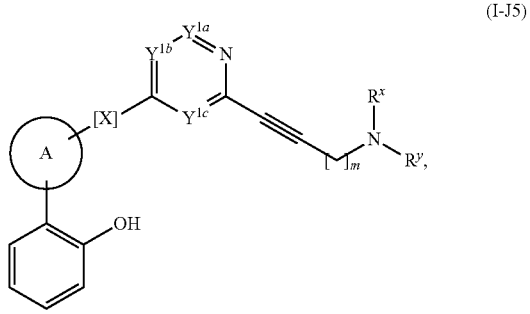

(I-J5)

or a stereoisomer or tautomer thereof, or a pharmaceutically acceptable salt of any of the foregoing, wherein each of $Y^{1a}$ $Y^{1b}$ and $Y^{1c}$ is independently N or CH, m is 1 or 2, and

[X], $R^x$, and $R^y$ are as defined above or elsewhere herein for a compound of formula (I). In another variation,

[X], $R^x$, and $R^y$ of formula (I-J4) are as defined for a compound of formula (I'), or a stereoisomer or tautomer thereof, or a pharmaceutically acceptable salt of any of the foregoing. In some embodiments of formula (I-J5), [X] is 3-15 membered heterocyclyl or 5-20 membered heteroaryl. In some embodiments of formula (I-J5), $Y^{1a}$ and $Y^{1b}$ are each CH. In some embodiments of formula (I-J5), $Y^{1a}$ is CH and $Y^{1b}$ is N. In some embodiments of formula (I-J5), at least one of $Y^{1a}$ $Y^{1b}$ and $Y^{1c}$ is CH. In some embodiments of formula (I-J5) [X] is

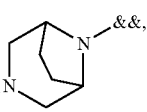

wherein & denotes the point of attachment to

and && denotes the point of attachment to the remainder of the molecule. In some embodiments of formula (I-J5), m is 1. In some embodiments of formula (I-J5), m is 2.

In some embodiments of formula (I-J5),

is selected from the group consisting of:

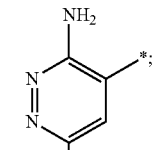

(a)

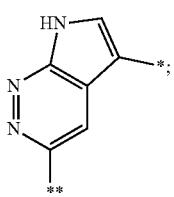

(b)

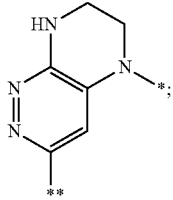

(c)

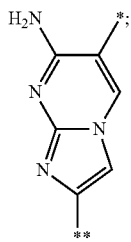

(d)

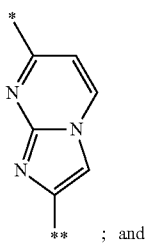

; and

-continued

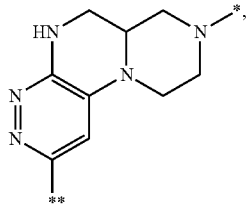

(f)

wherein, for (a)-(f), * denotes the point of attachment to [X], or, if [X] is absent, * denotes the point of attachment to the phenol, and ** denotes the point of attachment to the remainder of the molecule;

[X] is absent or selected from a

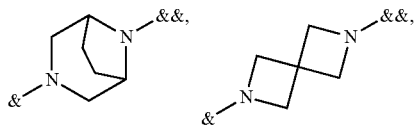

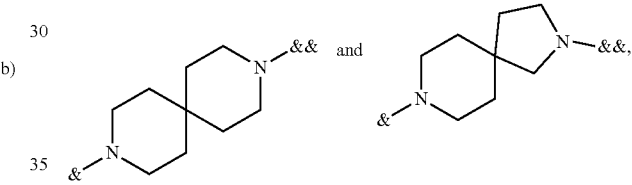

wherein & denotes the point of attachment to

and && denotes the point of attachment to the remainder of the molecule;

$Y^{1a}$ $X^{1b}$ and $X^{1c}$ are each independently CH or N, wherein at least one of $X_1$, $X_2$ and $X_3$ is CH;

m is 1 or 2; and $R^x$ and $R^y$ are each independently hydrogen or $C_1$-$C_{10}$alkyl optionally substituted with one or more hydroxy, or $R^x$ and $R^y$, together with the N atom to which they are attached, form a 4 to 12-membered heterocycle, wherein the 4 to 10-membered heterocycle is optionally substituted with at least one substituent selected from halogen, hydroxy, oxo, $C_1$-$C_4$alkyl optionally substituted with one or more —OH, $C_3$-$C_7$cycloalkyl, $C_1$-$C_4$alkoxy and $C_1$-$C_4$haloalkyl and —C(O)—N($R^h$)($R^i$), wherein $R^h$ and $R^i$ are each independently selected from hydrogen and $C_1$-$C_4$alkyl, wherein said $C_1$-$C_4$alkyl is further optionally substituted with one or more hydroxy.

In some embodiments, provided herein is a compound of formula (I'), wherein the compound is of formula (I-J6):

(I-J6)

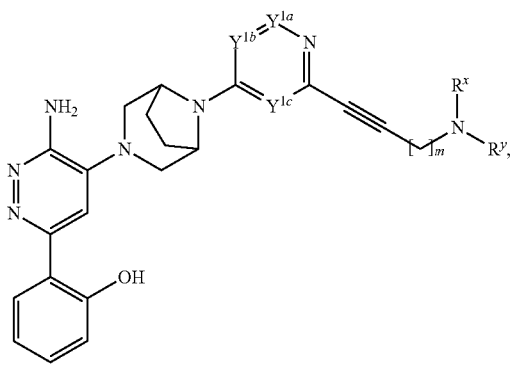

or a stereoisomer or tautomer thereof, or a pharmaceutically acceptable salt of any of the foregoing, wherein each of $Y^{1a}$ $Y^{1b}$ and $Y^{1c}$ is independently N or CH, m is 1 or 2, and $R^x$ and $R^y$ are as defined above or elsewhere herein for a compound of formula (I). In another variation, $R^x$ and $R^y$ of formula (I-J6) are as defined for a compound of formula (I'), or a stereoisomer or tautomer thereof, or a pharmaceutically acceptable salt of any of the foregoing. In some embodiments of a compound of formula (I-J6), $Y^{1a}$ $Y^{1b}$ and $Y^{1c}$ are each independently CH or N, wherein at least one of $Y^{1a}$ $Y^{1b}$ and $Y^{1c}$ is CH, m is 1 or 2, and $R^x$ and $R^y$ are each independently hydrogen or $C_{1-10}$alkyl optionally substituted with one or more hydroxy, or $R^x$ and $R^y$, together with the N atom to which each is attached, form a 4 to 12-membered heterocycle, wherein the 4 to 10-membered heterocycle is optionally substituted with at least one substituent selected from halogen, hydroxy, oxo, $C_1$-$C_4$alkyl, $C_3$-$C_7$cycloalkyl, $C_1$-$C_4$alkoxy and $C_1$-$C_4$haloalkyl and —C(O)—N($R^i$)($R^h$), wherein $R^i$ and $R^h$ are each independently selected from hydrogen and $C_1$-$C_4$alkyl, wherein said $C_1$-$C_4$alkyl is further optionally substituted with one or more hydroxy. In embodiments, $Y^{1a}$ and $Y^{1b}$ are each CH. In embodiments, $Y^{1a}$ is CH and $Y^{1b}$ is N. In embodiments, m is 1. In embodiments, m is 2.

In some embodiments, provided herein is a compound of formula (I'), wherein the compound is of formula (I-J7):

(I-J7)

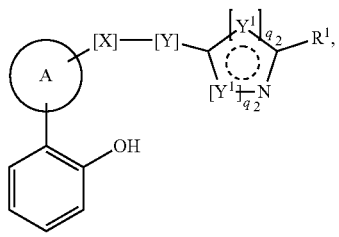

or a stereoisomer or tautomer thereof, or a pharmaceutically acceptable salt of any of the foregoing, wherein each $Y^1$ is independently N or CH, and $q_1$ and $q_2$ are each integers and the sum of $q_1$ and $q_2$ is 2 or 3, and

[X], [Y], and $R^1$ are as defined above or elsewhere herein for a compound of formula (I). In another variation,

[X], [Y], and $R^1$ of formula (I-J7) are as defined for a compound of formula (I'), or a stereoisomer or tautomer thereof, or a pharmaceutically acceptable salt of any of the foregoing.

In some embodiments, provided herein is a compound of formula (I'), wherein the compound is of formula (I-K):

(I-K)

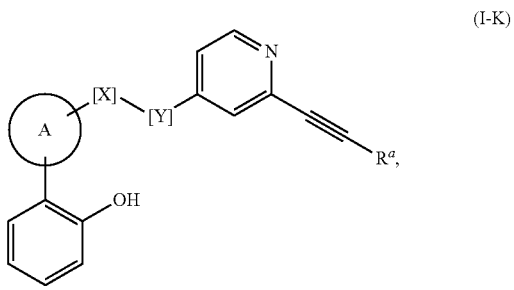

or a stereoisomer or tautomer thereof, or a pharmaceutically acceptable salt of any of the foregoing, wherein,

[X], [Y], and $R^a$ are as defined above or elsewhere herein for a compound of formula (I). In another variation,

[X], [Y], and $R^a$ of formula (I-K) are as defined for a compound of formula (I'), or a stereoisomer or tautomer thereof, or a pharmaceutically acceptable salt of any of the foregoing. In some embodiments of formula (I-K), [X] is 3-15 membered heterocyclyl or 5-20 membered heteroaryl. In some embodiments of formula (I-K), [Y] is absent. In some embodiments of formula (I-J), [X] is 3-15 membered heterocyclyl or 5-20 membered heteroaryl. In some embodiments of formula (I-J), [X] is 3-15 membered heterocyclyl or 5-20 membered heteroaryl each of which independently comprises at least one nitrogen heteroatom. In some embodiments of formula (I-J), [Y] is absent and [X] is 3-15 membered heterocyclyl or 5-20 membered heteroaryl each of which comprises at least one nitrogen heteroatom. In some embodiments, [Y] is absent and [X] is 3-15 membered heterocyclyl comprising at least 1 nitrogen heteroatom. In some embodiments, [Y] is absent and [X] is 3-15 membered heterocyclyl comprising at least 2 nitrogen heteroatoms.

In some embodiments, provided herein is a compound of formula (I'), wherein the compound is of formula (I-K1):

(I-K1)

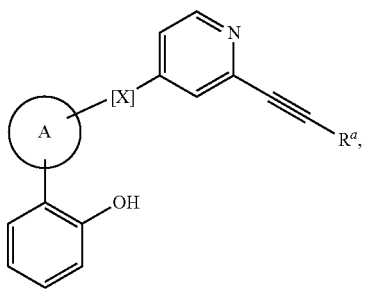

or a stereoisomer or tautomer thereof, or a pharmaceutically acceptable salt of any of the foregoing, wherein

[X], and $R^a$ are as defined above or elsewhere herein for a compound of formula (I). In another variation,

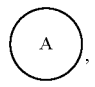

[X], and $R^a$ of formula (I-K1) are as defined for a compound of formula (I'), or a stereoisomer or tautomer thereof, or a pharmaceutically acceptable salt of any of the foregoing. In some embodiments of formula (I-K1), [X] is 3-15 membered heterocyclyl or 5-20 membered heteroaryl. In some embodiments of formula (I-K1),

is

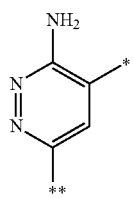

and [X] is

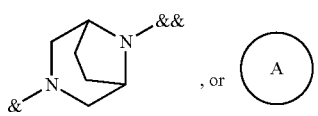

is

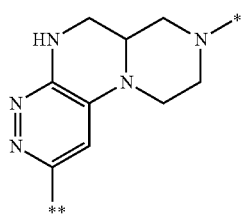

and [X] is absent, wherein * denotes the point of attachment to [X], or, if [X] is absent, * denotes the point of attachment to [Y], or if [X] and [Y] are absent, * denotes the point of attachment to [Z], and ** denotes the point of attachment to the remainder of the molecule, and wherein & denotes the point of attachment to

and && denotes the point of attachment to the remainder of the molecule; and $R^a$ is —$CH_2$—$R^b$, wherein $R^b$ is 4- to 9-membered heterocycle, optionally substituted with —OH, halo, $C_{1-2}$ alkyl, or cyclopropyl, wherein each $C_{1-2}$ alkyl is optionally substituted with —OH or halo, or $R^a$ is 6-membered heterocycle.

In some embodiments, provided herein is a compound of formula (I'), wherein the compound is of formula (I-K2):

(I-K2)

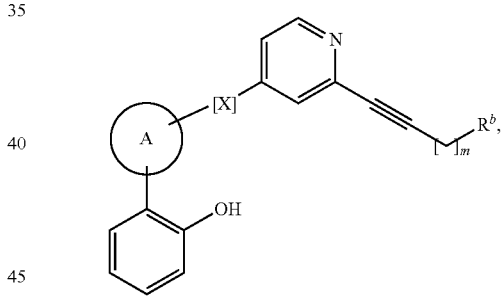

or a stereoisomer or tautomer thereof, or a pharmaceutically acceptable salt of any of the foregoing, wherein

[X], and $R^b$ are as defined above or elsewhere herein for a compound of formula (I). In another variation,

[X], and $R^b$ of formula (I-K2) are as defined for a compound of formula (I'), or a stereoisomer or tautomer thereof, or a pharmaceutically acceptable salt of any of the foregoing. In some embodiments of formula (I-K2), [X] is 3-15 membered heterocyclyl or 5-20 membered heteroaryl.

In some embodiments, provided herein is a compound of formula (I'), wherein the compound is of formula (I-K3):

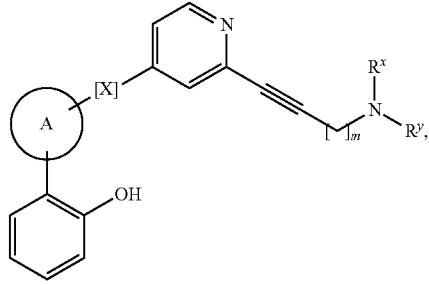
(I-K3)

or a stereoisomer or tautomer thereof, or a pharmaceutically acceptable salt of any of the foregoing, wherein

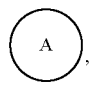

[X], $R^x$, and $R^y$ are as defined above or elsewhere herein for a compound of formula (I).

In another variation,

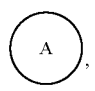

[X], $R^x$, and $R^y$ of formula (I-K3) are as defined for a compound of formula (I'), or a stereoisomer or tautomer thereof, or a pharmaceutically acceptable salt of any of the foregoing. In some embodiments of formula (I-K3), [X] is 3-15 membered heterocyclyl or 5-20 membered heteroaryl.

In some embodiments, provided herein is a compound of formula (I'), wherein the compound is of formula (I-K4):

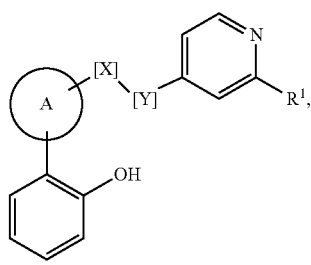
(I-K4)

or a stereoisomer or tautomer thereof, or a pharmaceutically acceptable salt of any of the foregoing, wherein

[X], [Y], and $R^1$ are as defined above or elsewhere herein for a compound of formula (I). In another variation,

[X], [Y], and $R^1$ of formula (I-K4) are as defined for a compound of formula (I'), or a stereoisomer or tautomer thereof, or a pharmaceutically acceptable salt of any of In some embodiments of formula (I-K4), [Y] is absent. In some embodiments of formula (I-K4), [X] is 3-15 membered heterocyclyl or 5-20 membered heteroaryl. In some embodiments of formula (I-K4), [X] is 3-15 membered heterocyclyl or 5-20 membered heteroaryl each of which independently comprises at least one nitrogen heteroatom. In some embodiments of formula (I-K4), [Y] is absent and [X] is 3-15 membered heterocyclyl or 5-20 membered heteroaryl each of which comprises at least one nitrogen heteroatom. In some embodiments, [Y] is absent and [X] is 3-15 membered heterocyclyl comprising at least 1 nitrogen heteroatom. In some embodiments, [Y] is absent and [X] is 3-15 membered heterocyclyl comprising at least 2 nitrogen heteroatoms.

In some embodiments, provided herein is a compound of formula (I'), wherein the compound is of formula (I-K5):

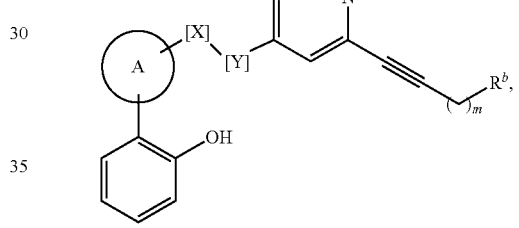
(I-K5)

or a stereoisomer or tautomer thereof, or a pharmaceutically acceptable salt of any of the foregoing, wherein m is 1 or 2, and

[X], [Y], and $R^b$ are as defined above or elsewhere herein for a compound of formula (I). In another variation,

[X], [Y], and $R^c$ of formula (I-K5) are as defined for a compound of formula (I'), or a stereoisomer or tautomer thereof, or a pharmaceutically acceptable salt of any of In some embodiments of formula (I-K5), [Y] is absent. In some embodiments of formula (I-K5), [X] is 3-15 membered heterocyclyl or 5-20 membered heteroaryl. In some embodiments of formula (I-K5), [X] is 3-15 membered heterocyclyl or 5-20 membered heteroaryl each of which independently comprises at least one nitrogen heteroatom. In some embodiments of formula (I-K5), [Y] is absent and [X] is 3-15 membered heterocyclyl or 5-20 membered heteroaryl each of which comprises at least one nitrogen heteroatom. In some embodiments of formula (I-K5), [Y] is absent and [X] is 3-15 membered heterocyclyl comprising at least 1 nitrogen heteroatom. In some embodiments of formula (I-K5), [Y] is absent and [X] is 3-15 membered heterocyclyl comprising at least 2 nitrogen heteroatoms. In some embodiments of formula (I-K5), [Y] is absent and [X] is

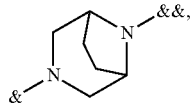

wherein & denotes the point of attachment to

and && denotes the point of attachment to the remainder of the molecule. In some embodiments of formula (I-K5), $R^b$ is a monocyclic heterocycyl comprising at least one N, optionally substituted with one or more $R^c$. In some embodiments of formula (I-K5), $R^b$ is a polycyclic heterocycyl comprising at least one N, optionally substituted with one or more $R^c$. In some embodiments of formula (I-K5), $R^b$ is a fused polycyclic heterocycyl comprising at least one N, optionally substituted with one or more $R^c$. In some embodiments of formula (I-K5), $R^b$ is a spirocyclic polycyclic heterocycyl comprising at least one N, optionally substituted with one or more $R^c$.

In some embodiments, provided herein is a compound of formula (I'), wherein the compound is of formula (I-K6):

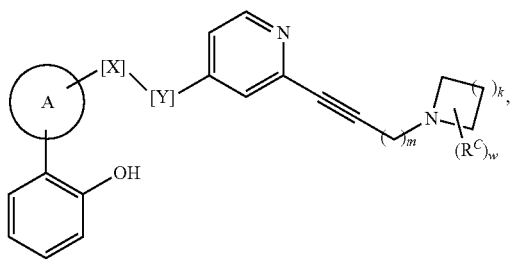

(I-K6)

or a stereoisomer or tautomer thereof, or a pharmaceutically acceptable salt of any of the foregoing, wherein m is 1 or 2, k is an integer from 1-4, w is an integer from 0-12 and

[X], [Y], and $R^c$ are as defined above or elsewhere herein for a compound of formula (I). In another variation,

[X], [Y], and $R^c$ of formula (I-K6) are as defined for a compound of formula (I'), or a stereoisomer or tautomer thereof, or a pharmaceutically acceptable salt of any of the foregoing. In some embodiments of formula (I-K6), [Y] is absent. In some embodiments of formula (I-K6), [X] is 3-15 membered heterocyclyl or 5-20 membered heteroaryl. In some embodiments of formula (I-K6), [X] is 3-15 membered heterocyclyl or 5-20 membered heteroaryl each of which independently comprises at least one nitrogen heteroatom. In some embodiments of formula (I-K6), [Y] is absent and [X] is 3-15 membered heterocyclyl or 5-20 membered heteroaryl each of which comprises at least one nitrogen heteroatom. In some embodiments of formula (I-K6), [Y] is absent and [X] is 3-15 membered heterocyclyl comprising at least 1 nitrogen heteroatom. In some embodiments of formula (I-K6), [Y] is absent and [X] is 3-15 membered heterocyclyl comprising at least 2 nitrogen heteroatoms. In some embodiments of formula (I-K6), [Y] is absent and [X] is

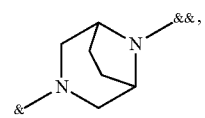

wherein & denotes the point of attachment to

and && denotes the point of attachment to the remainder of the molecule. In some embodiments w is 0. In some embodiments w is 1. In some embodiments w is 2. In some embodiments, w is 3. In some embodiments, w is an integer from 1 to 12, from 1 to 10, from 1 to 8, from 1 to 6, or from 1 to 4. In some embodiments, k is 4. In some embodiments, k is 3. In some embodiments, k is 2. In some embodiments, k is 1. In some embodiments, k is 4 and w is an integer from 0 to 3. In some embodiments, k is 4, m is 1, and w is an integer from 0 to 3.

In embodiments, provided is a a compound of formula (I') or (I), or any applicable subformulae thereof, or a stereoisomer or tautomer thereof, or a pharmaceutically acceptable salt of any of the foregoing, wherein

is

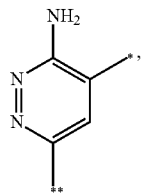

and [Z] is 5-20 membered heteroaryl comprising at least one nitrogen heteroatom. In embodiments,

is

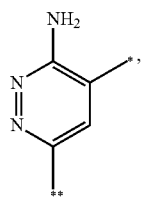

and [Z] is pyridinyl. In embodiments,

is

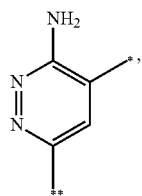

[Z] is pyridinyl, and [X] is 3-15 membered heterocyclyl. In embodiments,

is

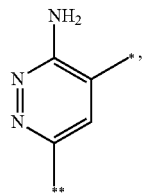

[Z] is pyridinyl, and [X] is 5-20 membered heteroaryl. In embodiments,

is

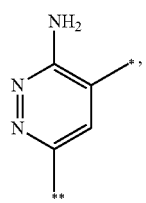

[Z] is pyridinyl, and [X] is 3-15 membered heterocyclyl comprising at least one nitrogen heteroatom. In embodiments,

is

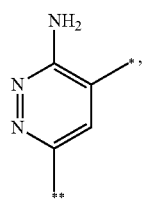

[Z] is pyridinyl, and [X] is 3-15 membered heterocyclyl comprising at least two nitrogen heteroatoms. In embodiments,

is

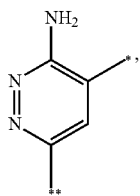

[Z] is pyridinyl, and [X] is 5-20 membered heteroaryl comprising at least one nitrogen heteroatom. In embodiments,

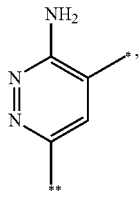

is

[Z] is pyridinyl, and [X] is 5-20 membered heteroaryl comprising at least two nitrogen heteroatoms.

In some embodiments of a compound of formula (I'), (I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), [X] is absent or selected from

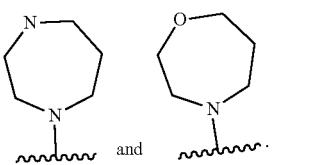

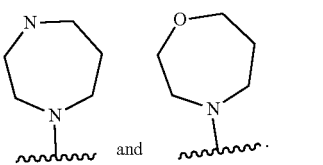

wherein & denotes the point of attachment to

and && denotes the point of attachment to the remainder of the molecule.

In some embodiments of a compound of formula (I'), (I), (I-J), (I-K), and any applicable subformulae thereof, $R^b$ is a monocyclic heterocycle. In some embodiments, the monocyclic heterocycle is selected from the group consisting of

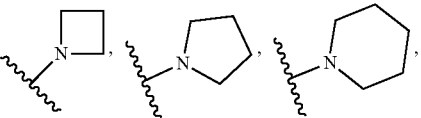

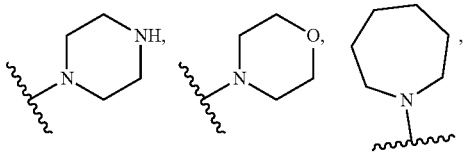

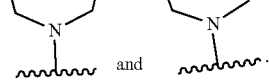

In some embodiments, $R^b$ is a fused bicyclic heterocycle. In embodiments, the fused bicyclic heterocycle is selected from the group consisting of

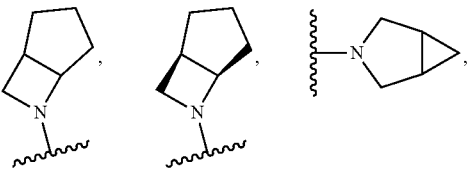

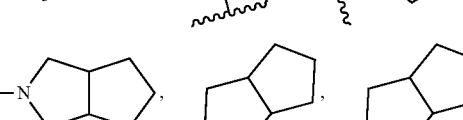

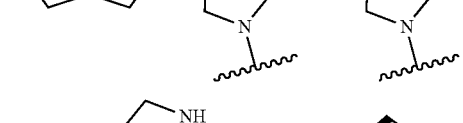

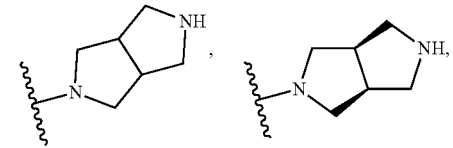

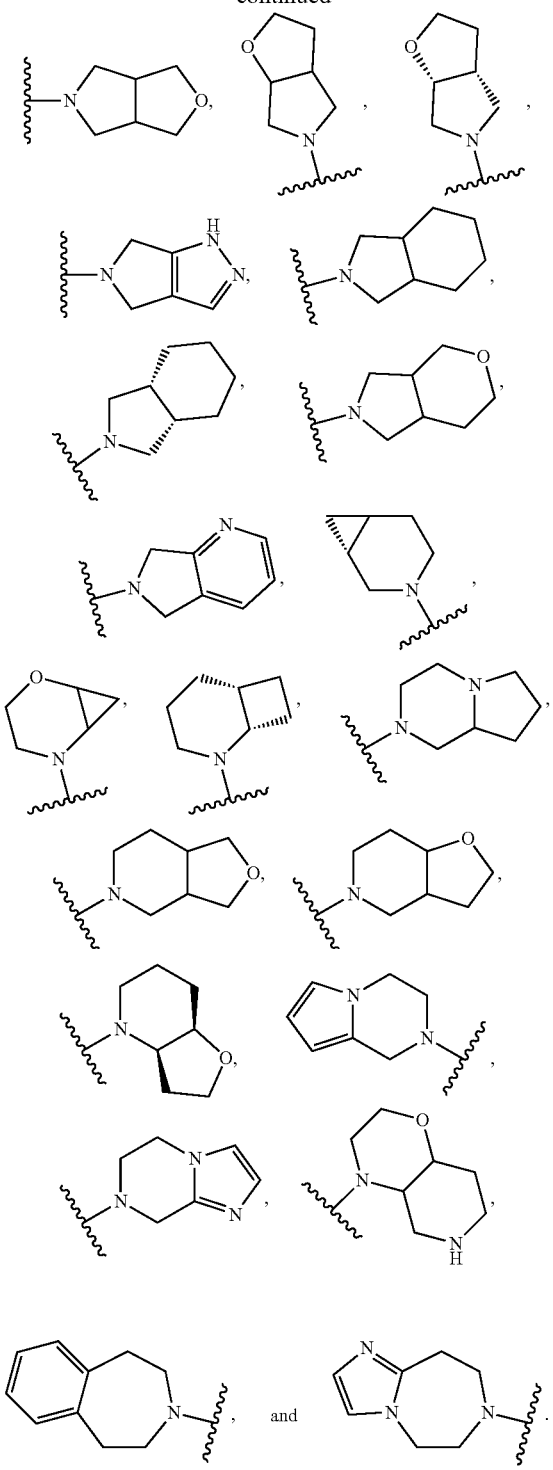
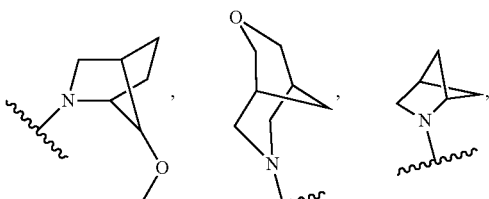
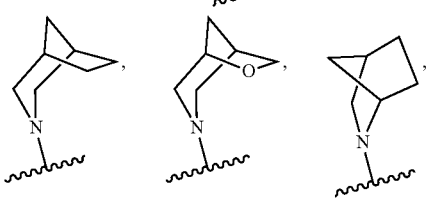
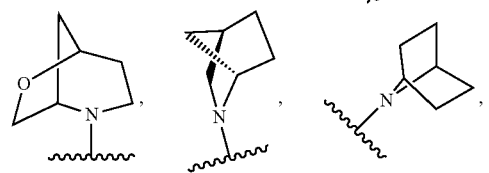

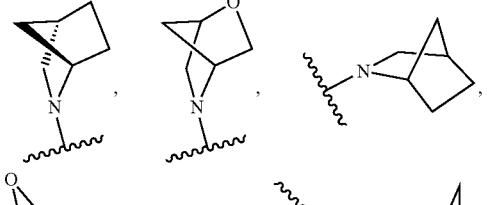
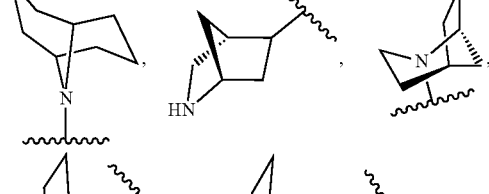
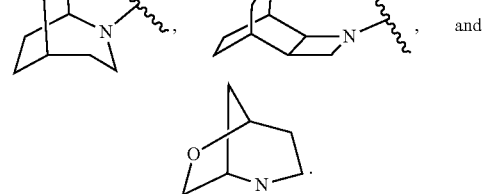
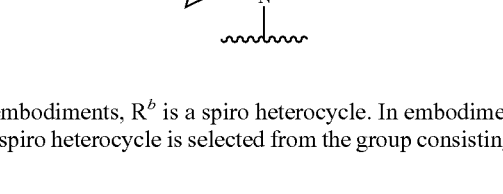
, and
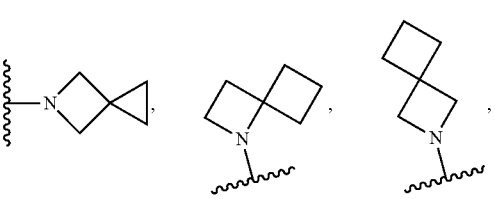
In embodiments, R$^b$ is a spiro heterocycle. In embodiments, the spiro heterocycle is selected from the group consisting of
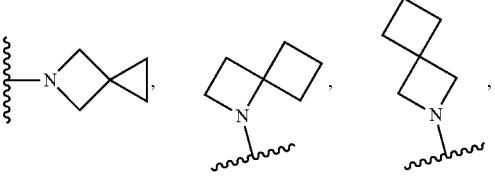
In embodiments, R$^b$ is a bridged heterocycle. In embodiments the bridged heterocycle is selected from the group consisting of

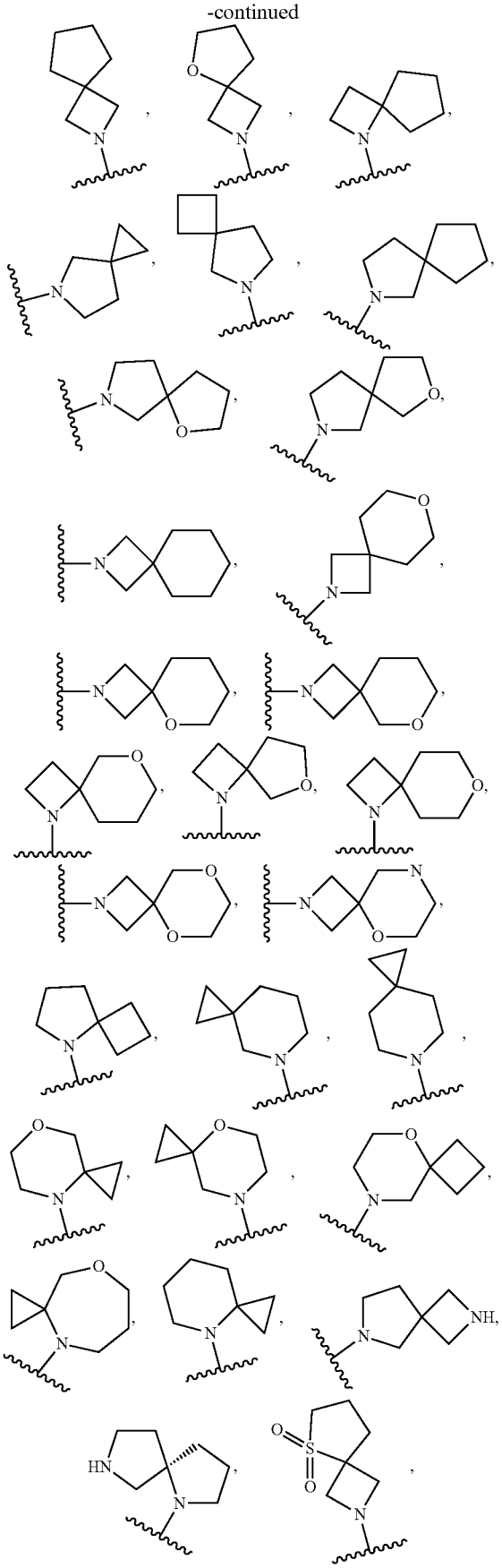

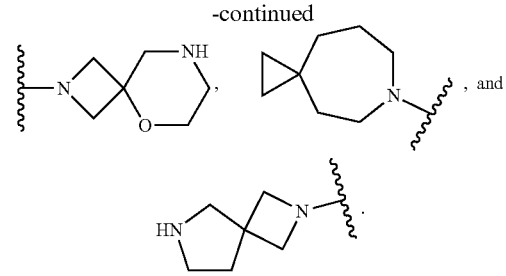

In some embodiments of a compound of formula (I'), (I), (I-J), (I-K), and any applicable subformulae thereof, $R^a$ is a monocyclic heterocycle. In some embodiments, the monocyclic heterocycle is selected from the group consisting of

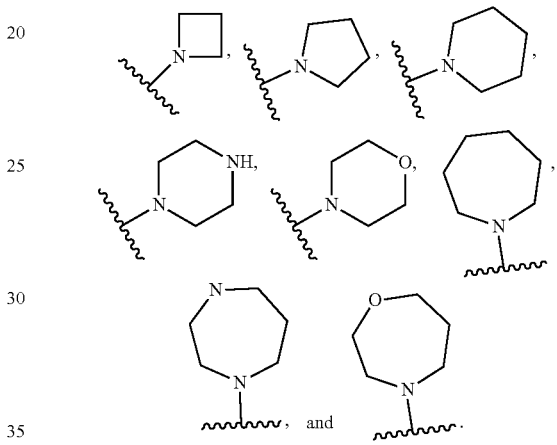

some embodiments, $R^a$ is a fused bicyclic heterocycle. In embodiments, the fused bicyclic heterocycle is selected from the group consisting of

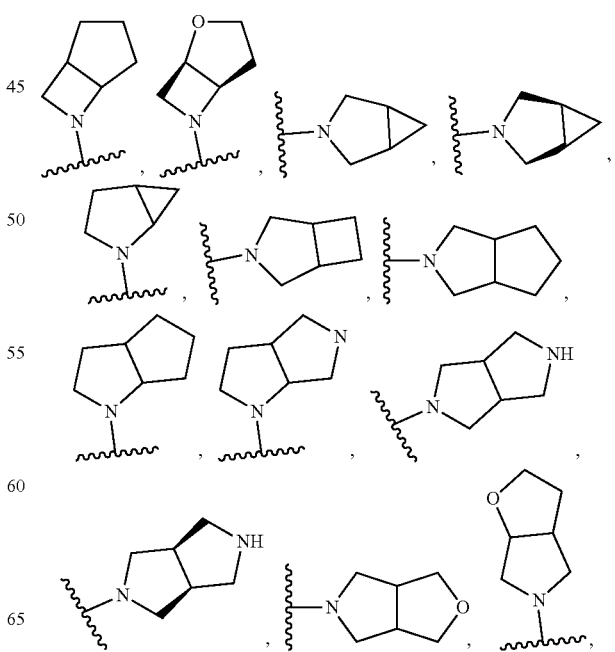

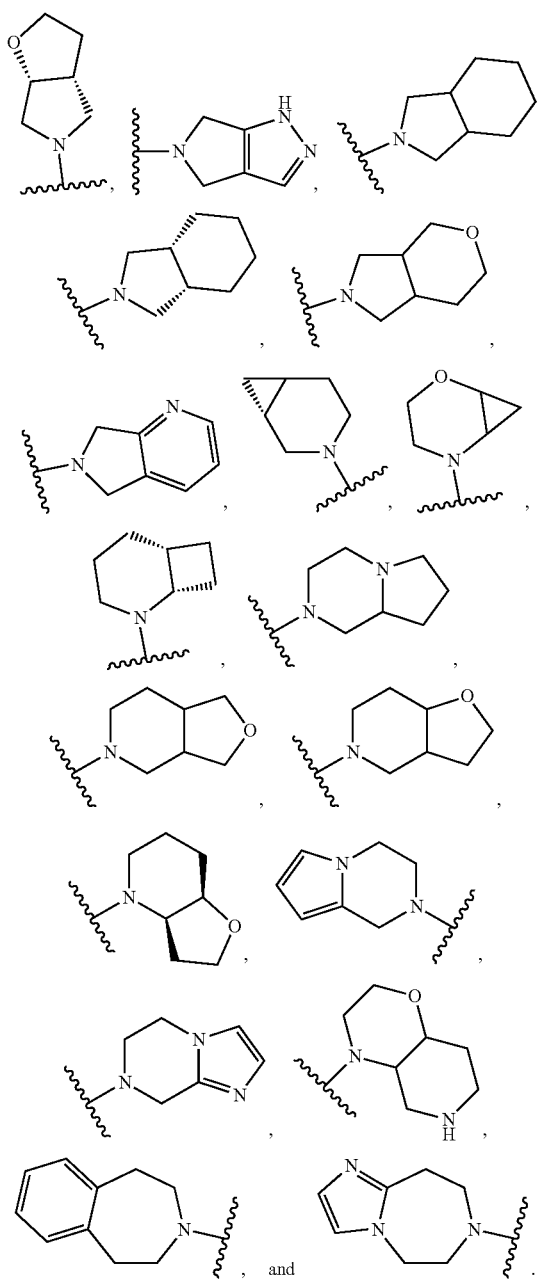
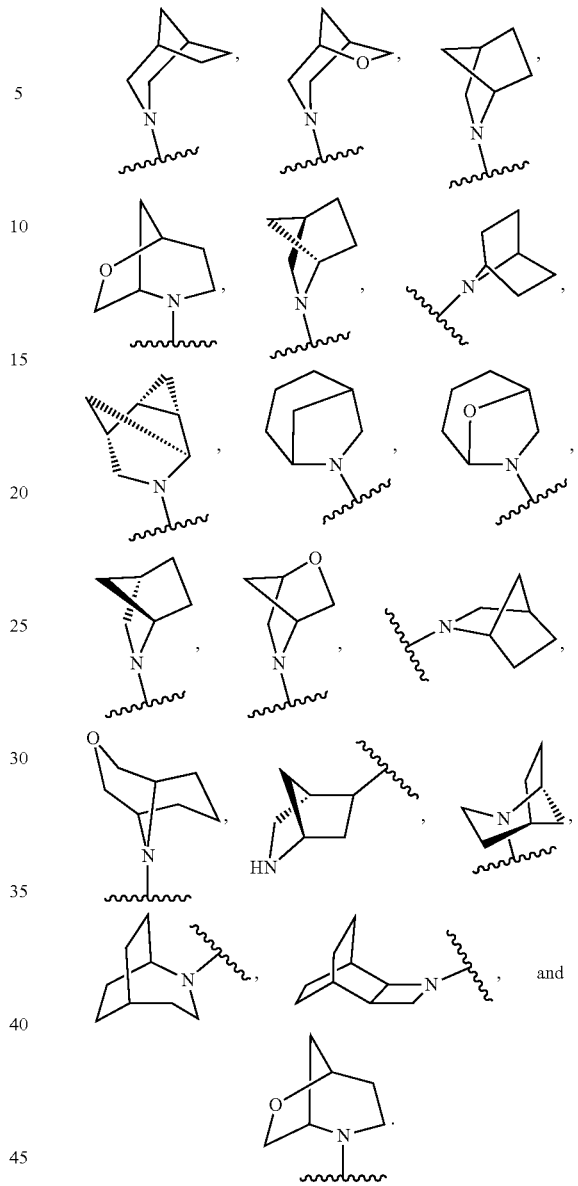
In embodiments, $R^a$ is a bridged heterocycle. In embodiments the bridged heterocycle is selected from the group consisting of
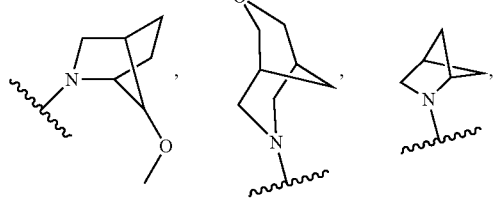
In embodiments, $R^a$ is a spiro heterocycle. In embodiments, the spiro heterocycle is selected from the group consisting of
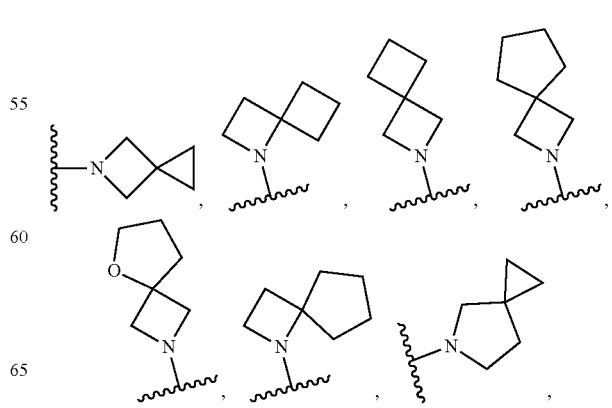

225
-continued

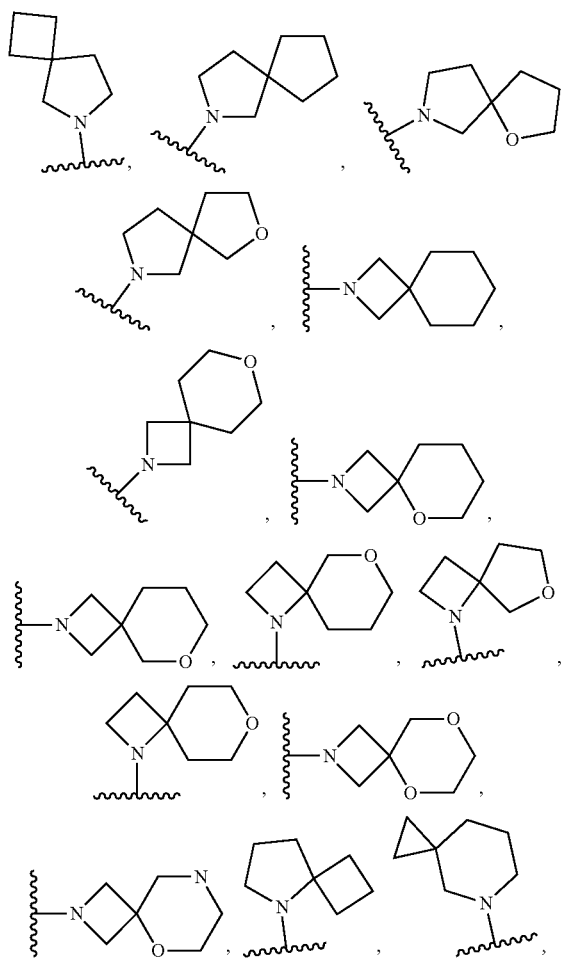

226
-continued

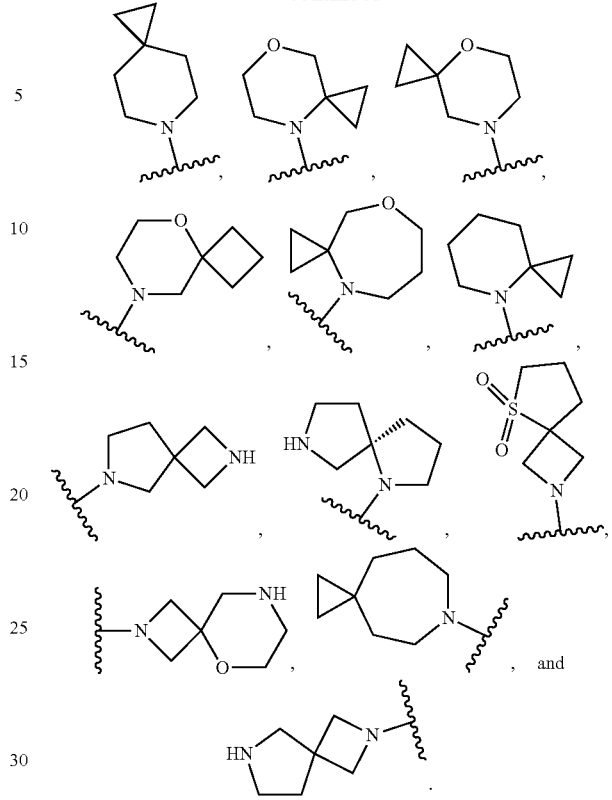

In embodiments, the present disclosure is directed to a compound of formula (I), (I'), (II), or (II'), or a stereoisomer or tautomer thereof, or a pharmaceutically acceptable salt of any of the foregoing, wherein the compound, or a stereoisomer or tautomer thereof, or a pharmaceutically acceptable salt of any of the foregoing, is selected from the group consisting of the compounds in Table 1.

TABLE 1

| No. | Structure | Name |
| --- | --- | --- |
| 1 | 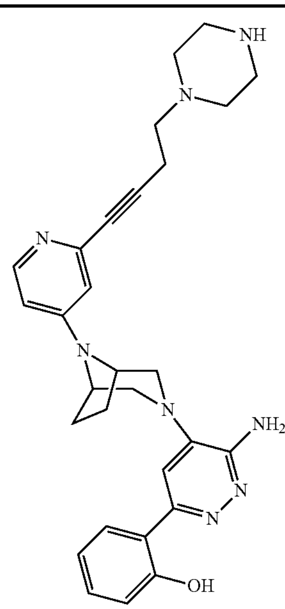 | 2-(6-amino-5-(8-(2-(4-(piperazin-1-yl)but-1-yn-1-yl)pyridin-4-yl)-3,8-diazabicyclo[3.2.1]octan-3-yl)pyridazin-3-yl)phenol |

TABLE 1-continued

| No. | Structure | Name |
|---|---|---|
| 2 | 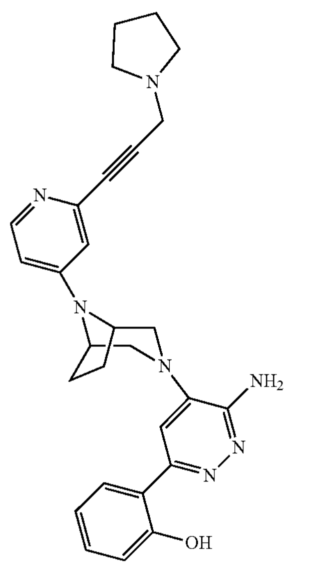 [SMILES: Nc1nnc(-c2ccccc2O)cc1N1CC2CCC(C1)N2c1ccnc(C#CCN2CCCC2)c1] | 2-(6-amino-5-(8-(2-(3-(pyrrolidin-1-yl)prop-1-yn-1-yl)pyridin-4-yl)-3,8-diazabicyclo[3.2.1]octan-3-yl)pyridazin-3-yl)phenol |
| 3 | 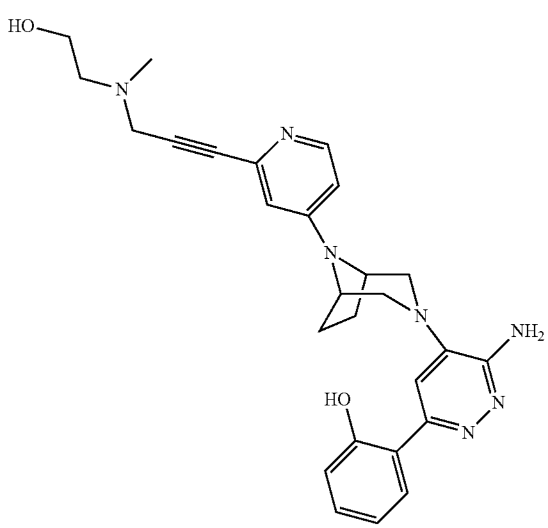 [SMILES: CN(CC#Cc1cc(N2C3CCC2CN(c2cc(-c4ccccc4O)nnc2N)C3)ccn1)CCO] | 2-(6-amino-5-(8-(2-(3-((2-hydroxyethyl)(methyl)amino)prop-1-yn-1-yl)pyridin-4-yl)-3,8-diazabicyclo[3.2.1]octan-3-yl)pyridazin-3-yl)phenol |

TABLE 1-continued

| No. | Structure | Name |
|---|---|---|
| 4 | 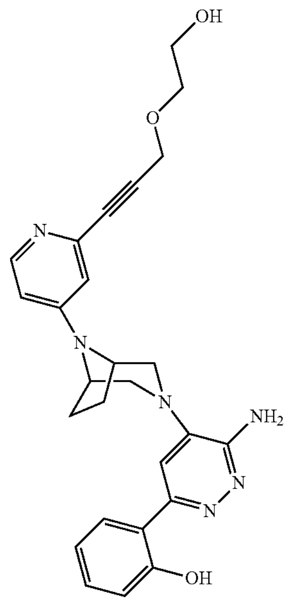 [SMILES: Nc1nnc(-c2ccccc2O)cc1N1CC2CCC(C1)N2c1ccnc(C#CCOCCO)c1] | 2-(6-amino-5-(8-(2-(3-(2-hydroxyethoxy)prop-1-yn-1-yl)pyridin-4-yl)-3,8-diazabicyclo[3.2.1]octan-3-yl)pyridazin-3-yl)phenol |
| 5 | 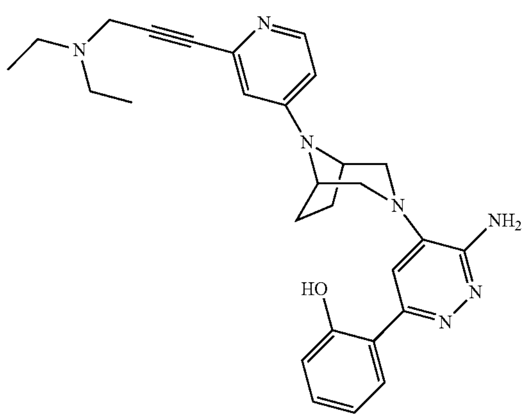 [SMILES: CCN(CC)CC#Cc1cc(N2C3CCC2CN(c2cc(-c4ccccc4O)nnc2N)C3)ccn1] | 2-(6-amino-5-(8-(2-(3-(diethylamino)prop-1-yn-1-yl)pyridin-4-yl)-3,8-diazabicyclo[3.2.1]octan-3-yl)pyridazin-3-yl)phenol |
| 6 | 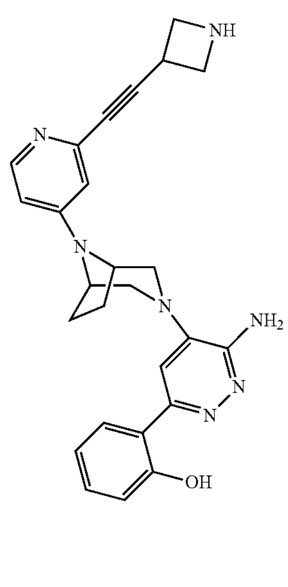 [SMILES: Nc1nnc(-c2ccccc2O)cc1N1CC2CCC(C1)N2c1ccnc(C#CC2CNC2)c1] | 2-(6-amino-5-(8-(2-(azetidin-3-ylethynyl)pyridin-4-yl)-3,8-diazabicyclo[3.2.1]octan-3-yl)pyridazin-3-yl)phenol |

TABLE 1-continued
| No. | Structure | Name |
|---|---|---|
| 7 | 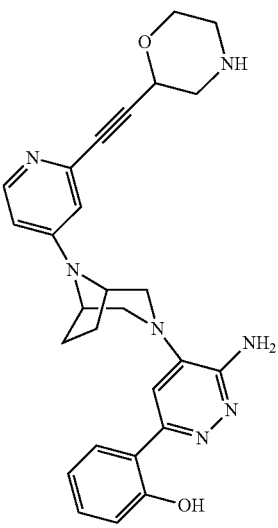 [SMILES: Nc1nnc(-c2ccccc2O)cc1N1CC2CCC(C1)N2c1ccnc(C#CC2CNCCO2)c1] | 2-(6-amino-5-(8-(2-(morpholin-2-ylethynyl)pyridin-4-yl)-3,8-diazabicyclo[3.2.1]octan-3-yl)pyridazin-3-yl)phenol |
| 8 | 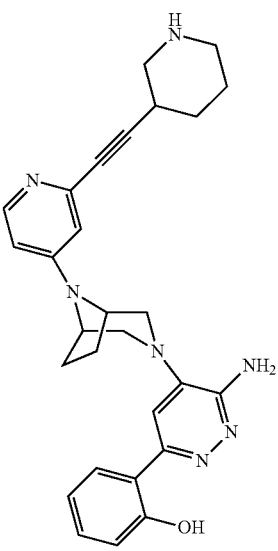 [SMILES: Nc1nnc(-c2ccccc2O)cc1N1CC2CCC(C1)N2c1ccnc(C#CC2CCCNC2)c1] | 2-(6-amino-5-(8-(2-(piperidin-3-ylethynyl)pyridin-4-yl)-3,8-diazabicyclo[3.2.1]octan-3-yl)pyridazin-3-yl)phenol |

TABLE 1-continued
| No. | Structure | Name |
|---|---|---|
| 9 | 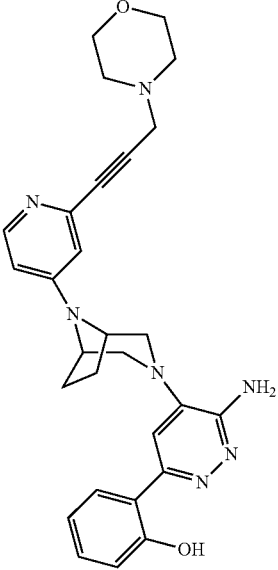 [SMILES: Nc1nnc(-c2ccccc2O)cc1N1CC2CCC(C1)N2c1ccnc(C#CCN2CCOCC2)c1] | 2-(6-amino-5-(8-(2-(3-morpholinoprop-1-yn-1-yl)pyridin-4-yl)-3,8-diazabicyclo[3.2.1]octan-3-yl)pyridazin-3-yl)phenol |
| 10 | 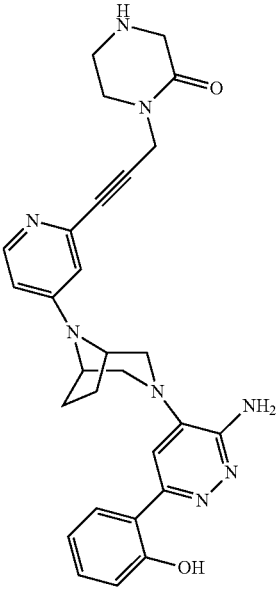 [SMILES: Nc1nnc(-c2ccccc2O)cc1N1CC2CCC(C1)N2c1ccnc(C#CCN2CCNCC2=O)c1] | 1-(3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)piperazin-2-one |

TABLE 1-continued
| No. | Structure | Name |
|---|---|---|
| 11 | 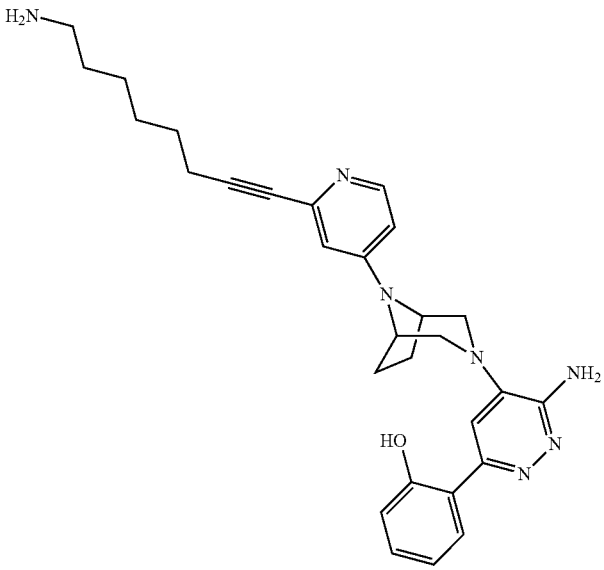 [SMILES: NCCCCCCC#Cc1cc(N2C3CCC2CN(c2cc(-c4ccccc4O)nnc2N)C3)ccn1] | 2-(6-amino-5-(8-(2-(8-aminooct-1-yn-1-yl)pyridin-4-yl)-3,8-diazabicyclo[3.2.1]octan-3-yl)pyridazin-3-yl)phenol |
| 12 | 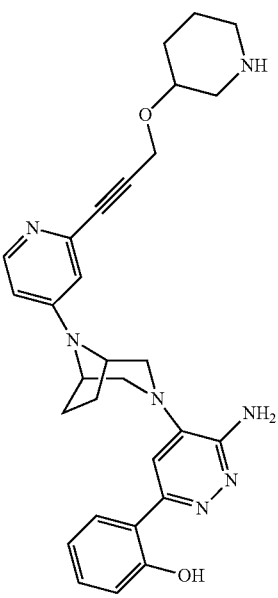 [SMILES: Nc1nnc(-c2ccccc2O)cc1N1CC2CCC(C1)N2c1ccnc(C#CCOC2CCCNC2)c1] | 2-(6-amino-5-(8-(2-(3-(piperidin-3-yloxy)prop-1-yn-1-yl)pyridin-4-yl)-3,8-diazabicyclo[3.2.1]octan-3-yl)pyridazin-3-yl)phenol |

TABLE 1-continued

| No. | Structure | Name |
|---|---|---|
| 13 | 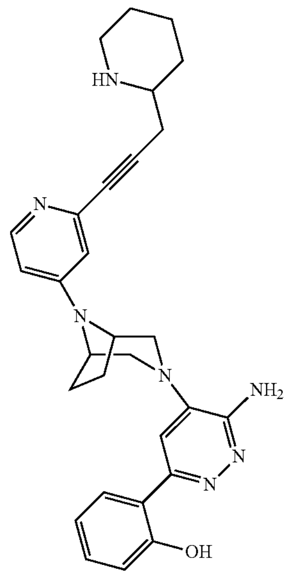 [SMILES: Nc1nnc(-c2ccccc2O)cc1N1CC2CCC(C1)N2c1ccnc(C#CCC2CCCCN2)c1] | 2-(6-amino-5-(8-(2-(3-(piperidin-2-yl)prop-1-yn-1-yl)pyridin-4-yl)-3,8-diazabicyclo[3.2.1]octan-3-yl)pyridazin-3-yl)phenol |
| 14 | 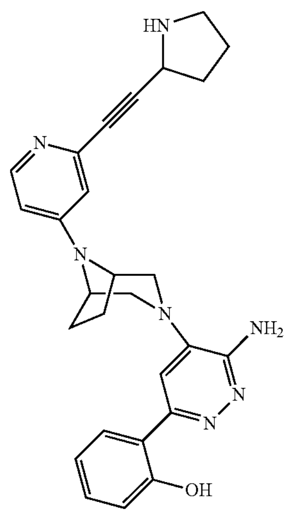 [SMILES: Nc1nnc(-c2ccccc2O)cc1N1CC2CCC(C1)N2c1ccnc(C#CC2CCCN2)c1] | 2-(6-amino-5-(8-(2-(pyrrolidin-2-ylethynyl)pyridin-4-yl)-3,8-diazabicyclo[3.2.1]octan-3-yl)pyridazin-3-yl)phenol |
| 15 | 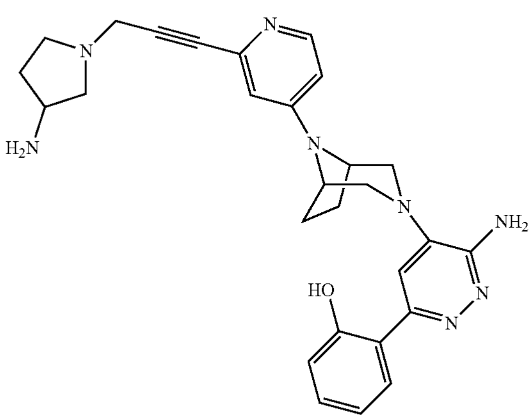 [SMILES: Nc1nnc(-c2ccccc2O)cc1N1CC2CCC(C1)N2c1ccnc(C#CCN2CCC(N)C2)c1] | 2-(6-amino-5-(8-(2-(3-(3-aminopyrrolidin-1-yl)prop-1-yn-1-yl)pyridin-4-yl)-3,8-diazabicyclo[3.2.1]octan-3-yl)pyridazin-3-yl)phenol |

TABLE 1-continued
| No. | Structure | Name |
|---|---|---|
| 16 | 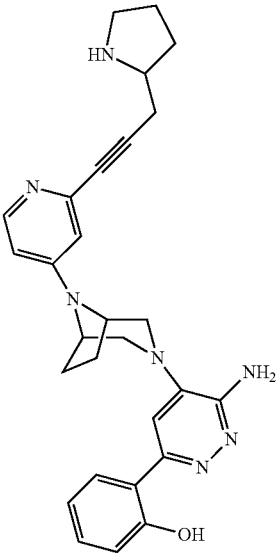 [SMILES: Nc1nnc(-c2ccccc2O)cc1N1CC2CCC(C1)N2c1ccnc(C#CCC2CCCN2)c1] | 2-(6-amino-5-(8-(2-(3-(pyrrolidin-2-yl)prop-1-yn-1-yl)pyridin-4-yl)-3,8-diazabicyclo[3.2.1]octan-3-yl)pyridazin-3-yl)phenol |
| 17 | 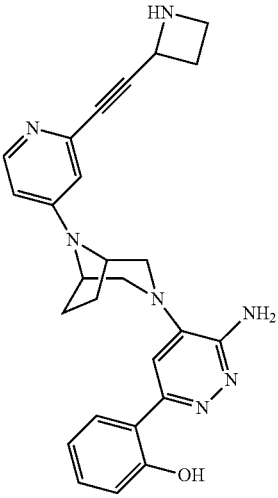 [SMILES: Nc1nnc(-c2ccccc2O)cc1N1CC2CCC(C1)N2c1ccnc(C#CC2CCN2)c1] | 2-(6-amino-5-(8-(2-(azetidin-2-ylethynyl)pyridin-4-yl)-3,8-diazabicyclo[3.2.1]octan-3-yl)pyridazin-3-yl)phenol |

TABLE 1-continued

| No. | Structure | Name |
|-----|-----------|------|
| 18 | 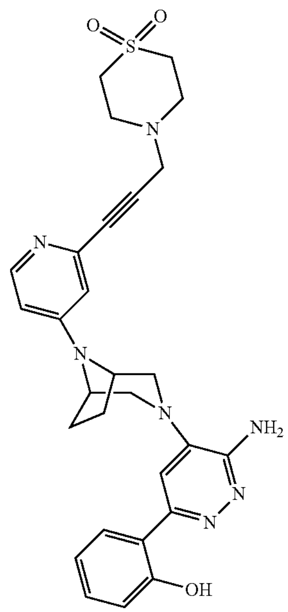 [SMILES: Nc1nnc(-c2ccccc2O)cc1N1CC2CCC(C1)N2c1ccnc(C#CCN2CCS(=O)(=O)CC2)c1] | 4-(3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)thiomorpholine1,1-dioxide |
| 19 | 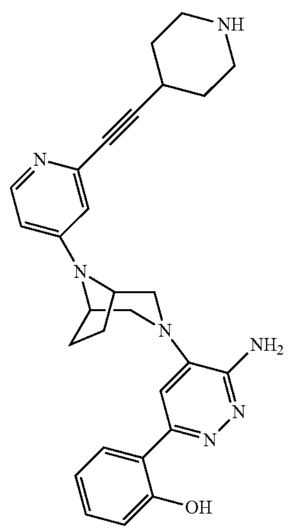 [SMILES: Nc1nnc(-c2ccccc2O)cc1N1CC2CCC(C1)N2c1ccnc(C#CC2CCNCC2)c1] | 2-(6-amino-5-(8-(2-(piperidin-4-ylethynyl)pyridin-4-yl)-3,8-diazabicyclo[3.2.1]octan-3-yl)pyridazin-3-yl)phenol |
| 20 | 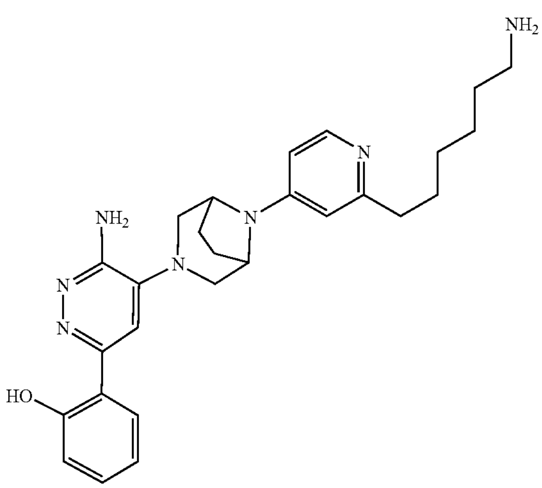 [SMILES: NCCCCCCc1cc(N2C3CCC2CN(c2cc(-c4ccccc4O)nnc2N)C3)ccn1] | 2-(6-amino-5-(8-(2-(6-aminohexyl)pyridin-4-yl)-3,8-diazabicyclo[3.2.1]octan-3-yl)pyridazin-3-yl)phenol |

TABLE 1-continued

| No. | Structure | Name |
|---|---|---|
| 21 | 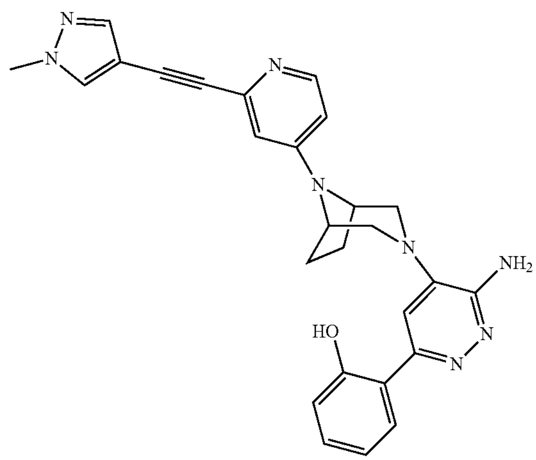 [SMILES: Cn1cc(C#Cc2cc(N3C4CCC3CN(c3cc(-c5ccccc5O)nnc3N)C4)ccn2)cn1] | 2-(6-amino-5-(8-(2-((1-methyl-1H-pyrazol-4-yl)ethynyl)pyridin-4-yl)-3,8-diazabicyclo[3.2.1]octan-3-yl)pyridazin-3-yl)phenol |
| 22 | 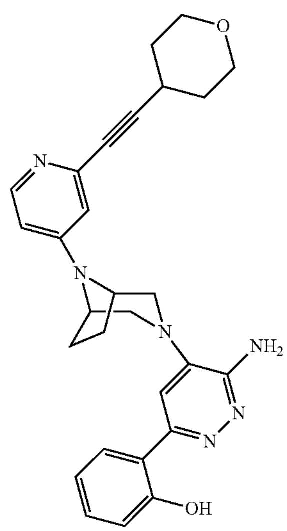 [SMILES: Nc1nnc(-c2ccccc2O)cc1N1CC2CCC(C1)N2c1ccnc(C#CC2CCOCC2)c1] | 2-(6-amino-5-(8-(2-((tetrahydro-2H-pyran-4-yl)ethynyl)pyridin-4-yl)-3,8-diazabicyclo[3.2.1]octan-3-yl)pyridazin-3-yl)phenol |
| 23 | 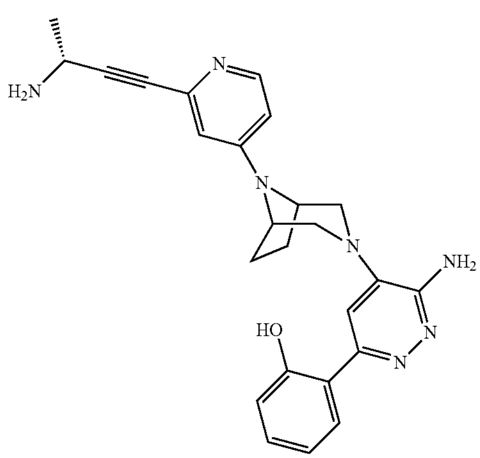 [SMILES: C[C@@H](N)C#Cc1cc(N2C3CCC2CN(c2cc(-c4ccccc4O)nnc2N)C3)ccn1] | 2-(6-amino-5-(8-(2-((R)-3-aminobut-1-yn-1-yl)pyridin-4-yl)-3,8-diazabicyclo[3.2.1]octan-3-yl)pyridazin-3-yl)phenol |

TABLE 1-continued
| No. | Structure | Name |
|---|---|---|
| 24 | 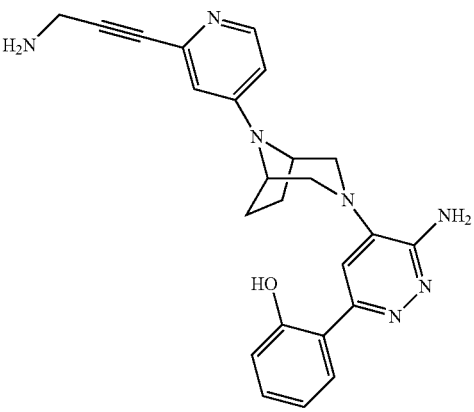 [SMILES: NCC#Cc1cc(N2C3CCC2CN(c2cc(-c4ccccc4O)nnc2N)C3)ccn1] | 2-(6-amino-5-(8-(2-(3-aminoprop-1-yn-1-yl)pyridin-4-yl)-3,8-diazabicyclo[3.2.1]octan-3-yl)pyridazin-3-yl)phenol |
| 25 | 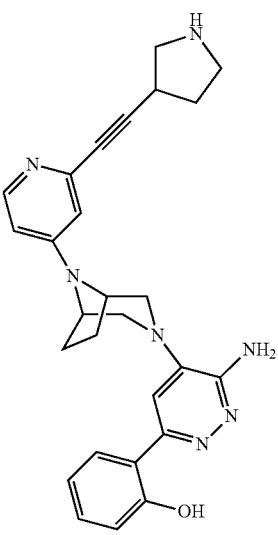 [SMILES: Nc1nnc(-c2ccccc2O)cc1N1CC2CCC(C1)N2c1ccnc(C#CC2CCNC2)c1] | 2-(6-amino-5-(8-(2-(pyrrolidin-3-ylethynyl)pyridin-4-yl)-3,8-diazabicyclo[3.2.1]octan-3-yl)pyridazin-3-yl)phenol |
| 26 | 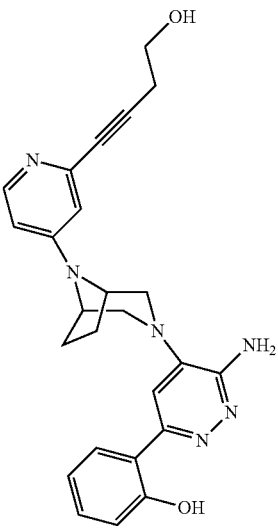 [SMILES: Nc1nnc(-c2ccccc2O)cc1N1CC2CCC(C1)N2c1ccnc(C#CCCO)c1] | 2-(6-amino-5-(8-(2-(4-hydroxybut-1-yn-1-yl)pyridin-4-yl)-3,8-diazabicyclo[3.2.1]octan-3-yl)pyridazin-3-yl)phenol |

TABLE 1-continued
| No. | Structure | Name |
|---|---|---|
| 27 | 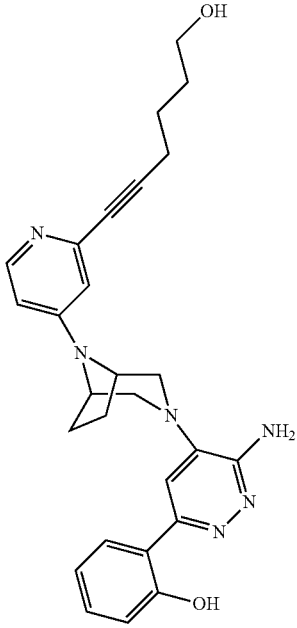 [SMILES: Nc1nnc(-c2ccccc2O)cc1N1CC2CCC(C1)N2c1ccnc(C#CCCCCO)c1] | 2-(6-amino-5-(8-(2-(6-hydroxyhex-1-yn-1-yl)pyridin-4-yl)-3,8-diazabicyclo[3.2.1]octan-3-yl)pyridazin-3-yl)phenol |
| 28 | 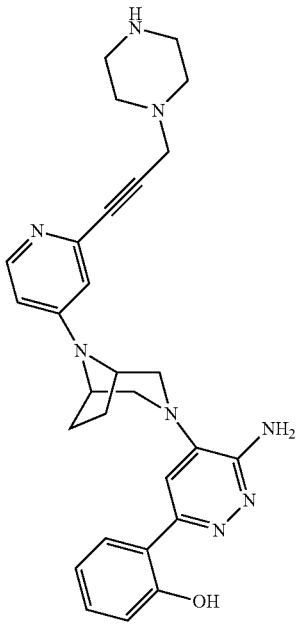 [SMILES: Nc1nnc(-c2ccccc2O)cc1N1CC2CCC(C1)N2c1ccnc(C#CCN2CCNCC2)c1] | 2-(6-amino-5-(8-(2-(3-(piperazin-1-yl)prop-1-yn-1-yl)pyridin-4-yl)-3,8-diazabicyclo[3.2.1]octan-3-yl)pyridazin-3-yl)phenol |

| No. | Structure | Name |
|---|---|---|
| 29 | 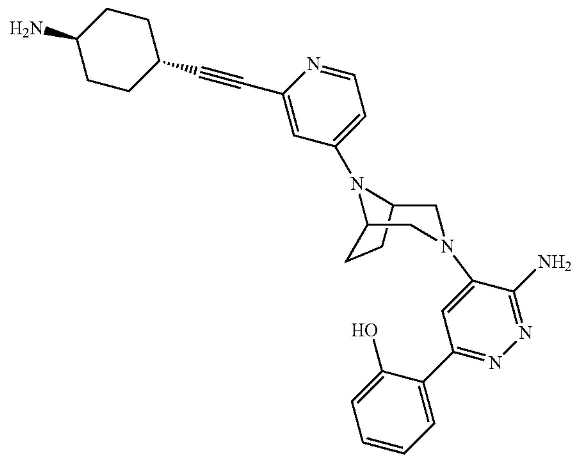 [SMILES: Nc1nnc(-c2ccccc2O)cc1N1CC2CCC(C1)N2c1ccnc(C#C[C@H]2CC[C@H](N)CC2)c1] | 2-(6-amino-5-(8-(2-(((1r,4r)-4-aminocyclohexyl)ethynyl)pyridin-4-yl)-3,8-diazabicyclo[3.2.1]octan-3-yl)pyridazin-3-yl)phenol |
| 30 | 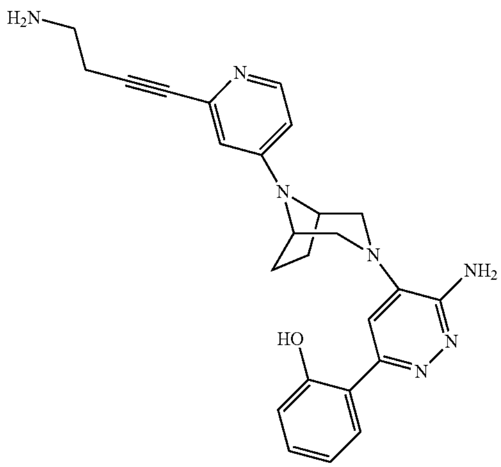 [SMILES: NCCC#Cc1cc(N2C3CCC2CN(c2cc(-c4ccccc4O)nnc2N)C3)ccn1] | 2-(6-amino-5-(8-(2-(4-aminobut-1-yn-1-yl)pyridin-4-yl)-3,8-diazabicyclo[3.2.1]octan-3-yl)pyridazin-3-yl)phenol |
| 31 | 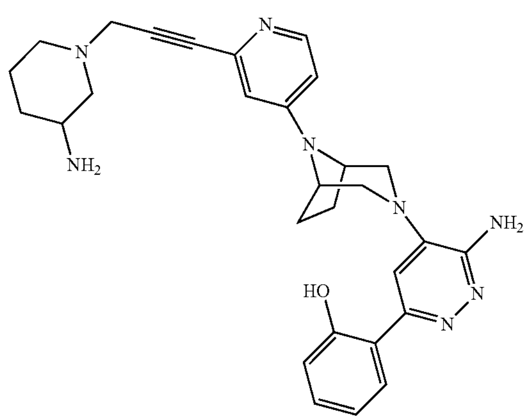 [SMILES: Nc1nnc(-c2ccccc2O)cc1N1CC2CCC(C1)N2c1ccnc(C#CCN2CCCC(N)C2)c1] | 2-(6-amino-5-(8-(2-(3-(3-aminopiperidin-1-yl)prop-1-yn-1-yl)pyridin-4-yl)-3,8-diazabicyclo[3.2.1]octan-3-yl)pyridazin-3-yl)phenol |

TABLE 1-continued

| No. | Structure | Name |
|---|---|---|
| 32 | 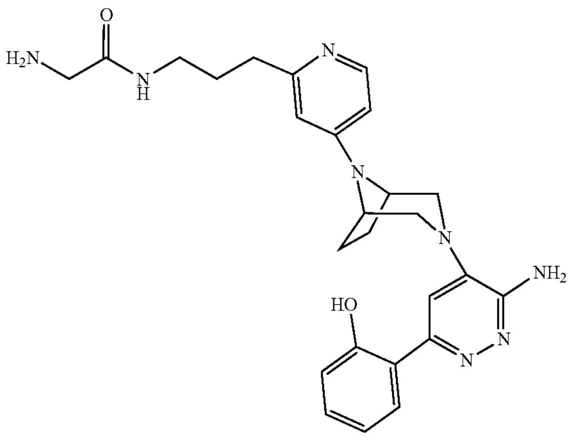 [SMILES: NCC(=O)NCCCc1cc(N2C3CCC2CN(c2cc(-c4ccccc4O)nnc2N)C3)ccn1] | 2-amino-N-(3-(4-(3-(3-amino-6-(2-hydroxyphenyl)pyridazin-4-yl)-3,8-diazabicyclo[3.2.1]octan-8-yl)pyridin-2-yl)propyl)acetamide |
| 33 | 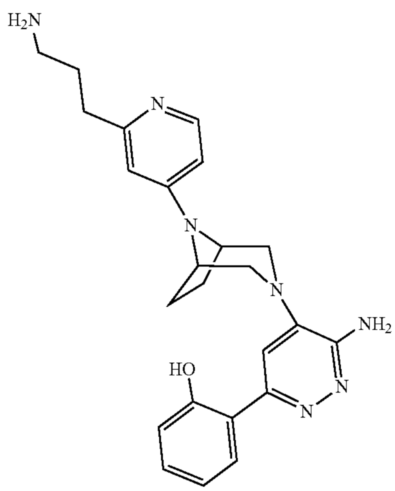 [SMILES: NCCCc1cc(N2C3CCC2CN(c2cc(-c4ccccc4O)nnc2N)C3)ccn1] | 2-(6-amino-5-(8-(2-(3-aminopropyl)pyridin-4-yl)-3,8-diazabicyclo[3.2.1]octan-3-yl)pyridazin-3-yl)phenol |
| 34 | 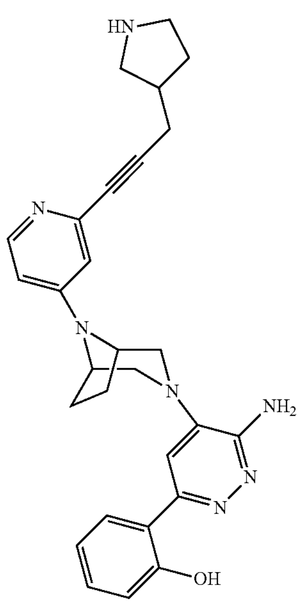 [SMILES: Nc1nnc(-c2ccccc2O)cc1N1CC2CCC(C1)N2c1ccnc(C#CCC2CCNC2)c1] | 2-(6-amino-5-(8-(2-(3-(pyrrolidin-3-yl)prop-1-yn-1-yl)pyridin-4-yl)-3,8-diazabicyclo[3.2.1]octan-3-yl)pyridazin-3-yl)phenol |

TABLE 1-continued

| No. | Structure | Name |
|---|---|---|
| 35 | 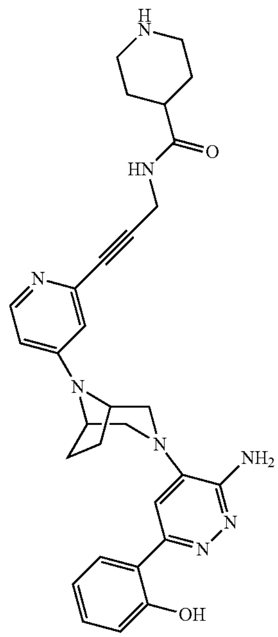 [SMILES: Nc1nnc(-c2ccccc2O)cc1N1CC2CCC(C1)N2c1ccnc(C#CCNC(=O)C2CCNCC2)c1] | N-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidine-4-carboxamide |
| 36 | 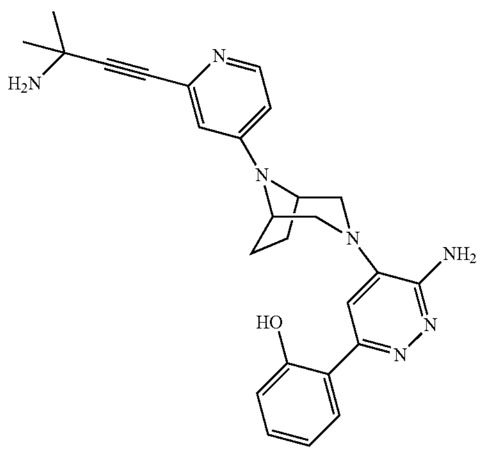 [SMILES: CC(C)(N)C#Cc1cc(N2C3CCC2CN(c2cc(-c4ccccc4O)nnc2N)C3)ccn1] | 2-[6-amino-5-[8-[2-(3-amino-3-methyl-but-1-ynyl)-4-pyridyl]-3,8-diazabicyclo[3.2.1]octan-3-yl]pyridazin-3-yl]phenol |
| 37 | 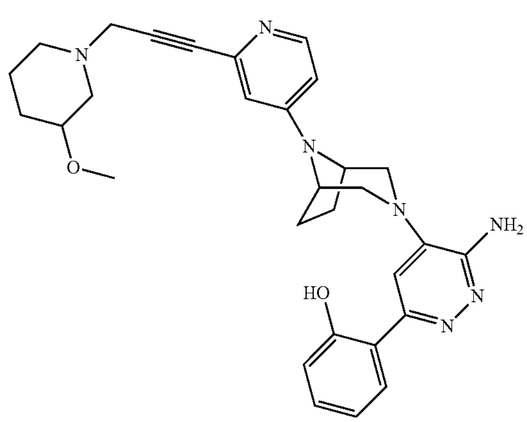 [SMILES: COC1CCCN(CC#Cc2cc(N3C4CCC3CN(c3cc(-c5ccccc5O)nnc3N)C4)ccn2)C1] | 2-[6-amino-5-[8-[2-[3-(3-methoxy-1-piperidyl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 38 | 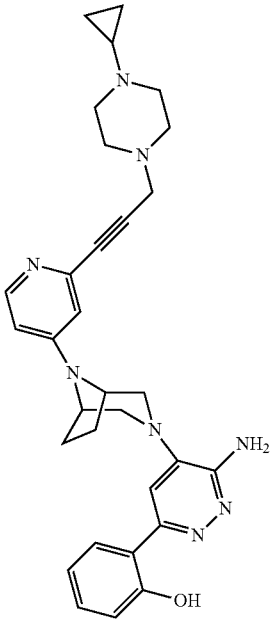 [SMILES: Nc1nnc(-c2ccccc2O)cc1N1CC2CCC(C1)N2c1ccnc(C#CCN2CCN(C3CC3)CC2)c1] | 2-[6-amino-5-[8-[2-[3-(4-cyclopropylpiperazin-1-yl)prop-1-ynyl]-4-pyridyl]-3,8-diazabicyclo[3.2.1]octan-3-yl]pyridazin-3-yl]phenol |
| 39 | 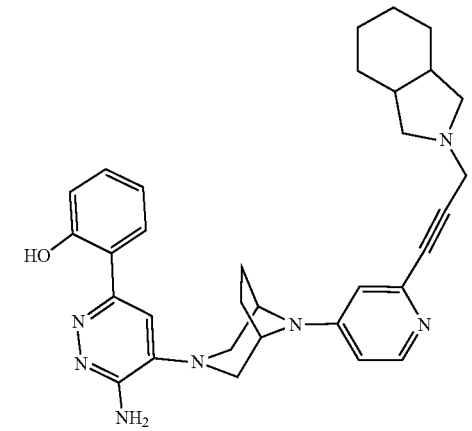 [SMILES: Nc1nnc(-c2ccccc2O)cc1N1CC2CCC(C1)N2c1ccnc(C#CCN2CC3CCCCC3C2)c1] | 2-[5-[8-[2-[3-(1,3,3a,4,5,6,7,7a-octahydroisoindol-2-yl)prop-1-ynyl]-4-pyridyl]-3,8-diazabicyclo[3.2.1]octan-3-yl]-6-amino-pyridazin-3-yl]phenol |
| 40 | 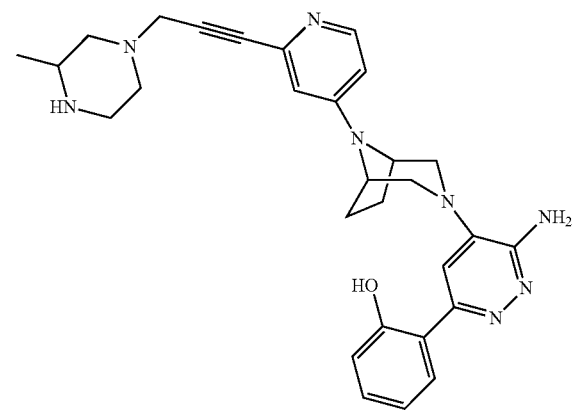 [SMILES: CC1CN(CC#Cc2cc(N3C4CCC3CN(c3cc(-c5ccccc5O)nnc3N)C4)ccn2)CCN1] | 2-[6-amino-5-[8-[2-[3-(3-methylpiperazin-1-yl)prop-1-ynyl]-4-pyridyl]-3,8-diazabicyclo[3.2.1]octan-3-yl]pyridazin-3-yl]phenol |

| No. | Structure | Name |
|---|---|---|
| 41 | 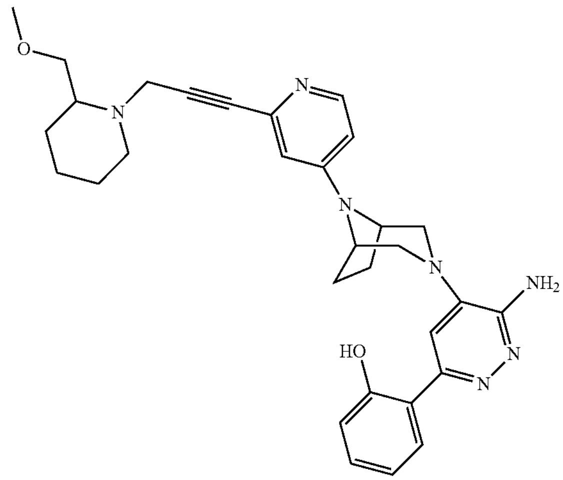 [SMILES: COCC1CCCCN1CC#Cc1cc(N2C3CCC2CN(c2cc(-c4ccccc4O)nnc2N)C3)ccn1] | 2-[6-amino-5-[8-[2-[3-[2-(methoxymethyl)-1-piperidyl]prop-1-ynyl]-4-pyridyl]-3,8-diazabicyclo[3.2.1]octan-3-yl]pyridazin-3-yl]phenol |
| 42 | 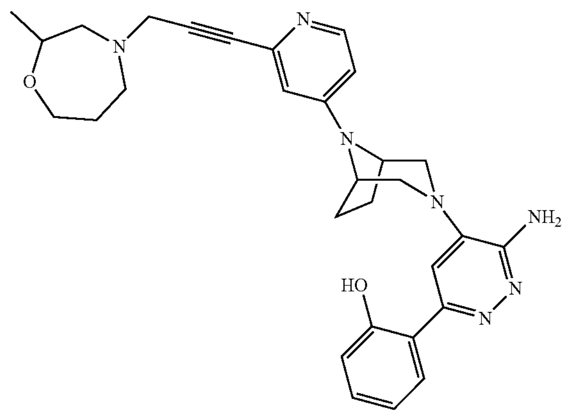 [SMILES: CC1CN(CC#Cc2cc(N3C4CCC3CN(c3cc(-c5ccccc5O)nnc3N)C4)ccn2)CCCO1] | 2-[6-amino-5-[8-[2-[3-(2-methyl-1,4-oxazepan-4-yl)prop-1-ynyl]-4-pyridyl]-3,8-diazabicyclo[3.2.1]octan-3-yl]pyridazin-3-yl]phenol |
| 43 | 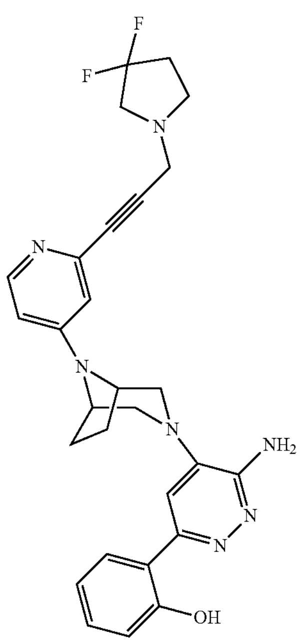 [SMILES: Nc1nnc(-c2ccccc2O)cc1N1CC2CCC(C1)N2c1ccnc(C#CCN2CCC(F)(F)C2)c1] | 2-[6-amino-5-[8-[2-[3-(3,3-difluoropyrrolidin-1-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 44 | 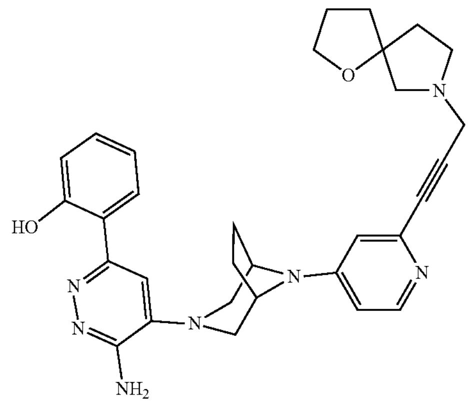 [SMILES: Nc1nnc(-c2ccccc2O)cc1N1CC2CCC(C1)N2c1ccnc(C#CCN2CCC3(CCCO3)C2)c1] | 2-[6-amino-5-[8-[2-[3-(1-oxa-7-azaspiro[4.4]nonan-7-yl)prop-1-ynyl]-4-pyridyl]-3,8-diazabicyclo[3.2.1]octan-3-yl]pyridazin-3-yl]phenol |
| 45 | 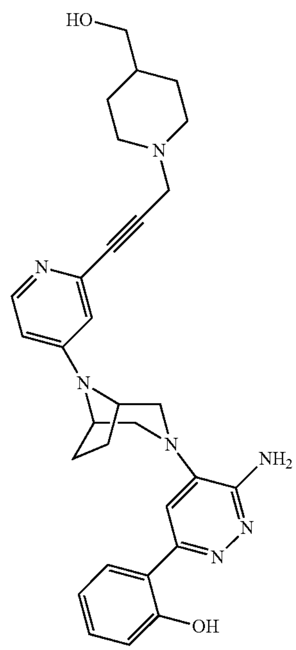 [SMILES: Nc1nnc(-c2ccccc2O)cc1N1CC2CCC(C1)N2c1ccnc(C#CCN2CCC(CO)CC2)c1] | 2-[6-amino-5-[8-[2-[3-[4-(hydroxymethyl)-1-piperidyl]prop-1-ynyl]-4-pyridyl]-3,8-diazabicyclo[3.2.1]octan-3-yl]pyridazin-3-yl]phenol |
| 46 | 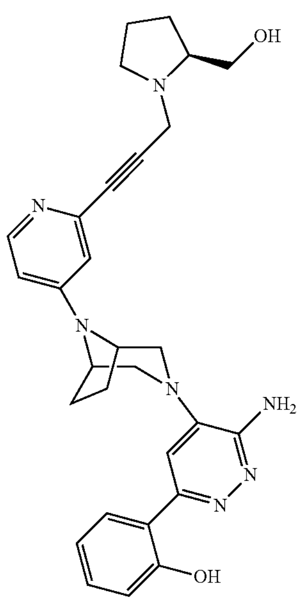 [SMILES: Nc1nnc(-c2ccccc2O)cc1N1CC2CCC(C1)N2c1ccnc(C#CCN2CCC[C@H]2CO)c1] | 2-[6-amino-5-[8-[2-[3-[(2S)-2-(hydroxymethyl)pyrrolidin-1-yl]prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 47 | 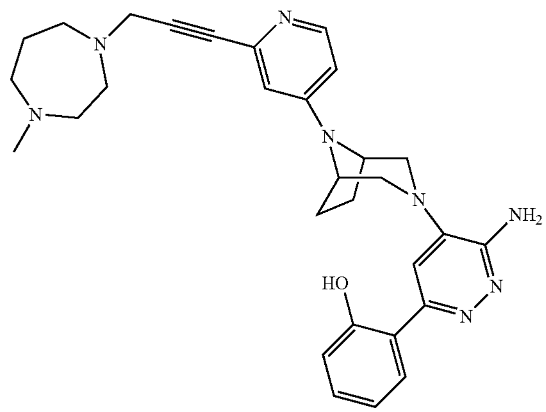 [SMILES: CN1CCCN(CC#Cc2cc(N3C4CCC3CN(c3cc(-c5ccccc5O)nnc3N)C4)ccn2)CC1] | 2-[6-amino-5-[8-[2-[3-(4-methyl-1,4-diazepan-1-yl)prop-1-ynyl]-4-pyridyl]-3,8-diazabicyclo[3.2.1]octan-3-yl]pyridazin-3-yl]phenol |
| 48 | 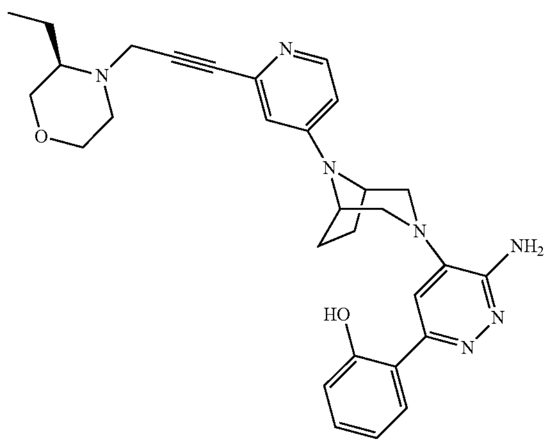 [SMILES: CC[C@@H]1COCCN1CC#Cc1cc(N2C3CCC2CN(c2cc(-c4ccccc4O)nnc2N)C3)ccn1] | 2-[6-amino-5-[8-[2-[3-[(3R)-3-ethylmorpholin-4-yl]prop-1-ynyl]-4-pyridyl]-3,8-diazabicyclo[3.2.1]octan-3-yl]pyridazin-3-yl]phenol |
| 49 | 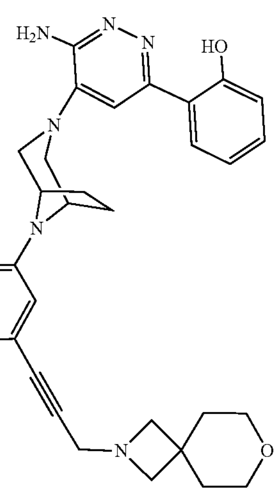 | 2-[6-amino-5-[8-[2-[3-(7-oxa-2-azaspiro[3.5]nonan-2-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 50 | 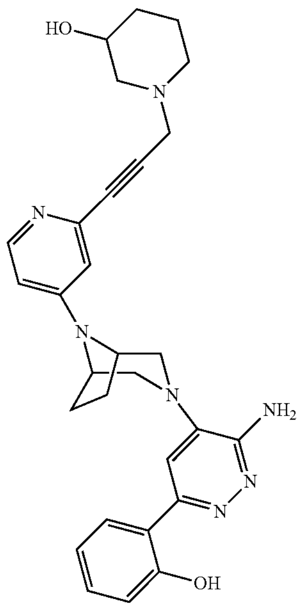 [SMILES: Nc1nnc(-c2ccccc2O)cc1N1CC2CCC(C1)N2c1ccnc(C#CCN2CCCC(O)C2)c1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidin-3-ol |
| 51 | 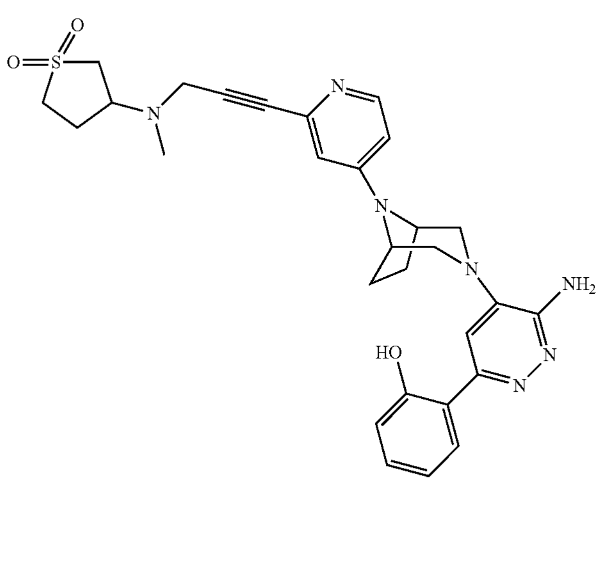 [SMILES: CN(CC#Cc1cc(N2C3CCC2CN(c2cc(-c4ccccc4O)nnc2N)C3)ccn1)C1CCS(=O)(=O)C1] | 2-[6-amino-5-[8-[2-[3-[(1,1-dioxothiolan-3-yl)-methyl-amino]prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 52 | 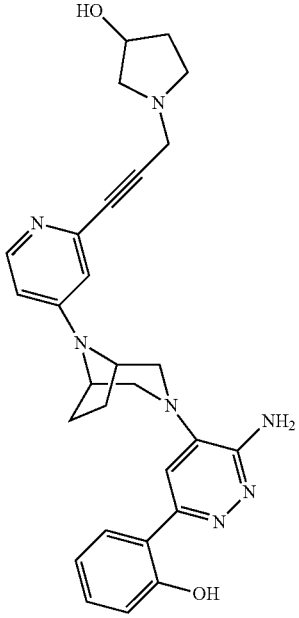 [SMILES: Nc1nnc(-c2ccccc2O)cc1N1CC2CCC(C1)N2c1ccnc(C#CCN2CCC(O)C2)c1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]pyrrolidin-3-ol |
| 53 | 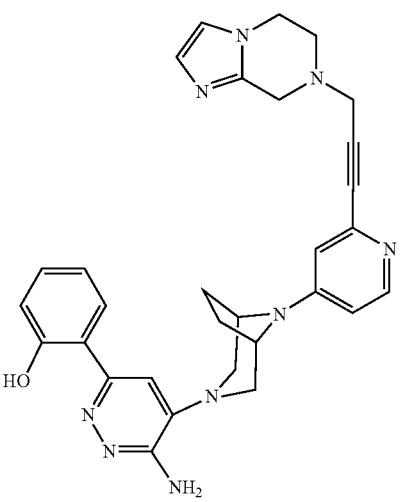 [SMILES: Nc1nnc(-c2ccccc2O)cc1N1CC2CCC(C1)N2c1ccnc(C#CCN2CCn3ccnc3C2)c1] | 2-[6-amino-5-[8-[2-[3-(6,8-dihydro-5H-imidazo[1,2-a]pyrazin-7-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 54 | 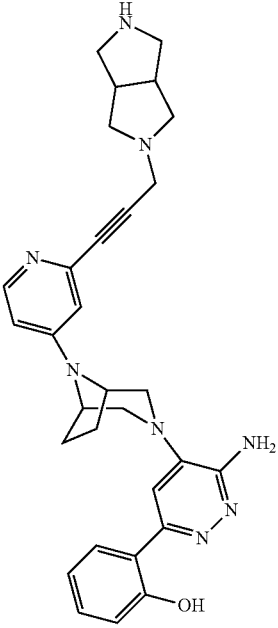 [SMILES: Nc1nnc(-c2ccccc2O)cc1N1CC2CCC(C1)N2c1ccnc(C#CCN2CC3CNCC3C2)c1] | 2-[5-[8-[2-[3-(2,3,3a,4,6,6a-hexahydro-1H-pyrrolo[3,4-c]pyrrol-5-yl)prop-1-ynyl]-4-pyridyl]-3,8-diazabicyclo[3.2.1]octan-3-yl]-6-amino-pyridazin-3-yl]phenol |
| 55 | 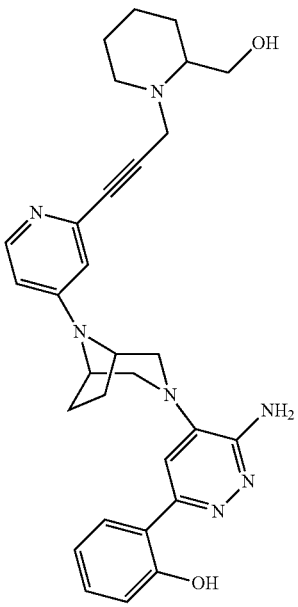 [SMILES: Nc1nnc(-c2ccccc2O)cc1N1CC2CCC(C1)N2c1ccnc(C#CCN2CCCCC2CO)c1] | 2-[6-amino-5-[8-[2-[3-[2-(hydroxymethyl)-1-piperidyl]prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 56 | 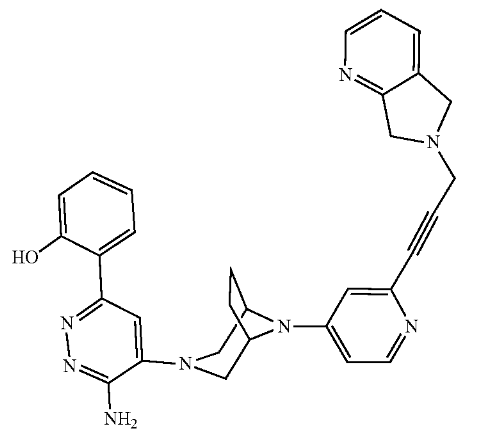 [SMILES: Nc1nnc(-c2ccccc2O)cc1N1CC2CCC(C1)N2c1ccnc(C#CCN2Cc3cccnc3C2)c1] | 2-[6-amino-5-[8-[2-[3-(5,7-dihydropyrrolo[3,4-b]pyridin-6-yl)prop-1-ynyl]-4-pyridyl]-3,8-diazabicyclo[3.2.1]octan-3-yl]pyridazin-3-yl]phenol |
| 57 | 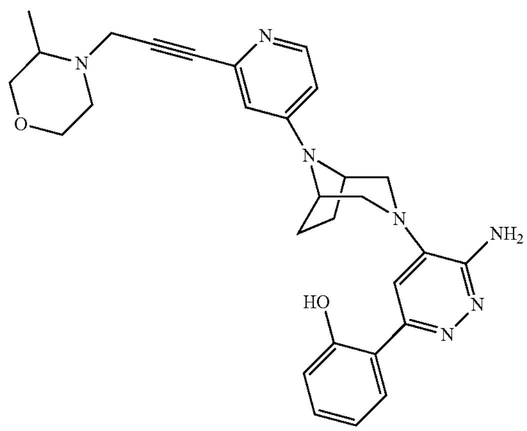 [SMILES: CC1COCCN1CC#Cc1cc(N2C3CCC2CN(c2cc(-c4ccccc4O)nnc2N)C3)ccn1] | 2-[6-amino-5-[8-[2-[3-(3-methylmorpholin-4-yl)prop-1-ynyl]-4-pyridyl]-3,8-diazabicyclo[3.2.1]octan-3-yl]pyridazin-3-yl]phenol |
| 58 | 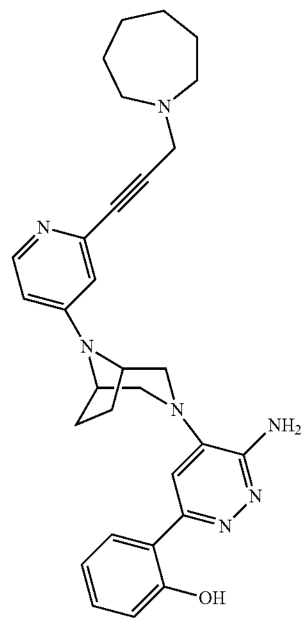 [SMILES: Nc1nnc(-c2ccccc2O)cc1N1CC2CCC(C1)N2c1ccnc(C#CCN2CCCCCC2)c1] | 2-[6-amino-5-[8-[2-[3-(azepan-1-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 59 | 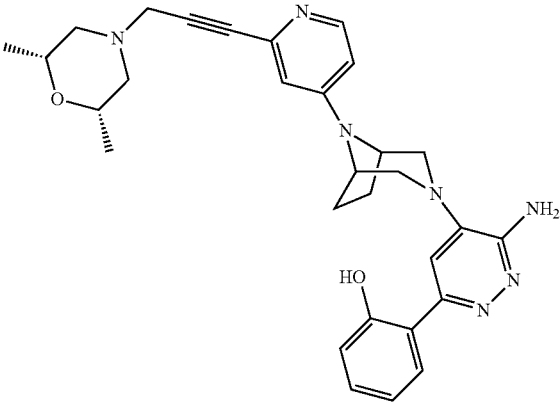 [SMILES: C[C@@H]1CN(CC#Cc2cc(N3C4CCC3CN(c3cc(-c5ccccc5O)nnc3N)C4)ccn2)C[C@H](C)O1] | 2-[6-amino-5-[8-[2-[3-[(2S,6R)-2,6-dimethylmorpholin-4-yl]prop-1-ynyl]-4-pyridyl]-3,8-diazabicyclo[3.2.1]octan-3-yl]pyridazin-3-yl]phenol |
| 60 | 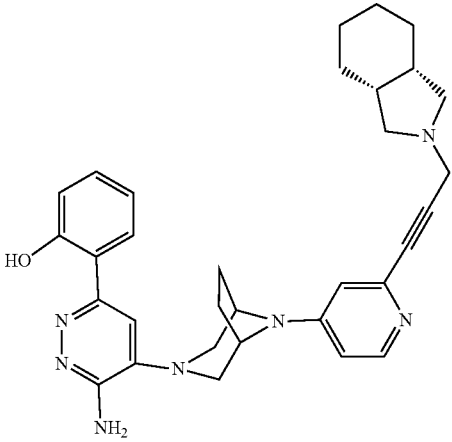 [SMILES: Nc1nnc(-c2ccccc2O)cc1N1CC2CCC(C1)N2c1ccnc(C#CCN2C[C@H]3CCCC[C@H]3C2)c1] | 2-[5-[8-[2-[3-[(3aS,7aR)-1,3,3a,4,5,6,7,7a-octahydroisoindol-2-yl]prop-1-ynyl]-4-pyridyl]-3,8-diazabicyclo[3.2.1]octan-3-yl]-6-amino-pyridazin-3-yl]phenol |
| 61 | 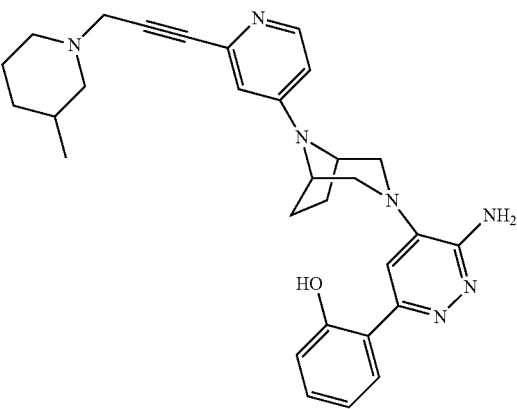 [SMILES: CC1CCCN(CC#Cc2cc(N3C4CCC3CN(c3cc(-c5ccccc5O)nnc3N)C4)ccn2)C1] | 2-[6-amino-5-[8-[2-[3-(3-methyl-1-piperidyl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 62 | 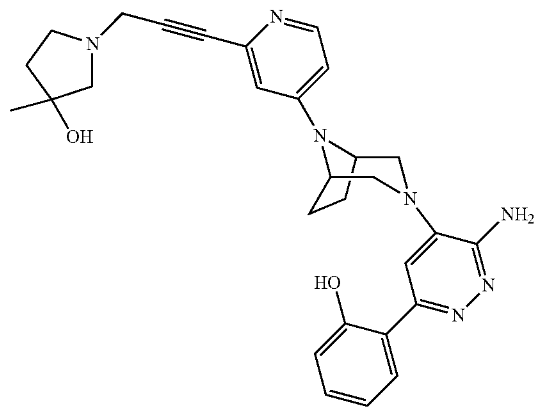 [SMILES: CC1(O)CCN(CC#Cc2cc(N3C4CCC3CN(c3cc(-c5ccccc5O)nnc3N)C4)ccn2)C1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-pyrrolidin-3-ol |
| 63 | 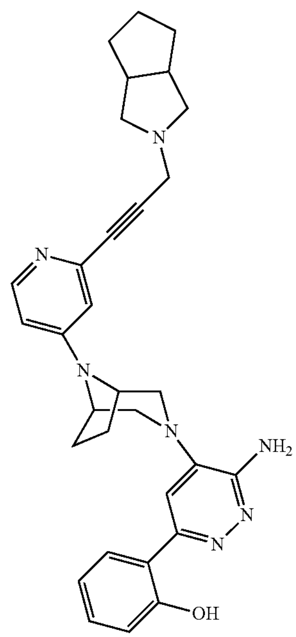 [SMILES: Nc1nnc(-c2ccccc2O)cc1N1CC2CCC(C1)N2c1ccnc(C#CCN2CC3CCCC3C2)c1] | 2-[5-[8-[2-[3-(3,3a,4,5,6,6a-hexahydro-1H-cyclopenta[c]pyrrol-2-yl)prop-1-ynyl]-4-pyridyl]-3,8-diazabicyclo[3.2.1]octan-3-yl]-6-amino-pyridazin-3-yl]phenol |
| 64 | 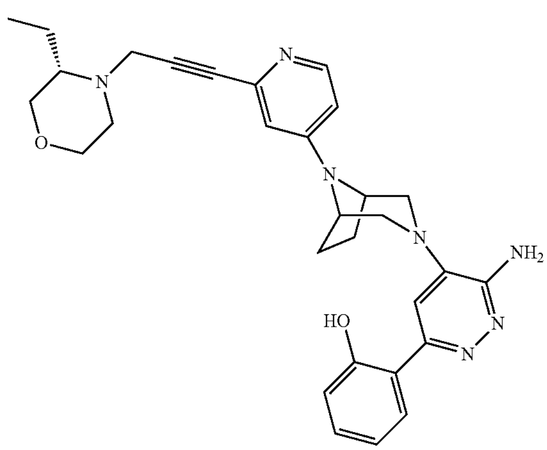 [SMILES: CC[C@H]1COCCN1CC#Cc1cc(N2C3CCC2CN(c2cc(-c4ccccc4O)nnc2N)C3)ccn1] | 2-[6-amino-5-[8-[2-[3-[(3S)-3-ethylmorpholin-4-yl]prop-1-ynyl]-4-pyridyl]-3,8-diazabicyclo[3.2.1]octan-3-yl]pyridazin-3-yl]phenol |

| No. | Structure | Name |
|---|---|---|
| 65 | 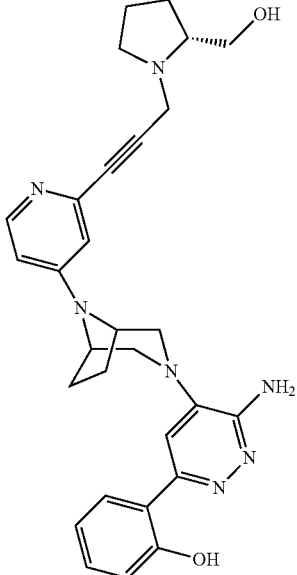 | 2-[6-amino-5-[8-[2-[3-[(2R)-2-(hydroxymethyl)pyrrolidin-1-yl]prop-1-ynyl]-4-pyridyl]-3,8-diazabicyclo[3.2.1]octan-3-yl]pyridazin-3-yl]phenol |
| 66 | 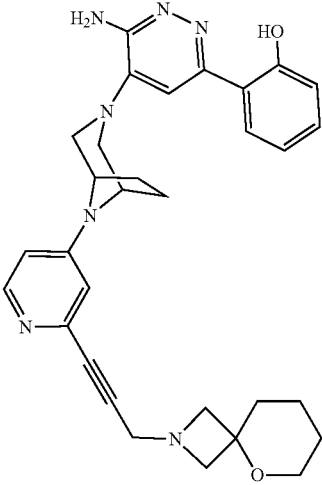 [SMILES: Nc1nnc(-c2ccccc2O)cc1N1CC2CCC(C1)N2c1ccnc(C#CCN2CC3(CCCCO3)C2)c1] | 2-[6-amino-5-[8-[2-[3-(5-oxa-2-azaspiro[3.5]nonan-2-yl)prop-1-ynyl]-4-pyridyl]-3,8-diazabicyclo[3.2.1]octan-3-yl]pyridazin-3-yl]phenol |
| 67 | 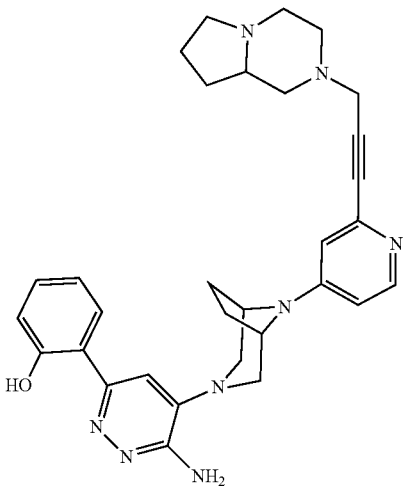 [SMILES: Nc1nnc(-c2ccccc2O)cc1N1CC2CCC(C1)N2c1ccnc(C#CCN2CCN3CCCC3C2)c1] | 2-[5-[8-[2-[3-(3,4,6,7,8,8a-hexahydro-1H-pyrrolo[1,2-a]pyrazin-2-yl)prop-1-ynyl]-4-pyridyl]-3,8-diazabicyclo[3.2.1]octan-3-yl]-6-amino-pyridazin-3-yl]phenol |

TABLE 1-continued
| No. | Structure | Name |
|---|---|---|
| 68 | 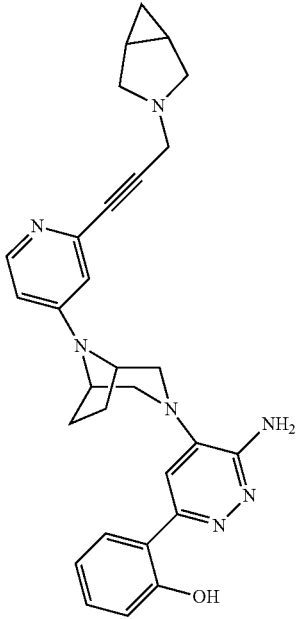 [SMILES: Nc1nnc(-c2ccccc2O)cc1N1CC2CCC(C1)N2c1ccnc(C#CCN2CC3CC3C2)c1] | 2-[6-amino-5-[8-[2-[3-(3-azabicyclo[3.1.0]hexan-3-yl)prop-1-ynyl]-4-pyridyl]-3,8-diazabicyclo[3.2.1]octan-3-yl]pyridazin-3-yl]phenol; |
| 69 | 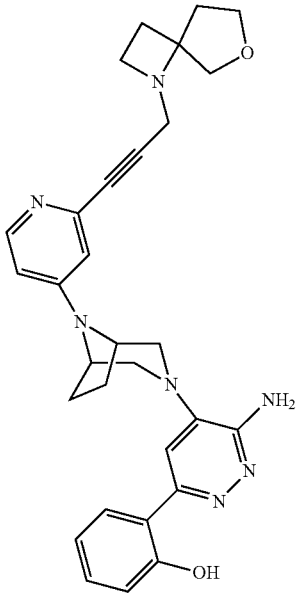 [SMILES: Nc1nnc(-c2ccccc2O)cc1N1CC2CCC(C1)N2c1ccnc(C#CCN2CCC23CCOC3)c1] | 2-[6-amino-5-[8-[2-[3-(7-oxa-1-azaspiro[3.4]octan-1-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 70 | 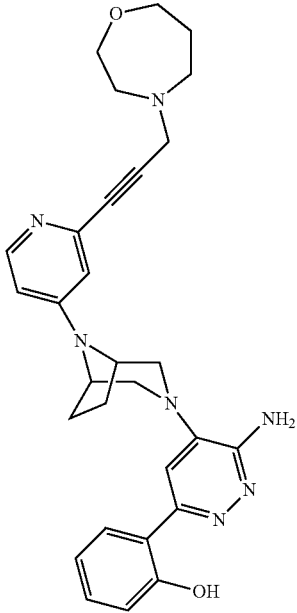 [SMILES: Nc1nnc(-c2ccccc2O)cc1N1CC2CCC(C1)N2c1ccnc(C#CCN2CCCOCC2)c1] | 2-[6-amino-5-[8-[2-[3-(1,4-oxazepan-4-yl)prop-1-ynyl]-4-pyridyl]-3,8-diazabicyclo[3.2.1]octan-3-yl]pyridazin-3-yl]phenol |
| 71 | 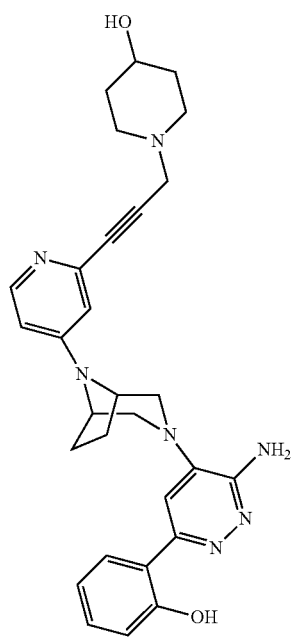 [SMILES: Nc1nnc(-c2ccccc2O)cc1N1CC2CCC(C1)N2c1ccnc(C#CCN2CCC(O)CC2)c1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidin-4-ol |

TABLE 1-continued

| No. | Structure | Name |
|---|---|---|
| 72 | 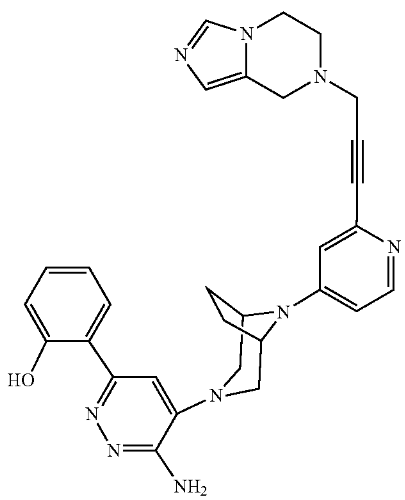 | 2-[6-amino-5-[8-[2-[3-(6,8-dihydro-5H-imidazo[1,5-a]pyrazin-7-yl)prop-1-ynyl]-4-pyridyl]-3,8-diazabicyclo[3.2.1]octan-3-yl]pyridazin-3-yl]phenol |
| 73 | 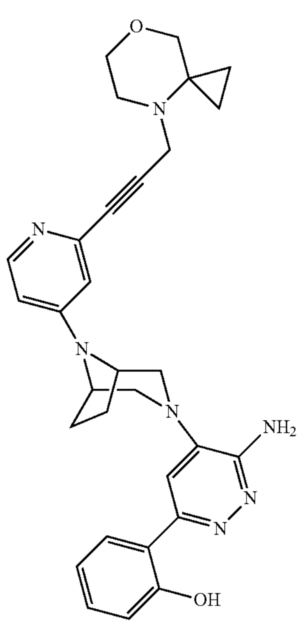 [SMILES: Nc1nnc(-c2ccccc2O)cc1N1CC2CCC(C1)N2c1ccnc(C#CCN2CCOCC23CC3)c1] | 2-[6-amino-5-[8-[2-[3-(7-oxa-4-azaspiro[2.5]octan-4-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 74 | 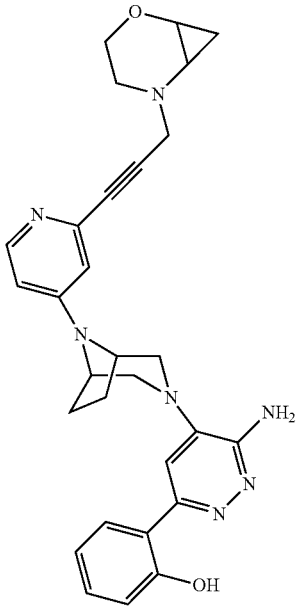 [SMILES: Nc1nnc(-c2ccccc2O)cc1N1CC2CCC(C1)N2c1ccnc(C#CCN2CCOC3CC32)c1] | 2-[6-amino-5-[8-[2-[3-(2-oxa-5-azabicyclo[4.1.0]heptan-5-yl)prop-1-ynyl]-4-pyridyl]-3,8-diazabicyclo[3.2.1]octan-3-yl]pyridazin-3-yl]phenol |
| 75 | 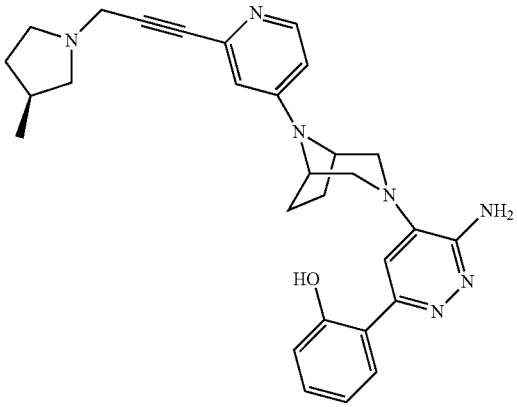 [SMILES: C[C@H]1CCN(CC#Cc2cc(N3C4CCC3CN(c3cc(-c5ccccc5O)nnc3N)C4)ccn2)C1] | 2-[6-amino-5-[8-[2-[3-[(3S)-3-methylpyrrolidin-1-yl]prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 76 | 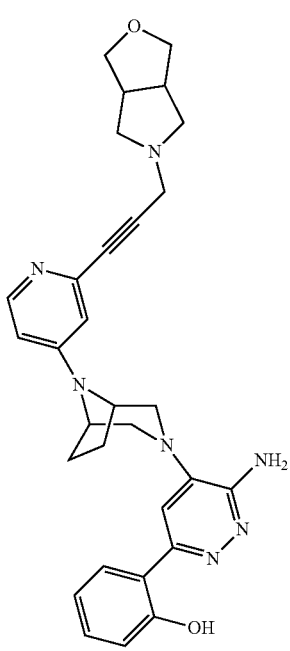 [SMILES: Nc1nnc(-c2ccccc2O)cc1N1CC2CCC(C1)N2c1ccnc(C#CCN2CC3COCC3C2)c1] | 2-[5-[8-[2-[3-(1,3,3a,4,6,6a-hexahydrofuro[3,4-c]pyrrol-5-yl)prop-1-ynyl]-4-pyridyl]-3,8-diazabicyclo[3.2.1]octan-3-yl]-6-amino-pyridazin-3-yl]phenol |
| 77 | 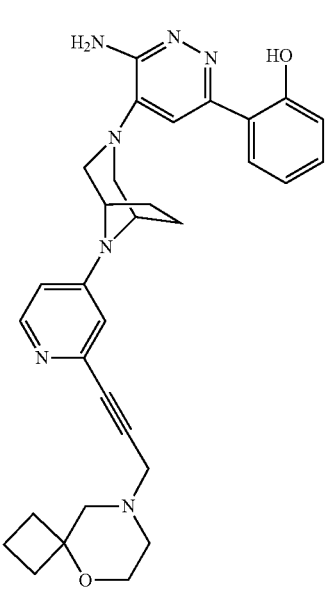 [SMILES: Nc1nnc(-c2ccccc2O)cc1N1CC2CCC(C1)N2c1ccnc(C#CCN2CCOC3(CCC3)C2)c1] | 2-[6-amino-5-[8-[2-[3-(5-oxa-8-azaspiro[3.5]nonan-8-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 78 | 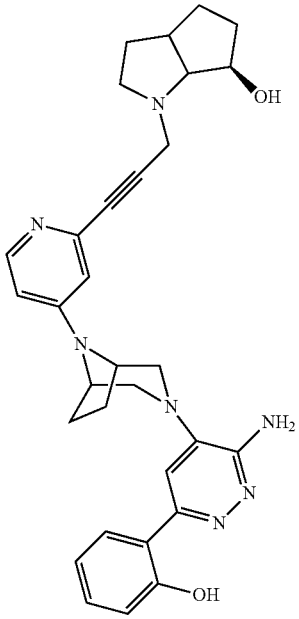 [SMILES: Nc1nnc(-c2ccccc2O)cc1N1CC2CCC(C1)N2c1ccnc(C#CCN2CCC3CC[C@@H](O)C32)c1] | (6R)-1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3,3a,4,5,6,6a-hexahydro-2H-cyclopenta[b]pyrrol-6-ol |
| 79 | 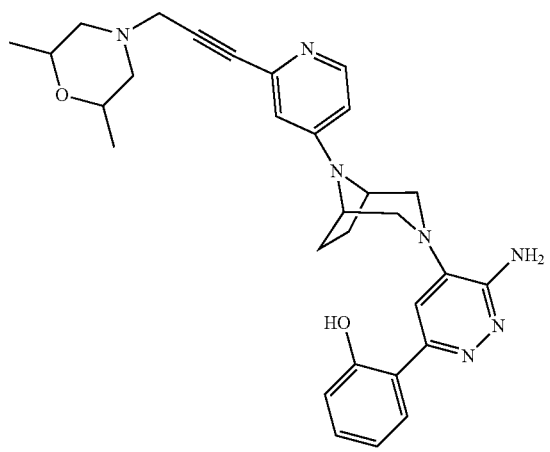 [SMILES: CC1CN(CC#Cc2cc(N3C4CCC3CN(c3cc(-c5ccccc5O)nnc3N)C4)ccn2)CC(C)O1] | 2-[6-amino-5-[8-[2-[3-(2,6-dimethylmorpholin-4-yl)prop-1-ynyl]-4-pyridyl]-3,8-diazabicyclo[3.2.1]octan-3-yl]pyridazin-3-yl]phenol |

| No. | Structure | Name |
|---|---|---|
| 80 | 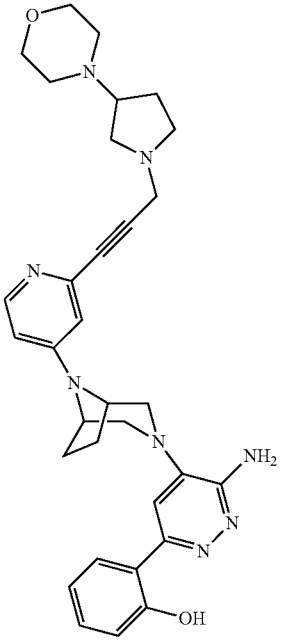 [SMILES: Nc1nnc(-c2ccccc2O)cc1N1CC2CCC(C1)N2c1ccnc(C#CCN2CCC(N3CCOCC3)C2)c1] | 2-[6-amino-5-[8-[2-[3-(3-morpholinopyrrolidin-1-yl)prop-1-ynyl]-4-pyridyl]-3,8-diazabicyclo[3.2.1]octan-3-yl]pyridazin-3-yl]phenol |
| 81 | 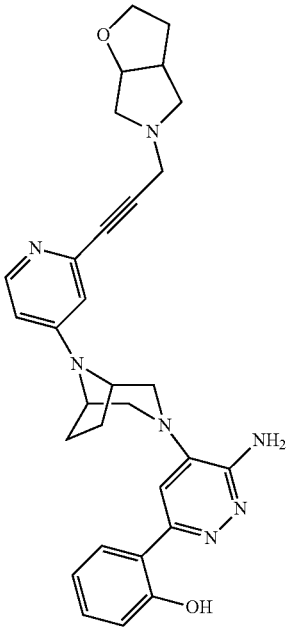 | 2-[5-[8-[2-[3-(2,3,3a,4,6,6a-hexahydrofuro[2,3-c]pyrrol-5-yl)prop-1-ynyl]-4-pyridyl]-3,8-diazabicyclo[3.2.1]octan-3-yl]-6-amino-pyridazin-3-yl]phenol |

TABLE 1-continued
| No. | Structure | Name |
|---|---|---|
| 82 | 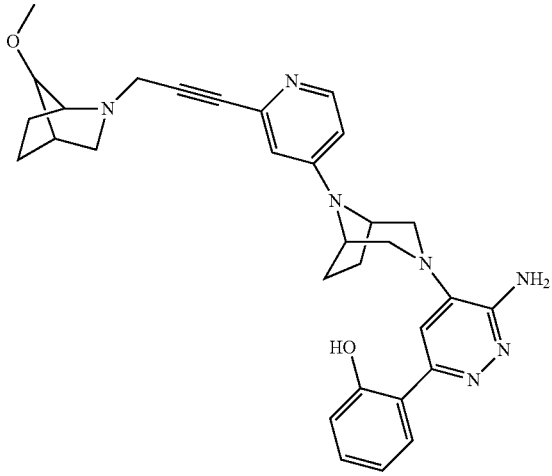 [SMILES: COC1C2CCC1N(CC#Cc1cc(N3C4CCC3CN(c3cc(-c5ccccc5O)nnc3N)C4)ccn1)C2] | 2-[6-amino-5-[8-[2-[3-(7-methoxy-2-azabicyclo[2.2.1]heptan-2-yl)prop-1-ynyl]-4-pyridyl]-3,8-diazabicyclo[3.2.1]octan-3-yl]pyridazin-3-yl]phenol |
| 83 | 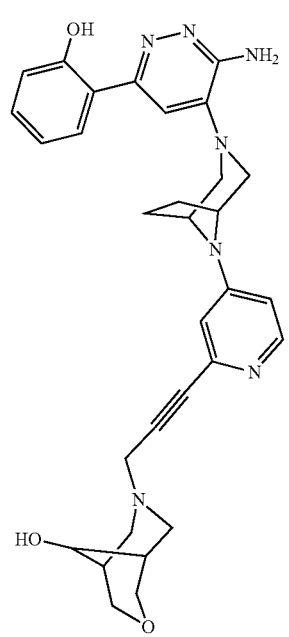 [SMILES: Nc1nnc(-c2ccccc2O)cc1N1CC2CCC(C1)N2c1ccnc(C#CCN2CC3COCC(C2)C3O)c1] | 7-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-oxa-7-azabicyclo[3.3.1]nonan-9-ol |

TABLE 1-continued
| No. | Structure | Name |
|---|---|---|
| 84 | 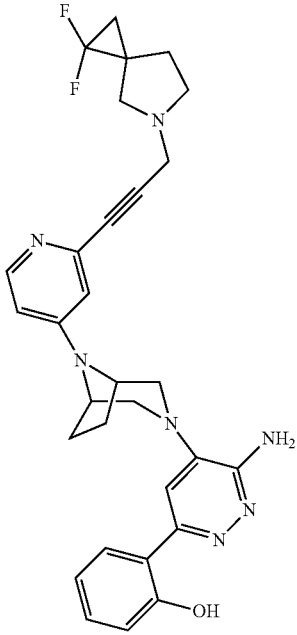 [SMILES: Nc1nnc(-c2ccccc2O)cc1N1CC2CCC(C1)N2c1ccnc(C#CCN2CCC3(C2)CC3(F)F)c1] | 2-[6-amino-5-[8-[2-[3-(2,2-difluoro-5-azaspiro[2.4]heptan-5-yl)prop-1-ynyl]-4-pyridyl]-3,8-diazabicyclo[3.2.1]octan-3-yl]pyridazin-3-yl]phenol |
| 85 | 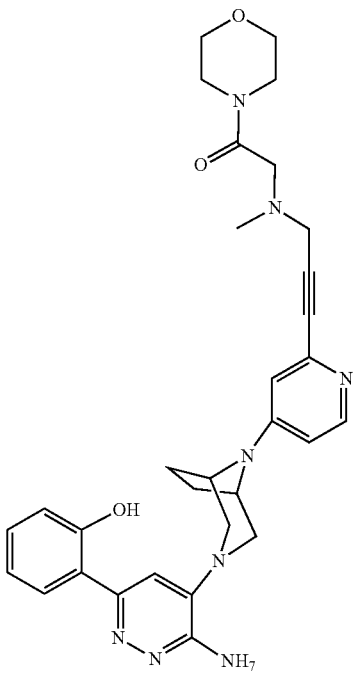 | 2-[3-[4-[3-[3-amino-6-(2-hydroxyphenyl)pyridazin-4-yl]-3,8-diazabicyclo[3.2.1]octan-8-yl]-2-pyridyl]prop-2-ynyl-methyl-amino]-1-morpholino-ethanone |

TABLE 1-continued
| No. | Structure | Name |
|---|---|---|
| 86 | 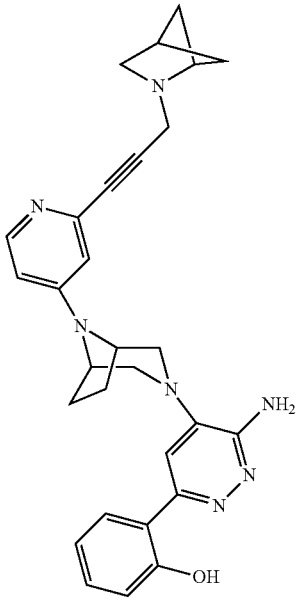 [SMILES: Nc1nnc(-c2ccccc2O)cc1N1CC2CCC(C1)N2c1ccnc(C#CCN2CC3CC2C3)c1] | 2-[6-amino-5-[8-[2-[3-(2-azabicyclo[2.1.1]hexan-2-yl)prop-1-ynyl]-4-pyridyl]-3,8-diazabicyclo[3.2.1]octan-3-yl]pyridazin-3-yl]phenol |
| 87 | 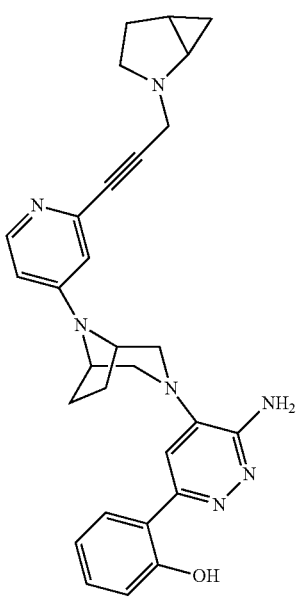 [SMILES: Nc1nnc(-c2ccccc2O)cc1N1CC2CCC(C1)N2c1ccnc(C#CCN2CCC3CC32)c1] | 2-[6-amino-5-[8-[2-[3-(2-azabicyclo[3.1.0]hexan-2-yl)prop-1-ynyl]-4-pyridyl]-3,8-diazabicyclo[3.2.1]octan-3-yl]pyridazin-3-yl]phenol |

| No. | Structure | Name |
|---|---|---|
| 88 | 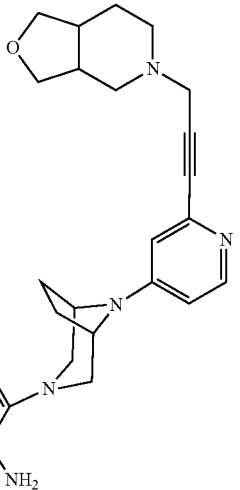 | 2-[5-[8-[2-[3-(3,3a,4,6,7,7a-hexahydro-1H-furo[3,4-c]pyridin-5-yl)prop-1-ynyl]-4-pyridyl]-3,8-diazabicyclo[3.2.1]octan-3-yl]-6-amino-pyridazin-3-yl]phenol |
| 89 | 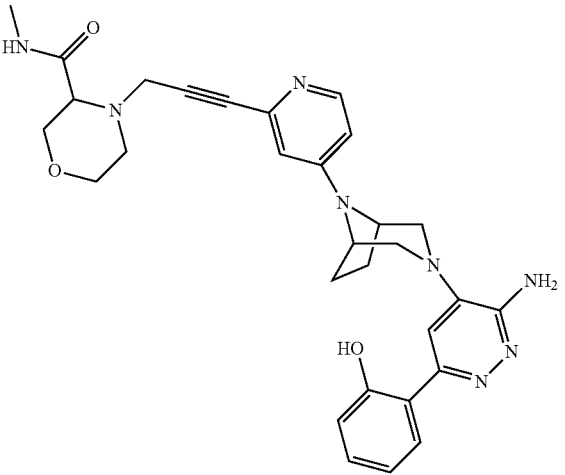 | 4-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-morpholine-3-carboxamide |
| 90 | 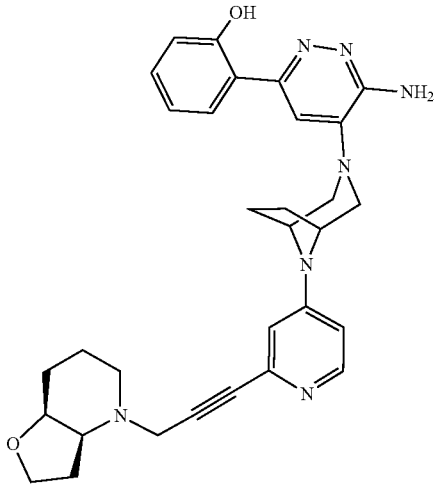 [SMILES: Nc1nnc(-c2ccccc2O)cc1N1CC2CCC(C1)N2c1ccnc(C#CCN2CCC[C@@H]3OCC[C@@H]32)c1] | 2-[5-[8-[2-[3-[(3aS,7aS)-3,3a,5,6,7,7a-hexahydro-2H-furo[3,2-b]pyridin-4-yl]prop-1-ynyl]-4-pyridyl]-3,8-diazabicyclo[3.2.1]octan-3-yl]-6-amino-pyridazin-3-yl]phenol |

TABLE 1-continued
| No. | Structure | Name |
|---|---|---|
| 91 | 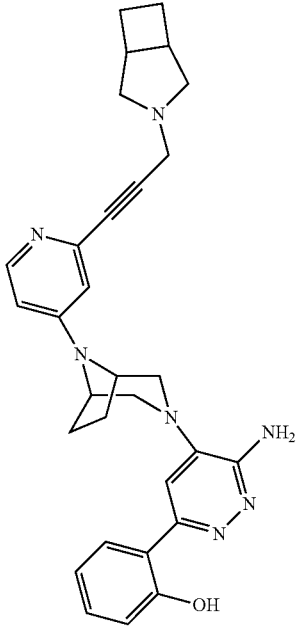 [SMILES: Nc1nnc(-c2ccccc2O)cc1N1CC2CCC(C1)N2c1ccnc(C#CCN2CC3CCC3C2)c1] | 2-[6-amino-5-[8-[2-[3-(3-azabicyclo[3.2.0]heptan-3-yl)prop-1-ynyl]-4-pyridyl]-3,8-diazabicyclo[3.2.1]octan-3-yl]pyridazin-3-yl]phenol |
| 92 | 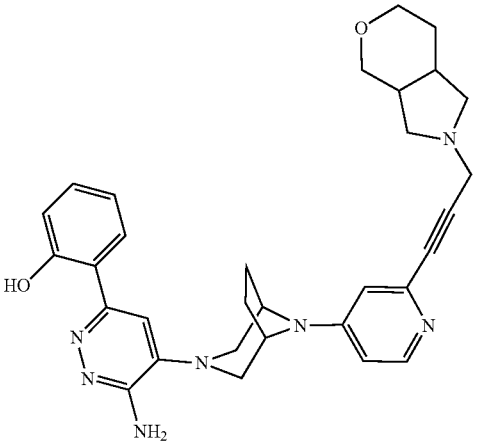 [SMILES: Nc1nnc(-c2ccccc2O)cc1N1CC2CCC(C1)N2c1ccnc(C#CCN2CC3CCOCC3C2)c1] | 2-[5-[8-[2-[3-(3,3a,4,6,7,7a-hexahydro-1H-pyrano[3,4-c]pyrrol-2-yl)prop-1-ynyl]-4-pyridyl]-3,8-diazabicyclo[3.2.1]octan-3-yl]-6-amino-pyridazin-3-yl]phenol |

TABLE 1-continued

| No. | Structure | Name |
|---|---|---|
| 93 | 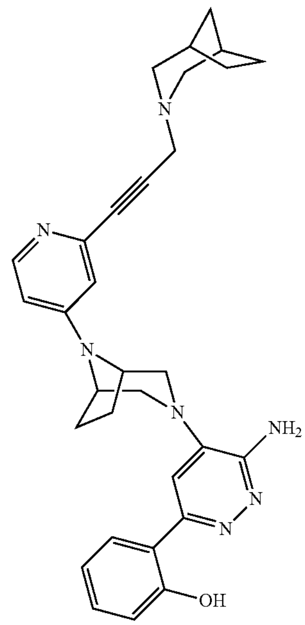 | 2-[6-amino-5-[8-[2-[3-(3-azabicyclo[3.2.1]octan-3-yl)prop-1-ynyl]-4-pyridyl]-3,8-diazabicyclo[3.2.1]octan-3-yl]pyridazin-3-yl]phenol |
| 94 | 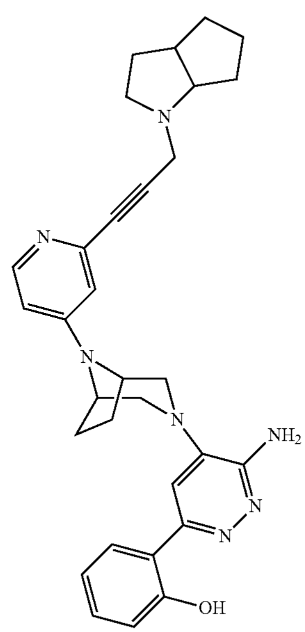 [SMILES: Nc1nnc(-c2ccccc2O)cc1N1CC2CCC(C1)N2c1ccnc(C#CCN2CCC3CCCC32)c1] | 2-[5-[8-[2-[3-(3,3a,4,5,6,6a-hexahydro-2H-cyelopenta[b]pyrrol-1-yl)prop-1-ynyl]-4-pyridyl]-3,8-diazabicyclo[3.2.1]octan-3-yl]-6-amino-pyridazin-3-yl]phenol |

TABLE 1-continued
| No. | Structure | Name |
|---|---|---|
| 95 | 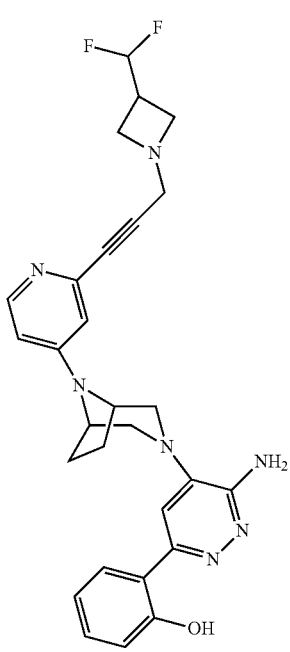 [SMILES: Nc1nnc(-c2ccccc2O)cc1N1CC2CCC(C1)N2c1ccnc(C#CCN2CC(C(F)F)C2)c1] | 2-[6-amino-5-[8-[2-[3-[3-(difluoromethyl)azetidin-1-yl]prop-1-ynyl]-4-pyridyl]-3,8-diazabicyclo[3.2.1]octan-3-yl]pyridazin-3-yl]phenol |
| 96 | 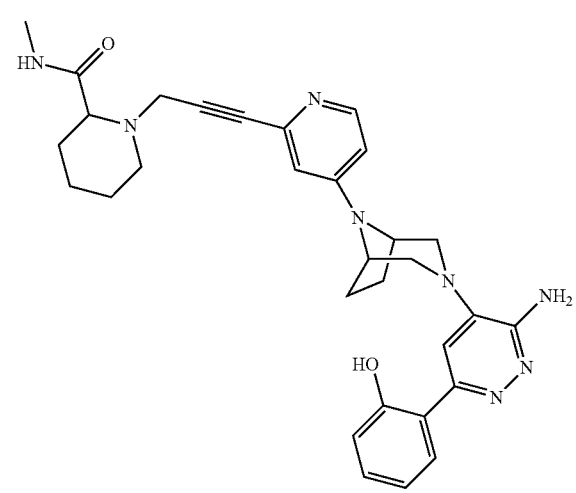 [SMILES: CNC(=O)C1CCCCN1CC#Cc1cc(N2C3CCC2CN(c2cc(-c4ccccc4O)nnc2N)C3)ccn1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-piperidine-2-carboxamide |

TABLE 1-continued
| No. | Structure | Name |
|---|---|---|
| 97 | 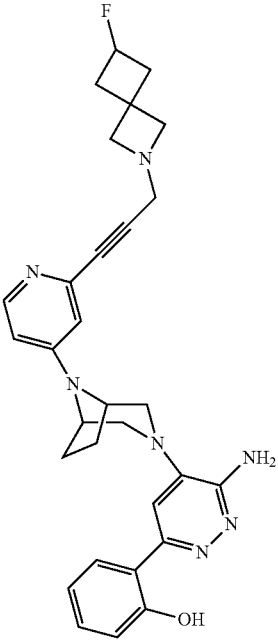 [SMILES: Nc1nnc(-c2ccccc2O)cc1N1CC2CCC(C1)N2c1ccnc(C#CCN2CC3(CC(F)C3)C2)c1] | 2-[6-amino-5-[8-[2-[3-(6-fluoro-2-azaspiro[3.3]heptan-2-yl)prop-1-ynyl]-4-pyridyl]-3,8-diazabicyclo[3.2.1]octan-3-yl]pyridazin-3-yl]phenol |
| 98 | 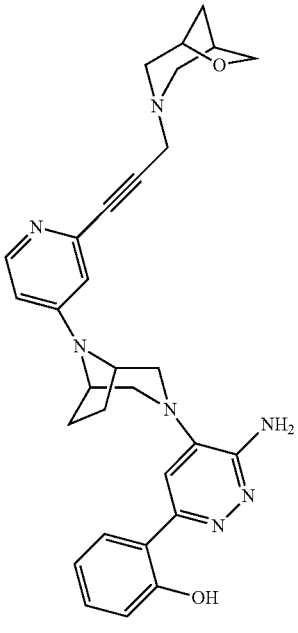 [SMILES: Nc1nnc(-c2ccccc2O)cc1N1CC2CCC(C1)N2c1ccnc(C#CCN2CC3COC(C3)C2)c1] | 2-[6-amino-5-[8-[2-[3-(6-oxa-3-azabicyclo[3.2.1]octan-3-yl)prop-1-ynyl]-4-pyridyl]-3,8-diazabicyclo[3.2.1]octan-3-yl]pyridazin-3-yl]phenol |

| No. | Structure | Name |
|---|---|---|
| 99 | 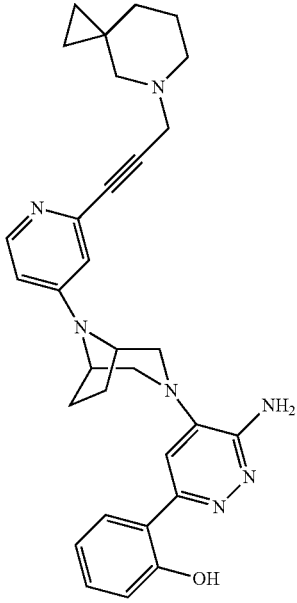 [SMILES: Nc1nnc(-c2ccccc2O)cc1N1CC2CCC(C1)N2c1ccnc(C#CCN2CCCC3(CC3)C2)c1] | 2-[6-amino-5-[8-[2-[3-(5-azaspiro[2.5]octan-5-yl)prop-1-ynyl]-4-pyridyl]-3,8-diazabicyclo[3.2.1]octan-3-yl]pyridazin-3-yl]phenol |
| 100 | 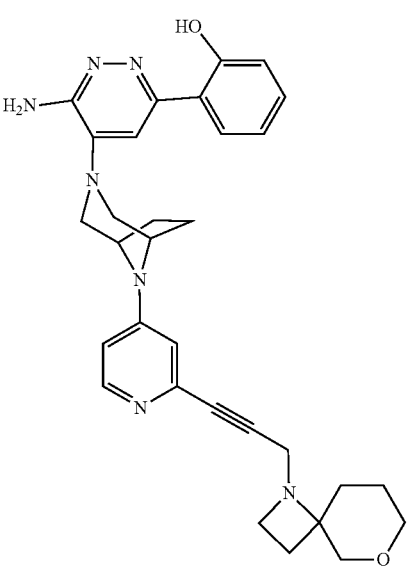 [SMILES: Nc1nnc(-c2ccccc2O)cc1N1CC2CCC(C1)N2c1ccnc(C#CCN2CCC23CCCOC3)c1] | 2-[6-amino-5-[8-[2-[3-(8-oxa-1-azaspiro[3.5]nonan-1-yl)prop-1-ynyl]-4-pyridyl]-3,8-diazabicyclo[3.2.1]octan-3-yl]pyridazin-3-yl]phenol |

| No. | Structure | Name |
|---|---|---|
| 101 | 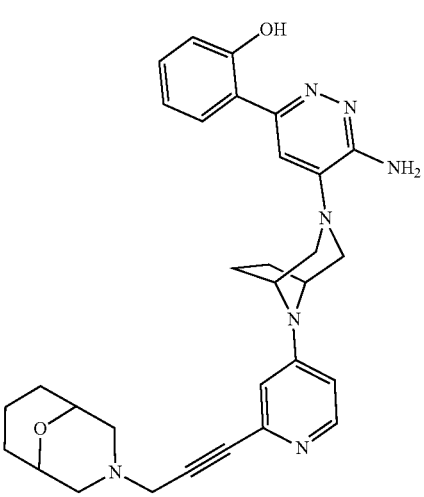 [SMILES: Nc1nnc(-c2ccccc2O)cc1N1CC2CCC(C1)N2c1ccnc(C#CCN2CC3CCCC(C2)O3)c1] | 2-[6-amino-5-[8-[2-[3-(9-oxa-3-azabicyclo[3.3.1]nonan-3-yl)prop-1-ynyl]-4-pyridyl]-3,8-diazabicyclo[3.2.1]octan-3-yl]pyridazin-3-yl]phenol |
| 102 | 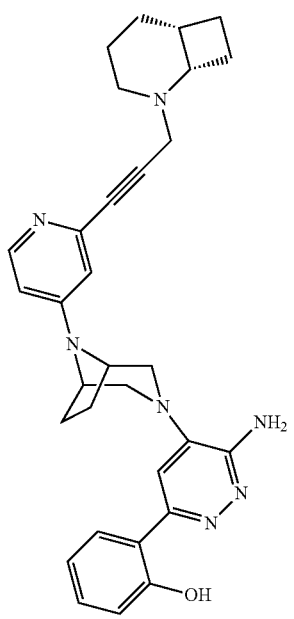 [SMILES: Nc1nnc(-c2ccccc2O)cc1N1CC2CCC(C1)N2c1ccnc(C#CCN2CCC[C@@H]3CC[C@@H]32)c1] | 2-[6-amino-5-[8-[2-[3-[(1S,6R)-2-azabicyclo[4.2.0]octan-2-yl]prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 103 | 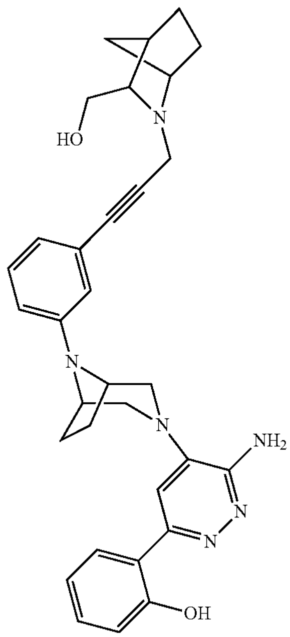 [SMILES: Nc1nnc(-c2ccccc2O)cc1N1CC2CCC(C1)N2c1cccc(C#CCN2C3CCC(C3)C2CO)c1] | 2-[6-amino-5-[8-[2-[3-[3-(hydroxymethyl)-2-azabicyclo[2.2.1]heptan-2-yl]prop-1-ynyl]-4-pyridyl]-3,8-diazabicyclo[3.2.1]octan-3-yl]pyridazin-3-yl]phenol |
| 104 | 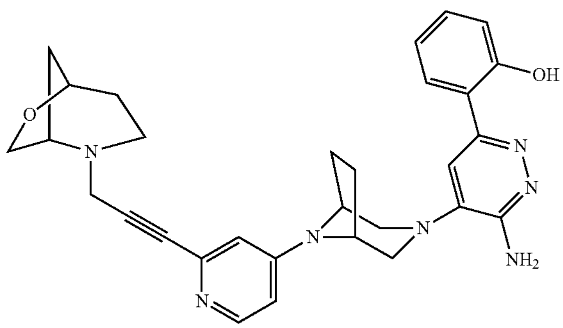 [SMILES: Nc1nnc(-c2ccccc2O)cc1N1CC2CCC(C1)N2c1ccnc(C#CCN2CCC3CC2CO3)c1] | 2-[6-amino-5-[8-[2-[3-(6-oxa-2-azabicyclo[3.2.1]octan-2-yl)prop-1-ynyl]-4-pyridyl]-3,8-diazabicyclo[3.2.1]octan-3-yl]pyridazin-3-yl]phenol |
| 105 | 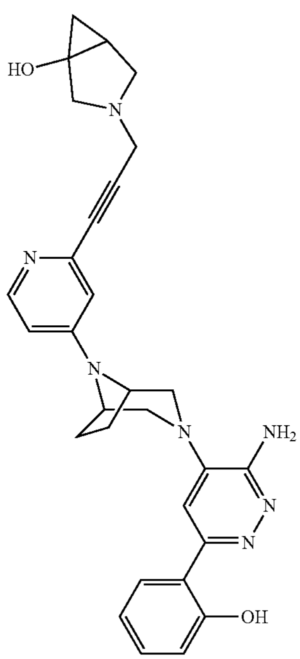 [SMILES: Nc1nnc(-c2ccccc2O)cc1N1CC2CCC(C1)N2c1ccnc(C#CCN2CC3CC3(O)C2)c1] | 3-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-azabicyclo[3.1.0]hexan-1-ol |

| No. | Structure | Name |
|---|---|---|
| 106 | 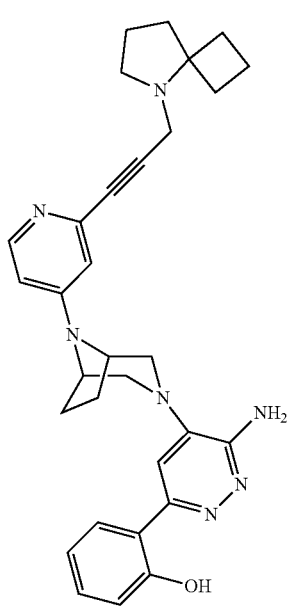 [SMILES: Nc1nnc(-c2ccccc2O)cc1N1CC2CCC(C1)N2c1ccnc(C#CCN2CCCC23CCC3)c1] | 2-[6-amino-5-[8-[2-[3-(5-azaspiro[3.4]octan-5-yl)prop-1-ynyl]-4-pyridyl]-3,8-diazabicyclo[3.2.1]octan-3-yl]pyridazin-3-yl]phenol |
| 107 | 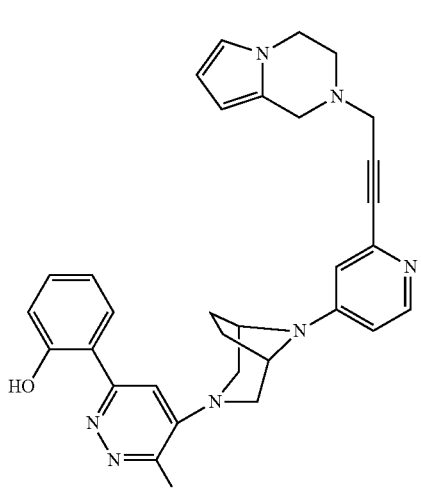 | 2-[6-amino-5-[8-[2-[3-(3,4-dihydro-1H-pyrrolo[1,2-a]pyrazin-2-yl)prop-1-ynyl]-4-pyridyl]-3,8-diazabicyclo[3.2.1]octan-3-yl]pyridazin-3-yl]phenol |

| No. | Structure | Name |
|---|---|---|
| 108 | 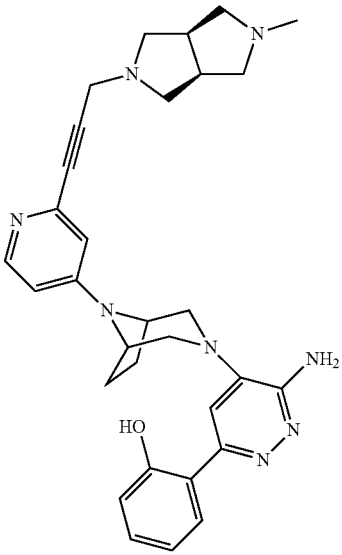 [SMILES: CN1C[C@@H]2CN(CC#Cc3cc(N4C5CCC4CN(c4cc(-c6ccccc6O)nnc4N)C5)ccn3)C[C@@H]2C1] | 2-[5-[8-[2-[3-[(3aS,6aR)-2-methyl-1,3,3a,4,6,6a-hexahydropyrrolo[3,4-c]pyrrol-5-yl]prop-1-ynyl]-4-pyridyl]-3,8-diazabicyclo[3.2.1]octan-3-yl]-6-amino-pyridazin-3-yl]phenol |
| 109 | 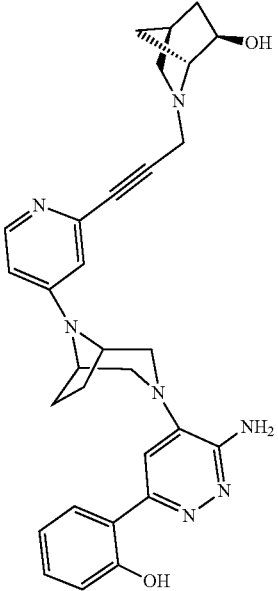 [SMILES: Nc1nnc(-c2ccccc2O)cc1N1CC2CCC(C1)N2c1ccnc(C#CCN2C[C@@H]3C[C@@H](O)[C@H]2C3)c1] | (1R,4S,6R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[2.2.1]heptan-6-ol |
| 110 | 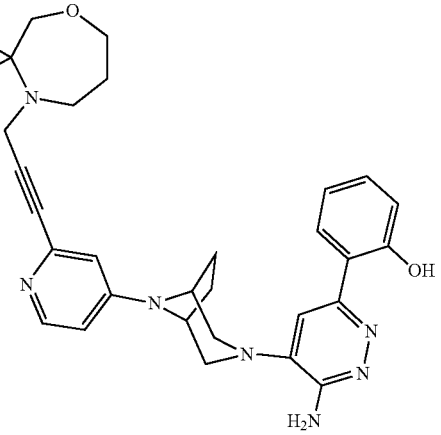 | 2-[6-amino-5-[8-[2-[3-(8-oxa-4-azaspiro[2.6]nonan-4-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 111 | 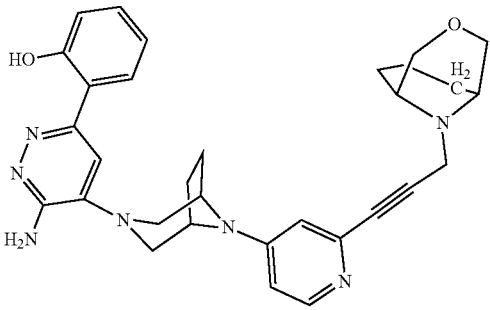 | 2-[6-amino-5-[8-[2-[3-(3-oxa-9-azabicyclo[3.3.1]nonan-9-yl)prop-1-ynyl]-4-pyridyl]-3,8-diazabicyclo[3.2.1]octan-3-yl]pyridazin-3-yl]phenol |
| 112 | 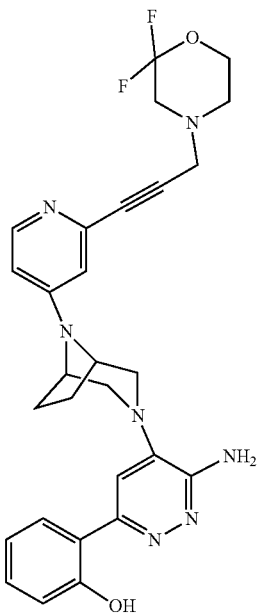 [SMILES: Nc1nnc(-c2ccccc2O)cc1N1CC2CCC(C1)N2c1ccnc(C#CCN2CCOC(F)(F)C2)c1] | 2-[6-amino-5-[8-[2-[3-(2,2-difluoromorpholin-4-yl)prop-1-ynyl]-4-pyridyl]-3,8-diazabicyclo[3.2.1]octan-3-yl]pyridazin-3-yl]phenol |
| 113 | 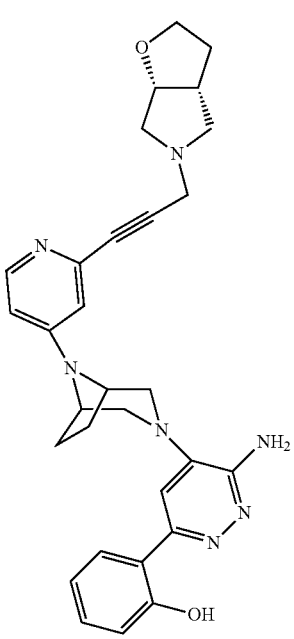 [SMILES: Nc1nnc(-c2ccccc2O)cc1N1CC2CCC(C1)N2c1ccnc(C#CCN2C[C@H]3CCO[C@H]3C2)c1] | 2-[5-[8-[2-[3-[(3aR,6aR)-2,3,3a,4,6,6a-hexahydrofuro[2,3-c]pyrrol-5-yl]prop-1-ynyl]-4-pyridyl]-3,8-diazabicyclo[3.2.1]octan-3-yl]-6-amino-pyridazin-3-yl]phenol |

TABLE 1-continued
| No. | Structure | Name |
| --- | --- | --- |
| 114 | 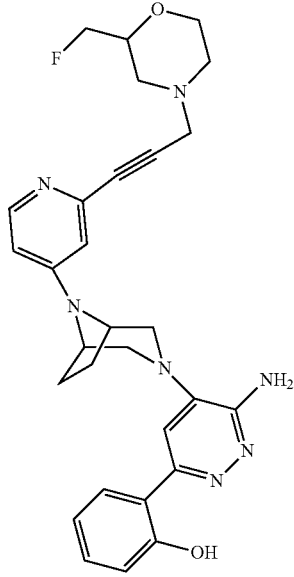 [SMILES: Nc1nnc(-c2ccccc2O)cc1N1CC2CCC(C1)N2c1ccnc(C#CCN2CCOC(CF)C2)c1] | 2-[6-amino-5-[8-[2-[3-[2-(fluoromethyl)morpholin-4-yl]prop-1-ynyl]-4-pyridyl]-3,8-diazabicyclo[3.2.1]octan-3-yl]pyridazin-3-yl]phenol |
| 115 | 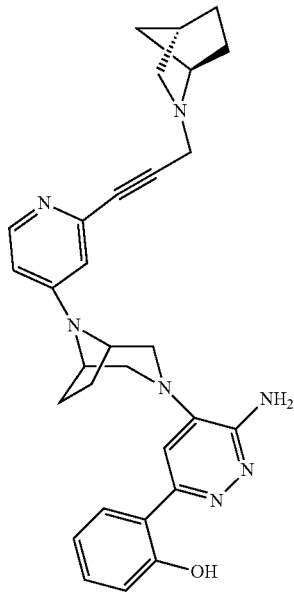 [SMILES: Nc1nnc(-c2ccccc2O)cc1N1CC2CCC(C1)N2c1ccnc(C#CCN2C[C@H]3CC[C@@H]2C3)c1] | 2-[6-amino-5-[8-[2-[3-[(1R,4S)-2-azabicyclo[2.2.1]heptan-2-yl]prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 116 | 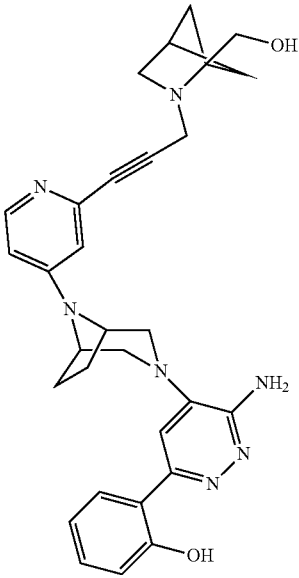 [SMILES: Nc1nnc(-c2ccccc2O)cc1N1CC2CCC(C1)N2c1ccnc(C#CCN2CC3CC2(CO)C3)c1] | 2-[6-amino-5-[8-[2-[3-[1-(hydroxymethyl)-2-azabicyclo[2.1.1]hexan-2-yl]prop-1-ynyl]-4-pyridyl]-3,8-diazabicyclo[3.2.1]octan-3-yl]pyridazin-3-yl]phenol |
| 117 | 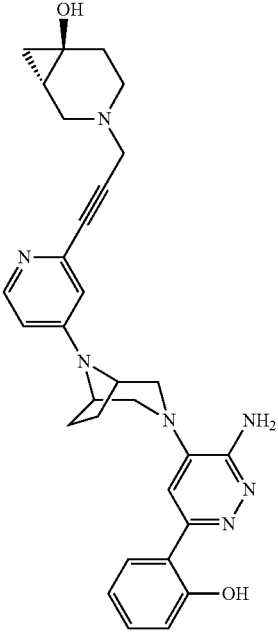 [SMILES: Nc1nnc(-c2ccccc2O)cc1N1CC2CCC(C1)N2c1ccnc(C#CCN2CC[C@@]3(O)C[C@H]3C2)c1] | (1S,6S)-3-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-azabicyclo[4.1.0]heptan-6-ol |

TABLE 1-continued
| No. | Structure | Name |
|---|---|---|
| 118 | 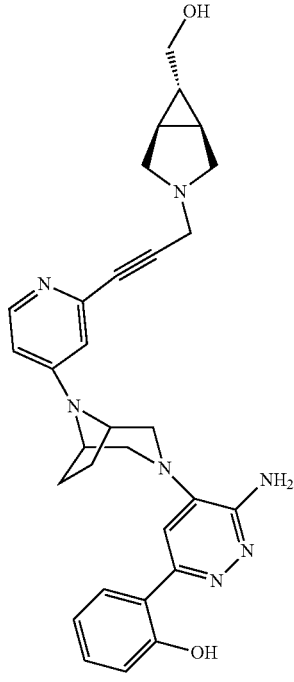 [SMILES: Nc1nnc(-c2ccccc2O)cc1N1CC2CCC(C1)N2c1ccnc(C#CCN2C[C@@H]3[C@@H](CO)[C@@H]3C2)c1] | 2-[6-amino-5-[8-[2-[3-[(1S,5R)-6-(hydroxymethyl)-3-azabicyclo[3.1.0]hexan-3-yl]prop-1-ynyl]-4-pyridyl]-3,8-diazabicyclo[3.2.1]octan-3-yl]pyridazin-3-yl]phenol |
| 119 | 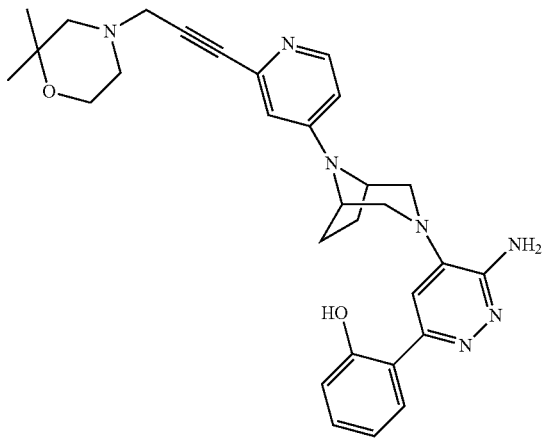 [SMILES: CC1(C)CN(CC#Cc2cc(N3C4CCC3CN(c3cc(-c5ccccc5O)nnc3N)C4)ccn2)CCO1] | 2-[6-amino-5-[8-[2-[3-(2,2-dimethylmorpholin-4-yl)prop-1-ynyl]-4-pyridyl]-3,8-diazabicyclo[3.2.1]octan-3-yl]pyridazin-3-yl]phenol |

| No. | Structure | Name |
|---|---|---|
| 120 | 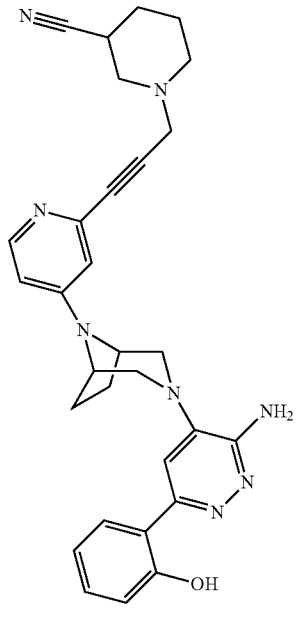 [SMILES: N#CC1CCCN(CC#Cc2cc(N3C4CCC3CN(c3cc(-c5ccccc5O)nnc3N)C4)ccn2)C1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidine-3-carbonitrile |
| 121 | 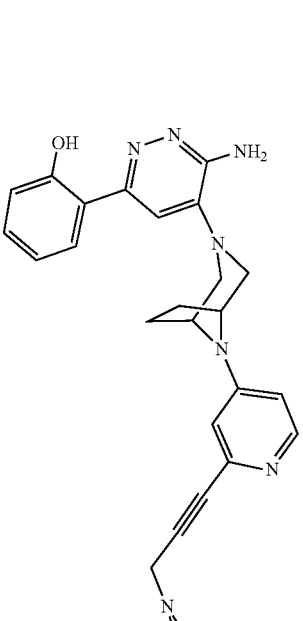 | 2-[6-amino-5-[8-[2-[3-[1-(hydroxymethyl)-7-azabicyclo[2.2.1]heptan-7-yl]prop-1-ynyl]-4-pyridyl]-3,8-diazabicyclo[3.2.1]octan-3-yl]pyridazin-3-yl]phenol |

| No. | Structure | Name |
|---|---|---|
| 122 | 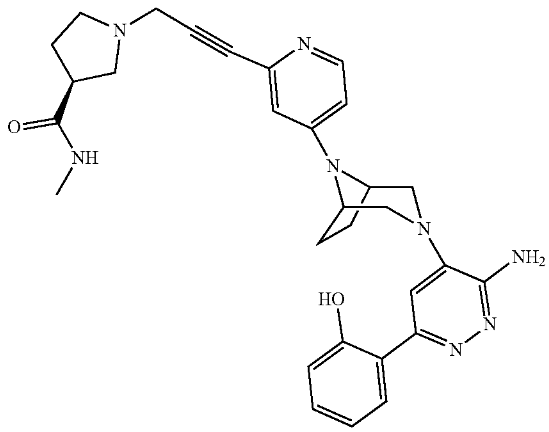 [SMILES: CNC(=O)[C@H]1CCN(CC#Cc2cc(N3C4CCC3CN(c3cc(-c5ccccc5O)nnc3N)C4)ccn2)C1] | (3S)-1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-pyrrolidine-3-carboxamide |
| 123 | 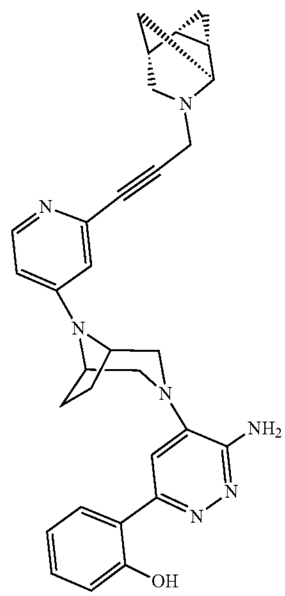 [SMILES: Nc1nnc(-c2ccccc2O)cc1N1CC2CCC(C1)N2c1ccnc(C#CCN2C[C@@H]3C[C@H]2[C@H]2C[C@@H]32)c1] | 2-[6-amino-5-[8-[2-[3-[(1R,2S,4S,5S)-6-azatricyclo[3.2.1.0²,⁴]octan-6-yl]prop-1-ynyl]-4-pyridyl]-3,8-diazabicyclo[3.2.1]octan-3-yl]pyridazin-3-yl]phenol |
| 124 | 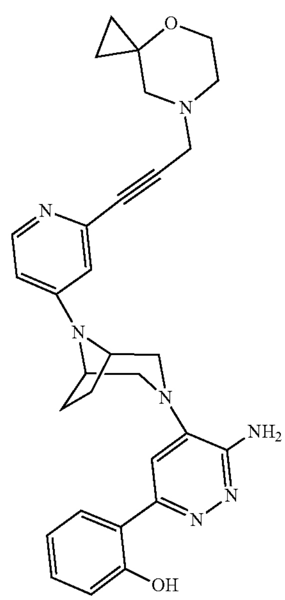 [SMILES: Nc1nnc(-c2ccccc2O)cc1N1CC2CCC(C1)N2c1ccnc(C#CCN2CCOC3(CC3)C2)c1] | 2-[6-amino-5-[8-[2-[3-(4-oxa-7-azaspiro[2.5]octan-7-yl)prop-1-ynyl]-4-pyridyl]-3,8-diazabicyclo[3.2.1]octan-3-yl]pyridazin-3-yl]phenol |

| No. | Structure | Name |
| --- | --- | --- |
| 125 | 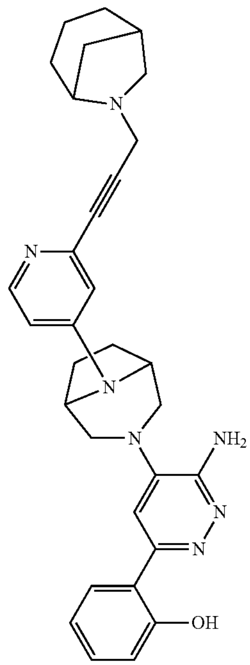 [SMILES: Nc1nnc(-c2ccccc2O)cc1N1CC2CCC(C1)N2c1ccnc(C#CCN2CC3CCCC2C3)c1] | 2-[6-amino-5-[8-[2-[3-(6-azabicyclo[3.2.1]octan-6-yl)prop-1-ynyl]-4-pyridyl]-3,8-diazabicyclo[3.2.1]octan-3-yl]pyridazin-3-yl]phenol |
| 126 | 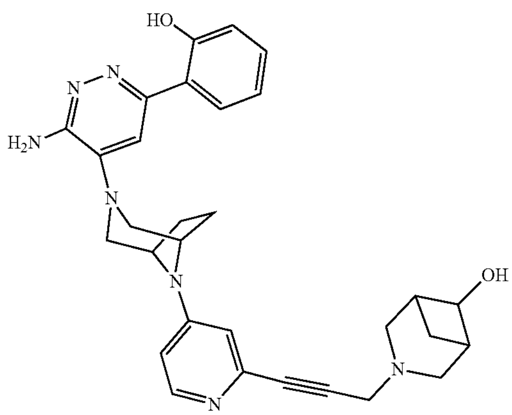 [SMILES: Nc1nnc(-c2ccccc2O)cc1N1CC2CCC(C1)N2c1ccnc(C#CCN2CC3CC(C2)C3O)c1] | 3-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-azabicyclo[3.1.1]heptan-6-ol |
| 127 | 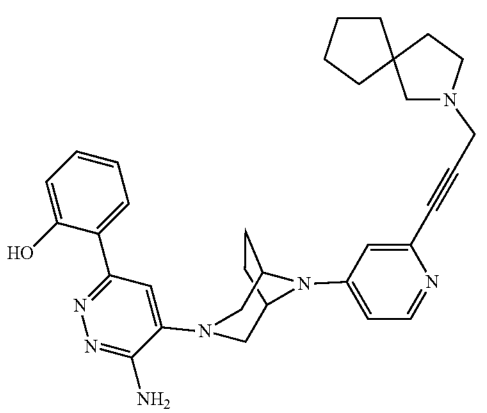 [SMILES: Nc1nnc(-c2ccccc2O)cc1N1CC2CCC(C1)N2c1ccnc(C#CCN2CCC3(CCCC3)C2)c1] | 2-[6-amino-5-[8-[2-[3-(2-azaspiro[4.4]nonan-2-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 128 | 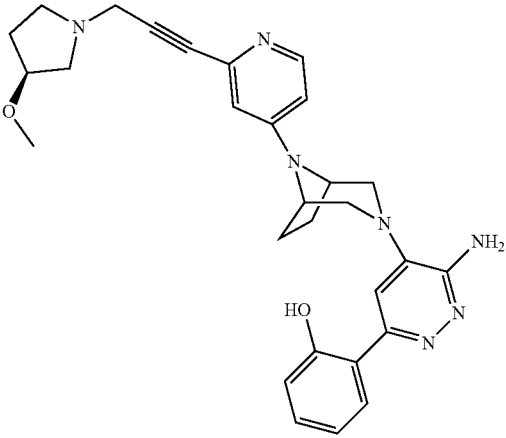 [SMILES: CO[C@H]1CCN(CC#Cc2cc(N3C4CCC3CN(c3cc(-c5ccccc5O)nnc3N)C4)ccn2)C1] | 2-[6-amino-5-[8-[2-[3-[(3S)-3-methoxypyrrolidin-1-yl]prop-1-ynyl]-4-pyridyl]-3,8-diazabicyclo[3.2.1]octan-3-yl]pyridazin-3-yl]phenol |
| 129 | 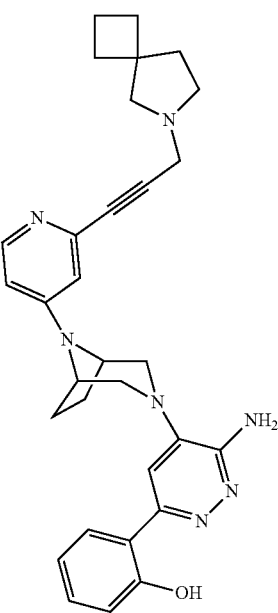 [SMILES: Nc1nnc(-c2ccccc2O)cc1N1CC2CCC(C1)N2c1ccnc(C#CCN2CCC3(CCC3)C2)c1] | 2-[6-amino-5-[8-[2-[3-(6-azaspiro[3.4]octan-6-yl)prop-1-ynyl]-4-pyridyl]-3,8-diazabicyclo[3.2.1]octan-3-yl]pyridazin-3-yl]phenol |

TABLE 1-continued

| No. | Structure | Name |
|-----|-----------|------|
| 130 | 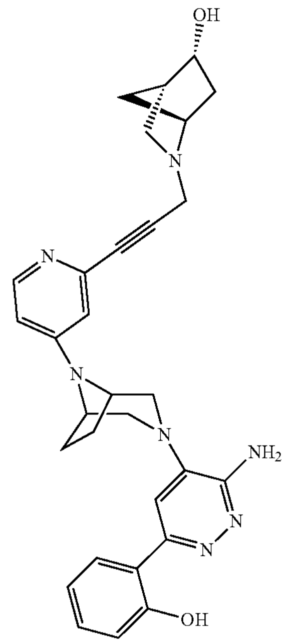 [SMILES: Nc1nnc(-c2ccccc2O)cc1N1CC2CCC(C1)N2c1ccnc(C#CCN2C[C@@H]3C[C@H]2C[C@H]3O)c1] | (1S,4S,5R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[2.2.1]heptan-5-ol |
| 131 | 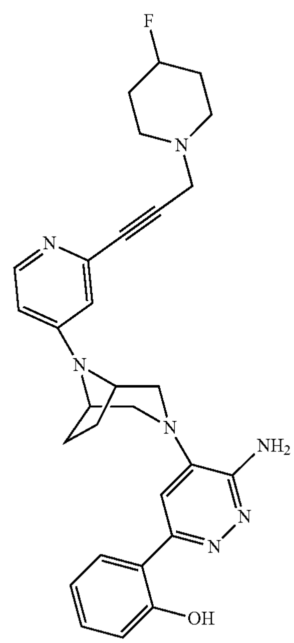 [SMILES: Nc1nnc(-c2ccccc2O)cc1N1CC2CCC(C1)N2c1ccnc(C#CCN2CCC(F)CC2)c1] | 2-[6-amino-5-[8-[2-[3-(4-fluoro-1-piperidyl)prop-1-ynyl]-4-pyridyl]-3,8-diazabicyclo[3.2.1]octan-3-yl]pyridazin-3-yl]phenol |

TABLE 1-continued

| No. | Structure | Name |
|-----|-----------|------|
| 132 | 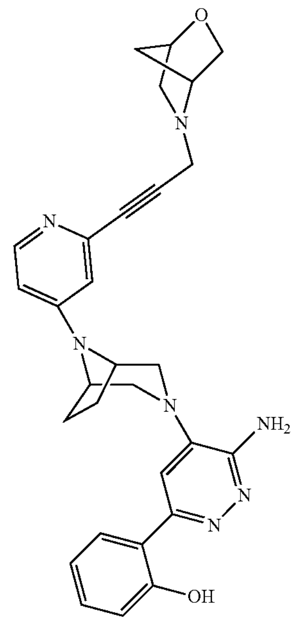 [SMILES: Nc1nnc(-c2ccccc2O)cc1N1CC2CCC(C1)N2c1ccnc(C#CCN2CC3CC2CO3)c1] | 2-[6-amino-5-[8-[2-[3-(2-oxa-5-azabicyclo[2.2.1]heptan-5-yl)prop-1-ynyl]-4-pyridyl]-3,8-diazabicyclo[3.2.1]octan-3-yl]pyridazin-3-yl]phenol |
| 133 | 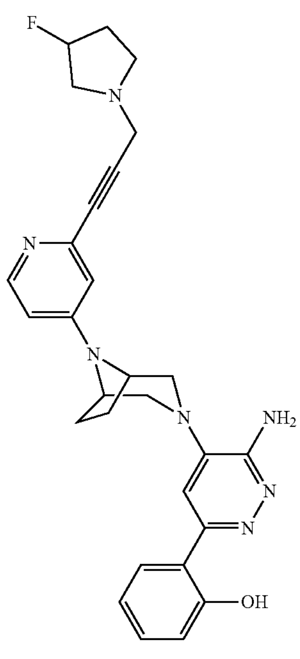 [SMILES: Nc1nnc(-c2ccccc2O)cc1N1CC2CCC(C1)N2c1ccnc(C#CCN2CCC(F)C2)c1] | 2-[6-amino-5-[8-[2-[3-(3-fluoropyrrolidin-1-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 134 | 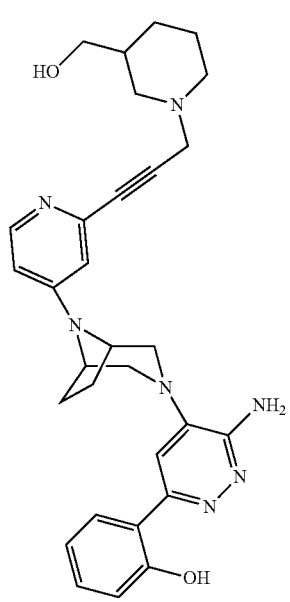 [SMILES: Nc1nnc(-c2ccccc2O)cc1N1CC2CCC(C1)N2c1ccnc(C#CCN2CCCC(CO)C2)c1] | 2-[6-amino-5-[8-[2-[3-[3-(hydroxymethyl)-1-piperidyl]prop-1-ynyl]-4-pyridyl]-3,8-diazabicyclo[3.2.1]octan-3-yl]pyridazin-3-yl]phenol |
| 135 | 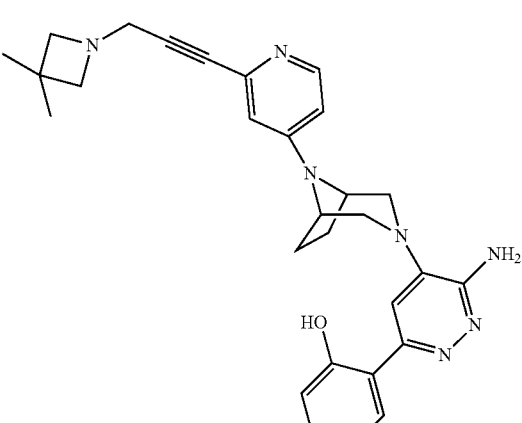 | 2-[6-amino-5-[8-[2-[3-(3,3-dimethylazetidin-1-yl)prop-1-ynyl]-4-pyridyl]-3,8-diazabicyclo[3.2.1]octan-3-yl]pyridazin-3-yl]phenol |

| No. | Structure | Name |
|---|---|---|
| 136 | 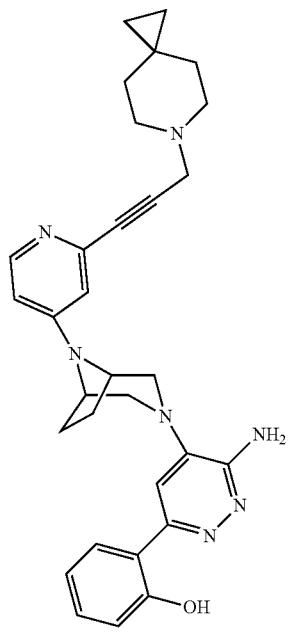 [SMILES: Nc1nnc(-c2ccccc2O)cc1N1CC2CCC(C1)N2c1ccnc(C#CCN2CCC3(CC2)CC3)c1] | 2-[6-amino-5-[8-[2-[3-(6-azaspiro[2.5]octan-6-yl)prop-1-ynyl]-4-pyridyl]-3,8-diazabicyclo[3.2.1]octan-3-yl]pyridazin-3-yl]phenol |
| 137 | 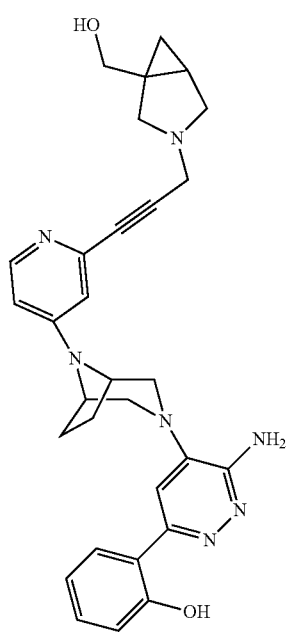 [SMILES: Nc1nnc(-c2ccccc2O)cc1N1CC2CCC(C1)N2c1ccnc(C#CCN2CC3CC3(CO)C2)c1] | 2-[6-amino-5-[8-[2-[3-[1-(hydroxymethyl)-3-azabicyclo[3.1.0]hexan-3-yl]prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 138 | 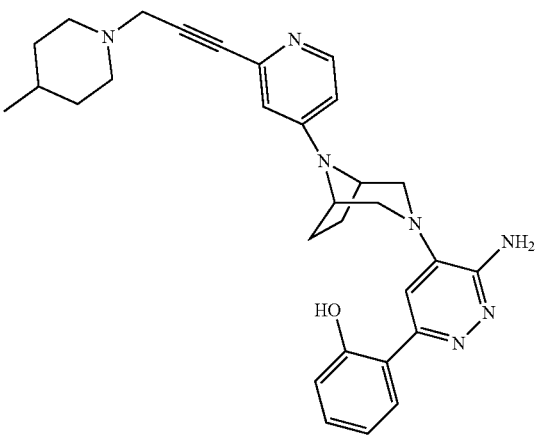 [SMILES: CC1CCN(CC#Cc2cc(N3C4CCC3CN(c3cc(-c5ccccc5O)nnc3N)C4)ccn2)CC1] | 2-[6-amino-5-[8-[2-[3-(4-methyl-1-piperidyl)prop-1-ynyl]-4-pyridyl]-3,8-diazabicyclo[3.2.1]octan-3-yl]pyridazin-3-yl]phenol |
| 139 | 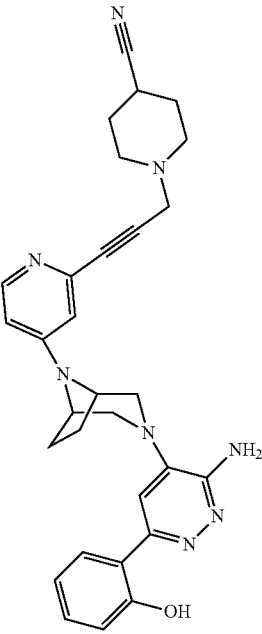 [SMILES: N#CC1CCN(CC#Cc2cc(N3C4CCC3CN(c3cc(-c5ccccc5O)nnc3N)C4)ccn2)CC1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidine-4-carbonitrile |
| 140 | 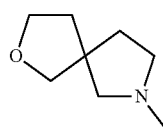 | 2-[6-amino-5-[8-[2-[3-(2-oxa-7-azaspiro[4.4]nonan-7-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 141 | 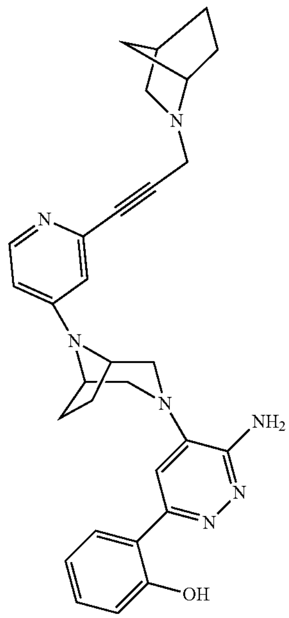 [SMILES: Nc1nnc(-c2ccccc2O)cc1N1CC2CCC(C1)N2c1ccnc(C#CCN2CC3CCC2C3)c1] | 2-[6-amino-5-[8-[2-[3-(2-azabicyclo[2.2.1]heptan-2-yl)prop-1-ynyl]-4-pyridyl]-3,8-diazabicyclo[3.2.1]octan-3-yl]pyridazin-3-yl]phenol |
| 142 | 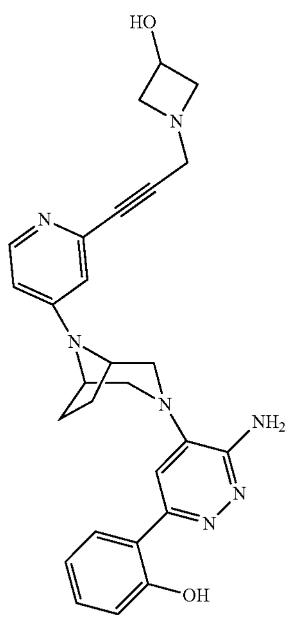 [SMILES: Nc1nnc(-c2ccccc2O)cc1N1CC2CCC(C1)N2c1ccnc(C#CCN2CC(O)C2)c1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-ol |

| No. | Structure | Name |
|---|---|---|
| 143 | 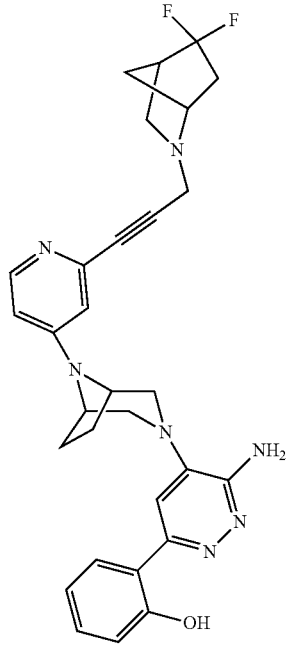 [SMILES: Nc1nnc(-c2ccccc2O)cc1N1CC2CCC(C1)N2c1ccnc(C#CCN2CC3CC2CC3(F)F)c1] | 2-[6-amino-5-[8-[2-[3-(5,5-difluoro-2-azabicyclo[2.2.1]heptan-2-yl)prop-1-ynyl]-4-pyridyl]-3,8-diazabicyclo[3.2.1]octan-3-yl]pyridazin-3-yl]phenol |
| 144 | 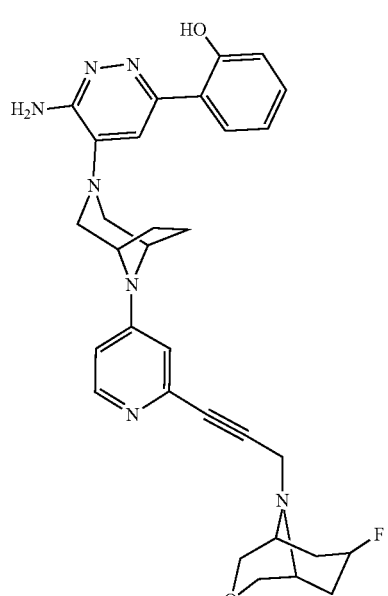 | 2-[6-amino-5-[8-[2-[3-(7-fluoro-3-oxa-9-azabicyclo[3.3.1]nonan-9-yl)prop-1-ynyl]-4-pyridyl]-3,8-diazabicyclo[3.2.1]octan-3-yl]pyridazin-3-yl]phenol |

| No. | Structure | Name |
|---|---|---|
| 145 | 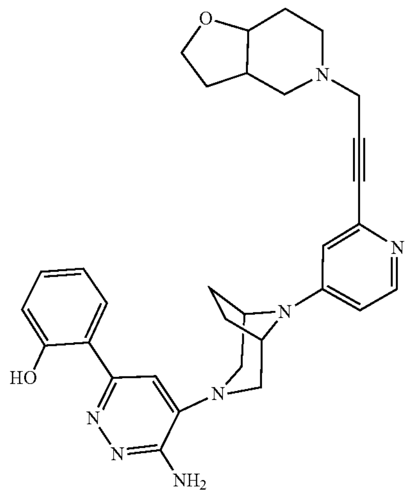 [SMILES: Nc1nnc(-c2ccccc2O)cc1N1CC2CCC(C1)N2c1ccnc(C#CCN2CCC3OCCC3C2)c1] | 2-[5-[8-[2-[3-(3,3a,4,6,7,7a-hexahydro-2H-furo[3,2-c]pyridin-5-yl)prop-1-ynyl]-4-pyridyl]-3,8-diazabicyclo[3.2.1]octan-3-yl]-6-amino-pyridazin-3-yl]phenol |
| 146 | 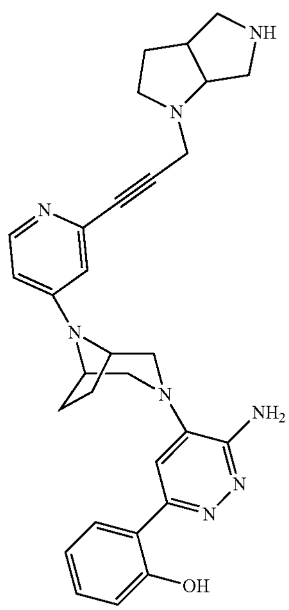 [SMILES: Nc1nnc(-c2ccccc2O)cc1N1CC2CCC(C1)N2c1ccnc(C#CCN2CCC3CNCC32)c1] | 2-[5-[8-[2-[3-(3,3a,4,5,6,6a-hexahydro-2H-pyrrolo[3,4-b]pyrrol-1-yl)prop-1-ynyl]-4-pyridyl]-3,8-diazabicyclo[3.2.1]octan-3-yl]-6-amino-pyridazin-3-yl]phenol |
| 147 | 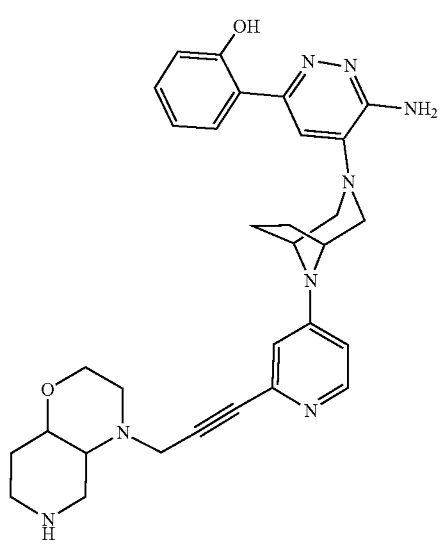 [SMILES: Nc1nnc(-c2ccccc2O)cc1N1CC2CCC(C1)N2c1ccnc(C#CCN2CCOC3CCNCC32)c1] | 2-[5-[8-[2-[3-(2,3,4a,5,6,7,8,8a-octahydropyrido[4,3-b][1,4]oxazin-4-yl)prop-1-ynyl]-4-pyridyl]-3,8-diazabicyclo[3.2.1]octan-3-yl]-6-amino-pyridazin-3-yl]phenol |

| No. | Structure | Name |
|---|---|---|
| 148 | 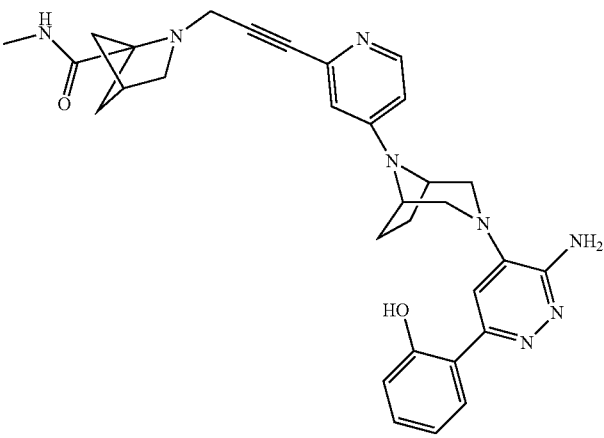 [SMILES: CNC(=O)C12CC(CN1CC#Cc1cc(N3C4CCC3CN(c3cc(-c5ccccc5O)nnc3N)C4)ccn1)C2] | 2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-2-azabicyclo[2.1.1]hexane-1-carboxamide |
| 149 | 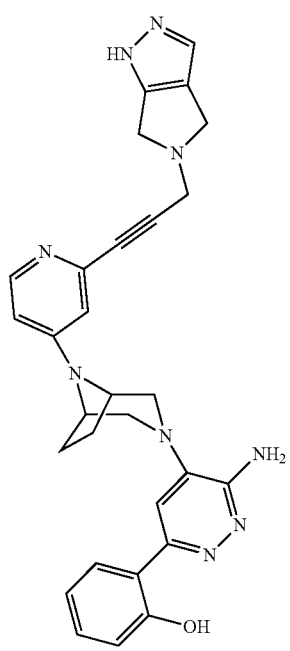 [SMILES: Nc1nnc(-c2ccccc2O)cc1N1CC2CCC(C1)N2c1ccnc(C#CCN2Cc3cn[nH]c3C2)c1] | 2-[6-amino-5-[8-[2-[3-(4,6-dihydro-1H-pyrrolo[3,4-c]pyrazol-5-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 150 | 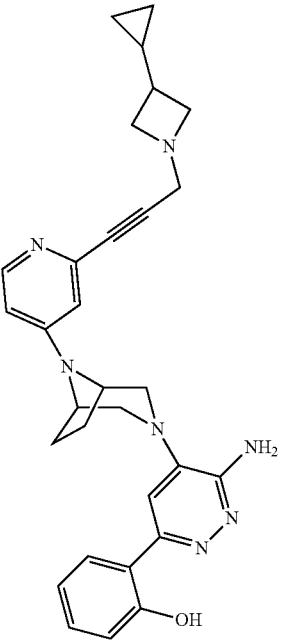 [SMILES: Nc1nnc(-c2ccccc2O)cc1N1CC2CCC(C1)N2c1ccnc(C#CCN2CC(C3CC3)C2)c1] | 2-[6-amino-5-[8-[2-[3-(3-cyclopropylazetidin-1-yl)prop-1-ynyl]-4-pyridyl]-3,8-diazabicyclo[3.2.1]octan-3-yl]pyridazin-3-yl]phenol |
| 151 | 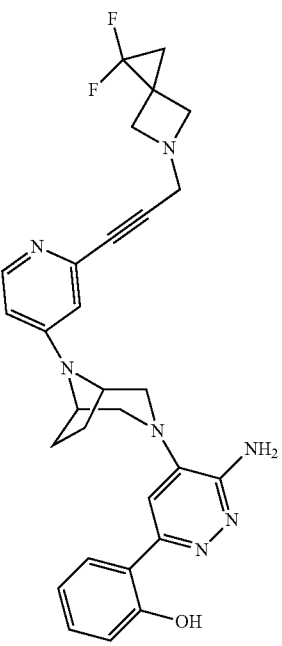 [SMILES: Nc1nnc(-c2ccccc2O)cc1N1CC2CCC(C1)N2c1ccnc(C#CCN2CC3(C2)CC3(F)F)c1] | 2-[6-amino-5-[8-[2-[3-(2,2-difluoro-5-azaspiro[2.3]hexan-5-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 152 | 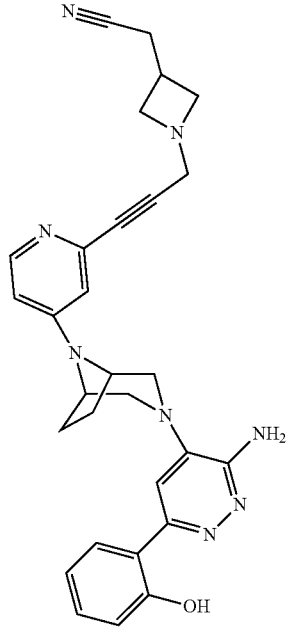 [SMILES: N#CCC1CN(CC#Cc2cc(N3C4CCC3CN(c3cc(-c5ccccc5O)nnc3N)C4)ccn2)C1] | 2-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-yl]acetonitrile |
| 153 | 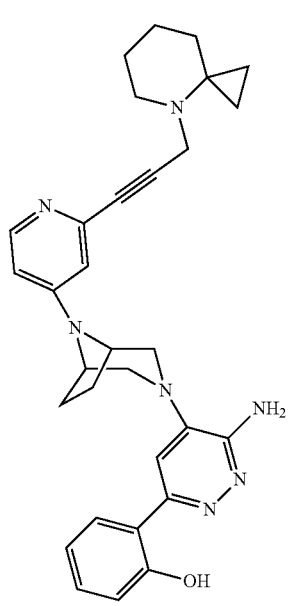 [SMILES: Nc1nnc(-c2ccccc2O)cc1N1CC2CCC(C1)N2c1ccnc(C#CCN2CCCCC23CC3)c1] | 2-[6-amino-5-[8-[2-[3-(4-azaspiro[2.5]octan-4-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 154 | 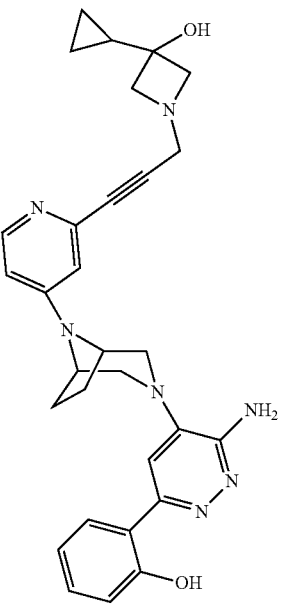 [SMILES: Nc1nnc(-c2ccccc2O)cc1N1CC2CCC(C1)N2c1ccnc(C#CCN2CC(O)(C3CC3)C2)c1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-cyclopropyl-azetidin-3-ol |
| 155 | 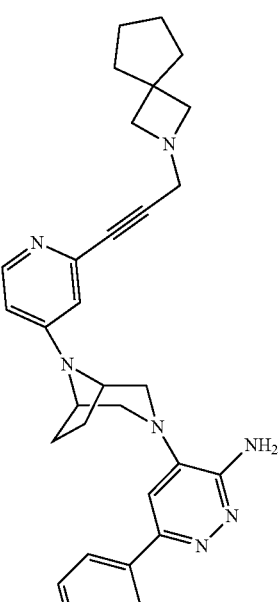 | 2-[6-amino-5-[8-[2-[3-(2-azaspiro[3.4]octan-2-yl)prop-1-ynyl]-4-pyridyl]-3,8-diazabicyclo[3.2.1]octan-3-yl]pyridazin-3-yl]phenol |

| No. | Structure | Name |
|---|---|---|
| 156 | 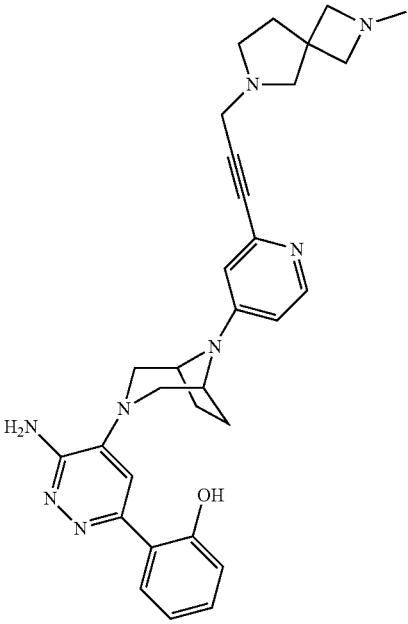 [SMILES: CN1CC2(CCN(CC#Cc3cc(N4C5CCC4CN(c4cc(-c6ccccc6O)nnc4N)C5)ccn3)C2)C1] | 2-[6-amino-5-[8-[2-[3-(2-methyl-2,6-diazaspiro[3.4]octan-6-yl)prop-1-ynyl]-4-pyridyl]-3,8-diazabicyclo[3.2.1]octan-3-yl]pyridazin-3-yl]phenol |
| 157 | 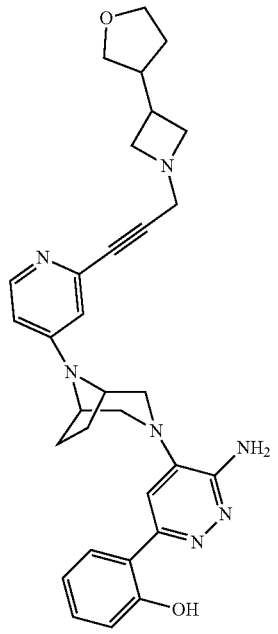 [SMILES: Nc1nnc(-c2ccccc2O)cc1N1CC2CCC(C1)N2c1ccnc(C#CCN2CC(C3CCOC3)C2)c1] | 2-[6-amino-5-[8-[2-[3-(3-tetrahydrofuran-3-ylazetidin-1-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 158 | 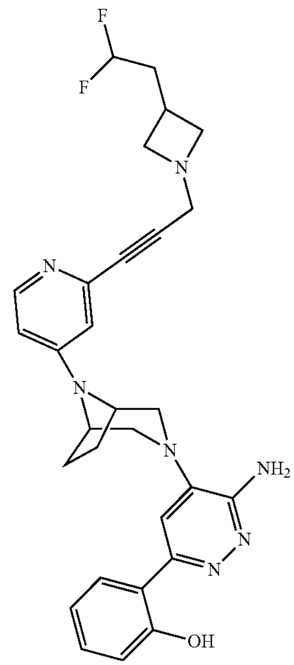 [SMILES: Nc1nnc(-c2ccccc2O)cc1N1CC2CCC(C1)N2c1ccnc(C#CCN2CC(CC(F)F)C2)c1] | 2-[6-amino-5-[8-[2-[3-[3-(2,2-difluoroethyl)azetidin-1-yl]prop-1-ynyl]-4-pyridyl]-3,8-diazabicyclo[3.2.1]octan-3-yl]pyridazin-3-yl]phenol |
| 159 | 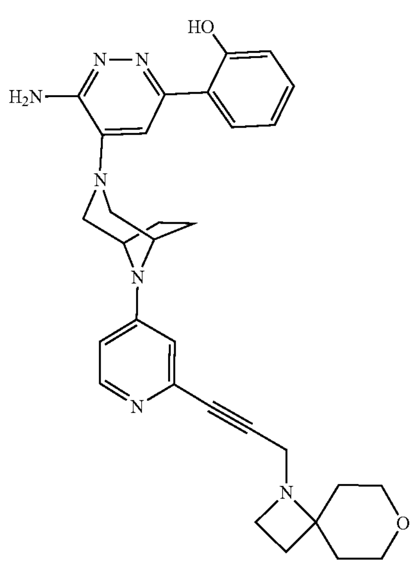 [SMILES: Nc1nnc(-c2ccccc2O)cc1N1CC2CCC(C1)N2c1ccnc(C#CCN2CCC23CCOCC3)c1] | 2-[6-amino-5-[8-[2-[3-(7-oxa-1-azaspiro[3.5]nonan-1-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 160 | 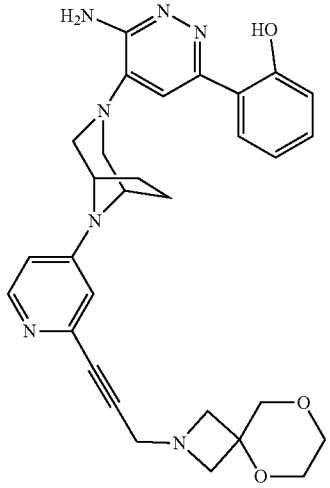 [SMILES: Nc1nnc(-c2ccccc2O)cc1N1CC2CCC(C1)N2c1ccnc(C#CCN2CC3(COCCO3)C2)c1] | 2-[6-amino-5-[8-[2-[3-(5,8-dioxa-2-azaspiro[3.5]nonan-2-yl)prop-1-ynyl]-4-pyridyl]-3,8-diazabicyclo[3.2.1]octan-3-yl]pyridazin-3-yl]phenol |
| 161 | 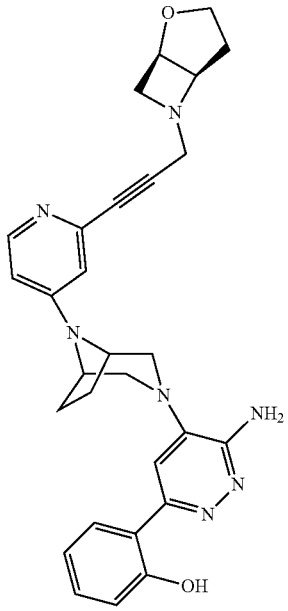 [SMILES: Nc1nnc(-c2ccccc2O)cc1N1CC2CCC(C1)N2c1ccnc(C#CCN2C[C@H]3OCC[C@H]32)c1] | 2-[6-amino-5-[8-[2-[3-[(1R,5R)-2-oxa-6-azabicyclo[3.2.0]heptan-6-yl]prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 162 | 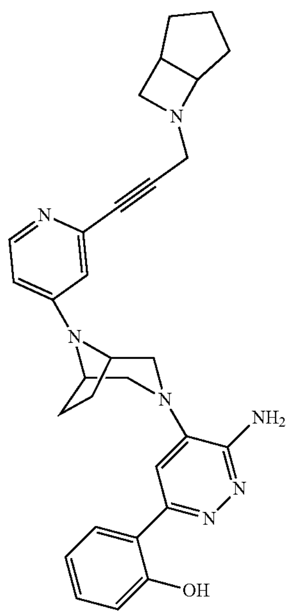 [SMILES: Nc1nnc(-c2ccccc2O)cc1N1CC2CCC(C1)N2c1ccnc(C#CCN2CC3CCCC32)c1] | 2-[6-amino-5-[8-[2-[3-(6-azabicyclo[3.2.0]heptan-6-yl)prop-1-ynyl]-4-pyridyl]-3,8-diazabicyclo[3.2.1]octan-3-yl]pyridazin-3-yl]phenol |
| 163 | 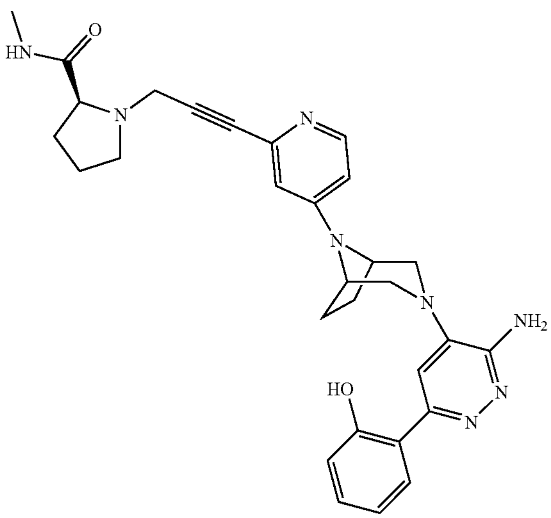 [SMILES: CNC(=O)[C@@H]1CCCN1CC#Cc1cc(N2C3CCC2CN(c2cc(-c4ccccc4O)nnc2N)C3)ccn1] | (2S)-1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-pyrrolidine-2-carboxamide |
| 164 | 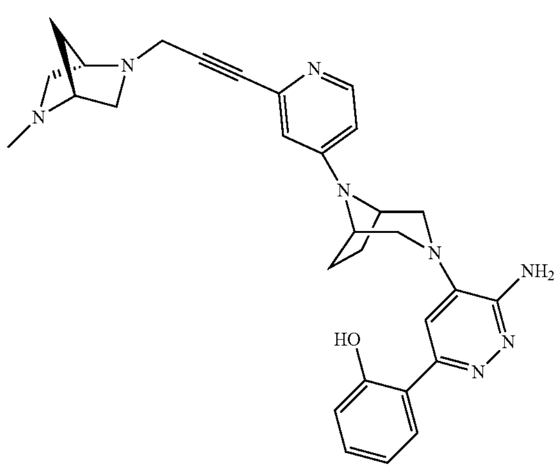 [SMILES: CN1C[C@@H]2C[C@H]1CN2CC#Cc1cc(N2C3CCC2CN(c2cc(-c4ccccc4O)nnc2N)C3)ccn1] | 2-[6-amino-5-[8-[2-[3-[(1S,4S)-5-methyl-2,5-diazabicyclo[2.2.1]heptan-2-yl]prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 165 | 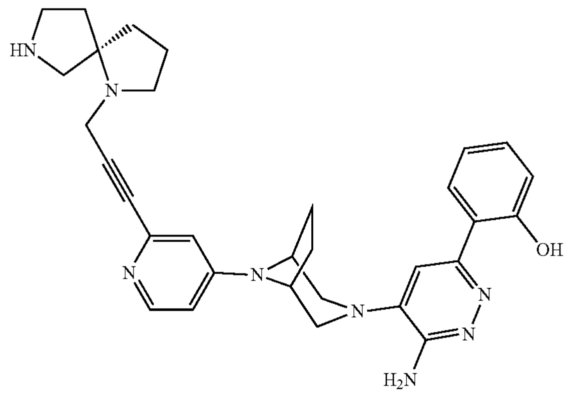 [SMILES: Nc1nnc(-c2ccccc2O)cc1N1CC2CCC(C1)N2c1ccnc(C#CCN2CCC[C@]23CCNC3)c1] | 2-[6-amino-5-[8-[2-[3-[(5R)-1,7-diazaspiro[4.4]nonan-1-yl]prop-1-ynyl]-4-pyridyl]-3,8-diazabicyclo[3.2.1]octan-3-yl]pyridazin-3-yl]phenol |
| 166 | 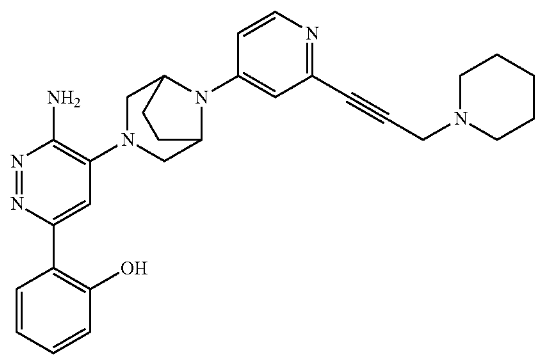 [SMILES: Nc1nnc(-c2ccccc2O)cc1N1CC2CCC(C1)N2c1ccnc(C#CCN2CCCCC2)c1] | 2-[6-amino-5-[8-[2-[3-(1-piperidyl)prop-1-ynyl]-4-pyridyl]-3,8-diazabicyclo[3.2.1]octan-3-yl]pyridazin-3-yl]phenol |
| 167 | 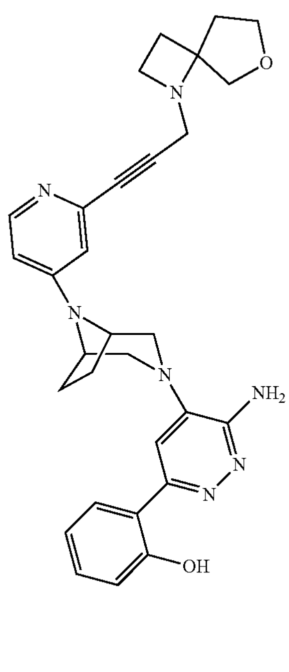 [SMILES: Nc1nnc(-c2ccccc2O)cc1N1CC2CCC(C1)N2c1ccnc(C#CCN2CCC23CCOC3)c1] | 2-[6-amino-5-[8-[2-[3-(7-oxa-1-azaspiro[3.4]octan-1-yl)prop-1-ynyl]-4-pyridyl]-3,8-diazabicyclo[3.2.1]octan-3-yl]pyridazin-3-yl]phenol |

TABLE 1-continued

| No. | Structure | Name |
| --- | --- | --- |
| 168 | 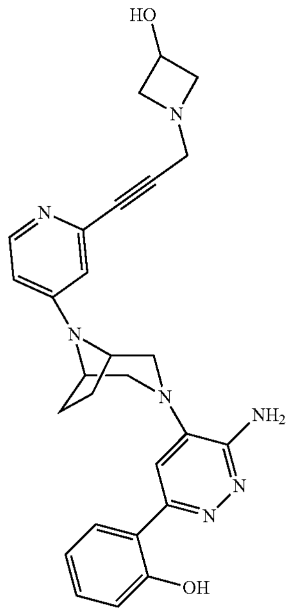 [SMILES: Nc1nnc(-c2ccccc2O)cc1N1CC2CCC(C1)N2c1ccnc(C#CCN2CC(O)C2)c1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-ol |
| 169 | 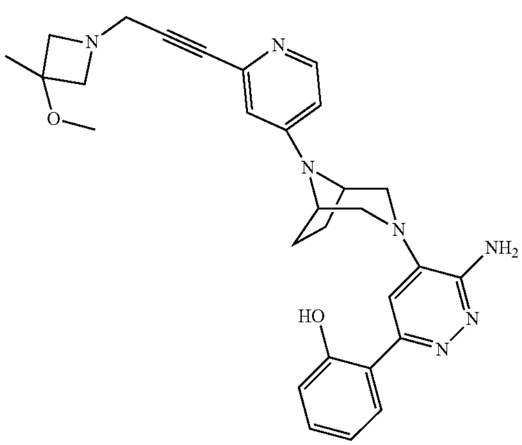 [SMILES: COC1(C)CN(CC#Cc2cc(N3C4CCC3CN(c3cc(-c5ccccc5O)nnc3N)C4)ccn2)C1] | 2-[6-amino-5-[8-[2-[3-(3-methoxy-3-methyl-azetidin-1-yl)prop-1-ynyl]-4-pyridyl]-3,8-diazabicyclo[3.2.1]octan-3-yl]pyridazin-3-yl]phenol |
| 170 | 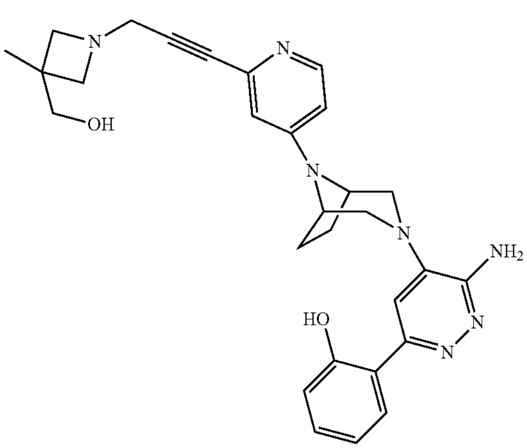 [SMILES: CC1(CO)CN(CC#Cc2cc(N3C4CCC3CN(c3cc(-c5ccccc5O)nnc3N)C4)ccn2)C1] | 2-[6-amino-5-[8-[2-[3-[3-(hydroxymethyl)-3-methyl-azetidin-1-yl]prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 171 | 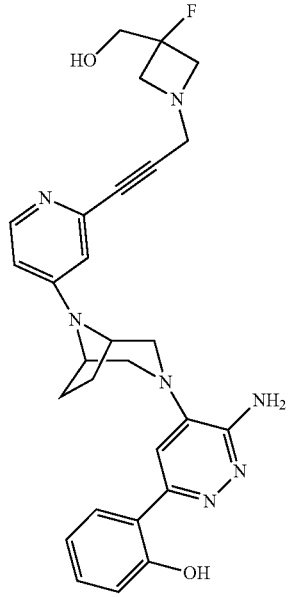 [SMILES: Nc1nnc(-c2ccccc2O)cc1N1CC2CCC(C1)N2c1ccnc(C#CCN2CC(F)(CO)C2)c1] | 2-[6-amino-5-[8-[2-[3-[3-fluoro-3-(hydroxymethyl)azetidin-1-yl]prop-1-ynyl]-4-pyridyl]-3,8-diazabicyclo[3.2.1]octan-3-yl]pyridazin-3-yl]phenol |
| 172 | 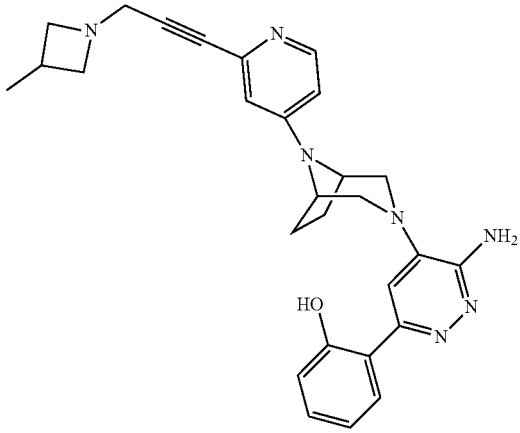 [SMILES: CC1CN(CC#Cc2cc(N3C4CCC3CN(c3cc(-c5ccccc5O)nnc3N)C4)ccn2)C1] | 2-[6-amino-5-[8-[2-[3-(3-methylazetidin-1-yl)prop-1-ynyl]-4-pyridyl]-3,8-diazabicyclo[3.2.1]octan-3-yl]pyridazin-3-yl]phenol |
| 173 | 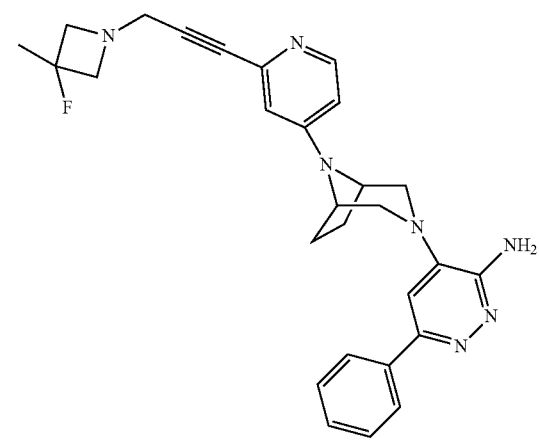 [SMILES: CC1(F)CN(CC#Cc2cc(N3C4CCC3CN(c3cc(-c5ccccc5)nnc3N)C4)ccn2)C1] | 2-[6-amino-5-[8-[2-[3-(3-fluoro-3-methyl-azetidin-1-yl)prop-1-ynyl]-4-pyridyl]-3,8-diazabicyclo[3.2.1]octan-3-yl]pyridazin-3-yl]phenol |

| No. | Structure | Name |
|---|---|---|
| 174 | 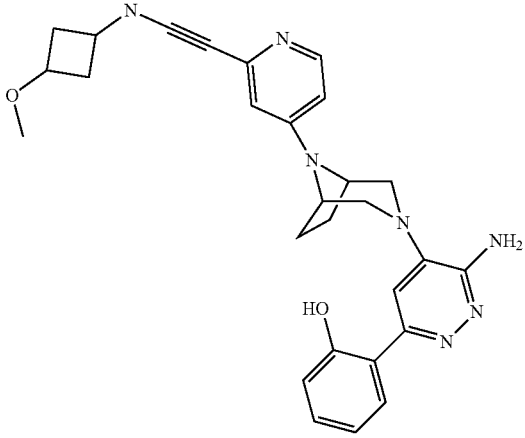 [SMILES: COC1CC(NC#Cc2cc(N3C4CCC3CN(c3cc(-c5ccccc5O)nnc3N)C4)ccn2)C1] | 2-[6-amino-5-[8-[2-[3-(3-methoxyazetidin-1-yl)prop-1-ynyl]-4-pyridyl]-3,8-diazabicyclo[3.2.1]octan-3-yl]pyridazin-3-yl]phenol |
| 175 | 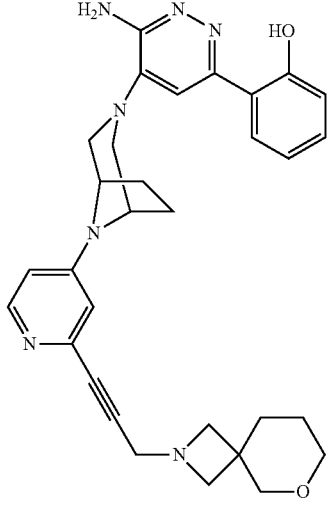 [SMILES: Nc1nnc(-c2ccccc2O)cc1N1CC2CCC(C1)N2c1ccnc(C#CCN2CC3(CCCOC3)C2)c1] | 2-[6-amino-5-[8-[2-[3-(6-oxa-2-azaspiro[3.5]nonan-2-yl)prop-1-ynyl]-4-pyridyl]-3,8-diazabicyclo[3.2.1]octan-3-yl]pyridazin-3-yl]phenol |
| 176 | 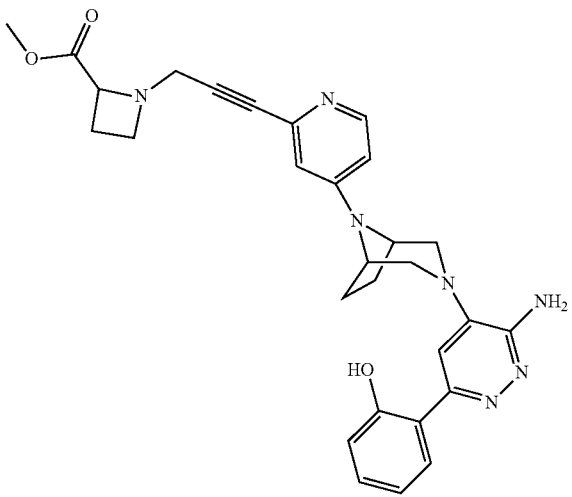 [SMILES: COC(=O)C1CCN1CC#Cc1cc(N2C3CCC2CN(c2cc(-c4ccccc4O)nnc2N)C3)ccn1] | methyl 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-2-carboxylate |

| No. | Structure | Name |
|---|---|---|
| 177 | 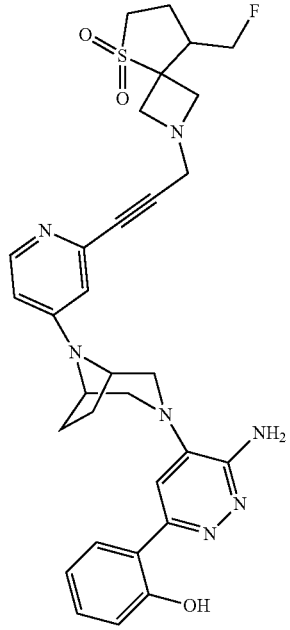 [SMILES: Nc1nnc(-c2ccccc2O)cc1N1CC2CCC(C1)N2c1ccnc(C#CCN2CC3(C2)C(CF)CCS3(=O)=O)c1] | 2-[6-amino-5-[8-[2-[3-[8-(fluoromethyl)-5,5-dioxo-5lambda6-thia-2-azaspiro[3.4]octan-2-yl]prop-1-ynyl]-4-pyridyl]-3,8-diazabicyclo[3.2.1]octan-3-yl]pyridazin-3-yl]phenol |
| 178 | 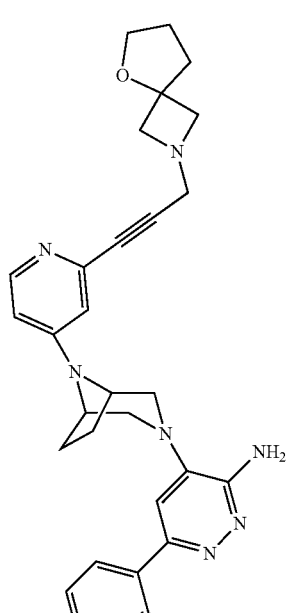 | 2-[6-amino-5-[8-[2-[3-(5-oxa-2-azaspiro[3.4]octan-2-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 179 | 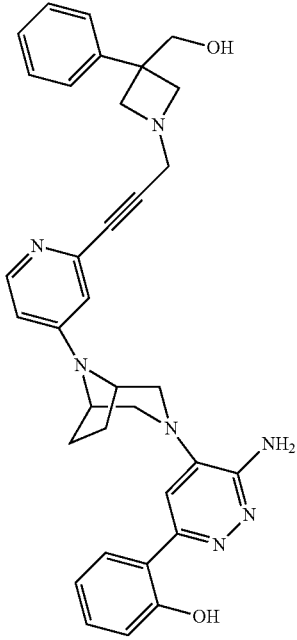 [SMILES: Nc1nnc(-c2ccccc2O)cc1N1CC2CCC(C1)N2c1ccnc(C#CCN2CC(CO)(c3ccccc3)C2)c1] | 2-[6-amino-5-[8-[2-[3-[3-(hydroxymethyl)-3-phenyl-azetidin-1-yl]prop-1-ynyl]-4-pyridyl]-3,8-diazabicyclo[3.2.1]octan-3-yl]pyridazin-3-yl]phenol |
| 180 | 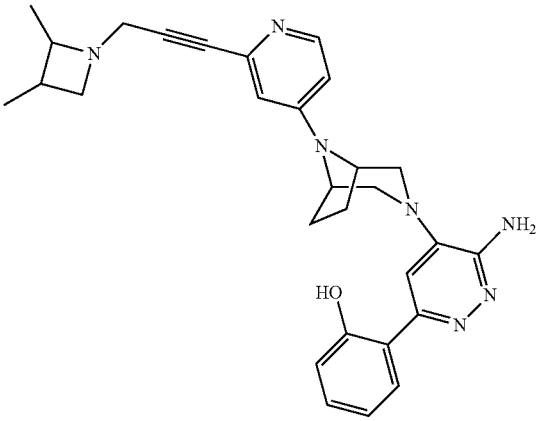 [SMILES: CC1CN(CC#Cc2cc(N3C4CCC3CN(c3cc(-c5ccccc5O)nnc3N)C4)ccn2)C1C] | 2-[6-amino-5-[8-[2-[3-(2,3-dimethylazetidin-1-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 181 | 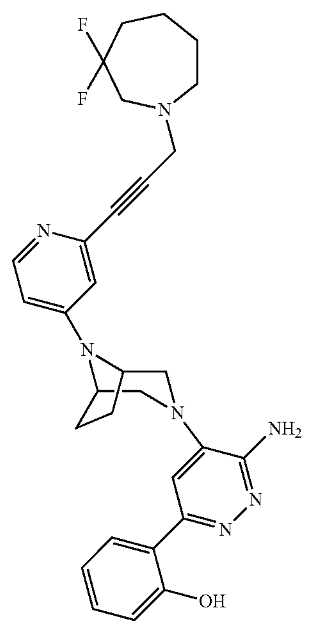 [SMILES: Nc1nnc(-c2ccccc2O)cc1N1CC2CCC(C1)N2c1ccnc(C#CCN2CCCCC(F)(F)C2)c1] | 2-[6-amino-5-[8-[2-[3-(3,3-difluoroazepan-1-yl)prop-1-ynyl]-4-pyridyl]-3,8-diazabicyclo[3.2.1]octan-3-yl]pyridazin-3-yl]phenol |
| 182 | 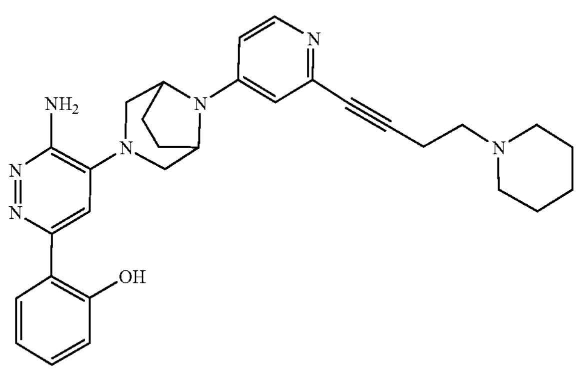 [SMILES: Nc1nnc(-c2ccccc2O)cc1N1CC2CCC(C1)N2c1ccnc(C#CCCN2CCCCC2)c1] | 2-[6-amino-5-[8-[2-[4-(1-piperidyl)but-1-ynyl]-4-pyridyl]-3,8-diazabicyclo[3.2.1]octan-3-yl]pyridazin-3-yl]phenol |
| 183 | 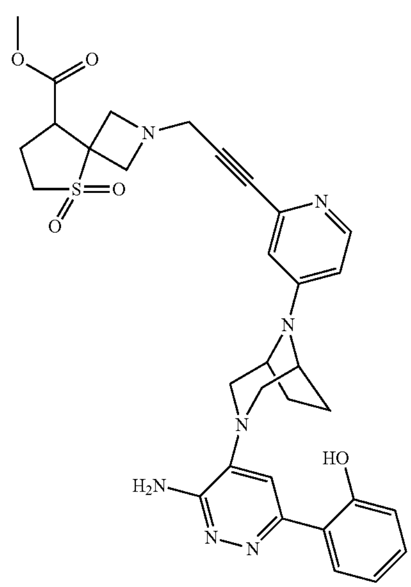 [SMILES: COC(=O)C1CCS(=O)(=O)C12CN(CC#Cc1cc(N3C4CCC3CN(c3cc(-c5ccccc5O)nnc3N)C4)ccn1)C2] | methyl 2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-dioxo-5lambda6-thia-2-azaspiro[3.4]octane-8-carboxylate |

TABLE 1-continued

| No. | Structure | Name |
|---|---|---|
| 184 | 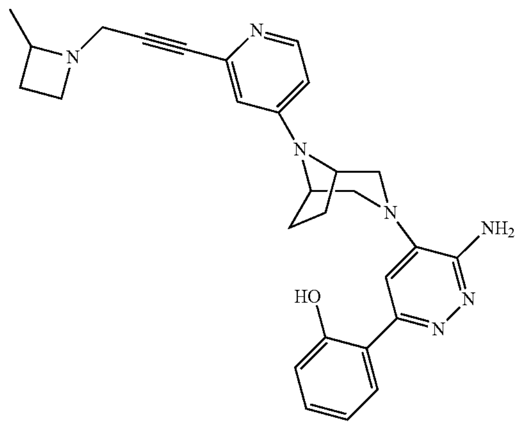 [SMILES: CC1CCN1CC#Cc1cc(N2C3CCC2CN(c2cc(-c4ccccc4O)nnc2N)C3)ccn1] | 2-[6-amino-5-[8-[2-[3-(2-methylazetidin-1-yl)prop-1-ynyl]-4-pyridyl]-3,8-diazabicyclo[3.2.1]octan-3-yl]pyridazin-3-yl]phenol |
| 185 | 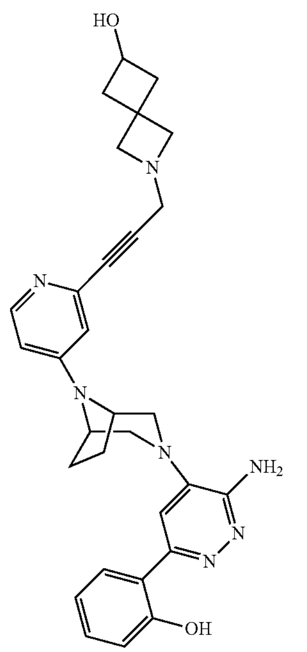 [SMILES: Nc1nnc(-c2ccccc2O)cc1N1CC2CCC(C1)N2c1ccnc(C#CCN2CC3(CC(O)C3)C2)c1] | 2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azaspiro[3.3]heptan-6-ol |
| 186 | 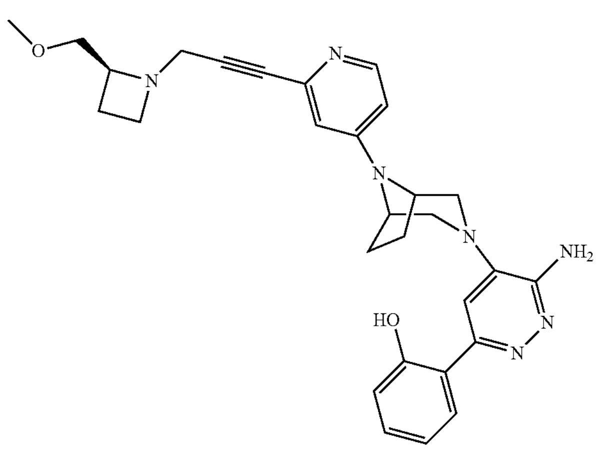 [SMILES: COC[C@@H]1CCN1CC#Cc1cc(N2C3CCC2CN(c2cc(-c4ccccc4O)nnc2N)C3)ccn1] | 2-[6-amino-5-[8-[2-[3-[(2S)-2-(methoxymethyl)azetidin-1-yl]prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 187 | 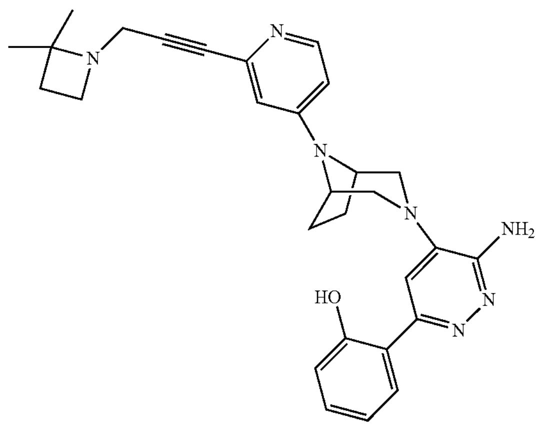 [SMILES: CC1(C)CCN1CC#Cc1cc(N2C3CCC2CN(c2cc(-c4ccccc4O)nnc2N)C3)ccn1] | 2-[6-amino-5-[8-[2-[3-(2,2-dimethylazetidin-1-yl)prop-1-ynyl]-4-pyridyl]-3,8-diazabicyclo[3.2.1]octan-3-yl]pyridazin-3-yl]phenol |
| 188 | 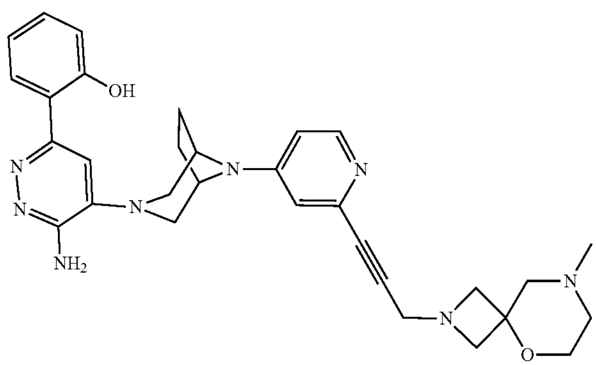 [SMILES: CN1CCOC2(C1)CN(CC#Cc1cc(N3C4CCC3CN(c3cc(-c5ccccc5O)nnc3N)C4)ccn1)C2] | 2-[6-amino-5-[8-[2-[3-(8-methyl-5-oxa-2,8-diazaspiro[3.5]nonan-2-yl)prop-1-ynyl]-4-pyridyl]-3,8-diazabicyclo[3.2.1]octan-3-yl]pyridazin-3-yl]phenol |
| 189 | 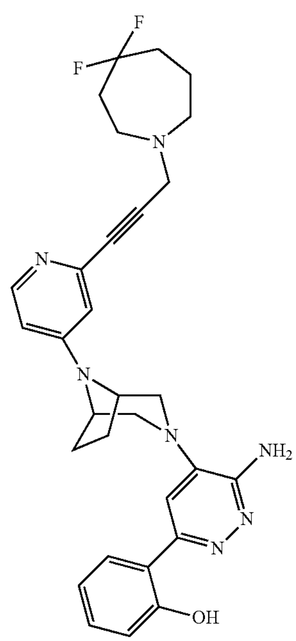 [SMILES: Nc1nnc(-c2ccccc2O)cc1N1CC2CCC(C1)N2c1ccnc(C#CCN2CCCC(F)(F)CC2)c1] | 2-[6-amino-5-[8-[2-[3-(4,4-difluoroazepan-1-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 190 | 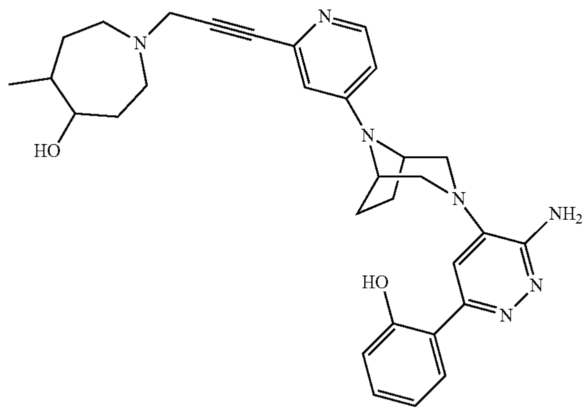 [SMILES: CC1CCN(CC#Cc2cc(N3C4CCC3CN(c3cc(-c5ccccc5O)nnc3N)C4)ccn2)CCC1O] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5-methyl-azepan-4-ol |
| 191 | 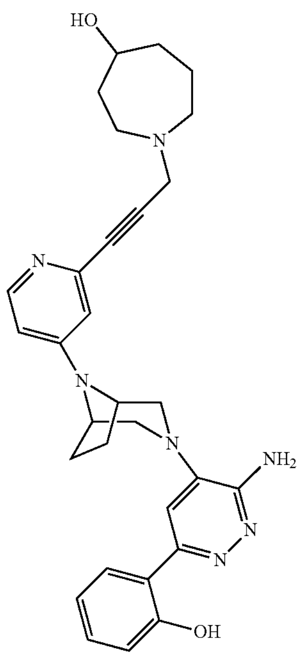 [SMILES: Nc1nnc(-c2ccccc2O)cc1N1CC2CCC(C1)N2c1ccnc(C#CCN2CCCC(O)CC2)c1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azepan-4-ol |
| 192 | 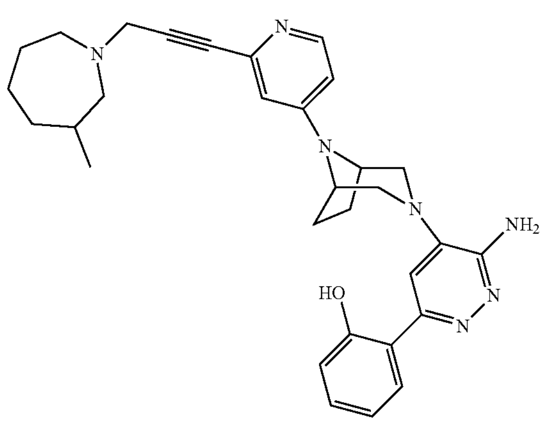 [SMILES: CC1CCCCN(CC#Cc2cc(N3C4CCC3CN(c3cc(-c5ccccc5O)nnc3N)C4)ccn2)C1] | 2-[6-amino-5-[8-[2-[3-(3-methylazepan-1-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 193 | 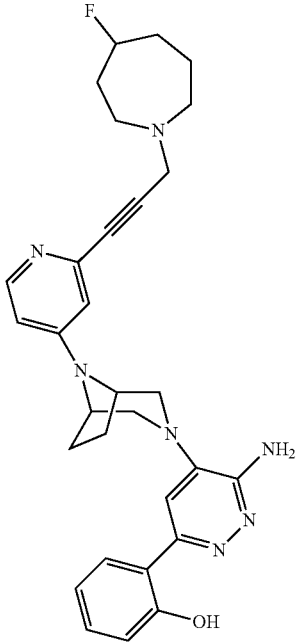 [SMILES: Nc1nnc(-c2ccccc2O)cc1N1CC2CCC(C1)N2c1ccnc(C#CCN2CCCC(F)CC2)c1] | 2-[6-amino-5-[8-[2-[3-(4-fluoroazepan-1-yl)prop-1-ynyl]-4-pyridyl]-3,8-diazabicyclo[3.2.1]octan-3-yl]pyridazin-3-yl]phenol |
| 194 | 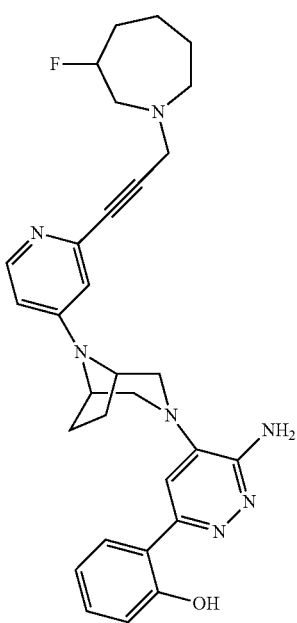 [SMILES: Nc1nnc(-c2ccccc2O)cc1N1CC2CCC(C1)N2c1ccnc(C#CCN2CCCCC(F)C2)c1] | 2-[6-amino-5-[8-[2-[3-(3-fluoroazepan-1-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 195 | 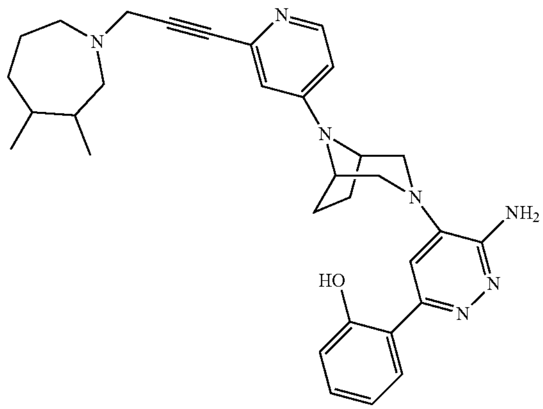 [SMILES: CC1CCCN(CC#Cc2cc(N3C4CCC3CN(c3cc(-c5ccccc5O)nnc3N)C4)ccn2)CC1C] | 2-[6-amino-5-[8-[2-[3-(3,4-dimethylazepan-1-yl)prop-1-ynyl]-4-pyridyl]-3,8-diazabicyclo[3.2.1]octan-3-yl]pyridazin-3-yl]phenol |
| 196 | 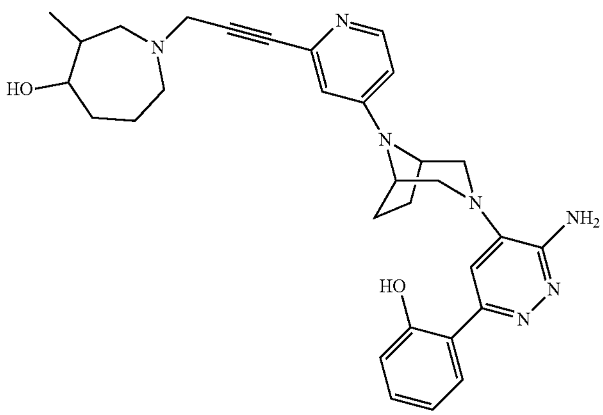 [SMILES: CC1CN(CC#Cc2cc(N3C4CCC3CN(c3cc(-c5ccccc5O)nnc3N)C4)ccn2)CCCC1O] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-4-ol |
| 197 | 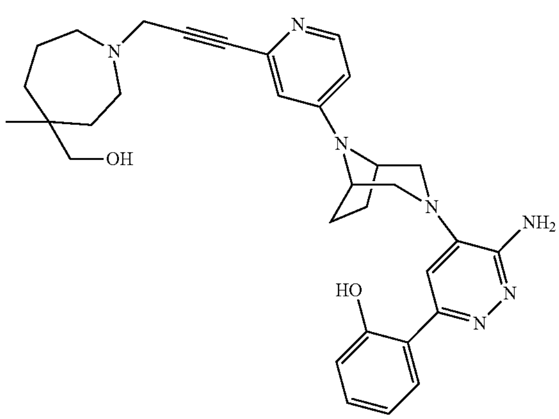 [SMILES: CC1(CO)CCCN(CC#Cc2cc(N3C4CCC3CN(c3cc(-c5ccccc5O)nnc3N)C4)ccn2)CC1] | 2-[6-amino-5-[8-[2-[3-[4-(hydroxymethyl)-4-methyl-azepan-1-yl]prop-1-ynyl]-4-pyridyl]-3,8-diazabicyclo[3.2.1]octan-3-yl]pyridazin-3-yl]phenol |

| No. | Structure | Name |
|---|---|---|
| 198 | 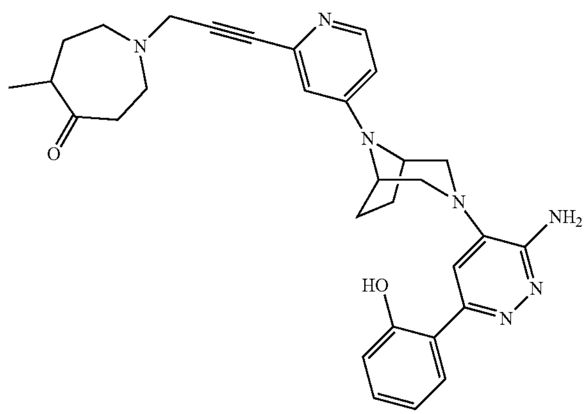 [SMILES: CC1CCN(CC#Cc2cc(N3C4CCC3CN(c3cc(-c5ccccc5O)nnc3N)C4)ccn2)CCC1=O] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5-methyl-azepan-4-one |
| 199 | 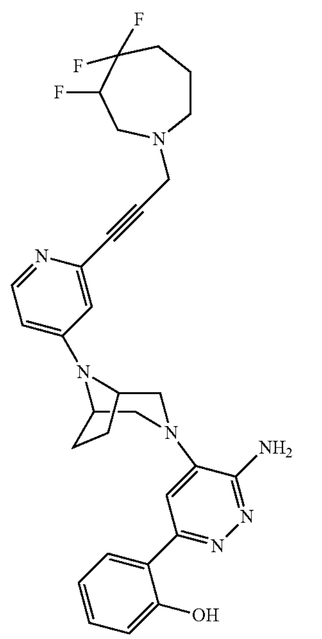 [SMILES: Nc1nnc(-c2ccccc2O)cc1N1CC2CCC(C1)N2c1ccnc(C#CCN2CCCC(F)(F)C(F)C2)c1] | 2-[6-amino-5-[8-[2-[3-(3,4,4-trifluoroazepan-1-yl)prop-1-ynyl]-4-pyridyl]-3,8-diazabicyclo[3.2.1]octan-3-yl]pyridazin-3-yl]phenol |
| 200 | 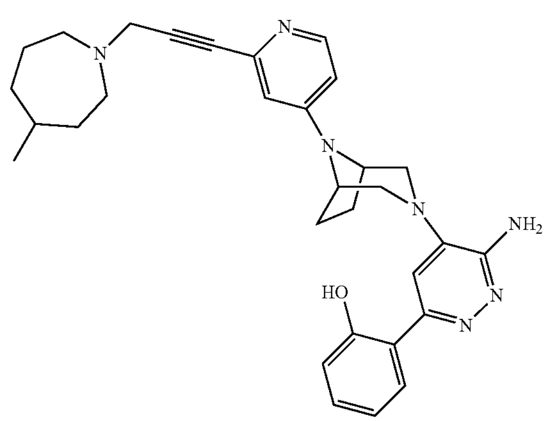 [SMILES: CC1CCCN(CC#Cc2cc(N3C4CCC3CN(c3cc(-c5ccccc5O)nnc3N)C4)ccn2)CC1] | 2-[6-amino-5-[8-[2-[3-(4-methylazepan-1-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 201 | 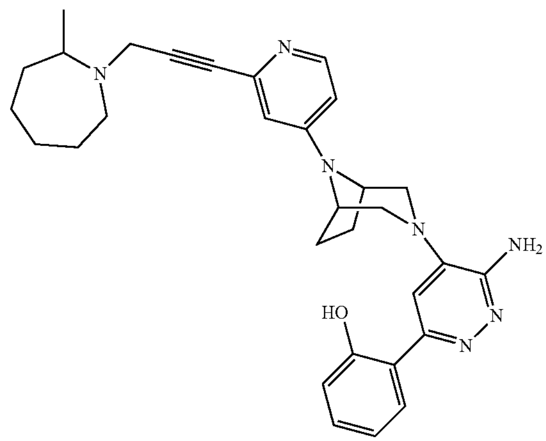 [SMILES: CC1CCCCCN1CC#Cc1cc(N2C3CCC2CN(c2cc(-c4ccccc4O)nnc2N)C3)ccn1] | 2-[6-amino-5-[8-[2-[3-(2-methylazepan-1-yl)prop-1-ynyl]-4-pyridyl]-3,8-diazabicyclo[3.2.1]octan-3-yl]pyridazin-3-yl]phenol |
| 202 | 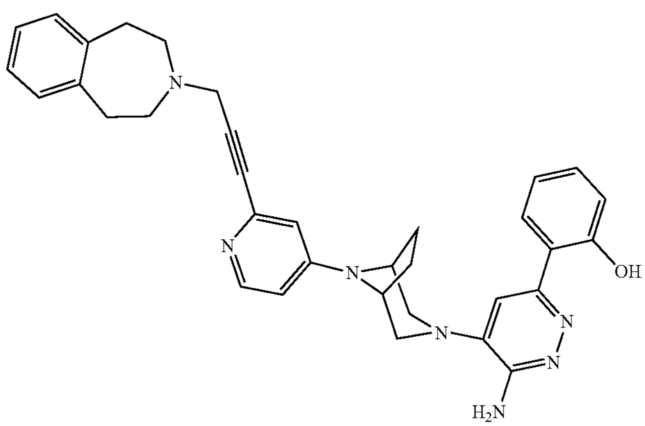 [SMILES: Nc1nnc(-c2ccccc2O)cc1N1CC2CCC(C1)N2c1ccnc(C#CCN2CCc3ccccc3CC2)c1] | 2-[6-amino-5-[8-[2-[3-(1,2,4,5-tetrahydro-3-benzazepin-3-yl)prop-1-ynyl]-4-pyridyl]-3,8-diazabicyclo[3.2.1]octan-3-yl]pyridazin-3-yl]phenol |
| 203 | 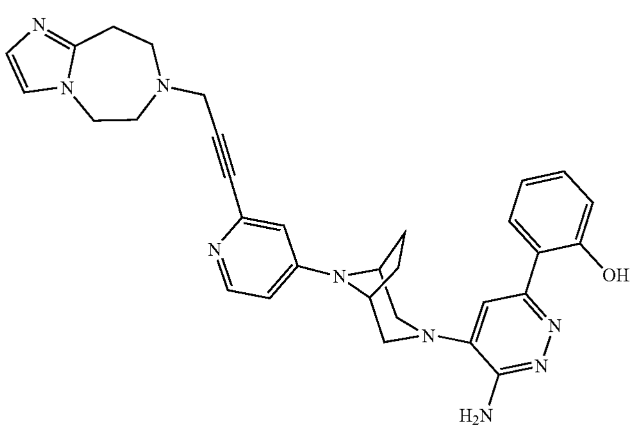 [SMILES: Nc1nnc(-c2ccccc2O)cc1N1CC2CCC(C1)N2c1ccnc(C#CCN2CCc3nccn3CC2)c1] | 2-[6-amino-5-[8-[2-[3-(5,6,8,9-tetrahydroimidazo[1,2-d][1,4]diazepin-7-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 204 | 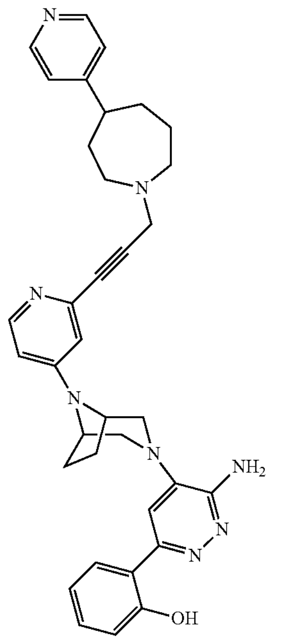 [SMILES: Nc1nnc(-c2ccccc2O)cc1N1CC2CCC(C1)N2c1ccnc(C#CCN2CCCC(c3ccncc3)CC2)c1] | 2-[6-amino-5-[8-[2-[3-[4-(4-pyridyl)-1,4-diazepan-1-yl]prop-1-ynyl]-4-pyridyl]-3,8-diazabicyclo[3.2.1]octan-3-yl]pyridazin-3-yl]phenol |
| 205 | 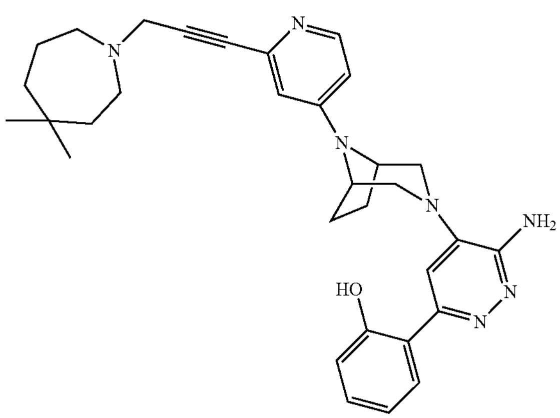 [SMILES: CC1(C)CCCN(CC#Cc2cc(N3C4CCC3CN(c3cc(-c5ccccc5O)nnc3N)C4)ccn2)CC1] | 2-[6-amino-5-[8-[2-[3-(4,4-dimethylazepan-1-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 206 | 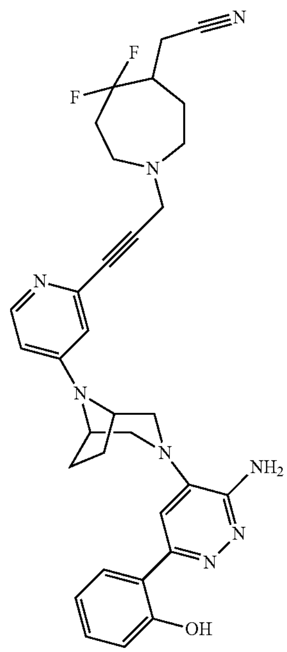 [SMILES: N#CCC1CCN(CC#Cc2cc(N3C4CCC3CN(c3cc(-c5ccccc5O)nnc3N)C4)ccn2)CCC1(F)F] | 2-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-difluoro-azepan-4-yl]acetonitrile |
| 207 | 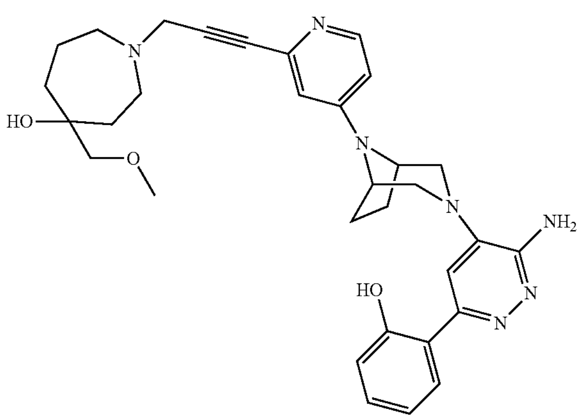 [SMILES: COCC1(O)CCCN(CC#Cc2cc(N3C4CCC3CN(c3cc(-c5ccccc5O)nnc3N)C4)ccn2)CC1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4-(methoxymethyl)azepan-4-ol |
| 208 | 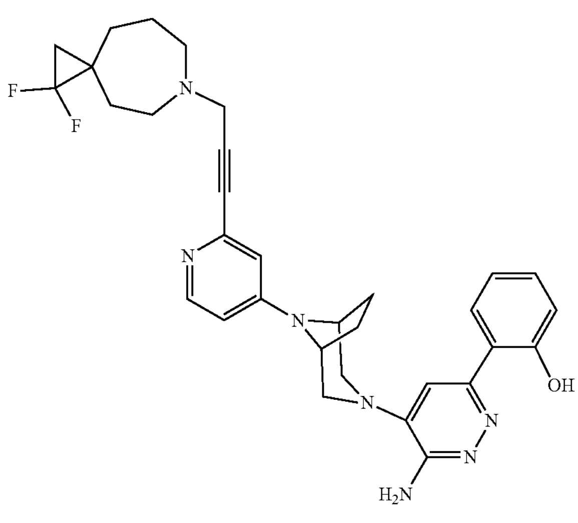 [SMILES: Nc1nnc(-c2ccccc2O)cc1N1CC2CCC(C1)N2c1ccnc(C#CCN2CCCC3(CC2)CC3(F)F)c1] | 2-[6-amino-5-[8-[2-[3-(2,2-difluoro-7-azaspiro[2.6]nonan-7-yl)prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 209 | 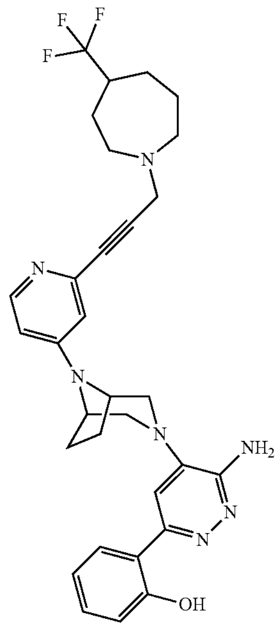 [SMILES: Nc1nnc(-c2ccccc2O)cc1N1CC2CCC(C1)N2c1ccnc(C#CCN2CCCC(C(F)(F)F)CC2)c1] | 2-[6-amino-5-[8-[2-[3-[4-(trifluoromethyl)azepan-1-yl]prop-1-ynyl]-4-pyridyl]-3,8-diazabicyclo[3.2.1]octan-3-yl]pyridazin-3-yl]phenol |
| 210 | 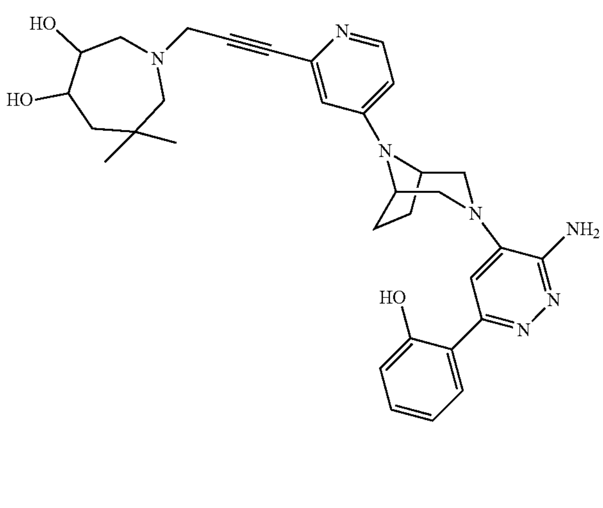 [SMILES: CC1(C)CC(O)C(O)CN(CC#Cc2cc(N3C4CCC3CN(c3cc(-c5ccccc5O)nnc3N)C4)ccn2)C1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepane-3,4-diol |

| No. | Structure | Name |
|---|---|---|
| 211 | 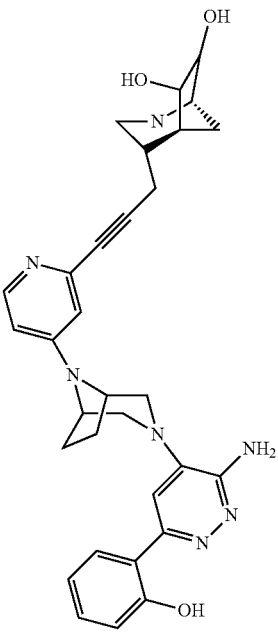 [SMILES: Nc1nnc(-c2ccccc2O)cc1N1CC2CCC(C1)N2c1ccnc(C#CCC2CN[C@H]3C[C@@H]2C(O)C3O)c1] | (1S,5R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[3.2.1]octane-6,7-diol |
| 212 | 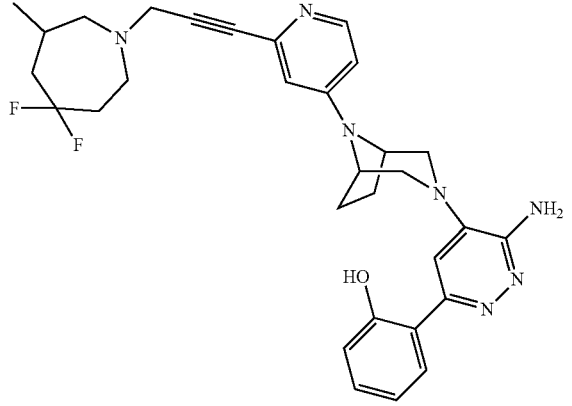 [SMILES: CC1CN(CC#Cc2cc(N3C4CCC3CN(c3cc(-c5ccccc5O)nnc3N)C4)ccn2)CCC(F)(F)C1] | 2-[6-amino-5-[8-[2-[3-(5,5-difluoro-3-methyl-azepan-1-yl)prop-1-ynyl]-4-pyridyl]-3,8-diazabicyclo[3.2.1]octan-3-yl]pyridazin-3-yl]phenol |
| 213 | 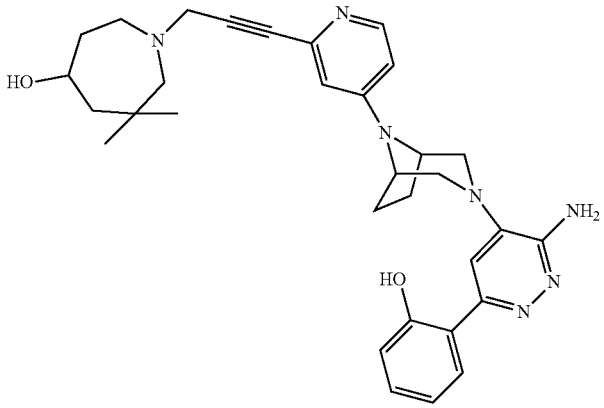 [SMILES: CC1(C)CC(O)CCN(CC#Cc2cc(N3C4CCC3CN(c3cc(-c5ccccc5O)nnc3N)C4)ccn2)C1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepan-4-ol |

TABLE 1-continued

| No. | Structure | Name |
|---|---|---|
| 214 | 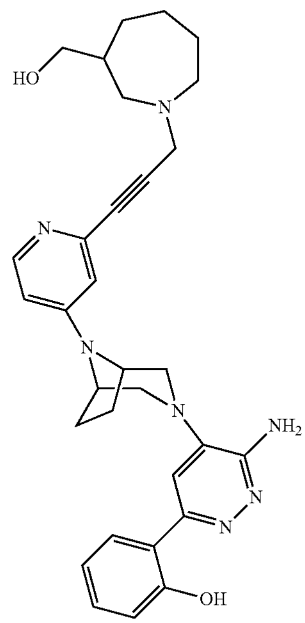 [SMILES: Nc1nnc(-c2ccccc2O)cc1N1CC2CCC(C1)N2c1ccnc(C#CCN2CCCCC(CO)C2)c1] | 2-[6-amino-5-[8-[2-[3-[3-(hydroxymethyl)azepan-1-yl]prop-1-ynyl]-4-pyridyl]-3,8-diazabicyclo[3.2.1]octan-3-yl]pyridazin-3-yl]phenol |
| 215 | 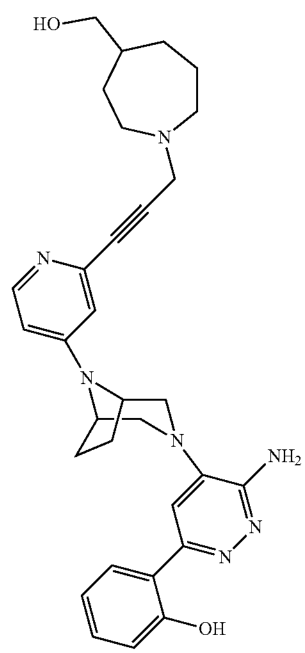 [SMILES: Nc1nnc(-c2ccccc2O)cc1N1CC2CCC(C1)N2c1ccnc(C#CCN2CCCC(CO)CC2)c1] | 2-[6-amino-5-[8-[2-[3-[4-(hydroxymethyl)azepan-1-yl]prop-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 216 | 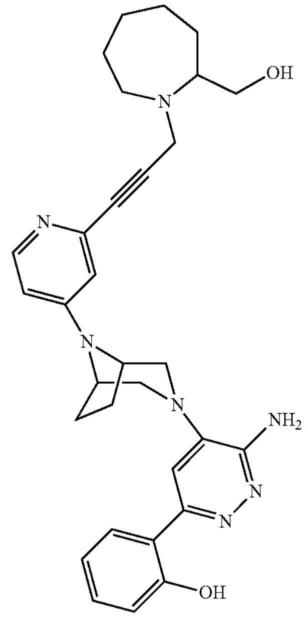 [SMILES: Nc1nnc(-c2ccccc2O)cc1N1CC2CCC(C1)N2c1ccnc(C#CCN2CCCCCC2CO)c1] | 2-[6-amino-5-[8-[2-[3-[2-(hydroxymethyl)azepan-1-yl]prop-1-ynyl]-4-pyridyl]-3,8-diazabicyclo[3.2.1]octan-3-yl]pyridazin-3-yl]phenol |
| 217 | 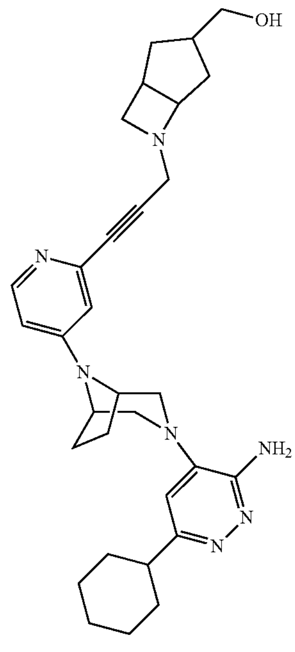 [SMILES: Nc1nnc(C2CCCCC2)cc1N1CC2CCC(C1)N2c1ccnc(C#CCN2CC3CC(CO)CC32)c1] | 2-[6-amino-5-[8-[2-[3-[3-(hydroxymethyl)-6-azabicyclo[3.2.0]heptan-6-yl]prop-1-ynyl]-4-pyridyl]-3,8-diazabicyclo[3.2.1]octan-3-yl]pyridazin-3-yl]phenol |
| 218 | 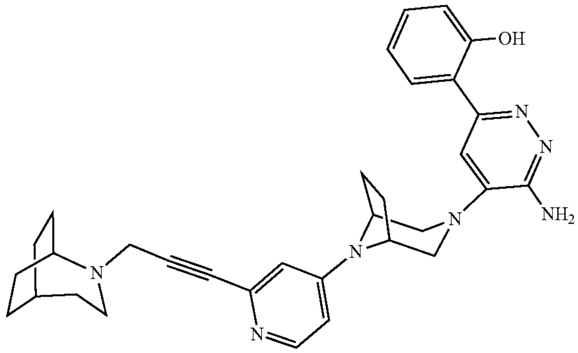 [SMILES: Nc1nnc(-c2ccccc2O)cc1N1CC2CCC(C1)N2c1ccnc(C#CCN2CCC3CCC2CC3)c1] | 2-[6-amino-5-[8-[2-[3-(2-azabicyclo[3.2.2]nonan-2-yl)prop-1-ynyl]-4-pyridyl]-3,8-diazabicyclo[3.2.1]octan-3-yl]pyridazin-3-yl]henol |

TABLE 1-continued

| No. | Structure | Name |
|---|---|---|
| 219 | 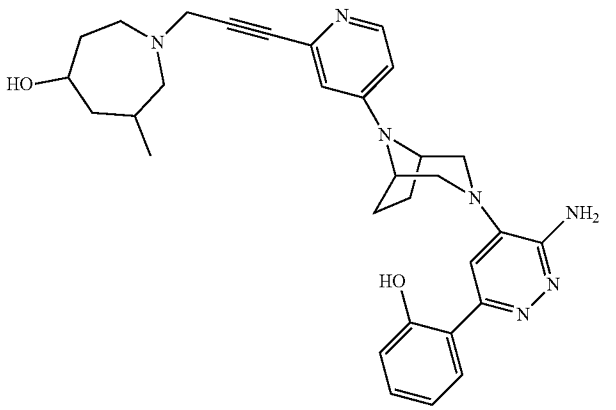 [SMILES: CC1CC(O)CCN(CC#Cc2cc(N3C4CCC3CN(c3cc(-c5ccccc5O)nnc3N)C4)ccn2)C1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6-methyl-azepan-4-ol |
| 220 | 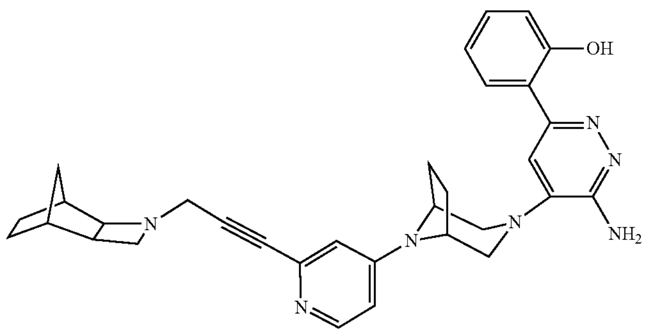 [SMILES: Nc1nnc(-c2ccccc2O)cc1N1CC2CCC(C1)N2c1ccnc(C#CCN2CC3C4CCC(C4)C32)c1] | 2-[6-amino-5-[8-[2-[3-(3-azatricyclo[4.2.1.02,5]nonan-3-yl)prop-1-ynyl]-4-pyridyl]-3,8-diazabicyclo[3.2.1]octan-3-yl]pyridazin-3-yl]phenol |
| 221 | 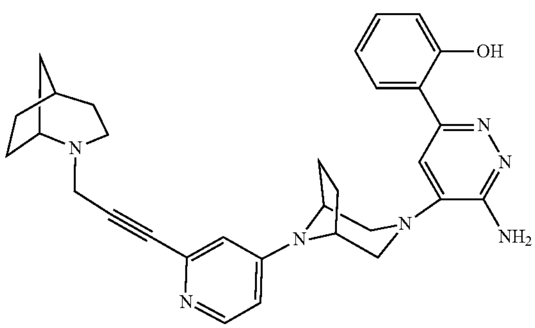 [SMILES: Nc1nnc(-c2ccccc2O)cc1N1CC2CCC(C1)N2c1ccnc(C#CCN2CCC3CCC2C3)c1] | 2-[6-amino-5-[8-[2-[3-(2-azabicyclo[3.2.1]octan-2-yl)prop-1-ynyl]-4-pyridyl]-3,8-diazabicyclo[3.2.1]octan-3-yl]pyridazin-3-yl]phenol |
| 222 | 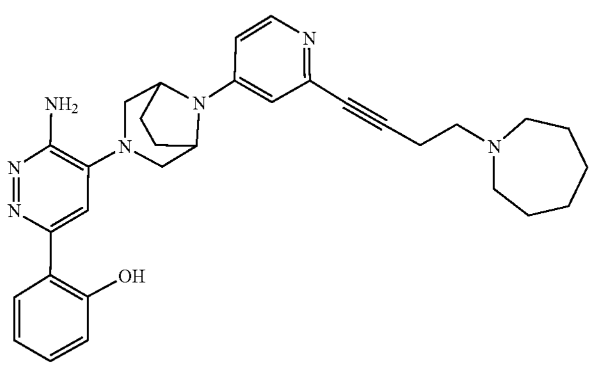 [SMILES: Nc1nnc(-c2ccccc2O)cc1N1CC2CCC(C1)N2c1ccnc(C#CCCN2CCCCCC2)c1] | 2-[6-amino-5-[8-[2-[4-(azepan-1-yl)but-1-ynyl]-4-pyridyl]-3,8-diazabicyclo[3.2.1]octan-3-yl]pyridazin-3-yl]phenol |

TABLE 1-continued

| No. | Structure | Name |
|---|---|---|
| 223 | 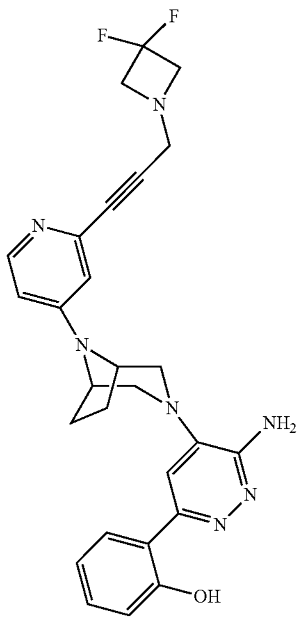 [SMILES: Nc1nnc(-c2ccccc2O)cc1N1CC2CCC(C1)N2c1ccnc(C#CCN2CC(F)(F)C2)c1] | 2-[6-amino-5-[8-[2-[3-(3,3-difluoroazetidin-1-yl)prop-1-ynyl]-4-pyridyl]-3,8-diazabicyclo[3.2.1]octan-3-yl]pyridazin-3-yl]phenol |
| 224 | 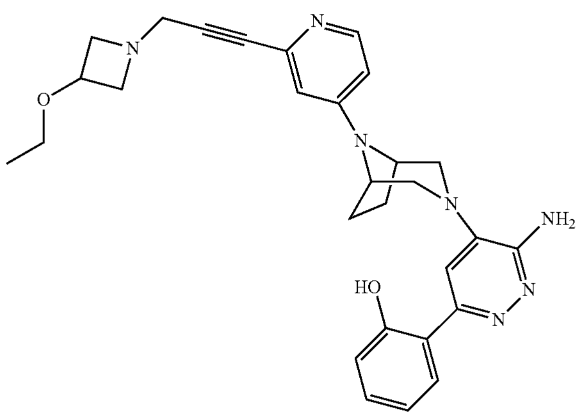 [SMILES: CCOC1CN(CC#Cc2cc(N3C4CCC3CN(c3cc(-c5ccccc5O)nnc3N)C4)ccn2)C1] | 2-[6-amino-5-[8-[2-[3-(3-ethoxyazetidin-1-yl)prop-1-ynyl]-4-pyridyl]-3,8-diazabicyclo[3.2.1]octan-3-yl]pyridazin-3-yl]phenol |
| 225 | 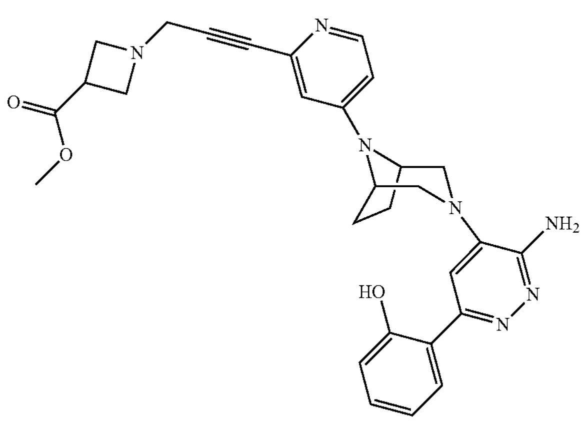 [SMILES: COC(=O)C1CN(CC#Cc2cc(N3C4CCC3CN(c3cc(-c5ccccc5O)nnc3N)C4)ccn2)C1] | methyl -[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-3-carboxylate |

TABLE 1-continued
| No. | Structure | Name |
|---|---|---|
| 226 | 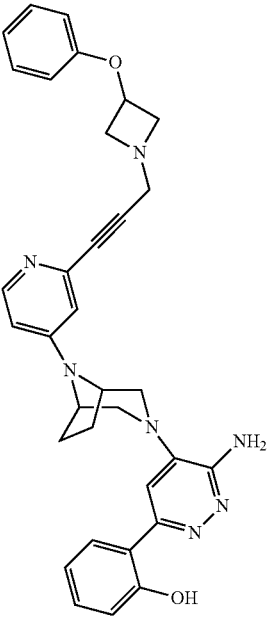 [SMILES: Nc1nnc(-c2ccccc2O)cc1N1CC2CCC(C1)N2c1ccnc(C#CCN2CC(Oc3ccccc3)C2)c1] | 2-[6-amino-5-[8-[2-[3-(3-phenoxyazetidin-1-yl)prop-1-ynyl]-4-pyridyl]-3,8-diazabicyclo[3.2.1]octan-3-yl]pyridazin-3-yl]phenol |
| 227 | 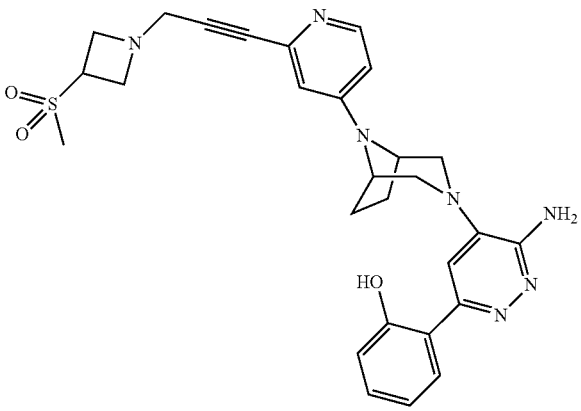 [SMILES: CS(=O)(=O)C1CN(CC#Cc2cc(N3C4CCC3CN(c3cc(-c5ccccc5O)nnc3N)C4)ccn2)C1] | 2-[6-amino-5-[8-[2-[3-(3-methylsulfonylazetidin-1-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 228 | 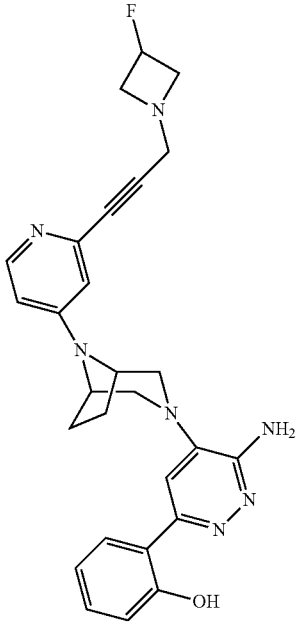 [SMILES: Nc1nnc(-c2ccccc2O)cc1N1CC2CCC(C1)N2c1ccnc(C#CCN2CC(F)C2)c1] | 2-[6-amino-5-[8-[2-[3-(3-fluoroazetidin-1-yl)prop-1-ynyl]-4-pyridyl]-3,8-diazabicyclo[3.2.1]octan-3-yl]pyridazin-3-yl]phenol |
| 229 | 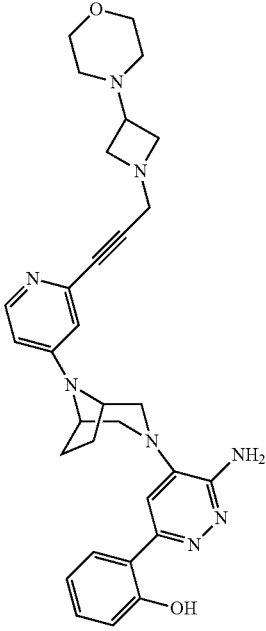 [SMILES: Nc1nnc(-c2ccccc2O)cc1N1CC2CCC(C1)N2c1ccnc(C#CCN2CC(N3CCOCC3)C2)c1] | 2-[6-amino-5-[8-[2-[3-(3-morpholinoazetidin-1-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 230 | 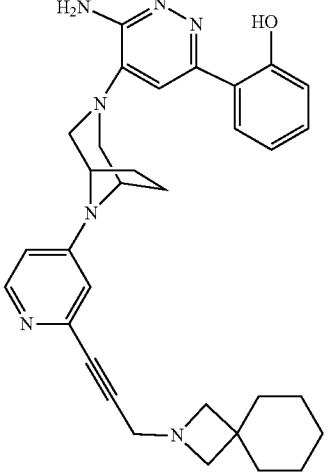 | 2-[6-amino-5-[8-[2-[3-(2-azaspiro[3.5]nonan-2-yl)prop-1-ynyl]-4-pyridyl]-3,8-diazabicyclo[3.2.1]octan-3-yl]pyridazin-3-yl]phenol |
| 231 | 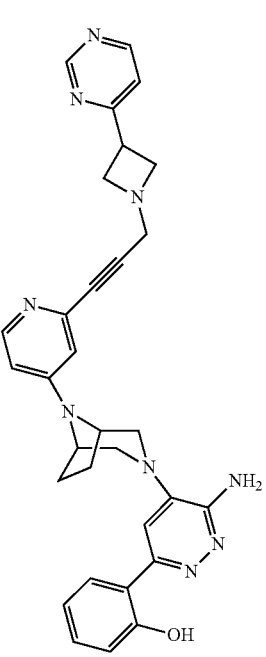 [SMILES: Nc1nnc(-c2ccccc2O)cc1N1CC2CCC(C1)N2c1ccnc(C#CCN2CC(c3ccncn3)C2)c1] | 2-[6-amino-5-[8-[2-[3-(3-pyrimidin-4-ylazetidin-1-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 232 | 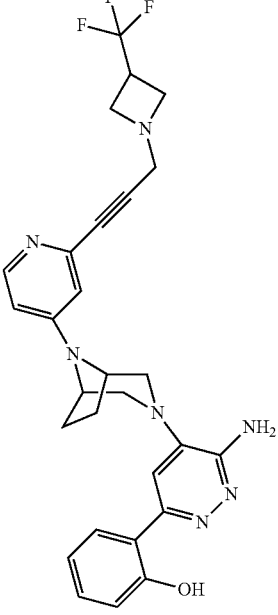 | 2-[6-amino-5-[8-[2-[3-[3-(trifluoromethyl)azetidin-1-yl]prop-1-ynyl]-4-pyridyl]-3,8-diazabicyclo[3.2.1]octan-3-yl]pyridazin-3-yl]phenol |
| 233 | 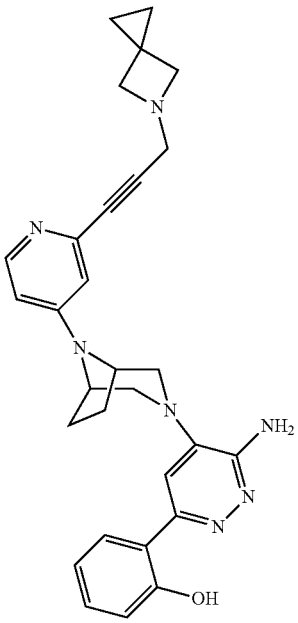 [SMILES: Nc1nnc(-c2ccccc2O)cc1N1CC2CCC(C1)N2c1ccnc(C#CCN2CC3(CC3)C2)c1] | 2-[6-amino-5-[8-[2-[3-(5-azaspiro[2.3]hexan-5-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 234 | 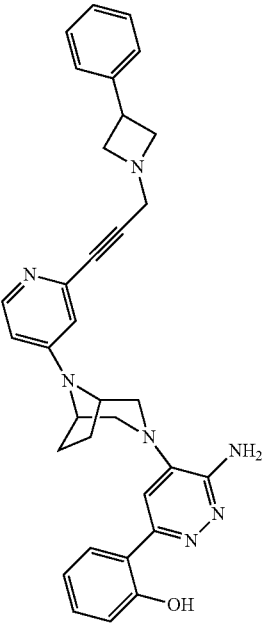 [SMILES: Nc1nnc(-c2ccccc2O)cc1N1CC2CCC(C1)N2c1ccnc(C#CCN2CC(c3ccccc3)C2)c1] | 2-[6-amino-5-[8-[2-[3-(3-phenylazetidin-1-yl)prop-1-ynyl]-4-pyridyl]-3,8-diazabicyclo[3.2.1]octan-3-yl]pyridazin-3-yl]phenol |
| 235 | 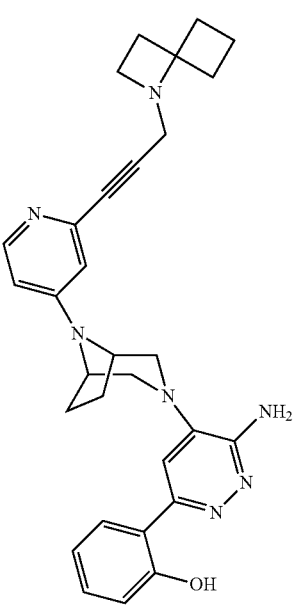 [SMILES: Nc1nnc(-c2ccccc2O)cc1N1CC2CCC(C1)N2c1ccnc(C#CCN2CCC23CCC3)c1] | 2-[6-amino-5-[8-[2-[3-(1-azaspiro[3.3]heptan-1-yl)prop-1-ynyl]-4-pyridyl]-3,8-diazabicyclo[3.2.1]octan-3-yl]pyridazin-3-yl]phenol |

TABLE 1-continued
| No. | Structure | Name |
|---|---|---|
| 236 | 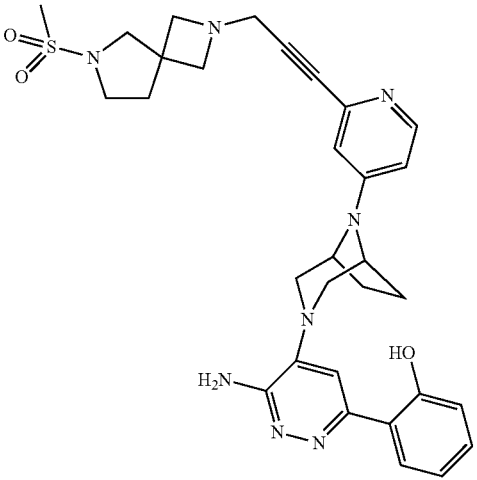 [SMILES: CS(=O)(=O)N1CCC2(CN(CC#Cc3cc(N4C5CCC4CN(c4cc(-c6ccccc6O)nnc4N)C5)ccn3)C2)C1] | 2-[6-amino-5-[8-[2-[3-(7-methylsulfonyl-2,7-diazaspiro[3.4]octan-2-yl)prop-1-ynyl]-4-pyridyl]-3,8-diazabicyclo[3.2.1]octan-3-yl]pyridazin-3-yl]phenol |
| 237 | 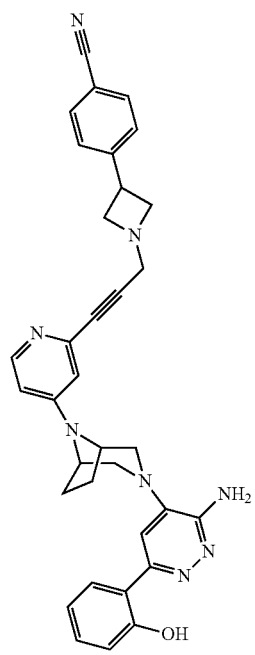 [SMILES: N#Cc1ccc(C2CN(CC#Cc3cc(N4C5CCC4CN(c4cc(-c6ccccc6O)nnc4N)C5)ccn3)C2)cc1] | 4-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-yl]benzonitrile |

| No. | Structure | Name |
|---|---|---|
| 238 | 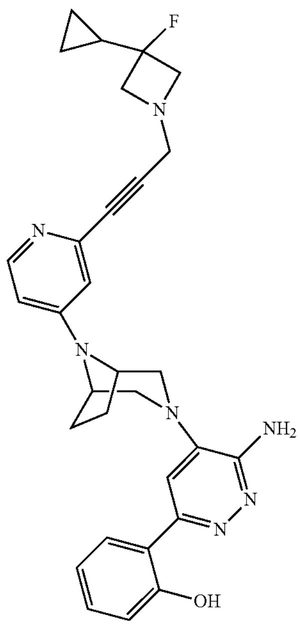 [SMILES: Nc1nnc(-c2ccccc2O)cc1N1CC2CCC(C1)N2c1ccnc(C#CCN2CC(F)(C3CC3)C2)c1] | 2-[6-amino-5-[8-[2-[3-(3-cyclopropyl-3-fluoro-azetidin-1-yl)prop-1-ynyl]-4-pyridyl]-3,8-diazabicyclo[3.2.1]octan-3-yl]pyridazin-3-yl]phenol |
| 239 | 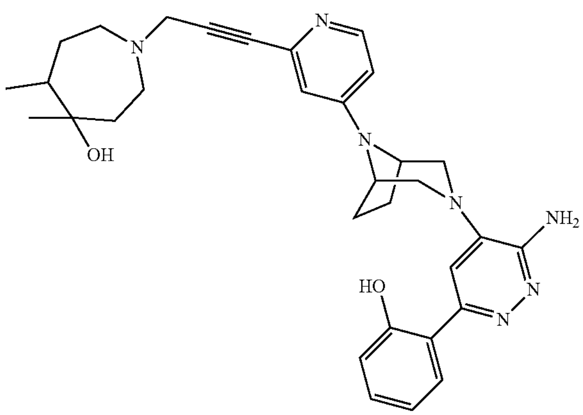 [SMILES: CC1CCN(CC#Cc2cc(N3C4CCC3CN(c3cc(-c5ccccc5O)nnc3N)C4)ccn2)CCC1(C)O] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4,5-dimethyl-azepan-4-ol |
| 240 | 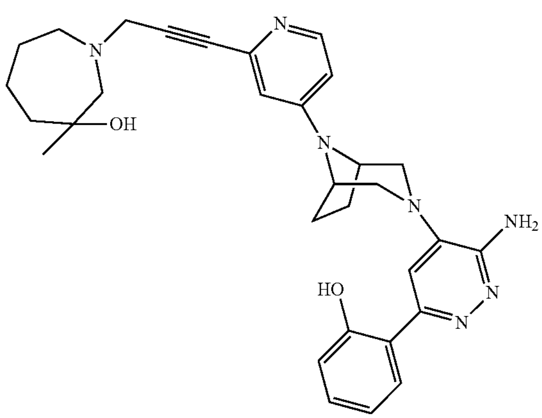 [SMILES: CC1(O)CCCCN(CC#Cc2cc(N3C4CCC3CN(c3cc(-c5ccccc5O)nnc3N)C4)ccn2)C1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-3-ol |

TABLE 1-continued
| No. | Structure | Name |
|---|---|---|
| 241 | 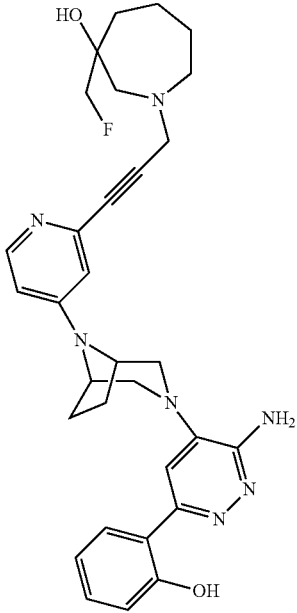 [SMILES: Nc1nnc(-c2ccccc2O)cc1N1CC2CCC(C1)N2c1ccnc(C#CCN2CCCCC(O)(CF)C2)c1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-(fluoromethyl)azepan-3-ol |
| 242 | 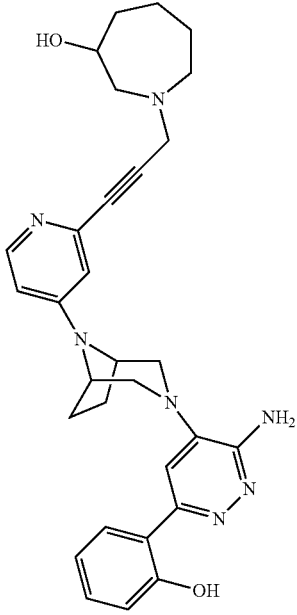 [SMILES: Nc1nnc(-c2ccccc2O)cc1N1CC2CCC(C1)N2c1ccnc(C#CCN2CCCCC(O)C2)c1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azepan-3-ol |

TABLE 1-continued

| No. | Structure | Name |
|---|---|---|
| 243 | 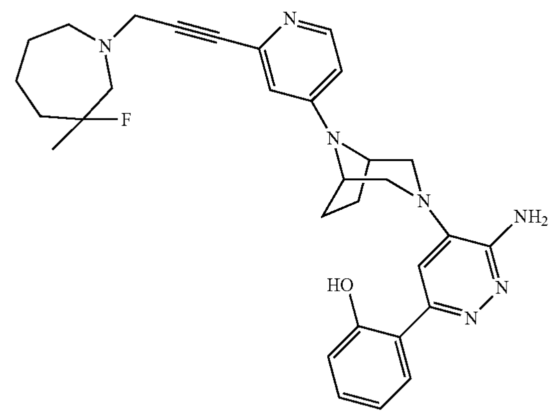 [SMILES: CC1(F)CCCCN(CC#Cc2cc(N3C4CCC3CN(c3cc(-c5ccccc5O)nnc3N)C4)ccn2)C1] | 2-[6-amino-5-[8-[2-[3-(3-fluoro-3-methyl-azepan-1-yl)prop-1-ynyl]-4-pyridyl]-3,8-diazabicyclo[3.2.1]octan-3-yl]pyridazin-3-yl]phenol |
| 244 | 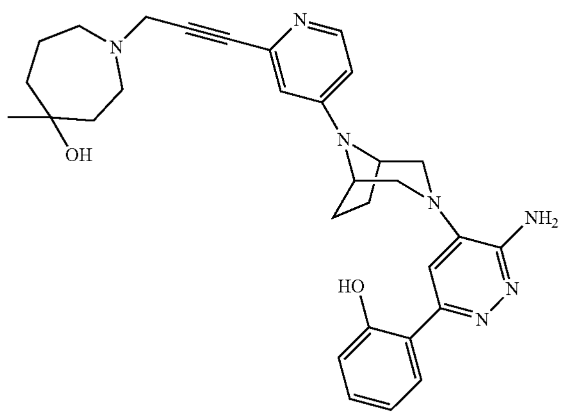 [SMILES: CC1(O)CCCN(CC#Cc2cc(N3C4CCC3CN(c3cc(-c5ccccc5O)nnc3N)C4)ccn2)CC1] | 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4-methyl-azepan-4-ol |
| 245 | 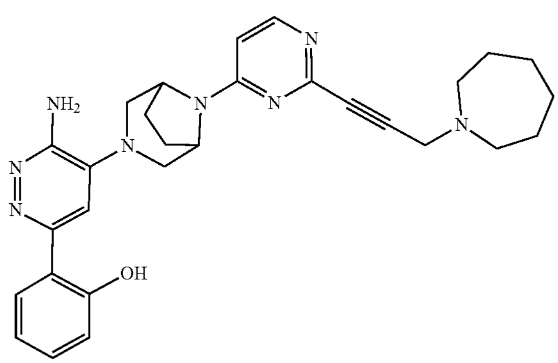 [SMILES: Nc1nnc(-c2ccccc2O)cc1N1CC2CCC(C1)N2c1ccnc(C#CCN2CCCCCC2)n1] | 2-[6-amino-5-[8-[2-[3-(azepan-1-yl)prop-1-ynyl]pyrimidin-4-yl]-3,8-diazabicyclo[3.2.1]octan-3-yl]pyridazin-3-yl]phenol |
| 246 | 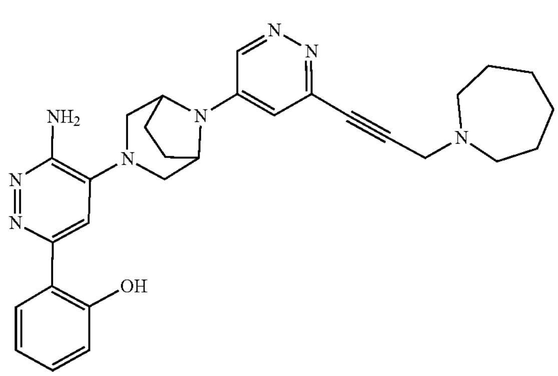 [SMILES: Nc1nnc(-c2ccccc2O)cc1N1CC2CCC(C1)N2c1cnnc(C#CCN2CCCCCC2)c1] | 2-[6-amino-5-[8-[6-[3-(azepan-1-yl)prop-1-ynyl]pyridazin-4-yl]-3,8-diazabicyclo[3.2.1]octan-3-yl]pyridazin-3-yl]phenol |

TABLE 1-continued

| No. | Structure | Name |
|---|---|---|
| 247 | 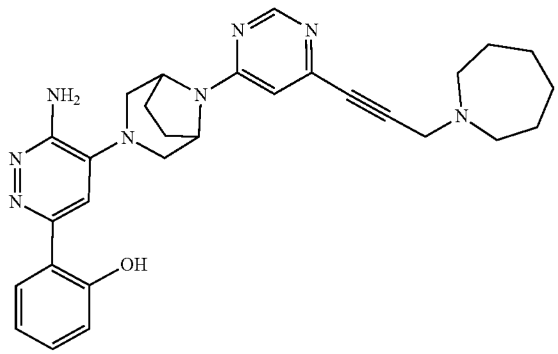 [SMILES: Nc1nnc(-c2ccccc2O)cc1N1CC2CCC(C1)N2c1cc(C#CCN2CCCCCC2)ncn1] | 2-[6-amino-5-[8-[6-[3-(azepan-1-yl)prop-1-ynyl]pyrimidin-4-yl]-3,8-diazabicyclo[3.2.1]octan-3-yl]pyridazin-3-yl]phenol |
| 248 | 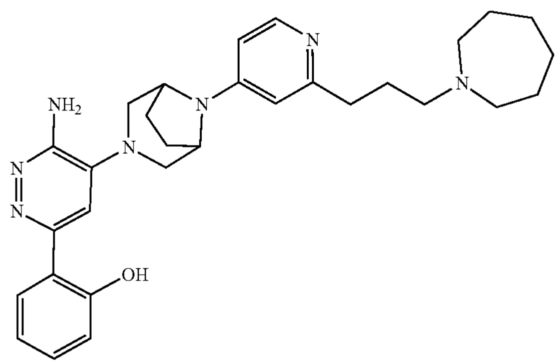 [SMILES: Nc1nnc(-c2ccccc2O)cc1N1CC2CCC(C1)N2c1ccnc(CCCN2CCCCCC2)c1] | 2-[6-amino-5-[8-[2-[(E)-3-(azepan-1-yl)prop-1-enyl]-4-pyridyl]-3,8-diazabicyclo[3.2.1]octan-3-yl]pyridazin-3-yl]phenol |
| 249 | 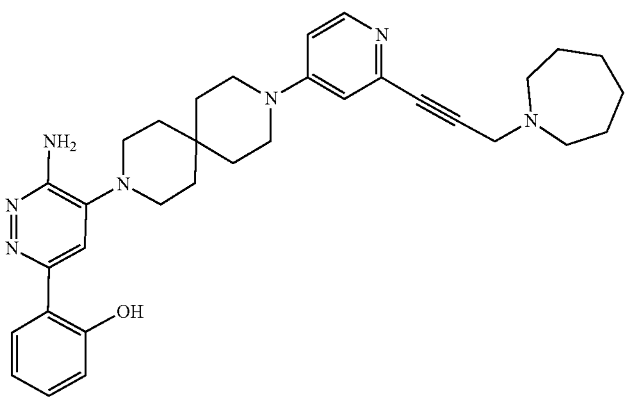 [SMILES: Nc1nnc(-c2ccccc2O)cc1N1CCC2(CCN(c3ccnc(C#CCN4CCCCCC4)c3)CC2)CC1] | 2-[6-amino-5-[9-[2-[3-(azepan-1-yl)prop-1-ynyl]-4-pyridyl]-3,9-diazaspiro[5.5]undecan-3-yl]pyridazin-3-yl]phenol |
| 250 | 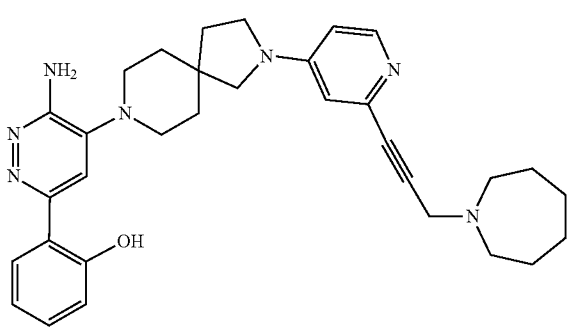 [SMILES: Nc1nnc(-c2ccccc2O)cc1N1CCC2(CCN(c3ccnc(C#CCN4CCCCCC4)c3)C2)CC1] | 2-[6-amino-5-[2-[2-[3-(azepan-1-yl)prop-1-ynyl]-4-pyridyl]-2,8-diazaspiro[4.5]decan-8-yl]pyridazin-3-yl]phenol |

TABLE 1-continued

| No. | Structure | Name |
|---|---|---|
| 251 | 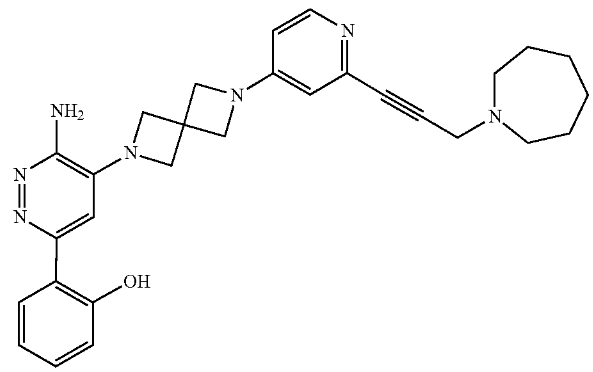 [SMILES: Nc1nnc(-c2ccccc2O)cc1N1CC2(CN(c3ccnc(C#CCN4CCCCCC4)c3)C2)C1] | 2-[6-amino-5-[6-[2-[3-(azepan-1-yl)prop-1-ynyl]-4-pyridyl]-2,6-diazaspiro[3.3]heptan-2-yl]pyridazin-3-yl]phenol |
| 252 | 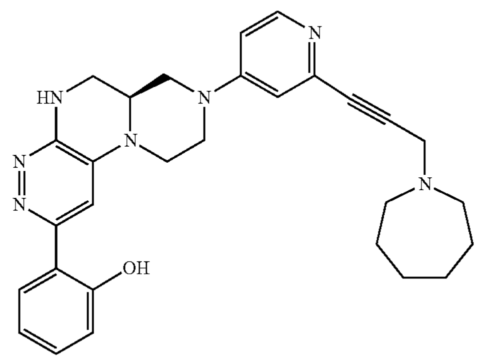 [SMILES: Oc1ccccc1-c1cc2c(nn1)NC[C@H]1CN(c3ccnc(C#CCN4CCCCCC4)c3)CCN21] | 2-[(10S)-12-[2-[3-(azepan-1-yl)prop-1-ynyl]-4-pyridyl]-1,5,6,8,12-pentazatricyclo[8.4.0.02,7]tetradeca-2(7),3,5-trien-4-yl]phenol |
| 253 | 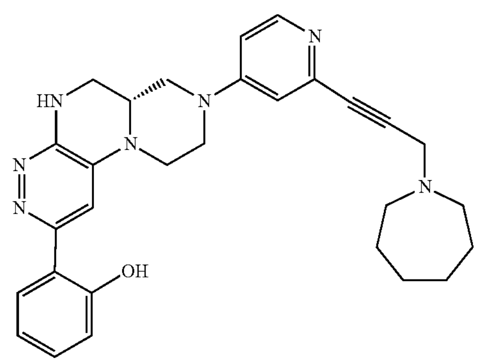 [SMILES: Oc1ccccc1-c1cc2c(nn1)NC[C@@H]1CN(c3ccnc(C#CCN4CCCCCC4)c3)CCN21] | 2-[(10R)-12-[2-[3-(azepan-1-yl)prop-1-ynyl]-4-pyridyl]-1,5,6,8,12-pentazatricyclo[8.4.0.02,7]tetradeca-2(7),3,5-trien-4-yl]phenol |

Note that, in Table 1, compound names were auto-generated using ChemDraw® software version 18.2.0.48.

In embodiments, the present disclosure is directed to a compound selected from the group consisting of:

2-(6-amino-5-(8-(2-(4-(piperazin-1-yl)but-1-yn-1-yl)pyridin-4-yl)-3,8-diazabicyclo[3.2.1]octan-3-yl)pyridazin-3-yl)phenol;

2-(6-amino-5-(8-(2-(3-(pyrrolidin-1-yl)prop-1-yn-1-yl)pyridin-4-yl)-3,8-diazabicyclo[3.2.1]octan-3-yl)pyridazin-3-yl)phenol;

2-(6-amino-5-(8-(2-(3-((2-hydroxyethyl)(methyl)amino)prop-1-yn-1-yl)pyridin-4-yl)-3,8-diazabicyclo[3.2.1]octan-3-yl)pyridazin-3-yl)phenol;

2-(6-amino-5-(8-(2-(3-(2-hydroxyethoxy)prop-1-yn-1-yl)pyridin-4-yl)-3,8-diazabicyclo[3.2.1]octan-3-yl)pyridazin-3-yl)phenol;

2-(6-amino-5-(8-(2-(3-(diethylamino)prop-1-yn-1-yl)pyridin-4-yl)-3,8-diazabicyclo[3.2.1]octan-3-yl)pyridazin-3-yl)phenol;

2-(6-amino-5-(8-(2-(azetidin-3-ylethynyl)pyridin-4-yl)-3,8-diazabicyclo[3.2.1]octan-3-yl)pyridazin-3-yl)phenol;

2-(6-amino-5-(8-(2-(morpholin-2-ylethynyl)pyridin-4-yl)-3,8-diazabicyclo[3.2.1]octan-3-yl)pyridazin-3-yl)phenol;

2-(6-amino-5-(8-(2-(piperidin-3-ylethynyl)pyridin-4-yl)-3,8-diazabicyclo[3.2.1]octan-3-yl)pyridazin-3-yl)phenol;

2-(6-amino-5-(8-(2-(3-morpholinoprop-1-yn-1-yl)pyridin-4-yl)-3,8-diazabicyclo[3.2.1]octan-3-yl)pyridazin-3-yl)phenol;

1-(3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)piperazin-2-one;

2-(6-amino-5-(8-(2-(8-aminooct-1-yn-1-yl)pyridin-4-yl)-3,8-diazabicyclo[3.2.1]octan-3-yl)pyridazin-3-yl)phenol;

2-(6-amino-5-(8-(2-(3-(piperidin-3-yloxy)prop-1-yn-1-yl)pyridin-4-yl)-3,8-diazabicyclo[3.2.1]octan-3-yl)pyridazin-3-yl)phenol;

2-(6-amino-5-(8-(2-(3-(piperidin-2-yl)prop-1-yn-1-yl)pyridin-4-yl)-3,8-diazabicyclo[3.2.1]octan-3-yl)pyridazin-3-yl)phenol;

2-(6-amino-5-(8-(2-(pyrrolidin-2-ylethynyl)pyridin-4-yl)-3,
8-diazabicyclo[3.2.1]octan-3-yl)pyridazin-3-yl)phenol;
2-(6-amino-5-(8-(2-(3-(3-aminopyrrolidin-1-yl)prop-1-yn-
1-yl)pyridin-4-yl)-3,8-diazabicyclo[3.2.1]octan-3-yl)
pyridazin-3-yl)phenol;
2-(6-amino-5-(8-(2-(3-(pyrrolidin-2-yl)prop-1-yn-1-yl)pyri-
din-4-yl)-3,8-diazabicyclo[3.2.1]octan-3-yl)pyridazin-3-
yl)phenol;
2-(6-amino-5-(8-(2-(azetidin-2-ylethynyl)pyridin-4-yl)-3,8-
diazabicyclo[3.2.1]octan-3-yl)pyridazin-3-yl)phenol;
4-(3-(4-(3-(3-amino-6-(2-hydroxyphenyl)pyridazin-4-yl)-3,
8-diazabicyclo[3.2.1]octan-8-yl)pyridin-2-yl)prop-2-yn-
1-yl)thiomorpholine 1,1-dioxide;
2-(6-amino-5-(8-(2-(piperidin-4-ylethynyl)pyridin-4-yl)-3,
8-diazabicyclo[3.2.1]octan-3-yl)pyridazin-3-yl)phenol;
2-(6-amino-5-(8-(2-(6-aminohexyl)pyridin-4-yl)-3,8-diaz-
abicyclo[3.2.1]octan-3-yl)pyridazin-3-yl)phenol;
2-(6-amino-5-(8-(2-((1-methyl-1H-pyrazol-4-yl)ethynyl)
pyridin-4-yl)-3,8-diazabicyclo[3.2.1]octan-3-yl)
pyridazin-3-yl)phenol;
2-(6-amino-5-(8-(2-((tetrahydro-2H-pyran-4-yl)ethynyl)
pyridin-4-yl)-3,8-diazabicyclo[3.2.1]octan-3-yl)
pyridazin-3-yl)phenol;
2-(6-amino-5-(8-(2-(3-aminobut-1-yn-1-yl)pyridin-4-yl)-3,
8-diazabicyclo[3.2.1]octan-3-yl)pyridazin-3-yl)phenol;
2-(6-amino-5-(8-(2-(3-aminoprop-1-yn-1-yl)pyridin-4-yl)-
3,8-diazabicyclo[3.2.1]octan-3-yl)pyridazin-3-yl)phenol;
2-(6-amino-5-(8-(2-(pyrrolidin-3-ylethynyl)pyridin-4-yl)-3,
8-diazabicyclo[3.2.1]octan-3-yl)pyridazin-3-yl)phenol;
2-(6-amino-5-(8-(2-(4-hydroxybut-1-yn-1-yl)pyridin-4-yl)-
3,8-diazabicyclo[3.2.1]octan-3-yl)pyridazin-3-yl)phenol;
2-(6-amino-5-(8-(2-(6-hydroxyhex-1-yn-1-yl)pyridin-4-yl)-
3,8-diazabicyclo[3.2.1]octan-3-yl)pyridazin-3-yl)phenol;
2-(6-amino-5-(8-(2-(3-(piperazin-1-yl)prop-1-yn-1-yl)pyri-
din-4-yl)-3,8-diazabicyclo[3.2.1]octan-3-yl)pyridazin-3-
yl)phenol;
2-(6-amino-5-(8-(2-((4-aminocyclohexyl)ethynyl)pyridin-
4-yl)-3,8-diazabicyclo[3.2.1]octan-3-yl)pyridazin-3-yl)
phenol;
2-(6-amino-5-(8-(2-(4-aminobut-1-yn-1-yl)pyridin-4-yl)-3,
8-diazabicyclo[3.2.1]octan-3-yl)pyridazin-3-yl)phenol;
2-(6-amino-5-(8-(2-(3-(3-aminopiperidin-1-yl)prop-1-yn-1-
yl)pyridin-4-yl)-3,8-diazabicyclo[3.2.1]octan-3-yl)
pyridazin-3-yl)phenol;
2-amino-N-(3-(4-(3-(3-amino-6-(2-hydroxyphenyl)
pyridazin-4-yl)-3,8-diazabicyclo[3.2.1]octan-8-yl)pyri-
din-2-yl)propyl)acetamide;
2-(6-amino-5-(8-(2-(3-aminopropyl)pyridin-4-yl)-3,8-diaz-
abicyclo[3.2.1]octan-3-yl)pyridazin-3-yl)phenol; and
2-(6-amino-5-(8-(2-(3-(pyrrolidin-3-yl)prop-1-yn-1-yl)pyri-
din-4-yl)-3,8-diazabicyclo[3.2.1]octan-3-yl)pyridazin-3-
yl)phenol,
or a stereoisomer or tautomer thereof, or a pharmaceuti-
cally acceptable salt of any of the foregoing.

In embodiments, the present disclosure is directed to a compound selected from the group consisting of:

N-[3-[4-[3-[3-amino-6-(2-hydroxyphenyl)pyridazin-4-yl]-
3,8-diazabicyclo[3.2.1]octan-8-yl]-2-pyridyl]prop-2-
ynyl]piperidine-4-carboxamide;
2-[6-amino-5-[8-[2-(3-amino-3-methyl-but-1-ynyl)-4-
pyridyl]-3,8-diazabicyclo[3.2.1]octan-3-yl]pyridazin-3-
yl]phenol;
2-[6-amino-5-[8-[2-[3-(3-methoxy-1-piperidyl)prop-1-
ynyl]-4-pyridyl]-3,8-diazabicyclo[3.2.1]octan-3-yl]
pyridazin-3-yl]phenol;
2-[6-amino-5-[8-[2-[3-(4-cyclopropylpiperazin-1-yl)prop-
1-ynyl]-4-pyridyl]-3,8-diazabicyclo[3.2.1]octan-3-yl]
pyridazin-3-yl]phenol;
2-[5-[8-[2-[3-(1,3,3a,4,5,6,7,7a-octahydroisoindol-2-yl)
prop-1-ynyl]-4-pyridyl]-3,8-diazabicyclo[3.2.1]octan-3-
yl]-6-amino-pyridazin-3-yl]phenol;
2-[6-amino-5-[8-[2-[3-(3-methylpiperazin-1-yl)prop-1-
ynyl]-4-pyridyl]-3,8-diazabicyclo[3.2.1]octan-3-yl]
pyridazin-3-yl]phenol;
2-[6-amino-5-[8-[2-[3-[2-(methoxymethyl)-1-piperidyl]
prop-1-ynyl]-4-pyridyl]-3,8-diazabicyclo[3.2.1]octan-3-
yl]pyridazin-3-yl]phenol;
2-[6-amino-5-[8-[2-[3-(2-methyl-1,4-oxazepan-4-yl)prop-
1-ynyl]-4-pyridyl]-3,8-diazabicyclo[3.2.1]octan-3-yl]
pyridazin-3-yl]phenol;
2-[6-amino-5-[8-[2-[3-(3,3-difluoropyrrolidin-1-yl)prop-1-
ynyl]-4-pyridyl]-3,8-diazabicyclo[3.2.1]octan-3-yl]
pyridazin-3-yl]phenol;
2-[6-amino-5-[8-[2-[3-(1-oxa-7-azaspiro[4.4]nonan-7-yl)
prop-1-ynyl]-4-pyridyl]-3,8-diazabicyclo[3.2.1]octan-3-
yl]pyridazin-3-yl]phenol;
2-[6-amino-5-[8-[2-[3-[4-(hydroxymethyl)-1-piperidyl]
prop-1-ynyl]-4-pyridyl]-3,8-diazabicyclo[3.2.1]octan-3-
yl]pyridazin-3-yl]phenol;
2-[6-amino-5-[8-[2-[3-[(2S)-2-(hydroxymethyl)pyrrolidin-
1-yl]prop-1-ynyl]-4-pyridyl]-3,8-diazabicyclo[3.2.1]oc-
tan-3-yl]pyridazin-3-yl]phenol;
2-[6-amino-5-[8-[2-[3-(4-methyl-1,4-diazepan-1-yl)prop-1-
ynyl]-4-pyridyl]-3,8-diazabicyclo[3.2.1]octan-3-yl]
pyridazin-3-yl]phenol;
2-[6-amino-5-[8-[2-[3-[(3R)-3-ethylmorpholin-4-yl]prop-1-
ynyl]-4-pyridyl]-3,8-diazabicyclo[3.2.1]octan-3-yl]
pyridazin-3-yl]phenol;
2-[6-amino-5-[8-[2-[3-(7-oxa-2-azaspiro[3.5]nonan-2-yl)
prop-1-ynyl]-4-pyridyl]-3,8-diazabicyclo[3.2.1]octan-3-
yl]pyridazin-3-yl]phenol;
1-[3-[4-[3-[3-amino-6-(2-hydroxyphenyl)pyridazin-4-yl]-3,
8-diazabicyclo[3.2.1]octan-8-yl]-2-pyridyl]prop-2-ynyl]
piperidin-3-ol;
2-[6-amino-5-[8-[2-[3-[(1,1-dioxothiolan-3-yl)-methyl-
amino]prop-1-ynyl]-4-pyridyl]-3,8-diazabicyclo[3.2.1]
octan-3-yl]pyridazin-3-yl]phenol;
1-[3-[4-[3-[3-amino-6-(2-hydroxyphenyl)pyridazin-4-yl]-3,
8-diazabicyclo[3.2.1]octan-8-yl]-2-pyridyl]prop-2-ynyl]
pyrrolidin-3-ol;
2-[6-amino-5-[8-[2-[3-(6,8-dihydro-5H-imidazo[1,2-a]
pyrazin-7-yl)prop-1-ynyl]-4-pyridyl]-3,8-diazabicyclo
[3.2.1]octan-3-yl]pyridazin-3-yl]phenol;
2-[5-[8-[2-[3-(2,3,3a,4,6,6a-hexahydro-1H-pyrrolo[3,4-c]
pyrrol-5-yl)prop-1-ynyl]-4-pyridyl]-3,8-diazabicyclo
[3.2.1]octan-3-yl]-6-amino-pyridazin-3-yl]phenol;
2-[6-amino-5-[8-[2-[3-[2-(hydroxymethyl)-1-piperidyl]
prop-1-ynyl]-4-pyridyl]-3,8-diazabicyclo[3.2.1]octan-3-
yl]pyridazin-3-yl]phenol;
2-[6-amino-5-[8-[2-[3-(5,7-dihydropyrrolo[3,4-b]pyridin-6-
yl)prop-1-ynyl]-4-pyridyl]-3,8-diazabicyclo[3.2.1]octan-
3-yl]pyridazin-3-yl]phenol;
2-[6-amino-5-[8-[2-[3-(3-methylmorpholin-4-yl)prop-1-
ynyl]-4-pyridyl]-3,8-diazabicyclo[3.2.1]octan-3-yl]
pyridazin-3-yl]phenol;
2-[6-amino-5-[8-[2-[3-(azepan-1-yl)prop-1-ynyl]-4-
pyridyl]-3,8-diazabicyclo[3.2.1]octan-3-yl]pyridazin-3-
yl]phenol;
2-[6-amino-5-[8-[2-[3-[(2S,6R)-2,6-dimethylmorpholin-4-
yl]prop-1-ynyl]-4-pyridyl]-3,8-diazabicyclo[3.2.1]octan-
3-yl]pyridazin-3-yl]phenol;

2-[5-[8-[2-[3-[(3aS,7aR)-1,3,3a,4,5,6,7,7a-octahydroisoindol-2-yl]prop-1-ynyl]-4-pyridyl]-3,8-diazabicyclo[3.2.1]octan-3-yl]-6-amino-pyridazin-3-yl]phenol;

2-[6-amino-5-[8-[2-[3-(3-methyl-1-piperidyl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-pyrrolidin-3-ol;

2-[5-[8-[2-[3-(3,3a,4,5,6,6a-hexahydro-1H-cyclopenta[c]pyrrol-2-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-[(3S)-3-ethylmorpholin-4-yl]prop-1-ynyl]-4-pyridyl]-3,8-diazabicyclo[3.2.1]octan-3-yl]pyridazin-3-yl]phenol;

2-[6-amino-5-[8-[2-[3-1[(2R)-2-(hydroxymethyl)pyrrolidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(5-oxa-2-azaspiro[3.5]nonan-2-yl)prop-1-ynyl]-4-pyridyl]-3,8-diazabicyclo[3.2.1]octan-3-yl]pyridazin-3-yl]phenol;

2-[5-[8-[2-[3-(3,4,6,7,8,8a-hexahydro-1H-pyrrolo[1,2-a]pyrazin-2-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-(3-azabicyclo[3.1.0]hexan-3-yl)prop-1-ynyl]-4-pyridyl]-3,8-diazabicyclo[3.2.1]octan-3-yl]pyridazin-3-yl]phenol;

2-[6-amino-5-[8-[2-[3-(7-oxa-1-azaspiro[3.4]octan-1-yl)prop-1-ynyl]-4-pyridyl]-3,8-diazabicyclo[3.2.1]octan-3-yl]pyridazin-3-yl]phenol;

2-[6-amino-5-[8-[2-[3-(1,4-oxazepan-4-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidin-4-ol;

2-[6-amino-5-[8-[2-[3-(6,8-dihydro-5H-imidazo[1,5-a]pyrazin-7-yl)prop-1-ynyl]-4-pyridyl]-3,8-diazabicyclo[3.2.1]octan-3-yl]pyridazin-3-yl]phenol;

2-[6-amino-5-[8-[2-[3-(7-oxa-4-azaspiro[2.5]octan-4-yl)prop-1-ynyl]-4-pyridyl]-3,8-diazabicyclo[3.2.1]octan-3-yl]pyridazin-3-yl]phenol;

2-[6-amino-5-[8-[2-[3-(2-oxa-5-azabicyclo[4.1.0]heptan-5-yl)prop-1-ynyl]-4-pyridyl]-3,8-diazabicyclo[3.2.1]octan-3-yl]pyridazin-3-yl]phenol;

2-[6-amino-5-[8-[2-[3-[(3S)-3-methylpyrrolidin-1-yl]prop-1-ynyl]-4-pyridyl]-3,8-diazabicyclo[3.2.1]octan-3-yl]pyridazin-3-yl]phenol;

2-[5-[8-[2-[3-(1,3,3a,4,6,6a-hexahydrofuro[3,4-c]pyrrol-5-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-(5-oxa-8-azaspiro[3.5]nonan-8-yl)prop-1-ynyl]-4-pyridyl]-3,8-diazabicyclo[3.2.1]octan-3-yl]pyridazin-3-yl]phenol;

(6R)-1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3,3a,4,5,6,6a-hexahydro-2H-cyclopenta[b]pyrrol-6-ol;

2-[6-amino-5-[8-[2-[3-(2,6-dimethylmorpholin-4-yl)prop-1-ynyl]-4-pyridyl]-3,8-diazabicyclo[3.2.1]octan-3-yl]pyridazin-3-yl]phenol;

2-[6-amino-5-[8-[2-[3-(3-morpholinopyrrolidin-1-yl)prop-1-ynyl]-4-pyridyl]-3,8-diazabicyclo[3.2.1]octan-3-yl]pyridazin-3-yl]phenol;

2-[5-[8-[2-[3-(2,3,3a,4,6,6a-hexahydrofuro[2,3-c]pyrrol-5-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-(7-methoxy-2-azabicyclo[2.2.1]heptan-2-yl)prop-1-ynyl]-4-pyridyl]-3,8-diazabicyclo[3.2.1]octan-3-yl]pyridazin-3-yl]phenol;

7-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-oxa-7-azabicyclo[3.3.1]nonan-9-ol;

2-[6-amino-5-[8-[2-[3-(2,2-difluoro-5-azaspiro[2.4]heptan-5-yl)prop-1-ynyl]-4-pyridyl]-3,8-diazabicyclo[3.2.1]octan-3-yl]pyridazin-3-yl]phenol;

2-[3-[4-[3-[3-amino-6-(2-hydroxyphenyl)pyridazin-4-yl]-3,8-diazabicyclo[3.2.1]octan-8-yl]-2-pyridyl]prop-2-ynyl-methyl-amino]-1-morpholino-ethanone;

2-[6-amino-5-[8-[2-[3-(2-azabicyclo[2.1.1]hexan-2-yl)prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[3.1.0]hexan-2-yl)prop-1-ynyl]-4-pyridyl]-3,8-diazabicyclo[3.2.1]octan-3-yl]pyridazin-3-yl]phenol;

2-[5-[8-[2-[3-(3,3a,4,6,7,7a-hexahydro-1H-furo[3,4-c]pyridin-5-yl)prop-1-ynyl]-4-pyridyl]-3,8-diazabicyclo[3.2.1]octan-3-yl]-6-amino-pyridazin-3-yl]phenol;

4-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-morpholine-3-carboxamide;

2-[5-[8-[2-[3-[(3aS,7aS)-3,3a,5,6,7,7a-hexahydro-2H-furo[3,2-b]pyridin-4-yl]prop-1-ynyl]-4-pyridyl]-3,8-diazabicyclo[3.2.1]octan-3-yl]-6-amino-pyridazin-3-yl]phenol;

2-[6-amino-5-[8-[2-[3-(3-azabicyclo[3.2.0]heptan-3-yl)prop-1-ynyl]-4-pyridyl]-3,8-diazabicyclo[3.2.1]octan-3-yl]pyridazin-3-yl]phenol;

2-[5-[8-[2-[3-(3,3a,4,6,7,7a-hexahydro-1H-pyrano[3,4-c]pyrrol-2-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-(3-azabicyclo[3.2.1]octan-3-yl)prop-1-ynyl]-4-pyridyl]-3,8-diazabicyclo[3.2.1]octan-3-yl]pyridazin-3-yl]phenol;

2-[5-[8-[2-[3-(3,3a,4,5,6,6a-hexahydro-2H-cyclopenta[b]pyrrol-1-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-[3-(difluoromethyl)azetidin-1-yl]prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-piperidine-2-carboxamide;

2-[6-amino-5-[8-[2-[3-(6-fluoro-2-azaspiro[3.3]heptan-2-yl)prop-1-ynyl]-4-pyridyl]-3,8-diazabicyclo[3.2.1]octan-3-yl]pyridazin-3-yl]phenol;

2-[6-amino-5-[8-[2-[3-(6-oxa-3-azabicyclo[3.2.1]octan-3-yl)prop-1-ynyl]-4-pyridyl]-3,8-diazabicyclo[3.2.1]octan-3-yl]pyridazin-3-yl]phenol;

2-[6-amino-5-[8-[2-[3-(5-azaspiro[2.5]octan-5-yl)prop-1-ynyl]-4-pyridyl]-3,8-diazabicyclo[3.2.1]octan-3-yl]pyridazin-3-yl]phenol;

2-[6-amino-5-[8-[2-[3-(8-oxa-1-azaspiro[3.5]nonan-1-yl)prop-1-ynyl]-4-pyridyl]-3,8-diazabicyclo[3.2.1]octan-3-yl]pyridazin-3-yl]phenol;

2-[6-amino-5-[8-[2-[3-(9-oxa-3-azabicyclo[3.3.1]nonan-3-yl)prop-1-ynyl]-4-pyridyl]-3,8-diazabicyclo[3.2.1]octan-3-yl]pyridazin-3-yl]phenol;

2-[6-amino-5-[8-[2-[3-[(1S,6R)-2-azabicyclo[4.2.0]octan-2-yl]prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-2-azabicyclo[2.2.1]heptan-2-yl]prop-1-ynyl]-4-pyridyl]-3,8-diazabicyclo[3.2.1]octan-3-yl]pyridazin-3-yl]phenol;

2-[6-amino-5-[8-[2-[3-(6-oxa-2-azabicyclo[3.2.1]octan-2-yl)prop-1-ynyl]-4-pyridyl]-3,8-diazabicyclo[3.2.1]octan-3-yl]pyridazin-3-yl]phenol;

3-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-azabicyclo[3.1.0]hexan-1-ol;

2-[6-amino-5-[8-[2-[3-(5-azaspiro[3.4]octan-5-yl)prop-1-ynyl]-4-pyridyl]-3,8-diazabicyclo[3.2.1]octan-3-yl]pyridazin-3-yl]phenol;

2-[6-amino-5-[8-[2-[3-(3,4-dihydro-1H-pyrrolo[1,2-a]pyrazin-2-yl)prop-1-ynyl]-4-pyridyl]-3,8-diazabicyclo[3.2.1]octan-3-yl]pyridazin-3-yl]phenol;

2-[5-[8-[2-[3-[(3aS,6aR)-2-methyl-1,3,3a,4,6,6a-hexahydropyrrolo[3,4-c]pyrrol-5-yl]prop-1-ynyl]-4-pyridyl]-3,8-diazabicyclo[3.2.1]octan-3-yl]-6-amino-pyridazin-3-yl]phenol;

(1R,4S,6R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[2.2.1]heptan-6-ol;

2-[6-amino-5-[8-[2-[3-(8-oxa-4-azaspiro[2.6]nonan-4-yl)prop-1-ynyl]-4-pyridyl]-3,8-diazabicyclo[3.2.1]octan-3-yl]pyridazin-3-yl]phenol;

2-[6-amino-5-[8-[2-[3-(3-oxa-9-azabicyclo[3.3.1]nonan-9-yl)prop-1-ynyl]-4-pyridyl]-3,8-diazabicyclo[3.2.1]octan-3-yl]pyridazin-3-yl]phenol;

2-[6-amino-5-[8-[2-[3-(2,2-difluoromorpholin-4-yl)prop-1-ynyl]-4-pyridyl]-3,8-diazabicyclo[3.2.1]octan-3-yl]pyridazin-3-yl]phenol;

2-[5-[8-[2-[3-[(3aR,6aR)-2,3,3a,4,6,6a-hexahydrofuro[2,3-c]pyrrol-5-yl]prop-1-ynyl]-4-pyridyl]-3,8-diazabicyclo[3.2.1]octan-3-yl]-6-amino-pyridazin-3-yl]phenol;

2-[6-amino-5-[8-[2-[3-[2-(fluoromethyl)morpholin-4-yl]prop-1-ynyl]-4-pyridyl]-3,8-diazabicyclo[3.2.1]octan-3-yl]pyridazin-3-yl]phenol;

2-[6-amino-5-[8-[2-[3-[(1R,4S)-2-azabicyclo[2.2.1]heptan-2-yl]prop-1-ynyl]-4-pyridyl]-3,8-diazabicyclo[3.2.1]octan-3-yl]pyridazin-3-yl]phenol;

2-[6-amino-5-[8-[2-[3-[1-(hydroxymethyl)-2-azabicyclo[2.1.1]hexan-2-yl]prop-1-ynyl]-4-pyridyl]-3,8-diazabicyclo[3.2.1]octan-3-yl]pyridazin-3-yl]phenol;

(1S,6S)-3-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-azabicyclo[4.1.0]heptan-6-ol;

2-[6-amino-5-[8-[2-[3-[(1S,5R)-6-(hydroxymethyl)-3-azabicyclo[3.1.0]hexan-3-yl]prop-1-ynyl]-4-pyridyl]-3,8-diazabicyclo[3.2.1]octan-3-yl]pyridazin-3-yl]phenol;

2-[6-amino-5-[8-[2-[3-(2,2-dimethylmorpholin-4-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidine-3-carbonitrile;

2-[6-amino-5-[8-[2-[3-[1-(hydroxymethyl)-7-azabicyclo[2.2.1]heptan-7-yl]prop-1-ynyl]-4-pyridyl]-3,8-diazabicyclo[3.2.1]octan-3-yl]pyridazin-3-yl]phenol;

(3S)-1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-pyrrolidine-3-carboxamide;

2-[6-amino-5-[8-[2-[3-[(1R,2S,4S,5S)-6-azatricyclo[3.2.1.02,4]octan-6-yl]prop-1-ynyl]-4-pyridyl]-3,8-diazabicyclo[3.2.1]octan-3-yl]pyridazin-3-yl]phenol;

2-[6-amino-5-[8-[2-[3-(4-oxa-7-azaspiro[2.5]octan-7-yl)prop-1-ynyl]-4-pyridyl]-3,8-diazabicyclo[3.2.1]octan-3-yl]pyridazin-3-yl]phenol;

2-[6-amino-5-[8-[2-[3-(6-azabicyclo[3.2.1]octan-6-yl)prop-1-ynyl]-4-pyridyl]-3,8-diazabicyclo[3.2.1]octan-3-yl]pyridazin-3-yl]phenol;

3-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-azabicyclo[3.1.1]heptan-6-ol;

2-[6-amino-5-[8-[2-[3-(2-azaspiro[4.4]nonan-2-yl)prop-1-ynyl]-4-pyridyl]-3,8-diazabicyclo[3.2.1]octan-3-yl]pyridazin-3-yl]phenol;

2-[6-amino-5-[8-[2-[3-[(3S)-3-methoxypyrrolidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(6-azaspiro[3.4]octan-6-yl)prop-1-ynyl]-4-pyridyl]-3,8-diazabicyclo[3.2.1]octan-3-yl]pyridazin-3-yl]phenol;

(1S,4S,5R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[2.2.1]heptan-5-ol;

2-[6-amino-5-[8-[2-[3-(4-fluoro-1-piperidyl)prop-1-ynyl]-4-pyridyl]-3,8-diazabicyclo[3.2.1]octan-3-yl]pyridazin-3-yl]phenol;

2-[6-amino-5-[8-[2-[3-(2-oxa-5-azabicyclo[2.2.1]heptan-5-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoropyrrolidin-1-yl)prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-1-piperidyl]prop-1-ynyl]-4-pyridyl]-3,8-diazabicyclo[3.2.1]octan-3-yl]pyridazin-3-yl]phenol;

2-[6-amino-5-[8-[2-[3-(3,3-dimethylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(6-azaspiro[2.5]octan-6-yl)prop-1-ynyl]-4-pyridyl]-3,8-diazabicyclo[3.2.1]octan-3-yl]pyridazin-3-yl]phenol;

2-[6-amino-5-[8-[2-[3-[1-(hydroxymethyl)-3-azabicyclo[3.1.0]hexan-3-yl]prop-1-ynyl]-4-pyridyl]-3,8-diazabicyclo[3.2.1]octan-3-yl]pyridazin-3-yl]phenol;

2-[6-amino-5-[8-[2-[3-(4-methyl-1-piperidyl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidine-4-carbonitrile;

2-[6-amino-5-[8-[2-[3-(2-oxa-7-azaspiro[4.4]nonan-7-yl)prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[2.2.1]heptan-2-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-ol;

2-[6-amino-5-[8-[2-[3-(5,5-difluoro-2-azabicyclo[2.2.1]heptan-2-yl)prop-1-ynyl]-4-pyridyl]-3,8-diazabicyclo[3.2.1]octan-3-yl]pyridazin-3-yl]phenol;

2-[6-amino-5-[8-[2-[3-(7-fluoro-3-oxa-9-azabicyclo[3.3.1]nonan-9-yl)prop-1-ynyl]-4-pyridyl]-3,8-diazabicyclo[3.2.1]octan-3-yl]pyridazin-3-yl]phenol;

2-[5-[8-[2-[3-(3,3a,4,6,7,7a-hexahydro-2H-furo[3,2-c]pyridin-5-yl)prop-1-ynyl]-4-pyridyl]-3,8-diazabicyclo[3.2.1]octan-3-yl]-6-amino-pyridazin-3-yl]phenol;

2-[5-[8-[2-[3-(3,3a,4,5,6,6a-hexahydro-2H-pyrrolo[3,4-b]pyrrol-1-yl)prop-1-ynyl]-4-pyridyl]-3,8-diazabicyclo[3.2.1]octan-3-yl]-6-amino-pyridazin-3-yl]phenol;

2-[5-[8-[2-[3-(2,3,4a,5,6,7,8,8a-octahydropyrido[4,3-b][1,4]oxazin-4-yl)prop-1-ynyl]-4-pyridyl]-3,8-diazabicyclo[3.2.1]octan-3-yl]-6-amino-pyridazin-3-yl]phenol;

2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-2-azabicyclo[2.1.1]hexane-1-carboxamide;

2-[6-amino-5-[8-[2-[3-(4,6-dihydro-1H-pyrrolo[3,4-c]pyrazol-5-yl)prop-1-ynyl]-4-pyridyl]-3,8-diazabicyclo[3.2.1]octan-3-yl]pyridazin-3-yl]phenol;

2-[6-amino-5-[8-[2-[3-(3-cyclopropylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(2,2-difluoro-5-azaspiro[2.3]hexan-5-yl)prop-1-ynyl]-4-pyridyl]-3,8-diazabicyclo[3.2.1]octan-3-yl]pyridazin-3-yl]phenol;

2-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-yl]acetonitrile;

2-[6-amino-5-[8-[2-[3-(4-azaspiro[2.5]octan-4-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-cyclopropyl-azetidin-3-ol;

2-[6-amino-5-[8-[2-[3-(2-azaspiro[3.4]octan-2-yl)prop-1-ynyl]-4-pyridyl]-3,8-diazabicyclo[3.2.1]octan-3-yl]pyridazin-3-yl]phenol;

2-[6-amino-5-[8-[2-[3-(2-methyl-2,6-diazaspiro[3.4]octan-6-yl)prop-1-ynyl]-4-pyridyl]-3,8-diazabicyclo[3.2.1]octan-3-yl]pyridazin-3-yl]phenol;

2-[6-amino-5-[8-[2-[3-(3-tetrahydrofuran-3-ylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-[3-(2,2-difluoroethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(7-oxa-1-azaspiro[3.5]nonan-1-yl)prop-1-ynyl]-4-pyridyl]-3,8-diazabicyclo[3.2.1]octan-3-yl]pyridazin-3-yl]phenol;

2-[6-amino-5-[8-[2-[3-(5,8-dioxa-2-azaspiro[3.5]nonan-2-yl)prop-1-ynyl]-4-pyridyl]-3,8-diazabicyclo[3.2.1]octan-3-yl]pyridazin-3-yl]phenol;

2-[6-amino-5-[8-[2-[3-[(1R,5R)-2-oxa-6-azabicyclo[3.2.0]heptan-6-yl]prop-1-ynyl]-4-pyridyl]-3,8-diazabicyclo[3.2.1]octan-3-yl]pyridazin-3-yl]phenol;

2-[6-amino-5-[8-[2-[3-(6-azabicyclo[3.2.0]heptan-6-yl)prop-1-ynyl]-4-pyridyl]-3,8-diazabicyclo[3.2.1]octan-3-yl]pyridazin-3-yl]phenol;

(2S)-1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-pyrrolidine-2-carboxamide;

2-[6-amino-5-[8-[2-[3-1[(1S,4S)-5-methyl-2,5-diazabicyclo[2.2.1]heptan-2-yl]prop-1-ynyl]-4-pyridyl]-3,8-diazabicyclo[3.2.1]octan-3-yl]pyridazin-3-yl]phenol;

2-[6-amino-5-[8-[2-[3-[(5R)-1,7-diazaspiro[4.4]nonan-1-yl]prop-1-ynyl]-4-pyridyl]-3,8-diazabicyclo[3.2.1]octan-3-yl]pyridazin-3-yl]phenol;

2-[6-amino-5-[8-[2-[3-(1-piperidyl)prop-1-ynyl]-4-pyridyl]-3,8-diazabicyclo[3.2.1]octan-3-yl]pyridazin-3-yl]phenol;

2-[6-amino-5-[8-[2-[3-(7-oxa-1-azaspiro[3.4]octan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-ol;

2-[6-amino-5-[8-[2-[3-(3-methoxy-3-methyl-azetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-3-methyl-azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-[3-fluoro-3-(hydroxymethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(3-methylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoro-3-methyl-azetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-methoxyazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(6-oxa-2-azaspiro[3.5]nonan-2-yl)prop-1-ynyl]-4-pyridyl]-3,8-diazabicyclo[3.2.1]octan-3-yl]pyridazin-3-yl]phenol;

methyl 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-2-carboxylate;

2-[6-amino-5-[8-[2-[3-[8-(fluoromethyl)-5,5-dioxo-5lambda6-thia-2-azaspiro[3.4]octan-2-yl]prop-1-ynyl]-4-pyridyl]-3,8-diazabicyclo[3.2.1]octan-3-yl]pyridazin-3-yl]phenol;

2-[6-amino-5-[8-[2-[3-(5-oxa-2-azaspiro[3.4]octan-2-yl)prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-3-phenyl-azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(2,3-dimethylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3,3-difluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[4-(1-piperidyl)but-1-ynyl]-4-pyridyl]-3,8-diazabicyclo[3.2.1]octan-3-yl]pyridazin-3-yl]phenol;

methyl 2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-dioxo-5lambda6-thia-2-azaspiro[3.4]octane-8-carboxylate;

2-[6-amino-5-[8-[2-[3-(2-methylazetidin-1-yl)prop-1-ynyl]-4-pyridyl]-3,8-diazabicyclo[3.2.1]octan-3-yl]pyridazin-3-yl]phenol;

2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azaspiro[3.3]heptan-6-ol;

2-[6-amino-5-[8-[2-[3-[(2S)-2-(methoxymethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(2,2-dimethylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(8-methyl-5-oxa-2,8-diazaspiro[3.5]nonan-2-yl)prop-1-ynyl]-4-pyridyl]-3,8-diazabicyclo[3.2.1]octa189n-3-yl]pyridazin-3-yl]phenol;

2-[6-amino-5-[8-[2-[3-(4,4-difluoroazepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5-methyl-azepan-4-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azepan-4-ol;

2-[6-amino-5-[8-[2-[3-(3-methylazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(4-fluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(3,4-dimethylazepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-4-ol;

2-[6-amino-5-[8-[2-[3-[4-(hydroxymethyl)-4-methyl-azepan-1-yl]prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5-methyl-azepan-4-one;

2-[6-amino-5-[8-[2-[3-(3,4,4-trifluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(4-methylazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(2-methylazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(1,2,4,5-tetrahydro-3-benzazepin-3-yl)prop-1-ynyl]-4-pyridyl]-3,8-diazabicyclo[3.2.1]octan-3-yl]pyridazin-3-yl]phenol;

2-[6-amino-5-[8-[2-[3-(5,6,8,9-tetrahydroimidazo[1,2-d][1,4]diazepin-7-yl)prop-1-ynyl]-4-pyridyl]-3,8-diazabicyclo[3.2.1]octan-3-yl]pyridazin-3-yl]phenol;

2-[6-amino-5-[8-[2-[3-[4-(4-pyridyl)-1,4-diazepan-1-yl]prop-1-ynyl]-4-pyridyl]-3,8-diazabicyclo[3.2.1]octan-3-yl]pyridazin-3-yl]phenol;

2-[6-amino-5-[8-[2-[3-(4,4-dimethylazepan-1-yl)prop-1-ynyl]-4-pyridyl]-3,8-diazabicyclo[3.2.1]octan-3-yl]pyridazin-3-yl]phenol;

2-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-difluoro-azepan-4-yl]acetonitrile;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4-(methoxymethyl)azepan-4-ol;

2-[6-amino-5-[8-[2-[3-(2,2-difluoro-7-azaspiro[2.6]nonan-7-yl)prop-1-ynyl]-4-pyridyl]-3,8-diazabicyclo[3.2.1]octan-3-yl]pyridazin-3-yl]phenol;

2-[6-amino-5-[8-[2-[3-[4-(trifluoromethyl)azepan-1-yl]prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepane-3,4-diol;

(1S,5R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[3.2.1]octane-6,7-diol;

2-[6-amino-5-[8-[2-[3-(5,5-difluoro-3-methyl-azepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepan-4-ol;

2-[6-amino-5-[8-[2-[3-[3-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[4-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[2-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-6-azabicyclo[3.2.0]heptan-6-yl]prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[3.2.2]nonan-2-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6-methyl-azepan-4-ol;

2-[6-amino-5-[8-[2-[3-(3-azatricyclo[4.2.1.02,5]nonan-3-yl)prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[3.2.1]octan-2-yl)prop-1-ynyl]-4-pyridyl]-3,8-diazabicyclo[3.2.1]octan-3-yl]pyridazin-3-yl]phenol;

2-[6-amino-5-[8-[2-[4-(azepan-1-yl)but-1-ynyl]-4-pyridyl]-3,8-diazabicyclo[3.2.1]octan-3-yl]pyridazin-3-yl]phenol;

2-[6-amino-5-[8-[2-[3-(3,3-difluoroazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-ethoxyazetidin-1-yl)prop-1-ynyl]-4-pyridyl]-3,8-diazabicyclo[3.2.1]octan-3-yl]pyridazin-3-yl]phenol;

methyl 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-3-carboxylate;

2-[6-amino-5-[8-[2-[3-(3-phenoxyazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-methylsulfonylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoroazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-morpholinoazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(2-azaspiro[3.5]nonan-2-yl)prop-1-ynyl]-4-pyridyl]-3,8-diazabicyclo[3.2.1]octan-3-yl]pyridazin-3-yl]phenol;

2-[6-amino-5-[8-[2-[3-(3-pyrimidin-4-ylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-[3-(trifluoromethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(5-azaspiro[2.3]hexan-5-yl)prop-1-ynyl]-4-pyridyl]-3,8-diazabicyclo[3.2.1]octan-3-yl]pyridazin-3-yl]phenol;

2-[6-amino-5-[8-[2-[3-(3-phenylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(1-azaspiro[3.3]heptan-1-yl)prop-1-ynyl]-4-pyridyl]-3,8-diazabicyclo[3.2.1]octan-3-yl]pyridazin-3-yl]phenol;

2-[6-amino-5-[8-[2-[3-(7-methylsulfonyl-2,7-diazaspiro[3.4]octan-2-yl)prop-1-ynyl]-4-pyridyl]-3,8-diazabicyclo[3.2.1]octan-3-yl]pyridazin-3-yl]phenol;

4-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-yl]benzonitrile;

2-[6-amino-5-[8-[2-[3-(3-cyclopropyl-3-fluoro-azetidi; n-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4,5-dimethyl-azepan-4-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-3-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-(fluoromethyl)azepan-3-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azepan-3-ol;

2-[6-amino-5-[8-[2-[3-(3-fluoro-3-methyl-azepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4-methyl-azepan-4-ol;

2-[6-amino-5-[8-[2-[3-(azepan-1-yl)prop-1-ynyl]pyrimidin-4-yl]-3,8-diazabicyclo[3.2.1]octan-3-yl]pyridazin-3-yl]phenol;

2-[6-amino-5-[8-[6-[3-(azepan-1-yl)prop-1-ynyl]pyridazin-4-yl]-3,8-diazabicyclo[3.2.1]octan-3-yl]pyridazin-3-yl]phenol;

2-[6-amino-5-[8-[6-[3-(azepan-1-yl)prop-1-ynyl]pyrimidin-4-yl]-3,8-diazabicyclo[3.2.1]octan-3-yl]pyridazin-3-yl]phenol; and 2-[6-amino-5-[8-[2-[3-(azepan-1-yl)prop-1-enyl]-4-pyridyl]-3,8-diazabicyclo[3.2.1]octan-3-yl]pyridazin-3-yl]phenol. 2-[6-amino-5-[8-[2-[3-(7-oxa-1-azaspiro[3.4]octan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-ol;

2-[6-amino-5-[8-[2-[3-(3-methoxy-3-methyl-azetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-3-methyl-azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-[3-fluoro-3-(hydroxymethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(3-methylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoro-3-methyl-azetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-methoxyazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(6-oxa-2-azaspiro[3.5]nonan-2-yl)prop-1-ynyl]-4-pyridyl]-3,8-diazabicyclo[3.2.1]octan-3-yl]pyridazin-3-yl]phenol;

methyl 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-2-carboxylate 2-[6-amino-5-[8-[2-[3-[8-(fluoromethyl)-5,5-dioxo-5lambda6-thia-2-azaspiro[3.4]octan-2-yl]prop-1-ynyl]-4-pyridyl]-3,8-diazabicyclo[3.2.1]octan-3-yl]pyridazin-3-yl]phenol;

2-[6-amino-5-[8-[2-[3-(5-oxa-2-azaspiro[3.4]octan-2-yl)prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-3-phenyl-azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(2,3-dimethylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3,3-difluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[4-(1-piperidyl)but-1-ynyl]-4-pyridyl]-3,8-diazabicyclo[3.2.1]octan-3-yl]pyridazin-3-yl]phenol methyl 2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-dioxo-5lambda6-thia-2-azaspiro[3.4]octane-8-carboxylate 2-[6-amino-5-[8-[2-[3-(2-methylazetidin-1-yl)prop-1-ynyl]-4-pyridyl]-3,8-diazabicyclo[3.2.1]octan-3-yl]pyridazin-3-yl]phenol;

2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azaspiro[3.3]heptan-6-ol;

2-[6-amino-5-[8-[2-[3-[(2S)-2-(methoxymethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(2,2-dimethylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(8-methyl-5-oxa-2,8-diazaspiro[3.5]nonan-2-yl)prop-1-ynyl]-4-pyridyl]-3,8-diazabicyclo[3.2.1]octan-3-yl]pyridazin-3-yl]phenol;

2-[6-amino-5-[8-[2-[3-(4,4-difluoroazepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5-methyl-azepan-4-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azepan-4-ol;

2-[6-amino-5-[8-[2-[3-(3-methylazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(4-fluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(3,4-dimethylazepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-4-ol;

2-[6-amino-5-[8-[2-[3-[4-(hydroxymethyl)-4-methyl-azepan-1-yl]prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3, 8-diazabicyclo[3.2.1]octan-8-yl]-2-pyridyl]prop-2-ynyl]-5-methyl-azepan-4-one;

2-[6-amino-5-[8-[2-[3-(3,4,4-trifluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(4-methylazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(2-methylazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(1,2,4,5-tetrahydro-3-benzazepin-3-yl)prop-1-ynyl]-4-pyridyl]-3,8-diazabicyclo[3.2.1]octan-3-yl]pyridazin-3-yl]phenol;

2-[6-amino-5-[8-[2-[3-(5,6,8,9-tetrahydroimidazo[1,2-d][1,4]diazepin-7-yl)prop-1-ynyl]-4-pyridyl]-3,8-diazabicyclo[3.2.1]octan-3-yl]pyridazin-3-yl]phenol;

2-[6-amino-5-[8-[2-[3-[4-(4-pyridyl)-1,4-diazepan-1-yl]prop-1-ynyl]-4-pyridyl]-3,8-diazabicyclo[3.2.1]octan-3-yl]pyridazin-3-yl]phenol;

2-[6-amino-5-[8-[2-[3-(4,4-dimethylazepan-1-yl)prop-1-ynyl]-4-pyridyl]-3,8-diazabicyclo[3.2.1]octan-3-yl]pyridazin-3-yl]phenol;

2-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-difluoro-azepan-4-yl]acetonitrile;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4-(methoxymethyl)azepan-4-ol;

2-[6-amino-5-[8-[2-[3-(2,2-difluoro-7-azaspiro[2.6]nonan-7-yl)prop-1-ynyl]-4-pyridyl]-3,8-diazabicyclo[3.2.1]octan-3-yl]pyridazin-3-yl]phenol;

2-[6-amino-5-[8-[2-[3-[4-(trifluoromethyl)azepan-1-yl]prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepane-3,4-diol;

(1S,5R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[3.2.1]octane-6,7-diol;

2-[6-amino-5-[8-[2-[3-(5,5-difluoro-3-methyl-azepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepan-4-ol;

2-[6-amino-5-[8-[2-[3-[3-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[4-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[2-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-6-azabicyclo[3.2.0]heptan-6-yl]prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[3.2.2]nonan-2-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6-methyl-azepan-4-ol;

2-[6-amino-5-[8-[2-[3-(3-azatricyclo[4.2.1.02,5]nonan-3-yl)prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[3.2.1]octan-2-yl)prop-1-ynyl]-4-pyridyl]-3,8-diazabicyclo[3.2.1]octan-3-yl]pyridazin-3-yl]phenol;

2-[6-amino-5-[8-[2-[4-(azepan-1-yl)but-1-ynyl]-4-pyridyl]-3,8-diazabicyclo[3.2.1]octan-3-yl]pyridazin-3-yl]phenol;

2-[6-amino-5-[8-[2-[3-(3,3-difluoroazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-ethoxyazetidin-1-yl)prop-1-ynyl]-4-pyridyl]-3,8-diazabicyclo[3.2.1]octan-3-yl]pyridazin-3-yl]phenol;

methyl 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-3-carboxylate;

2-[6-amino-5-[8-[2-[3-(3-phenoxyazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-methylsulfonylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoroazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-morpholinoazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(2-azaspiro[3.5]nonan-2-yl)prop-1-ynyl]-4-pyridyl]-3,8-diazabicyclo[3.2.1]octan-3-yl]pyridazin-3-yl]phenol;

2-[6-amino-5-[8-[2-[3-(3-pyrimidin-4-ylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-[3-(trifluoromethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(5-azaspiro[2.3]hexan-5-yl)prop-1-ynyl]-4-pyridyl]-3,8-diazabicyclo[3.2.1]octan-3-yl]pyridazin-3-yl]phenol;

2-[6-amino-5-[8-[2-[3-(3-phenylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(1-azaspiro[3.3]heptan-1-yl)prop-1-ynyl]-4-pyridyl]-3,8-diazabicyclo[3.2.1]octan-3-yl]pyridazin-3-yl]phenol;

2-[6-amino-5-[8-[2-[3-(7-methylsulfonyl-2,7-diazaspiro[3.4]octan-2-yl)prop-1-ynyl]-4-pyridyl]-3,8-diazabicyclo[3.2.1]octan-3-yl]pyridazin-3-yl]phenol;

4-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-yl]benzonitrile 2-[6-amino-5-[8-[2-[3-(3-cyclopropyl-3-fluoro-azetidin-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4,5-dimethyl-azepan-4-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-3-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-(fluoromethyl)azepan-3-ol;

1-[3-[4-[3-[3-amino-6-(2-hydroxyphenyl)pyridazin-4-yl]-3,
8-diazabicyclo[3.2.1]octan-8-yl]-2-pyridyl]prop-2-ynyl]
azepan-3-ol;
2-[6-amino-5-[8-[2-[3-(3-fluoro-3-methyl-azepan-1-yl)
prop-1-ynyl]-4-pyridyl]-3,8-diazabicyclo[3.2.1]octan-3-
yl]pyridazin-3-yl]phenol; and
1-[3-[4-[3-[3-amino-6-(2-hydroxyphenyl)pyridazin-4-yl]-3,
8-diazabicyclo[3.2.1]octan-8-yl]-2-pyridyl]prop-2-ynyl]-
4-methyl-azepan-4-ol,
    or a stereoisomer or tautomer thereof, or a pharmaceutically acceptable salt of any of the foregoing.

In embodiments, the present disclosure is directed to a compound selected from the group consisting of:
2-[6-amino-5-[9-[2-[3-(azepan-1-yl)prop-1-ynyl]-4-
pyridyl]-3,9-diazaspiro[5.5]undecan-3-yl]pyridazin-3-yl]
phenol;
2-[6-amino-5-[2-[2-[3-(azepan-1-yl)prop-1-ynyl]-4-
pyridyl]-2,8-diazaspiro[4.5]decan-8-yl]pyridazin-3-yl]
phenol;
2-[6-amino-5-[6-[2-[3-(azepan-1-yl)prop-1-ynyl]-4-
pyridyl]-2,6-diazaspiro[3.3]heptan-2-yl]pyridazin-3-yl]
phenol;
2-[(10S)-12-[2-[3-(azepan-1-yl)prop-1-ynyl]-4-pyridyl]-1,
5,6,8,12-pentazatricyclo[8.4.0.02,7]tetradeca-2(7),3,5-
trien-4-yl]phenol; and
2-[(10R)-12-[2-[3-(azepan-1-yl)prop-1-ynyl]-4-pyridyl]-1,
5,6,8,12-pentazatricyclo[8.4.0.02,7]tetradeca-2(7),3,5-
trien-4-yl]phenol,
    or a stereoisomer or tautomer thereof, or a pharmaceutically acceptable salt of any of the foregoing.

In embodiments, the present disclosure is directed to a compound selected from the group consisting of:
2-(6-amino-5-(8-(2-(4-(piperazin-1-yl)but-1-yn-1-yl)pyridin-4-yl)-3,8-diazabicyclo[3.2.1]octan-3-yl)pyridazin-3-yl)phenol;
2-(6-amino-5-(8-(2-(3-(pyrrolidin-1-yl)prop-1-yn-1-yl)pyridin-4-yl)-3,8-diazabicyclo[3.2.1]octan-3-yl)pyridazin-3-yl)phenol;
2-(6-amino-5-(8-(2-(3-((2-hydroxyethyl)(methyl)amino)prop-1-yn-1-yl)pyridin-4-yl)-3,8-diazabicyclo[3.2.1]octan-3-yl)pyridazin-3-yl)phenol;
2-(6-amino-5-(8-(2-(3-(2-hydroxyethoxy)prop-1-yn-1-yl)pyridin-4-yl)-3,8-diazabicyclo[3.2.1]octan-3-yl)pyridazin-3-yl)phenol;
2-(6-amino-5-(8-(2-(3-(diethylamino)prop-1-yn-1-yl)pyridin-4-yl)-3,8-diazabicyclo[3.2.1]octan-3-yl)pyridazin-3-yl)phenol;
2-(6-amino-5-(8-(2-(azetidin-3-ylethynyl)pyridin-4-yl)-3,8-diazabicyclo[3.2.1]octan-3-yl)pyridazin-3-yl)phenol;
2-(6-amino-5-(8-(2-(morpholin-2-ylethynyl)pyridin-4-yl)-3,8-diazabicyclo[3.2.1]octan-3-yl)pyridazin-3-yl)phenol;
2-(6-amino-5-(8-(2-(piperidin-3-ylethynyl)pyridin-4-yl)-3,8-diazabicyclo[3.2.1]octan-3-yl)pyridazin-3-yl)phenol;
2-(6-amino-5-(8-(2-(3-morpholinoprop-1-yn-1-yl)pyridin-4-yl)-3,8-diazabicyclo[3.2.1]octan-3-yl)pyridazin-3-yl)phenol;
1-(3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)piperazin-2-one;
2-(6-amino-5-(8-(2-(8-aminooct-1-yn-1-yl)pyridin-4-yl)-3,8-diazabicyclo[3.2.1]octan-3-yl)pyridazin-3-yl)phenol;
2-(6-amino-5-(8-(2-(3-(piperidin-3-yloxy)prop-1-yn-1-yl)pyridin-4-yl)-3,8-diazabicyclo[3.2.1]octan-3-yl)pyridazin-3-yl)phenol;
2-(6-amino-5-(8-(2-(3-(piperidin-2-yl)prop-1-yn-1-yl)pyridin-4-yl)-3,8-diazabicyclo[3.2.1]octan-3-yl)pyridazin-3-yl)phenol;
2-(6-amino-5-(8-(2-(pyrrolidin-2-ylethynyl)pyridin-4-yl)-3,8-diazabicyclo[3.2.1]octan-3-yl)pyridazin-3-yl)phenol;
2-(6-amino-5-(8-(2-(3-(3-aminopyrrolidin-1-yl)prop-1-yn-1-yl)pyridin-4-yl)-3,8-diazabicyclo[3.2.1]octan-3-yl)pyridazin-3-yl)phenol;
2-(6-amino-5-(8-(2-(3-(pyrrolidin-2-yl)prop-1-yn-1-yl)pyridin-4-yl)-3,8-diazabicyclo[3.2.1]octan-3-yl)pyridazin-3-yl)phenol;
2-(6-amino-5-(8-(2-(azetidin-2-ylethynyl)pyridin-4-yl)-3,8-diazabicyclo[3.2.1]octan-3-yl)pyridazin-3-yl)phenol;
4-(3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)thiomorpholine 1,1-dioxide;
2-(6-amino-5-(8-(2-(piperidin-4-ylethynyl)pyridin-4-yl)-3,8-diazabicyclo[3.2.1]octan-3-yl)pyridazin-3-yl)phenol;
2-(6-amino-5-(8-(2-(6-aminohexyl)pyridin-4-yl)-3,8-diazabicyclo[3.2.1]octan-3-yl)pyridazin-3-yl)phenol;
2-(6-amino-5-(8-(2-((1-methyl-1H-pyrazol-4-yl)ethynyl)pyridin-4-yl)-3,8-diazabicyclo[3.2.1]octan-3-yl)pyridazin-3-yl)phenol;
2-(6-amino-5-(8-(2-((tetrahydro-2H-pyran-4-yl)ethynyl)pyridin-4-yl)-3,8-diazabicyclo[3.2.1]octan-3-yl)pyridazin-3-yl)phenol;
2-(6-amino-5-(8-(2-(3-aminobut-1-yn-1-yl)pyridin-4-yl)-3,8-diazabicyclo[3.2.1]octan-3-yl)pyridazin-3-yl)phenol;
2-(6-amino-5-(8-(2-(3-aminoprop-1-yn-1-yl)pyridin-4-yl)-3,8-diazabicyclo[3.2.1]octan-3-yl)pyridazin-3-yl)phenol;
2-(6-amino-5-(8-(2-(pyrrolidin-3-ylethynyl)pyridin-4-yl)-3,8-diazabicyclo[3.2.1]octan-3-yl)pyridazin-3-yl)phenol;
2-(6-amino-5-(8-(2-(4-hydroxybut-1-yn-1-yl)pyridin-4-yl)-3,8-diazabicyclo[3.2.1]octan-3-yl)pyridazin-3-yl)phenol;
2-(6-amino-5-(8-(2-(6-hydroxyhex-1-yn-1-yl)pyridin-4-yl)-3,8-diazabicyclo[3.2.1]octan-3-yl)pyridazin-3-yl)phenol;
2-(6-amino-5-(8-(2-(3-(piperazin-1-yl)prop-1-yn-1-yl)pyridin-4-yl)-3,8-diazabicyclo[3.2.1]octan-3-yl)pyridazin-3-yl)phenol;
2-(6-amino-5-(8-(2-((4-aminocyclohexyl)ethynyl)pyridin-4-yl)-3,8-diazabicyclo[3.2.1]octan-3-yl)pyridazin-3-yl)phenol;
2-(6-amino-5-(8-(2-(4-aminobut-1-yn-1-yl)pyridin-4-yl)-3,8-diazabicyclo[3.2.1]octan-3-yl)pyridazin-3-yl)phenol;
2-(6-amino-5-(8-(2-(3-(3-aminopiperidin-1-yl)prop-1-yn-1-yl)pyridin-4-yl)-3,8-diazabicyclo[3.2.1]octan-3-yl)pyridazin-3-yl)phenol;
2-amino-N-(3-(4-(3-(3-amino-6-(2-hydroxyphenyl)pyridazin-4-yl)-3,8-diazabicyclo[3.2.1]octan-8-yl)pyridin-2-yl)propyl)acetamide;
2-(6-amino-5-(8-(2-(3-aminopropyl)pyridin-4-yl)-3,8-diazabicyclo[3.2.1]octan-3-yl)pyridazin-3-yl)phenol; and
2-(6-amino-5-(8-(2-(3-(pyrrolidin-3-yl)prop-1-yn-1-yl)pyridin-4-yl)-3,8-diazabicyclo[3.2.1]octan-3-yl)pyridazin-3-yl)phenol,
    or a stereoisomer or tautomer thereof, or a pharmaceutically acceptable salt of any of the foregoing.

In embodiments, the present disclosure is directed to a compound selected from the group consisting of:
N-[3-[4-[3-[3-amino-6-(2-hydroxyphenyl)pyridazin-4-yl]-
3,8-diazabicyclo[3.2.1]octan-8-yl]-2-pyridyl]prop-2-
ynyl]piperidine-4-carboxamide;
2-[6-amino-5-[8-[2-(3-amino-3-methyl-but-1-ynyl)-4-
pyridyl]-3,8-diazabicyclo[3.2.1]octan-3-yl]pyridazin-3-
yl]phenol;
2-[6-amino-5-[8-[2-[3-(3-methoxy-1-piperidyl)prop-1-
ynyl]-4-pyridyl]-3,8-diazabicyclo[3.2.1]octan-3-yl]
pyridazin-3-yl]phenol;

2-[6-amino-5-[8-[2-[3-(4-cyclopropylpiperazin-1-yl)prop-1-ynyl]-4-pyridyl]-3,8-diazabicyclo[3.2.1]octan-3-yl]pyridazin-3-yl]phenol;

2-[5-[8-[2-[3-(1,3,3a,4,5,6,7,7a-octahydroisoindol-2-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-(3-methylpiperazin-1-yl)prop-1-ynyl]-4-pyridyl]-3,8-diazabicyclo[3.2.1]octan-3-yl]pyridazin-3-yl]phenol;

2-[6-amino-5-[8-[2-[3-[2-(methoxymethyl)-1-piperidyl]prop-1-ynyl]-4-pyridyl]-3,8-diazabicyclo[3.2.1]octan-3-yl]pyridazin-3-yl]phenol;

2-[6-amino-5-[8-[2-[3-(2-methyl-1,4-oxazepan-4-yl)prop-1-ynyl]-4-pyridyl]-3,8-diazabicyclo[3.2.1]octan-3-yl]pyridazin-3-yl]phenol;

2-[6-amino-5-[8-[2-[3-(3,3-difluoropyrrolidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(1-oxa-7-azaspiro[4.4]nonan-7-yl)prop-1-ynyl]-4-pyridyl]-3,8-diazabicyclo[3.2.1]octan-3-yl]pyridazin-3-yl]phenol;

2-[6-amino-5-[8-[2-[3-[4-(hydroxymethyl)-1-piperidyl]prop-1-ynyl]-4-pyridyl]-3,8-diazabicyclo[3.2.1]octan-3-yl]pyridazin-3-yl]phenol;

2-[6-amino-5-[8-[2-[3-[(2S)-2-(hydroxymethyl)pyrrolidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(4-methyl-1,4-diazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-[(3R)-3-ethylmorpholin-4-yl]prop-1-ynyl]-4-pyridyl]-3,8-diazabicyclo[3.2.1]octan-3-yl]pyridazin-3-yl]phenol;

2-[6-amino-5-[8-[2-[3-(7-oxa-2-azaspiro[3.5]nonan-2-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidin-3-ol;

2-[6-amino-5-[8-[2-[3-1[(1,1-dioxothiolan-3-yl)-methylamino]prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]pyrrolidin-3-ol;

2-[6-amino-5-[8-[2-[3-(6,8-dihydro-5H-imidazo[1,2-a]pyrazin-7-yl)prop-1-ynyl]-4-pyridyl]-3,8-diazabicyclo[3.2.1]octan-3-yl]pyridazin-3-yl]phenol;

2-[5-[8-[2-[3-(2,3,3a,4,6,6a-hexahydro-1H-pyrrolo[3,4-c]pyrrol-5-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-[2-(hydroxymethyl)-1-piperidyl]prop-1-ynyl]-4-pyridyl]-3,8-diazabicyclo[3.2.1]octan-3-yl]pyridazin-3-yl]phenol;

2-[6-amino-5-[8-[2-[3-(5,7-dihydropyrrolo[3,4-b]pyridin-6-yl)prop-1-ynyl]-4-pyridyl]-3,8-diazabicyclo[3.2.1]octan-3-yl]pyridazin-3-yl]phenol;

2-[6-amino-5-[8-[2-[3-(3-methylmorpholin-4-yl)prop-1-ynyl]-4-pyridyl]-3,8-diazabicyclo[3.2.1]octan-3-yl]pyridazin-3-yl]phenol;

2-[6-amino-5-[8-[2-[3-(azepan-1-yl)prop-1-ynyl]-4-pyridyl]-3,8-diazabicyclo[3.2.1]octan-3-yl]pyridazin-3-yl]phenol;

2-[6-amino-5-[8-[2-[3-[(2S,6R)-2,6-dimethylmorpholin-4-yl]prop-1-ynyl]-4-pyridyl]-3,8-diazabicyclo[3.2.1]octan-3-yl]pyridazin-3-yl]phenol;

2-[5-[8-[2-[3-[(3aS,7aR)-1,3,3a,4,5,6,7,7a-octahydroisoindol-2-yl]prop-1-ynyl]-4-pyridyl]-3,8-diazabicyclo[3.2.1]octan-3-yl]-6-amino-pyridazin-3-yl]phenol;

2-[6-amino-5-[8-[2-[3-(3-methyl-1-piperidyl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-pyrrolidin-3-ol;

2-[5-[8-[2-[3-(3,3a,4,5,6,6a-hexahydro-1H-cyclopenta[c]pyrrol-2-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-[(3S)-3-ethylmorpholin-4-yl]prop-1-ynyl]-4-pyridyl]-3,8-diazabicyclo[3.2.1]octan-3-yl]pyridazin-3-yl]phenol;

2-[6-amino-5-[8-[2-[3-[(2R)-2-(hydroxymethyl)pyrrolidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(5-oxa-2-azaspiro[3.5]nonan-2-yl)prop-1-ynyl]-4-pyridyl]-3,8-diazabicyclo[3.2.1]octan-3-yl]pyridazin-3-yl]phenol;

2-[5-[8-[2-[3-(3,4,6,7,8,8a-hexahydro-1H-pyrrolo[1,2-a]pyrazin-2-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-(3-azabicyclo[3.1.0]hexan-3-yl)prop-1-ynyl]-4-pyridyl]-3,8-diazabicyclo[3.2.1]octan-3-yl]pyridazin-3-yl]phenol;

2-[6-amino-5-[8-[2-[3-(7-oxa-1-azaspiro[3.4]octan-1-yl)prop-1-ynyl]-4-pyridyl]-3,8-diazabicyclo[3.2.1]octan-3-yl]pyridazin-3-yl]phenol;

2-[6-amino-5-[8-[2-[3-(1,4-oxazepan-4-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidin-4-ol;

2-[6-amino-5-[8-[2-[3-(6,8-dihydro-5H-imidazo[1,5-a]pyrazin-7-yl)prop-1-ynyl]-4-pyridyl]-3,8-diazabicyclo[3.2.1]octan-3-yl]pyridazin-3-yl]phenol;

2-[6-amino-5-[8-[2-[3-(7-oxa-4-azaspiro[2.5]octan-4-yl)prop-1-ynyl]-4-pyridyl]-3,8-diazabicyclo[3.2.1]octan-3-yl]pyridazin-3-yl]phenol;

2-[6-amino-5-[8-[2-[3-(2-oxa-5-azabicyclo[4.1.0]heptan-5-yl)prop-1-ynyl]-4-pyridyl]-3,8-diazabicyclo[3.2.1]octan-3-yl]pyridazin-3-yl]phenol;

2-[6-amino-5-[8-[2-[3-[(3S)-3-methylpyrrolidin-1-yl]prop-1-ynyl]-4-pyridyl]-3,8-diazabicyclo[3.2.1]octan-3-yl]pyridazin-3-yl]phenol;

2-[5-[8-[2-[3-(1,3,3a,4,6,6a-hexahydrofuro[3,4-c]pyrrol-5-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-(5-oxa-8-azaspiro[3.5]nonan-8-yl)prop-1-ynyl]-4-pyridyl]-3,8-diazabicyclo[3.2.1]octan-3-yl]pyridazin-3-yl]phenol;

(6R)-1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3,3a,4,5,6,6a-hexahydro-2H-cyclopenta[b]pyrrol-6-ol;

2-[6-amino-5-[8-[2-[3-(2,6-dimethylmorpholin-4-yl)prop-1-ynyl]-4-pyridyl]-3,8-diazabicyclo[3.2.1]octan-3-yl]pyridazin-3-yl]phenol;

2-[6-amino-5-[8-[2-[3-(3-morpholinopyrrolidin-1-yl)prop-1-ynyl]-4-pyridyl]-3,8-diazabicyclo[3.2.1]octan-3-yl]pyridazin-3-yl]phenol;

2-[5-[8-[2-[3-(2,3,3a,4,6,6a-hexahydrofuro[2,3-c]pyrrol-5-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-(7-methoxy-2-azabicyclo[2.2.1]heptan-2-yl)prop-1-ynyl]-4-pyridyl]-3,8-diazabicyclo[3.2.1]octan-3-yl]pyridazin-3-yl]phenol;

7-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-oxa-7-azabicyclo[3.3.1]nonan-9-ol;

2-[6-amino-5-[8-[2-[3-(2,2-difluoro-5-azaspiro[2.4]heptan-5-yl)prop-1-ynyl]-4-pyridyl]-3,8-diazabicyclo[3.2.1]octan-3-yl]pyridazin-3-yl]phenol;

2-[3-[4-[3-[3-amino-6-(2-hydroxyphenyl)pyridazin-4-yl]-3,8-diazabicyclo[3.2.1]octan-8-yl]-2-pyridyl]prop-2-ynyl-methyl-amino]-1-morpholino-ethanone;

2-[6-amino-5-[8-[2-[3-(2-azabicyclo[2.1.1]hexan-2-yl)prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[3.1.0]hexan-2-yl)prop-1-ynyl]-4-pyridyl]-3,8-diazabicyclo[3.2.1]octan-3-yl]pyridazin-3-yl]phenol;

2-[5-[8-[2-[3-(3,3a,4,6,7,7a-hexahydro-1H-furo[3,4-c]pyridin-5-yl)prop-1-ynyl]-4-pyridyl]-3,8-diazabicyclo[3.2.1]octan-3-yl]-6-amino-pyridazin-3-yl]phenol;

4-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-morpholine-3-carboxamide;

2-[5-[8-[2-[3-[(3aS,7aS)-3,3a,5,6,7,7a-hexahydro-2H-furo[3,2-b]pyridin-4-yl]prop-1-ynyl]-4-pyridyl]-3,8-diazabicyclo[3.2.1]octan-3-yl]-6-amino-pyridazin-3-yl]phenol;

2-[6-amino-5-[8-[2-[3-(3-azabicyclo[3.2.0]heptan-3-yl)prop-1-ynyl]-4-pyridyl]-3,8-diazabicyclo[3.2.1]octan-3-yl]pyridazin-3-yl]phenol;

2-[5-[8-[2-[3-(3,3a,4,6,7,7a-hexahydro-1H-pyrano[3,4-c]pyrrol-2-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-(3-azabicyclo[3.2.1]octan-3-yl)prop-1-ynyl]-4-pyridyl]-3,8-diazabicyclo[3.2.1]octan-3-yl]pyridazin-3-yl]phenol;

2-[5-[8-[2-[3-(3,3a,4,5,6,6a-hexahydro-2H-cyclopenta[b]pyrrol-1-yl)prop-1-ynyl]-4-pyridyl]-3,8-diazabicyclo[3.2.1]octan-3-yl]-6-amino-pyridazin-3-yl]phenol;

2-[6-amino-5-[8-[2-[3-[3-(difluoromethyl)azetidin-1-yl]prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-piperidine-2-carboxamide;

2-[6-amino-5-[8-[2-[3-(6-fluoro-2-azaspiro[3.3]heptan-2-yl)prop-1-ynyl]-4-pyridyl]-3,8-diazabicyclo[3.2.1]octan-3-yl]pyridazin-3-yl]phenol;

2-[6-amino-5-[8-[2-[3-(6-oxa-3-azabicyclo[3.2.1]octan-3-yl)prop-1-ynyl]-4-pyridyl]-3,8-diazabicyclo[3.2.1]octan-3-yl]pyridazin-3-yl]phenol;

2-[6-amino-5-[8-[2-[3-(5-azaspiro[2.5]octan-5-yl)prop-1-ynyl]-4-pyridyl]-3,8-diazabicyclo[3.2.1]octan-3-yl]pyridazin-3-yl]phenol;

2-[6-amino-5-[8-[2-[3-(8-oxa-1-azaspiro[3.5]nonan-1-yl)prop-1-ynyl]-4-pyridyl]-3,8-diazabicyclo[3.2.1]octan-3-yl]pyridazin-3-yl]phenol;

2-[6-amino-5-[8-[2-[3-(9-oxa-3-azabicyclo[3.3.1]nonan-3-yl)prop-1-ynyl]-4-pyridyl]-3,8-diazabicyclo[3.2.1]octan-3-yl]pyridazin-3-yl]phenol;

2-[6-amino-5-[8-[2-[3-[(1S,6R)-2-azabicyclo[4.2.0]octan-2-yl]prop-1-ynyl]-4-pyridyl]-3,8-diazabicyclo[3.2.1]octan-3-yl]pyridazin-3-yl]phenol;

2-[6-amino-5-[8-[2-[3-(hydroxymethyl)-2-azabicyclo[2.2.1]heptan-2-yl]prop-1-ynyl]-4-pyridyl]-3,8-diazabicyclo[3.2.1]octan-3-yl]pyridazin-3-yl]phenol;

2-[6-amino-5-[8-[2-[3-(6-oxa-2-azabicyclo[3.2.1]octan-2-yl)prop-1-ynyl]-4-pyridyl]-3,8-diazabicyclo[3.2.1]octan-3-yl]pyridazin-3-yl]phenol;

3-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-azabicyclo[3.1.0]hexan-1-ol;

2-[6-amino-5-[8-[2-[3-(5-azaspiro[3.4]octan-5-yl)prop-1-ynyl]-4-pyridyl]-3,8-diazabicyclo[3.2.1]octan-3-yl]pyridazin-3-yl]phenol;

2-[6-amino-5-[8-[2-[3-(3,4-dihydro-1H-pyrrolo[1,2-a]pyrazin-2-yl)prop-1-ynyl]-4-pyridyl]-3,8-diazabicyclo[3.2.1]octan-3-yl]pyridazin-3-yl]phenol;

2-[5-[8-[2-[3-[(3aS,6aR)-2-methyl-1,3,3a,4,6,6a-hexahydropyrrolo[3,4-c]pyrrol-5-yl]prop-1-ynyl]-4-pyridyl]-3,8-diazabicyclo[3.2.1]octan-3-yl]-6-amino-pyridazin-3-yl]phenol;

(1R,4S,6R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[2.2.1]heptan-6-ol;

2-[6-amino-5-[8-[2-[3-(8-oxa-4-azaspiro[2.6]nonan-4-yl)prop-1-ynyl]-4-pyridyl]-3,8-diazabicyclo[3.2.1]octan-3-yl]pyridazin-3-yl]phenol;

2-[6-amino-5-[8-[2-[3-(3-oxa-9-azabicyclo[3.3.1]nonan-9-yl)prop-1-ynyl]-4-pyridyl]-3,8-diazabicyclo[3.2.1]octan-3-yl]pyridazin-3-yl]phenol;

2-[6-amino-5-[8-[2-[3-(2,2-difluoromorpholin-4-yl)prop-1-ynyl]-4-pyridyl]-3,8-diazabicyclo[3.2.1]octan-3-yl]pyridazin-3-yl]phenol;

2-[5-[8-[2-[3-[(3aR,6aR)-2,3,3a,4,6,6a-hexahydrofuro[2,3-c]pyrrol-5-yl]prop-1-ynyl]-4-pyridyl]-3,8-diazabicyclo[3.2.1]octan-3-yl]-6-amino-pyridazin-3-yl]phenol;

2-[6-amino-5-[8-[2-[3-[2-(fluoromethyl)morpholin-4-yl]prop-1-ynyl]-4-pyridyl]-3,8-diazabicyclo[3.2.1]octan-3-yl]pyridazin-3-yl]phenol;

2-[6-amino-5-[8-[2-[3-[(1R,4S)-2-azabicyclo[2.2.1]heptan-2-yl]prop-1-ynyl]-4-pyridyl]-3,8-diazabicyclo[3.2.1]octan-3-yl]pyridazin-3-yl]phenol;

2-[6-amino-5-[8-[2-[3-[1-(hydroxymethyl)-2-azabicyclo[2.1.1]hexan-2-yl]prop-1-ynyl]-4-pyridyl]-3,8-diazabicyclo[3.2.1]octan-3-yl]pyridazin-3-yl]phenol;

(1S,6S)-3-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-azabicyclo[4.1.0]heptan-6-ol;

2-[6-amino-5-[8-[2-[3-[(1S,5R)-6-(hydroxymethyl)-3-azabicyclo[3.1.0]hexan-3-yl]prop-1-ynyl]-4-pyridyl]-3,8-diazabicyclo[3.2.1]octan-3-yl]pyridazin-3-yl]phenol;

2-[6-amino-5-[8-[2-[3-(2,2-dimethylmorpholin-4-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidine-3-carbonitrile;

2-[6-amino-5-[8-[2-[3-[1-(hydroxymethyl)-7-azabicyclo[2.2.1]heptan-7-yl]prop-1-ynyl]-4-pyridyl]-3,8-diazabicyclo[3.2.1]octan-3-yl]pyridazin-3-yl]phenol;

(3S)-1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-N-methyl-pyrrolidine-3-carboxamide;

2-[6-amino-5-[8-[2-[3-[(1R,2S,4S,5S)-6-azatricyclo[3.2.1.0²,⁴]octan-6-yl]prop-1-ynyl]-4-pyridyl]-3,8-diazabicyclo[3.2.1]octan-3-yl]pyridazin-3-yl]phenol;

2-[6-amino-5-[8-[2-[3-(4-oxa-7-azaspiro[2.5]octan-7-yl)prop-1-ynyl]-4-pyridyl]-3,8-diazabicyclo[3.2.1]octan-3-yl]pyridazin-3-yl]phenol;

2-[6-amino-5-[8-[2-[3-(6-azabicyclo[3.2.1]octan-6-yl)prop-1-ynyl]-4-pyridyl]-3,8-diazabicyclo[3.2.1]octan-3-yl]pyridazin-3-yl]phenol;

3-[3-[4-[3-[3-amino-6-(2-hydroxyphenyl)pyridazin-4-yl]-3,
8-diazabicyclo[3.2.1]octan-8-yl]-2-pyridyl]prop-2-ynyl]-
3-azabicyclo[3.1.1]heptan-6-ol;

2-[6-amino-5-[8-[2-[3-(2-azaspiro[4.4]nonan-2-yl)prop-1-
ynyl]-4-pyridyl]-3,8-diazabicyclo[3.2.1]octan-3-yl]
pyridazin-3-yl]phenol;

2-[6-amino-5-[8-[2-[3-[(3S)-3-methoxypyrrolidin-1-yl]
prop-1-ynyl]-4-pyridyl]-3,8-diazabicyclo[3.2.1]octan-3-
yl]pyridazin-3-yl]phenol;

2-[6-amino-5-[8-[2-[3-(6-azaspiro[3.4]octan-6-yl)prop-1-
ynyl]-4-pyridyl]-3,8-diazabicyclo[3.2.1]octan-3-yl]
pyridazin-3-yl]phenol;

(1S,4S,5R)-2-[3-[4-[3-[3-amino-6-(2-hydroxyphenyl)
pyridazin-4-yl]-3,8-diazabicyclo[3.2.1]octan-8-yl]-2-
pyridyl]prop-2-ynyl]-2-azabicyclo[2.2.1]heptan-5-ol;

2-[6-amino-5-[8-[2-[3-(4-fluoro-1-piperidyl)prop-1-ynyl]-
4-pyridyl]-3,8-diazabicyclo[3.2.1]octan-3-yl]pyridazin-
3-yl]phenol;

2-[6-amino-5-[8-[2-[3-(2-oxa-5-azabicyclo[2.2.1]heptan-5-
yl)prop-1-ynyl]-4-pyridyl]-3,8-diazabicyclo[3.2.1]octan-
3-yl]pyridazin-3-yl]phenol;

2-[6-amino-5-[8-[2-[3-(3-fluoropyrrolidin-1-yl)prop-1-
ynyl]-4-pyridyl]-3,8-diazabicyclo[3.2.1]octan-3-yl]
pyridazin-3-yl]phenol;

2-[6-amino-5-[8-[2-[3-[3-(hydroxymethyl)-1-piperidyl]
prop-1-ynyl]-4-pyridyl]-3,8-diazabicyclo[3.2.1]octan-3-
yl]pyridazin-3-yl]phenol;

2-[6-amino-5-[8-[2-[3-(3,3-dimethylazetidin-1-yl)prop-1-
ynyl]-4-pyridyl]-3,8-diazabicyclo[3.2.1]octan-3-yl]
pyridazin-3-yl]phenol;

2-[6-amino-5-[8-[2-[3-(6-azaspiro[2.5]octan-6-yl)prop-1-
ynyl]-4-pyridyl]-3,8-diazabicyclo[3.2.1]octan-3-yl]
pyridazin-3-yl]phenol;

2-[6-amino-5-[8-[2-[3-[1-(hydroxymethyl)-3-azabicyclo
[3.1.0]hexan-3-yl]prop-1-ynyl]-4-pyridyl]-3,8-diazabicy-
clo[3.2.1]octan-3-yl]pyridazin-3-yl]phenol;

2-[6-amino-5-[8-[2-[3-(4-methyl-1-piperidyl)prop-1-ynyl]-
4-pyridyl]-3,8-diazabicyclo[3.2.1]octan-3-yl]pyridazin-
3-yl]phenol;

1-[3-[4-[3-[3-amino-6-(2-hydroxyphenyl)pyridazin-4-yl]-3,
8-diazabicyclo[3.2.1]octan-8-yl]-2-pyridyl]prop-2-ynyl]
piperidine-4-carbonitrile;

2-[6-amino-5-[8-[2-[3-(2-oxa-7-azaspiro[4.4]nonan-7-yl)
prop-1-ynyl]-4-pyridyl]-3,8-diazabicyclo[3.2.1]octan-3-
yl]pyridazin-3-yl]phenol;

2-[6-amino-5-[8-[2-[3-(2-azabicyclo[2.2.1]heptan-2-yl)
prop-1-ynyl]-4-pyridyl]-3,8-diazabicyclo[3.2.1]octan-3-
yl]pyridazin-3-yl]phenol;

1-[3-[4-[3-[3-amino-6-(2-hydroxyphenyl)pyridazin-4-yl]-3,
8-diazabicyclo[3.2.1]octan-8-yl]-2-pyridyl]prop-2-ynyl]
azetidin-3-ol;

2-[6-amino-5-[8-[2-[3-(5,5-difluoro-2-azabicyclo[2.2.1]
heptan-2-yl)prop-1-ynyl]-4-pyridyl]-3,8-diazabicyclo
[3.2.1]octan-3-yl]pyridazin-3-yl]phenol;

2-[6-amino-5-[8-[2-[3-(7-fluoro-3-oxa-9-azabicyclo[3.3.1]
nonan-9-yl)prop-1-ynyl]-4-pyridyl]-3,8-diazabicyclo
[3.2.1]octan-3-yl]pyridazin-3-yl]phenol;

2-[5-[8-[2-[3-(3,3a,4,6,7,7a-hexahydro-2H-furo[3,2-c]pyri-
din-5-yl)prop-1-ynyl]-4-pyridyl]-3,8-diazabicyclo[3.2.1]
octan-3-yl]-6-amino-pyridazin-3-yl]phenol;

2-[5-[8-[2-[3-(3,3a,4,5,6,6a-hexahydro-2H-pyrrolo[3,4-b]
pyrrol-1-yl)prop-1-ynyl]-4-pyridyl]-3,8-diazabicyclo
[3.2.1]octan-3-yl]-6-amino-pyridazin-3-yl]phenol;

2-[5-[8-[2-[3-(2,3,4a,5,6,7,8,8a-octahydropyrido[4,3-b][1,
4]oxazin-4-yl)prop-1-ynyl]-4-pyridyl]-3,8-diazabicyclo
[3.2.1]octan-3-yl]-6-amino-pyridazin-3-yl]phenol;

2-[3-[4-[3-[3-amino-6-(2-hydroxyphenyl)pyridazin-4-yl]-3,
8-diazabicyclo[3.2.1]octan-8-yl]-2-pyridyl]prop-2-ynyl]-
N-methyl-2-azabicyclo[2.1.1]hexane-1-carboxamide;

2-[6-amino-5-[8-[2-[3-(4,6-dihydro-1H-pyrrolo[3,4-c]pyra-
zol-5-yl)prop-1-ynyl]-4-pyridyl]-3,8-diazabicyclo[3.2.1]
octan-3-yl]pyridazin-3-yl]phenol;

2-[6-amino-5-[8-[2-[3-(3-cyclopropylazetidin-1-yl)prop-1-
ynyl]-4-pyridyl]-3,8-diazabicyclo[3.2.1]octan-3-yl]
pyridazin-3-yl]phenol;

2-[6-amino-5-[8-[2-[3-(2,2-difluoro-5-azaspiro[2.3]hexan-
5-yl)prop-1-ynyl]-4-pyridyl]-3,8-diazabicyclo[3.2.1]oc-
tan-3-yl]pyridazin-3-yl]phenol;

2-[1-[3-[4-[3-[3-amino-6-(2-hydroxyphenyl)pyridazin-4-
yl]-3,8-diazabicyclo[3.2.1]octan-8-yl]-2-pyridyl]prop-2-
ynyl]azetidin-3-yl]acetonitrile;

2-[6-amino-5-[8-[2-[3-(4-azaspiro[2.5]octan-4-yl)prop-1-
ynyl]-4-pyridyl]-3,8-diazabicyclo[3.2.1]octan-3-yl]
pyridazin-3-yl]phenol;

1-[3-[4-[3-[3-amino-6-(2-hydroxyphenyl)pyridazin-4-yl]-3,
8-diazabicyclo[3.2.1]octan-8-yl]-2-pyridyl]prop-2-ynyl]-
3-cyclopropyl-azetidin-3-ol;

2-[6-amino-5-[8-[2-[3-(2-azaspiro[3.4]octan-2-yl)prop-1-
ynyl]-4-pyridyl]-3,8-diazabicyclo[3.2.1]octan-3-yl]
pyridazin-3-yl]phenol;

2-[6-amino-5-[8-[2-[3-(2-methyl-2,6-diazaspiro[3.4]octan-
6-yl)prop-1-ynyl]-4-pyridyl]-3,8-diazabicyclo[3.2.1]oc-
tan-3-yl]pyridazin-3-yl]phenol;

2-[6-amino-5-[8-[2-[3-(3-tetrahydrofuran-3-ylazetidin-1-yl)
prop-1-ynyl]-4-pyridyl]-3,8-diazabicyclo[3.2.1]octan-3-
yl]pyridazin-3-yl]phenol;

2-[6-amino-5-[8-[2-[3-[3-(2,2-difluoroethyl)azetidin-1-yl]
prop-1-ynyl]-4-pyridyl]-3,8-diazabicyclo[3.2.1]octan-3-
yl]pyridazin-3-yl]phenol;

2-[6-amino-5-[8-[2-[3-(7-oxa-1-azaspiro[3.5]nonan-1-yl)
prop-1-ynyl]-4-pyridyl]-3,8-diazabicyclo[3.2.1]octan-3-
yl]pyridazin-3-yl]phenol;

2-[6-amino-5-[8-[2-[3-(5,8-dioxa-2-azaspiro[3.5]nonan-2-
yl)prop-1-ynyl]-4-pyridyl]-3,8-diazabicyclo[3.2.1]octan-
3-yl]pyridazin-3-yl]phenol;

2-[6-amino-5-[8-[2-[3-[(1R,5R)-2-oxa-6-azabicyclo[3.2.0]
heptan-6-yl]prop-1-ynyl]-4-pyridyl]-3,8-diazabicyclo
[3.2.1]octan-3-yl]pyridazin-3-yl]phenol;

2-[6-amino-5-[8-[2-[3-(6-azabicyclo[3.2.0]heptan-6-yl)
prop-1-ynyl]-4-pyridyl]-3,8-diazabicyclo[3.2.1]octan-3-
yl]pyridazin-3-yl]phenol;

(2S)-1-[3-[4-[3-[3-amino-6-(2-hydroxyphenyl)pyridazin-4-
yl]-3,8-diazabicyclo[3.2.1]octan-8-yl]-2-pyridyl]prop-2-
ynyl]-N-methyl-pyrrolidine-2-carboxamide;

2-[6-amino-5-[8-[2-[3-1[(1S,4S)-5-methyl-2,5-diazabicyclo
[2.2.1]heptan-2-yl]prop-1-ynyl]-4-pyridyl]-3,8-diazabi-
cyclo[3.2.1]octan-3-yl]pyridazin-3-yl]phenol;

2-[6-amino-5-[8-[2-[3-[(5R)-1,7-diazaspiro[4.4]nonan-1-yl]
prop-1-ynyl]-4-pyridyl]-3,8-diazabicyclo[3.2.1]octan-3-
yl]pyridazin-3-yl]phenol;

2-[6-amino-5-[8-[2-[3-(1-piperidyl)prop-1-ynyl]-4-
pyridyl]-3,8-diazabicyclo[3.2.1]octan-3-yl]pyridazin-3-
yl]phenol;

2-[6-amino-5-[8-[2-[3-(7-oxa-1-azaspiro[3.4]octan-1-yl)
prop-1-ynyl]-4-pyridyl]-3,8-diazabicyclo[3.2.1]octan-3-
yl]pyridazin-3-yl]phenol;

1-[3-[4-[3-[3-amino-6-(2-hydroxyphenyl)pyridazin-4-yl]-3,
8-diazabicyclo[3.2.1]octan-8-yl]-2-pyridyl]prop-2-ynyl]
azetidin-3-ol;

2-[6-amino-5-[8-[2-[3-(3-methoxy-3-methyl-azetidin-1-yl)
prop-1-ynyl]-4-pyridyl]-3,8-diazabicyclo[3.2.1]octan-3-
yl]pyridazin-3-yl]phenol;

2-[6-amino-5-[8-[2-[3-[3-(hydroxymethyl)-3-methyl-azetidin-1-yl]prop-1-ynyl]-4-pyridyl]-3,8-diazabicyclo[3.2.1]octan-3-yl]pyridazin-3-yl]phenol;
2-[6-amino-5-[8-[2-[3-[3-fluoro-3-(hydroxymethyl)azetidin-1-yl]prop-1-ynyl]-4-pyridyl]-3,8-diazabicyclo[3.2.1]octan-3-yl]pyridazin-3-yl]phenol;
2-[6-amino-5-[8-[2-[3-(3-methylazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(3-fluoro-3-methyl-azetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(3-methoxyazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(6-oxa-2-azaspiro[3.5]nonan-2-yl)prop-1-ynyl]-4-pyridyl]-3,8-diazabicyclo[3.2.1]octan-3-yl]pyridazin-3-yl]phenol;
methyl 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-2-carboxylate;
2-[6-amino-5-[8-[2-[3-[8-(fluoromethyl)-5,5-dioxo-5lambda6-thia-2-azaspiro[3.4]octan-2-yl]prop-1-ynyl]-4-pyridyl]-3,8-diazabicyclo[3.2.1]octan-3-yl]pyridazin-3-yl]phenol;
2-[6-amino-5-[8-[2-[3-(5-oxa-2-azaspiro[3.4]octan-2-yl)prop-1-ynyl]-4-pyridyl]-3,8-diazabicyclo[3.2.1]octan-3-yl]pyridazin-3-yl]phenol;
2-[6-amino-5-[8-[2-[3-[3-(hydroxymethyl)-3-phenyl-azetidin-1-yl]prop-1-ynyl]-4-pyridyl]-3,8-diazabicyclo[3.2.1]octan-3-yl]pyridazin-3-yl]phenol;
2-[6-amino-5-[8-[2-[3-(2,3-dimethylazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(3,3-difluoroazepan-1-yl)prop-1-ynyl]-4-pyridyl]-3,8-diazabicyclo[3.2.1]octan-3-yl]pyridazin-3-yl]phenol;
2-[6-amino-5-[8-[2-[4-(1-piperidyl)but-1-ynyl]-4-pyridyl]-3,8-diazabicyclo[3.2.1]octan-3-yl]pyridazin-3-yl]phenol;
methyl 2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-dioxo-5lambda6-thia-2-azaspiro[3.4]octane-8-carboxylate;
2-[6-amino-5-[8-[2-[3-(2-methylazetidin-1-yl)prop-1-ynyl]-4-pyridyl]-3,8-diazabicyclo[3.2.1]octan-3-yl]pyridazin-3-yl]phenol;
2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azaspiro[3.3]heptan-6-ol;
2-[6-amino-5-[8-[2-[3-[(2S)-2-(methoxymethyl)azetidin-1-yl]prop-1-ynyl]-4-pyridyl]-3,8-diazabicyclo[3.2.1]octan-3-yl]pyridazin-3-yl]phenol;
2-[6-amino-5-[8-[2-[3-(2,2-dimethylazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(8-methyl-5-oxa-2,8-diazaspiro[3.5]nonan-2-yl)prop-1-ynyl]-4-pyridyl]-3,8-diazabicyclo[3.2.1]octa189n-3-yl]pyridazin-3-yl]phenol;
2-[6-amino-5-[8-[2-[3-(4,4-difluoroazepan-1-yl)prop-1-ynyl]-4-pyridyl]-3,8-diazabicyclo[3.2.1]octan-3-yl]pyridazin-3-yl]phenol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5-methyl-azepan-4-ol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azepan-4-ol;
2-[6-amino-5-[8-[2-[3-(3-methylazepan-1-yl)prop-1-ynyl]-4-pyridyl]-3,8-diazabicyclo[3.2.1]octan-3-yl]pyridazin-3-yl]phenol;
2-[6-amino-5-[8-[2-[3-(4-fluoroazepan-1-yl)prop-1-ynyl]-4-pyridyl]-3,8-diazabicyclo[3.2.1]octan-3-yl]pyridazin-3-yl]phenol;
2-[6-amino-5-[8-[2-[3-(3-fluoroazepan-1-yl)prop-1-ynyl]-4-pyridyl]-3,8-diazabicyclo[3.2.1]octan-3-yl]pyridazin-3-yl]phenol;
2-[6-amino-5-[8-[2-[3-(3,4-dimethylazepan-1-yl)prop-1-ynyl]-4-pyridyl]-3,8-diazabicyclo[3.2.1]octan-3-yl]pyridazin-3-yl]phenol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-4-ol;
2-[6-amino-5-[8-[2-[3-[4-(hydroxymethyl)-4-methyl-azepan-1-yl]prop-1-ynyl]-4-pyridyl]-3,8-diazabicyclo[3.2.1]octan-3-yl]pyridazin-3-yl]phenol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5-methyl-azepan-4-one;
2-[6-amino-5-[8-[2-[3-(3,4,4-trifluoroazepan-1-yl)prop-1-ynyl]-4-pyridyl]-3,8-diazabicyclo[3.2.1]octan-3-yl]pyridazin-3-yl]phenol;
2-[6-amino-5-[8-[2-[3-(4-methylazepan-1-yl)prop-1-ynyl]-4-pyridyl]-3,8-diazabicyclo[3.2.1]octan-3-yl]pyridazin-3-yl]phenol;
2-[6-amino-5-[8-[2-[3-(2-methylazepan-1-yl)prop-1-ynyl]-4-pyridyl]-3,8-diazabicyclo[3.2.1]octan-3-yl]pyridazin-3-yl]phenol;
2-[6-amino-5-[8-[2-[3-(1,2,4,5-tetrahydro-3-benzazepin-3-yl)prop-1-ynyl]-4-pyridyl]-3,8-diazabicyclo[3.2.1]octan-3-yl]pyridazin-3-yl]phenol;
2-[6-amino-5-[8-[2-[3-(5,6,8,9-tetrahydroimidazo[1,2-d][1,4]diazepin-7-yl)prop-1-ynyl]-4-pyridyl]-3,8-diazabicyclo[3.2.1]octan-3-yl]pyridazin-3-yl]phenol;
2-[6-amino-5-[8-[2-[3-[4-(4-pyridyl)-1,4-diazepan-1-yl]prop-1-ynyl]-4-pyridyl]-3,8-diazabicyclo[3.2.1]octan-3-yl]pyridazin-3-yl]phenol;
2-[6-amino-5-[8-[2-[3-(4,4-dimethylazepan-1-yl)prop-1-ynyl]-4-pyridyl]-3,8-diazabicyclo[3.2.1]octan-3-yl]pyridazin-3-yl]phenol;
2-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-difluoro-azepan-4-yl]acetonitrile;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4-(methoxymethyl)azepan-4-ol;
2-[6-amino-5-[8-[2-[3-(2,2-difluoro-7-azaspiro[2.6]nonan-7-yl)prop-1-ynyl]-4-pyridyl]-3,8-diazabicyclo[3.2.1]octan-3-yl]pyridazin-3-yl]phenol;
2-[6-amino-5-[8-[2-[3-[4-(trifluoromethyl)azepan-1-yl]prop-1-ynyl]-4-pyridyl]-3,8-diazabicyclo[3.2.1]octan-3-yl]pyridazin-3-yl]phenol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepane-3,4-diol;
(1S,5R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[3.2.1]octane-6,7-diol;
2-[6-amino-5-[8-[2-[3-(5,5-difluoro-3-methyl-azepan-1-yl)prop-1-ynyl]-4-pyridyl]-3,8-diazabicyclo[3.2.1]octan-3-yl]pyridazin-3-yl]phenol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepan-4-ol;

2-[6-amino-5-[8-[2-[3-[3-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[4-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[2-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-6-azabicyclo[3.2.0]heptan-6-yl]prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[3.2.2]nonan-2-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6-methyl-azepan-4-ol;

2-[6-amino-5-[8-[2-[3-(3-azatricyclo[4.2.1.02,5]nonan-3-yl)prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[3.2.1]octan-2-yl)prop-1-ynyl]-4-pyridyl]-3,8-diazabicyclo[3.2.1]octan-3-yl]pyridazin-3-yl]phenol;

2-[6-amino-5-[8-[2-[4-(azepan-1-yl)but-1-ynyl]-4-pyridyl]-3,8-diazabicyclo[3.2.1]octan-3-yl]pyridazin-3-yl]phenol;

2-[6-amino-5-[8-[2-[3-(3,3-difluoroazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-ethoxyazetidin-1-yl)prop-1-ynyl]-4-pyridyl]-3,8-diazabicyclo[3.2.1]octan-3-yl]pyridazin-3-yl]phenol;

methyl 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-3-carboxylate;

2-[6-amino-5-[8-[2-[3-(3-phenoxyazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-methylsulfonylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoroazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-morpholinoazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(2-azaspiro[3.5]nonan-2-yl)prop-1-ynyl]-4-pyridyl]-3,8-diazabicyclo[3.2.1]octan-3-yl]pyridazin-3-yl]phenol;

2-[6-amino-5-[8-[2-[3-(3-pyrimidin-4-ylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-[3-(trifluoromethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(5-azaspiro[2.3]hexan-5-yl)prop-1-ynyl]-4-pyridyl]-3,8-diazabicyclo[3.2.1]octan-3-yl]pyridazin-3-yl]phenol;

2-[6-amino-5-[8-[2-[3-(3-phenylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(1-azaspiro[3.3]heptan-1-yl)prop-1-ynyl]-4-pyridyl]-3,8-diazabicyclo[3.2.1]octan-3-yl]pyridazin-3-yl]phenol;

2-[6-amino-5-[8-[2-[3-(7-methylsulfonyl-2,7-diazaspiro[3.4]octan-2-yl)prop-1-ynyl]-4-pyridyl]-3,8-diazabicyclo[3.2.1]octan-3-yl]pyridazin-3-yl]phenol;

4-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-yl]benzonitrile;

2-[6-amino-5-[8-[2-[3-(3-cyclopropyl-3-fluoro-azetidin-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4,5-dimethyl-azepan-4-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-3-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-(fluoromethyl)azepan-3-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azepan-3-ol;

2-[6-amino-5-[8-[2-[3-(3-fluoro-3-methyl-azepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4-methyl-azepan-4-ol;

2-[6-amino-5-[8-[2-[3-(azepan-1-yl)prop-1-ynyl]pyrimidin-4-yl]-3,8-diazabicyclo[3.2.1]octan-3-yl]pyridazin-3-yl]phenol;

2-[6-amino-5-[8-[6-[3-(azepan-1-yl)prop-1-ynyl]pyridazin-4-yl]-3,8-diazabicyclo[3.2.1]octan-3-yl]pyridazin-3-yl]phenol;

2-[6-amino-5-[8-[6-[3-(azepan-1-yl)prop-1-ynyl]pyrimidin-4-yl]-3,8-diazabicyclo[3.2.1]octan-3-yl]pyridazin-3-yl]phenol; and 2-[6-amino-5-[8-[2-[3-(azepan-1-yl)prop-1-enyl]-4-pyridyl]-3,8-diazabicyclo[3.2.1]octan-3-yl]pyridazin-3-yl]phenol. 2-[6-amino-5-[8-[2-[3-(7-oxa-1-azaspiro[3.4]octan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-ol;

2-[6-amino-5-[8-[2-[3-(3-methoxy-3-methyl-azetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-3-methyl-azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-[3-fluoro-3-(hydroxymethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(3-methylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoro-3-methyl-azetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-methoxyazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(6-oxa-2-azaspiro[3.5]nonan-2-yl)prop-1-ynyl]-4-pyridyl]-3,8-diazabicyclo[3.2.1]octan-3-yl]pyridazin-3-yl]phenol;

methyl 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-2-carboxylate 2-amino-5-[8-[2-[3-[8-(fluoromethyl)-5,5-dioxo-5lambda6-thia-2-azaspiro[3.4]octan-2-yl]prop-1-ynyl]-4-pyridyl]-3,8-diazabicyclo[3.2.1]octan-3-yl]pyridazin-3-yl]phenol;

2-[6-amino-5-[8-[2-[3-(5-oxa-2-azaspiro[3.4]octan-2-yl)prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-3-phenyl-azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(2,3-dimethylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(3,3-difluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[4-(1-piperidyl)but-1-ynyl]-4-pyridyl]-3,8-diazabicyclo[3.2.1]octan-3-yl]pyridazin-3-yl]phenol methyl 2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-dioxo-5lambda6-thia-2-azaspiro[3.4]octane-8-carboxylate 2-[6-amino-5-[8-[2-[3-(2-methylazetidin-1-yl)prop-1-ynyl]-4-pyridyl]-3,8-diazabicyclo[3.2.1]octan-3-yl]pyridazin-3-yl]phenol;

2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azaspiro[3.3]heptan-6-ol;

2-[6-amino-5-[8-[2-[3-[(2S)-2-(methoxymethyl)azetidin-1-yl]prop-1-ynyl]-4-pyridyl]-3,8-diazabicyclo[3.2.1]octan-3-yl]pyridazin-3-yl]phenol;

2-[6-amino-5-[8-[2-[3-(2,2-dimethylazetidin-1-yl)prop-1-ynyl]-4-pyridyl]-3,8-diazabicyclo[3.2.1]octan-3-yl]pyridazin-3-yl]phenol;

2-[6-amino-5-[8-[2-[3-(8-methyl-5-oxa-2,8-diazaspiro[3.5]nonan-2-yl)prop-1-ynyl]-4-pyridyl]-3,8-diazabicyclo[3.2.1]octan-3-yl]pyridazin-3-yl]phenol;

2-[6-amino-5-[8-[2-[3-(4,4-difluoroazepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5-methyl-azepan-4-ol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azepan-4-ol;

2-[6-amino-5-[8-[2-[3-(3-methylazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(4-fluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(3-fluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(3,4-dimethylazepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-4-ol;

2-[6-amino-5-[8-[2-[3-[4-(hydroxymethyl)-4-methyl-azepan-1-yl]prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5-methyl-azepan-4-one;

2-[6-amino-5-[8-[2-[3-(3,4,4-trifluoroazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(4-methylazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(2-methylazepan-1-yl)prop-1-ynyl]-4-pyridyl]-3,8-diazabicyclo[3.2.1]octan-3-yl]pyridazin-3-yl]phenol;

2-[6-amino-5-[8-[2-[3-(1,2,4,5-tetrahydro-3-benzazepin-3-yl)prop-1-ynyl]-4-pyridyl]-3,8-diazabicyclo[3.2.1]octan-3-yl]pyridazin-3-yl]phenol;

2-[6-amino-5-[8-[2-[3-(5,6,8,9-tetrahydroimidazo[1,2-d][1,4]diazepin-7-yl)prop-1-ynyl]-4-pyridyl]-3,8-diazabicyclo[3.2.1]octan-3-yl]pyridazin-3-yl]phenol;

2-[6-amino-5-[8-[2-[3-[4-(4-pyridyl)-1,4-diazepan-1-yl]prop-1-ynyl]-4-pyridyl]-3,8-diazabicyclo[3.2.1]octan-3-yl]pyridazin-3-yl]phenol;

2-[6-amino-5-[8-[2-[3-(4,4-dimethylazepan-1-yl)prop-1-ynyl]-4-pyridyl]-3,8-diazabicyclo[3.2.1]octan-3-yl]pyridazin-3-yl]phenol;

2-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-5,5-difluoro-azepan-4-yl]acetonitrile;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4-(methoxymethyl)azepan-4-ol;

2-[6-amino-5-[8-[2-[3-(2,2-difluoro-7-azaspiro[2.6]nonan-7-yl)prop-1-ynyl]-4-pyridyl]-3,8-diazabicyclo[3.2.1]octan-3-yl]pyridazin-3-yl]phenol;

2-[6-amino-5-[8-[2-[3-[4-(trifluoromethyl)azepan-1-yl]prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepane-3,4-diol;

(1S,5R)-2-[3-[4-[3-[3-amino-6-(2-hydroxyphenyl)pyridazin-4-yl]-3,8-diazabicyclo[3.2.1]octan-8-yl]-2-pyridyl]prop-2-ynyl]-2-azabicyclo[3.2.1]octane-6,7-diol;

2-[6-amino-5-[8-[2-[3-(5,5-difluoro-3-methyl-azepan-1-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6,6-dimethyl-azepan-4-ol;

2-[6-amino-5-[8-[2-[3-[3-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[4-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[2-(hydroxymethyl)azepan-1-yl]prop-1-ynyl]-4-pyridyl]-3,8-diazabicyclo[3.2.1]octan-3-yl]pyridazin-3-yl]phenol;

2-[6-amino-5-[8-[2-[3-[3-(hydroxymethyl)-6-azabicyclo[3.2.0]heptan-6-yl]prop-1-ynyl]-4-pyridyl]-3,8-diazabicyclo[3.2.1]octan-3-yl]pyridazin-3-yl]phenol;

2-[6-amino-5-[8-[2-[3-(2-azabicyclo[3.2.2]nonan-2-yl)prop-1-ynyl]-4-pyridyl]-3,8-diazabicyclo[3.2.1]octan-3-yl]pyridazin-3-yl]phenol;

1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-6-methyl-azepan-4-ol;

2-[6-amino-5-[8-[2-[3-(3-azatricyclo[4.2.1.02,5]nonan-3-yl)prop-1-ynyl]-4-pyridyl]-3,8-diazabicyclo[3.2.1]octan-3-yl]pyridazin-3-yl]phenol;
2-[6-amino-5-[8-[2-[3-(2-azabicyclo[3.2.1]octan-2-yl)prop-1-ynyl]-4-pyridyl]-3,8-diazabicyclo[3.2.1]octan-3-yl]pyridazin-3-yl]phenol;
2-[6-amino-5-[8-[2-[4-(azepan-1-yl)but-1-ynyl]-4-pyridyl]-3,8-diazabicyclo[3.2.1]octan-3-yl]pyridazin-3-yl]phenol;
2-[6-amino-5-[8-[2-[3-(3,3-difluoroazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(3-ethoxyazetidin-1-yl)prop-1-ynyl]-4-pyridyl]-3,8-diazabicyclo[3.2.1]octan-3-yl]pyridazin-3-yl]phenol;
methyl 1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidine-3-carboxylate;
2-[6-amino-5-[8-[2-[3-(3-phenoxyazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(3-methylsulfonylazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(3-fluoroazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(3-morpholinoazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(2-azaspiro[3.5]nonan-2-yl)prop-1-ynyl]-4-pyridyl]-3,8-diazabicyclo[3.2.1]octan-3-yl]pyridazin-3-yl]phenol;
2-[6-amino-5-[8-[2-[3-(3-pyrimidin-4-ylazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-[3-(trifluoromethyl)azetidin-1-yl]prop-1-ynyl]-4-pyridyl]-3,8-diazabicyclo[3.2.1]octan-3-yl]pyridazin-3-yl]phenol;
2-[6-amino-5-[8-[2-[3-(5-azaspiro[2.3]hexan-5-yl)prop-1-ynyl]-4-pyridyl]-3,8-diazabicyclo[3.2.1]octan-3-yl]pyridazin-3-yl]phenol;
2-[6-amino-5-[8-[2-[3-(3-phenylazetidin-1-yl)prop-1-ynyl]-4-pyridyl]-3,8-diazabicyclo[3.2.1]octan-3-yl]pyridazin-3-yl]phenol;
2-[6-amino-5-[8-[2-[3-(1-azaspiro[3.3]heptan-1-yl)prop-1-ynyl]-4-pyridyl]-3,8-diazabicyclo[3.2.1]octan-3-yl]pyridazin-3-yl]phenol;
2-[6-amino-5-[8-[2-[3-(7-methylsulfonyl-2,7-diazaspiro[3.4]octan-2-yl)prop-1-ynyl]-4-pyridyl]-3,8-diazabicyclo[3.2.1]octan-3-yl]pyridazin-3-yl]phenol;
4-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-yl]benzonitrile
2-[6-amino-5-[8-[2-[3-(3-cyclopropyl-3-fluoro-azetidin-1-yl)prop-1-ynyl]-4-pyridyl]-3,8-diazabicyclo[3.2.1]octan-3-yl]pyridazin-3-yl]phenol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4,5-dimethyl-azepan-4-ol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-methyl-azepan-3-ol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-3-(fluoromethyl)azepan-3-ol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azepan-3-ol;
2-[6-amino-5-[8-[2-[3-(3-fluoro-3-methyl-azepan-1-yl)prop-1-ynyl]-4-pyridyl]-3,8-diazabicyclo[3.2.1]octan-3-yl]pyridazin-3-yl]phenol;
1-[3-[4-[3-[3-amino-6-(2-hydroxyphenyl)pyridazin-4-yl]-3,8-diazabicyclo[3.2.1]octan-8-yl]-2-pyridyl]prop-2-ynyl]-4-methyl-azepan-4-ol;
2-[6-amino-5-[9-[2-[3-(azepan-1-yl)prop-1-ynyl]-4-pyridyl]-3,9-diazaspiro[5.5]undecan-3-yl]pyridazin-3-yl]phenol;
2-[6-amino-5-[2-[2-[3-(azepan-1-yl)prop-1-ynyl]-4-pyridyl]-2,8-diazaspiro[4.5]decan-8-yl]pyridazin-3-yl]phenol;
2-[6-amino-5-[6-[2-[3-(azepan-1-yl)prop-1-ynyl]-4-pyridyl]-2,6-diazaspiro[3.3]heptan-2-yl]pyridazin-3-yl]phenol;
2-[(10S)-12-[2-[3-(azepan-1-yl)prop-1-ynyl]-4-pyridyl]-1,5,6,8,12-pentazatricyclo[8.4.0.02,7]tetradeca-2(7),3,5-trien-4-yl]phenol; and
2-[(10R)-12-[2-[3-(azepan-1-yl)prop-1-ynyl]-4-pyridyl]-1,5,6,8,12-pentazatricyclo[8.4.0.02,7]tetradeca-2(7),3,5-trien-4-yl]phenol,
or a stereoisomer or tautomer thereof, or a pharmaceutically acceptable salt of any of the foregoing.

Compounds of the present disclosure, as described herein, may exist in solid or liquid form. In the solid state, the compound may exist in crystalline or noncrystalline form, or as a mixture thereof. For example, pharmaceutically acceptable solvates may be formed from crystalline or non-crystalline compounds. In crystalline solvates, solvent molecules are incorporated into the crystalline lattice during crystallization. Solvates wherein water is the solvent incorporated into the crystalline lattice are typically referred to as "hydrates." Hydrates include stoichiometric hydrates as well as compositions containing variable amounts of water. Such compounds described herein that exist in crystalline form, including the various solvates thereof, may exhibit polymorphism (i.e. the capacity to occur in different crystalline structures). These different crystalline forms are typically known as "polymorphs." The subject matter disclosed herein includes such polymorphs. Polymorphs have the same chemical composition but differ in packing, geometrical arrangement, and other descriptive properties of the crystalline solid state.

Compounds described herein or a salts thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (II'), (II), (II-A), (II-A1), (II-B), (II-B1), or a salt (e.g., a pharmaceutically acceptable salt) thereof, may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes combinations and subsets of the particular groups defined hereinabove.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds as disclosed herein and salts (e.g., pharmaceutically acceptable salts) thereof that contain the aforementioned isotopes and/or other isotopes of other atoms are within the scope of the subject matter disclosed herein. Isotopically-labelled compounds are disclosed herein, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are commonly used for their ease of preparation and detectability. $^{11}C$ and $^{18}F$ isotopes are useful in PET (positron emission tomography), and $^{125}I$ isotopes are useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I can generally be prepared by carrying out the procedures disclosed in the Schemes and/or in the Examples below, by substituting a readily available isotopically labelled reagent for a non-isotopically labelled reagent.

III. Formulations

In an additional aspect, the description provides therapeutic or pharmaceutical compositions comprising an effective amount of at least one of the compounds as described herein, including, e.g., at least one compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (II'), (II), (II-A), (II-A1), (II-B), or (II-B1), or a salt (e.g., a pharmaceutically acceptable salt) thereof, and combinations thereof. In some embodiments, the description provides therapeutic or pharmaceutical compositions comprising an effective amount of at least one compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, and combinations thereof. In some embodiments, the description provides therapeutic or pharmaceutical compositions comprising an effective amount of at least one compound of formula (II), (II-A), (II-A1), (II-B), or (II-B1), or a salt (e.g., a pharmaceutically acceptable salt) thereof, and combinations thereof. Pharmaceutical compositions comprising an effective amount of at least one compound according to the present disclosure, and optionally one or more of the compounds otherwise described herein, in effective amounts, in combination with a pharmaceutically effective amount of a carrier, additive or excipient, and optionally an additional bioactive agent, represents a further aspect of the disclosure.

In certain embodiments, the compositions comprise pharmaceutically acceptable salts, in particular, acid or base addition salts of compounds as described herein. The acids that are used to prepare the pharmaceutically acceptable acid addition salts of the aforementioned base compounds include those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate[i.e., 1,1'-methylene-bis-(2-hydroxy-3naphthoate)] salts, among numerous others.

Pharmaceutically acceptable base addition salts may also be used to produce pharmaceutically acceptable salt forms of the compounds or derivatives. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compositions as described herein may in certain embodiments be administered in single or divided unit doses by the oral, parenteral or topical routes. Administration of the compounds may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, by inhalation spray, rectally, vaginally, or via an implanted reservoir, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound according to the present disclosure, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but may also be administered in suppository and transdermal or other topical forms. Intramuscular injections in liposomal form may also be used to control or sustain the release of compound at an injection site.

Thus in one aspect, pharmaceutical formulations of compounds as described herein can be prepared for parenteral administration with a pharmaceutically acceptable parenteral vehicle and in a unit dosage injectable form. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. A compound of the present disclosure, having the desired degree of purity, is optionally mixed with one or more pharmaceutically acceptable excipients (Remington's Pharmaceutical Sciences (1980) 16th edition, Osol, A. Ed.; herein incorporated by reference in its entirety), in the form of a lyophilized formulation for reconstitution or an aqueous solution.

The compositions of the present disclosure may be formulated in a conventional manner using one or more pharmaceutically acceptable carriers and may also be administered in controlled-release formulations. The compounds of the disclosure can be formulated in accordance with standard pharmaceutical practice as a pharmaceutical composition. According to this aspect, there is provided a pharmaceutical composition comprising a compound of the present disclosure, e.g., a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), (II'), (II), (II-A), (II-A1), (II-B), or (II-B1), or a salt (e.g., a pharmaceutically acceptable salt) thereof, in association with one or more pharmaceutically acceptable excipients. In some embodiments, provided is a pharmaceutical composition comprising a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, in association with one or more pharmaceutically acceptable excipients. In some embodiments provided is a pharmaceutical composition comprising a compound of formula (II), (II-A), (II-A1), (II-B), or (II-B1), or a salt (e.g., a pharmaceutically acceptable salt) thereof, in association with one or more pharmaceutically acceptable excipients.

A typical formulation is prepared by mixing the compounds of the disclosure with excipients, such as carriers and/or diluents. Suitable carriers, diluents and other excipients are well known to those skilled in the art and include materials such as carbohydrates, waxes, water soluble and/or swellable polymers, hydrophilic or hydrophobic materials, gelatin, oils, solvents, water and the like. The particular carrier, diluent or other excipient used will depend upon the means and purpose for which the compound is being applied. Other pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solvents are generally selected based on solvents recognized by persons skilled in the art as safe to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (fewer than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG).

The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the compound of the present disclosure or aid in the manufacturing of the pharmaceutical product. The formulations may be prepared using conventional dissolution and mixing procedures.

Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The pharmaceutical compositions may be in the form of a sterile injectable preparation, such as a sterile injectable aqueous or oleaginous suspension. In particular, formulations to be used for in vivo administration must be sterile. Such sterilization is readily accomplished by filtration through sterile filtration membranes. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables, as well as natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Alternatively, the pharmaceutical compositions can be formulated in a suitable lotion or cream containing the active components suspended or dissolved in one or more pharmaceutically acceptable carriers.

For ophthalmic use, the pharmaceutical compositions may be formulated as micronized suspensions in isotonic, pH adjusted sterile saline or as solutions in isotonic, pH-adjusted sterile saline, either with our without a preservative. Alternatively, for ophthalmic uses, the pharmaceutical compositions may be formulated in an ointment.

The pharmaceutical compositions of this disclosure may also be administered by nasal aerosol or inhalation. Such compositions are prepared according to techniques well-known in the art of pharmaceutical formulation.

The compositions of the present disclosure ordinarily can be stored as a solid composition, a lyophilized formulation or as an aqueous solution.

The compound of the present disclosure can be formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the present disclosure can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

The active compound (e.g., a compound of the present disclosure or a salt thereof) is included in the pharmaceutically acceptable carrier or diluent in an amount sufficient to deliver to a patient a therapeutically effective amount for the desired indication, without causing serious toxic effects in the patient treated. A preferred dose of the active compound for the herein-mentioned conditions is in the range from about 10 ng/kg to 300 mg/kg, preferably 0.1 to 100 mg/kg per day, more generally 0.5 to about 25 mg per kilogram body weight of the recipient/patient per day. One typical daily dosage might range from about 1 µg/kg to 100 mg/kg or more, depending on the factors mentioned above. A typical topical dosage will range from 0.01-5% wt/wt in a suitable carrier.

The compound is conveniently administered in any suitable unit dosage form, including, but not limited to, one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.00001-0.01 mM, or in other embodiments, about 0.1-30 mM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

In embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety).

In embodiments, the composition includes a pharmaceutically acceptable salt form of one or more of the compounds described herein which are presented to, e.g., increase the solubility of the compound in the gastric juices of the patient's gastrointestinal tract in order to promote dissolution and the bioavailability of the compounds. In embodiments, the pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally or by any other desired route.

IV. Indications and Methods of Treatment

It is contemplated that the compounds disclosed herein may be used to treat various diseases or disorders. Generally, the disease or disorder to be treated is a hyperproliferative disease such as cancer.

A compound of the present disclosure or a salt thereof may be administered by any route appropriate to the condition to be treated. The compound will typically be administered parenterally, i.e. infusion, subcutaneous, intramuscular, intravenous, intradermal, intrathecal and epidural.

A "BRM-mediated disease, disorder, or condition" is characterized by the participation of BRM in the inception, manifestation of one or more symptoms or disease markers, severity, or progression of a disease, disorder, or condition. A BRM-mediated disease, disorder, or condition may be associated with SMARCA1, BRAHMA or BRM accumulation and aggregation. A BRM-mediated disease, disorder, or condition may be SMARCA2-dependent.

BRM-mediated diseases, disorders, or conditions include cancers, including, but not limited to, squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, and Philadelphia chromosome positive CML.

In embodiments, the BRM-mediated disease, disorder, or condition is a BRG1 (SMARCA4)-related disease, disorder, or condition such as an SWI/SNF associated cancer with a BRG1 mutation or a BRG1-deficient cancer or a cancer with decreased expression of BRG1 relative to normal BRG1 expression (e.g., relative to the expression of non-mutated BRG1 or BRG1 in a similarly situated non-cancerous cell with a wildtype BRG1).

BRG1-related disorders include cancers, including, but not limited to, lung cancer such as small-cell lung cancer and non-small cell lung cancer, colorectal cancer, bladder cancer, cancer of unknown primary, glioma, breast cancer, melanoma, nonmelanoma skin cancer, endometrial cancer, esophagogastric cancer, pancreatic cancer, hepatobiliary cancer, soft tissue sarcoma, ovarian cancer, head cancer, neck cancer, renal cell carcinoma, bone cancer, non-Hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, adrenocortical carcinoma, appendiceal cancer, small bowel cancer, and penile cancer.

In embodiments, BRM-mediated disease, disorder, or condition is cancer. In embodiments, BRM-mediated disease, disorder, or condition is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, non-small cell lung cancer, colorectal cancer, cancer of unknown primary, nonmelanoma skin cancer, endometrial cancer, esophagogastric cancer, hepatobiliary cancer, soft tissue sarcoma, bone cancer, small-cell lung cancer, embryonal tumor, germ cell tumor, salivary gland cancer, gastrointestinal neuroendocrine tumor, uterine sarcoma, gastrointestinal stromal tumor, CNS cancer, thymic tumor, adrenocortical carcinoma, appendiceal cancer, small bowel cancer, and penile cancer.

In embodiments, the BRM-mediated disease, disorder, or condition is lung cancer or non-small cell lung cancer.

In embodiments, the present disclosure is directed to the use of a compound of the present disclosure formula (III'), or a salt (e.g., a pharmaceutically acceptable salt) thereof) for modulation of BRM (in vitro or in vivo). In embodiments, the present disclosure is directed to the use of a compound of the present disclosure formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a salt (e.g., a pharmaceutically acceptable salt) thereof) for modulation of BRM (in vitro or in vivo). In embodiments, the present disclosure is directed to the use of a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof) for modulation of BRM (in vitro or in vivo). In embodiments, the present disclosure is directed to the use of a compound of formula (II), (II-A), (II-A1), (II-B), or (II-B1), or a salt (e.g., a pharmaceutically acceptable salt) thereof) for modulation of BRM (in vitro or in vivo).

In certain embodiments, the present disclosure is directed to a method of treating a condition, disease, or disorder in a subject (e.g., a human subject) in need thereof, comprising administering to the subject (e.g., a human subject) an effective amount of a compound of formula (III'), or a salt (e.g., a pharmaceutically acceptable salt) thereof, or a pharmaceutical composition of the present disclosure that comprises said compound or salt and one or more pharmaceutically acceptable excipients. In certain embodiments, the present disclosure is directed to a method of treating a condition, disease, or disorder in a subject (e.g., a human subject) in need thereof, comprising administering to the subject (e.g., a human subject) an effective amount of a compound of the present disclosure (e.g., a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1)), or a salt (e.g., a pharmaceutically acceptable salt) thereof, or a pharmaceutical composition of the present disclosure that comprises said compound or salt and one or more pharmaceutically acceptable excipients. In certain embodiments, the present disclosure is directed to a method of treating a condition, disease, or disorder in a subject (e.g., a human subject) in need thereof, comprising administering to the subject (e.g., a human subject) an effective amount of a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, or a pharmaceutical composition of the present disclosure that comprises said compound or salt and one or more pharmaceutically acceptable excipients. In certain embodiments, the present disclosure is directed to a method of treating a condition, disease, or disorder in a subject (e.g., a human subject) in need thereof, comprising administering to the subject (e.g., a human subject) an effective amount of a compound of formula (II), (II-A), (II-A1), (II-B), or (II-B1), or a salt (e.g., a pharmaceutically acceptable salt) thereof, or a pharmaceutical composition of the present disclosure that comprises said compound or salt and one or more pharmaceutically acceptable excipients.

In embodiments, the condition, disease, or disorder is a BRM-mediated disorder. Thus, another embodiment includes a method for treating a BRM-mediated condition, disease, or disorder in a subject in need thereof, comprising administering to the subject an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a salt (e.g., a pharmaceutically acceptable salt) thereof, or a pharmaceutical composition of the present disclosure that comprises said compound or salt and one or more pharmaceutically acceptable excipients. Another embodiment includes a method for treating a BRM-mediated condition, disease, or disorder in a subject in need thereof, comprising administering to the subject an effective amount of a compound of formula (III'), or a salt (e.g., a pharmaceutically acceptable salt) thereof, or a pharmaceutical composition of the present disclosure that comprises said compound or salt and one or more pharmaceutically acceptable excipients. Another embodiment includes a method for treating a BRM-mediated condition, disease, or disorder in a subject in need thereof, comprising administering to the subject an effective amount of a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, or a pharmaceutical composition of the present disclosure that comprises said compound or salt and one or more pharmaceutically acceptable excipients. Another embodiment includes a method for treating a BRM-mediated condition, disease, or disorder in a subject in need thereof, comprising administering to the subject an effective amount of a compound of formula (II), (II-A), (II-A1), (II-B), or (II-B1), or a salt (e.g., a pharmaceutically acceptable salt) thereof, or a pharmaceutical composition of the present disclosure that comprises said compound or salt and one or more pharmaceutically acceptable excipients. BRM-mediated disorders include, but are not limited to, those disorders described herein.

Another embodiment is directed to a method of degrading a BRM-containing protein in a cell, the method comprising exposing the cell to a composition comprising an effective amount of a compound of the present disclosure (e.g., a compound of formula (III'), or a salt (e.g., a pharmaceutically acceptable salt) thereof), wherein the compound effectuates the degradation of the BRM-containing protein. Another embodiment is directed to a method of degrading a BRM-containing protein in a cell, the method comprising exposing the cell to a composition comprising an effective amount of a compound of the present disclosure (e.g., a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a salt (e.g., a pharmaceutically acceptable salt) thereof), wherein the compound effectuates the degradation of the BRM-containing protein. Another embodiment is directed to a method of degrading a BRM-containing protein in a cell, the method comprising exposing the cell to a composition comprising an effective amount of a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, wherein the compound effectuates the degradation of the BRM-containing protein. Another embodiment is directed to a method of degrading a BRM-containing protein in a cell, the method comprising exposing the cell to a composition comprising an effective amount of a compound of formula (II), (II-A), (II-A1), (II-B), or (II-B1), or a salt (e.g., a pharmaceutically acceptable salt) thereof, wherein the compound effectuates the degradation of the BRM-containing protein. The term "degrading", when used in connection with degrading a BRM-containing protein in a cell, means the level of the protein in the cell is reduced. The cell may be, for example, any animal cell, including human cells.

Another embodiment includes a method of treating cancer in an subject comprising administering to the subject an effective amount of a compound of formula (III'), or a salt (e.g., a pharmaceutically acceptable salt) thereof, or a pharmaceutically acceptable composition comprising said compound or salt. Another embodiment includes a method of treating cancer in an subject comprising administering to the subject an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a salt (e.g., a pharmaceutically acceptable salt) thereof, or a pharmaceutically acceptable composition comprising said compound or salt. Another embodiment includes a method of treating cancer in an subject comprising administering to the subject an effective amount of a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, or a pharmaceutically acceptable composition comprising said compound or salt. Another embodiment includes a method of treating cancer in an subject comprising administering to the subject an effective amount of a compound of formula (II), (II-A), (II-A1), (II-B), or (II-B1), or a salt (e.g., a pharmaceutically acceptable salt) thereof, or a pharmaceutically acceptable composition comprising said compound or salt.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In embodiments, provided herein is a method of modulating BRM in a cell, comprising exposing the cell to (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In embodiments, provided herein is a method of modulating BRM in a cell, comprising exposing the cell to (1) an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, and (ii) one or more pharmaceutically acceptable excipients. In embodiments, provided herein is a method of modulating BRM in a cell, comprising exposing the cell to (1) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, and (ii) one or more pharmaceutically acceptable excipients. In embodiments, provided herein is a method of modulating BRM in a cell, comprising exposing the cell to (1) an effective amount of a compound of formula (II') or formula (II), such as a compound of formula (II'), (II), (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II') or formula (II), such as a compound of formula (II'), (II), (II-A), (II-A1), (II-B), or (II-B1), or a stereoisomer or tautomer thereof, or a pharmaceutically acceptable salt of any of the foregoing, and (ii) one or more pharmaceutically acceptable excipients.

In embodiments, provided herein is a method of degrading BRM in a cell, comprising exposing the cell to (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In embodiments, provided herein is a method of degrading BRM in a cell, comprising exposing the cell to (1) an effective amount of a compound of formula (I'), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), or (I-J3), or a stereoisomer or tautomer thereof, or a pharmaceutically acceptable salt of any of the foregoing, or (2) a pharmaceutical composition, comprising (i) an effective amount of a compound of formula (I'), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), or (I-J3), or a stereoisomer or tautomer thereof, or a pharmaceutically acceptable salt of any of the foregoing, and (ii) one or more pharmaceutically acceptable excipients. In embodiments, provided herein is a method of degrading BRM in a cell, comprising exposing the cell to (1) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, and (ii) one or more pharmaceutically acceptable excipients. In embodiments, provided herein is a method of degrading BRM in a cell, comprising exposing the cell to (1) an effective amount of a compound of formula (II') or formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II') or formula (II), such as a compound of formula (II'), (II), (II-A), (II-A1), (II-B), or (II-B1), or a stereoisomer or tautomer thereof, or a pharmaceutically acceptable salt of any of the foregoing, and (ii) one or more pharmaceutically acceptable excipients.

In embodiments, provided herein is a method of treating a BRM-mediated disease, disorder, or condition in an individual in need thereof, comprising administering to the individual (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In embodiments, provided herein is a method of treating a BRM-mediated disease, disorder, or condition in an individual in need thereof, comprising administering to the individual (1) an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, and (ii) one or more pharmaceutically acceptable excipients. In embodiments, provided herein is a method of treating a BRM-mediated disease, disorder, or condition in an individual in need thereof, comprising administering to the individual (1) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, and (ii) one or more pharmaceutically acceptable excipients. In embodiments, provided herein is a method of treating a BRM-mediated disease, disorder, or condition in an individual in need thereof, comprising exposing the cell to (1) an effective amount of a compound of formula (II') or formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II') or formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In embodiments, the BRM-mediated disease, disorder, or condition is a BRG-1-related disease, disorder, or condition.

In embodiments, provided herein is a method of increasing the efficacy of cancer treatment in an individual in need thereof, comprising administering to the individual (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In embodiments, provided herein is a method of increasing the efficacy of cancer treatment in an individual in need thereof, comprising administering to the individual (1) an effective amount of a compound of formula (I'), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-J), (I-J1), (I-J2), or (I-J3), or a stereoisomer or tautomer thereof, or a pharmaceutically acceptable salt of any of the foregoing, or (2) a pharmaceutical composition, comprising (i) an effective amount of a compound of formula (I'), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (1-J1), (I-J2), or (I-J3), or a stereoisomer or tautomer thereof, or a pharmaceutically acceptable salt of any of the foregoing, and (ii) one or more pharmaceutically acceptable excipients. In embodiments, provided herein is a method of increasing the efficacy of cancer treatment in an individual in need thereof, comprising administering to the individual (1) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, and (ii) one or more pharmaceutically acceptable excipients. In embodiments, provided herein is a method of increasing the efficacy of cancer treatment in an individual in need thereof, comprising exposing the cell to (1) an effective amount of a compound of formula (II') or formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II') or formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In embodiments, provided herein is a method of preventing or delaying development of cancer resistance to a cytotoxic agent in a human, comprising administering to the individual (1) an effective amount of a compound of formula (III'), or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In embodiments, provided herein is a method of preventing or delaying development of cancer resistance to a cytotoxic agent in a human, comprising administering to the individual (1) an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, and (ii) one or more pharmaceutically acceptable excipients. In embodiments, provided herein is a method of preventing or delaying development of cancer resistance to a cytotoxic agent in a human, comprising administering to the individual (1) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, and (ii) one or more pharmaceutically acceptable excipients. In embodiments, provided herein is a method of preventing or delaying development of cancer resistance to a cytotoxic agent in a human, comprising exposing the cell to (1) an effective amount of a compound of formula (II') or formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II') or formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In embodiments, provided herein is a method of extending the duration of response to a cancer therapy in a human, comprising administering to the individual (1) an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, and (ii) one or more pharmaceutically acceptable excipients. In embodiments, provided herein is a method of extending the duration of response to a cancer therapy in a human, comprising administering to the individual (1) an effective amount of a compound of formula (III'), such as a compound of formula or a stereoisomer or tautomer thereof, or a pharmaceutically acceptable salt of any of the foregoing, or (2) a pharmaceutical composition, comprising (i) an effective amount of a compound of formula (III'), or a stereoisomer or tautomer thereof, or a pharmaceutically acceptable salt of any of the foregoing, and (ii) one or more pharmaceutically acceptable excipients. In embodiments, provided herein is a method of extending the duration of response to a cancer therapy in a human, comprising administering to the individual (1) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a stereoisomer or tautomer thereof, or a pharmaceutically acceptable salt of any of the foregoing, or (2) a pharmaceutical composition, comprising (i) an effective amount of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, and (ii) one or more pharmaceutically acceptable excipients. In embodiments, provided herein is a method of extending the duration of response to a cancer therapy in a human, comprising exposing the cell to (1) an effective amount of a compound of formula (II') or formula (II), such as a compound of formula (II-A), (II-A1), (II-B), or (II-B1), or a stereoisomer or tautomer thereof, or a pharmaceutically acceptable salt of any of the foregoing, or (2) a pharmaceutical composition, comprising (i) an effective amount of a compound of formula (II') or formula (II), such as a compound of formula (II-A), (II-A1), (II-B), or (II-B1), or a stereoisomer or tautomer thereof, or a pharmaceutically acceptable salt of any of the foregoing, and (ii) one or more pharmaceutically acceptable excipients.

In embodiments, provided herein is the use of a compound of formula (III'), or a stereoisomer or tautomer thereof, or a pharmaceutically acceptable salt of any of the foregoing, in the manufacture of a medicament for use in the treatment of a disease, disorder, or condition mediated by BRM or BRG1. In embodiments, provided herein is the use of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, in the manufacture of a medicament for use in the treatment of a disease, disorder, or condition mediated by BRM or BRG1. In embodiments, provided herein is the use of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, in the manufacture of a medicament for use in the treatment of a disease, disorder, or condition mediated by BRM or BRG1. In embodiments, provided herein is the use of a compound of formula (II') or formula (II), such as a compound of formula (II-A), (II-A1), (II-B), or (II-B1), or a stereoisomer or tautomer thereof, or a pharmaceutically acceptable salt of any of the foregoing, in the manufacture of a medicament for use in the treatment of a disease, disorder, or condition mediated by BRM or BRG1. In embodiments, provided herein is the use of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, in the manufacture of a medicament for use in the treatment of a disease, disorder, or condition mediated by BRM. In embodiments, provided herein is the use of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, in the manufacture of a medicament for use in the treatment of a disease, disorder, or condition mediated by BRM. In embodiments, provided herein is the use of a compound of formula (II') or formula (II), such as a compound of formula (II-A), (II-A1), (II-B), or (II-B1), or a stereoisomer or tautomer thereof, or a pharmaceutically acceptable salt of any of the foregoing, in the manufacture of a medicament for use in the treatment of a disease, disorder, or condition mediated by BRM.

In embodiments, provided herein is the use of a compound of formula (III'), or a stereoisomer or tautomer thereof, or a pharmaceutically acceptable salt of any of the foregoing, in the manufacture of a medicament for use in the treatment of cancer. In embodiments, provided herein is the use of a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, in the manufacture of a medicament for use in the treatment of cancer. In embodiments, provided herein is the use of a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, in the manufacture of a medicament for use in the treatment of cancer. In embodiments, provided herein is the use of a compound of formula (II') or formula (II), such as a compound of formula (II-A), (II-A1), (II-B), or (II-B1), or a stereoisomer or tautomer thereof, or a pharmaceutically acceptable salt of any of the foregoing, in the manufacture of a medicament for use in the treatment of cancer. In embodiments, provided herein is a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, for use in the treatment of a disease, disorder, or condition mediated by BRM or BRG1. In embodiments, provided herein is a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, for use in the treatment of a disease, disorder, or condition mediated by BRM or BRG1. In embodiments, provided herein is the use of a compound of formula (II') or formula (II), such as a compound of formula (II-A), (II-A1), (II-B), or (II-B1), or a stereoisomer or tautomer thereof, or a pharmaceutically acceptable salt of any of the foregoing, for use in the treatment of a disease, disorder, or condition mediated by BRM or BRG1.

In embodiments, provided herein is a compound of formula (III'), or a stereoisomer or tautomer thereof, or a pharmaceutically acceptable salt of any of the foregoing, for use in the treatment of a disease, disorder, or condition mediated by BRM. In embodiments, provided herein is a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, for use in the treatment of a disease, disorder, or condition mediated by BRM. In embodiments, provided herein is a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, for use in the treatment of a disease, disorder, or condition mediated by BRM. In embodiments, provided herein is the use of a compound of formula (II') or formula (II), such as a compound of formula (II-A), (II-A1), (II-B), or (II-B1), or a stereoisomer or tautomer thereof, or a pharmaceutically acceptable salt of any of the foregoing, for use in the treatment of a disease, disorder, or condition mediated by BRM.

In embodiments, provided herein is a compound of formula (III'), or a stereoisomer or tautomer thereof, or a pharmaceutically acceptable salt of any of the foregoing, for use in the treatment of cancer. In embodiments, provided herein is a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a stereoisomer or tautomer thereof, or a pharmaceutically acceptable salt of any of the foregoing, for use in the treatment of cancer. In embodiments, provided herein is a compound of formula (I), such as a compound of formula (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), or (I-G), or a stereoisomer or tautomer thereof, or a pharmaceutically acceptable salt of any of the foregoing, for use in the treatment of cancer. In embodiments, provided herein is the use of a compound of formula (II') or formula (II), such as a compound of formula (II-A), (II-A1), (II-B), or (II-B1), or a stereoisomer or tautomer thereof, or a pharmaceutically acceptable salt of any of the foregoing, for use in the treatment of cancer.

Co-Administration

A compound of the present disclosure can be used either alone or in combination with other agents in a therapy. For instance, a compound of formula (III'), or a salt (e.g., a pharmaceutically acceptable salt) thereof, may be co-administered with at least one additional therapeutic agent. In some embodiments, a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a salt (e.g., a pharmaceutically acceptable salt) thereof, may be co-administered with at least one additional therapeutic agent. In some embodiments, a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G) or a salt (e.g., a pharmaceutically acceptable salt) thereof, may be co-administered with at least one additional therapeutic agent. In some embodiments, a compound of formula (II), (II-A), (II-A1), (II-B), or (II-B1) or a salt (e.g., a pharmaceutically acceptable salt) thereof, may be co-administered with at least one additional therapeutic agent. Such combination therapies noted above encompass combined administration (where two or more therapeutic agents are included in the same or separate formulations), and separate administration, in which case, administration of the compound of the present disclosure can occur prior to, simultaneously (e.g., concurrently), and/or following, administration of the additional therapeutic agent and/or adjuvant. A compound of the present disclosure or a salt thereof can also be used in combination with radiation therapy.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present disclosure may be co-administered to a patient at the same time, the term embraces both administration of two or more agents at the same time or at different times, provided that effective concentrations of coadministered compounds or compositions are found in the subject at a given time.

The term "additional therapeutic agent" is used to describe an agent, other than a compound as described herein, which is used in combination with the disclosed compounds as an agent with biological activity to assist in effecting an intended therapy, inhibition and/or prevention/ prophylaxis for which the disclosed compounds are used. Additional therapeutic agents for use herein may include those agents which have pharmacological activity or therapeutic effect similar to that for which the disclosed compounds are used or administered. In embodiments, the compound as described herein, the additional therapeutic agent or both are present in an effective amount or, in certain embodiments, a synergistically effective amount.

The present disclosure includes a method of treating cancer in a subject comprising administering to the subject an effective amount of (a) a compound of formula (III'), or a salt (e.g., a pharmaceutically acceptable salt) thereof, and (b) one or more anti-cancer agents such as cytotoxic agents or chemotherapeutic agents. The present disclosure includes a method of treating cancer in a subject comprising administering to the subject an effective amount of (a) a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), or (II-B1), or a salt (e.g., a pharmaceutically acceptable salt) thereof, and (b) one or more anti-cancer agents such as cytotoxic agents or chemotherapeutic agents. In some embodiments, provided is a method of treating cancer in a subject comprising administering to the subject an effective amount of (a) a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, and (b) one or more anti-cancer agents such as cytotoxic agents or chemotherapeutic agents. In some embodiments, provided is a method of treating cancer in a subject comprising administering to the subject an effective amount of (a) a compound of formula (II), (II-A), (II-A1), (II-B), or (II-B1) or a salt (e.g., a pharmaceutically acceptable salt) thereof, and (b) one or more anti-cancer agents such as cytotoxic agents or chemotherapeutic agents.

Another embodiment includes a method of increasing efficacy of a cancer treatment in a subject comprising administering to the subject an effective amount of (a) a compound of formula (III'), or a salt (e.g., a pharmaceutically acceptable salt) thereof, and (b) one or more anti-cancer agents such as cytotoxic agents or chemotherapeutic agents. Another embodiment includes a method of increasing efficacy of a cancer treatment in a subject comprising administering to the subject an effective amount of (a) a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), or (IV'-N5), (II'), (II), (II-A), (II-A1), (II-B), or (II-B1), or a salt (e.g., a pharmaceutically acceptable salt) thereof, and (b) one or more anti-cancer agents such as cytotoxic agents or chemotherapeutic agents. Another embodiment includes a method of increasing efficacy of a cancer treatment in a subject comprising administering to the subject an effective amount of (a) a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, and (b) one or more anti-cancer agents such as cytotoxic agents or chemotherapeutic agents. Another embodiment includes a method of increasing efficacy of a cancer treatment in a subject comprising administering to the subject an effective amount of (a) a compound of formula (II), (II-A), (II-A1), (II-B), or (II-B1), or a salt (e.g., a pharmaceutically acceptable salt) thereof, and (b) one or more anti-cancer agents such as cytotoxic agents or chemotherapeutic agents.

The term "cytotoxic agent" or "chemotherapeutic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

In embodiments the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism.

Administration

A compound of the present disclosure or a pharmaceutically acceptable salt thereof (and any additional therapeutic agent) and pharmaceutical compositions comprising a compound of the present disclosure or a pharmaceutically acceptable salt thereof (and any additional therapeutic agent) can be formulated, dosed and administered in a fashion, i.e., amounts, concentrations, schedules, course, vehicles and route of administration, consistent with good medical practice.

In embodiments, such compounds, salts, compositions and agents are administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Route of administration may be determined based, at least in part, on whether the administration is brief or chronic. Administration may occur on dosing schedules including, but not limited to, single or multiple administrations over various time-points, bolus administration, and pulse infusion.

For the prevention or treatment of disease, the appropriate dosage of a compound of the present disclosure or a pharmaceutically acceptable salt thereof (when used alone or in combination with one or more other additional therapeutic agents) will depend on factors such as the type of disease to be treated, the severity and course of the disease, the cause of the disorder, the site of delivery of the agent, the method of administration, the scheduling of administration, the type of compound(s) to be administered, whether the compound or a salt thereof is administered for preventive or therapeutic purposes, the clinical condition of the individual patient, previous therapy received by the patient, the patient's clinical history and response to the compound, and other factors known to medical practitioners.

Depending at least in part on these factors, the compound of the present disclosure or a pharmaceutically acceptable salt thereof is suitably administered at a "therapeutically effective amount" to the patient by one or more separate administrations, or by continuous infusion at suitable dosage or dosages such as about 10 ng/kg to 300 mg/kg (e.g. 0.1 mg/kg-10 mg/kg). One typical daily dosage might range from about 1 µg/kg to 100 mg/kg or more. Such doses may be administered intermittently, e.g. every week or every three weeks (e.g. such that the patient receives from about two to about twenty, or e.g. about six doses). An initial higher loading dose, followed by one or more lower doses may be administered. However, other dosage regimens may be useful. The progress of this therapy is easily monitored by conventional techniques and assays and may generally be sustained until a desired suppression of at least one disease symptom or biological marker occurs.

The "therapeutically effective amount" of the compound to be administered will be governed by such considerations, and is Such amount is preferably below the amount that is toxic to the host or renders the host significantly more susceptible to unwanted side effects.

V. Articles of Manufacture

In another aspect, described herein are articles of manufacture, for example, a "kit", containing materials useful for the treatment of the diseases and disorders described above is provided. The kit comprises a container comprising a compound of the present disclosure or a salt thereof. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products.

Suitable containers include, for example, bottles, vials, syringes, blister pack, etc. A "vial" is a container suitable for holding a liquid or lyophilized preparation. In embodiments, the vial is a single-use vial, e.g. a 20-cc single-use vial with a stopper. The container may be formed from a variety of materials such as glass or plastic. The container may hold a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), (II-B1), or (III'), or a salt (e.g., a pharmaceutically acceptable salt) thereof, or a formulation thereof which is effective for treating the condition and may have a sterile access port (for example, the container may be an intravenous solution bag or a vial having a stopper pierceable by a hypodermic injection needle). The container may hold a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, or a formulation thereof which is effective for treating the condition and may have a sterile access port (for example, the container may be an intravenous solution bag or a vial having a stopper pierceable by a hypodermic injection needle). The container may hold a compound of formula (II), (II-A), (II-A1), (II-B), (II-B1), or a salt (e.g., a pharmaceutically acceptable salt) thereof, or a formulation thereof which is effective for treating the condition and may have a sterile access port (for example, the container may be an intravenous solution bag or a vial having a stopper pierceable by a hypodermic injection needle).

At least one active agent in the composition is a compound of the present disclosure or a salt thereof. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In embodiments, the label or package inserts indicates that the composition comprising a compound of the present disclosure or a salt thereof can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound or a salt thereof and, if present, the second pharmaceutical formulation. For example, if the kit comprises a first composition comprising a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), (II-B1), or (III'), or a salt (e.g., a pharmaceutically acceptable salt) thereof, and a second pharmaceutical formulation, the kit may further comprise directions for the simultaneous, sequential or separate administration of the first and second pharmaceutical compositions to a patient in need thereof. If the kit comprises a first composition comprising a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, and a second pharmaceutical formulation, the kit may further comprise directions for the simultaneous, sequential or separate administration of the first and second pharmaceutical compositions to a patient in need thereof. If the kit comprises a first composition comprising a compound of formula (II), (II-A), (II-A1), (II-B), (II-B1), or a salt (e.g., a pharmaceutically acceptable salt) thereof, and a second pharmaceutical formulation, the kit may further comprise directions for the simultaneous, sequential or separate administration of the first and second pharmaceutical compositions to a patient in need thereof.

In an embodiment, the kits are suitable for the delivery of solid oral forms of a compound of the present disclosure or a salt thereof, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of the present disclosure, e.g., a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-L5), (IV'-M), (IV'-M1), (IV'-M2), (IV'-M3), (IV'-M4), (IV'-M5), (IV'-N), (IV'-N1), (IV'-N2), (IV'-N3), (IV'-N4), (IV'-N5), (II'), (II), (II-A), (II-A1), (II-B), (II-B1), or (III'), or a salt (e.g., a pharmaceutically acceptable salt) thereof, contained therein; and optionally (b) a second container with a second pharmaceutical formulation contained therein, wherein the second pharmaceutical formulation comprises a second compound with anti-hyperproliferative activity. In some embodiments, a kit may comprise (a) a first container with a compound of the present disclosure, e.g., a compound of formula (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), or a salt (e.g., a pharmaceutically acceptable salt) thereof, contained therein; and optionally (b) a second container with a second pharmaceutical formulation contained therein, wherein the second pharmaceutical formulation comprises a second compound with anti-hyperproliferative activity. In some embodiments, a kit may comprise (a) a first container with a compound of the present disclosure, e.g., a compound of formula (II), (II-A), (II-A1), (II-B), (II-B1), or a salt (e.g., a pharmaceutically acceptable salt) thereof, contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a compound of the present disclosure or a salt thereof and a second therapeutic agent, the kit may comprise a container for containing the separate compositions such as a divided bottle or a divided foil packet; however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

VI. Process Embodiments

In some embodiments, provided is a process for making a compound of formula (I'), (I), (II'), (II), (III'), or (IV'), or any applicable subformulae thereof (including, for example, a compound of formula (I-F)) comprising reacting a compound of formula S1 (wherein $PG^1$ is a protecting group) according to Scheme A-1 to yield a compound of formula (I-F).

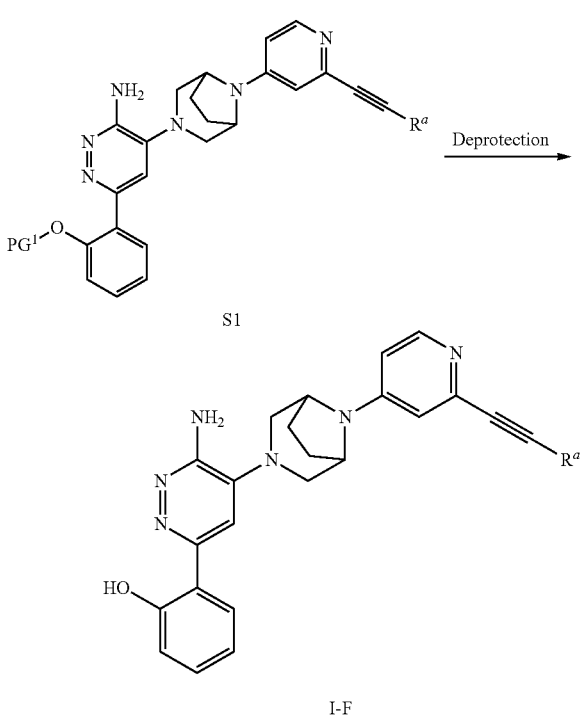

Scheme A-1

In some embodiments, $PG^1$ is methoxymethyl ether. In some embodiments, the deprotection step of scheme A-1 comprises treatment with acid. In some such embodiments, the acid comprises hydrochloric acid. In some embodiments, $R^a$ also comprises a protecting group. In some such embodiments, the protecting group comprised by $R^a$ is different from $PG^1$. In some such embodiments, the process comprises an additional deprotection step to remove the protecting group comprised by $R^a$.

In some embodiments, provided is a process for making a compound of formula S1 comprising reacting a compound of formula S2 with a compound of formula S3 according to scheme A-2 to yield a compound of formula S1.

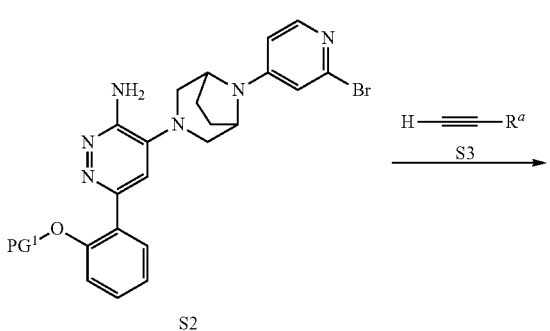

Scheme A-2

-continued

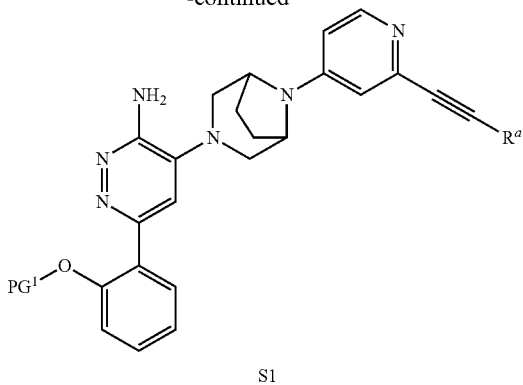

S1

In some embodiments, the process further comprises addition of Cu, Pd, and a base. In some such embodiments, the process comprises addition of Cu(I), Pd(II), and a base. In some such embodiments, the process comprises addition of CuI, Pd(PPh$_3$)$_2$Cl$_2$, and K$_2$CO$_3$. In some embodiments, the process is comprises heating. In some such embodiments, the reaction mixture is heated to at least about 100° C.

In some embodiments, provided is a process for making a compound of formula S2 comprising reacting a compound of formula S4 with a compound of formula S5 according to scheme A-3 to yield a compound of formula S2.

Scheme A-3

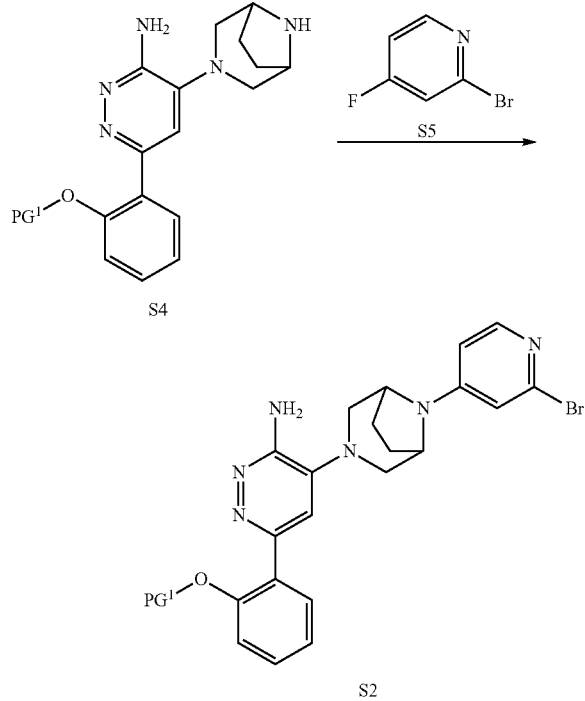

In some embodiments, the process comprises addition of an organic base. In some such embodiments, the process comprises addition of a tertiary amine. In some such embodiments the process comprises addition of N,N-diisopropylethylamine (DIEA). In some embodiments, the process comprises heating. In some such embodiments, the process comprises heating the reaction mixture to at least about 100° C. In some embodiments, the process is performed in a solvent comprising DMSO.

In some embodiments, provided is a process for making a compound of formula S4 comprising reacting a compound of formula S6 (wherein PG$^2$ is a protecting group) according to scheme A-4 to yield a compound of formula S4.

Scheme A-4

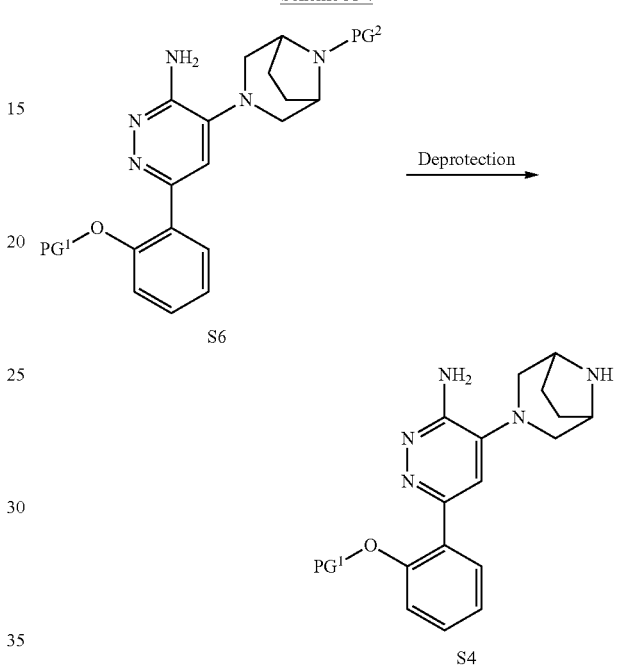

In some embodiments, PG$^2$ is benzyloxycarbonyl. In some embodiments, the deprotection step of scheme A-4 comprises addition of a Pd(II)-containing compound. In some such embodiments, the deprotection step comprises treatment with Pd(OH)$_2$/C. In some embodiments, the deprotection step is performed in a solvent comprising an alcohol solvent. In some such embodiments, the solvent comprises methanol (MeOH).

In some embodiments, provided is a process for making a compound of formula S6, comprising reacting a compound of formula S7 with a compound of formula S8 according to scheme A-5 to yield a compound of formula S6.

Scheme A-5

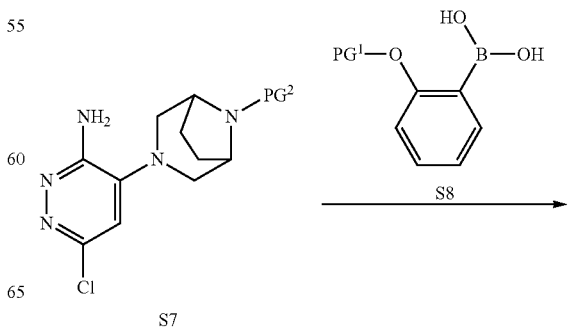

-continued

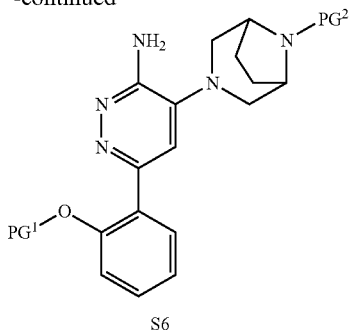

S6

In some embodiments, the process of Scheme A-5 comprises addition of Pd. In some such embodiments, the process comprises addition of a Pd⁰ compound. In some such embodiments, the process comprises addition of $Pd(PPh_3)_4$. In some embodiments, the process comprises heating. In some such embodiments, the process comprises heating to at least about 100° C. In some embodiments, the process is performed in a solvent comprising dioxane.

In some embodiments, provided is a process for making a compound of formula S7, comprising reacting a compound of formula S9 with a compound of formula S10 according to scheme A-6 to yield a compound of formula S7.

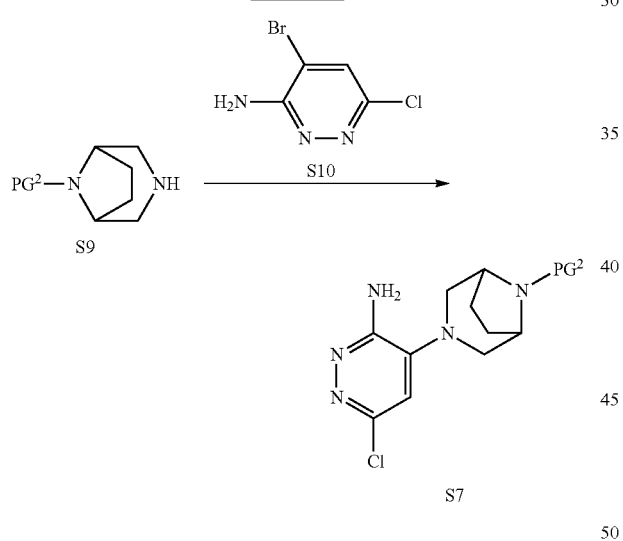

Scheme A-6

In some embodiments, the process of Scheme A-6 comprises addition of an organic base. In some such embodiments, the process comprises addition of a tertiary amine. In some such embodiments, the process comprises addition of DIPEA. In some embodiments, the process comprises heating. In some embodiments, the process comprises heating to at least about 130° C. In some embodiments, the process is performed in a solvent comprising dimethylsulfoxide (DMSO).

In some embodiments, provided is a process for making a compound of formula (I'), (I), (II'), or (II), or any applicable subformulae thereof (including, for example, a compound of formula (I-B) or formula (I-B2)) comprising reacting a compound of formula S13 (wherein $PG^1$ is a protecting group) according to scheme B-1 to yield a compound of formula (I-B2) wherein R may be $R^g$ or $—(CH_2)_{(n-2)}—R^g$.

Scheme B-1

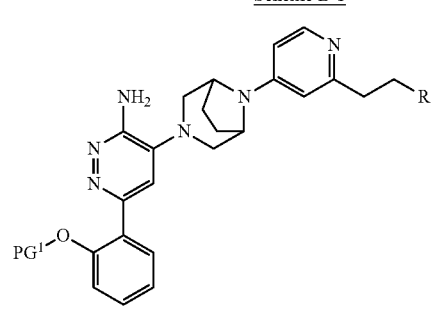

S13

Deprotection

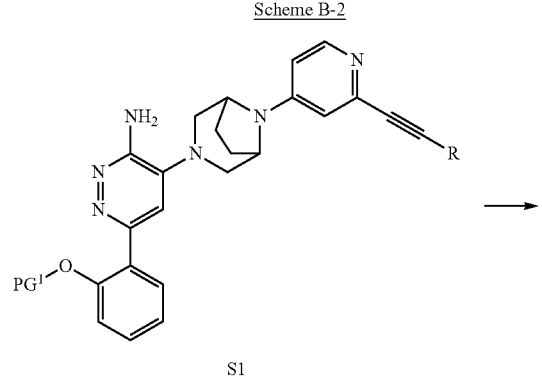

I-B2

In some embodiments, $PG^1$ is methoxymethyl ether. In some embodiments, the deprotection step of scheme A-1 comprises treatment with acid. In some such embodiments, the acid comprises hydrochloric acid.

In some embodiments, provided is a process for making a compound of formula S13 comprising reacting a compound of formula S1 according to scheme B-2 to yield a compound of formula S13 wherein R may be $R^g$ or $—(CH_2)_{(n-2)}—R^g$.

Scheme B-2

S1

-continued

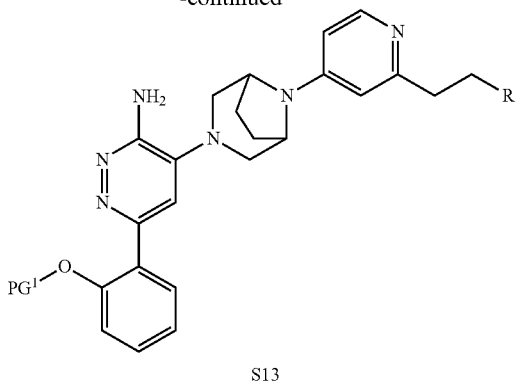

S13

In some embodiments, the process of Scheme B-2 comprises hydrogenation. In some such embodiments, the process comprises addition of Pd/C and SiEt$_3$H. In some embodiments the process comprises heating. In some such embodiments, the process comprises heating to at least about 50° C. In some embodiments, the process is performed in a solvent comprising an alcohol solvent. In some such embodiments, the process is performed in a solvent comprising MeOH. In some embodiments, the process is performed in the presence of acid. In some such embodiments, the acid comprises HCl.

In some embodiments, provided is a process for making a compound of formula (I'), (I), (II'), or (II), or any applicable subformulae thereof (including, for example, a compound of formula (I-C)) comprising reacting a compound of formula S14 (wherein PG$^1$ is a protecting group) according to scheme C-1 to yield a compound of formula (I-C).

Scheme C-1

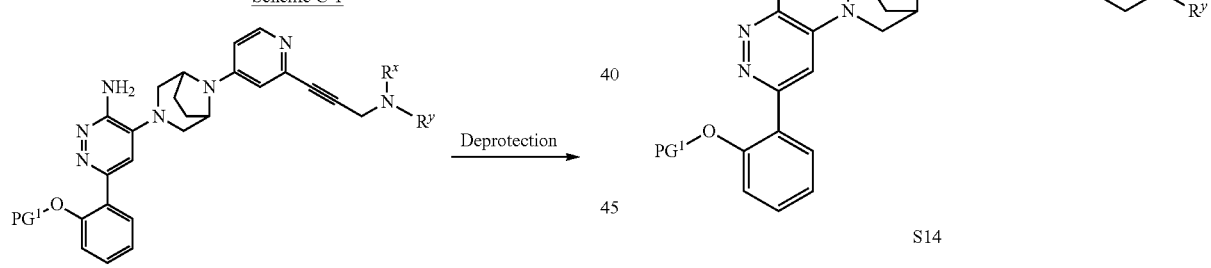

In some embodiments, PG$^1$ is methoxymethyl ether. In some embodiments, the deprotection step of scheme A-1 comprises treatment with acid. In some such embodiments, the acid comprises hydrochloric acid. In other such embodiments, the acid comprises an organic acid. In some such embodiments, the acid comprises HCl. In some embodiments the reaction is performed in a solvent comprising an alcohol solvent. In some such embodiments, the reaction is performed in a solvent comprising MeOH.

In some embodiments, provided is a process for making a compound of formula S14, comprising reacting a compound of formula S15 (wherein X is a leaving group) with a compound of formula S16 according to scheme C-2 to yield a compound of formula S14.

Scheme C-2

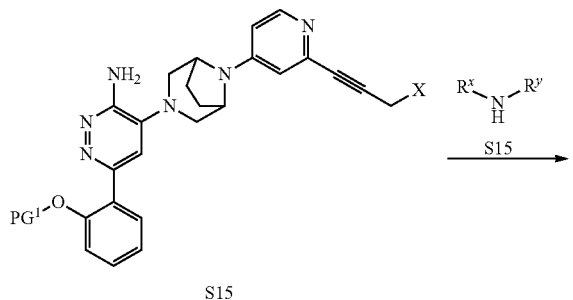

S15

S14

In some embodiments, the process of Scheme C-2 comprises addition of an organic base. In some such embodiments, the process comprises addition of a tertiary amine. In some such embodiments, the process comprises addition of DIEA. In some embodiments, the process performed in a solvent comprising DCM. In some embodiments, X is a halogen. In some such embodiments, X is Br. In some embodiments, X is a sulfonate group. In some embodiments, X is methylsulfonate (OMs).

In some embodiments, provided is a process for making a compound of formula 515, comprising reacting a compound of formula S17 according to scheme C-3 to yield a compound of formula S15.

Scheme C-3

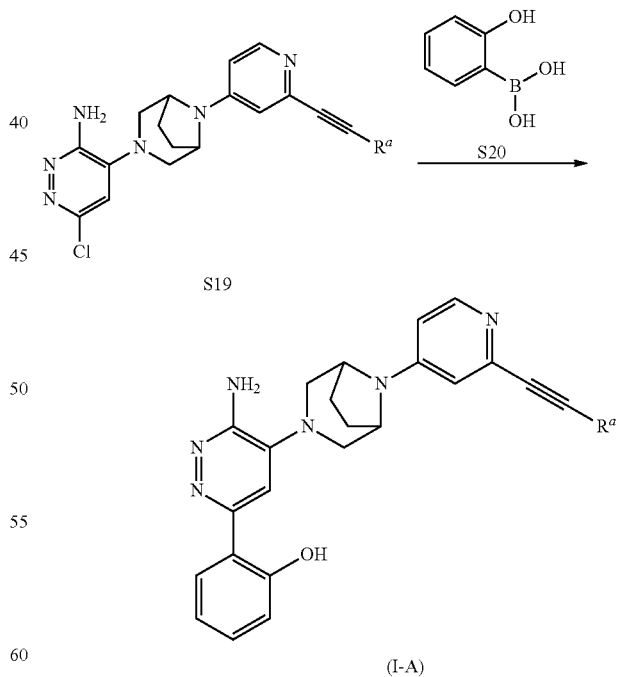

In some embodiments, X is a halogen. In some such embodiments, X is Br. In some embodiments, X is OMs. In some embodiments, the process of Scheme C-3 comprises addition of CBr₄ and PS-PPh₃. In other embodiments, the process comprises addition of methanesulfonyl chloride (MsCl). In some embodiments, the process is performed in a solvent comprising DCM.

In some embodiments, provided is a process for making a compound of formula S17 comprising reacting a compound of formula S2 with a compound of formula S18 according to scheme C-4 to yield a compound of formula S17.

Scheme C-4

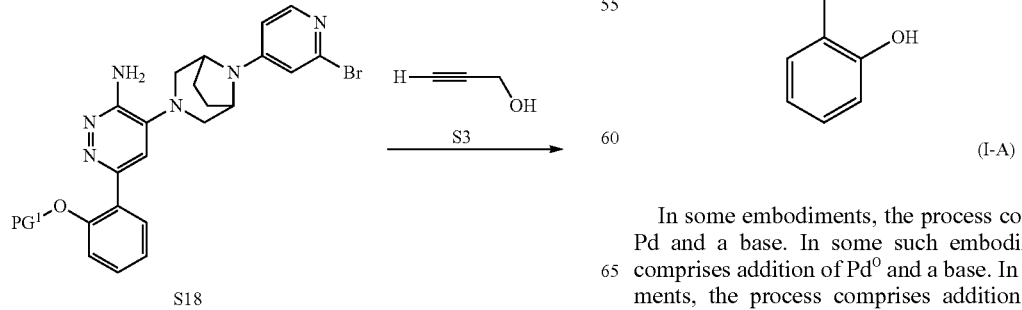

In some embodiments, the process further comprises addition of Cu, Pd, and a base. In some such embodiments, the process comprises addition of Cu(I), Pd⁰, and a base. In some such embodiments, the process comprises addition of CuI, Pd(PPh₃)₄, PPh₃, and TEA. In some embodiments, the process is comprises heating. In some such embodiments, the reaction mixture is heated to at least about 80° C. In some embodiments, the reaction is performed in a solvent comprising DMF.

In some embodiments, provided is a process for making a compound of formula (I'), (I), (II'), or (II), or any applicable subformulae thereof (including, for example, a compound of formula (I-A)) comprising reacting a compound of formula S19 with a compound of formula S20 according to Scheme D-1 to yield a compound of formula (I-D).

Scheme D-1

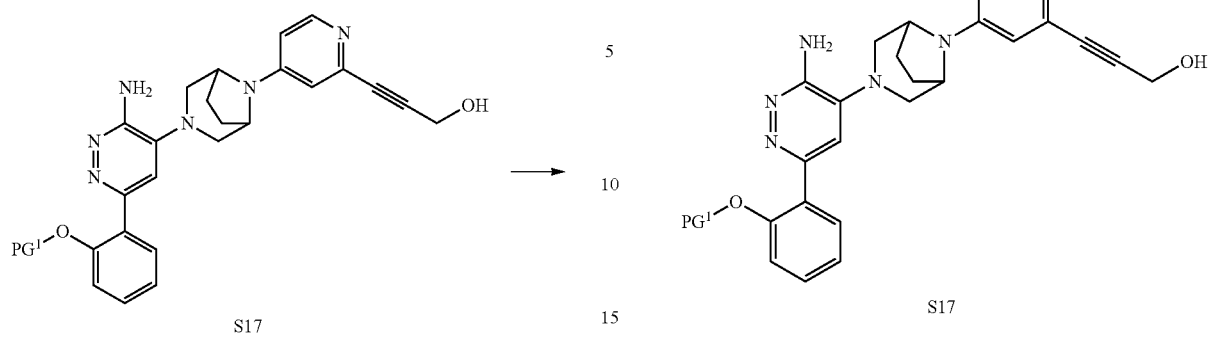

In some embodiments, the process comprises addition of Pd and a base. In some such embodiments, the process comprises addition of Pd⁰ and a base. In some such embodiments, the process comprises addition of Pd(PPh₃)₄ and K₂CO₃. In some embodiments, the process comprises heating. In some such embodiments, the process comprises heating to at least about 90° C.

In some embodiments, provided is a process for making a compound of formula S19 comprising reacting a compound of formula S21 with a compound of formula S22 according to Scheme D-2 to yield a compound of formula S19.

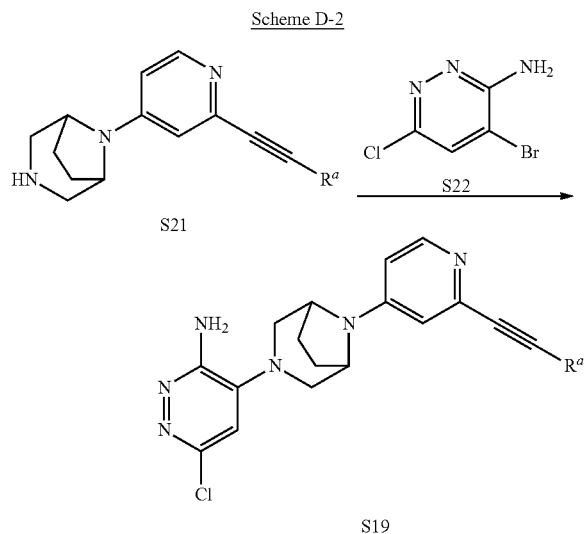

Scheme D-2

In some embodiments, the process comprises addition of an organic base. In some such embodiments, the process comprises addition of a tertiary amine. In some such embodiments, the process comprises addition of DIEA. In some embodiments, the process comprises heating. In some such embodiments, the process comprises heating to at least about 130° C. In some embodiments, the process is performed in a solvent comprising DMSO.

In some embodiments, provided is a process for making a compound of formula S21 comprising reacting a compound of formula S23 according to Scheme D-3 to yield a compound of formula 521.

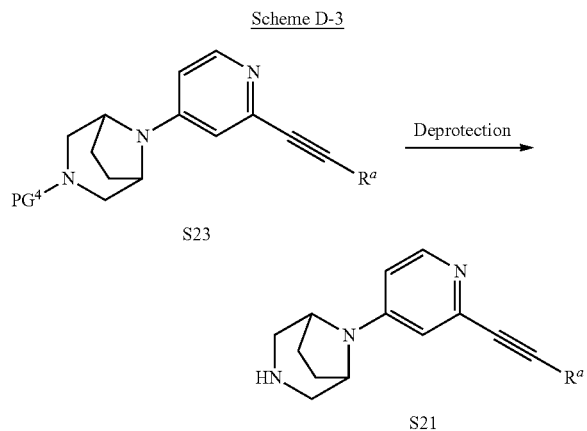

Scheme D-3

In some embodiments, the process comprises addition of an organic base. In some such embodiments, the process comprises addition of a tertiary amine. In some such embodiments, the process comprises addition of TEA. In some embodiments, the reaction comprises cooling. In some such embodiments, the reaction comprises cooling to about 0° C.

In some embodiments, provided is a process for making a compound of formula S23 comprising reacting a compound of formula S24 with a compound of formula S25 according to Scheme D-4 to yield a compound of formula S23.

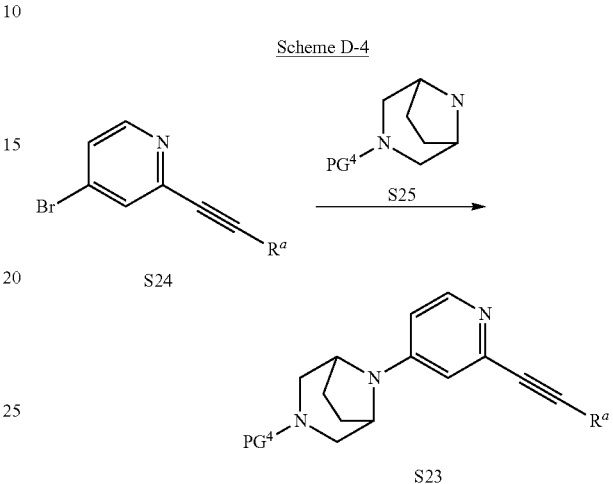

Scheme D-4

In some embodiments, the process comprises addition of Pd and a base. In some such embodiments, the process comprises addition of Ruphos Pd G3 and $Cs_2CO_3$. In some embodiments, the process comprises heating. In some such embodiments, the process comprises heating to at least about 110° C. In some embodiments, the process is performed in a solvent comprising toluene.

In some embodiments, provided is a process for making a compound of formula S24 (including, for example, a compound of formula (I-D)) comprising reacting a compound of formula S26 with a compound of formula S27 according to Scheme D-5 to yield a compound of formula S24.

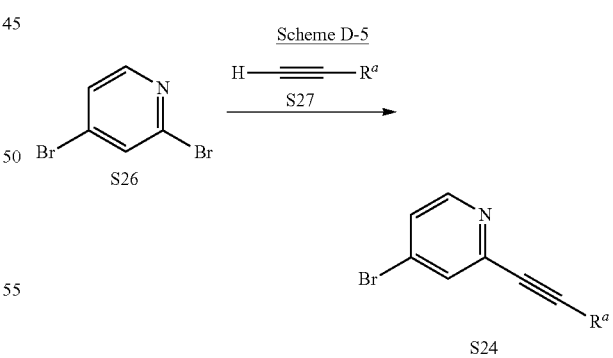

Scheme D-5

In some embodiments, the process comprises addition of Pd, Cu and a base. In some such embodiments, the process comprises addition of Pd, Cu, and a tertiary amine. In some such embodiments, the process comprises addition of $Pd^0$, $Cu(I)$, and a tertiary amine. In some such embodiments, the process comprises addition of $Pd(PPh_3)$, CuI, $PPh_3$, and TEA. In some embodiments, the reaction is performed in a solvent comprising DMF.

VII. Enumerated Embodiments

Enumerated Embodiments (A)

Embodiment A1 A compound of formula (I):

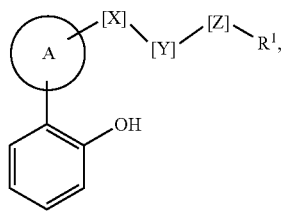
(I)

or a stereoisomer or tautomer thereof, or a pharmaceutically acceptable salt of any of the foregoing, wherein:

is selected from the group consisting of:

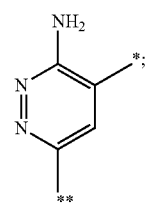
(a)

(b)

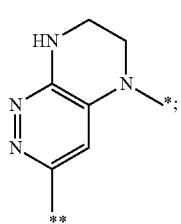
(c)

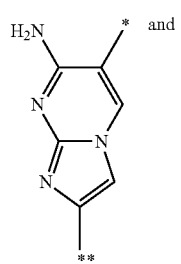
(d)

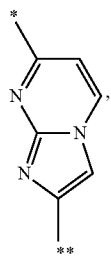
(e)

wherein, for (a)-(e), * denotes the point of attachment to [X], or, if [X] is absent, * denotes the point of attachment to [Y], and ** denotes the point of attachment to the remainder of the molecule;

and wherein:

(i) [X] is 3-15 membered heterocyclyl or 5-20 membered heteroaryl, provided that, when

is (a), then [X] is not

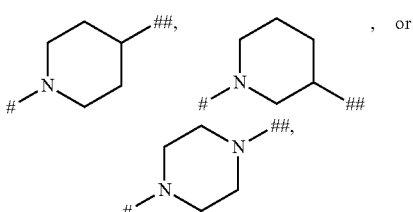

wherein # denotes the point of attachment

and ## denotes the point of attachment to R¹,

[Y] is absent, and

[Z] is absent; or (ii) [X] is 3-15 membered heterocyclyl or 5-20 membered heteroaryl, wherein the 3-15 membered heterocyclyl of [X] is optionally substituted with one or more —OH or $C_{1-6}$alkyl,

[Y] is absent, and

[Z] is 3-15 membered heterocyclyl or 5-20 membered heteroaryl, provided that, when

is (a) and [X] is

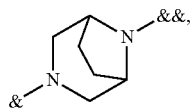

wherein & denotes the point of attachment to

and && denotes the point of attachment to [Z], then [Z] is not

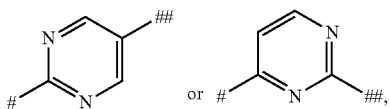

wherein # denotes the point of attachment to [X] and ## denotes the point of attachment to $R^1$; or
(iii) [X] is 3-15 membered heterocyclyl or 5-20 membered heteroaryl,
[Y] is methylene, wherein the methylene of [Y] is optionally substituted with one or more methyl group, and
[Z] is 3-15 membered heterocyclyl; or
(iv) [X] is absent,
[Y] is ethenylene, wherein the ethenylene of [Y] is optionally substituted with one or more halo, and
[Z] is 5-20 membered heteroaryl,
provided that

is (a), (b), (d), or (e); or
(v) [X] is absent,
[Y] is ethynylene, and
[Z] is 5-20 membered heteroaryl,
provided that

is (a), (b), (d), or (e); or
(vi) [X] is absent,
[Y] is cyclopropyl or cyclobutyl, and
[Z] is 5-20 membered heteroaryl,
provided that

is (a), (b), (d), or (e); and
$R^1$ is:
(a) —C≡C—$R^a$, wherein
(i) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$ cycloalkyl of $R^c$ is optionally substituted with one or more halo, and
the 3-15 membered heterocyclyl of $R^c$ is optionally substituted with one or more $C_{1-6}$ alkyl or —C(O)—$C_{1-6}$alkyl, and
the $C_{1-6}$alkoxy of $R^b$ is optionally substituted with one or more —OH, or
(ii) $R^a$ is $C_{3-10}$ cycloalkyl, wherein the $C_{3-10}$ cycloalkyl of $R^a$ is optionally substituted with one or more $R^z$, or
(iii) $R^a$ is 3-15 membered heterocyclyl, wherein the 3-15 membered heterocyclyl of $R^a$ is optionally substituted with one or more $R^z$, or
(iv) $R^a$ is 5-20 membered heteroaryl, wherein the 5-20 membered heteroaryl of $R^a$ is optionally substituted with one or more $R^z$, or
(b) —$(CH_2)_n$—$R^g$, wherein
n is an integer from 1-6, and
$R^g$ is —N($R^x$)($R^y$) or —OH;
$R^z$ is, independently at each occurrence, —OH, —CN, halo, $C_{1-6}$alkyl, $C_{1-6}$alkoxy, —N($R^x$)($R^y$), or —C(O)—N($R^x$)($R^y$); and
the $R^x$ and $R^y$ of —C(O)N($R^x$)($R^y$) and —N($R^x$)($R^y$) are, independently of each other and independently at each occurrence, H, —C(O)—$(CH_2)_p$—N($R^p$)($R^q$), 5-20 membered heteroaryl, or $C_{1-6}$alkyl, wherein
p is an integer from 1-6,
$R^p$ and $R^q$ are, independently of each other and independently at each occurrence H, or $C_{1-6}$alkyl, and
the $C_{1-6}$alkyl of $R^x$ or $R^y$ is optionally substituted with one or more —OH, 3-15 membered heterocyclyl, or —C(O)-(3-15 membered heterocyclyl).

Embodiment A2 The compound of embodiment A1, or a stereoisomer or tautomer thereof, or a pharmaceutically acceptable salt of any of the foregoing, wherein

is

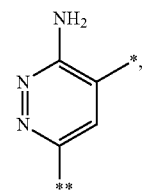

such that the compound of formula (I) is a compound of formula (I-A):

501

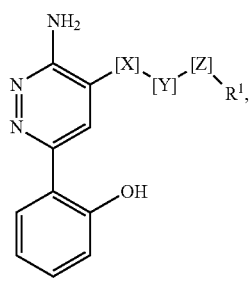
(I-A)

or a stereoisomer or tautomer thereof, or a pharmaceutically acceptable salt of any of the foregoing.

Embodiment A3 The compound of embodiment A2, or a stereoisomer or tautomer thereof, or a pharmaceutically acceptable salt of any of the foregoing, wherein [X] is 3-15 membered heterocyclyl or 5-20 membered heteroaryl, provided that [X] is not

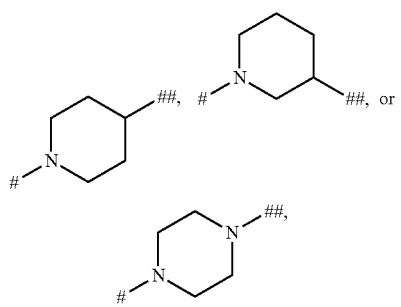

or wherein # denotes the point of attachment to (A)

and ## denotes the point of attachment to $R^1$; [Y] is absent; and [Z] is absent.

Embodiment A4 The compound of embodiment A3, or a stereoisomer or tautomer thereof, or a pharmaceutically acceptable salt of any of the foregoing, wherein the compound is selected from the group consisting of

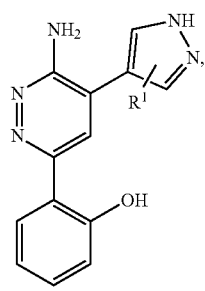

502

-continued

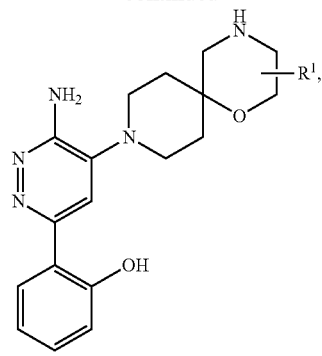

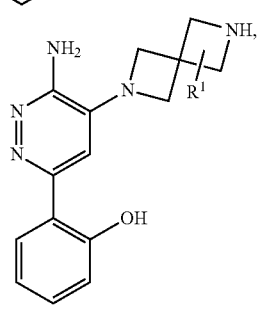

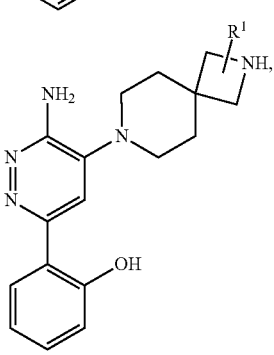

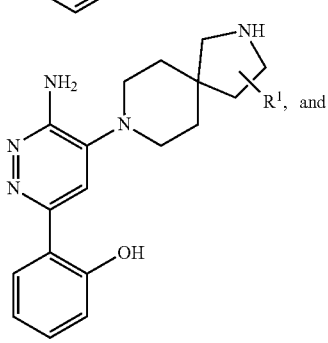

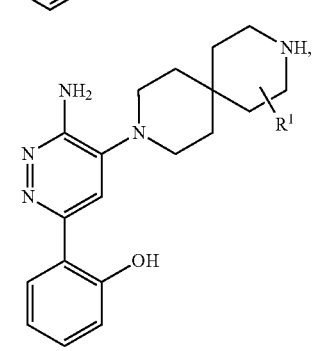

or a stereoisomer or tautomer thereof, or a pharmaceutically acceptable salt of any of the foregoing.

Embodiment A5 The compound of embodiment A2, or a stereoisomer or tautomer thereof, or a pharmaceutically acceptable salt of any of the foregoing, wherein [X] is 3-15 membered heterocyclyl or 5-20 membered heteroaryl, wherein the 3-15 membered heterocyclyl of [X] is optionally substituted with one or more —OH or $C_{1-6}$alkyl; [Y] is absent; and [Z] is 3-15 membered heterocyclyl or 5-20 membered heteroaryl, provided that, when [X] is

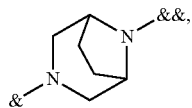

& wherein & denotes the point of attachment to

and && denotes the point of attachment to [Z], then [Z] is not

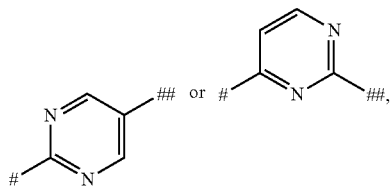

wherein # denotes the point of attachment to [X] and ## denotes the point of attachment to $R^1$.

Embodiment A6 The compound of embodiment A5, or a stereoisomer or tautomer thereof, or a pharmaceutically acceptable salt of any of the foregoing, wherein the compound is selected from the group consisting of

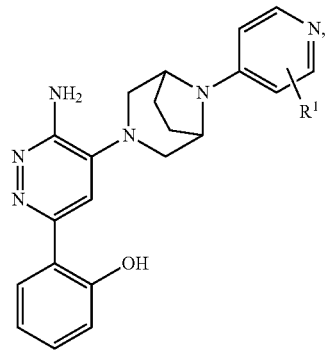

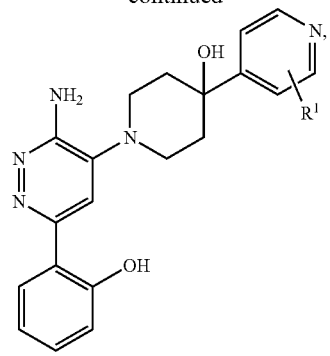

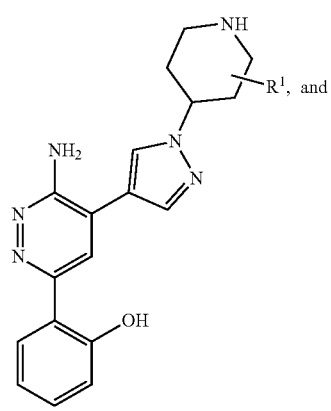

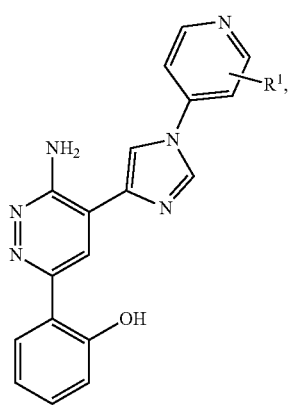

or a stereoisomer or tautomer thereof, or a pharmaceutically acceptable salt of any of the foregoing.

Embodiment A7 The compound of embodiment A6, or a stereoisomer or tautomer thereof, or a pharmaceutically acceptable salt of any of the foregoing, wherein the compound is

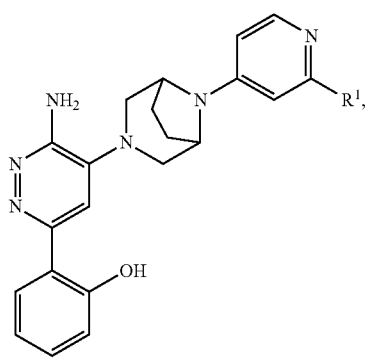

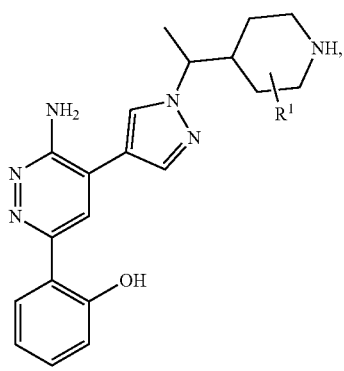

or a stereoisomer or tautomer thereof, or a pharmaceutically acceptable salt of any of the foregoing.

Embodiment A8 The compound of embodiment A7, or a stereoisomer or tautomer thereof, or a pharmaceutically acceptable salt of any of the foregoing, wherein the compound, or a stereoisomer or tautomer thereof, or a pharmaceutically acceptable salt of any of the foregoing, is selected from compounds 1 to 34 of Table 1.

Embodiment A9 The compound of embodiment A2, or a stereoisomer or tautomer thereof, or a pharmaceutically acceptable salt of any of the foregoing, wherein [X] is 3-15 membered heterocyclyl or 5-20 membered heteroaryl, [Y] is methylene, wherein the methylene of [Y] is optionally substituted with one or more methyl group, and [Z] is 3-15 membered heterocyclyl.

Embodiment A10 The compound of embodiment A9, or a stereoisomer or tautomer thereof, or a pharmaceutically acceptable salt of any of the foregoing, wherein the compound is selected from the group consisting of

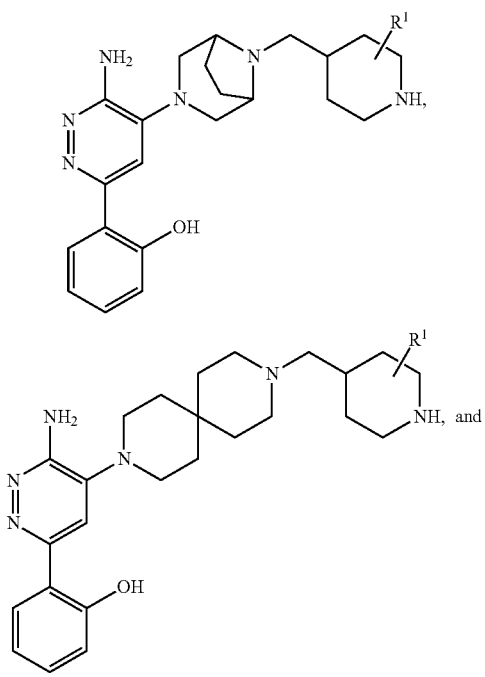

or a stereoisomer or tautomer thereof, or a pharmaceutically acceptable salt of any of the foregoing.

Embodiment A11 The compound of embodiment A2, or a stereoisomer or tautomer thereof, or a pharmaceutically acceptable salt of any of the foregoing, wherein [X] is absent, [Y] is ethenylene, wherein the ethenylene of [Y] is optionally substituted with one or more halo, and [Z] is 5-20 membered heteroaryl.

Embodiment A12 The compound of embodiment A11, or a stereoisomer or tautomer thereof, or a pharmaceutically acceptable salt of any of the foregoing, wherein the compound is selected from the group consisting of

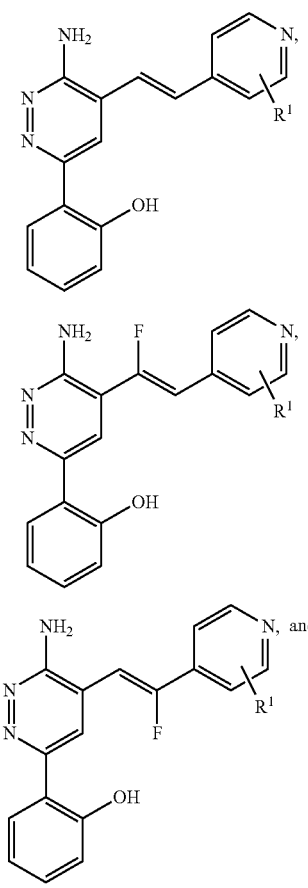

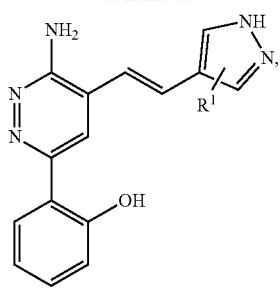

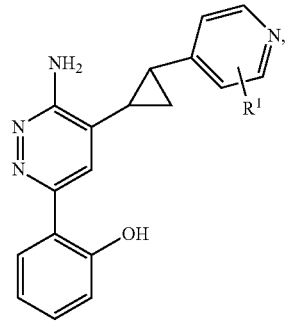

or a stereoisomer or tautomer thereof, or a pharmaceutically acceptable salt of any of the foregoing.

Embodiment A13 The compound of embodiment A2, or a stereoisomer or tautomer thereof, or a pharmaceutically acceptable salt of any of the foregoing, wherein [X] is absent, [Y] is ethynylene, and [Z] is 5-20 membered heteroaryl.

Embodiment A14 The compound of embodiment A13, or a stereoisomer or tautomer thereof, or a pharmaceutically acceptable salt of any of the foregoing, wherein the compound is selected from the group consisting of

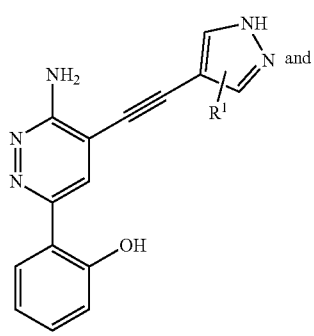

and

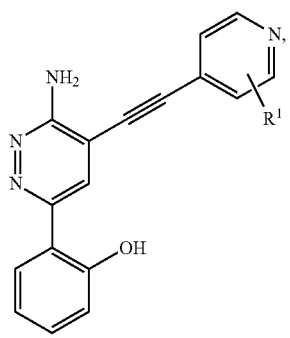

or a stereoisomer or tautomer thereof, or a pharmaceutically acceptable salt of any of the foregoing.

Embodiment A15 The compound of embodiment A2, or a stereoisomer or tautomer thereof, or a pharmaceutically acceptable salt of any of the foregoing, wherein [X] is absent, [Y] is cyclopropyl or cyclobutyl, and [Z] is 5-20 membered heteroaryl.

Embodiment A16 The compound of embodiment A15, or a stereoisomer or tautomer thereof, or a pharmaceutically acceptable salt of any of the foregoing, wherein the compound is or a stereoisomer or tautomer thereof, or a pharmaceutically acceptable salt of any of the foregoing.

Embodiment A17 The compound of embodiment A1, or a stereoisomer or tautomer thereof, or a pharmaceutically acceptable salt of any of the foregoing, wherein

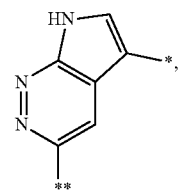

is

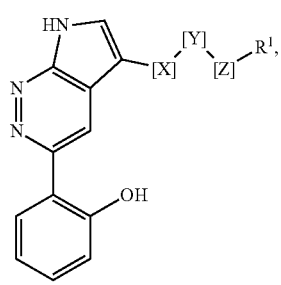

such that the compound of formula (I) is a compound of formula (I-B):

(I-B)

or a stereoisomer or tautomer thereof, or a pharmaceutically acceptable salt of any of the foregoing.

Embodiment A18 The compound of embodiment A1, or a stereoisomer or tautomer thereof, or a pharmaceutically acceptable salt of any of the foregoing, wherein is

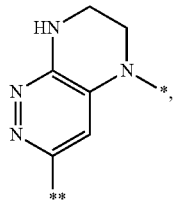

such that the compound of formula (I) is a compound of formula (I-C):

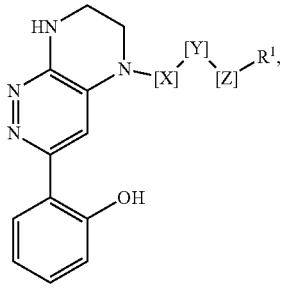
(I-C)

or a stereoisomer or tautomer thereof, or a pharmaceutically acceptable salt of any of the foregoing.

Embodiment A19 The compound of embodiment A1, or a stereoisomer or tautomer thereof, or a pharmaceutically acceptable salt of any of the foregoing, wherein

Ⓐ is

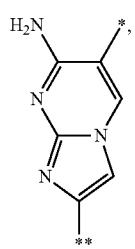

such that the compound of formula (I) is a compound of formula (I-D):

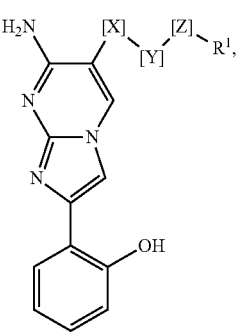
(I-D)

or a stereoisomer or tautomer thereof, or a pharmaceutically acceptable salt of any of the foregoing.

Embodiment A20 The compound of embodiment A1, or a stereoisomer or tautomer thereof, or a pharmaceutically acceptable salt of any of the foregoing, wherein

Ⓐ is

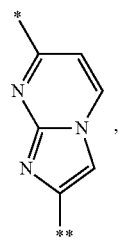

such that the compound of formula (I) is a compound of formula (I-E):

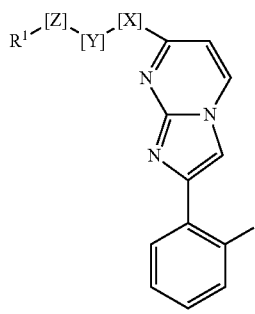
(I-E)

or a stereoisomer or tautomer thereof, or a pharmaceutically acceptable salt of any of the foregoing.

Embodiment A21 The compound of embodiment A20, or a stereoisomer or tautomer thereof, or a pharmaceutically acceptable salt of any of the foregoing, wherein [X] is 3-15 membered heterocyclyl; [Y] is absent; and [Z] is 5-20 membered heteroaryl.

Embodiment A22 The compound of embodiment A21, or a stereoisomer or tautomer thereof, or a pharmaceutically acceptable salt of any of the foregoing, wherein the compound is

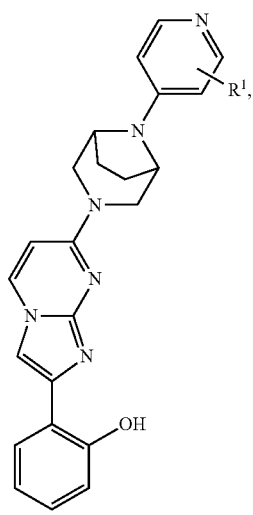

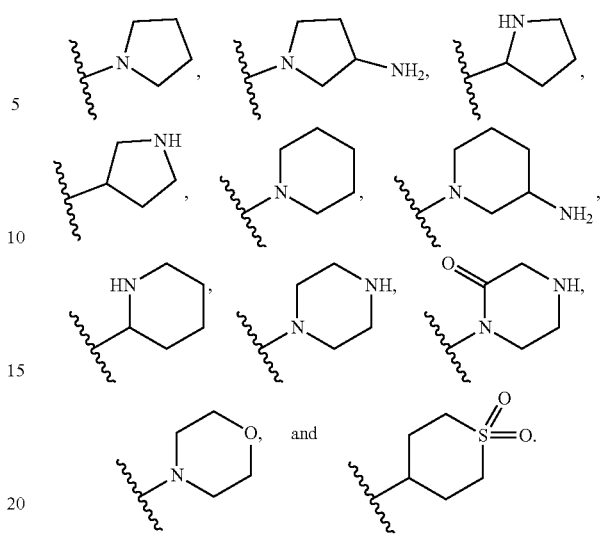

or a stereoisomer or tautomer thereof, or a pharmaceutically acceptable salt of any of the foregoing.

Embodiment A23 The compound of any one of embodiments A1-A22, or a stereoisomer or tautomer thereof, or a pharmaceutically acceptable salt of any of the foregoing, wherein $R^1$ is —C≡C—$R^a$.

Embodiment A24 The compound embodiment A23, or a stereoisomer or tautomer thereof, or a pharmaceutically acceptable salt of any of the foregoing, wherein $R^a$ is $C_{1-6}$alkyl, wherein the $C_{1-6}$alkyl of $R^a$ is optionally substituted with one or more $R^b$.

Embodiment A25 The compound of embodiment A23 or embodiment A24, or a stereoisomer or tautomer thereof, or a pharmaceutically acceptable salt of any of the foregoing, wherein $R^1$ is

Embodiment A26 The compound of embodiment A24 or embodiment A25, or a stereoisomer or tautomer thereof, or a pharmaceutically acceptable salt of any of the foregoing, wherein $R^b$ is 3-15 membered heterocyclyl, wherein the 3-15 membered heterocyclyl of $R^b$ is optionally substituted with one or more $R^c$.

Embodiment A27 The compound of embodiment A24 or embodiment A25, or a stereoisomer or tautomer thereof, or a pharmaceutically acceptable salt of any of the foregoing, wherein $R^b$ is 4-6 membered heterocyclyl, wherein the 4-6 membered heterocyclyl of $R^b$ is optionally substituted with one or more $R^c$.

Embodiment A28 The compound of embodiment A26 or embodiment A27, or a stereoisomer or tautomer thereof, or a pharmaceutically acceptable salt of any of the foregoing, wherein each $R^c$ is independently oxo or —$NH_2$.

Embodiment A29 The compound of any one of embodiments A24-A28, or a stereoisomer or tautomer thereof, or a pharmaceutically acceptable salt of any of the foregoing, wherein $R^b$ is selected from the group consisting of Embodiment A30 The compound of embodiment A24 or embodiment A25, or a stereoisomer or tautomer thereof, or a pharmaceutically acceptable salt of any of the foregoing, wherein $R^b$ is —N($R^x$)($R^y$).

Embodiment A31 The compound of embodiment A30, or a stereoisomer or tautomer thereof, or a pharmaceutically acceptable salt of any of the foregoing, wherein $R^x$ and $R^y$ are each independently H or $C_{1-6}$alkyl, wherein the $C_{1-6}$alkyl is optionally substituted with one or more —OH.

Embodiment A32 The compound of any one of embodiments A24, A25, A30, and A31, or a stereoisomer or tautomer thereof, or a pharmaceutically acceptable salt of any of the foregoing, wherein $R^b$ is selected from the group consisting of

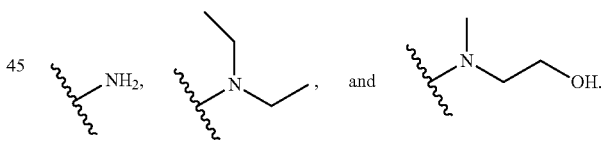

Embodiment A33 The compound of embodiment A24 or embodiment A25, or a stereoisomer or tautomer thereof, or a pharmaceutically acceptable salt of any of the foregoing, wherein $R^b$ is —OH.

Embodiment A34 The compound of embodiment A24 or embodiment A25, or a stereoisomer or tautomer thereof, or a pharmaceutically acceptable salt of any of the foregoing, wherein $R^b$ is —O-(3-15 membered heterocyclyl).

Embodiment A35 The compound of embodiment A24 or embodiment A25, or a stereoisomer or tautomer thereof, or a pharmaceutically acceptable salt of any of the foregoing, wherein $R^b$ is —O-(4-6 membered heterocyclyl).

Embodiment A36 The compound of any one of embodiments A24, A25, A34, and 35, or a stereoisomer or tautomer thereof, or a pharmaceutically acceptable salt of any of the foregoing, wherein $R^b$ is

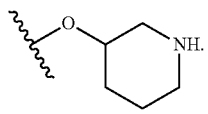 [SMILES: *OC1CCCNC1]

Embodiment A37 The compound of embodiment A24 or embodiment A25, or a stereoisomer or tautomer thereof, or a pharmaceutically acceptable salt of any of the foregoing, wherein $R^b$ is $C_{1-6}$alkoxy, wherein the $C_{1-6}$alkoxy of $R^b$ is optionally substituted with one or more —OH.

Embodiment A38 The compound of any one of embodiments A24, A25, and A37, or a stereoisomer or tautomer thereof, or a pharmaceutically acceptable salt of any of the foregoing, wherein $R^b$ is H

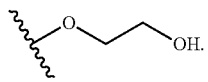

Embodiment A39 The compound of embodiment A23, or a stereoisomer or tautomer thereof, or a pharmaceutically acceptable salt of any of the foregoing, wherein $R^a$ is $C_{3-10}$cycloalykl, wherein the $C_{3-10}$ cycloalkyl of $R^a$ is optionally substituted with one or more $R^z$.

Embodiment A40 The compound of embodiment A23, or a stereoisomer or tautomer thereof, or a pharmaceutically acceptable salt of any of the foregoing, wherein $R^a$ is $C_{4-6}$cycloalykl, wherein the $C_{4-6}$cycloalkyl of $R^a$ is optionally substituted with one or more $R^z$.

Embodiment A41 The compound of embodiment A40, or a stereoisomer or tautomer thereof, or a pharmaceutically acceptable salt of any of the foregoing, wherein the $C_{4-6}$cycloalkyl of $R^a$ is optionally substituted with one or more —NH$_2$.

Embodiment A42 The compound of any one of embodiments A39-A41, or a stereoisomer or tautomer thereof, or a pharmaceutically acceptable salt of any of the foregoing, wherein $R^a$ is

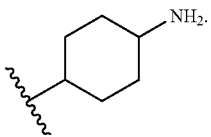 [SMILES: *C1CCC(N)CC1]

Embodiment A43 The compound of embodiment A23, or a stereoisomer or tautomer thereof, or a pharmaceutically acceptable salt of any of the foregoing, wherein $R^a$ is 3-15 membered heterocyclyl, wherein the 3-15 membered heterocyclyl of $R^a$ is optionally substituted with one or more $R^z$.

Embodiment A44 The compound of embodiment A23, or a stereoisomer or tautomer thereof, or a pharmaceutically acceptable salt of any of the foregoing, wherein $R^a$ is 4-6 membered heterocyclyl, wherein the 4-6 membered heterocyclyl of $R^a$ is optionally substituted with one or more $R^z$.

Embodiment A45 The compound of embodiment A44, or a stereoisomer or tautomer thereof, or a pharmaceutically acceptable salt of any of the foregoing, wherein the 4-6 membered heterocyclyl of $R^a$ is unsubstituted.

Embodiment A46 The compound of any one of embodiments A43-A45, or a stereoisomer or tautomer thereof, or a pharmaceutically acceptable salt of any of the foregoing, wherein $R^a$ is selected from the group consisting of

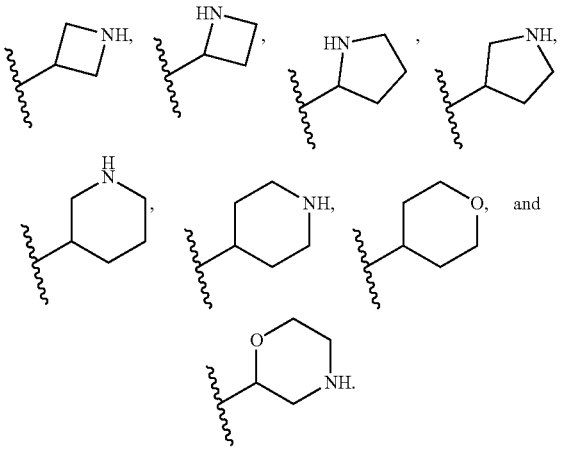

Embodiment A47 The compound of embodiment A23, or a stereoisomer or tautomer thereof, or a pharmaceutically acceptable salt of any of the foregoing, wherein $R^a$ is 5-20 membered heteroaryl, wherein the 5-20 membered heteroaryl of $R^a$ is optionally substituted with one or more $R^z$.

Embodiment A48 The compound of embodiment A23, or a stereoisomer or tautomer thereof, or a pharmaceutically acceptable salt of any of the foregoing, wherein $R^a$ is 5-6 membered heteroaryl, wherein the 5-6 membered heteroaryl of $R^a$ is optionally substituted with one or more $R^z$.

Embodiment A49 The compound of embodiment A48, or a stereoisomer or tautomer thereof, or a pharmaceutically acceptable salt of any of the foregoing, wherein the 5-6 membered heteroaryl of $R^a$ is optionally substituted with one or more $C_{1-6}$alkyl.

Embodiment A50 The compound of any one of embodiments A47-A49, or a stereoisomer or tautomer thereof, or a pharmaceutically acceptable salt of any of the foregoing, wherein $R^a$ is

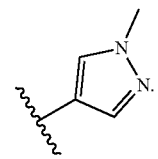 [SMILES: *c1cnn(C)c1]

Embodiment A51 The compound of any one of embodiments A1-A22, or a stereoisomer or tautomer thereof, or a pharmaceutically acceptable salt of any of the foregoing, wherein $R^1$ is —(CH$_2$)$_n$—$R^g$, wherein n is an integer from 1-6 and $R^g$ is —N($R^x$)($R^y$) or —OH.

Embodiment A52 The compound of embodiment A51, or a stereoisomer or tautomer thereof, or a pharmaceutically acceptable salt of any of the foregoing, wherein $R^g$ is —N($R^x$)($R^y$).

Embodiment A53 The compound of embodiment A52, or a stereoisomer or tautomer thereof, or a pharmaceutically acceptable salt of any of the foregoing, wherein $R^x$ and $R^y$ are both H.

Embodiment A54 The compound of embodiment A52, or a stereoisomer or tautomer thereof, or a pharmaceutically acceptable salt of any of the foregoing, wherein one of $R^x$ and $R^y$ is H and the other of $R^x$ and $R^y$ is —C(O)—CH$_2$—NH$_2$.

Embodiment A55 The compound of any one of embodiments A51-A54, or a stereoisomer or tautomer thereof, or a pharmaceutically acceptable salt of any of the foregoing, wherein n is 3.

Embodiment A56 The compound of embodiment A1, or a stereoisomer or tautomer thereof, or a pharmaceutically acceptable salt of any of the foregoing, wherein the compound is selected from compounds 1 to 34 of Table 1, or a stereoisomer or tautomer thereof, or a pharmaceutically acceptable salt of any of the foregoing.

Embodiment A57 A pharmaceutical composition, comprising: (i) an effective amount of a compound of any one of embodiments A1-A56, or a stereoisomer or tautomer thereof, or a pharmaceutically acceptable salt of any of the foregoing; and (ii) one or more pharmaceutically acceptable excipients.

Embodiment A58 The pharmaceutical composition of embodiment A57, further comprising an additional bioactive agent.

Embodiment A59 A method of modulating BRM in a cell, comprising exposing the cell to a composition comprising an effective amount of a compound according to any of embodiments A1-A56, or a stereoisomer or tautomer thereof, or a pharmaceutically acceptable salt of any of the foregoing, or a pharmaceutical composition of embodiment A57 or embodiment A58.

Embodiment A60 A method of inhibiting BRM in a cell, comprising exposing the cell to a composition comprising an effective amount of a compound according to any of embodiments A1-A56, or a stereoisomer or tautomer thereof, or a pharmaceutically acceptable salt of any of the foregoing, or a pharmaceutical composition of embodiment A57 or embodiment A58.

Embodiment A61 A method of degrading BRM in a cell, comprising exposing the cell to a composition comprising an effective amount of a compound according to any of embodiments A1-A56, or a stereoisomer or tautomer thereof, or a pharmaceutically acceptable salt of any of the foregoing, or a pharmaceutical composition of embodiment A57 or embodiment A58.

Embodiment A62 A method of treating a BRM-mediated disease, disorder, or condition in a human in need thereof, comprising administering to the human an effective amount of a compound of any one of embodiments A1-A56, or stereoisomer or tautomer thereof, or a pharmaceutically acceptable salt of any of the foregoing, or a composition of embodiment A57 or embodiment A58.

Embodiment A63 The method of embodiment A62, wherein the disease, disorder, or condition is cancer.

Embodiment A64 The method of embodiment A63, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, and Philadelphia chromosome positive CML.

Embodiment A65 A method of treating a BRG1-mediated disease, disorder, or condition in a human in need thereof, comprising administering to the human an effective amount of a compound of any one of embodiments A1-A56, or stereoisomer or tautomer thereof, or a pharmaceutically acceptable salt of any of the foregoing, or a composition of embodiment A57 or embodiment A58.

Embodiment A66 The method of embodiment A65, wherein the disease, disorder, or condition is cancer.

Embodiment A67 The method of embodiment A66, wherein the cancer is selected from the group consisting of non-small cell lung cancer, colorectal cancer, bladder cancer, cancer of unknown primary, glioma, breast cancer, melanoma, nonmelanoma skin cancer, endometrial cancer, esophagogastric cancer, pancreatic cancer, hepatobiliary cancer, soft tissue sarcoma, ovarian cancer, head cancer, neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment A68 A method of increasing the efficacy of a cancer treatment in a human, comprising administering to the human an effective amount of a compound of any one of embodiments A1-A56, or stereoisomer or tautomer thereof, or a pharmaceutically acceptable salt of any of the foregoing, or a pharmaceutical composition of embodiment A57 or embodiment A58.

Embodiment A69 A method of preventing or delaying development of cancer resistance to a cytotoxic agent in a human, comprising administering to the human an effective amount of a compound of any one of embodiments A1-A56, or stereoisomer or tautomer thereof, or a pharmaceutically acceptable salt of any of the foregoing, or a pharmaceutical composition of embodiment A57 or embodiment A58.

Embodiment A70 A method of extending the duration of response to a cancer therapy in a human, comprising administering to the human an effective amount of a compound of any one of embodiments A1-A56, or stereoisomer or tautomer thereof, or a pharmaceutically acceptable salt of any of the foregoing, or a composition of embodiment A57 or embodiment A58.

Embodiment A71 The method of any one of embodiments A68-A70, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, non-small cell lung cancer, colorectal cancer, cancer of unknown primary, nonmelanoma skin cancer, endometrial cancer, esophagogastric cancer, hepatobiliary cancer, soft tissue sarcoma, bone cancer, small-cell lung cancer, embryonal tumor, germ cell tumor, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment A72 Use of a compound of any one of embodiments A1-A56, or a stereoisomer or tautomer thereof, or a pharmaceutically acceptable salt of any of the foregoing, or a pharmaceutical composition of embodiment A57 or embodiment A58, in the manufacture of a medicament for use in the treatment of a disease, disorder, or condition modulated by BRM.

Embodiment A73 The use of embodiment A72, wherein the disease, disorder, or condition is cancer.

Embodiment A74 The use of embodiment A73, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, and Philadelphia chromosome positive CML.

Embodiment A75 Use of a compound of any one of embodiments A1-A56, or a stereoisomer or tautomer thereof, or a pharmaceutically acceptable salt of any of the foregoing, or a pharmaceutical composition of embodiment A57 or embodiment A58, in the manufacture of a medicament for use in the treatment of a disease, disorder, or condition modulated by BRG1.

Embodiment A76 The use of embodiment A75, wherein the disease, disorder, or condition is cancer.

Embodiment A77 The use of embodiment A76, wherein the cancer is selected from the group consisting of non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head cancer, neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment A78 Use of a compound of any one of embodiments A1-A56, or a stereoisomer or tautomer thereof, or a pharmaceutically acceptable salt of any of the foregoing, or a pharmaceutical composition of embodiment A57 or embodiment A58, in the manufacture of a medicament for use in the treatment of cancer.

Embodiment A79 The use of embodiment A78, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, non-small cell lung cancer, colorectal cancer, cancer of unknown primary, nonmelanoma skin cancer, endometrial cancer, esophagogastric cancer, hepatobiliary cancer, soft tissue sarcoma, bone cancer, small-cell lung cancer, embryonal tumor, germ cell tumor, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment A80 A compound of any one of embodiments A1-A56, or a stereoisomer or tautomer thereof, or a pharmaceutically acceptable salt of any of the foregoing, for use in the treatment of a disease, disorder, or condition modulated by BRM.

Embodiment A81 The compound of embodiment A80, or a stereoisomer or tautomer thereof, or a pharmaceutically acceptable salt of any of the foregoing, wherein the disease, disorder, or condition is cancer.

Embodiment A82 The compound of embodiment A81, or a stereoisomer or tautomer thereof, or a pharmaceutically acceptable salt of any of the foregoing, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, and Philadelphia chromosome positive CML.

Embodiment A83 A compound of any one of embodiments A1-A56, or a stereoisomer or tautomer thereof, or a pharmaceutically acceptable salt of any of the foregoing, for use in the treatment of a disease, disorder, or condition modulated by BRG1.

Embodiment A84 The compound of embodiment A83, or a stereoisomer or tautomer thereof, or a pharmaceutically acceptable salt of any of the foregoing, wherein the disease, disorder, or condition is cancer.

Embodiment A85 The compound of embodiment A84, or a stereoisomer or tautomer thereof, or a pharmaceutically acceptable salt of any of the foregoing, wherein the cancer is selected from the group consisting of non-small cell lung cancer, colorectal cancer, bladder cancer, cancer of unknown primary, glioma, breast cancer, melanoma, nonmelanoma skin cancer, endometrial cancer, esophagogastric cancer, pancreatic cancer, hepatobiliary cancer, soft tissue sarcoma, ovarian cancer, head cancer, neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment A86 A compound of any one of embodiments A1-A56, or a stereoisomer or tautomer thereof, or a pharmaceutically acceptable salt of any of the foregoing, for use in the treatment of cancer.

Embodiment A87 The compound of embodiment A86, or a stereoisomer or tautomer thereof, or a pharmaceutically acceptable salt of any of the foregoing, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, non-small cell lung cancer, colorectal cancer, cancer of unknown primary, nonmelanoma skin cancer, endometrial cancer, esophagogastric cancer, hepatobiliary cancer, soft tissue sarcoma, bone cancer, small-cell lung cancer, embryonal tumor, germ cell tumor, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment A88 A pharmaceutical composition of embodiment A57 or embodiment A58 for use in the treatment of a disease, disorder, or condition modulated by BRM.

Embodiment A89 The pharmaceutical composition of embodiment A88, wherein the disease, disorder, or condition is cancer.

Embodiment A90 The pharmaceutical composition of embodiment A89, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, and Philadelphia chromosome positive CML.

Embodiment A91 A pharmaceutical composition of embodiment A57 or embodiment A58 for use in the treatment of a disease, disorder, or condition modulated by BRG1.

Embodiment A92 The pharmaceutical composition of embodiment A91, wherein the disease, disorder, or condition is cancer.

Embodiment A93 The pharmaceutical composition of embodiment A92, wherein the cancer is selected from the group consisting of non-small cell lung cancer, colorectal cancer, bladder cancer, cancer of unknown primary, glioma, breast cancer, melanoma, nonmelanoma skin cancer, endometrial cancer, esophagogastric cancer, pancreatic cancer, hepatobiliary cancer, soft tissue sarcoma, ovarian cancer, head cancer, neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment A94 A pharmaceutical composition of embodiment A57 or embodiment A58 for use in the treatment of cancer.

Embodiment A95 The pharmaceutical composition of embodiment A94, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, non-small cell lung cancer, colorectal cancer, cancer of unknown primary, nonmelanoma skin cancer, endometrial cancer, esophagogastric cancer, hepatobiliary cancer, soft tissue sarcoma, bone cancer, small-cell lung cancer, embryonal tumor, germ cell tumor, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment A96 A process for preparing a compound of formula (I):

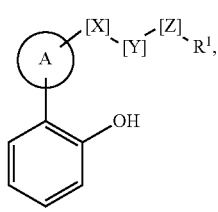
(I)

or a stereoisomer or tautomer thereof, or a pharmaceutically acceptable salt of any of the foregoing, wherein

is selected from the group consisting of:

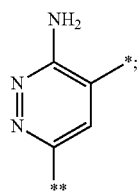
(a)

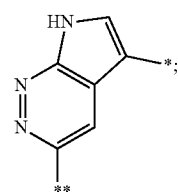
(b)

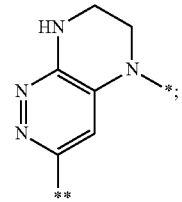
(c)

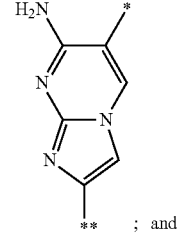
(d)

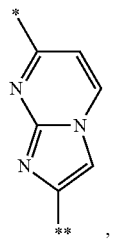
(e)

wherein, for (a)-(e), * denotes the point of attachment to [X], or, if [X] is absent, * denotes the point of attachment to [Y], and ** denotes the point of attachment to the remainder of the molecule;

and wherein:

(i) [X] is 3-15 membered heterocyclyl or 5-20 membered heteroaryl, provided that, when

is (a), then [X] is not

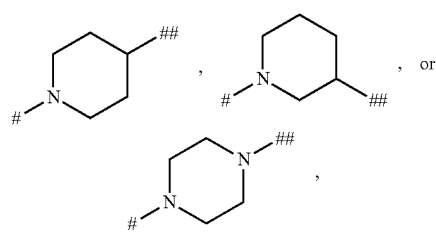

wherein # denotes the point of attachment to

and ## denotes the point of attachment to R$^1$,
[Y] is absent, and
[Z] is absent; or
(ii) [X] is 3-15 membered heterocyclyl or 5-20 membered heteroaryl, wherein the 3-15 membered heterocyclyl of [X] is optionally substituted with one or more —OH or C$_{1-6}$alkyl,
[Y] is absent, and
[Z] is 3-15 membered heterocyclyl or 5-20 membered heteroaryl,
provided that, when

is (a) and [X] is

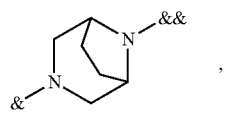

wherein & denotes the point of attachment to

and && denotes the point of attachment to [Z], then [Z] is not

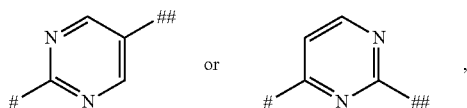

wherein # denotes the point of attachment to [X] and ## denotes the point of attachment to R$^1$; or
(iii) [X] is 3-15 membered heterocyclyl or 5-20 membered heteroaryl,
[Y] is methylene, wherein the methylene of [Y] is optionally substituted with one or more methyl group, and
[Z] is 3-15 membered heterocyclyl; or
(iv) [X] is absent,
[Y] is ethenylene, wherein the ethenylene of [Y] is optionally substituted with one or more halo, and
[Z] is 5-20 membered heteroaryl,
provided that

is (a), (b), (d), or (e); or (v) [X] is absent,
[Y] is ethynylene, and
[Z] is 5-20 membered heteroaryl,
provided that

is (a), (b), (d), or (e); or
(vi) [X] is absent,
[Y] is cyclopropyl or cyclobutyl, and
[Z] is 5-20 membered heteroaryl,
provided that is (a), (b), (d), or (e); and
R$^1$ is:
(a) —C≡C—R$^a$, wherein
(i) R$^a$ is C$_{1-6}$alkyl, wherein the C$_{1-6}$alkyl of R$^a$ is optionally substituted with one or more R$^b$, wherein each R$^b$ is independently 3-15 membered heterocyclyl, —O-(3-15 membered heterocyclyl), C$_{1-6}$alkoxy, —OH, —CN, halo, or —N(R$^x$)(R$^y$), wherein
the 3-15 membered heterocyclyl of R$^b$ is optionally substituted with one or more R$^c$, wherein each R$^c$ is independently —OH, —CN, halo, oxo, C$_{1-6}$alkyl, C$_{1-6}$alkoxy, C$_{3-10}$ cycloalkyl, 3-15 membered heterocyclyl, 5-20 membered heteroaryl, —C(O)-(3-15 membered heterocyclyl), —C(O)—C$_{1-6}$alkoxy, —C(O)—N(R$^x$)(R$^y$), or —N(R$^x$)(R$^y$), wherein
the C$_{1-6}$alkyl of R$^c$ is optionally substituted with one or more —OH, —CN, halo, C$_{1-6}$alkoxy, or 3-15 membered heterocyclyl,
the C$_{3-10}$ cycloalkyl of R$^c$ is optionally substituted with one or more halo, and
the 3-15 membered heterocyclyl of R$^c$ is optionally substituted with one or more C$_{1-6}$ alkyl or —C(O)—C$_{1-6}$alkyl, and
the C$_{1-6}$alkoxy of R$^b$ is optionally substituted with one or more OH, or
(ii) R$^a$ is C$_{3-10}$ cycloalkyl, wherein the C$_{3-10}$ cycloalkyl of R$^a$ is optionally substituted with one or more R$^z$, or
(iii) R$^a$ is 3-15 membered heterocyclyl, wherein the 3-15 membered heterocyclyl of R$^a$ is optionally substituted with one or more R$^z$, or
(iv) R$^a$ is 5-20 membered heteroaryl, wherein the 5-20 membered heteroaryl of R$^a$ is optionally substituted with one or more —OH, —CN, halo, C$_{1-6}$alkyl, —N(R$^x$)(R$^y$), or —C(O)—N(R$^x$)(R$^y$), or
(b) —(CH$_2$)$_n$—R$^g$, wherein
n is an integer from 1-6, and
R$^g$ is —N(R$^x$)(R$^y$) or —OH;
R$^z$ is, independently at each occurrence, —OH, —CN, halo, C$_{1-6}$alkyl, C$_{1-6}$alkoxy, —N(R$^x$)(R$^y$), or —C(O)—N(R$^x$)(R$^y$); and
the R$^x$ and R$^y$ of —C(O)N(R$^x$)(R$^y$) and —N(R$^x$)(R$^y$) are, independently of each other and independently at each occurrence, H, —C(O)—(CH$_2$)$_p$—N(R$^p$)(R$^q$), 5-20 membered heteroaryl, or C$_{1-6}$alkyl, wherein
p is an integer from 1-6, $R^p$ and $R^q$ are, independently of each other and independently at each occurrence H, or $C_{1-6}$alkyl, and the $C_{1-6}$alkyl of $R^x$ or $R^y$ is optionally substituted with one or more —OH, 3-15 membered heterocyclyl, or —C(O)-(3-15 membered heterocyclyl).

Embodiment A97 A compound, or a stereoisomer or tautomer thereof, or a pharmaceutically acceptable salt of any of the foregoing, prepared by the process of embodiment A96.

Embodiment A98 The invention as described hereinbefore in Enumerated Embodiments (A).

Enumerated Embodiments (B)

Embodiment B1 A compound of formula (II):

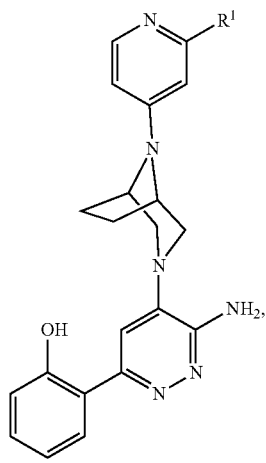

(II)

or a stereoisomer or tautomer thereof, or a pharmaceutically acceptable salt of any of the foregoing, wherein:

(i) $R^1$ is —C≡C—$R^a$, wherein
(a) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$cycloalkyl, 3-15 membered heterocyclyl, 5-20 membered heteroaryl, —C(O)-(3-15 membered heterocyclyl), —C(O)—$C_{1-6}$alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$cycloalkyl of $R^c$ is optionally substituted with one or more halo, and
the 3-15 membered heterocyclyl of $R^c$ is optionally substituted with one or more $C_{1-6}$alkyl or —C(O)—$C_{1-6}$alkyl, and
the $C_{1-6}$alkoxy of $R^b$ is optionally substituted with one or more —OH, or (b) $R^a$ is $C_{3-10}$cycloalkyl, wherein the $C_{3-10}$cycloalkyl of $R^a$ is optionally substituted with one or more $R^z$, or
(c) $R^a$ is 3-15 membered heterocyclyl, wherein the 3-15 membered heterocyclyl of $R^a$ is optionally substituted with one or more $R^z$, or
(d) $R^a$ is 5-20 membered heteroaryl, wherein the 5-20 membered heteroaryl of $R^a$ is optionally substituted with one or more $R^z$, or (ii) $R^1$ is —$(CH_2)_n$—$R^g$, wherein $R^g$ is —N($R^x$)($R^y$) or —OH, and n is an integer from 1-6;

wherein $R^z$ is, independently at each occurrence, —OH, —CN, halo, $C_{1-6}$alkyl, $C_{1-6}$alkoxy, —N($R^x$)($R^y$), or —C(O)—N($R^x$)($R^y$); and the $R^x$ and $R^y$ of —C(O)N($R^x$)($R^y$) and —N($R^x$)($R^y$) are, independently of each other and independently at each occurrence, H, —C(O)—$(CH_2)_p$—N($R^p$)($R^q$), 5-20 membered heteroaryl, or $C_{1-6}$ alkyl, wherein p is an integer from 1-6, $R^p$ and $R^q$ are, independently of each other and independently at each occurrence H, or $C_{1-6}$ alkyl, and the $C_{1-6}$alkyl of $R^x$ or $R^y$ is optionally substituted with one or more —OH, 3-15 membered heterocyclyl, or —C(O)-(3-15 membered heterocyclyl).

Embodiment B2 The compound of embodiment B1, or a stereoisomer or tautomer thereof, or a pharmaceutically acceptable salt of any of the foregoing, wherein $R^1$ is —C≡C—$R^a$, such that the compound of formula (II) is a compound of formula (II-A):

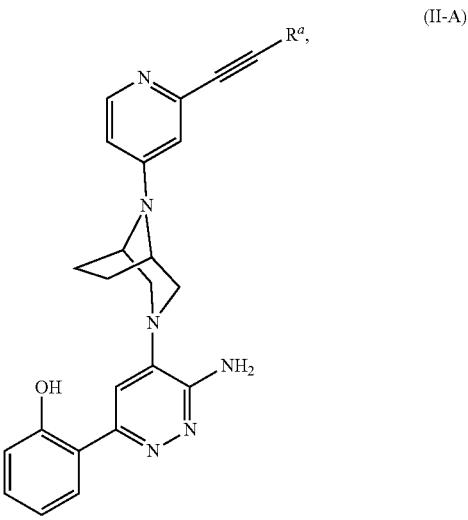

(II-A)

or a stereoisomer or tautomer thereof, or a pharmaceutically acceptable salt of any of the foregoing.

Embodiment B3 The compound of embodiment B1 or embodiment B2, or a stereoisomer or tautomer thereof, or a pharmaceutically acceptable salt of any of the foregoing, wherein $R^a$ is $C_{1-6}$alkyl, wherein the $C_{1-6}$alkyl of $R^a$ is optionally substituted with one or more $R^b$.

Embodiment B4 The compound of any one of embodiments B1-B3, or a stereoisomer or tautomer thereof, or a pharmaceutically acceptable salt of any of the foregoing, wherein the compound of formula (II) is a compound of formula (II-A1):

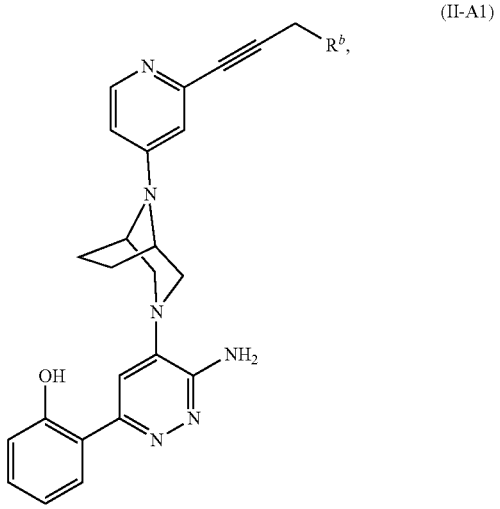

(II-A1)

or a stereoisomer or tautomer thereof, or a pharmaceutically acceptable salt of any of the foregoing.

Embodiment B5 The compound of embodiment B3 or embodiment B4, or a stereoisomer or tautomer thereof, or a pharmaceutically acceptable salt of any of the foregoing, wherein $R^b$ is 3-15 membered heterocyclyl, wherein the 3-15 membered heterocyclyl of $R^b$ is optionally substituted with one or more $R^c$.

Embodiment B6 The compound of embodiment B3 or embodiment B4, or a stereoisomer or tautomer thereof, or a pharmaceutically acceptable salt of any of the foregoing, wherein $R^b$ is 4-6 membered heterocyclyl, wherein the 4-6 membered heterocyclyl of $R^b$ is optionally substituted with one or more $R^c$.

Embodiment B7 The compound of embodiment B5 or embodiment B6, or a stereoisomer or tautomer thereof, or a pharmaceutically acceptable salt of any of the foregoing, wherein each $R^c$ is independently oxo or —NH$_2$.

Embodiment B8 The compound of any one of embodiments B3-B7, or a stereoisomer or tautomer thereof, or a pharmaceutically acceptable salt of any of the foregoing, wherein $R^b$ is selected from the group consisting of

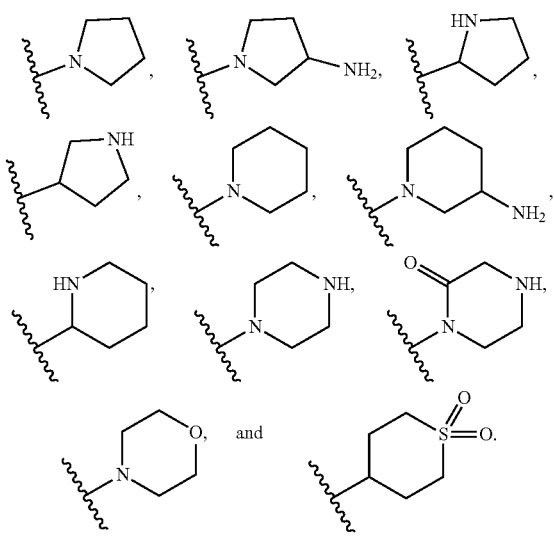

Embodiment B9 The compound of embodiment B3 or embodiment B4, or a stereoisomer or tautomer thereof, or a pharmaceutically acceptable salt of any of the foregoing, wherein $R^b$ is —N($R^x$)($R^y$).

Embodiment B10 The compound of embodiment B9, or a stereoisomer or tautomer thereof, or a pharmaceutically acceptable salt of any of the foregoing, wherein $R^x$ and $R^y$ are each independently H or $C_{1-6}$alkyl, wherein the $C_{1-6}$alkyl is optionally substituted with one or more —OH.

Embodiment B11 The compound of any one of embodiments B3, B4, B9, and B10, or a stereoisomer or tautomer thereof, or a pharmaceutically acceptable salt of any of the foregoing, wherein $R^b$ is selected from the group consisting of

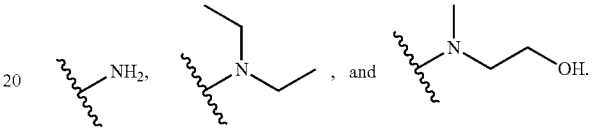

Embodiment B12 The compound of embodiment B3 or embodiment B4, or a stereoisomer or tautomer thereof, or a pharmaceutically acceptable salt of any of the foregoing, wherein $R^b$ is —OH.

Embodiment B13 The compound of embodiment B3 or embodiment B4, or a stereoisomer or tautomer thereof, or a pharmaceutically acceptable salt of any of the foregoing, wherein $R^b$ is —O-(3-15 membered heterocyclyl).

Embodiment B14 The compound of embodiment B3 or embodiment B4, or a stereoisomer or tautomer thereof, or a pharmaceutically acceptable salt of any of the foregoing, wherein $R^b$ is —O-(4-6 membered heterocyclyl).

Embodiment B15 The compound of any one of embodiments B3, B4, B13, and B14, or a stereoisomer or tautomer thereof, or a pharmaceutically acceptable salt of any of the foregoing, wherein R is

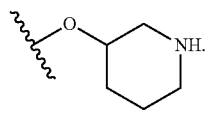 [SMILES: *OC1CCCNC1]

Embodiment B16 The compound of embodiment B3 or embodiment B4, or a stereoisomer or tautomer thereof, or a pharmaceutically acceptable salt of any of the foregoing, wherein $R^b$ is $C_{1-6}$alkoxy, wherein the $C_{1-6}$alkoxy of $R^b$ is optionally substituted with one or more —OH.

Embodiment B17 The compound of any one of embodiments B3, B4, and B16, or a stereoisomer or tautomer thereof, or a pharmaceutically acceptable salt of any of the foregoing, wherein $R^b$ is

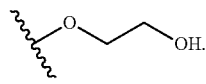 [SMILES: *OCCO]

Embodiment B18 The compound of embodiment B1 or embodiment B2, or a stereoisomer or tautomer thereof, or a pharmaceutically acceptable salt of any of the foregoing, wherein $R^a$ is $C_{3-10}$ cycloalkyl, wherein the $C_{3-10}$ cycloalkyl of R$^a$ is optionally substituted with one or more —OH, —CN, halo, C$_{1-6}$alkyl, —N(R$^x$)(R$^y$), or —C(O)—N(R$^x$)(R$^y$).

Embodiment B19 The compound of embodiment B1 or embodiment B2, or a stereoisomer or tautomer thereof, or a pharmaceutically acceptable salt of any of the foregoing, wherein R$^a$ is C$_{4-6}$cycloalkyl, wherein the C$_{4-6}$cycloalkyl of R$^a$ is optionally substituted with one or more —OH, —CN, halo, C$_{1-6}$alkyl, —N(R$^x$)(R$^y$), or —C(O)—N(R$^x$)(R$^y$).

Embodiment B20 The compound of embodiment B19, or a stereoisomer or tautomer thereof, or a pharmaceutically acceptable salt of any of the foregoing, wherein the C$_{4-6}$cycloalkyl of R$^a$ is optionally substituted with one or more —NH$_2$.

Embodiment B21 The compound of any one of embodiments B18-B20, or a stereoisomer or tautomer thereof, or a pharmaceutically acceptable salt of any of the foregoing, wherein R$^a$ is

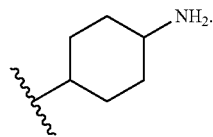 [SMILES: *C1CCC(N)CC1]

Embodiment B22 The compound of embodiment B1 or embodiment B2, or a stereoisomer or tautomer thereof, or a pharmaceutically acceptable salt of any of the foregoing, wherein R$^a$ is 3-15 membered heterocyclyl, wherein the 3-15 membered heterocyclyl of R$^a$ is optionally substituted with one or more R$^z$.

Embodiment B23 The compound of embodiment B1 or embodiment B2, or a stereoisomer or tautomer thereof, or a pharmaceutically acceptable salt of any of the foregoing, wherein R$^a$ is 4-6 membered heterocyclyl, wherein the 4-6 membered heterocyclyl of R$^a$ is optionally substituted with one or more R$^z$.

Embodiment B24 The compound of embodiment B23, or a stereoisomer or tautomer thereof, or a pharmaceutically acceptable salt of any of the foregoing, wherein the 4-6 membered heterocyclyl of R$^a$ is unsubstituted.

Embodiment B25 The compound of any one of embodiments B22-B24, or a stereoisomer or tautomer thereof, or a pharmaceutically acceptable salt of any of the foregoing, wherein R$^a$ is selected from the group consisting of

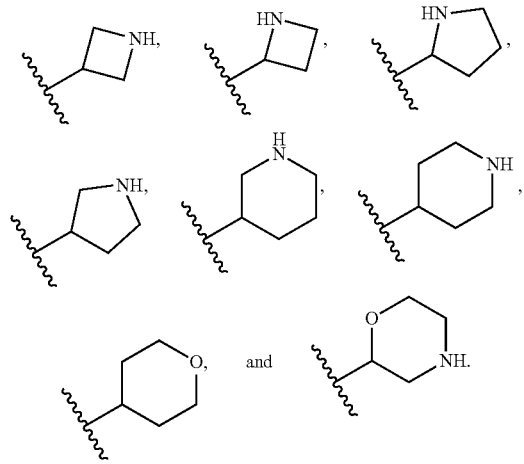

Embodiment B26 The compound of embodiment B1 or embodiment B2, or a stereoisomer or tautomer thereof, or a pharmaceutically acceptable salt of any of the foregoing, wherein R$^a$ is 5-20 membered heteroaryl, wherein the 5-20 membered heteroaryl of R$^a$ is optionally substituted with one or more R$^z$.

Embodiment B27 The compound of embodiment B1 or embodiment B2, or a stereoisomer or tautomer thereof, or a pharmaceutically acceptable salt of any of the foregoing, wherein R$^a$ is 5-6 membered heteroaryl, wherein the 5-6 membered heteroaryl of R$^a$ is optionally substituted with one or more R$^z$.

Embodiment B28 The compound of embodiment B27, or a stereoisomer or tautomer thereof, or a pharmaceutically acceptable salt of any of the foregoing, wherein the 5-6 membered heteroaryl of R$^a$ is optionally substituted with one or more C$_{1-6}$alkyl.

Embodiment B29 The compound of any one of embodiments B26-B28, or a stereoisomer or tautomer thereof, or a pharmaceutically acceptable salt of any of the foregoing, wherein R$^a$ is

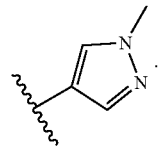 [SMILES: *c1cnn(C)c1]

Embodiment B30 The compound of embodiment B1, or a stereoisomer or tautomer thereof, or a pharmaceutically acceptable salt of any of the foregoing, wherein R$^1$ is —(CH$_2$)$_n$—R$^g$, wherein n is an integer from 1-6 and R$^g$ is —N(R$^x$)(R$^y$) or —OH.

Embodiment B31 The compound of embodiment B30, or a stereoisomer or tautomer thereof, or a pharmaceutically acceptable salt of any of the foregoing, wherein R$^g$ is —N(R$^x$)(R$^y$), such that the compound of formula (II) is a compound of formula (II-B):

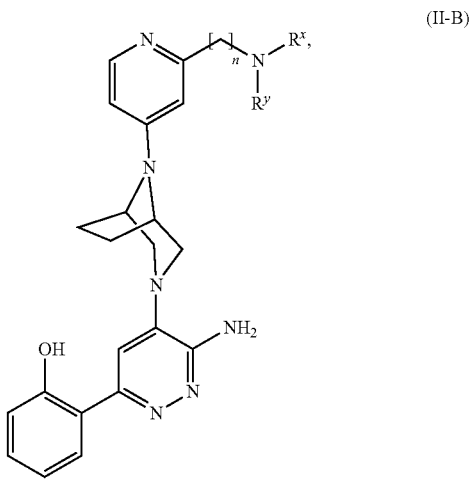

(II-B)

or a stereoisomer or tautomer thereof, or a pharmaceutically acceptable salt of any of the foregoing.

Embodiment B32 The compound of embodiment B31, or a stereoisomer or tautomer thereof, or a pharmaceutically acceptable salt of any of the foregoing, wherein R$^x$ and R$^y$ are both H.

Embodiment B33 The compound of embodiment B31, or a stereoisomer or tautomer thereof, or a pharmaceutically acceptable salt of any of the foregoing, wherein one of $R^x$ and $R^y$ is H and the other of $R^x$ and $R^y$ is —C(O)—CH$_2$—NH$_2$.

Embodiment B34 The compound of embodiment B32 or embodiment B33, or a stereoisomer or tautomer thereof, or a pharmaceutically acceptable salt of any of the foregoing, wherein n is 3.

Embodiment B35 The compound of embodiment B1, or a stereoisomer or tautomer thereof, or a pharmaceutically acceptable salt of any of the foregoing, wherein the compound is selected from compounds 1 to 34 of Table 1, or a stereoisomer or tautomer thereof, or a pharmaceutically acceptable salt of any of the foregoing.

Embodiment B36 A pharmaceutical composition, comprising (i) an effective amount of a compound of any one of embodiments B1-B35, or a stereoisomer or tautomer thereof, or a pharmaceutically acceptable salt of any of the foregoing, and (ii) one or more pharmaceutically acceptable excipients.

Embodiment B37 The pharmaceutical composition of embodiment B36, further comprising an additional bioactive agent.

Embodiment B38 A method of modulating BRM in a cell, comprising exposing the cell to an effective amount of a compound of any one of embodiments B1-B35, or a stereoisomer or tautomer thereof, or a pharmaceutically acceptable salt of any of the foregoing, or a pharmaceutical composition of embodiment B36 or embodiment B37.

Embodiment B39 A method of inhibiting BRM in a cell, comprising exposing the cell to an effective amount of a compound of any one of embodiments B1-B35, or a stereoisomer or tautomer thereof, or a pharmaceutically acceptable salt of any of the foregoing, or a pharmaceutical composition of embodiment B36 or embodiment B37.

Embodiment B40 A method of degrading BRM in a cell, comprising exposing the cell to an effective amount of a compound according to any one of embodiments B1-B35, or a stereoisomer or tautomer thereof, or a pharmaceutically acceptable salt of any of the foregoing, or a pharmaceutical composition of embodiment B36 or embodiment B37.

Embodiment B41 A method of treating a BRM-mediated disease, disorder, or condition in a human in need thereof, comprising administering to the human an effective amount of a compound of any one of embodiments B1-B35, or stereoisomer or tautomer thereof, or a pharmaceutically acceptable salt of any of the foregoing, or a pharmaceutical composition of embodiment B36 or embodiment B37.

Embodiment B42 The method of embodiment B41, wherein the disease, disorder, or condition is cancer.

Embodiment B43 The method of embodiment B41, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, and Philadelphia chromosome positive CML Embodiment B44 A method of treating a BRG1-mediated disease, disorder, or condition in a human in need thereof, comprising administering to the human an effective amount of a compound of any one of embodiments B1-B35, or stereoisomer or tautomer thereof, or a pharmaceutically acceptable salt of any of the foregoing, or a pharmaceutical composition of embodiment B36 or embodiment B37.

Embodiment B45 The method of embodiment B44, wherein the disease, disorder, or condition is cancer.

Embodiment B46 The method of embodiment B45, wherein the cancer is selected from the group consisting of non-small cell lung cancer, colorectal cancer, bladder cancer, cancer of unknown primary, glioma, breast cancer, melanoma, nonmelanoma skin cancer, endometrial cancer, esophagogastric cancer, pancreatic cancer, hepatobiliary cancer, soft tissue sarcoma, ovarian cancer, head cancer, neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment B47 A method of increasing the efficacy of a cancer treatment in a human, comprising administering to the human an effective amount of a compound of any one of embodiments B1-B35, or stereoisomer or tautomer thereof, or a pharmaceutically acceptable salt of any of the foregoing, or a pharmaceutical composition of embodiment B36 or embodiment B37.

Embodiment B48 A method of preventing or delaying development of cancer resistance to a cytotoxic agent in a human, comprising administering to the human an effective amount of a compound of any one of embodiments B1-B35, or stereoisomer or tautomer thereof, or a pharmaceutically acceptable salt of any of the foregoing, or a pharmaceutical composition of embodiment B36 or embodiment B37.

Embodiment' B49 A method of extending the duration of response to a cancer therapy in a human, comprising administering to the human an effective amount of a compound of any one of embodiments B1-B35, or stereoisomer or tautomer thereof, or a pharmaceutically acceptable salt of any of the foregoing, or a pharmaceutical composition of embodiment B36 or embodiment B37.

Embodiment B50 The method of any one of embodiments B47-B49, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, non-small cell lung cancer, colorectal cancer, cancer of unknown primary, nonmelanoma skin cancer, endometrial cancer, esophagogastric cancer, hepatobiliary cancer, soft tissue sarcoma, bone cancer, small-cell lung cancer, embryonal tumor, germ cell tumor, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment B51 Use of a compound of any one of embodiments B1-B35, or a stereoisomer or tautomer thereof, or a pharmaceutically acceptable salt of any of the foregoing, or a pharmaceutical composition of embodiment B B 36 or embodiment B 37, in the manufacture of a medicament for use in the treatment of a disease, disorder, or condition mediated by BRM.

Embodiment B52 The use of embodiment B 51, wherein the disease, disorder, or condition is cancer.

Embodiment B53 The use of embodiment B 52, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, and Philadelphia chromosome positive CML.

Embodiment B54 Use of a compound of any one of embodiments B1-B35, or a stereoisomer or tautomer thereof, or a pharmaceutically acceptable salt of any of the foregoing, or a pharmaceutical composition of embodiment B36 or embodiment B37, in the manufacture of a medicament for use in the treatment of a disease, disorder, or condition mediated by BRG1.

Embodiment B55 The use of embodiment B54, wherein the disease, disorder, or condition is cancer.

Embodiment B56 The use of embodiment B55, wherein the cancer is selected from the group consisting of non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head cancer, neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment B57 Use of a compound of any one of embodiments B1-B35, or a stereoisomer or tautomer thereof, or a pharmaceutically acceptable salt of any of the foregoing, or a pharmaceutical composition of embodiment B36 or embodiment B37, in the manufacture of a medicament for use in the treatment of cancer.

Embodiment B58 The use of embodiment B50, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, non-small cell lung cancer, colorectal cancer, cancer of unknown primary, nonmelanoma skin cancer, endometrial cancer, esophagogastric cancer, hepatobiliary cancer, soft tissue sarcoma, bone cancer, small-cell lung cancer, embryonal tumor, germ cell tumor, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment B59 A compound of any one of embodiments B1-B35, or a stereoisomer or tautomer thereof, or a pharmaceutically acceptable salt of any of the foregoing, or a pharmaceutical composition of embodiment B36 or embodiment B37, for use in the treatment of a disease, disorder, or condition mediated by BRM.

Embodiment B60 The compound of embodiment B59, or a stereoisomer or tautomer thereof, or a pharmaceutically acceptable salt of any of the foregoing, wherein the disease, disorder, or condition is cancer.

Embodiment B61 The compound of embodiment B60, or a stereoisomer or tautomer thereof, or a pharmaceutically acceptable salt of any of the foregoing, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, and Philadelphia chromosome positive CML.

Embodiment B62 A compound of any one of embodiments B1-B35, or a stereoisomer or tautomer thereof, or a pharmaceutically acceptable salt of any of the foregoing, or a pharmaceutical composition of embodiment B36 or embodiment B37, for use in the treatment of a disease, disorder, or condition mediated by BRG1.

Embodiment B63 The compound of embodiment B62, or a stereoisomer or tautomer thereof, or a pharmaceutically acceptable salt of any of the foregoing, wherein the disease, disorder, or condition is cancer.

Embodiment B64 The compound of embodiment B63, or a stereoisomer or tautomer thereof, or a pharmaceutically acceptable salt of any of the foregoing, wherein the cancer is selected from the group consisting of non-small cell lung cancer, colorectal cancer, bladder cancer, cancer of unknown primary, glioma, breast cancer, melanoma, nonmelanoma skin cancer, endometrial cancer, esophagogastric cancer, pancreatic cancer, hepatobiliary cancer, soft tissue sarcoma, ovarian cancer, head cancer, neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment B65 A compound of any one of embodiments B1-B35, or a stereoisomer or tautomer thereof, or a pharmaceutically acceptable salt of any of the foregoing, or a pharmaceutical composition of embodiment B36 or embodiment B37, for use in the treatment of cancer.

Embodiment B66 The compound of embodiment B65, or a stereoisomer or tautomer thereof, or a pharmaceutically acceptable salt of any of the foregoing, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, non-small cell lung cancer, colorectal cancer, cancer of unknown primary, nonmelanoma skin cancer, endometrial cancer, esophagogastric cancer, hepatobiliary cancer, soft tissue sarcoma, bone cancer, small-cell lung cancer, embryonal tumor, germ cell tumor, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment B67 A pharmaceutical composition of embodiment B36 or embodiment B37 for use in the treatment of a disease, disorder, or condition modulated by BRM.

Embodiment B68 The pharmaceutical composition of embodiment B67, wherein the disease, disorder, or condition is cancer.

Embodiment B69 The pharmaceutical composition of embodiment B68, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, and Philadelphia chromosome positive CML.

Embodiment B70 A pharmaceutical composition of embodiment B36 or embodiment B37 for use in the treatment of a disease, disorder, or condition modulated by BRG1.

Embodiment B71 The pharmaceutical composition of embodiment B70, wherein the disease, disorder, or condition is cancer.

Embodiment B72 The pharmaceutical composition of embodiment B71, wherein the cancer is selected from the group consisting of non-small cell lung cancer, colorectal cancer, bladder cancer, cancer of unknown primary, glioma, breast cancer, melanoma, nonmelanoma skin cancer, endometrial cancer, esophagogastric cancer, pancreatic cancer, hepatobiliary cancer, soft tissue sarcoma, ovarian cancer, head cancer, neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment B73 A pharmaceutical composition of embodiment B36 or embodiment B37 for use in the treatment of cancer.

Embodiment B74 The pharmaceutical composition of embodiment B73, wherein the cancer is selected from the group consisting of squamous-cell carcinoma, basal-cell carcinoma, adenocarcinoma, hepatocellular carcinomas, renal-cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, testicular cancer, thyroid cancer, uterine cancer, leukemia, lymphomas, Burkitt's lymphoma, Non-Hodgkin's lymphoma, melanoma, myeloproliferative diseases, sarcomas, Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal-cell tumors, meningiomas, meningeal sarcomas, neurofibromas, Schwannomas, astrocytoma, carcinosarcoma, Hodgkin's disease, Wilms' tumor, teratocarcinomas, T-lineage Acute lymphoblastic Leukemia (T-ALL), T-lineage Lymphoblastic Lymphoma (T-LL), Peripheral T-cell lymphoma, Adult T-cell Leukemia, Pre-B ALL, Pre-B Lymphomas, Large B-cell Lymphoma, B-cell ALL, Philadelphia chromosome positive ALL, Philadelphia chromosome positive CML, non-small cell lung cancer, colorectal cancer, cancer of unknown primary, nonmelanoma skin cancer, endometrial cancer, esophagogastric cancer, hepatobiliary cancer, soft tissue sarcoma, bone cancer, small-cell lung cancer, embryonal tumor, germ cell tumor, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Embodiment B75 A process for preparing a compound of formula (II):

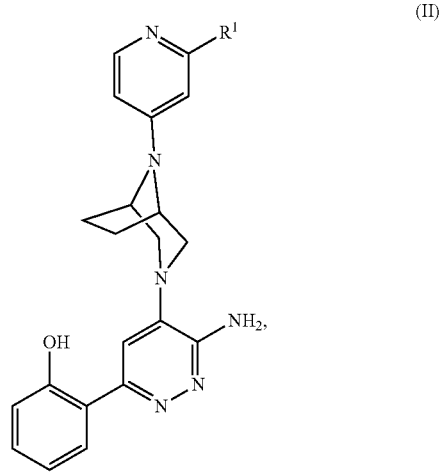

(II)

or a stereoisomer or tautomer thereof, or a pharmaceutically acceptable salt of any of the foregoing, wherein:
(i) $R^1$ is —C≡C—$R^a$, wherein
(a) $R^a$ is $C_{1-6}$alkyl, wherein the $C_{1-6}$alkyl of $R^a$ is optionally substituted with one or more $R^b$, wherein each $R^b$ is independently 3-15 membered heterocyclyl, —O-(3-15 membered heterocyclyl), $C_{1-6}$alkoxy, —OH, —CN, halo, or —N($R^x$)($R^y$), wherein
the 3-15 membered heterocyclyl of $R^b$ is optionally substituted with one or more $R^c$, wherein each $R^c$ is independently —OH, —CN, halo, oxo, $C_{1-6}$alkyl, $C_{1-6}$alkoxy, $C_{3-10}$ cycloalkyl, 3-15 membered heterocyclyl, 5-20 membered heteroaryl, —C(O)-(3-15 membered heterocyclyl), —C(O)—Cl-6alkoxy, —C(O)—N($R^x$)($R^y$), or —N($R^x$)($R^y$), wherein
the $C_{1-6}$alkyl of $R^c$ is optionally substituted with one or more —OH, —CN, halo, $C_{1-6}$alkoxy, or 3-15 membered heterocyclyl,
the $C_{3-10}$ cycloalkyl of $R^c$ is optionally substituted with one or more halo, and
the 3-15 membered heterocyclyl of $R^c$ is optionally substituted with one or more $C_{1-6}$alkyl or —C(O)—$C_{1-6}$alkyl, and
the $C_{1-6}$alkoxy of $R^b$ is optionally substituted with one or more —OH, or
(b) $R^a$ is $C_{3-10}$ cycloalkyl, wherein the $C_{3-10}$ cycloalkyl of $R^a$ is optionally substituted with one or more $R^z$, or
(c) $R^a$ is 3-15 membered heterocyclyl, wherein the 3-15 membered heterocyclyl of $R^a$ is optionally substituted with one or more $R^z$, or
(d) $R^a$ is 5-20 membered heteroaryl, wherein the 5-20 membered heteroaryl of $R^a$ is optionally substituted with one or more $R^z$, or
(ii) $R^1$ is —$(CH_2)_n$—$R^g$, wherein
n is an integer from 1-6, and
$R^g$ is —N($R^x$)($R^y$) or —OH,
wherein
$R^z$ is, independently at each occurrence, —OH, —CN, halo, $C_{1-6}$alkyl, $C_{1-6}$alkoxy, —N($R^x$)($R^y$), or —C(O)—N($R^x$)($R^y$); and
the $R^x$ and $R^y$ of —C(O)N($R^x$)($R^y$) and —N($R^x$)($R^y$) are, independently of each other and independently at each occurrence, H, —C(O)—$(CH_2)_p$—N($R^p$)($R^q$), 5-20 membered heteroaryl, or $C_{1-6}$ alkyl, wherein the $C_{1-6}$alkyl of $R^x$ or $R^y$ is optionally substituted with one or more —OH, 3-15 membered heterocyclyl, or —C(O)-(3-15 membered heterocyclyl).

Embodiment B76 A compound, or a stereoisomer or tautomer thereof, or a pharmaceutically acceptable salt of any of the foregoing, prepared by the process of embodiment B75.

Embodiment B77 The invention as described hereinbefore in Enumerated Embodiments (B).

EXAMPLES

The following examples are offered by way of illustration and not by way of limitation.

Abbreviations

Ac—acetyl
ACN—acetonitrile
ATP—adenosine triphosphate
Boc—tert—butyloxycarbonyl
Cbz—benzyloxycarbonyl
DCM—dichloromethane
DIEA/DIPEA—N,N—diisopropylethylamine
DMF—dimethylformamide
DMSO—dimethylsulfoxide
Et—ethyl
$Et_3N$—triethylamine
EtOAc—ethyl acetate EtOH—ethanol
FBS—fetal bovine serum
HPLC—high performance liquid chromatography
LCMS—liquid chromatography mass spectrometry
Me—methyl
MeOH—methanol
MOM—methoxymethyl
NMR—nuclear magnetic resonance
Pd/C—palladium on carbon
Ph—phenyl
t—Bu—tert—butyl
t—BuONO—tert—butyl nitrite
TCEP—tris(2-carboxyethyl)phosphine
TEA—triethylamine
TFA—trifluoroacetic acid
TLC—thin layer chromatography
UV—ultraviolet The following synthetic reaction schemes detailed in the General Scheme and Examples are merely illustrative of some of the methods by which the compounds of the present disclosure (or any embodiment or aspect thereof) can be synthesized. Various modifications to these synthetic reaction schemes can be made and will be suggested to one skilled in the art having referred to the disclosure contained in this Application.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40, each of which is hereby incorporated by reference in its entirety.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C.

Although certain exemplary embodiments are depicted and described herein, the compounds of the present disclosure (or an embodiment or aspect thereof) can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography, and/or by Preparative Thin Layer Chromatography (Prep TLC).

General LCMS conditions were performed under acidic and basic conditions. Acidic conditions: mobile Phase: 1.5 mL/4 L TFA in water (solvent A) and 0.75 mL/4 L TFA in acetonitrile (solvent B), using the elution gradient 0%-100% or 1%-100% or 10-100% (solvent B) over 3.85 minutes at a flow rate of 0.6 mL/min or 0.8 ml/min; Column: Waters, Xbridge C18 50*2.1 mm, 5 μm; Wavelength: UV 220 nm; Column temperature: 40° C.; MS ionization: ESI. Basic conditions: mobile Phase: 2 mL/4 L $NH_3 \cdot H_2O$ in water (solvent A) and acetonitrile (solvent B), using the elution gradient 0%-100% or 5%-100% or 15-100% (solvent B) over 3.40-3.90 minutes at a flow rate of 0.6 mL/min or 0.8 mL/min; Column: Waters, Xbridge C18 50*2.1 mm, 5 μm; Wavelength: UV 220 nm; Column temperature: 40° C.; MS ionization: ESI.

Specific LCMS Condition A: mobile phase: 1.5 mL/4LTFA in water (solvent A) and 0.75 mL/4LTFA in acetonitrile (solvent B), using the elution gradient 0%-100% (solvent B) over 3.85 minutes at a flow rate of 0.6 ml/min; Column: Waters, Xbridge C18 50*2.1 mm, 5 μm; Wavelength: UV 220 nm; Column temperature: 40° C.; MS ionization: ESI.

Specific LCMS Condition B: mobile phase: 1.5 mL/4LTFA in water (solvent A) and 0.75 mL/4LTFA in acetonitrile (solvent B), using the elution gradient 1%-100% (solvent B) over 3.85 minutes at a flow rate of 0.8 mL/min; Column: Waters, Xbridge C18 50*2.1 mm, 5 μm; Wavelength: UV 220 nm; Column temperature: 40° C.; MS ionization: ESI.

Specific LCMS Condition C: mobile phase: 1.5 mL/4LTFA in water (solvent A) and 0.75 mL/4LTFA in acetonitrile (solvent B), using the elution gradient 10%-100% (solvent B) over 3.85 minutes at a flow rate of 0.8 mL/min; Column: Waters, Xbridge C18 50*2.1 mm, 5 μm; Wavelength: UV 220 nm; Column temperature: 40° C.; MS ionization: ESI.

Specific LCMS Condition D: mobile phase 2 mL/4 L $NH_3 \cdot H_2O$ in water (solvent A) and acetonitrile (solvent B), using the elution gradient 0%-100% (solvent B) over 3.90 minutes at a flow rate of 0.6 mL/min; Column: Waters, Xbridge C18 50*2.1 mm, 5 μm; Wavelength: UV 220 nm; Column temperature: 30° C.; MS ionization: ESI.

Specific LCMS Condition E: mobile phase 2 mL/4 L $NH_3 \cdot H_2O$ in water (solvent A) and acetonitrile (solvent B), using the elution gradient 5%-100% (solvent B) over 3.60 minutes at a flow rate of 0.8 ml/min; Column: Waters, Xbridge C18 50*2.1 mm, 5 μm; Wavelength: UV 220 nm; Column temperature: 40° C.; MS ionization: ESI.

Specific LCMS Condition F: mobile phase 2 mL/4 L $NH_3 \cdot H_2O$ in water (solvent A) and acetonitrile (solvent B), using the elution gradient 15%-100% (solvent B) over 3.40 minutes at a flow rate of 0.8 mL/min; Column: Waters, Xbridge C18 50*2.1 mm, 5 μm; Wavelength: UV 220 nm; Column temperature: 40° C.; MS ionization: ESI.

All reactions involving air-sensitive reagents were performed under an inert atmosphere. Reagents were used as received from commercial suppliers unless otherwise noted.

The following generalized schemes are used to prepare the disclosed compounds, intermediates, and pharmaceutically acceptable salts thereof. Disclosed compounds and intermediates may be prepared using standard organic synthetic techniques and from commerically available starting materials and reagents. It will be appreciated that synthetic procedures employed in the preparation of disclosed compounds and intermediates will depend on the particular substituents present in the compound or intermediate and that various protection, deprotection, and conversion steps that are standard in organic synthesis may be required, but may not be illustrated in the following general schemes. It is also to be understood that any of the steps shown in any of the following general schemes may be used in any combination and in any order that is chemically feasible to achieve a desired intermediate or disclosed compound.

Scheme 1
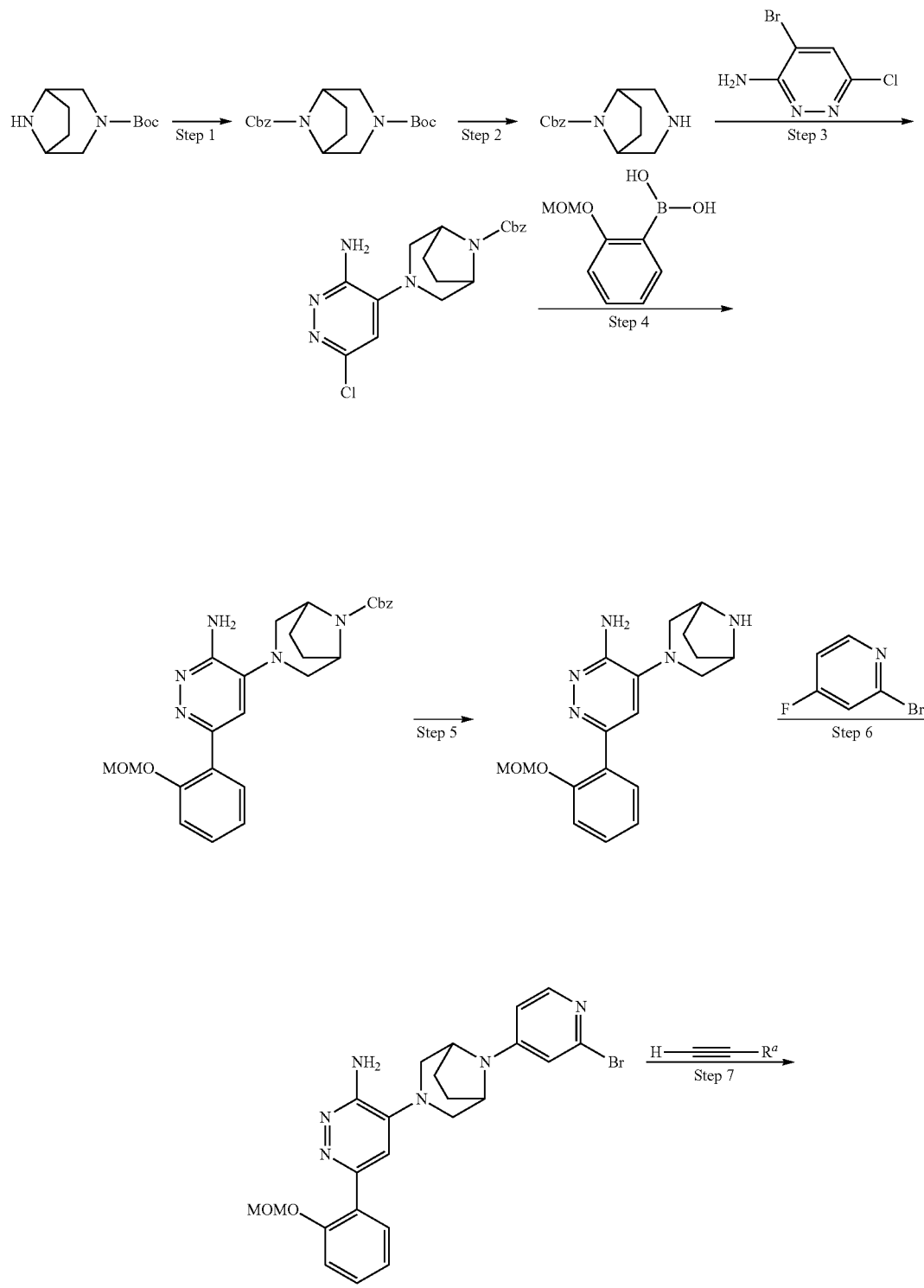

543    544

-continued

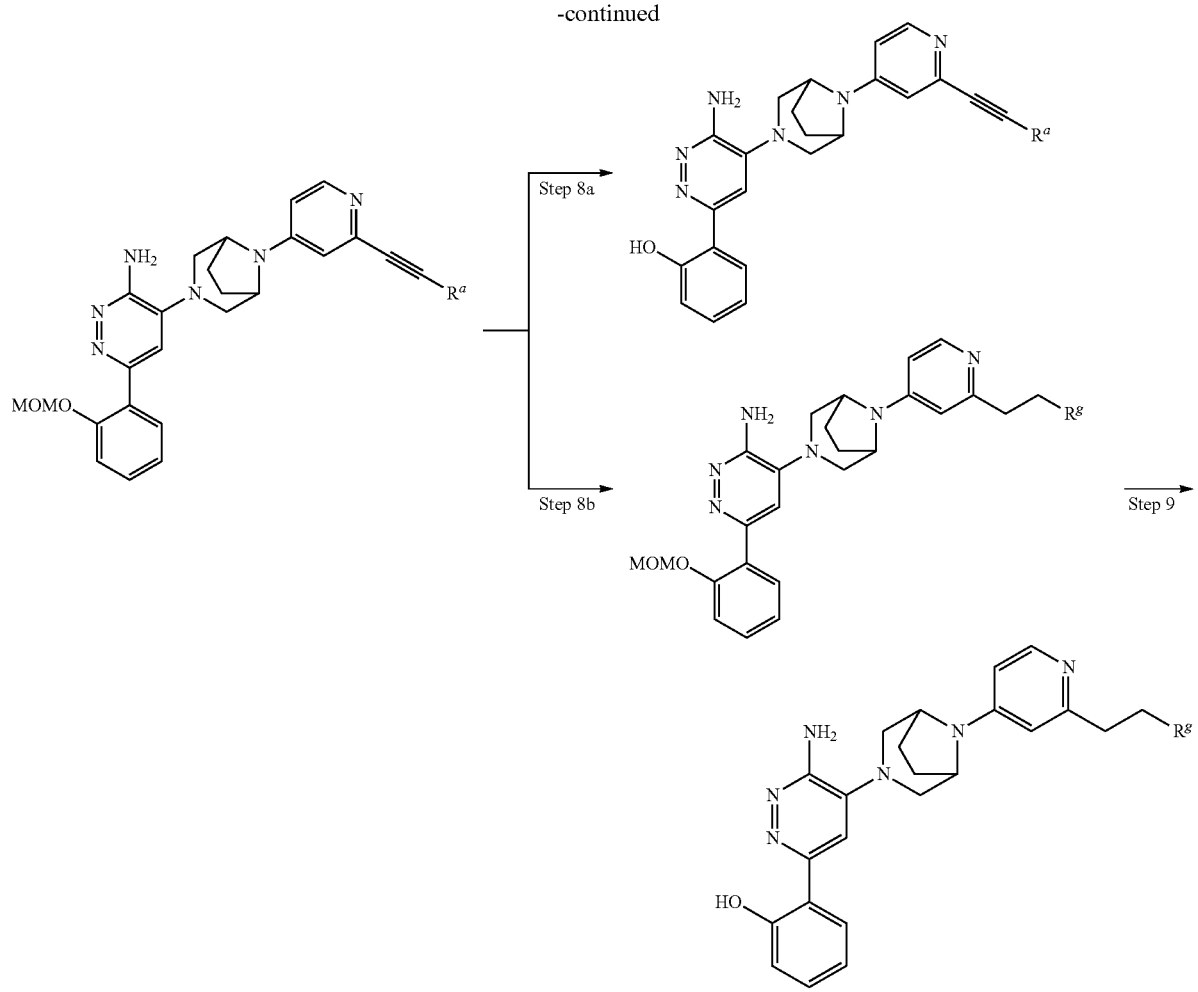

Note that, in Scheme 1, $R^a$ and $R^g$ are as defined for a compound of formula (I), or any variation or embodiment thereof, such as a compound of formula (I'), (I), (I-A), (I-A1), (I-A2), (I-A3), (I-A4), (I-A5), (I-A6), (I-A7), (I-A8), (I-A9), (I-B), (I-C), (I-D), (I-E), (I-E1), (I-F), (I-F1), (I-G), (I-H), (I-I), (I-J), (I-J1), (I-J2), (I-J3), (I-J4), (I-J5), (I-J6), (I-K), (I-K1), (I-K2), (I-K3), (I-K4), (I-K5), (I-K6), (IV'), (IV'-L), (IV'-L1), (IV'-L2), (IV'-L3), (IV'-L4), (IV'-M), (IV'-M1), (IV'-M2), (IV'-M3), (IV'-M4), (IV'-N), (IV'-N1), (IV'-N2), (IV'-N3), (IV'-N4), (II'), (II), (II-A), (II-A1), (II-B), (II-B1), or (III'), or a stereoisomer or tautomer thereof, or a pharmaceutically acceptable salt of any of the foregoing, as described elsewhere herein.

Scheme 2. General synthetic procedures A and B

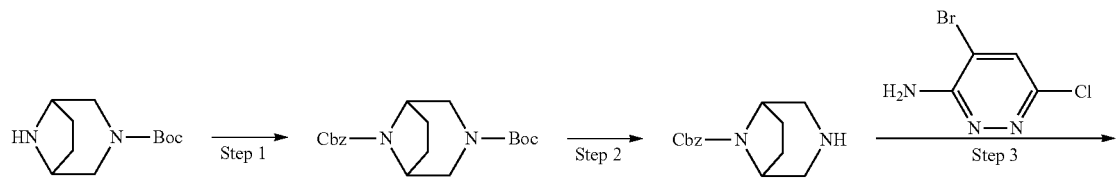

545 546
-continued
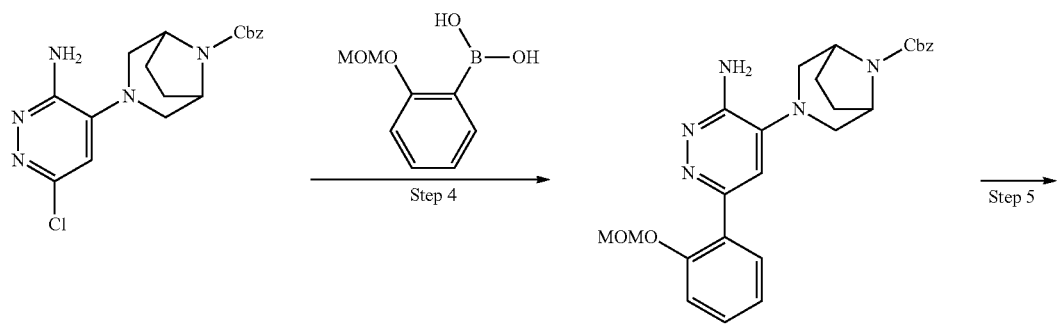
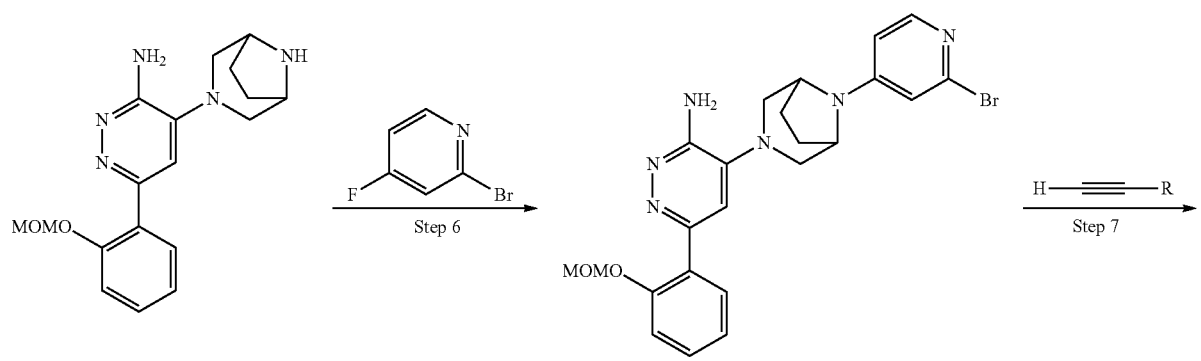
General procedure A
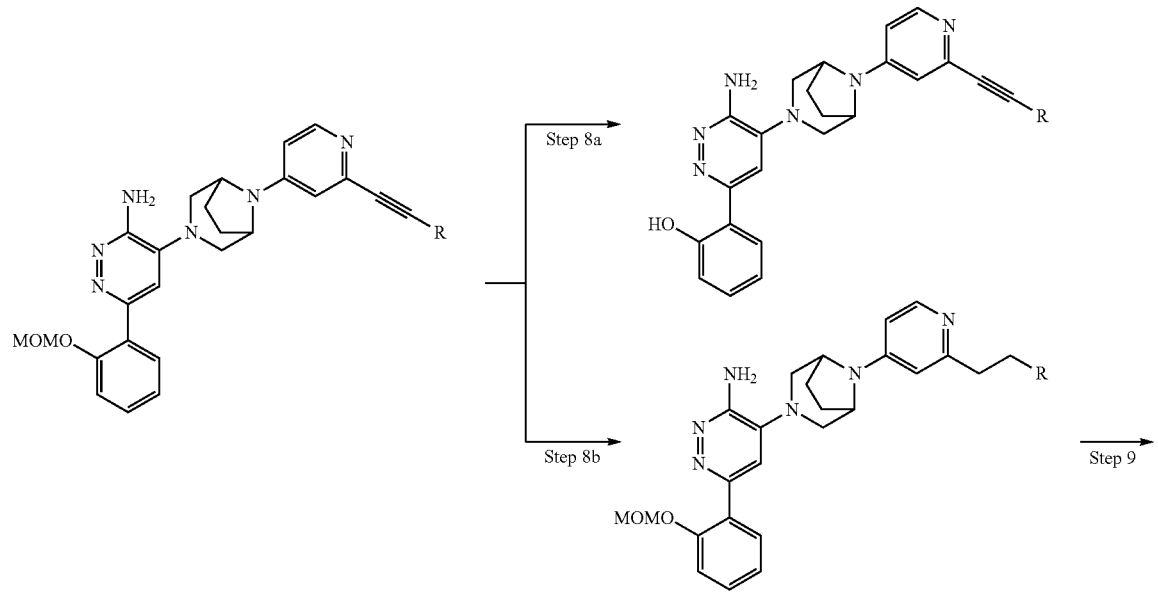
General procedure B

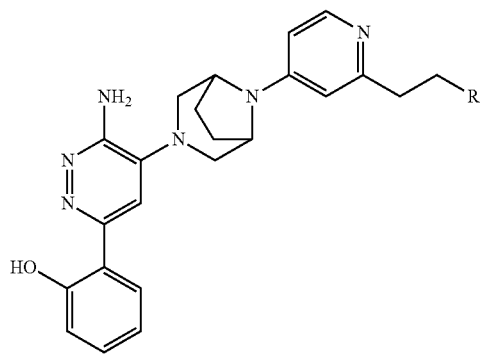
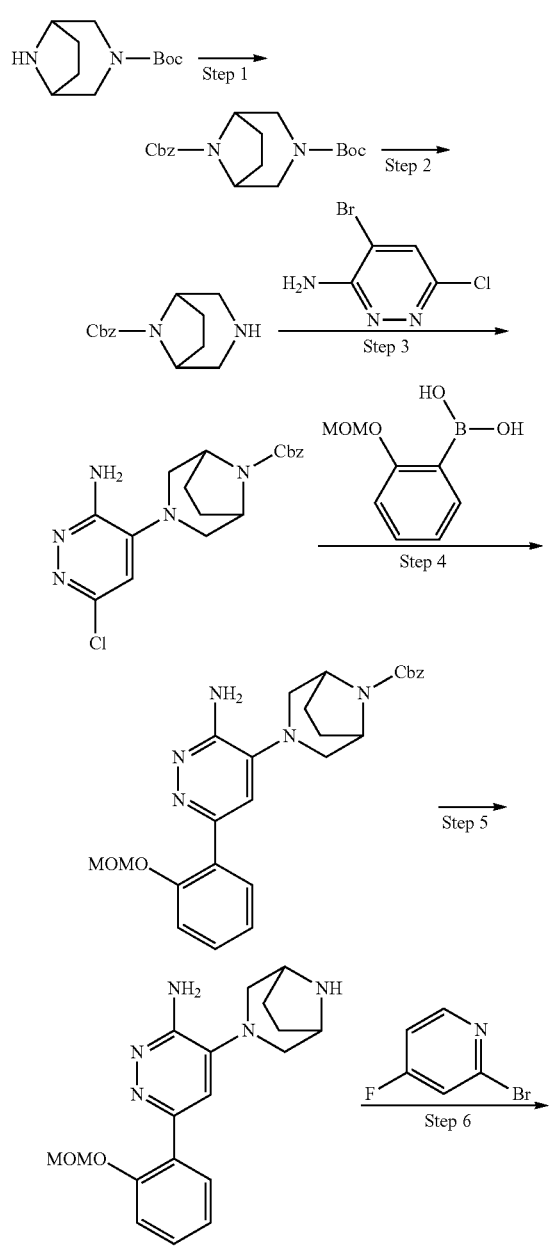
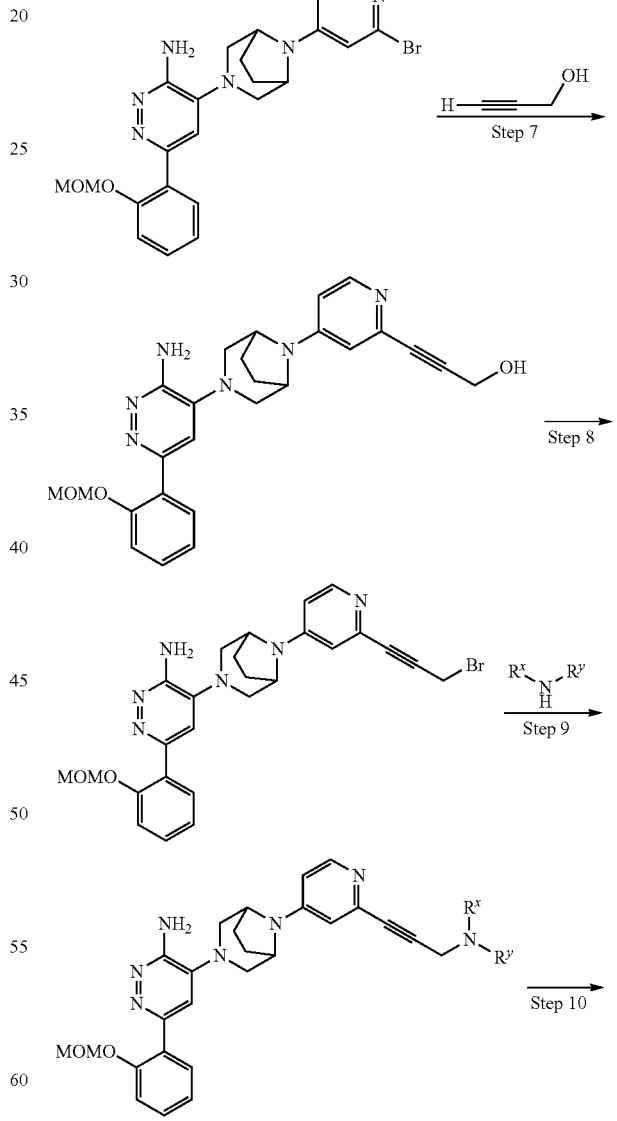

549

-continued

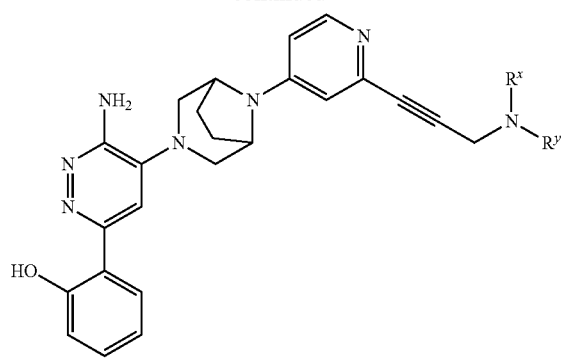

General procedure C

Example 1

2-(6-amino-5-(8-(2-(3-(pyrrolidin-1-yl)prop-1-yn-1-yl)pyridin-4-yl)-3,8-diazabicyclo[3.2.1]octan-3-yl)pyridazin-3-yl)phenol (Compound 2)

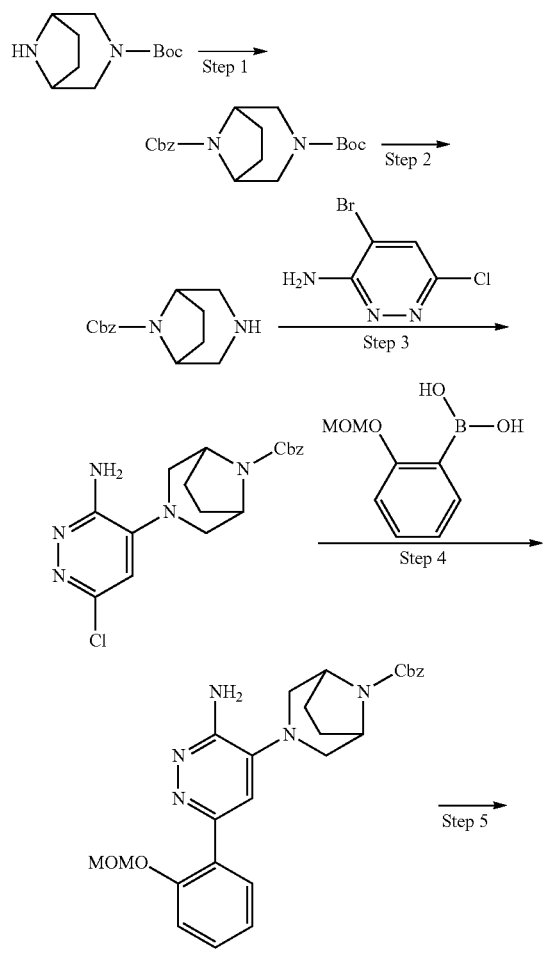

550

-continued

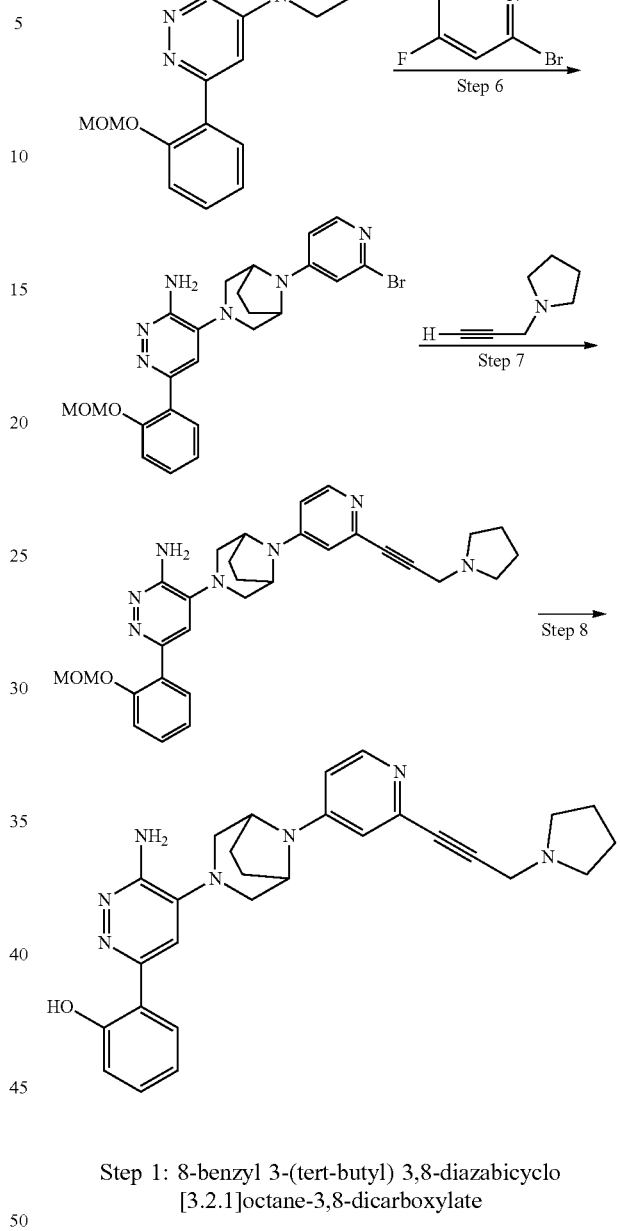

Step 1: 8-benzyl 3-(tert-butyl) 3,8-diazabicyclo[3.2.1]octane-3,8-dicarboxylate

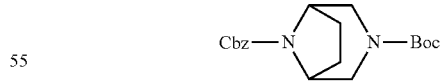

A mixture of tert-butyl 3,8-diazabicyclo[3.2.1]octane-3-carboxylate (125 g, 589 mmol, 1.00 eq) in DCM (620 mL), TEA (179 g, 1.77 mol, 246 mL, 3.00 eq) and CbzCl (151 g, 883 mmol, 126 mL, 1.50 eq) was added, and then the mixture was stirred at 25° C. for 3 hrs under N₂ atmosphere. TLC (Petroleum ether:Ethyl acetate=3:1) showed new spots (R$_f$=0.37) were formed. The solution was washed with water 50.0 mL, extracted with EtOAc 150×3 mL, washed with brine 50.0 mL and concentrated under reduced pressure to give a residue. The residue was purified by column chromatography (Petroleum ether/Ethyl acetate=3:1) to afford the title compound (89.0 g, 257 mmol, 43.6% yield) as a white solid. $^1$H NMR (400 MHz, CDCl$_3$): δ 7.38-7.34 (m, 5H), 5.15 (s, 2H), 4.30 (s, 2H), 3.87-3.70 (m, 2H), 3.03 (d, J=28.8 Hz, 2H), 1.95 (s, 2H), 1.88 (d, J=16.8 Hz, 2H), 1.45 (s, 9H).

Step 2: benzyl 3,8-diazabicyclo[3.2.1]octane-8-carboxylate

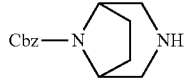

To a solution of 8-benzyl 3-(tert-butyl) 3,8-diazabicyclo[3.2.1]octane-3,8-dicarboxylate (89.0 g, 257 mmol, 1.00 eq) in EtOAc (150 mL) was added HCl/EtOAc (4 M, 321 mL, 5.00 eq). The mixture was stirred at 25° C. for 3 hrs. The solution was concentrated under reduced pressure to remove most of the solvent and filtered to afford the title compound (59.0 g, 209 mmol, 81.2% yield) as a crude white solid. $^1$H NMR (400 MHz, CDCl$_3$): δ 7.39-7.32 (m, 5H), 5.15 (s, 2H), 4.44 (s, 2H), 3.20 (s, 4H), 2.32-2.27 (m, 2H), 2.16-2.00 (m, 2H).

Step 3: benzyl 3-(3-amino-6-chloropyridazin-4-yl)-3,8-diazabicyclo[3.2.1]octane-8-carboxylate

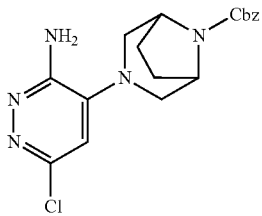 [SMILES: Nc1nnc(Cl)cc1N1CC2CCC(C1)N2C(=O)OCc1ccccc1]

A mixture of benzyl 3,8-diazabicyclo[3.2.1]octane-8-carboxylate (59.0 g, 209 mmol, 1.00 eq) in DMSO (410 mL), 4-bromo-6-chloro-pyridazin-3-amine (45.7 g, 219 mmol, 1.05 eq), DIPEA (108 g, 835 mmol, 145 mL, 4.00 eq) was added, and then the mixture was stirred at 130° C. for 16 hrs under N$_2$ atmosphere. The solution was added water 100 mL, and combined with another crude reaction mixture of the same product, extracted with EtOAc 150×3 mL, and then washed with brine 20.0 mL, concentrated under reduced pressure to afford the title compound (200 g, crude) as a white solid. $^1$H NMR (400 MHz, CDCl$_3$): δ 7.39-7.27 (m, 5H), 6.70 (s, 1H), 5.17 (s, 2H), 5.10 (s, 2H), 4.46 (s, 2H), 3.25 (d, J=9.6 Hz, 2H), 2.89 (d, J=33.6 Hz, 2H), 2.08-2.05 (m, 2H), 1.95-1.91 (m, 2H).

Step 4: benzyl 3-(3-amino-6-(2-(methoxymethoxy)phenyl)pyridazin-4-yl)-3,8-diazabicyclo[3.2.1]octane-8-carboxylate

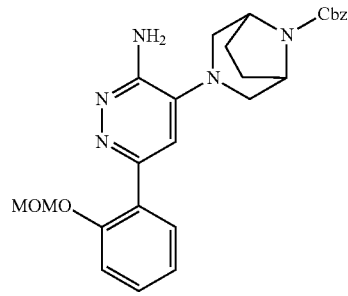

To a mixture of benzyl 3-(3-amino-6-chloropyridazin-4-yl)-3,8-diazabicyclo[3.2.1]octane-8-carboxylate (100 g, 268 mmol, 1.00 eq) in dioxane (800 mL) and H$_2$O (150 mL) was added (2-(methoxymethoxy)phenyl)boronic acid (73.0 g, 401 mmol, 1.50 eq), Pd(PPh$_3$)$_4$ (30.9 g, 26.8 mmol, 0.100 eq) and K$_2$CO$_3$ (73.9 g, 534 mmol, 2.00 eq), then the mixture was stirred at 100° C. for 2 hrs under N$_2$ atmosphere. The solution was added 100 mL water and combined with another crude reaction mixture of the same reaction. The mixture was extracted with EtOAc 200 mL×3, the organic was washed with brine 100 mL, dried over Na$_2$SO$_4$, concentrated under reduced pressure to give a residue. The residue was purified by column chromatography (Petroleum ether/Ethyl acetate=0:1) to afford the title compound (182 g, combined yield: 71.7%) as a yellow solid. $^1$H NMR (400 MHz, CDCl$_3$): δ 7.68 (d, J=1.2 Hz, 1H), 7.66-7.25 (m, 6H), 7.17 (d, J=6.0 Hz, 1H), 7.11-7.10 (m, 1H), 7.04 (s, 1H), 5.08 (s, 2H), 5.06 (s, 2H), 4.92 (s, 2H), 4.39 (s, 2H), 3.32 (s, 3H), 3.17 (d, J=10.0 Hz, 2H), 2.83 (d, J=46.8 Hz, 2H), 1.92-2.15 (m, 4H).

Step 5: 4-(3,8-diazabicyclo[3.2.1]octan-3-yl)-6-(2-(methoxymethoxy)phenyl)pyridazin-3-amine

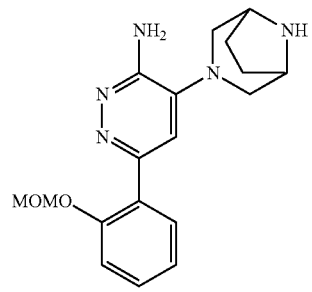

To a solution of benzyl 3-(3-amino-6-(2-(methoxymethoxy)phenyl)pyridazin-4-yl)-3,8-diazabicyclo[3.2.1]octane-8-carboxylate (182 g, 383 mmol, 1.00 eq) in MeOH (1.27 L) was added Pd(OH)$_2$/C (53.8 g, 38.3 mmol, 10.0% purity, 0.100 eq.) under N$_2$ atmosphere. The suspension was degassed and purged with H$_2$ 3 times. The mixture was stirred under H$_2$ at 35° C. for 16 hrs. The solution was filtered and the filtrate was concentrated under reduced pressure to afford the title compound (100 g, crude) as a brown solid.

Step 6: 4-(8-(2-bromopyridin-4-yl)-3,8-diazabicyclo[3.2.1]octan-3-yl)-6-(2-(methoxymethoxy)phenyl)pyridazin-3-amine

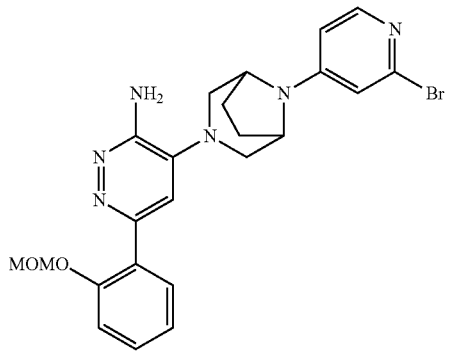

To a solution of 4-(3,8-diazabicyclo[3.2.1]octan-3-yl)-6-(2-(methoxymethoxy)phenyl)pyridazin-3-amine (16 g, 46.9 mmol) in DMSO (96 mL) was added 2-bromo-4-fluoropyridine (8.25 g, 46.9 mmol) and DIEA (60.6 g, 469 mmol, 81.6 mL) then the mixture was stirred for 5 hrs at 130° C. The reaction mixture was quenched by addition H$_2$O 100 mL, diluted with EtOAc 100 mL and extracted with EtOAc (100 mL×3). The combined organic layers were washed with brine 100 mL, dried over Na$_2$SO$_4$, filtered and concentrated under reduced pressure to give a residue. The crude product was triturated with MeOH:DCM=1:20 at 15° C. for 30 min, and then filtered and concentrated under reduced pressure to afford the title compound (17 g, 72.49% yield) as a light yellow solid. $^1$H NMR (400 MHz, CDCl$_3$): δ 8.00 (d, J=5.96 Hz, 1H), 7.72 (dd, J=7.63, 1.67 Hz, 1H), 7.22 (s, 1H) 7.31-7.38 (m, 1H), 7.15 (d, J=7.89 Hz, 1H), 7.10 (t, J=7.37 Hz, 1H), 6.77 (d, J=2.15 Hz, 1H), 6.54 (dd, J=5.96, 2.27 Hz, 1H), 5.13 (s, 2H), 5.10 (s, 2H), 4.37 (s, 2H), 3.36 (s, 3H), 3.23 (d, J=10.13 Hz, 2H), 3.02 (d, J=11.21 Hz, 2H), 2.10-2.24 (m, 4H).

Step 7: 6-(2-(methoxymethoxy)phenyl)-4-(8-(2-(3-(pyrrolidin-1-yl)prop-1-yn-1-yl)pyridin-4-yl)-3,8-diazabicyclo[3.2.1]octan-3-yl)pyridazin-3-amine

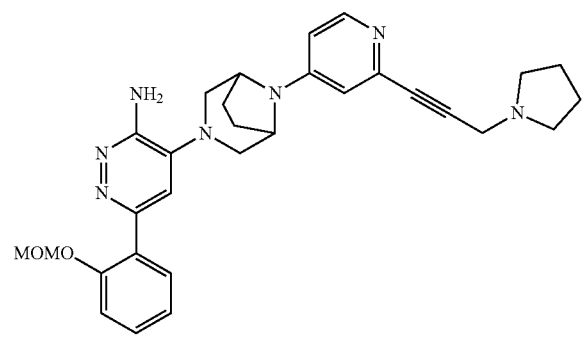

Under nitrogen, a solution of 4-(8-(2-bromopyridin-4-yl)-3,8-diazabicyclo[3.2.1]octan-3-yl)-6-(2-(methoxymethoxy)phenyl)pyridazin-3-amine (100 mg, 0.200 mmol, 1.0 eq) and 1-(prop-2-yn-1-yl)pyrrolidine (33 mg, 0.300 mmol, 1.5 eq) in DMF (2 mL) was added CuI (1.9 mg, 0.010 mmol, 0.030 eq), Pd(PPh$_3$)$_2$Cl$_2$ (7 mg, 0.010 mmol, 0.030 eq) and K$_2$CO$_3$ (83 mg, 0.600 mmol, 3.0 eq). The resulting solution was shaken at 100° C. for 16 hrs. The reaction mixture was concentrated by Speedvac and the residue was purified by prep-TLC and carried on assuming quantitative yield of the title compound.

Step 8: 2-(6-amino-5-(8-(2-(3-(pyrrolidin-1-yl)prop-1-yn-1-yl)pyridin-4-yl)-3,8-diazabicyclo[3.2.1]octan-3-yl)pyridazin-3-yl)phenol

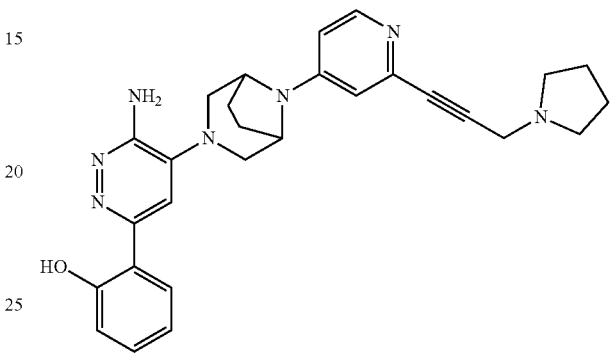

A solution of 6-(2-(methoxymethoxy)phenyl)-4-(8-(2-(3-(pyrrolidin-1-yl)prop-1-yn-1-yl)pyridin-4-yl)-3,8-diazabicyclo[3.2.1]octan-3-yl)pyridazin-3-amine (105 mg, 0.200 mmol, 1.0 eq.) in HCl (4 M in MeOH, 2 mL) was shaken at 30° C. for 2 hrs. The mixture was evaporated and diluted with 1.5 mL of MeOH. Then the pH was adjusted to 7-8 using aqueous NH$_3$·H$_2$O. The crude product was purified by prep-HPLC (® C18 150*25 mm*5 μm, Water (10 mM ammonium bicarbonate and 0.05% ammonia hydroxide v/v)-ACN, 36-61%) to afford the title compound (7.7 mg, 8% yield). $^1$H NMR (400 MHz, DMSO-d$_6$) δ 14.12 (s, 1H), 8.10 (d, J=5.9 Hz, 1H), 7.91 (dd, J=8.0, 1.6 Hz, 1H), 7.51 (s, 1H), 7.27-7.18 (m, 1H), 6.95 (d, J=2.4 Hz, 1H), 6.90-6.82 (m, 2H), 6.80 (dd, J=6.0, 2.5 Hz, 1H), 5.98 (s, 2H), 4.58 (t, J=3.4 Hz, 2H), 3.64 (s, 2H), 3.26 (dd, J=12.0, 2.3 Hz, 2H), 3.01 (d, J=11.6 Hz, 2H), 2.62 (d, J=6.0 Hz, 4H), 2.20 (q, J=6.2, 5.7 Hz, 2H), 1.97 (dd, J=8.0, 4.0 Hz, 2H), 1.79-1.68 (m, 4H).

LCMS (ESI): m/z 482.3 (M+H)$^+$.

Example 2

2-(6-amino-5-(8-(2-(3-morpholinoprop-1-yn-1-yl)pyridin-4-yl)-3,8-diazabicyclo[3.2.1]octan-3-yl)pyridazin-3-yl)phenol (Compound 9)

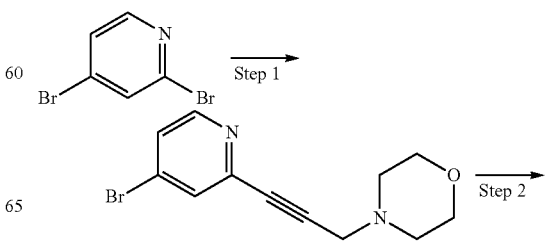

-continued

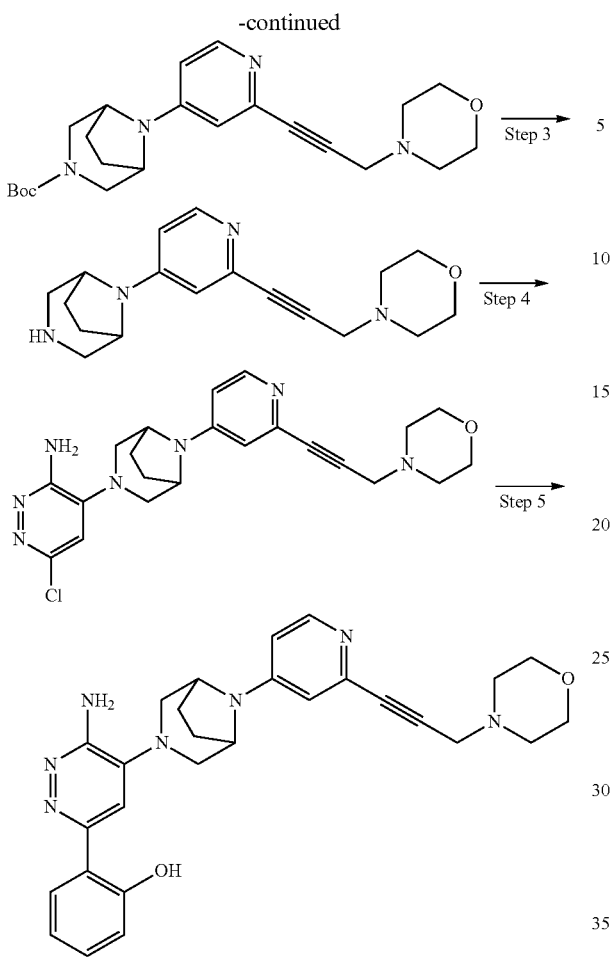

Step 1: 4-(3-(4-bromopyridin-2-yl)prop-2-yn-1-yl)morpholine

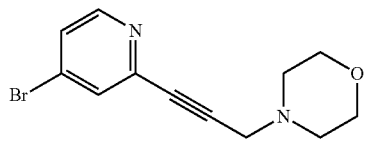 [SMILES: Brc1ccnc(C#CCN2CCOCC2)c1]

To a solution of 4-prop-2-ynylmorpholine (2.6 g, 21.11 mmol) in DMF (60 mL) was added 2,4-dibromopyridine (5.0 g, 21.11 mmol), Pd(PPh$_3$)$_4$ (3.6 g, 3.17 mmol), CuI (1.2 g, 6.33 mmol), PPh$_3$ (1.6 g, 6.33 mmol) and Et$_3$N (5.88 mL, 42.21 mmol) at 26° C. The reaction solution was stirred at 30° C. for 16 h under N$_2$ atmosphere. Then the reaction mixture was diluted with EtOAc (100 mL), washed with brine (30 mL×3), dried over Na$_2$SO$_4$ and concentrated. The residue was purified by column chromatography on silica gel (0-30% EtOAc in petroleum ether) to afford the title compound (2.4 g, 40%) as a yellow oil. $^1$H NMR (400 MHz, CDCl$_3$) δ 8.36 (d, J=5.2 Hz, 1H), 7.59 (d, J=1.6 Hz, 1H), 7.40 (d, J=5.2, 1.6 Hz, 1H), 3.68-3.85 (m, 4H), 3.56 (s, 2H), 2.66 (d, J=4.0 Hz, 4H). LCMS (ESI): m/z 282.8 (M+H)$^+$.

Step 2: tert-butyl 8-(2-(3-morpholinoprop-1-yn-1-yl)pyridin-4-yl)-3,8-diazabicyclo[3.2.1]octane-3-carboxylate

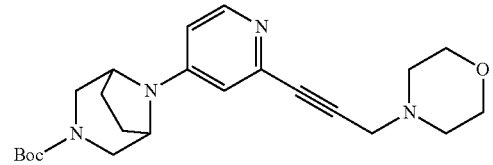 [SMILES: CC(C)(C)OC(=O)N1CC2CCC(C1)N2c1ccnc(C#CCN2CCOCC2)c1]

To a solution of Ruphos Pd G3 (428 mg, 0.51 mmol) in toluene (30 mL) was added Cs$_2$CO$_3$ (6.9 g, 21.34 mmol), tert-butyl 3,8-diazabicyclo[3.2.1]octane-3-carboxylate (1.8 g, 8.54 mmol), and 4-[3-(4-bromo-2-pyridyl)prop-2-ynyl]morpholine (2.4 g, 8.54 mmol), the resulting mixture was stirred at 110° C. for 16 h under N$_2$ atmosphere. Then the reaction mixture was cooled to room temperature, diluted with EtOAc (30 mL) and washed with brine (15 mL×2). The organic layer was dried over Na$_2$SO$_4$, filtered and concentrated. The residue was purified by flash chromatography on silica gel (0-10% MeOH in DCM) to afford the title compound (3 g, 85%) as a yellow oil. $^1$H NMR (400 MHz, DMSO-d$_6$) δ 8.05 (d, J=6.0 Hz, 1H), 6.89 (d, J=2.4 Hz, 1H), 6.73 (d, J=6.0, 2.4 Hz, 1H), 4.40 (s, 2H) 3.45-3.84 (m, 10H), 2.50 (s, 4H), 1.89 (d, J=4.0 Hz, 2H), 1.66 (d, J=6.8 Hz, 2H), 1.36 (s, 9H). LCMS (ESI): m/z 413.2 (M+H)$^+$.

Step 3: 4-(3-(4-(3,8-diazabicyclo[3.2.1]octan-8-yl)pyridin-2-yl)prop-2-yn-1-yl)morpholine

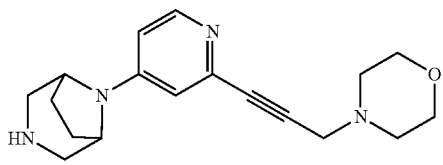 [SMILES: C(#Cc1cc(N2C3CCC2CNC3)ccn1)CN1CCOCC1]

To a solution of tert-butyl 8-[2-(3-morpholinoprop-1-ynyl)-4-pyridyl]-3,8-diazabicyclo[3.2.1]octane-3-carboxylate (3.0 g, 7.27 mmol) in DCM (30 mL) was added TFA (56.03 mL, 727.22 mmol) at 0° C. After stirring at 25° C. for 6 h, the mixture was concentrated and the residue was dissolved in EtOAc (30 mL), saturated Na$_2$CO$_3$ was added to adjust the pH to ~ 7.5. Then the mixture was extracted with ethyl acetate (50 mL×3). The combined organic phase was washed with brine (25 mL×2), dried over Na$_2$SO$_4$, filtered and concentrated. The residue was purified by flash chromatography on silica gel (0-10% MeOH in DCM) to afford the title compound (1.4 g, 62%) as a colorless oil. $^1$H NMR (400 MHz, CDCl$_3$) δ 8.16 (d, J=6.0 Hz, 1H), 6.69 (d, J=2.4 Hz, 1H), 6.45 (d, J=6.0, 2.4 Hz, 1H), 4.05-4.22 (m, 2H), 3.70-3.78 (m, 4H), 3.49 (s, 2H), 3.09 (d, J=11.6 Hz, 2H), 2.58-2.73 (m, 6H), 2.01-2.17 (m, 4H).

LCMS (ESI): m/z 313.0 (M+H)$^+$.

Step 4: 6-chloro-4-(8-(2-(3-morpholinoprop-1-yn-1-yl)pyridin-4-yl)-3,8-diazabicyclo[3.2.1]octan-3-yl)pyridazin-3-amine

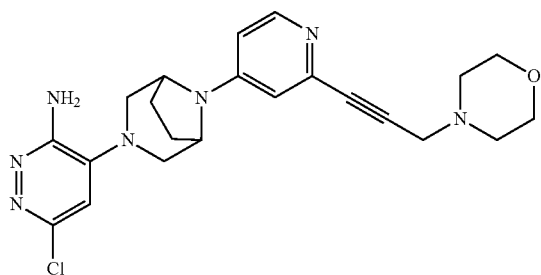 [SMILES: Nc1nnc(Cl)cc1N1CC2CCC(C1)N2c1ccnc(C#CCN2CCOCC2)c1]

A mixture of 4-bromo-6-chloro-pyridazin-3-amine (1.2 g, 5.83 mmol), DIEA (7.81 mL, 44.81 mmol) and 4-[3-[4-(3,8-diazabicyclo[3.2.1]octan-8-yl)-2-pyridyl]prop-2-ynyl]morpholine (1.4 g, 4.48 mmol) in DMSO (20 mL) was stirred at 130° C. under N$_2$ atmosphere for 16 h. Then the reaction mixture was cooled to room temperature, diluted with EtOAc (50 mL) and washed with brine (25 mL×3). The organic layer was dried over Na$_2$SO$_4$, filtered and concentrated. The residue was purified by column chromatography on silica gel (0-100% EtOAc in petroleum ether) to afford the title compound (500 mg, 25%) as a yellow solid. $^1$H NMR (400 MHz, CDCl$_3$) δ 8.22 (d, J=6.4 Hz, 1H), 6.57-6.86 (m, 3H), 4.47 (s, 2H), 3.81 (s, 4H), 3.65 (s, 2H), 3.31 (d, J=11.6 Hz, 2H), 3.00 (d, J=11.6 Hz, 2H), 2.76 (s, 4H), 2.10-2.27 (m, 4H). LCMS (ESI): m/z 440.1 (M+H)$^+$.

Step 5: 2-(6-amino-5-(8-(2-(3-morpholinoprop-1-yn-1-yl)pyridin-4-yl)-3,8-diazabicyclo[3.2.1]octan-3-yl)pyridazin-3-yl)phenol

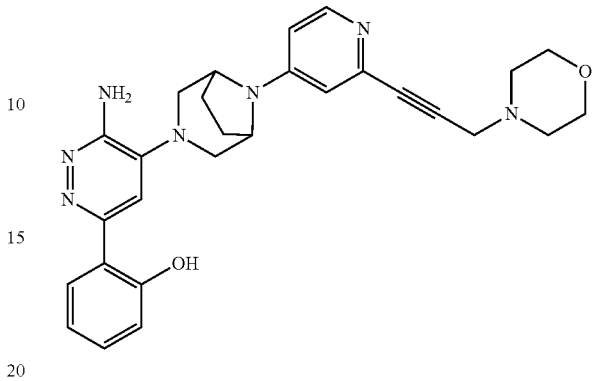

To a solution of 6-chloro-4-[8-[2-(3-morpholinoprop-1-ynyl)-4-pyridyl]-3,8-diazabicyclo[3.2.1]octan-3-yl]pyridazin-3-amine (100.0 mg, 0.23 mmol) in 1,4-dioxane (1 mL) and water (0.20 mL) was added 2-hydroxyphenylboronicacid (156.76 mg, 1.14 mmol), Pd(PPh$_3$)$_4$ (52.53 mg, 0.05 mmol) and K$_2$CO$_3$ (94.25 mg, 0.68 mmol) at 26° C. After stirring at 90° C. for 16 h, the reaction mixture was cooled to room temperature, diluted with EtOAc (30 mL) and washed with brine (15 mL×2). The organic layer was dried over Na$_2$SO$_4$, filtered and concentrated. The residue was purified by prep-HPLC (Phenomenex Synergi C18 150*30 mm*4 um, water (0.05% HCl)-ACN, 10-40%) to afford the title compound (35 mg, 30%) as a yellow solid. $^1$H NMR (400 MHz, DMSO-d$_6$) δ 8.33 (d, J=7.2 Hz, 1H), 7.49-7.61 (m, 3H), 7.19-7.45 (m, 3H), 6.94-7.16 (t, J=7.2 Hz, 1H), 4.99 (s, 1H), 4.93 (s, 1H), 4.35 (s, 4H), 3.95 (s, 4H), 3.62 (s, 2H), 3.22 (s, 4H), 2.25 (d, J=7.2 Hz, 2H), 2.02 (s, 2H).
LCMS (ESI): m/z 498.3 (M+H)$^+$.

Example 3

2-(6-amino-5-(8-(2-(piperidin-4-ylethynyl)pyridin-4-yl)-3,8-diazabicyclo[3.2.1]octan-3-yl)pyridazin-3-yl)phenol (Compound 19)

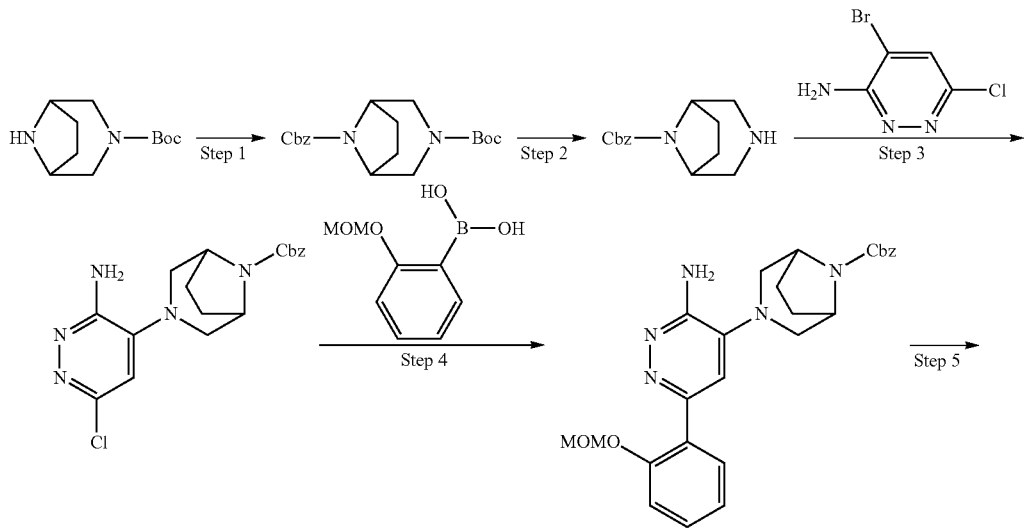

559
-continued
560
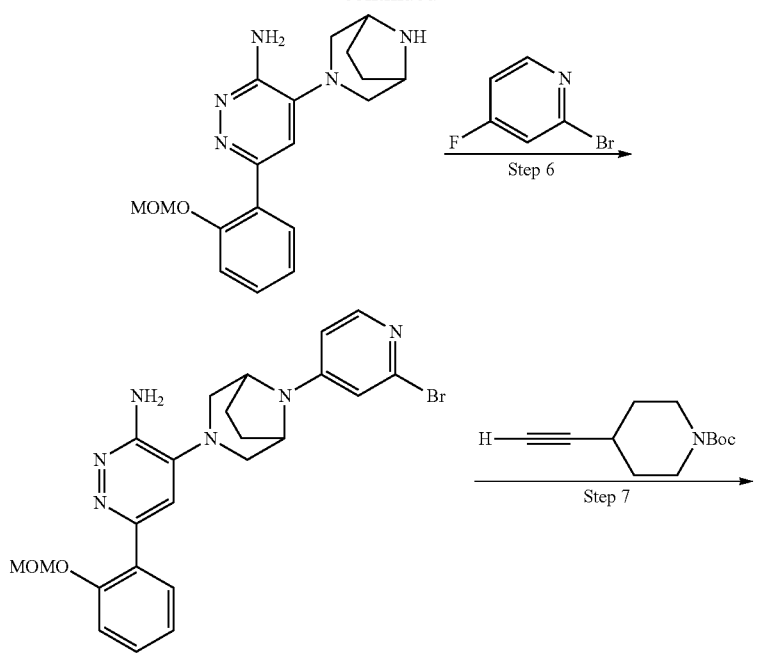
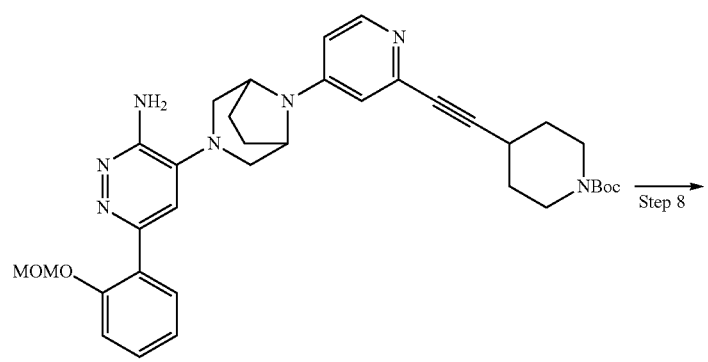
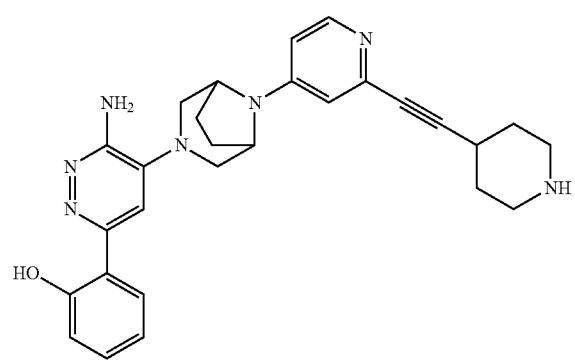 [SMILES: Nc1nnc(-c2ccccc2O)cc1N1CC2CCC(C1)N2c1ccnc(C#CC2CCNCC2)c1]

Step 1 to 6: procedure similar to those described elsewhere herein, e.g., in Scheme 1 and Example 1.

Step 7: tert-butyl 4-((4-(3-(3-amino-6-(2-(methoxymethoxy)phenyl)pyridazin-4-yl)-3,8-diazabicyclo[3.2.1]octan-8-yl)pyridin-2-yl)ethynyl)piperidine-1-carboxylate

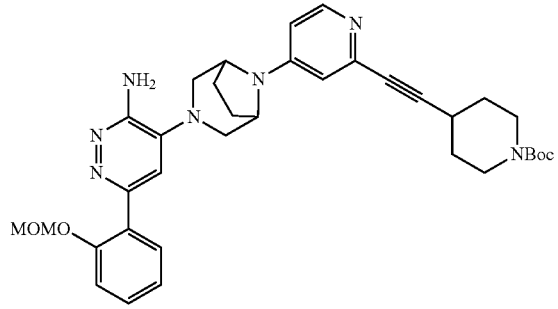

Under nitrogen, a solution of 4-(8-(2-bromopyridin-4-yl)-3,8-diazabicyclo[3.2.1]octan-3-yl)-6-(2-(methoxymethoxy)phenyl)pyridazin-3-amine (100 mg, 0.200 mmol, 1.0 eq) and tert-butyl 4-ethynylpiperidine-1-carboxylate (63 mg, 0.300 mmol, 1.5 eq) in DMF (2 mL) was added CuI (1.9 mg, 0.010 mmol, 0.030 eq), Pd(PPh$_3$)$_2$Cl$_2$ (7 mg, 0.010 mmol, 0.030 eq) and K$_2$CO$_3$ (83 mg, 0.600 mmol, 3.0 eq). The resulting solution was shaken at 100° C. for 16 hrs. The reaction mixture was concentrated by Speedvac and the residue was purified by prep-TLC and carried on assuming quantitative yield of the title compound.

Step 8: 2-(6-amino-5-(8-(2-(piperidin-4-ylethynyl)pyridin-4-yl)-3,8-diazabicyclo[3.2.1]octan-3-yl)pyridazin-3-yl)phenol

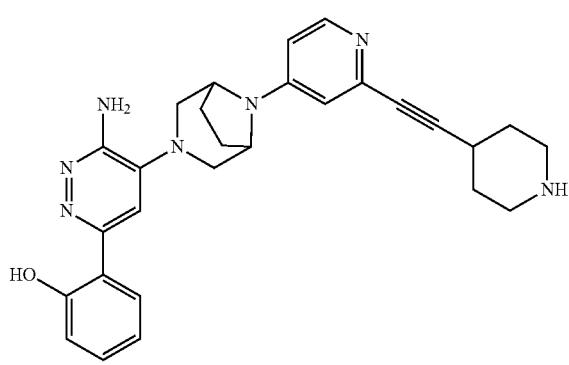 [SMILES: Nc1nnc(-c2ccccc2O)cc1N1CC2CCC(C1)N2c1ccnc(C#CC2CCNCC2)c1]

A solution of tert-butyl 4-((4-(3-(3-amino-6-(2-(methoxymethoxy)phenyl)pyridazin-4-yl)-3,8-diazabicyclo[3.2.1]octan-8-yl)pyridin-2-yl)ethynyl)piperidine-1-carboxylate (125 mg, 0.200 mmol, 1.0 eq) in HCl (4 M in MeOH, 2 mL) was shaken at 30° C. for 2 hrs. The mixture was evaporated and diluted with 1.5 mL of MeOH. Then the pH was adjusted to 7-8 using aqueous NH$_3$·H$_2$O. The crude product was purified by prep-HPLC (Xtimate® C18 150*25 mm*5 μm, Water (10 mM ammonium bicarbonate and 0.05% ammonia hydroxide v/v)-ACN, 42-67%) to afford the title compound (13 mg, 13% yield). $^1$H NMR (400 MHz, DMSO-d$_6$) δ 14.12 (s, 1H), 8.07 (d, J=5.8 Hz, 1H), 7.91 (dd, J=8.0, 1.7 Hz, 1H), 7.51 (s, 1H), 7.27-7.18 (m, 1H), 6.92-6.80 (m, 3H), 6.77 (dd, J=6.0, 2.5 Hz, 1H), 5.98 (s, 2H), 4.57 (s, 2H), 3.26 (dd, J=11.9, 2.3 Hz, 2H), 3.04-2.91 (m, 4H), 2.78-2.67 (m, 1H), 2.62 (ddd, J=12.5, 9.8, 2.9 Hz, 2H), 2.24-2.13 (m, 2H), 2.00-1.92 (m, 2H), 1.82 (dq, J=12.4, 3.9 Hz, 2H), 1.60-1.46 (m, 2H). LCMS (ESI): m/z 482.3 (M+H)$^+$.

Example 4

2-(6-amino-5-(8-(2-(3-aminopropyl)pyridin-4-yl)-3,8-diazabicyclo[3.2.1]octan-3-yl)pyridazin-3-yl)phenol (Compound 33)

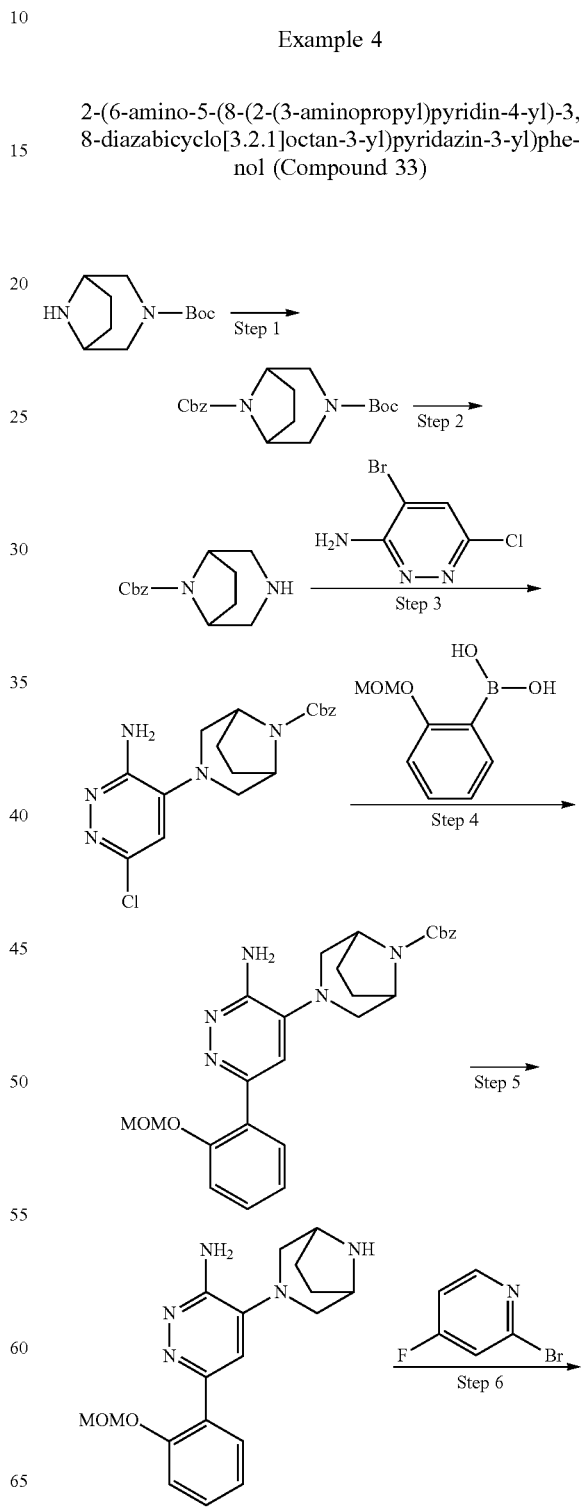

563

-continued

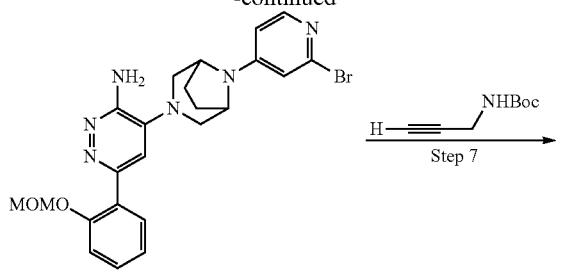

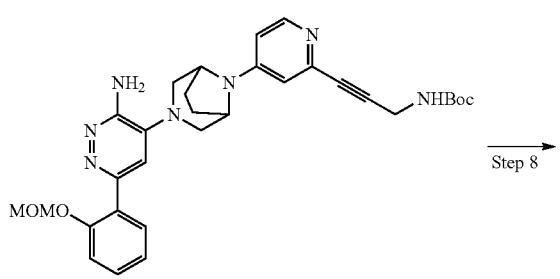

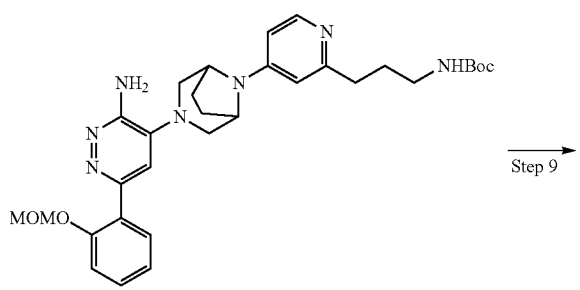

Step 1 to 6: procedure similar to those described elsewhere herein, e.g., in Scheme 1 and Example 1.

564

Step 7: tert-butyl (3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-yl)carbamate

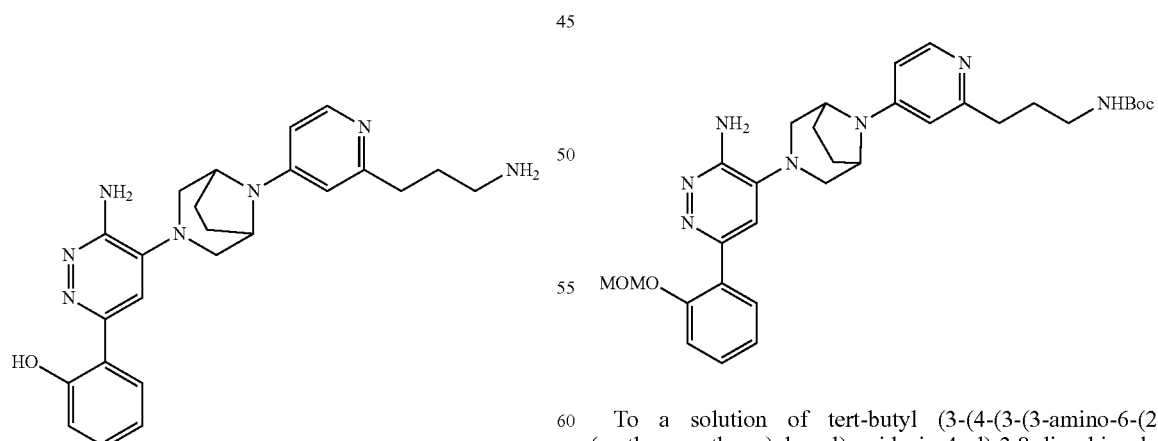

Under nitrogen, a solution of 4-(8-(2-bromopyridin-4-yl)-3,8-diazabicyclo[3.2.1]octan-3-yl)-6-(2-(methoxymethoxy)phenyl)pyridazin-3-amine (100 mg, 0.200 mmol, 1.0 eq) and tert-butyl prop-2-yn-1-ylcarbamate (47 mg, 0.300 mmol, 1.5 eq) in DMF (2 mL) was added CuI (1.9 mg, 0.010 mmol, 0.030 eq), Pd(PPh$_3$)$_2$Cl$_2$ (7 mg, 0.010 mmol, 0.030 eq) and K$_2$CO$_3$ (83 mg, 0.600 mmol, 3.0 eq). The resulting solution was shaken at 100° C. for 16 hrs. The reaction mixture was concentrated by Speedvac and the residue was purified by prep-TLC and carried on assuming quantitative yield of the title compound.

Step 8: tert-butyl (3-(4-(3-(3-amino-6-(2-(methoxymethoxy)phenyl)pyridazin-4-yl)-3,8-diazabicyclo[3.2.1]octan-8-yl)pyridin-2-yl)propyl)carbamate To a solution of tert-butyl (3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-yl)carbamate (114 mg, 0.200 mmol, 1.0 eq.) in MeOH (2 mL) was added Pd/C (60.0 mg) and SiEt$_3$H (0.4 mL). The resulting solution was shaken at 50° C. for 16 hrs. The mixture was filtered and the filtrate was concentrated to afford the crude title compound.

Step 9: 2-(6-amino-5-(8-(2-(3-aminopropyl)pyridin-4-yl)-3,8-diazabicyclo[3.2.1]octan-3-yl)pyridazin-3-yl)phenol

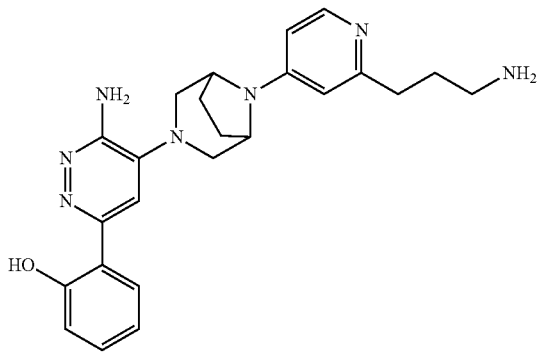 [SMILES: NCCCc1cc(N2C3CCC2CN(c2cc(-c4ccccc4O)nnc2N)C3)ccn1]

A solution of tert-butyl (3-(4-(3-(3-amino-6-(2-(methoxymethoxy)phenyl)pyridazin-4-yl)-3,8-diazabicyclo[3.2.1]octan-8-yl)pyridin-2-yl)propyl)carbamate (115 mg, 0.200 mmol, 1.0 eq.) in HCl (4 M in MeOH, 2 mL) was shaken at 30° C. for 2 hrs. The mixture was evaporated and diluted with 1.5 mL of MeOH. Then the pH was adjusted to 7-8 using aqueous $NH_3 \cdot H_2O$. The crude product was purified by prep-HPLC (Xtimate® C18 150*25 mm*5 μm, Water (10 mM ammonium bicarbonate and 0.05% ammonia hydroxide v/v)-ACN, 44-69%) to afford the title compound (11.7 mg, 14% yield). $^1$H NMR (400 MHz, DMSO-$d_6$) δ 8.06 (d, J=5.8 Hz, 1H), 7.90 (dd, J=8.1, 1.6 Hz, 1H), 7.49 (s, 1H), 7.22 (ddd, J=8.6, 7.2, 1.6 Hz, 1H), 6.90-6.80 (m, 2H), 6.69 (s, 1H), 6.65 (dd, J=5.8, 2.4 Hz, 1H), 5.97 (s, 2H), 4.53 (s, 2H), 3.36-3.23 (m, 2H), 3.02 (d, J=11.5 Hz, 2H), 2.58 (t, J=7.6 Hz, 3H), 2.24-2.15 (m, 2H), 2.01-1.91 (m, 2H), 1.72 (p, J=7.2 Hz, 2H). LCMS (ESI): m/z 432.3 (M+H)$^+$.

Example 5

2-(6-amino-5-(8-(2-(3-(4-(hydroxymethyl)piperidin-1-yl)prop-1-yn-1-yl)pyridin-4-yl)-3,8-diazabicyclo[3.2.1]octan-3-yl)pyridazin-3-yl)phenol (Compound 45)

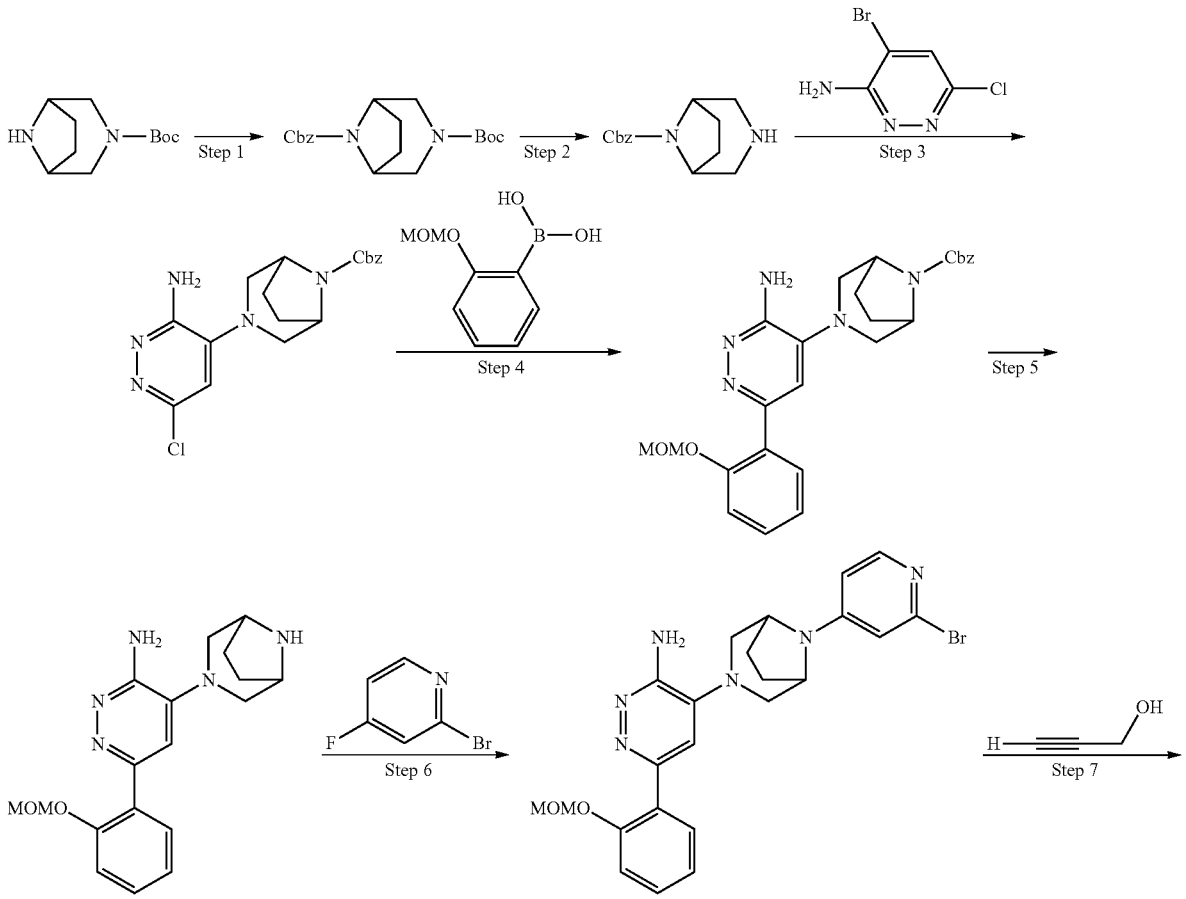

-continued
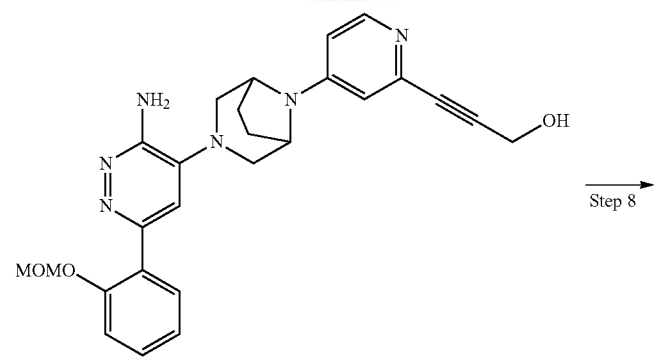
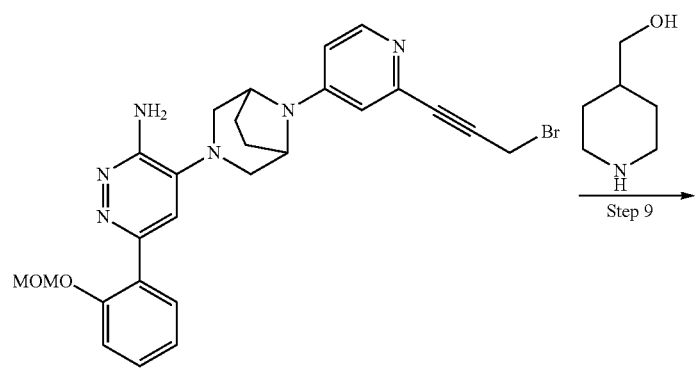
Step 8
Step 9
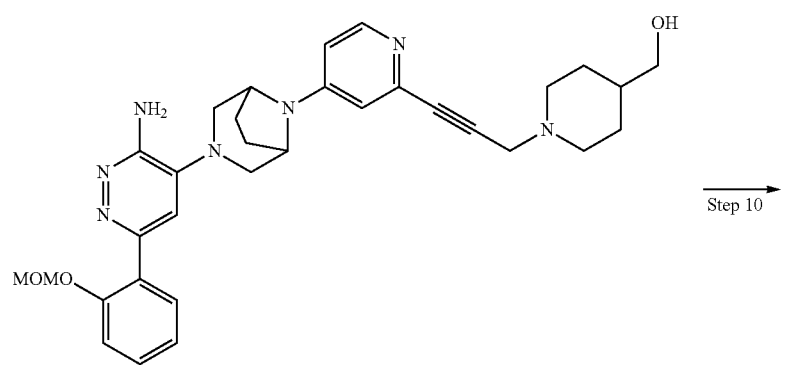
Step 10
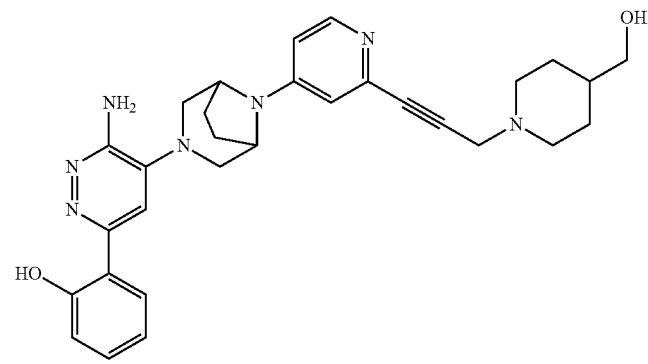

Steps 1 to 6: Procedure similar to those described elsewhere herein, e.g., in Scheme 1 and Example 1.

Step 7: 3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-ol

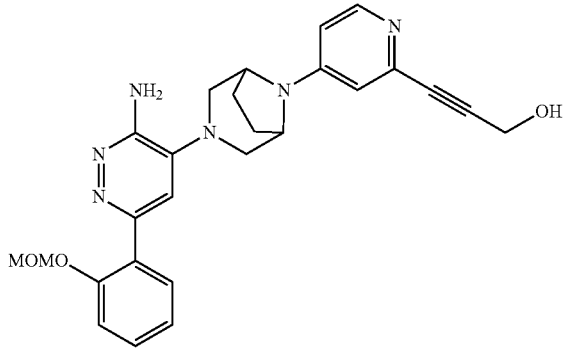

To a solution of 4-(8-(2-bromopyridin-4-yl)-3,8-diazabicyclo[3.2.1]octan-3-yl)-6-(2-(methoxymethoxy)phenyl)pyridazin-3-amine (30.0 g, 60.3 mmol, 1.00 eq) in DMF (210 mL) was added Pd(PPh₃)₄ (2.12 g, 3.02 mmol, 0.05 eq), CuI (574 mg, 3.02 mmol, 0.05 eq), PPh₃ (3.16 g, 12.1 mmol, 0.20 eq), Et₃N (18.3 g, 181 mmol, 25.2 mL, 3.00 eq) and prop-2-yn-1-ol (5.75 g, 102.59 mmol, 6.06 mL, 1.70 eq) at 20° C. under N₂. The reaction was stirred for 2 hrs at 80° C. under N₂. The mixture was poured into water (1.00 L). The aqueous phase was extracted with ethyl acetate (500 mL×3). The combined organic phase was washed with brine (300 mL), dried with anhydrous Na₂SO₄, filtered and concentrated under vacuum. The residue was purified by column chromatography (petroleum ether/ethyl acetate=100/1 to 0/1) to afford 3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-ol (19 g, 39.69 mmol, 65.8% yield) as a yellow solid. ¹H NMR (400 MHz, DMSO-d6): δ 8.08 (d, J=6.0 Hz, 1H), 7.58 (dd, J=2.0 Hz, 4.0 Hz 1H), 7.31-7.36 (m, 1H), 7.12-7.16 (m, 2H), 7.06 (t, J=7.6 Hz, 1H), 6.92 (d, J=2.4 Hz, 1H), 6.78 (dd, J=2.4 Hz, 6.0 Hz 1H), 5.71 (s, 2H), 5.34 (t, J=6.0 Hz, 1H), 5.13 (s, 2H), 4.54 (s, 2H), 4.28 (d, J=5.6 Hz, 2H), 3.22 (s, 3H), 3.16 (d, J=10.4 Hz, 2H), 2.84 (d, J=11.2 Hz, 2H), 2.17-2.22 (m, 2H), 1.95-1.99 (m, 2H).

Step 8: 4-(8-(2-(3-bromoprop-1-yn-1-yl)pyridin-4-yl)-3,8-diazabicyclo[3.2.1]octan-3-yl)-6-(2-(methoxymethoxy)phenyl)pyridazin-3-amine

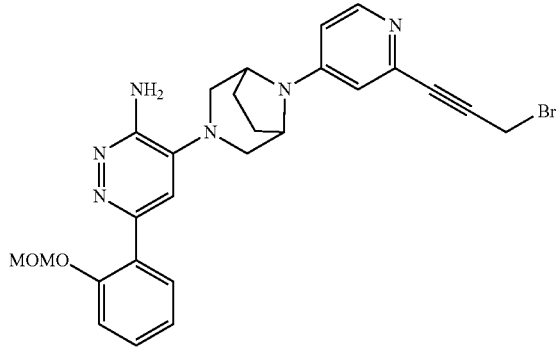

To a suspension of 3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-ol (70.0 mg, 0.15 mmol, 1.00 eq) in DCM (1.50 mL) was added CBr₄ (73.7 mg, 0.225 mmol, 1.50 eq). Then PS-PPh₃ (150 mg) was added under N₂. The reaction was shaken for 2 hrs at 30° C. After filtration, the filtrate was carried over to the next step.

Step 9: (1-(3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-yl)piperidin-4-yl)methanol

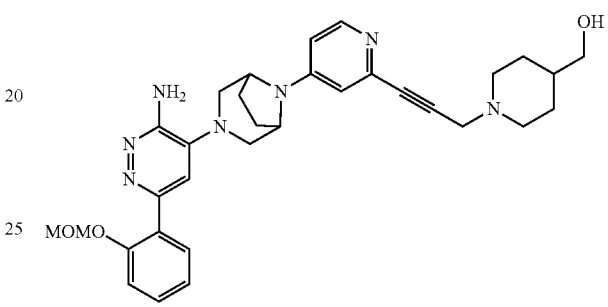

To a solution of piperidin-4-ylmethanol (57.6 mg, 0.50 mmol, 5.00 eq) in DCM (0.100 mL) was added solution of 4-(8-(2-(3-bromoprop-1-yn-1-yl)pyridin-4-yl)-3,8-diazabicyclo[3.2.1]octan-3-yl)-6-(2-(methoxymethoxy)phenyl)pyridazin-3-amine (53.5 mg, 0.10 mmol, 1.00 eq) and DIEA (64.6 mg, 0.500 mmol, 5.00 eq). Then mixture was shaken at 30° C. for 3 hrs. The solvent was concentrated by speedvac. The crude residue was carried over to the next step.

Step 10: 2-(6-amino-5-(8-(2-(3-(4-(hydroxymethyl)piperidin-1-yl)prop-1-yn-1-yl)pyridin-4-yl)-3,8-diazabicyclo[3.2.1]octan-3-yl)pyridazin-3-yl)phenol (Compound 45)

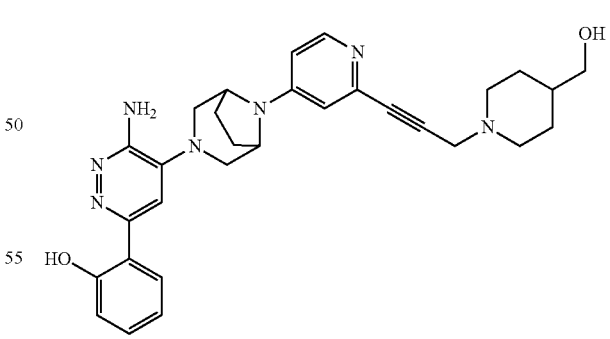

To a solution of (1-(3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-yl)piperidin-4-yl)methanol (57.0 mg, 0.100 mmol, 1.0 eq) in MeOH (0.500 mL) was added HCl-Dioxane (0.500 mL, 4M). The reaction mixture was shaken at 30° C. for 2 hrs. The solvent was concentrated by speedvac. The residue was purified by preparative TLC to afford 2-(6-amino-5-(8-(2-(3-(4-(hydroxymethyl)piperidin-1-yl)prop-1-yn-1-yl)pyridin-4-yl)-3,8-diazabicyclo[3.2.1]octan-3-yl)pyridazin-3-yl)phenol (Compound 45) (2.8 mg, 3.6% yield). $^1$H NMR (400 MHz, DMSO-d$_6$) δ 14.13 (br s, 1H), 8.09 (d, J=5.88 Hz, 1H), 7.88-7.94 (m, 1H), 7.51 (s, 1H), 7.19-7.26 (m, 1H), 6.94 (d, J=2.25 Hz, 1H), 6.82-6.89 (m, 2H), 6.80 (dd, J=2.38, 6.00 Hz, 1H), 5.98 (s, 2H), 4.58 (br s, 2H), 4.42 (t, J=5.32 Hz, 1H), 3.46 (s, 2H), 3.27 (br s, 1H), 3.22-3.26 (m, 3H), 3.01 (br d, J=11.51 Hz, 2H), 2.86 (br d, J=11.26 Hz, 2H), 2.07-2.23 (m, 4H), 1.90-2.01 (m, 2H), 1.67 (br d, J=11.01 Hz, 2H), 1.26-1.37 (m, 1H), 1.08-1.19 (m, 2H).

Example 6

2-(6-amino-5-(8-(2-(3-(azepan-1-yl)prop-1-yn-1-yl)pyridin-4-yl)-3,8-diazabicyclo[3.2.1]octan-3-yl)pyridazin-3-yl)phenol (Compound 58)

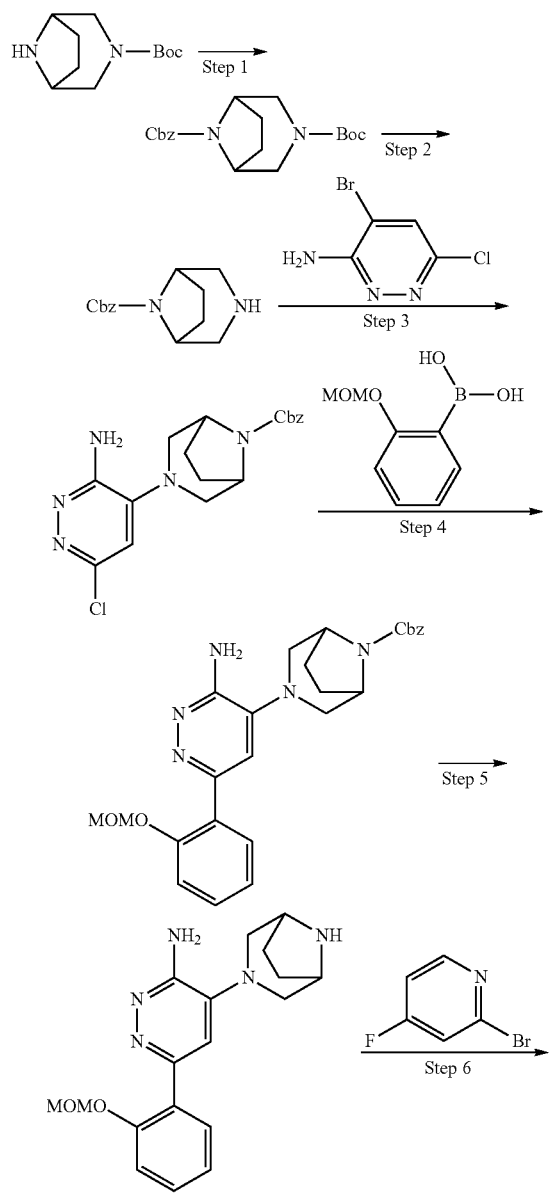

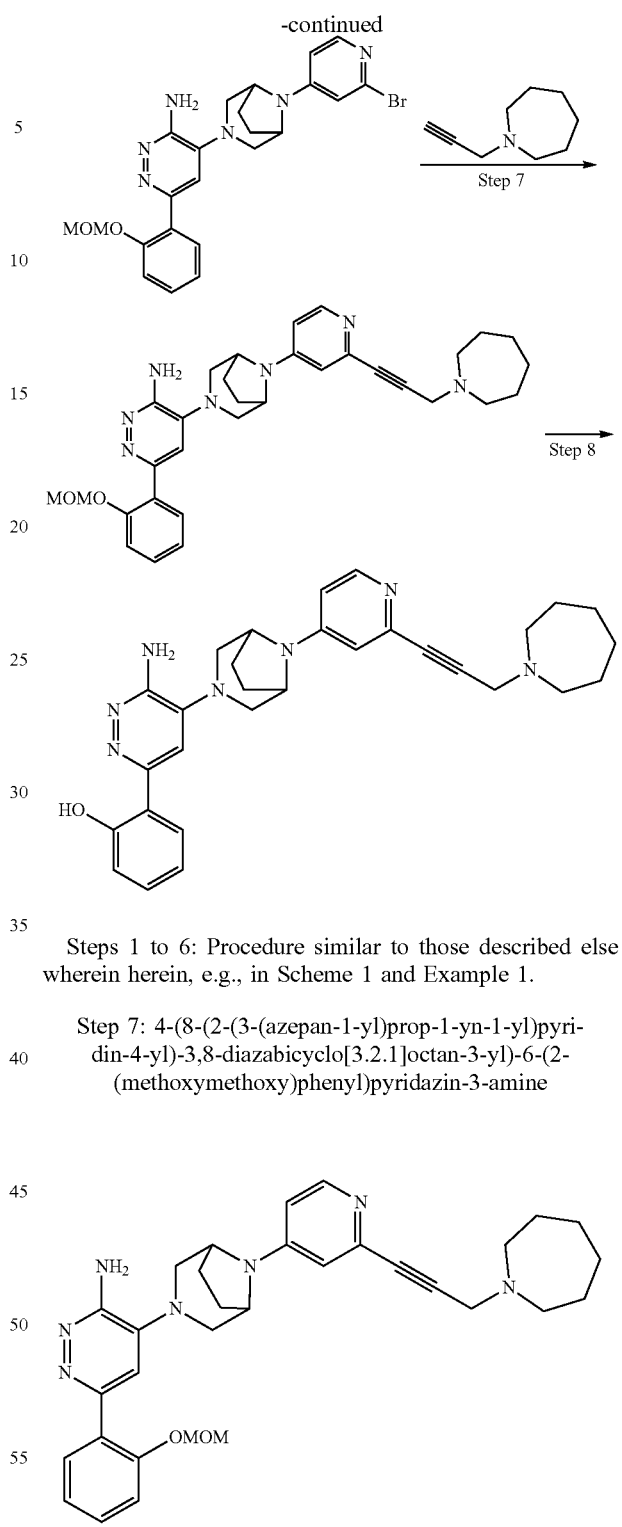

Steps 1 to 6: Procedure similar to those described elsewhere herein, e.g., in Scheme 1 and Example 1.

Step 7: 4-(8-(2-(3-(azepan-1-yl)prop-1-yn-1-yl)pyridin-4-yl)-3,8-diazabicyclo[3.2.1]octan-3-yl)-6-(2-(methoxymethoxy)phenyl)pyridazin-3-amine To a solution of 4-[8-(2-bromo-4-pyridyl)-3,8-diazabicyclo[3.2.1]octan-3-yl]-6-[2-(methoxymethoxy)phenyl]pyridazin-3-amine (300 mg, 0.603 mmol, 1.0 eq) and 1-prop-2-ynylazepane (413.83 mg, 3.02 mmol, 5 eq) in THF (5 mL) was added TEA (305.16 mg, 3.02 mmol, 5 eq) and Pd(dppf)Cl$_2$ (44.12 mg, 0.060 mmol, 0.1 eq), CuI (11.49 mg, 0.060 mmol, 0.1 eq). The mixture was stirred at 80° C. for 10 hr under N$_2$. The reaction mixture was concentrated under reduced pressure to remove solvent. The residue was diluted with H₂O (20 mL) and extracted with EtOAc (20 mL×2). The combined organic layers were dried over Na₂SO₄, filtered and concentrated under reduced pressure to give a residue to afford 4-(8-(2-(3-(azepan-1-yl)prop-1-yn-1-yl)pyridin-4-yl)-3,8-diazabicyclo[3.2.1]octan-3-yl)-6-(2-(methoxymethoxy)phenyl)pyridazin-3-amine as a brown solid (500 mg, crude).

Step 8: 2-(6-amino-5-(8-(2-(3-(azepan-1-yl)prop-1-yn-1-yl)pyridin-4-yl)-3,8-diazabicyclo[3.2.1]octan-3-yl)pyridazin-3-yl)phenol (Compound 58)

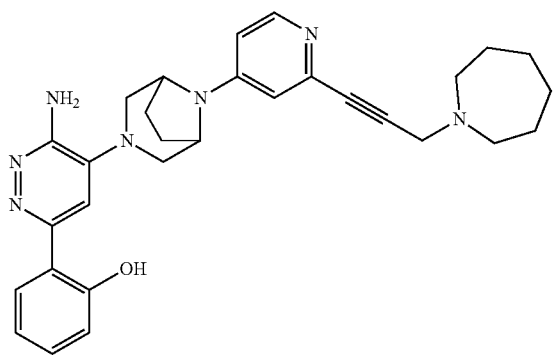

To a solution of 4-[8-[2-[3-(azepan-1-yl)prop-1-ynyl]-4-pyridyl]-3,8-diazabicyclo[3.2.1]octan-3-yl]-6-[2-(methoxymethoxy)phenyl]pyridazin-3-amine (500 mg, 0.903 mmol, 1.00 eq) in DCM (2 mL) was added HCl/EtOAc (4 M, 30.00 mL, 133 eq). The mixture was stirred at 25° C. for 5 hr. The reaction mixture was concentrated under reduced pressure. The crude product was purified by Pre-HPLC (Phenomenex Luna C18 75*30 mm*3 um, water (0.225% FA)-ACN, 1-30%) to afford 2-(6-amino-5-(8-(2-(3-(azepan-1-yl)prop-1-yn-1-yl)pyridin-4-yl)-3,8-diazabicyclo[3.2.1]octan-3-yl)pyridazin-3-yl)phenol (Compound 58) (26 mg, 8.4% yield over two steps). ¹H NMR (400 MHz, Methanol-d₄) δ 8.49 (br s, 1H), 8.11 (br d, J=6.1 Hz, 1H), 7.75 (br d, J=7.8 Hz, 1H), 7.51 (s, 1H), 7.25 (br t, J=7.5 Hz, 1H), 7.10 (s, 1H), 6.98-6.83 (m, 3H), 4.70-4.57 (m, 2H), 3.94 (s, 2H), 3.41 (br d, J=11.2 Hz, 2H), 3.19-3.04 (m, 6H), 2.37-2.07 (m, 4H), 1.85 (br s, 4H), 1.80-1.62 (m, 4H).

Example 7

2-(6-amino-5-(8-(2-(3-((S)-3-methylpyrrolidin-1-yl)prop-1-yn-1-yl)pyridin-4-yl)-3,8-diazabicyclo[3.2.1]octan-3-yl)pyridazin-3-yl)phenol (Compound 75)

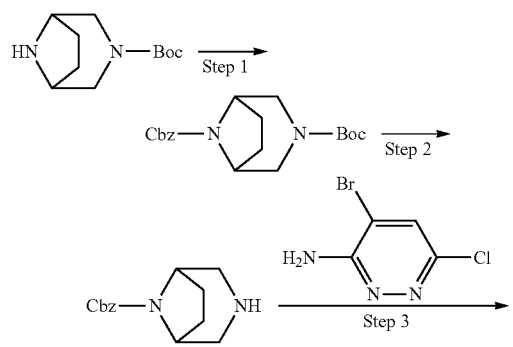

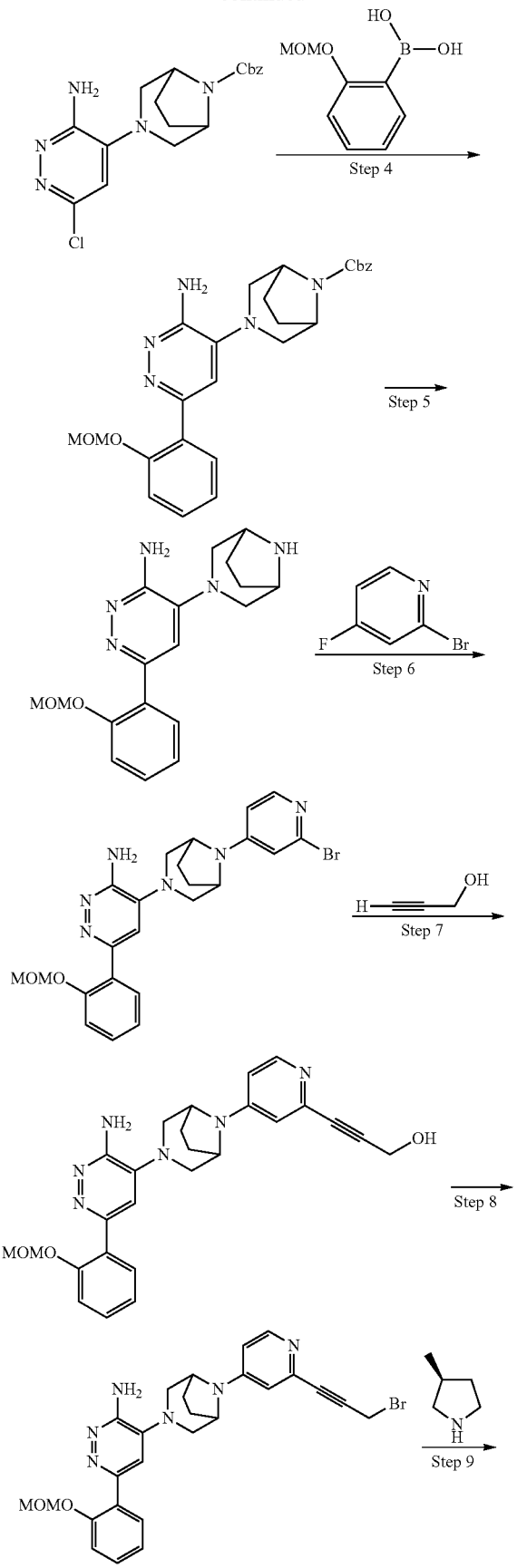

-continued

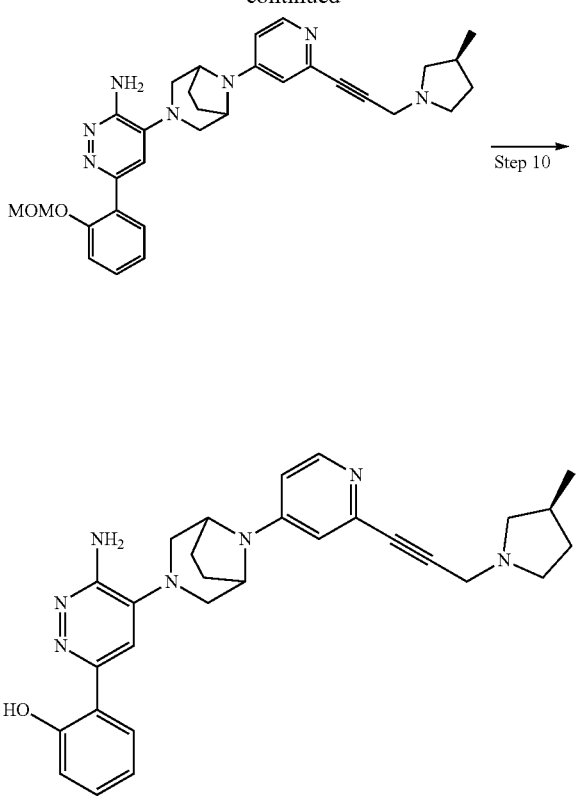

Step 1 to 8: Procedure similar to those described elsewhere herein, e.g., in Scheme 3 and Example 5.

Step 9: 6-(2-(methoxymethoxy)phenyl)-4-(8-(2-(3-((S)-3-methylpyrrolidin-1-yl)prop-1-yn-1-yl)pyridin-4-yl)-3,8-diazabicyclo[3.2.1]octan-3-yl)pyridazin-3-amine

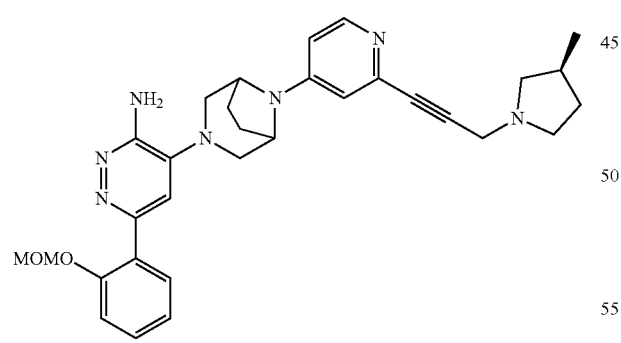

To a solution of (S)-3-methylpyrrolidine (42.6 mg, 0.50 mmol, 5.00 eq) in DCM (0.100 mL) was added solution of 4-(8-(2-(3-bromoprop-1-yn-1-yl)pyridin-4-yl)-3,8-diazabicyclo[3.2.1]octan-3-yl)-6-(2-(methoxymethoxy)phenyl)pyridazin-3-amine (53.5 mg, 0.10 mmol, 1.00 eq) and DIEA (64.6 mg, 0.500 mmol, 5.00 eq). Then mixture was shaken at 30° C. for 3 hrs. The solvent was concentrated by speedvac. The crude residue was carried over to the next step.

Step 10: 2-(6-amino-5-(8-(2-(3-((S)-3-methylpyrrolidin-1-yl)prop-1-yn-1-yl)pyridin-4-yl)-3,8-diazabicyclo[3.2.1]octan-3-yl)pyridazin-3-yl)phenol (Compound 75)

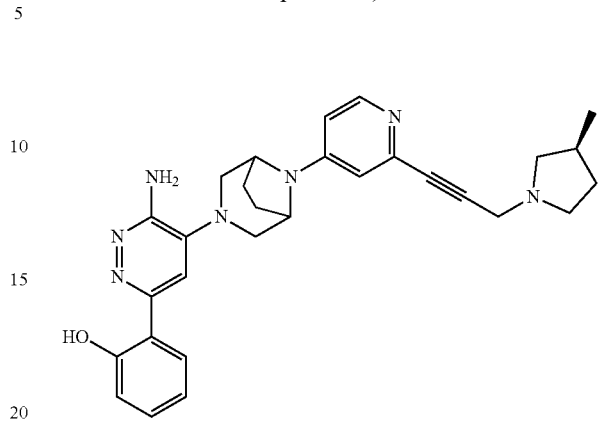

To a solution of 6-(2-(methoxymethoxy)phenyl)-4-(8-(2-(3-((S)-3-methylpyrrolidin-1-yl)prop-1-yn-1-yl)pyridin-4-yl)-3,8-diazabicyclo[3.2.1]octan-3-yl)pyridazin-3-amine (54.0 mg, 0.100 mmol, 1.0 eq) in MeOH (0.500 mL) was added HCl-Dioxane (0.500 mL, 4M). The reaction mixture was shaken at 30° C. for 2 hrs. The solvent was concentrated by speedvac. The residue was purified by prep-HPLC (Welch Xtimate® C18 150*25 mm*5 μm, water (0.225% FA)-ACN, 0-30%) to afford 2-(6-amino-5-(8-(2-(3-((S)-3-methylpyrrolidin-1-yl)prop-1-yn-1-yl)pyridin-4-yl)-3,8-diazabicyclo[3.2.1]octan-3-yl)pyridazin-3-yl)phenol (Compound 75) (5.7 mg, 12% yield). $^1$H NMR (400 MHz, DMSO-$d_6$) δ 8.09 (d, J=5.77 Hz, 1H), 7.88-7.94 (m, 1H), 7.51 (s, 1H), 7.18-7.26 (m, 1H), 6.94 (d, J=2.26 Hz, 1H), 6.77-6.90 (m, 3H), 5.99 (s, 2H), 4.57 (br s, 2H), 3.50-3.59 (m, 2H), 3.27 (br s, 1H), 3.25 (br s, 1H), 3.00 (br d, J=11.54 Hz, 2H), 2.80 (t, J=7.28 Hz, 1H), 2.57-2.68 (m, 2H), 2.12-2.24 (m, 4H), 1.90-2.01 (m, 3H), 1.23-1.33 (m, 1H), 0.99 (d, J=6.53 Hz, 3H).

Example 8

3-(3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)-3-azabicyclo[3.1.0]hexan-1-ol (Compound 105)

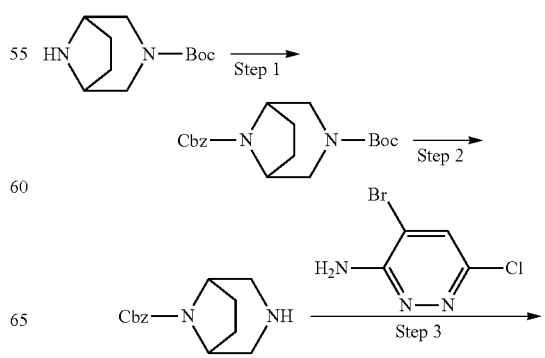

577
-continued

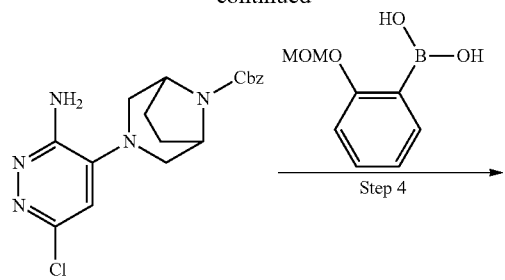
Step 4

Step 5

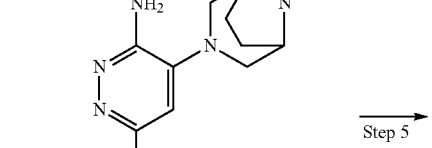
Step 6

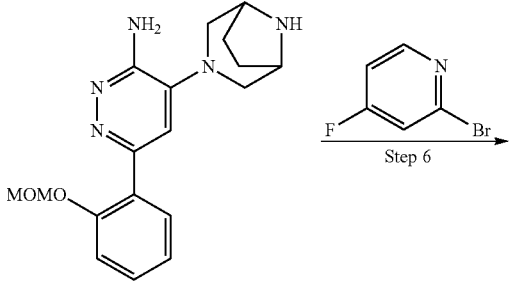
Step 7

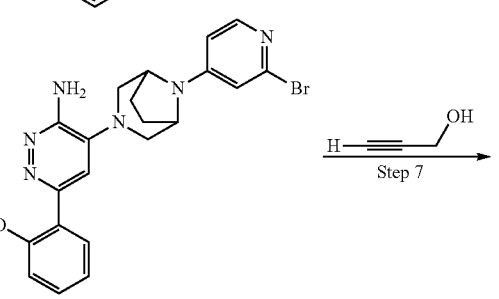
Step 8

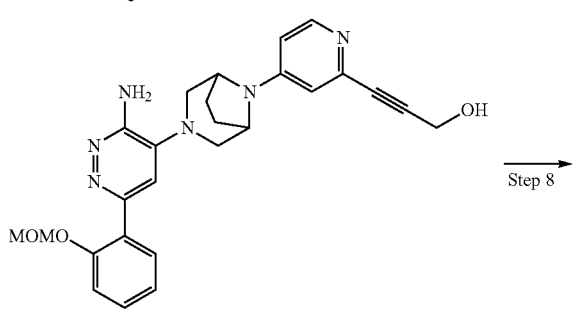
Step 9

578
-continued

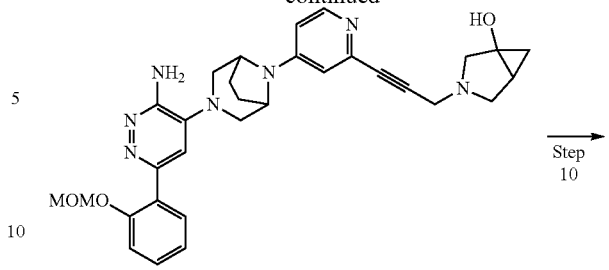
Step 10

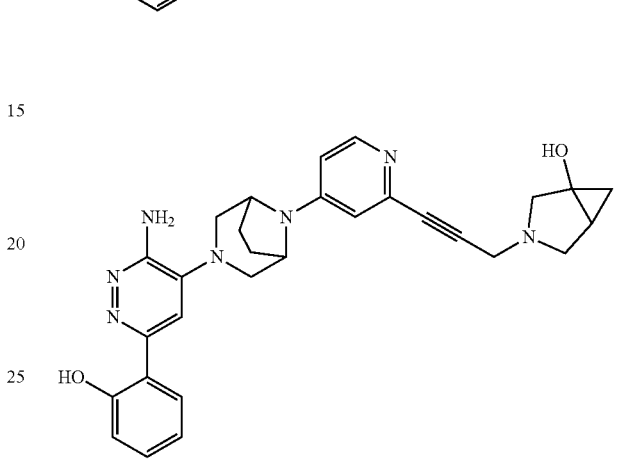

Step 1 to 8: Procedure similar to those described elsewhere herein, e.g., in Scheme 3 and Example 5.

Step 9: 3-(3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-yl)-3-azabicyclo[3.1.0]hexan-1-ol

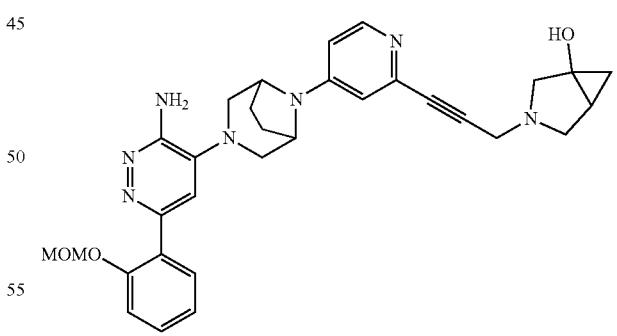

To a solution of 3-azabicyclo[3.1.0]hexan-1-ol (49.6 mg, 0.50 mmol, 5.00 eq) in DCM (0.100 mL) was added solution of 4-(8-(2-(3-bromoprop-1-yn-1-yl)pyridin-4-yl)-3,8-diazabicyclo[3.2.1]octan-3-yl)-6-(2-(methoxymethoxy)phenyl)pyridazin-3-amine (53.5 mg, 0.10 mmol, 1.00 eq) and DIEA (64.6 mg, 0.500 mmol, 5.00 eq). Then mixture was shaken at 30° C. for 3 hrs. The solvent was concentrated by speedvac. The crude residue was carried over to the next step.

Step 10: 3-(3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)-3-azabicyclo[3.1.0]hexan-1-ol (Compound 105)

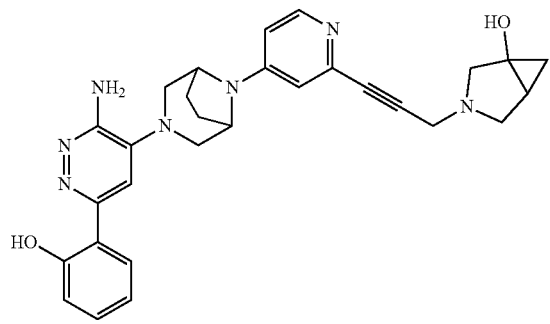 [SMILES: Nc1nnc(-c2ccccc2O)cc1N1CCN(c2ccnc(C#CCN3CC4CC4(O)C3)c2)CC1]

To a solution of 3-(3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-yl)-3-azabicyclo[3.1.0]hexan-1-ol (55.4 mg, 0.100 mmol, 1.0 eq) in MeOH (0.500 mL) was added HCl-Dioxane (0.500 mL, 4M). The reaction mixture was shaken at 30° C. for 2 hrs. The solvent was concentrated by speedvac. The residue was purified by prep-HPLC (Welch Xtimate® C18 150*25 mm*5 μm, water (0.225% FA)-ACN, 2-27%) to afford 3-(3-(4-(3-(3-amino-6-(2-hydroxyphenyl)pyridazin-4-yl)-3,8-diazabicyclo[3.2.1]octan-8-yl)pyridin-2-yl)prop-2-yn-1-yl)-3-azabicyclo[3.1.0]hexan-1-ol (Compound 105) (5.3 mg, 10% yield). $^1$H NMR (400 MHz, DMSO-$d_6$) δ 14.07 (br s, 1H), 8.10 (d, J=6.02 Hz, 1H), 7.88-7.95 (m, 1H), 7.51 (s, 1H), 7.18-7.25 (m, 1H), 6.96 (d, J=2.26 Hz, 1H), 6.76-6.90 (m, 3H), 5.99 (s, 2H), 5.68 (br s, 1H), 4.58 (br s, 2H), 3.49-3.63 (m, 2H), 3.28 (br s, 1H), 3.25 (br s, 1H), 2.93-3.05 (m, 3H), 2.72-2.77 (m, 2H), 2.65-2.69 (m, 1H), 2.19 (br d, J=7.28 Hz, 2H), 1.93-2.02 (m, 2H), 1.24-1.32 (m, 1H), 0.84 (t, J=4.39 Hz, 1H), 0.69 (dd, J=4.52, 8.78 Hz, 1H).

Example 9

2-(5-(8-(2-(3-(6-azaspiro[2.5]octan-6-yl)prop-1-yn-1-yl)pyridin-4-yl)-3,8-diazabicyclo[3.2.1]octan-3-yl)-6-aminopyridazin-3-yl)phenol (Compound 136)

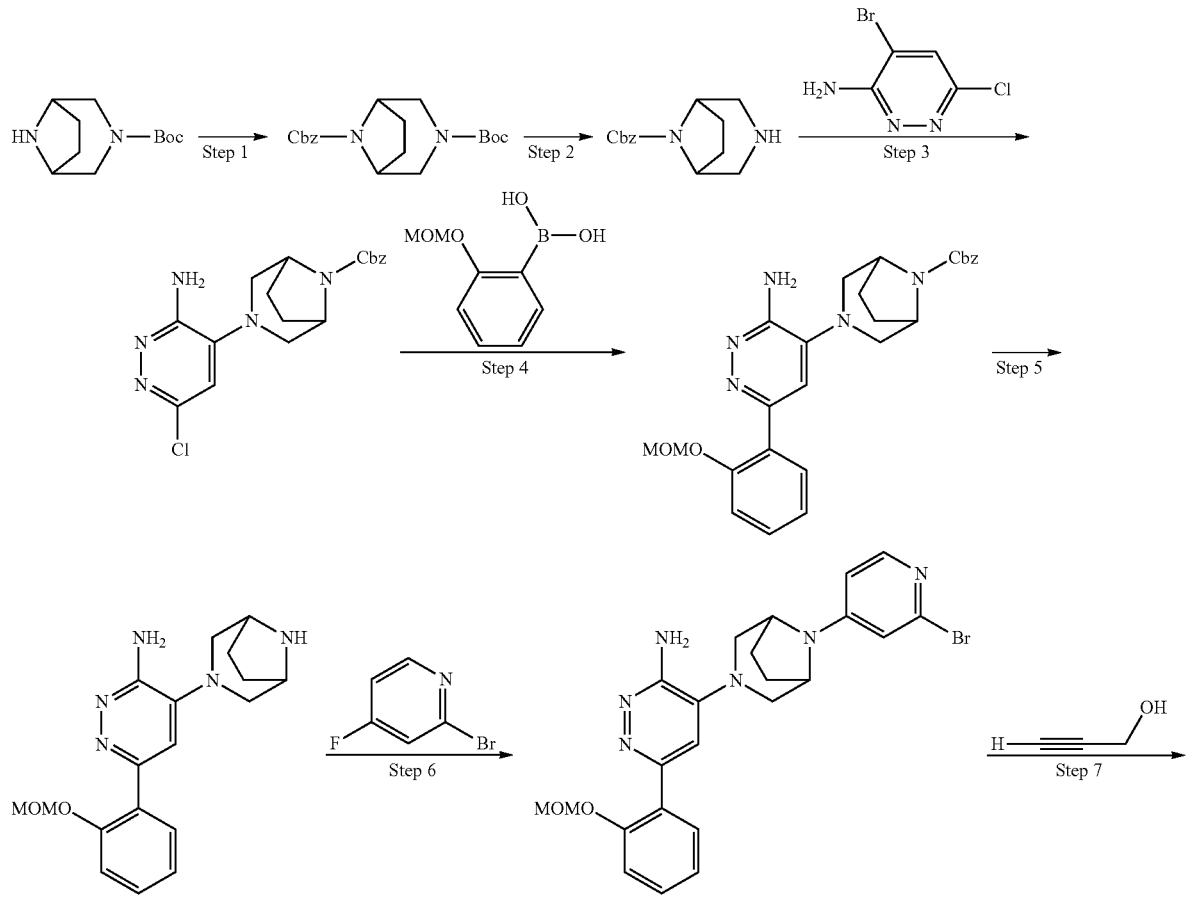

-continued
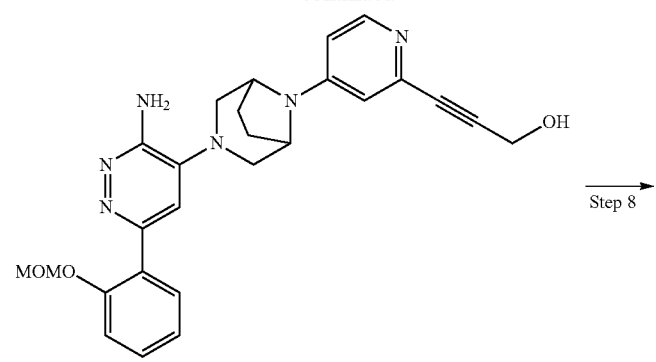
Step 8
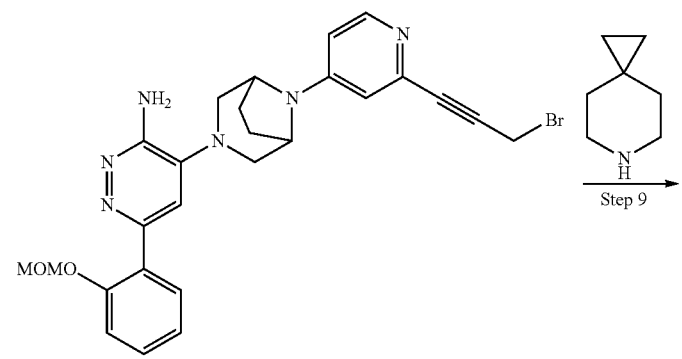
Step 9
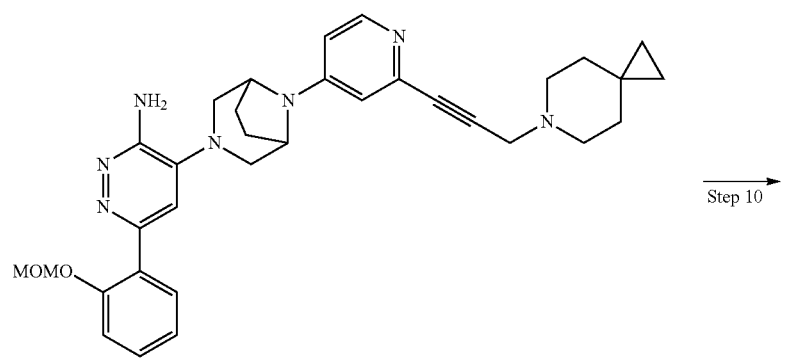
Step 10
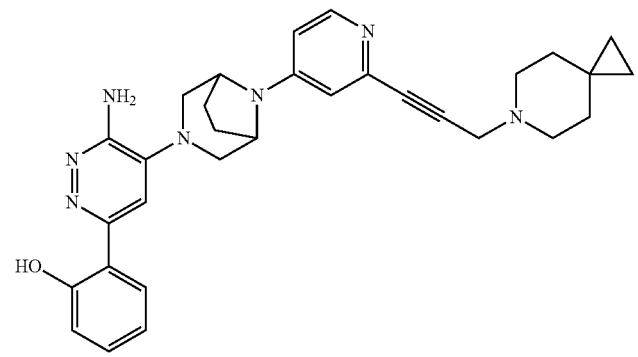

Step 1 to 8: Procedure similar to those described elsewhere herein, e.g., in Scheme 3 and Example 5.

Step 9: 4-(8-(2-(3-(6-azaspiro[2.5]octan-6-yl)prop-1-yn-1-yl)pyridin-4-yl)-3,8-diazabicyclo[3.2.1]octan-3-yl)-6-(2-(methoxymethoxy)phenyl)pyridazin-3-amine

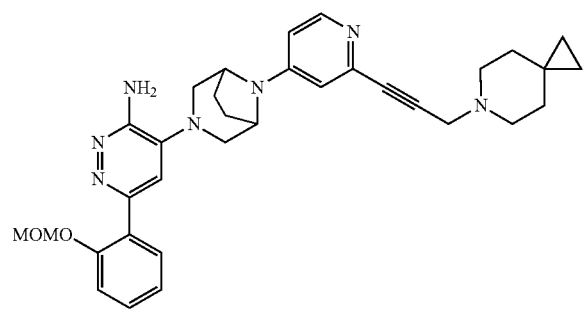

To a solution of 6-azaspiro[2.5]octane (55.6 mg, 0.50 mmol, 5.00 eq) in DCM (0.100 mL) was added solution of 4-(8-(2-(3-bromoprop-1-yn-1-yl)pyridin-4-yl)-3,8-diazabicyclo[3.2.1]octan-3-yl)-6-(2-(methoxymethoxy)phenyl)pyridazin-3-amine (53.5 mg, 0.10 mmol, 1.00 eq) and DIEA (64.6 mg, 0.500 mmol, 5.00 eq). Then mixture was shaken at 30° C. for 3 hrs. The solvent was concentrated by speedvac. The crude residue was carried over to the next step.

Step 10: 2-(5-(8-(2-(3-(6-azaspiro[2.5]octan-6-yl)prop-1-yn-1-yl)pyridin-4-yl)-3,8-diazabicyclo[3.2.1]octan-3-yl)-6-aminopyridazin-3-yl)phenol (Compound 136)

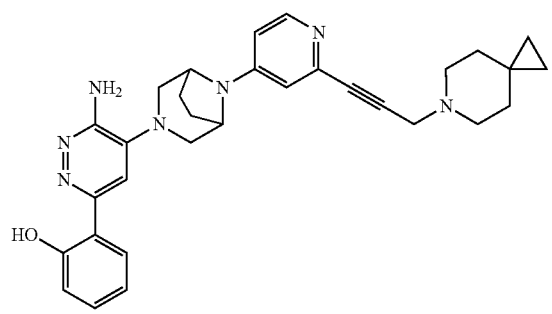 [SMILES: Nc1nnc(-c2ccccc2O)cc1N1CCN(c2ccnc(C#CCN3CCC4(CC3)CC4)c2)CC1]

To a solution of 4-(8-(2-(3-(6-azaspiro[2.5]octan-6-yl)prop-1-yn-1-yl)pyridin-4-yl)-3,8-diazabicyclo[3.2.1]octan-3-yl)-6-(2-(methoxymethoxy)phenyl)pyridazin-3-amine (56.6 mg, 0.100 mmol, 1.0 eq) in MeOH (0.500 mL) was added HCl-Dioxane (0.500 mL, 4M). The reaction mixture was shaken at 30° C. for 2 hrs. The solvent was concentrated by speedvac. The residue was purified by prep-HPLC (Welch Xtimate® C18 150*25 mm*5 μm, water (0.225% FA)-ACN, 0-24%) to afford 2-(5-(8-(2-(3-(6-azaspiro[2.5]octan-6-yl)prop-1-yn-1-yl)pyridin-4-yl)-3,8-diazabicyclo[3.2.1]octan-3-yl)-6-aminopyridazin-3-yl)phenol (Compound 136) (9.6 mg, 18% yield). $^1$H NMR (400 MHz, DMSO-$d_6$) δ 14.04 (br s, 1H), 8.10 (d, J=5.88 Hz, 1H), 7.91 (d, J=7.25 Hz, 1H), 7.51 (s, 1H), 7.22 (t, J=7.25 Hz, 1H), 6.95 (d, J=1.88 Hz, 1H), 6.77-6.89 (m, 3H), 5.99 (s, 2H), 4.57 (br s, 2H), 3.50 (s, 2H), 3.26 (br d, J=11.2 Hz, 2H), 3.01 (br d, J=11.51 Hz, 2H), 2.53 (m, 4H), 2.20 (br d, J=7.13 Hz, 2H), 1.86-2.07 (m, 2H), 1.22-1.51 (m, 4H), 0.25 (s, 4H).

Example 10

2-(5-(8-(2-(3-(6-azabicyclo[3.2.0]heptan-6-yl)prop-1-yn-1-yl)pyridin-4-yl)-3,8-diazabicyclo[3.2.1]octan-3-yl)-6-aminopyridazin-3-yl)phenol (Compound 162)

585

-continued

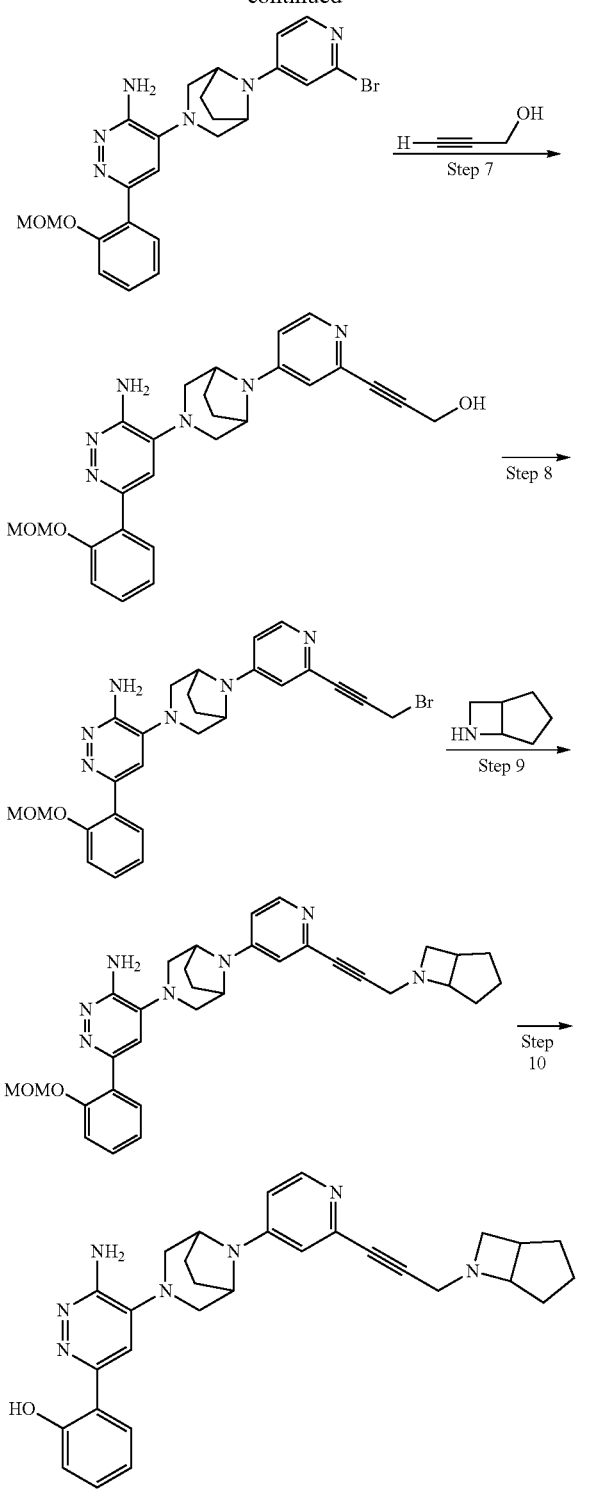

Step 1 to 8: Procedure similar to those described elsewherein herein, e.g., in Scheme 3 and Example 5.

586

Step 9: 4-(8-(2-(3-(6-azabicyclo[3.2.0]heptan-6-yl)prop-1-yn-1-yl)pyridin-4-yl)-3,8-diazabicyclo[3.2.1]octan-3-yl)-6-(2-(methoxymethoxy)phenyl)pyridazin-3-amine

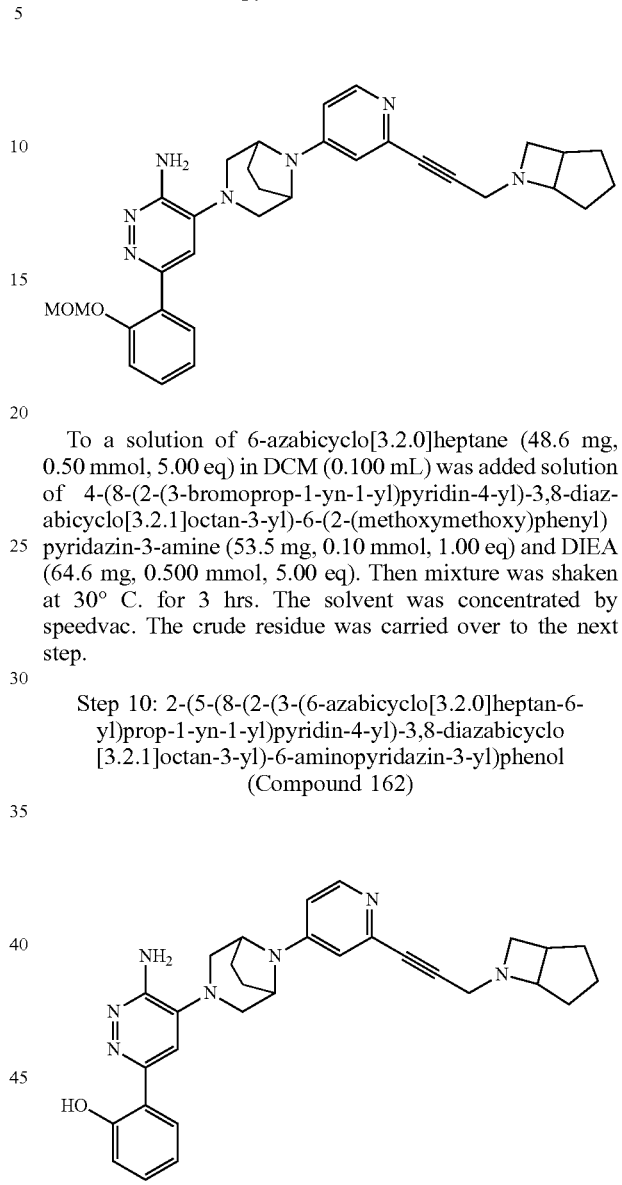

To a solution of 6-azabicyclo[3.2.0]heptane (48.6 mg, 0.50 mmol, 5.00 eq) in DCM (0.100 mL) was added solution of 4-(8-(2-(3-bromoprop-1-yn-1-yl)pyridin-4-yl)-3,8-diazabicyclo[3.2.1]octan-3-yl)-6-(2-(methoxymethoxy)phenyl)pyridazin-3-amine (53.5 mg, 0.10 mmol, 1.00 eq) and DIEA (64.6 mg, 0.500 mmol, 5.00 eq). Then mixture was shaken at 30° C. for 3 hrs. The solvent was concentrated by speedvac. The crude residue was carried over to the next step.

Step 10: 2-(5-(8-(2-(3-(6-azabicyclo[3.2.0]heptan-6-yl)prop-1-yn-1-yl)pyridin-4-yl)-3,8-diazabicyclo[3.2.1]octan-3-yl)-6-aminopyridazin-3-yl)phenol (Compound 162)

To a solution of 4-(8-(2-(3-(6-azabicyclo[3.2.0]heptan-6-yl)prop-1-yn-1-yl)pyridin-4-yl)-3,8-diazabicyclo[3.2.1]octan-3-yl)-6-(2-(methoxymethoxy)phenyl)pyridazin-3-amine (55.2 mg, 0.100 mmol, 1.0 eq) in MeOH (0.500 mL) was added HCl-Dioxane (0.500 mL, 4M). The reaction mixture was shaken at 30° C. for 2 hrs. The solvent was concentrated by speedvac. The residue was purified by prep-HPLC (Welch Xtimate® C18 150*25 mm*5 µm, water (0.225% FA)-ACN, 0-22%) to afford 2-(5-(8-(2-(3-(6-azabicyclo[3.2.0]heptan-6-yl)prop-1-yn-1-yl)pyridin-4-yl)-3,8-diazabicyclo[3.2.1]octan-3-yl)-6-aminopyridazin-3-yl)phenol (Compound 162) (7.9 mg, 16% yield). $^1$H NMR (400 MHz, DMSO-$d_6$) δ 14.12 (br s, 1H), 8.10 (d, J=5.88 Hz, 1H), 7.91 (d, J=6.88 Hz, 1H), 7.51 (s, 1H), 7.19-7.25 (m, 1H), 6.95 (d, J=2.13 Hz, 1H), 6.78-6.89 (m, 3H), 5.99 (s, 2H), 4.57 (br s, 2H), 3.81-3.88 (m, 1H), 3.42 (s, 2H), 3.26 (br d, J=11.2 Hz, 2H), 3.01 (br d, J=11.51 Hz, 2H), 2.92 (dd, J=3.25, 7.63 Hz, 1H), 2.69-2.78 (m, 1H), 2.20 (br d, J=7.13 Hz, 2H), 1.91-2.07 (m, 4H), 1.70-1.79 (m, 1H), 1.61-1.70 (m, 2H), 1.36-1.49 (m, 1H), 1.13-1.25 (m, 1H).
Example 11
2-(6-amino-5-(8-(2-(3-(piperidin-1-yl)prop-1-yn-1-yl)pyridin-4-yl)-3,8-diazabicyclo[3.2.1]octan-3-yl)pyridazin-3-yl)phenol (Compound 166)
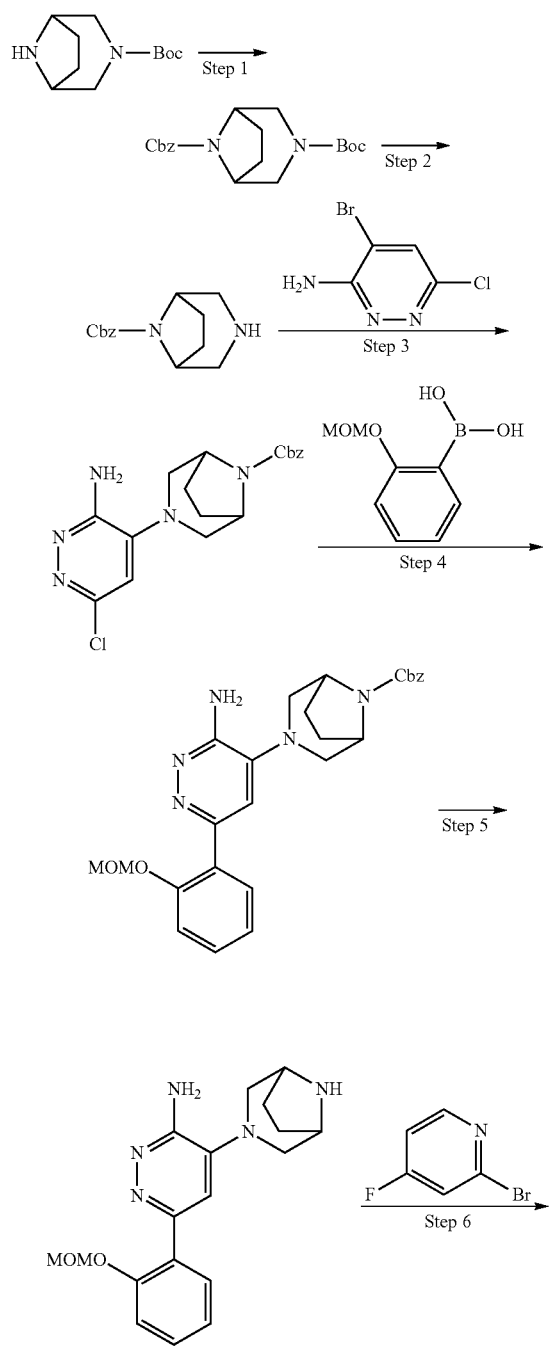
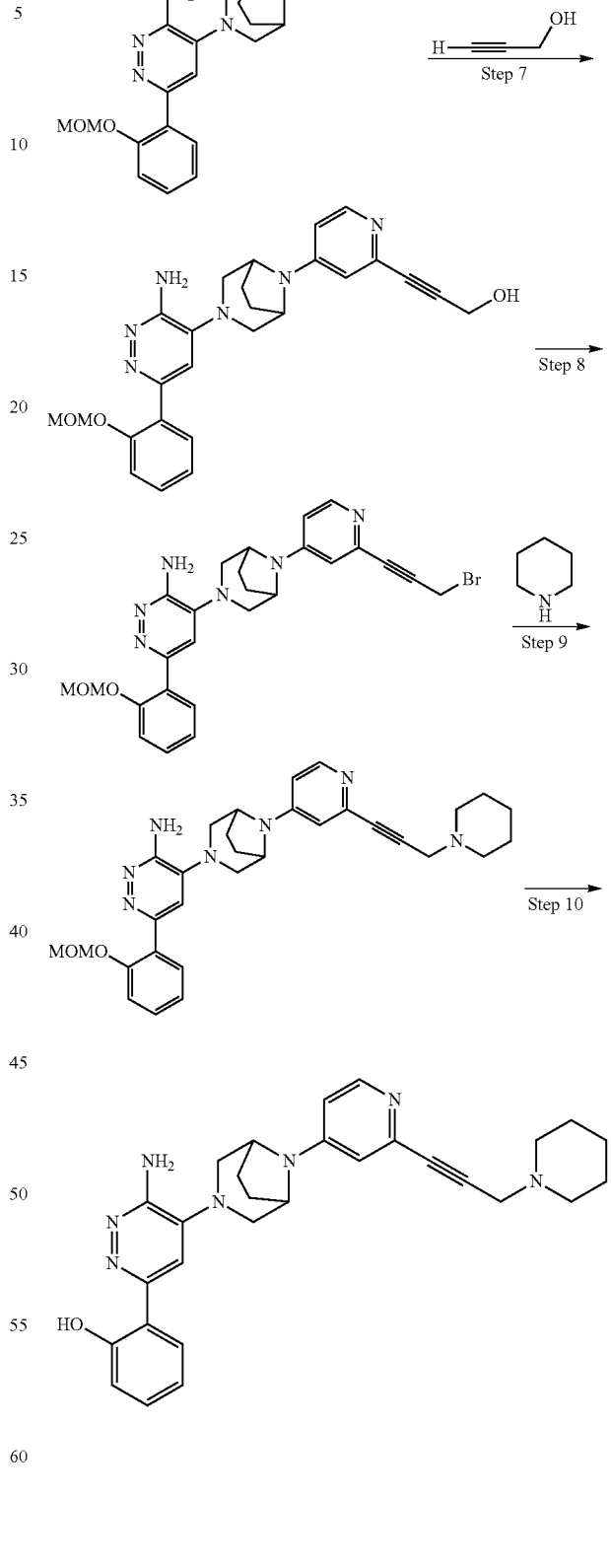
Step 1 to 7: Procedure similar to those described elsewhere herein, e.g., in Scheme 3 and Example 5.

Step 8: 3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-yl methanesulfonate

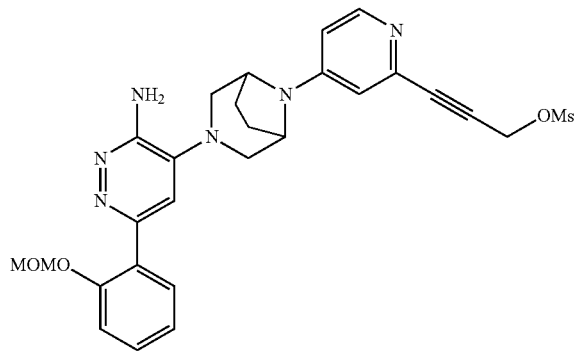

To a solution of 3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-ol (200 mg, 0.424 mmol, 1.00 eq) in DCM (10.0 mL) was added TEA (85.8 mg, 0.848 mmol, 2.00 eq) and MsCl (213 mg, 1.86 mmol, 4.38 eq). Then the mixture was stirred at 25° C. for 2 hrs. The reaction mixture was washed with water (5.00 mL×2), brine (10.0 mL). The organic layer was dried with $Na_2SO_4$ and concentrated under vacuum to afford 3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-yl methanesulfonate (0.700 g, crude) as a crude brown solid.

Step 9: 6-(2-(methoxymethoxy)phenyl)-4-(8-(2-(3-(piperidin-1-yl)prop-1-yn-1-yl)pyridin-4-yl)-3,8-diazabicyclo[3.2.1]octan-3-yl)pyridazin-3-amine

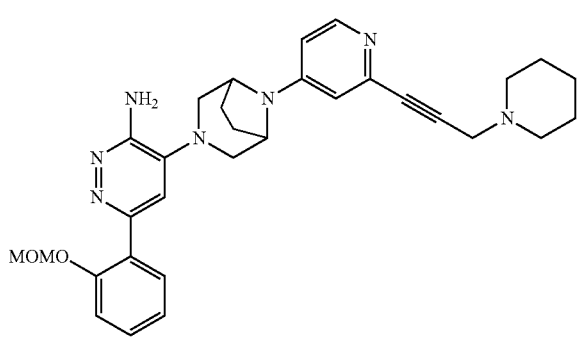

To a solution of 3-(4-(3-(3-amino-6-(2-(methoxymethoxy)phenyl)pyridazin-4-yl)-3,8-diazabicyclo[3.2.1]octan-8-yl)pyridin-2-yl)prop-2-yn-1-yl methanesulfonate (700 mg, 1.27 mmol, 1.00 eq) and piperidine (162 mg, 1.91 mmol, 1.50 eq) in DCM (5.00 mL) was added pyridine (201 mg, 2.54 mmol, 2.00 eq). The mixture was stirred at 25° C. for 3 hrs. The reaction mixture was concentrated under vacuum. The residue was purified by column chromatography (Ethyl acetate/MeOH=50/1 to 0/1) to afford 6-(2-(methoxymethoxy)phenyl)-4-(8-(2-(3-(piperidin-1-yl)prop-1-yn-1-yl)pyridin-4-yl)-3,8-diazabicyclo[3.2.1]octan-3-yl)pyridazin-3-amine (430 mg, 63% yield) as a yellow solid. $^1$H NMR (400 MHz, $CDCl_3$) δ 8.21 (d, 1H, J=6.0 Hz), 7.65 (dd, 1H, J=1.8, 7.6 Hz), 7.34 (ddd, 1H, J=1.8, 7.3, 8.3 Hz), 7.21 (s, 1H), 7.2-7.1 (m, 2H), 6.81 (d, 1H, J=2.4 Hz), 6.55 (dd, 1H, J=2.5, 6.0 Hz), 5.30 (br s, 2H), 4.40 (br s, 2H), 3.64 (br s, 2H), 3.34 (s, 3H), 3.19 (br d, 2H, J=11.6 Hz), 3.03 (br d, 3H, J=11.1 Hz), 2.74 (br s, 4H), 2.18-2.13 (m, 4H), 1.77-1.66 (m, 4H), 1.54-1.43 (m, 2H).

Step 10: 2-(6-amino-5-(8-(2-(3-(piperidin-1-yl)prop-1-yn-1-yl)pyridin-4-yl)-3,8-diazabicyclo[3.2.1]octan-3-yl)pyridazin-3-yl)phenol (Compound 166)

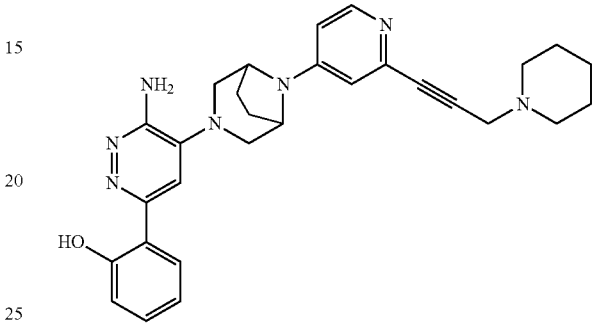

To a solution of 6-(2-(methoxymethoxy)phenyl)-4-(8-(2-(3-(piperidin-1-yl)prop-1-yn-1-yl)pyridin-4-yl)-3,8-diazabicyclo[3.2.1]octan-3-yl)pyridazin-3-amine (300 mg, 0.555 mmol, 1.00 eq) in EtOAc (2.00 mL) was added HCl/EtOAc (4 M, 10.0 mL). The mixture was stirred at 25° C. for 2 hrs. The reaction mixture was concentrated in vacuum. The residue was purified by prep-HPLC (Waters Xbridge BEH C18 100*30 mm*10 μm, water (10 mM ammonium bicarbonate and 0.05% ammonia hydroxide v/v)-ACN, 40%-70%) to afford 2-(6-amino-5-(8-(2-(3-(piperidin-1-yl)prop-1-yn-1-yl)pyridin-4-yl)-3,8-diazabicyclo[3.2.1]octan-3-yl)pyridazin-3-yl)phenol (Compound 166) (35.0 mg, 13% yield). $^1$H NMR (400 MHz, Methanol-$d_4$) δ 8.06 (d, J=6.0 Hz, 1H), 7.73 (br d, J=7.2 Hz, 1H), 7.48 (s, 1H), 7.23 (t, J=7.6 Hz, 1H), 7.00 (d, J=2.4 Hz, 1H), 6.89 (d, J=7.6 Hz, 1H), 6.81 (dd, J=6.0, 2.4 Hz, 1H), 4.52 (br s, 2H), 3.50 (s, 2H), 3.36 (br d, J=10.0 Hz, 2H), 2.26-2.23 (m, 2H), 2.16-2.13 (m, 2H), 1.68-1.63 (m, 4H), 1.50-1.49 (m, 2H).

Example 12 (Compound 245)

2-(6-amino-5-(8-(2-(3-(azepan-1-yl)prop-1-yn-1-yl)pyrimidin-4-yl)-3,8-diazabicyclo[3.2.1]octan-3-yl)pyridazin-3-yl)phenol

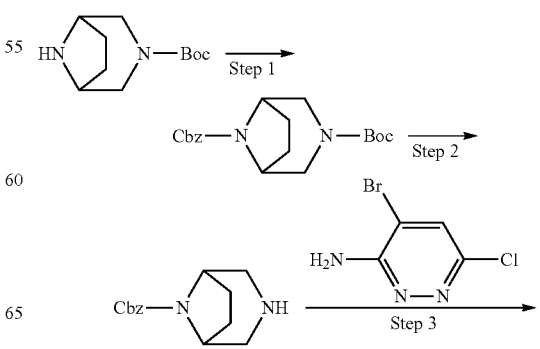

-continued

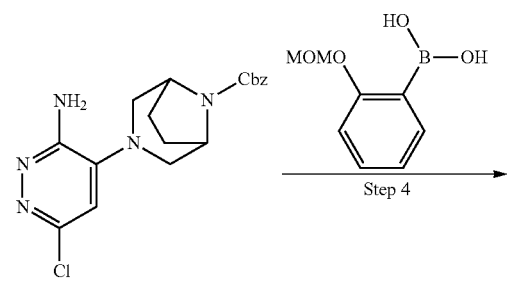

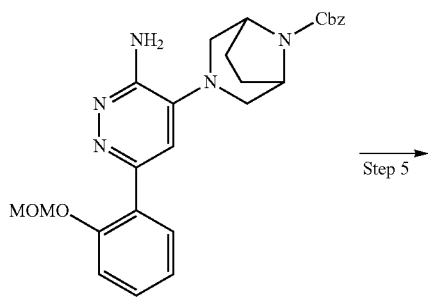

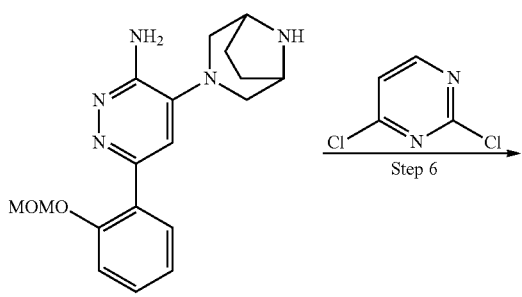

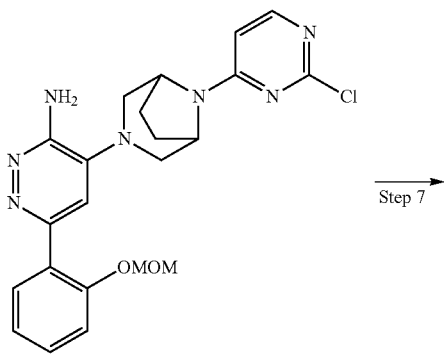

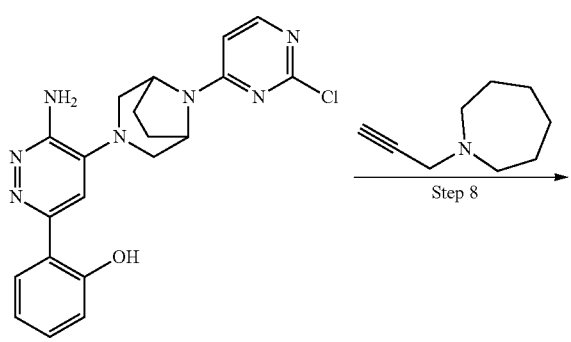

-continued

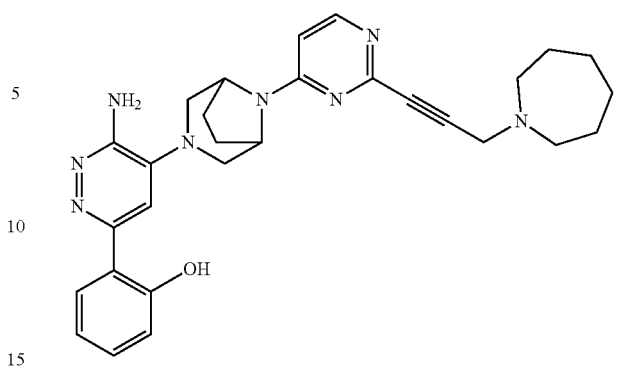

Step 1: 8-benzyl 3-(tert-butyl) 3,8-diazabicyclo[3.2.1]octane-3,8-dicarboxylate

A mixture of tert-butyl 3,8-diazabicyclo[3.2.1]octane-3-carboxylate (125 g, 589 mmol, 1.00 eq) in DCM (620 mL), TEA (179 g, 1.77 mol, 246 mL, 3.00 eq) and CbzCl (151 g, 883 mmol, 126 mL, 1.50 eq) was added, and then the mixture was stirred at 25° C. for 3 hrs under N₂ atmosphere. TLC (Petroleum ether:Ethyl acetate=3:1) showed new spots ($R_f$=0.37) were formed. The solution was washed with water 50.0 mL, extracted with EtOAc 150×3 mL, washed with brine 50.0 mL and concentrated under reduced pressure to give a residue. The residue was purified by column chromatography (Petroleum ether/Ethyl acetate=3:1) to afford the title compound (89.0 g, 257 mmol, 43.6% yield) as a white solid. ¹H NMR (400 MHz, CDCl₃): δ 7.38-7.34 (m, 5H), 5.15 (s, 2H), 4.30 (s, 2H), 3.87-3.70 (m, 2H), 3.03 (d, J=28.8 Hz, 2H), 1.95 (s, 2H), 1.88 (d, J=16.8 Hz, 2H), 1.45 (s, 9H).

Step 2: benzyl 3,8-diazabicyclo[3.2.1]octane-8-carboxylate

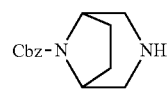 [SMILES: O=C(OCc1ccccc1)N1C2CCC1CNC2]

To a solution of 8-benzyl 3-(tert-butyl) 3,8-diazabicyclo[3.2.1]octane-3,8-dicarboxylate (89.0 g, 257 mmol, 1.00 eq) in EtOAc (150 mL) was added HCl/EtOAc (4 M, 321 mL, 5.00 eq). The mixture was stirred at 25° C. for 3 hrs. The solution was concentrated under reduced pressure to remove most of the solvent and filtered to afford the title compound (59.0 g, 209 mmol, 81.2% yield) as a crude white solid. ¹H NMR (400 MHz, CDCl₃): δ 7.39-7.32 (m, 5H), 5.15 (s, 2H), 4.44 (s, 2H), 3.20 (s, 4H), 2.32-2.27 (m, 2H), 2.16-2.00 (m, 2H)

Step 3: benzyl 3-(3-amino-6-chloropyridazin-4-yl)-3,8-diazabicyclo[3.2.1]octane-8-carboxylate

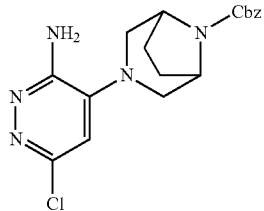

A mixture of benzyl 3,8-diazabicyclo[3.2.1]octane-8-carboxylate (59.0 g, 209 mmol, 1.00 eq) in DMSO (410 mL), 4-bromo-6-chloro-pyridazin-3-amine (45.7 g, 219 mmol, 1.05 eq), DIPEA (108 g, 835 mmol, 145 mL, 4.00 eq) was added, and then the mixture was stirred at 130° C. for 16 hrs under $N_2$ atmosphere. The solution was added water 100 mL, and combined with another crude reaction mixture of the same product, extracted with EtOAc 150×3 mL, and then washed with brine 20.0 mL, concentrated under reduced pressure to afford the title compound (200 g, crude) as a white solid. $^1$H NMR (400 MHz, $CDCl_3$): δ 7.39-7.27 (m, 5H), 6.70 (s, 1H), 5.17 (s, 2H), 5.10 (s, 2H), 4.46 (s, 2H), 3.25 (d, J=9.6 Hz, 2H), 2.89 (d, J=33.6 Hz, 2H), 2.08-2.05 (m, 2H), 1.95-1.91 (m, 2H)

Step 4: benzyl 3-(3-amino-6-(2-(methoxymethoxy)phenyl)pyridazin-4-yl)-3,8-diazabicyclo[3.2.1]octane-8-carboxylate

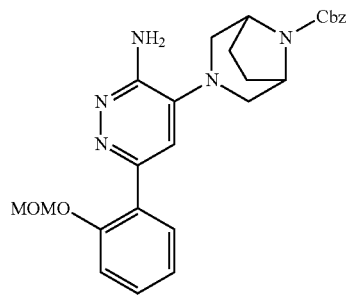

To a mixture of benzyl 3-(3-amino-6-chloropyridazin-4-yl)-3,8-diazabicyclo[3.2.1]octane-8-carboxylate (100 g, 268 mmol, 1.00 eq) in dioxane (800 mL) and $H_2O$ (150 mL) was added (2-(methoxymethoxy)phenyl)boronic acid (73.0 g, 401 mmol, 1.50 eq), Pd(PPh$_3$)$_4$ (30.9 g, 26.8 mmol, 0.100 eq) and $K_2CO_3$ (73.9 g, 534 mmol, 2.00 eq), then the mixture was stirred at 100° C. for 2 hrs under $N_2$ atmosphere. The solution was added 100 mL water and combined with another crude reaction mixture of the same reaction. The mixture was extracted with EtOAc 200 mL×3, the organic was washed with brine 100 mL, dried over $Na_2SO_4$, concentrated under reduced pressure to give a residue. The residue was purified by column chromatography (Petroleum ether/Ethyl acetate=0:1) to afford the title compound (182 g, combined yield: 71.7%) as a yellow solid. $^1$H NMR (400 MHz, $CDCl_3$): δ 7.68 (d, J=1.2 Hz, 1H), 7.66-7.25 (m, 6H), 7.17 (d, J=6.0 Hz, 1H), 7.11-7.10 (m, 1H), 7.04 (s, 1H), 5.08 (s, 2H), 5.06 (s, 2H), 4.92 (s, 2H), 4.39 (s, 2H), 3.32 (s, 3H), 3.17 (d, J=10.0 Hz, 2H), 2.83 (d, J=46.8 Hz, 2H), 1.92-2.15 (m, 4H).

Step 5: 4-(3,8-diazabicyclo[3.2.1]octan-3-yl)-6-(2-(methoxymethoxy)phenyl)pyridazin-3-amine

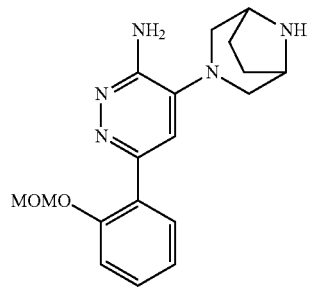

To a solution of benzyl 3-(3-amino-6-(2-(methoxymethoxy)phenyl)pyridazin-4-yl)-3,8-diazabicyclo[3.2.1]octane-8-carboxylate (182 g, 383 mmol, 1.00 eq) in MeOH (1.27 L) was added Pd(OH)$_2$/C (53.8 g, 38.3 mmol, 10.0% purity, 0.100 eq) under $N_2$ atmosphere. The suspension was degassed and purged with $H_2$ 3 times. The mixture was stirred under $H_2$ at 35° C. for 16 hrs. The solution was filtered and the filtrate was concentrated under reduced pressure to afford the title compound (100 g, crude) as a brown solid.

Step 6: 4-(8-(2-chloropyrimidin-4-yl)-3,8-diazabicyclo[3.2.1]octan-3-yl)-6-(2-(methoxymethoxy)phenyl)pyridazin-3-amine

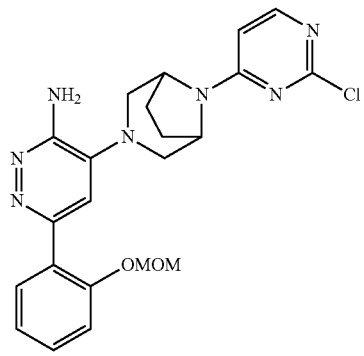

To a solution of 2,4-dichloropyrimidine (40.0 mg, 268.5 μmol, 1.0 eq) in EtOH (2 mL) was added 4-(3,8-diazabicyclo[3.2.1]octan-3-yl)-6-[2-(methoxymethoxy)phenyl]pyridazin-3-amine (100.8 mg, 295.3 μmol, 1.1 eq) and DIEA (93.53 μL, 537.0 μmol, 2.0 eq) at 25° C. The mixture was stirred at 25° C. for 2 hrs. TLC (DCM/MeOH=10/1, R$_f$=0.7) showed the reaction was completed. The reaction mixture was concentrated in vacuum to give a residue. The residue was purified by column chromatography (SiO$_2$, DCM/MeOH=100/1 to 10/1) to give the title compound (70 mg, 154.2 μmol, 57.4% yield) as a yellow solid. $^1$H NMR (400 MHz, DMSO-d$_6$): δ 8.08 (d, J=6.0 Hz, 1H), 7.58 (dd, J=7.6, 1.6 Hz, 1H), 7.38-7.31 (m, 1H), 7.20 (s, 1H), 7.16 (d, J=8.4 Hz, 1H), 7.07 (t, J=7.6 Hz, 1H), 6.82 (d, J=6.0 Hz, 1H), 5.76 (d, J=6.4 Hz, 2H), 5.16 (s, 2H), 4.96-4.45 (m, 2H), 3.31-3.28 (m, 2H), 3.27 (s, 3H), 2.91-2.72 (m, 2H), 2.21 (m, 2H), 1.96-1.94 (m, 2H).

Step 7: 2-(6-amino-5-(8-(2-chloropyrimidin-4-yl)-3,8-diazabicyclo[3.2.1]octan-3-yl)pyridazin-3-yl)phenol

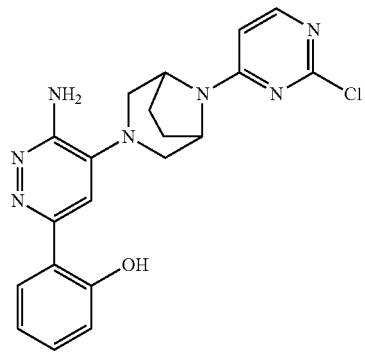 [SMILES: Nc1nnc(-c2ccccc2O)cc1N1CC2CCC(C1)N2c1ccnc(Cl)n1]

To a solution of 4-[8-(2-chloropyrimidin-4-yl)-3,8-diazabicyclo[3.2.1]octan-3-yl]-6-[2-(methoxymethoxy)phenyl]pyridazin-3-amine (70.0 mg, 154.2 µmol, 1.00 eq) in dioxane (5 mL) was added 4M HCl (0.4 mL, 1.6 mmol, 10 eq) in dioxane (5 mL). The reaction mixture was stirred at 25° C. for 16 hrs. TLC (DCM/MeOH=10/1, $R_f$=0.5) showed the reaction was completed. The mixture was concentrated in vacuum to give the titled compound (60 mg, 146.4 µmol, 94.9% yield) as a yellow solid. The crude product was directly used in the next step without further purification.

Step 8: 2-(6-amino-5-(8-(2-(3-(azepan-1-yl)prop-1-yn-1-yl)pyrimidin-4-yl)-3,8-diazabicyclo[3.2.1]octan-3-yl)pyridazin-3-yl)phenol

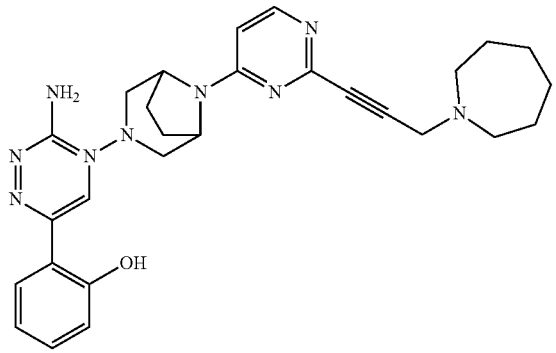

To a solution of 1-prop-2-ynylazepane (50.2 mg, 366.0 µmol, 5.00 eq) and bis(triphenylphosphine)palladium(ii)dichloride (5.1 mg, 7.3 µmol, 0.10 eq) in DMF (5 mL) was added PPh₃ (3.8 mg, 14.6 µmol, 0.20 eq), CuI (1.4 mg, 14.6 µmol, 0.10 eq), Et₃N (0.03 mL, 219.6 µmol, 3.00 eq) and 2-[6-amino-5-[8-(2-chloropyrimidin-4-yl)-3,8-diazabicyclo[3.2.1]octan-3-yl]pyridazin-3-yl]phenol (30.0 mg, 73.2 µmol, 1.00 eq). Then the reaction was stirred at 50° C. for 6 hrs. TLC (DCM/MeOH=10/1, $R_f$=0.3) showed the reaction was completed. The reaction mixture was filtered and the filtrate was collected. The residue was purified by prep-HPLC (column: Welch Xtimate® C18 150*30 mm*5 µm; mobile phase: [water(FA)-ACN]) to give the titled compound (9.9 mg, 18.2 µmol, 24.9% yield) as a yellow solid. $^1$H NMR (400 MHz, CDCl₃): δ 8.22 (s, 1H), 7.55 (d, J=8.0 Hz, 1H), 7.29-7.26 (m, 2H) 7.03 (d, J=8.4 Hz, 1H), 6.88 (t, J=7.2 Hz, 1H), 6.41 (d, J=5.6 Hz, 1H), 4.90-4.70 (m, 4H), 3.72 (s, 2H), 3.37-3.41 (m, 2H), 3.17-3.00 (m, 2H), 2.95-2.77 (m, 4H), 2.26-2.00 (m, 4H), 1.75-1.63 (m, 8H). LCMS (ESI): m/z 511.1 (M+H)⁺.

Example 13 (Compound 246)

2-(6-amino-5-(8-(6-(3-(azepan-1-yl)prop-1-yn-1-yl)pyridazin-4-yl)-3,8-diazabicyclo[3.2.1]octan-3-yl)pyridazin-3-yl)phenol

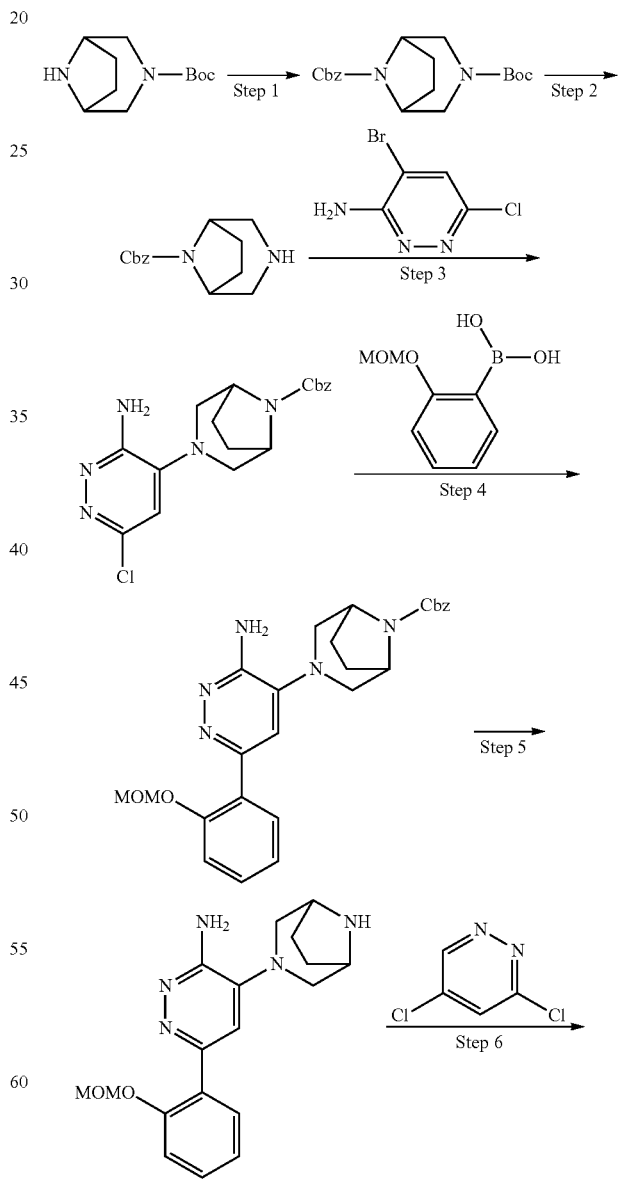

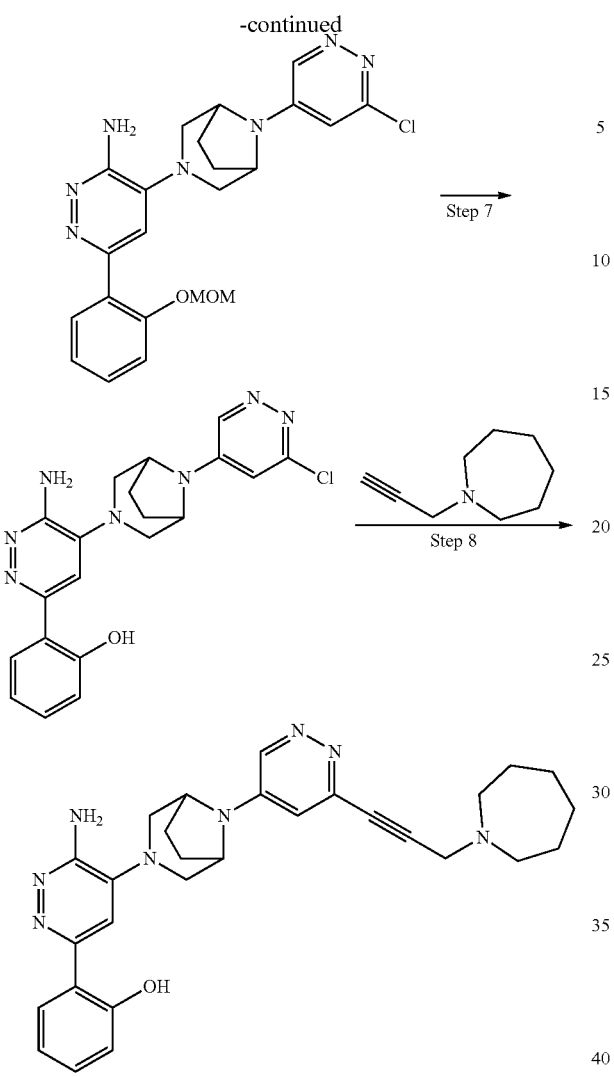

Step 1 to 5: procedure similar as described herein, e.g. in Example 12

Step 6: 4-(8-(6-chloropyridazin-4-yl)-3,8-diazabicyclo[3.2.1]octan-3-yl)-6-(2-(methoxymethoxy)phenyl)pyridazin-3-amine

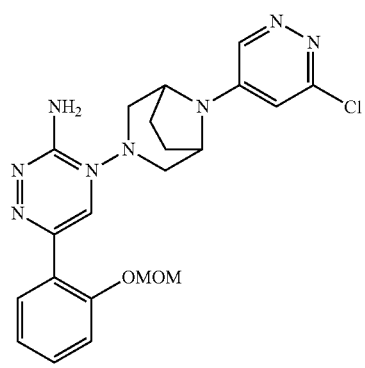

A mixture of 3,5-dichloropyridazine (327 mg, 2.2 mmol, 1.5 eq), 4-(3,8-diazabicyclo[3.2.1]octan-3-yl)-6-[2-(methoxymethoxy)phenyl]pyridazin-3-amine (500 mg, 1.46 mmol, 1 eq) and triethylamine (0.82 mL, 5.86 mmol, 5 eq) in ethanol (10 mL) was degassed and purged with N₂ for 3 times. Then the mixture was stirred at 90° C. for 5 h. TLC (MeOH/DCM=1/10, R$_f$=0.5) showed the reaction was completed. The reaction mixture was concentrated to give crude product, which was purified by column chromatography (SiO₂, MeOH/DCM=0 to 3/100) to afford the title compound (350 mg, 0.77 mmol, 52.6% yield) as a yellow solid.

Step 7: 2-(6-amino-5-(8-(6-chloropyridazin-4-yl)-3,8-diazabicyclo[3.2.1]octan-3-yl)pyridazin-3-yl)phenol

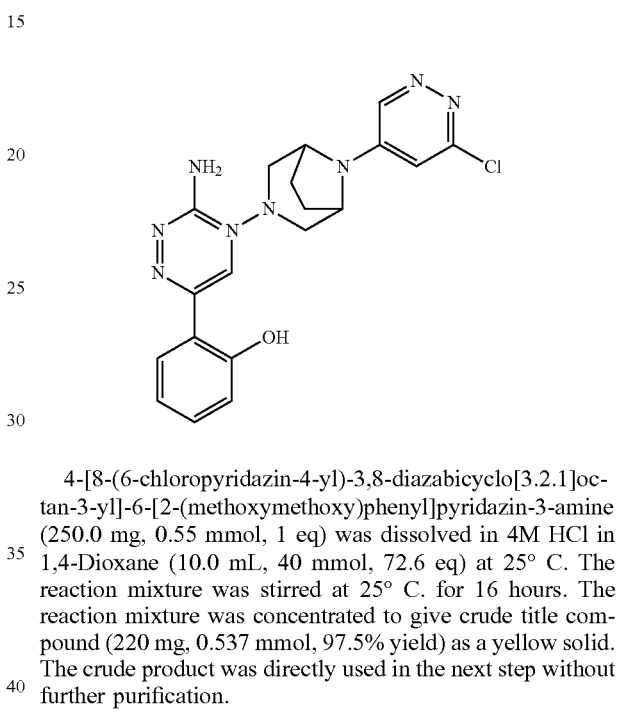

4-[8-(6-chloropyridazin-4-yl)-3,8-diazabicyclo[3.2.1]octan-3-yl]-6-[2-(methoxymethoxy)phenyl]pyridazin-3-amine (250.0 mg, 0.55 mmol, 1 eq) was dissolved in 4M HCl in 1,4-Dioxane (10.0 mL, 40 mmol, 72.6 eq) at 25° C. The reaction mixture was stirred at 25° C. for 16 hours. The reaction mixture was concentrated to give crude title compound (220 mg, 0.537 mmol, 97.5% yield) as a yellow solid. The crude product was directly used in the next step without further purification.

Step 8: 2-(6-amino-5-(8-(6-(3-(azepan-1-yl)prop-1-yn-1-yl)pyridazin-4-yl)-3,8-diazabicyclo[3.2.1]octan-3-yl)pyridazin-3-yl)phenol

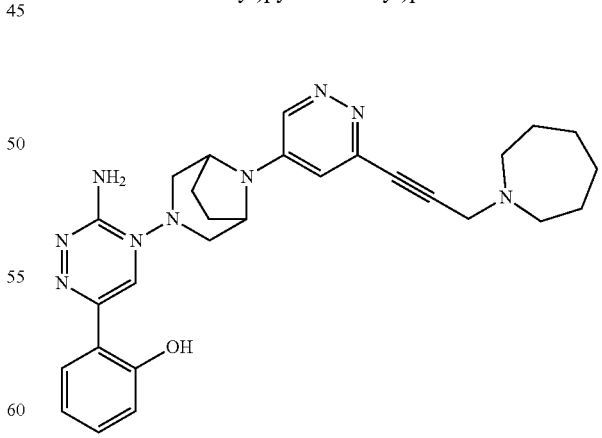

A solution of triethylamine (0.34 mL, 2.44 mmol, 10 eq), 2-[6-amino-5-[8-(6-chloropyridazin-4-yl)-3,8-diazabicyclo[3.2.1]octan-3-yl]pyridazin-3-yl]phenol (100.0 mg, 0.24 mmol, 1 eq), triphenylphosphine (12.8 mg, 0.05 mmol, 0.2 eq), copper(I) iodide (4.6 mg, 0.020 mmol, 0.1 eq), bis (triphenylphosphine)palladium(II)dichloride (17.1 mg, 0.020 mmol, 0.1 eq) and 1-prop-2-ynylazepane (167.4 mg, 1.22 mmol, 5 eq) in DMF (1.5 mL) was stirred at 80° C. for 16 hours. LCMS (5-95AB/1.5 min): R$_t$=0.630 min, [M+H]$^+$ 511.1, showed 20.8% of desired product. The residue was purified by pre-HPLC (column: Welch Xtimate® C18 (150*30 mm*5 µm); mobile phase: [water(FA)-ACN]; B %: 3%-33%, 7 min) to give the title compound (9.3 mg, 0.018 mmol, 7.2% yield) as a yellow solid. $^1$H NMR (400 MHz, DMSO-d$_6$): δ 8.90 (s, 1H), 7.89 (d, J=8.0 Hz, 1H), 7.54 (s, 1H), 7.22 (t, J=7.6 Hz, 1H), 7.08 (d, J=2.4 Hz, 1H), 6.93-6.80 (m, 2H), 6.02 (s, 2H), 4.72 (s, 2H), 3.62 (s, 2H), 3.25 (s, 2H), 3.02 (d, J=12.0 Hz, 2H), 2.70-2.66 (m, 4H), 2.23 (d, J=7.2 Hz, 2H), 2.02-1.93 (m, 2H), 1.65-1.52 (m, 8H). LCMS (ESI): m/z 511.1 (M+H)$^+$.

Example 14 Compound 247

2-(6-amino-5-(8-(6-(3-(azepan-1-yl)prop-1-yn-1-yl)pyrimidin-4-yl)-3,8-diazabicyclo[3.2.1]octan-3-yl)pyridazin-3-yl)phenol

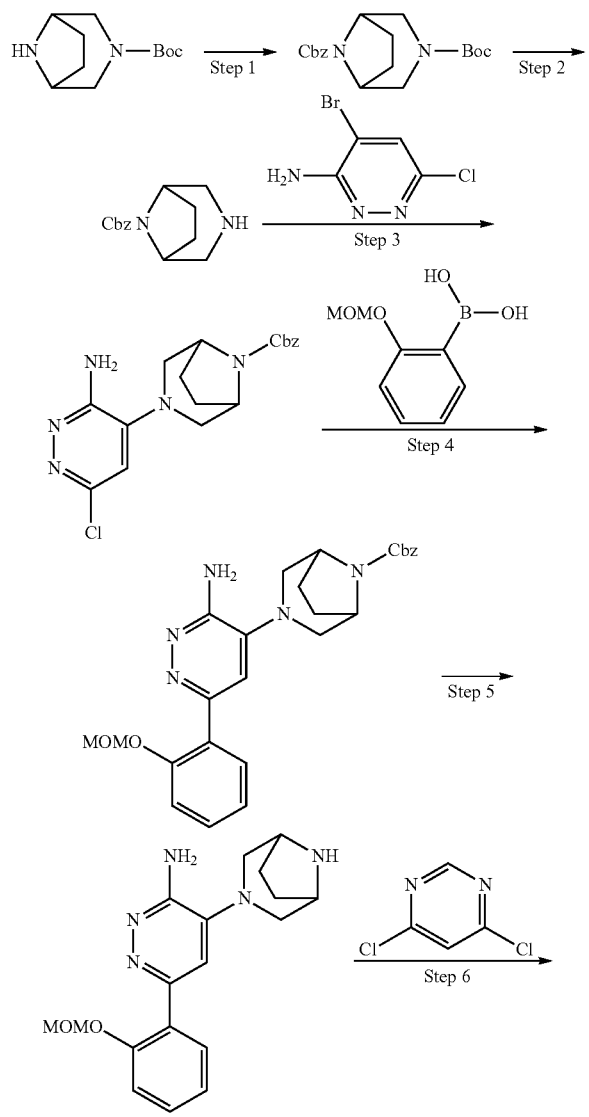

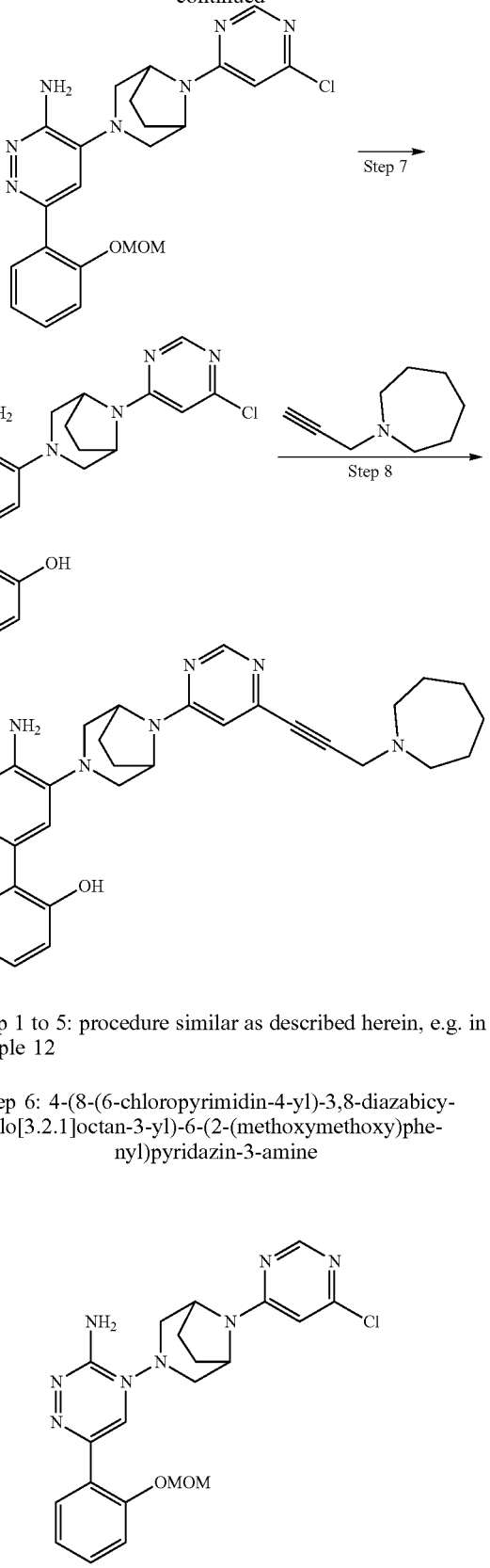

Step 1 to 5: procedure similar as described herein, e.g. in Example 12

Step 6: 4-(8-(6-chloropyrimidin-4-yl)-3,8-diazabicyclo[3.2.1]octan-3-yl)-6-(2-(methoxymethoxy)phenyl)pyridazin-3-amine A mixture of 4,6-dichloropyrimidine (1.31 g, 8.79 mmol, 1.5 eq), 4-(3,8-diazabicyclo[3.2.1]octan-3-yl)-6-[2-

(methoxymethoxy)phenyl]pyridazin-3-amine (2.0 g, 5.86 mmol, 1 eq) and triethylamine (3.27 mL, 23.43 mmol, 4 eq) in ethanol (20 mL) was degassed and purged with $N_2$ 3 times. Then the mixture was stirred at 90° C. for 5 h. TLC (methyl alcohol/Dichloromethane=1/10, $R_f$=0.5) showed the reaction was completed. The reaction mixture was concentrated to give crude product, which was purified by column chromatography ($SiO_2$, Dichloromethane/MeOH=100/0 to 20/1) to afford the title compound (1.8 g, 3.97 mmol, 67.7% yield) as a yellow solid.

Step 7: 2-(6-amino-5-(8-(6-chloropyrimidin-4-yl)-3,8-diazabicyclo[3.2.1]octan-3-yl)pyridazin-3-yl)phenol

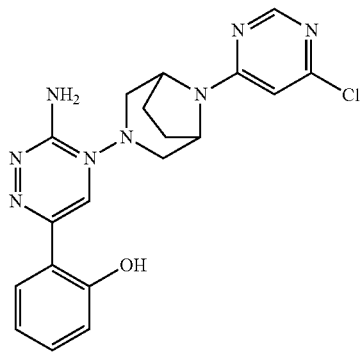

To a solution of 4-[8-(6-chloropyrimidin-4-yl)-3,8-diazabicyclo[3.2.1]octan-3-yl]-6-[2-(methoxymethoxy)phenyl]pyridazin-3-amine (1.8 g, 3.97 mmol, 1 eq) in 1,4-Dioxane (15 mL) was added 4M HCl in 1,4-Dioxane (15 mL, 60 mmol, 15 eq) at 25° C. The resulting mixture was stirred at 25° C. for 16 hours. LCMS (5-95AB/1.5 min): $R_t$=0.710 min, [M+H]$^+$ 410.0, showed 60% of desired product. The reaction mixture was concentrated to give crude title compound (1.6 g, 3.90 mmol, 98.4% yield) as a yellow solid. The crude product was directly used in the next step without further purification.

Step 8: 2-(6-amino-5-(8-(6-(3-(azepan-1-yl)prop-1-yn-1-yl)pyrimidin-4-yl)-3,8-diazabicyclo[3.2.1]octan-3-yl)pyridazin-3-yl)phenol

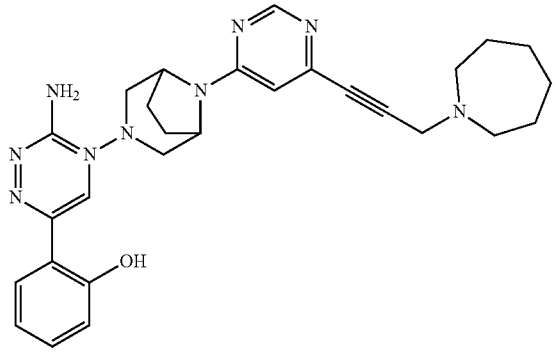

A solution of 2-[6-amino-5-[8-(6-chloropyrimidin-4-yl)-3,8-diazabicyclo[3.2.1]octan-3-yl]pyridazin-3-yl]phenol (100 mg, 0.24 mmol, 1 eq), bis(triphenylphosphine)palladium(II)dichloride (17.12 mg, 0.020 mmol, 0.1 eq), 1-prop-2-ynylazepane (167 mg, 1.22 mmol, 5 eq), triphenylphosphine (12.8 mg, 0.050 mmol, 0.2 eq), copper(I) iodide (4.6 mg, 0.020 mmol, 0.1 eq) and triethylamine (0.17 mL, 1.22 mmol, 5 eq) in N,N-Dimethylformamide (3 mL) was stirred at 80° C. for 16 hours. LCMS (5-95AB/1.5 min): $R_t$=0.649 min, [M+H]$^+$ 511.2, showed 30% of desired product. After cooling to room temperature, the mixture was filtered. The filtrate was purified by pre-HPLC (column: Welch Xtimate® C18 (150*30 mm*5 μm); mobile phase: [water(FA)-ACN]; B %: 3%-33%, 7 min) to give the titled compound (3.8 mg, 7.2 μmol, 3% yield) as a yellow solid. $^1$H NMR (400 MHz, DMSO-$d_6$): δ 8.45 (s, 1H), 8.16 (s, 1H), 7.92 (d, J=8.0 Hz, 1H), 7.55 (s, 1H), 7.27-7.18 (m, 1H), 6.95 (s, 1H), 6.89-6.82 (m, 2H), 6.03 (s, 2H), 5.06-4.60 (m, 2H), 3.59 (s, 2H), 3.27-3.26 (m, 2H), 3.01-2.98 (m, 2H), 2.67-2.66 (m, 4H), 2.24-2.20 (m, 2H), 2.00-1.91 (m, 2H), 1.64-1.52 (m, 8H). LCMS (ESI): m/z 511.1 (M+H)$^+$.

Example 15 Compound 248

(E)-2-(6-amino-5-(8-(2-(3-(azepan-1-yl)prop-1-en-1-yl)pyridin-4-yl)-3,8-diazabicyclo[3.2.1]octan-3-yl)pyridazin-3-yl)phenol

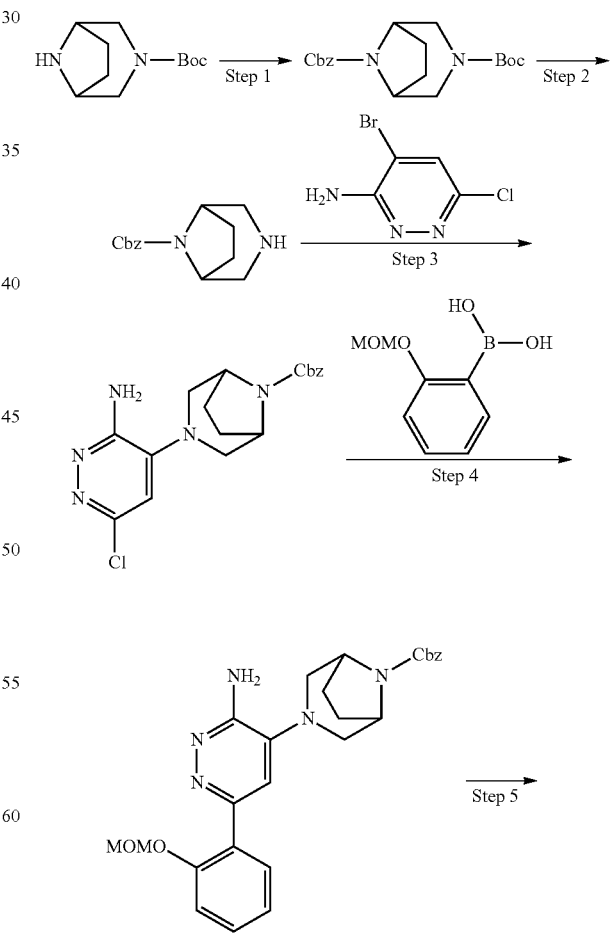

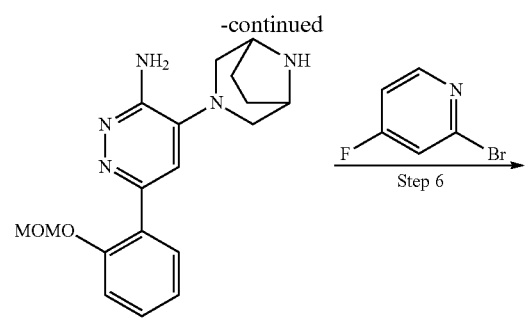

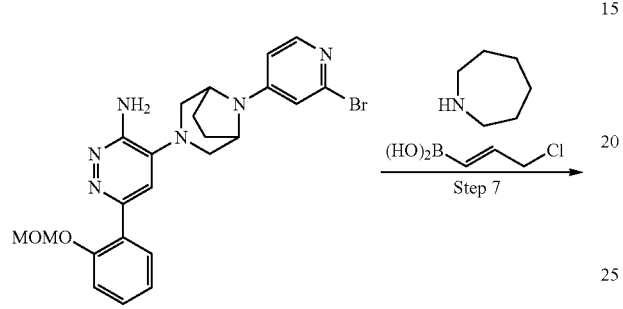

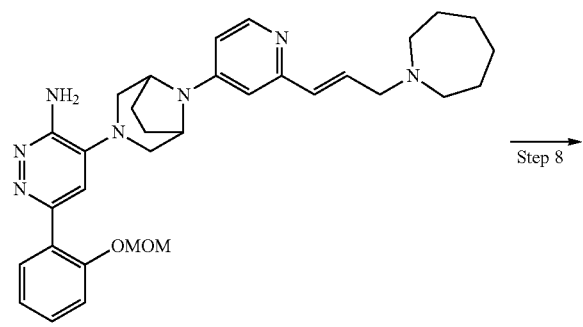

Step 1 to 5: procedure similar as described herein, e.g. in Example 12.

Step 6: 4-(8-(2-bromopyridin-4-yl)-3,8-diazabicyclo[3.2.1]octan-3-yl)-6-(2-(methoxymethoxy)phenyl)pyridazin-3-amine

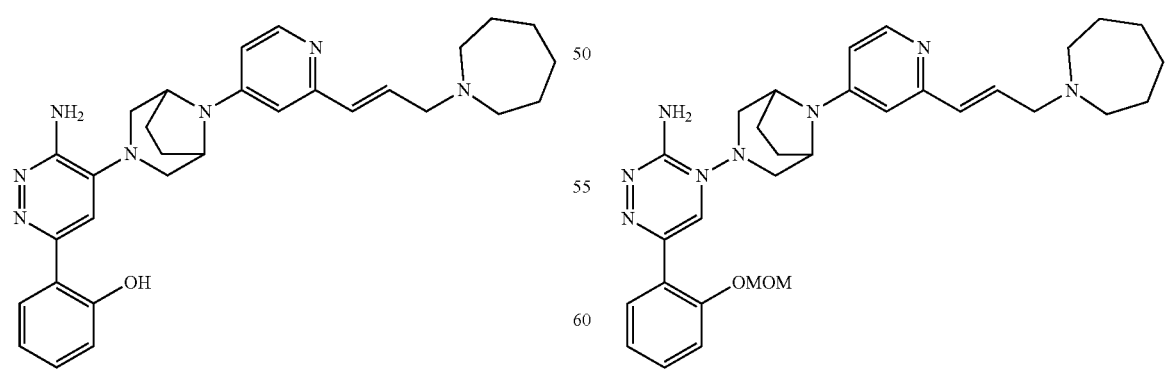

To a solution of 4-(3,8-diazabicyclo[3.2.1]octan-3-yl)-6-(2-(methoxymethoxy)phenyl)pyridazin-3-amine (16 g, 46.9 mmol) in DMSO (96 mL) was added 2-bromo-4-fluoropyridine (8.25 g, 46.9 mmol) and DIEA (60.6 g, 469 mmol, 81.6 mL) then the mixture was stirred for 5 hrs at 130° C. The reaction mixture was quenched by addition H$_2$O 100 mL, diluted with EtOAc 100 mL and extracted with EtOAc (100 mL×3). The combined organic layers were washed with brine 100 mL, dried over Na$_2$SO$_4$, filtered and concentrated under reduced pressure to give a residue. The crude product was triturated with MeOH:DCM=1:20 at 15° C. for 30 min, and then filtered and concentrated under reduced pressure to afford the title compound (17 g, 72.49% yield) as a light yellow solid. $^1$H NMR (400 MHz, CDCl$_3$): δ 8.00 (d, J=5.96 Hz, 1H), 7.72 (dd, J=7.63, 1.67 Hz, 1H), 7.22 (s, 1H) 7.31-7.38 (m, 1H), 7.15 (d, J=7.89 Hz, 1H), 7.10 (t, J=7.37 Hz, 1H), 6.77 (d, J=2.15 Hz, 1H), 6.54 (dd, J=5.96, 2.27 Hz, 1H), 5.13 (s, 2H), 5.10 (s, 2H), 4.37 (s, 2H), 3.36 (s, 3H), 3.23 (d, J=10.13 Hz, 2H), 3.02 (d, J=11.21 Hz, 2H), 2.10-2.24 (m, 4H).

Step 7: (E)-4-(8-(2-(3-(azepan-1-yl)prop-1-en-1-yl)pyridin-4-yl)-3,8-diazabicyclo[3.2.1]octan-3-yl)-6-(2-(methoxymethoxy)phenyl)pyridazin-3-amine To a mixture of 4-(8-(2-bromopyridin-4-yl)-3,8-diazabicyclo[3.2.1]octan-3-yl)-6-(2-(methoxymethoxy) phenyl) pyridazin-3-amine (500 mg, 1.01 mmol, 1.00 eq), (E)-(3-chloroprop-1-en-1-yl)boronic acid (242 mg, 2.01 mmol, 2.00 eq), Pd(dppf)Cl₂ (141 mg, 0.2 mmol, 0.2 eq) and Cs₂CO₃ (655 mg, 2.01 mmol, 2.00 eq) in DMSO (4 mL) was added azepane (0.23 mL, 2.00 eq) under N₂. The resulting mixture was stirred at 90° C. for 5 hrs. TLC (3% NH₃·H₂O in MeOH/DCM=1/10, R_f=0.45) showed the reaction was completed. The reaction mixture was purified by pre-HPLC (column: Xtimate® C18 150*40 mm*10 μm; mobile phase: [water(FA)-ACN]; B %: 1%-30%, 7 min) to give the titled compound (190 mg, 0.34 mmol, 34% yield) as a yellow solid.

Step 8: (E)-2-(6-amino-5-(8-(2-(3-(azepan-1-yl)prop-1-en-1-yl)pyridin-4-yl)-3,8-diazabicyclo[3.2.1]octan-3-yl)pyridazin-3-yl)phenol

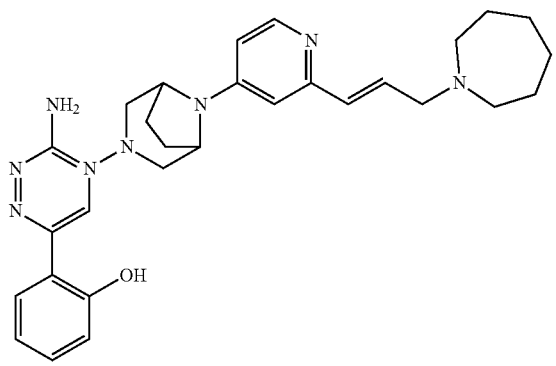

To a solution of (E)-4-(8-(2-(3-(azepan-1-yl)prop-1-en-1-yl)pyridin-4-yl)-3,8-diazabicyclo[3.2.1]octan-3-yl)-6-(2-(methoxymethoxy)phenyl)pyridazin-3-amine (50 mg, 0.09 mmol, 1 eq) in dioxane (2 mL) was added HCl/dioxane (4 M, 3 mL). Then the mixture was stirred at 25° C. for 3 h. TLC (3% NH₃·H₂O in MeOH/DCM=1/10, R_f=0.3) showed the reaction was completed. The reaction mixture was purified by prep-HPLC (column: Boston Green ODS 150*30 mm*5 μm; mobile phase: [water(FA)-ACN]; B %: 5%-35%, 7 min) to give the titled compound (19 mg, 0.037 mmol, 41.3% yield) as a brown solid. ¹H NMR (400 MHz, MeOD): δ 8.39 (s, 1H), 8.14 (d, J=6.4 Hz, 1H), 7.72 (dd, J=8.0, 1.2 Hz, 1H), 7.49 (s, 1H), 7.26-7.21 (m, 1H), 7.04 (d, J=2.4 Hz, 1H), 6.90-6.80 (m, 3H), 6.75-6.69 (m, 1H), 4.70 (s, 2H), 3.92 (d, J=6.8 Hz, 2H), 3.44 (d, J=10.8 Hz, 2H), 3.30-3.29 (m, 4H), 3.11 (d, J=11.6 Hz, 2H), 2.36-2.29 (m, 2H), 2.19-2.17 (m, 2H), 1.94-1.88 (m, 4H), 1.76-1.75 (m, 4H).

LCMS (ESI): m/z 512.1 (M+H)⁺.

Example 16 Compound 249

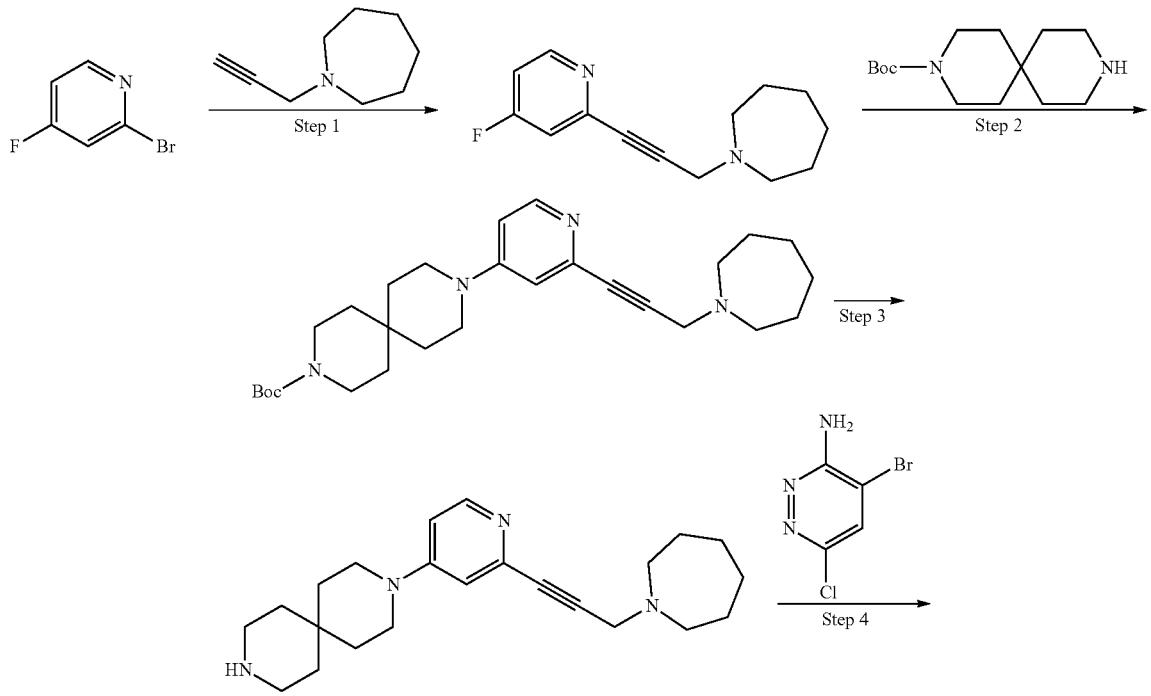

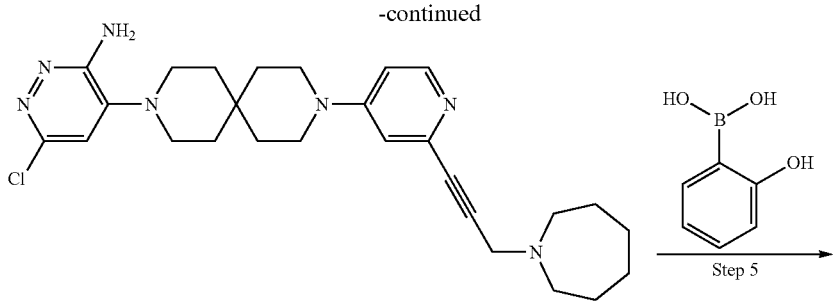

Step 5

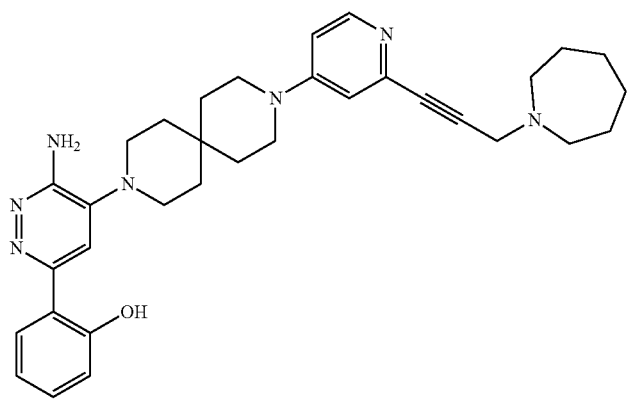

Step 1: 1-(3-(4-fluoropyridin-2-yl)prop-2-yn-1-yl)azepane

Step 2: tert-butyl 9-(2-(3-(azepan-1-yl)prop-1-yn-1-yl)pyridin-4-yl)-3,9-diazaspiro[5.5]undecane-3-carboxylate

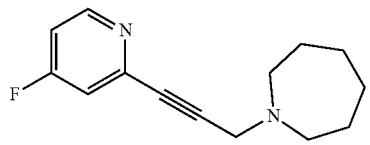 [SMILES: Fc1ccnc(C#CCN2CCCCCC2)c1]

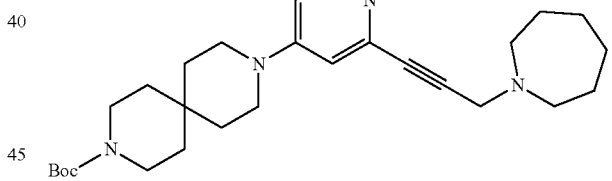

To a solution of 2-bromo-4-fluoropyridine (5.00 g, 28.4 mmol) in THF (35.0 mL) was added 1-(prop-2-yn-1-yl)azepane (5.07 g, 36.9 mmol, 1.30 eq), CuI (541 mg, 2.84 mmol, 0.10 eq), TEA (4.31 g, 42.6 mmol, 5.93 mL, 1.50 eq) and Pd(PPh$_3$)$_2$Cl$_2$ (598 mg, 852 μmol, 0.03 eq) with stirring at 25° C. The mixture was refluxed at 70° C. for 5 hrs under N$_2$. TLC (Petroleum ether/Ethyl acetate=3/1, product: R$_f$=0.08) indicated 2-bromo-4-fluoropyridine was consumed completely. The reaction mixture was diluted with water (30.0 mL) and extracted with EtOAc (30.0 mL×3). The combined organic layers were washed with brine, dried over Na$_2$SO$_4$, filtered and concentrated under reduced pressure to give a residue. The residue was purified by column chromatography (SiO$_2$, Petroleum ether:Ethyl acetate=10:1 to 0:1) to give the titled compound (3.80 g, 57.6% yield) as black oil.

To a solution of 1-(3-(4-fluoropyridin-2-yl)prop-2-yn-1-yl)azepane (2.00 g, 8.61 mmol) in DMF (15.0 mL) was added tert-butyl 3,9-diazaspiro[5.5]undecane-3-carboxylate (2.19 g, 8.61 mmol) and Cs$_2$CO$_3$ (8.42 g, 25.8 mmol) with stirring at 25° C. The mixture was refluxed at 100° C. for 12 hrs. TLC (Dichloromethane:Methanol=10:1, R$_f$=0.30) showed the reaction was completed. The reaction mixture was diluted with water (30.0 mL) and extracted with EtOAc (30.0 mL×3). The combined organic layers were washed with brine, dried over Na$_2$SO$_4$, filtered and concentrated under reduced pressure to give a residue. The residue was purified by column chromatography (SiO$_2$, Dichloromethane:Methanol=10:1 to 0:1) to afford the title compound (3.15 g, 78.4% yield) was obtained as black oil. $^1$H NMR: (400 MHz, CDCl$_3$) δ 8.17 (br d, J=1.10 Hz, 1H) 6.80 (d, J=0.66 Hz, 1H) 6.55 (br d, J=3.29 Hz, 1H) 3.59 (s, 2H) 3.44-3.33 (m, 4H) 3.33-3.23 (m, 4H) 2.81-2.71 (m, 4H) 1.75-1.63 (m, 5H) 1.63-1.52 (m, 10H) 1.52-1.26 (m, 10H).

Step 3: 3-(2-(3-(azepan-1-yl)prop-1-yn-1-yl)pyridin-4-yl)-3,9-diazaspiro[5.5]undecane

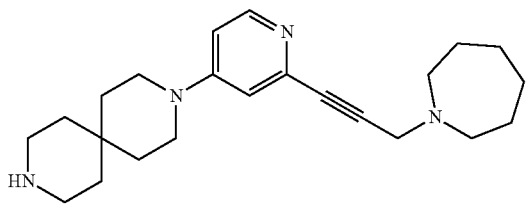 [SMILES: C(#Cc1cc(N2CCC3(CCNCC3)CC2)ccn1)CN1CCCCCC1]

A mixture of tert-butyl 9-(2-(3-(azepan-1-yl)prop-1-yn-1-yl)pyridin-4-yl)-3,9-diazaspiro[5.5]undecane-3-carboxylate (2.79 g, 5.98 mmol) in HCl/EtOAc (4 M, 25.0 mL) and EtOAc (10.0 mL) was stirred for 4 hrs at 25° C. TLC (Dichloromethane:Methanol=10:1, R$_f$=0.09) showed the reaction was complete. The reaction mixture was concentrated under reduced pressure to remove solvent. The title compound (2.69 g, crude) was used into the next step as a black oil without further purification.

Step 4: 4-(9-(2-(3-(azepan-1-yl)prop-1-yn-1-yl)pyridin-4-yl)-3,9-diazaspiro[5.5]undecan-3-yl)-6-chloropyridazin-3-amine

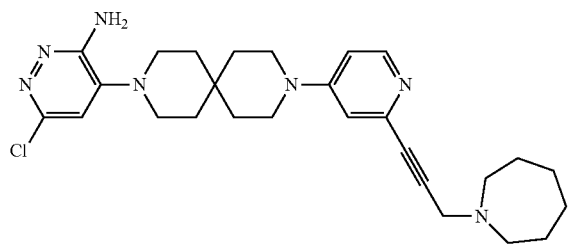 [SMILES: Nc1nnc(Cl)cc1N1CCC2(CCN(c3ccnc(C#CCN4CCCCCC4)c3)CC2)CC1]

To a solution of 3-(2-(3-(azepan-1-yl)prop-1-yn-1-yl)pyridin-4-yl)-3,9-diazaspiro[5.5]undecane (0.930 g, 2.30 mmol) in DMSO (20.0 mL) was added 4-bromo-6-chloropyridazin-3-amine (479 mg, 2.30 mmol), CsF (1.05 g, 6.89 mmol) and DIEA (890 mg, 6.89 mmol) with stirring at 25° C. The mixture was refluxed at 120° C. for 4 hrs. TLC (Dichloromethane:Methanol=10/1, R$_f$=0.40) showed the reaction was complete. The reaction mixture was diluted with water (30.0 mL) and extracted with EtOAc (30.0 mL×3). The combined organic layers were washed with brine, dried over Na$_2$SO$_4$, filtered and concentrated under reduced pressure to give a residue. The residue was purified by column chromatography (SiO$_2$, Dichloromethane:Methanol=10:1 to 0:1) to afford the title compound (0.260 g, 22.9% yield) as a black solid. $^1$H NMR: (400 MHz, CDCl$_3$) δ ppm 8.13 (d, J=6.02 Hz, 1H) 6.78 (d, J=2.51 Hz, 1H) 6.70 (s, 1H) 6.53 (dd, J=6.02, 2.64 Hz, 1H) 4.75 (br s, 2H) 3.32-3.24 (m, 4H) 3.02-2.93 (m, 4H) 2.79-2.69 (m, 4H) 1.75-1.52 (m, 16H).

Step 5: 2-(6-amino-5-(9-(2-(3-(azepan-1-yl)prop-1-yn-1-yl)pyridin-4-yl)-3,9-diazaspiro[5.5]undecan-3-yl)pyridazin-3-yl)phenol

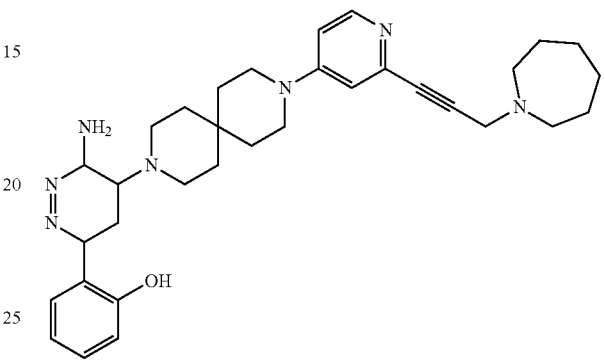

To a solution of 4-(9-(2-(3-(azepan-1-yl)prop-1-yn-1-yl)pyridin-4-yl)-3,9-diazaspiro[5.5]undecan-3-yl)-6-chloropyridazin-3-amine (120 mg, 243 μmol) in dioxane (5.00 mL) and H$_2$O (1.00 mL) was added (2-hydroxyphenyl)boronic acid (50.3 mg, 364 μmol), NaHCO$_3$ (61.2 mg, 729 μmol) and [2-(2-aminophenyl) phenyl]-chloro-palladium; bis(1-adamantyl)-butyl-phosphane (16.2 mg, 24.3 μmol). The mixture was refluxed at 100° C. for 3 hrs. LCMS showed desired mass was detected. The reaction mixture was concentrated under reduced pressure to remove solvent. The residue was purified by prep-HPLC (column: Phenomenex Luna C18 200*40 mm*10 μm; mobile phase: [water(FA)-ACN]; B %: 1%-25%, 8 min). The title compound (18.1 mg, 13.5% yield) was obtained as a yellow solid. $^1$H NMR: (400 MHz, MeOD) δ 8.48-8.41 (m, 1H) 8.10-8.05 (m, 1H) 7.83-7.78 (m, 1H) 7.57 (s, 1H) 7.30-7.25 (m, 1H) 7.09-7.06 (m, 1H) 6.96 (s, 2H) 6.92-6.88 (m, 1H) 3.93 (s, 2H) 3.58-3.50 (m, 4H) 3.24-3.18 (m, 4H) 3.15-3.09 (m, 4H) 1.90-1.81 (m, 8H) 1.79-1.70 (m, 8H). LCMS (ESI): m/z 552.2 (M+H)$^+$.

Example 17 Compound 250

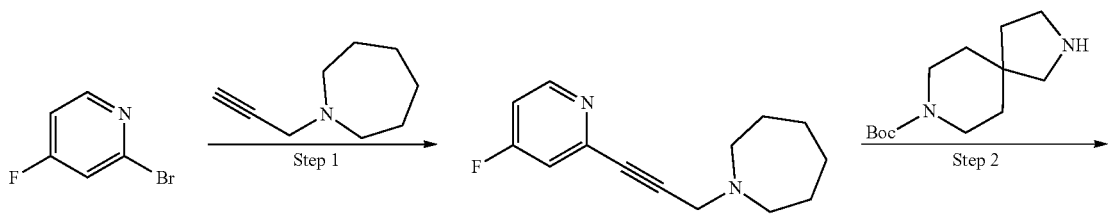

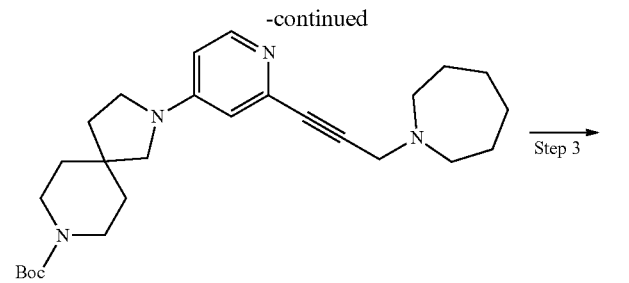

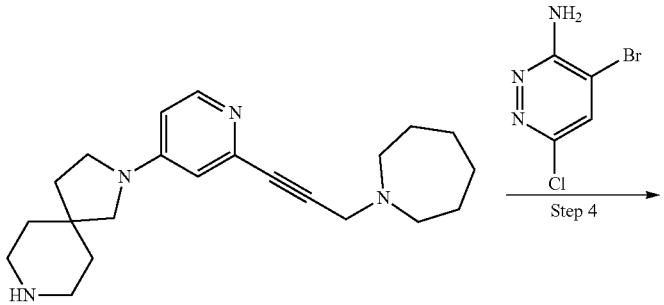

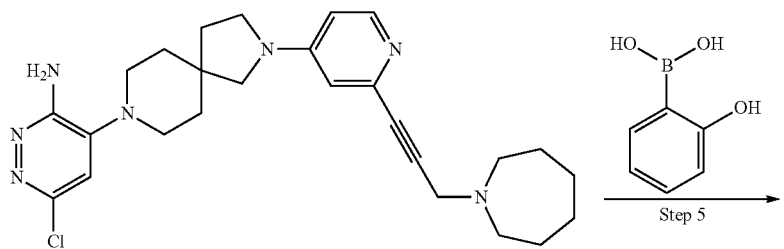

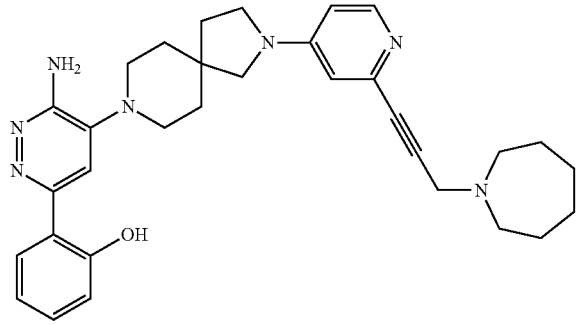

Step 1: 1-(3-(4-fluoropyridin-2-yl)prop-2-yn-1-yl)azepane

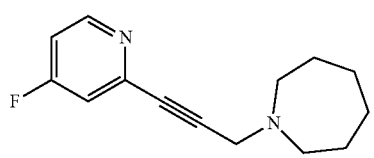 [SMILES: Fc1ccnc(C#CCN2CCCCCC2)c1]

To a solution of 2-bromo-4-fluoropyridine (5.00 g, 28.4 mmol, 1.00 eq) and 1-(prop-2-yn-1-yl)azepane (5.07 g, 36.9 mmol, 1.30 eq) in THF (35.0 mL) was added Pd(PPh$_3$)$_2$Cl$_2$ (598 mg, 852 μmol, 0.03 eq) and CuI (541 mg, 2.84 mmol, 0.10 eq) and TEA (4.31 g, 42.6 mmol, 5.93 mL, 1.50 eq), then the mixture was stirred at 80° C. for 6 hrs under N$_2$. TLC (Petroleum ether/Ethyl acetate=3/1, product: R$_f$=0.08) indicated 2-bromo-4-fluoropyridine was consumed completely. The reaction mixture was quenched by addition of H$_2$O 40 mL at 25° C., and then extracted with EtOAc (50 mL×2). The combined organic layers were dried over Na$_2$SO$_4$, filtered and concentrated under reduced pressure to give a residue. The residue was purified by column chromatography (SiO$_2$, Petroleum ether/Ethyl acetate=10/1 to 1/1) to afford the title compound (2.00 g, 8.61 mmol, 30.3% yield) as a yellow solid.

Step 2: tert-butyl 2-(2-(3-(azepan-1-yl)prop-1-yn-1-yl)pyridin-4-yl)-2,8-diazaspiro[4.5]decane-8-carboxylate

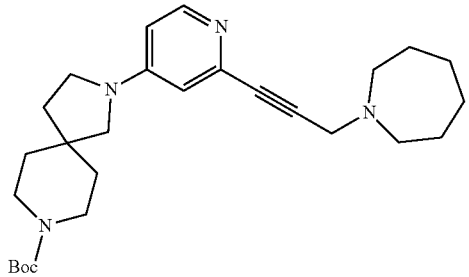 [SMILES: CC(C)(C)OC(=O)N1CCC2(CC1)CCN(c1ccnc(C#CCN3CCCCCC3)c1)C2]

A mixture of 1-(3-(4-fluoropyridin-2-yl)prop-2-yn-1-yl) azepane (1.88 g, 8.09 mmol, 1.00 eq), tert-butyl 2,8-diazaspiro[4.5]decane-8-carboxylate (2.14 g, 8.90 mmol, 1.10 eq) and Cs$_2$CO$_3$ (7.91 g, 24.3 mmol, 3.00 eq) in DMF (20 mL) was stirred at 100° C. for 3 hrs. TLC (Dichloromethane/Methanol=10/1, product: R$_f$=0.24) showed the reaction was completed. The reaction mixture was diluted with water 20 mL and extracted with EtOAc (20 mL×3). The combined organic layers were dried over Na$_2$SO$_4$, filtered and concentrated under reduced pressure to give a residue. The residue was purified by column chromatography (SiO2, Petroleum ether/Ethyl acetate=20/1 to 2/1) to afford the title compound (2.73 g, 6.03 mmol, 74.5% yield) was obtained as brown liquid. $^1$H NMR: (CDCl$_3$, 400 MHz) δ 8.16-8.15 (d, 1H), 6.54-6.54 (d, 1H), 6.30-6.29 (m, 1H), 3.60 (s, 2H), 3.51-3.46 (m, 2H), 3.41-3.35 (m, 4H), 3.17 (s, 2H), 3.88-3.81 (m, 4H), 1.93-1.90 (t, 2H), 1.72-1.70 (m, 4H), 1.63-1.61 (m, 4H), 1.58-1.55 (m, 4H), 1.46 (s, 9H)

Step 3: 2-(2-(3-(azepan-1-yl)prop-1-yn-1-yl)pyridin-4-yl)-2,8-diazaspiro[4.5]decane

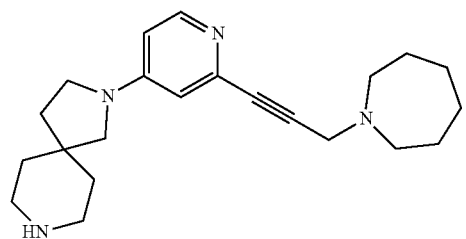 [SMILES: C(#Cc1cc(N2CCC3(CCNCC3)C2)ccn1)CN1CCCCCC1]

To a solution of tert-butyl 2-(2-(3-(azepan-1-yl)prop-1-yn-1-yl)pyridin-4-yl)-2,8-diazaspiro[4.5]decane-8-carboxylate (2.73 g, 6.03 mmol, 1.00 eq) in EtOAc (19.1 mL) was added HCl/EtOAc (4 M, 13.6 mL, 9.05 eq), then the mixture was stirred at 25° C. for 3 hrs. TLC (Dichloromethane/Methanol=10/1, product: R$_f$=0.10) showed the reaction was completed. The reaction mixture was filtered to collect the precipitate, and then the precipitate was dissolved in water and freeze-dried to give a residue. The title compound (1.96 g, 5.04 mmol, 83.6% yield, HCl) was obtained as brown solid.

Step 4: 4-(2-(2-(3-(azepan-1-yl)prop-1-yn-1-yl)pyridin-4-yl)-2,8-diazaspiro[4.5]decan-8-yl)-6-chloropyridazin-3-amine

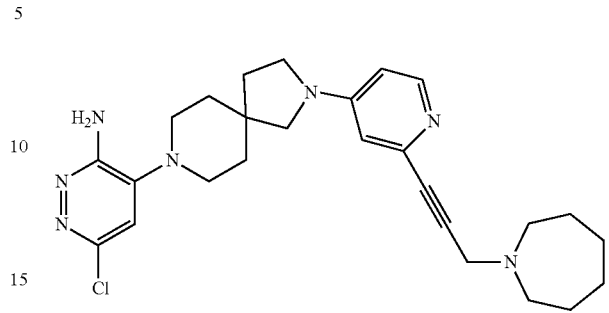

To a solution of 2-(2-(3-(azepan-1-yl)prop-1-yn-1-yl)pyridin-4-yl)-2,8-diazaspiro[4.5]decane (740 mg, 1.90 mmol, 1.00 eq, HCl) and 4-bromo-6-chloropyridazin-3-amine (396 mg, 1.90 mmol, 1.00 eq) in DMSO (10 mL) was added DIEA (983 mg, 7.61 mmol, 1.33 mL, 4.00 eq) and CsF (866 mg, 5.71 mmol, 210 μL, 3.00 eq), then the mixture was stirred at 120° C. for 1.5 hrs. LCMS indicated the reaction was complete. The reaction mixture was filtered to collect the filtrate, then the filtrate was diluted with H$_2$O 100 mL and extracted with EtOAc (50 mL×6). The combined organic layers were washed with brine (100 mL), dried over Na$_2$SO$_4$, filtered and concentrated under reduced pressure to give a residue. The residue was purified by column chromatography (SiO$_2$, Petroleum ether/Ethyl acetate=20/1 to 2/1) to afford the title compound (402 mg, 837 μmol, 44.0% yield) was obtained as yellow solid. $^1$H NMR: (CDCl$_3$, 400 MHz) δ 8.18-8.16 (d, 1H), 6.77 (s, 1H), 6.57-6.56 (d, 1H), 6.33-6.30 (m, 1H), 5.06 (s, 2H), 3.65 (s, 2H), 3.46-3.43 (m, 2H), 3.24 (m, 2H), 3.14-3.10 (m, 2H), 3.05-3.00 (m, 2H), 2.85-2.823 (m, 4H), 2.01-1.97 (m, 2H), 1.82-1.80 (m, 4H), 1.73-1.71 (m, 4H), 1.64-1.61 (m, 4H).

Step 5: 2-(6-amino-5-(2-(2-(3-(azepan-1-yl)prop-1-yn-1-yl)pyridin-4-yl)-2,8-diazaspiro[4.5]decan-8-yl)pyridazin-3-yl)phenol

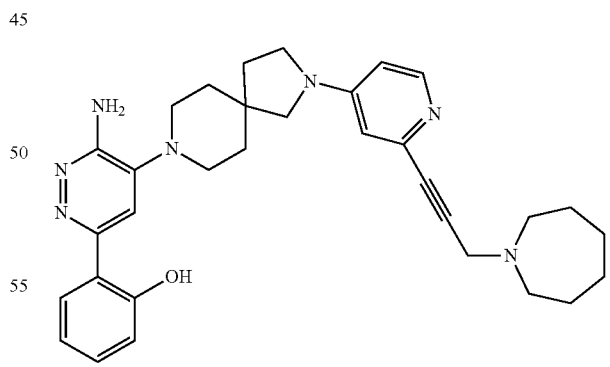

To a solution of 4-(2-(2-(3-(azepan-1-yl)prop-1-yn-1-yl)pyridin-4-yl)-2,8-diazaspiro[4.5]decan-8-yl)-6-chloropyridazin-3-amine (100 mg, 208 μmol, 1.00 eq), (2-hydroxyphenyl)boronic acid (43.1 mg, 312 μmol, 1.50 eq) in dioxane (4 mL) was added a solution of Na$_2$CO$_3$ (66.2 mg, 624 μmol, 3.00 eq) in H$_2$O (0.80 mL), and then [2-(2-aminophenyl)phenyl]-chloro-palladium; bis(1-adamantyl)-butyl-phosphane (1375477-29-4) (13.9 mg, 20.8 μmol, 0.10 eq) was added, and then the mixture was degassed and purged with N₂ for 3 times, and then the mixture was stirred at 100° C. for 4 hrs under N₂ atmosphere. LCMS indicated the reaction was complete. The reaction mixture was filtered to collect the filtrate, and then the filtrate was diluted with EtOAc (50 mL) and concentrated under reduced pressure to give a residue. The residue was purified by prep-HPLC (column: Phenomenex Luna C18 200*40 mm*10 μm; mobile phase: [water(FA)-ACN]; B %: 1%-25%, 8 min). The title compound (13.5 mg, 25.1 μmol, 12.0% yield) was obtained as light yellow solid. ¹H NMR: (CDCl₃, 400 MHz) δ 8.20-8.18 (d, 1H), 7.62-7.60 (d, 1H), 7.38 (s, 1H), 7.32-7.30 (m, 1H), 7.08-7.06 (d, 1H), 6.93-6.89 (t, 1H), 6.60 (s, 1H), 6.36-6.35 (m, 1H), 4.86 (s, 2H), 3.65 (s, 2H), 3.40-3.37 (t, 2H), 3.21 (s, 2H), 3.16-3.13 (m, 2H), 3.05-3.02 (m, 2H), 2.86-2.84 (m, 4H), 1.98-1.94 (t, 2H), 1.82-1.76 (m, 4H), 1.75-1.66 (m, 4H), 1.63-1.52 (m, 4H). LCMS (ESI): m/z 538.4 (M+H)⁺.

Example 18 Compound 251

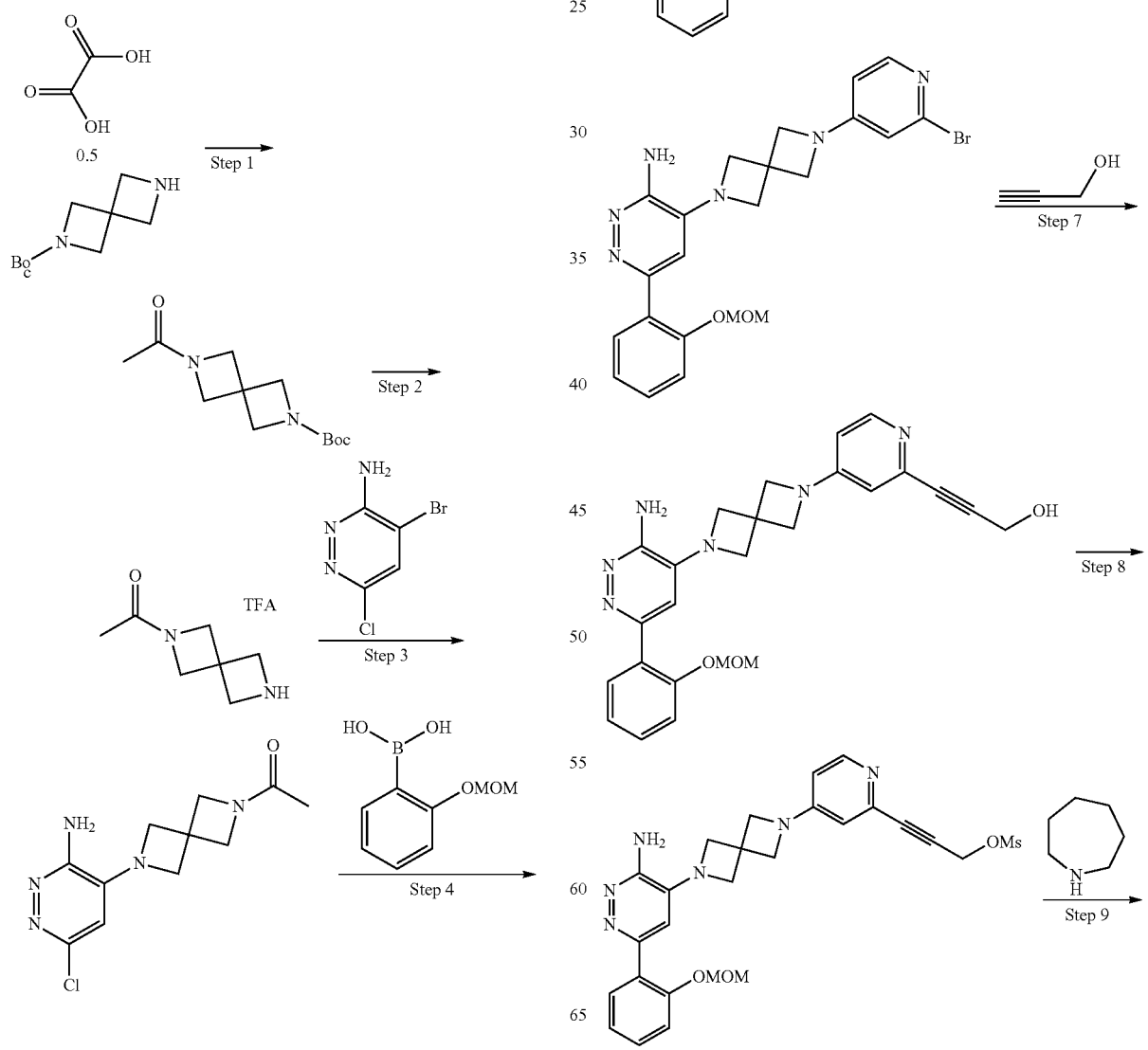

-continued

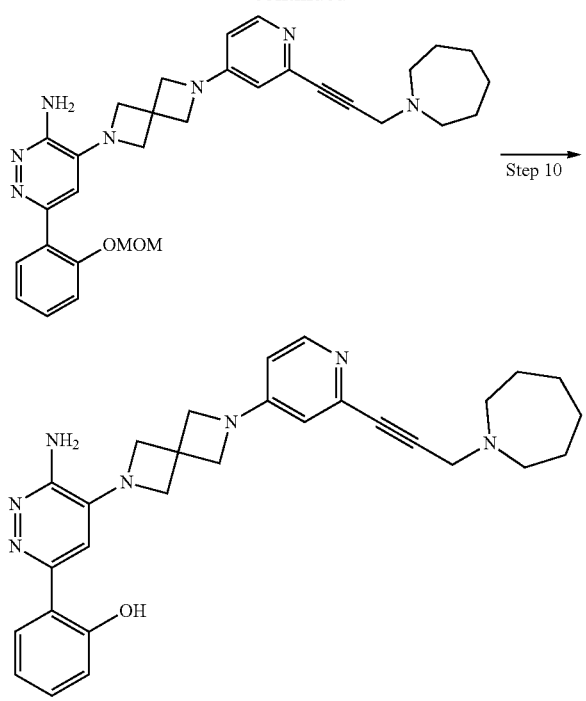

Step 10 →

Step 1: tert-butyl 6-acetyl-2,6-diazaspiro[3.3]heptane-2-carboxylate

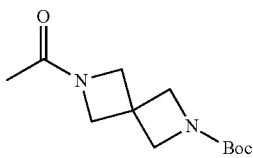 [SMILES: CC(=O)N1CC2(C1)CN(C(=O)OC(C)(C)C)C2]

To a solution of tert-butyl 2,6-diazaspiro[3.3]heptne-2-carboxylate (53.8 g, 22 mmol, 0.5OXALIC ACID) in DCM (350 mL) was added Ac₂O (56.4 g, 553 mmol, 51.8 mL) and NMM (111 g, 1.11 mol, 121 mL) at 0° C. Then the mixture was stirred at 40° C. for 12 hours. TLC (Dichloromethane/Methanol=10/1, product R$_f$=0.2) showed reactant 1 was consumed completely and a new spot was detected. LCMS (ET43580-132-P1A1, product RT=0.595 min) showed reactant 1 was consumed completely and a new peak with desired MS was detected. The reaction mixture was washed with ice-water (250 mL) with stirring, and then extracted with DCM (150 mL×5). The combined organic phases were washed with brine (100 mL) and dried over Na₂SO₄. Filtered and the filtrate was concentrated in vacuum to give a crude product. The crude product was purified by flash chromatography on a silica gel eluted with Dichloromethane/Methanol (from 100/1 to 5/1). The titled compound (51.0 g, 212 mmol, 95.8% yield) was obtained as a yellow oil. ¹H NMR: (CDCl₃, 400 MHz) δ4.04-4.21 (m, 8H), 1.84 (s, 3H), 1.41 (s, 9H).

Step 2: 1-(2,6-diazaspiro[3.3]heptan-2-yl)ethan-1-one

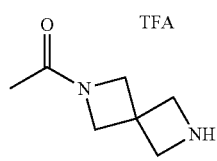

To a solution of tert-butyl 6-acetyl-2,6-diazaspiro[3.3]heptane-2-carboxylate (70.0 g, 291 mmol) in DCM (350 mL) was added TFA (323 g, 2.84 mol, 210 mL). Then the mixture was stirred at 25° C. for 2 hours. The reaction mixture was concentrated in vacuum to give a crude product. The crude product would be directly used in the next step without purification. The titled compound (74.0 g, crude, TFA) was obtained as a yellow oil.

Step 3: 1-(6-(3-amino-6-chloropyridazin-4-yl)-2,6-diazaspiro[3.3]heptan-2-yl)ethan-1-one

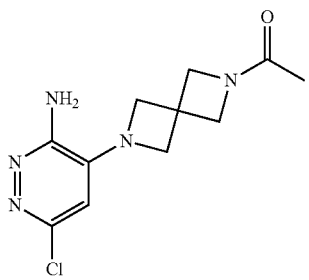 [SMILES: CC(=O)N1CC2(C1)CN(c1cc(Cl)nnc1N)C2]

To a solution of 1-(2,6-diazaspiro[3.3]heptan-2-yl)ethan-1-one (37.0 g, 145 mmol, TFA) in DMSO (222 mL) was added CSF (66.3 g, 436 mmol, 16.1 mL), DIEA (56.4 g, 436 mmol, 76.0 mL) and 4-bromo-6-chloro-pyridazin-3-amine (24.2 g, 116 mmol) at 25° C. Then the mixture was stirred at 80° C. for 2 hours. The reaction mixture was filtered and the filter cake was concentrated in vacuum to give a crude product. The crude product would be directly used in the next step without purification. The titled compound (72.0 g, 268 mmol, 92.3% yield) was obtained as a yellow solid.

Step 4: 1-(6-(3-amino-6-(2-(methoxymethoxy)phenyl)pyridazin-4-yl)-2,6-diazaspiro[3.3]heptan-2-yl)ethan-1-one

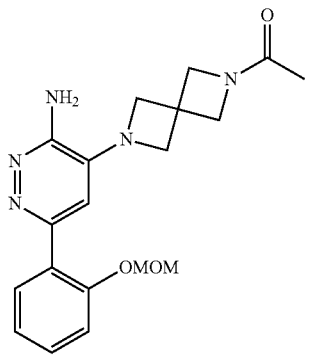

To a solution of 1-(6-(3-amino-6-chloropyridazin-4-yl)-2,6-diazaspiro[3.3]heptan-2-yl)ethan-1-one (50.0 g, 186 mmol) and 2-(methoxymethoxy)phenyl]boronic acid (50.9 g, 280 mmol) in dioxane (300 mL) and H₂O (60.0 g, 3.33 mol, 60.0 mL) was added K₂CO₃ (51.6 g, 373 mmol) followed by Pd(PPh₃)₄ (4.32 g, 3.74 mmol) at 25° C. under N₂. Then the mixture was degassed with N₂ for 3 times, heated to 90° C. and stirred for 16 hours. The reaction mixture was concentrated in vacuum to give a crude product. The product was added water (300 mL) with stirring, and then extracted with DCM (300 mL×4, 100 mL×2). The combined organic phases were washed with brine (150 mL) and dried over Na₂SO₄. Filtered and the filtrate was concentrated in vacuum to give a crude product. The crude product was triturated with MTBE (300 mL) at 25° C. for 30 min. The titled compound (48.0 g, 129 mmol, 69.5% yield) was obtained as a yellow solid.

Step 5: 6-(2-(methoxymethoxy)phenyl)-4-(2,6-diazaspiro[3.3]heptan-2-yl)pyridazin-3-amine

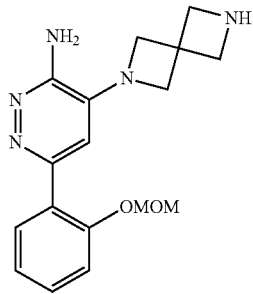

To a solution of 1-(6-(3-amino-6-(2-(methoxymethoxy)phenyl)pyridazin-4-yl)-2,6-diazaspiro[3.3]heptan-2-yl)ethan-1-one (48.0 g, 129 mmol) in MeOH (250 mL) was added NaOH (4 M, 150 mL). Then the mixture was stirred at 50° C. for 4 hours. The reaction mixture was cooled to 25° C. and added saturation citric acid aqueous solution to make pH=7. The crude product was purified by reversed-phase HPLC (0.1% NH₄HCO₃ condition). The titled compound (41.0 g, 125 mmol, 96.3% yield) was obtained as a yellow solid.

Step 6: 4-(6-(2-bromopyridin-4-yl)-2,6-diazaspiro[3.3]heptan-2-yl)-6-(2-(methoxymethoxy)phenyl)pyridazin-3-amine

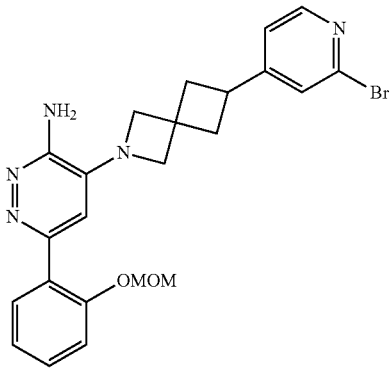

To a solution of 6-(2-(methoxymethoxy)phenyl)-4-(2,6-diazaspiro[3.3]heptan-2-yl)pyridazin-3-amine (41.0 g, 125 mmol) in DMSO (240 mL) was added DIEA (48.5 g, 375 mmol, 65.4 mL), 2-bromo-4-fluoro-pyridine (24.2 g, 137 mmol) at 25° C., warmed the mixture to 130° C. Then the mixture was stirred at 130° C. for 4 hours. TLC (Petroleum ether/Ethyl acetate=0/1, product R_f=0.4) showed reactant was consumed completely and a new spot was detected. The reaction mixture was poured into ice-water (1.00 L) with stirring and then filtered and the filter cake was concentrated in vacuum to give a crude product. The crude product was triturated with MTBE (250 mL) at 25° C. for 30 min. The titled compound (50.0 g, 103 mmol, 82.6% yield) was obtained as a yellow solid.

Step 7: 3-(4-(6-(3-amino-6-(2-(methoxymethoxy)phenyl)pyridazin-4-yl)-2,6-diazaspiro[3.3]heptan-2-yl)pyridin-2-yl)prop-2-yn-1-ol

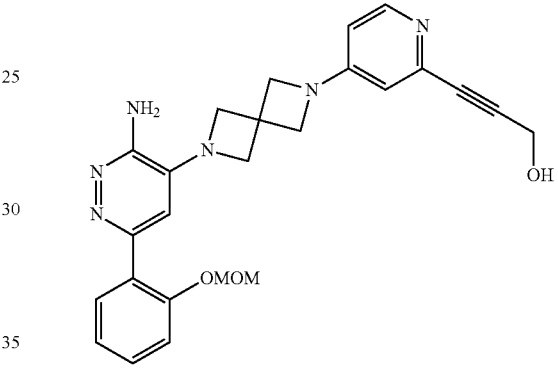

To a solution of 4-(6-(2-bromopyridin-4-yl)-2,6-diazaspiro[3.3]heptan-2-yl)-6-(2-(methoxymethoxy)phenyl)pyridazin-3-amine (50.0 g, 103 mmol) in DMF (300 mL) was added Et₃N (31.4 g, 310 mmol, 43.1 mL), CuI (985 mg, 5.17 mmol), PPh₃ (5.43 g, 20.6 mmol), Pd(PPh₃)₄ (5.98 g, 5.17 mmol) and prop-2-yn-1-ol (33.8 g, 604 mmol, 35.7 mL) under N₂ at 20° C., then the mixture was stirred at 50° C. for 2 hours. The residue was poured into water (1.50 L). The aqueous phase was extracted with DCM (800 mL×5, 300 mL×3). The combined organic phase was washed with brine (300 mL×3), dried with anhydrous Na₂SO₄, filtered and concentrated in vacuum. The crude product was purified by flash chromatography on a silica gel eluted with Dichloromethane/Methanol (from 100/1 to 5/1). The titled compound (15.0 g, 32.3 mmol, 31.3% yield, 98.9% purity) was obtained as a yellow solid. ¹H NMR (400 MHz, CDCl₃): δ 8.07 (d, J=5.6 Hz, 1H), 7.60 (d, J=7.6 Hz, 1H), 7.18-7.33 (m, 1H), 7.18 (s, 1H), 7.16-7.18 (m, 1H), 6.69 (s, 1H), 6.47 (s, 1H), 6.33-6.35 (m, 1H), 5.65 (s, 2H), 5.36-5.39 (m, 1H), 5.20 (s, 2H), 4.28 (d, J=5.6 Hz, 2H), 4.18 (s, 4H), 4.09 (s, 4H), 3.35 (s, 3H).

Step 8: 3-(4-(6-(3-amino-6-(2-(methoxymethoxy)phenyl)pyridazin-4-yl)-2,6-diazaspiro[3.3]heptan-2-yl)pyridin-2-yl)prop-2-yn-1-yl methanesulfonate

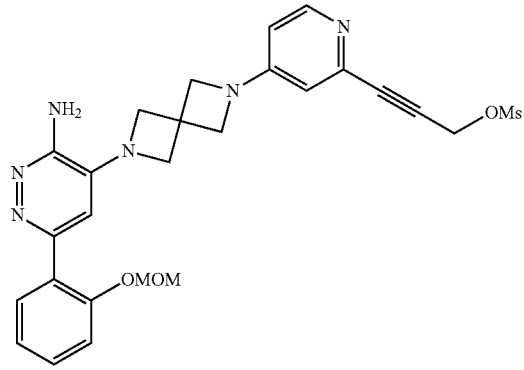

To a solution of 3-[4-[2-[3-amino-6-[2-(methoxymethoxy)phenyl]pyridazin-4-yl]-2,6-diazaspiro[3.3]heptan-6-yl]-2-pyridyl]prop-2-yn-1-ol (200 mg, 436 μmol, 1.00 eq) in DCM (3.00 mL) was added TEA (88.2 mg, 872 μmol, 121 μL, 2.00 eq) and MsCl (0.143 g, 1.25 mmol, 96.6 μL, 2.86 eq) at 0° C. The mixture was stirred at 25° C. for 2 hrs. TLC (Dichloromethane:Methanol=10/1, R$_f$=0.21) indicated most Reactant was consumed and one new point was detected according to TLC. The reaction mixture was quenched by addition H$_2$O (20 mL) at 25° C., then was filtered, the filtrate was extracted with DCM (20 mL×2). The combined organic layers were washed with H$_2$O (20 mL×2), dried over Na$_2$SO$_4$, filtered and concentrated under reduced pressure to give a residue. The titled compound (400 mg, 745 μmol, 56.9% yield) was obtained as a brown solid.

Step 9: 4-(6-(2-(3-(azepan-1-yl)prop-1-yn-1-yl)pyridin-4-yl)-2,6-diazaspiro[3.3]heptan-2-yl)-6-(2-(methoxymethoxy)phenyl)pyridazin-3-amine

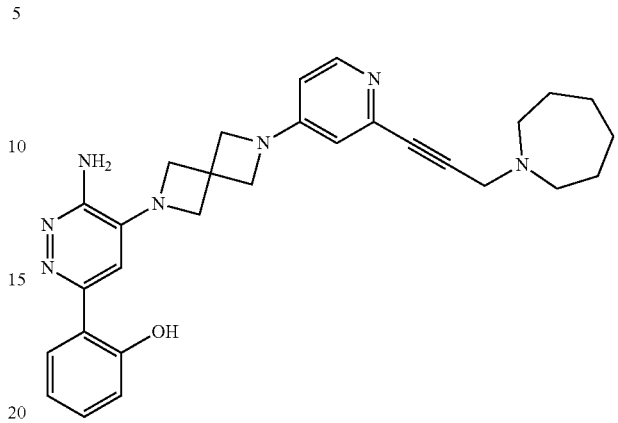

To a solution of 3-[4-[2-[3-amino-6-[2-(methoxymethoxy)phenyl]pyridazin-4-yl]-2,6-diazaspiro[3.3]heptan-6-yl]-2-pyridyl]prop-2-ynyl methanesulfonate (400 mg, 745 μmol, 1.00 eq) in MeCN (10.0 mL) was added K$_2$CO$_3$ (206 mg, 1.49 mmol, 2.00 eq) and azepane (0.48 g, 4.84 mmol, 545 μL, 6.49 eq). The mixture was stirred at 80° C. for 6 hrs. The reaction mixture was filtered and the filtrate was concentrated. Give the titled compound (160 mg, crude) was obtained as a brown gum.

Step 10: 2-(6-amino-5-(6-(2-(3-(azepan-1-yl)prop-1-yn-1-yl)pyridin-4-yl)-2,6-diazaspiro[3.3]heptan-2-yl)pyridazin-3-yl)phenol To a solution of 4-[6-[2-[3-(azepan-1-yl)prop-1-ynyl]-4-pyridyl]-2,6-diazaspiro[3.3]heptan-2-yl]-6-[2-(methoxymethoxy)phenyl]pyridazin-3-amine (140 mg, 259 μmol, 1.00 eq) in MeCN (3.00 mL) was added scandium (3+); trifluoromethanesulfonate (127 mg, 259 μmol, 1.00 eq) and EtOH (956 mg, 20.7 mmol, 80 eq). The mixture was stirred at 120° C. for 3 hrs in MW. Several new peaks were shown on LC-MS and desired compound was detected. The reaction mixture was filtered. The filtrate was purify by Pre-HPLC.column: Phenomenex Luna C18 75*30 mm*3 um; mobile phase: [water(FA)-ACN]; B %: 1%-20%, 8 min. The titled compound (6.00 mg, 11.9 μmol, 4.62% yield, 99% purity) was obtained as a brown solid. $^1$H NMR (400 MHz, MeOD): δ 8.10-8.08 (d, 1H, J=8.0 Hz), 7.73-7.71 (d, 1H, J=8.0 Hz), 7.31-7.29 (t, 1H, J=8.0 Hz), 6.96-6.92 (m, 3H), 6.66-6.65 (d, 1H, J=4.0 Hz), 6.50-6.48 (m, 1H), 4.51 (s, 4H), 4.31 (s, 4H), 4.04 (s, 2H), 3.21-3.18 (m, 4H), 1.86 (m, 4H), 1.74 (m, 4H). LCMS (ESI): m/z 496.1 (M+H)$^+$.

Example 19 and 20 Compounds 252 and 253

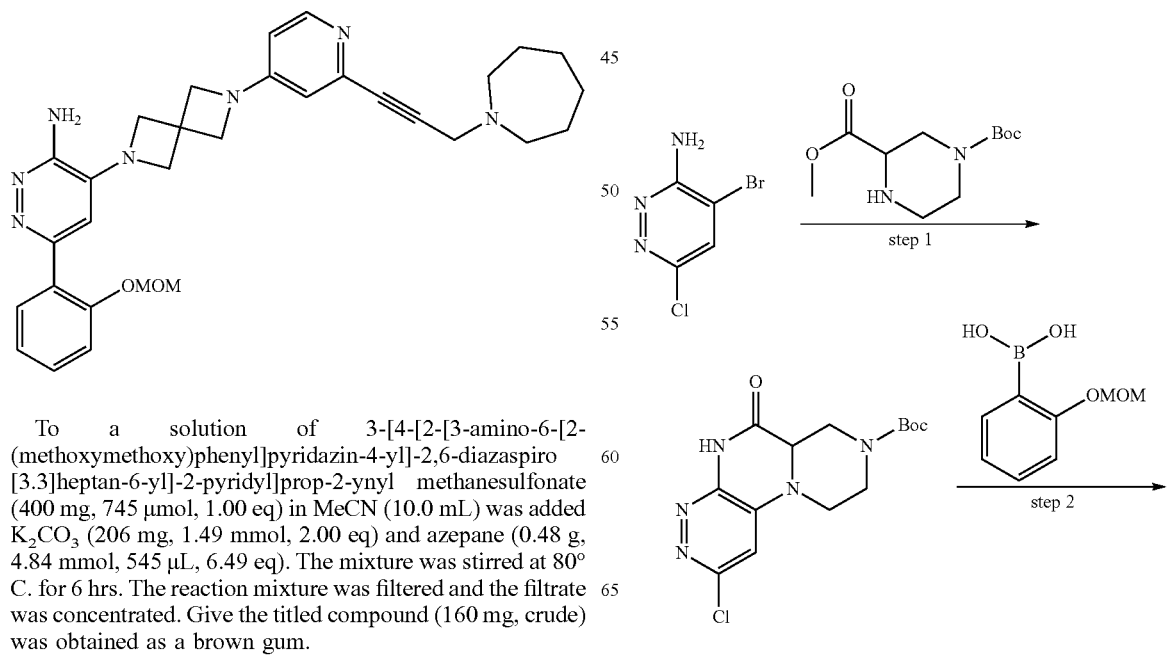

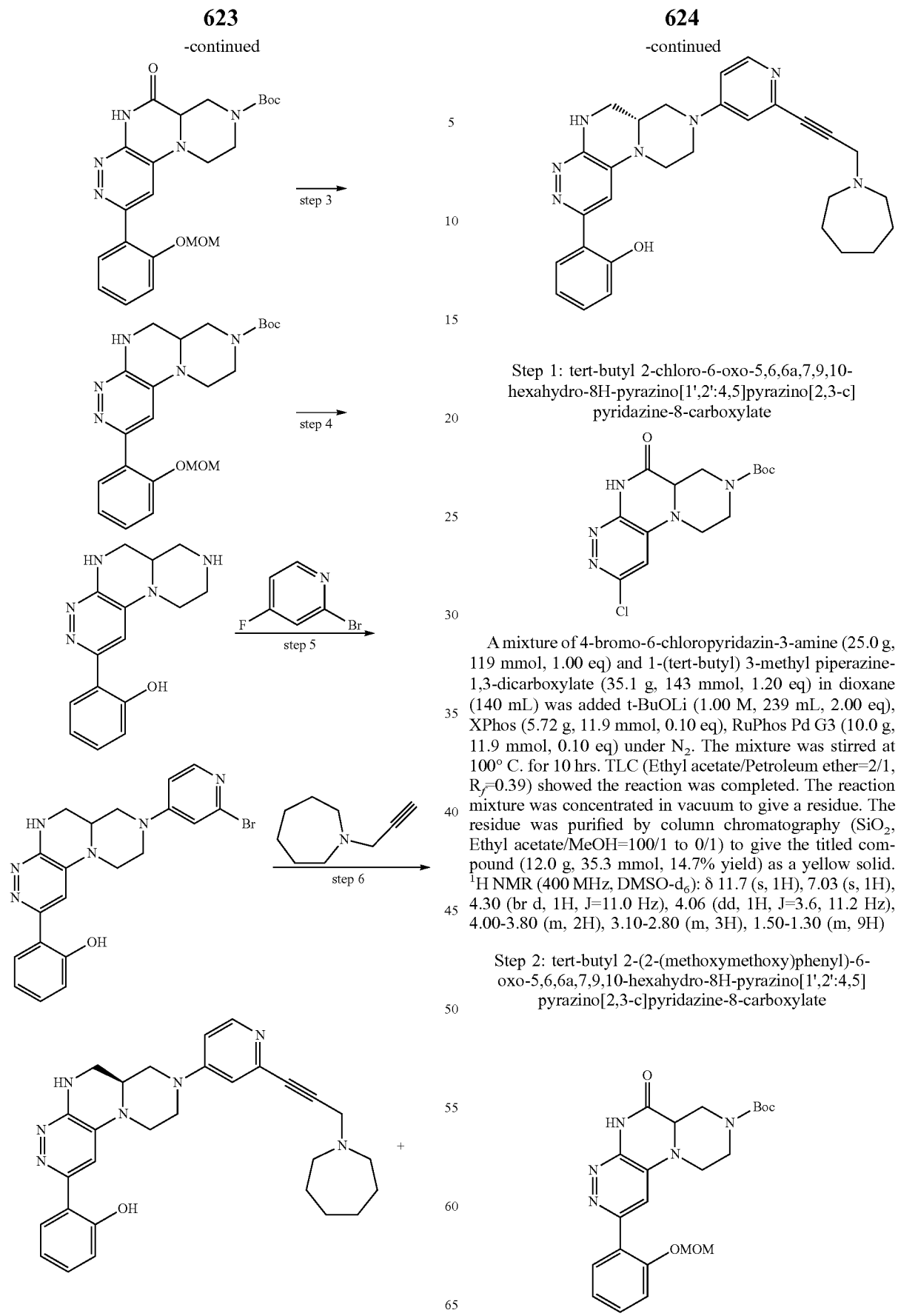

Step 1: tert-butyl 2-chloro-6-oxo-5,6,6a,7,9,10-hexahydro-8H-pyrazino[1',2':4,5]pyrazino[2,3-c]pyridazine-8-carboxylate A mixture of 4-bromo-6-chloropyridazin-3-amine (25.0 g, 119 mmol, 1.00 eq) and 1-(tert-butyl) 3-methyl piperazine-1,3-dicarboxylate (35.1 g, 143 mmol, 1.20 eq) in dioxane (140 mL) was added t-BuOLi (1.00 M, 239 mL, 2.00 eq), XPhos (5.72 g, 11.9 mmol, 0.10 eq), RuPhos Pd G3 (10.0 g, 11.9 mmol, 0.10 eq) under $N_2$. The mixture was stirred at 100° C. for 10 hrs. TLC (Ethyl acetate/Petroleum ether=2/1, $R_f$=0.39) showed the reaction was completed. The reaction mixture was concentrated in vacuum to give a residue. The residue was purified by column chromatography ($SiO_2$, Ethyl acetate/MeOH=100/1 to 0/1) to give the titled compound (12.0 g, 35.3 mmol, 14.7% yield) as a yellow solid. $^1$H NMR (400 MHz, DMSO-$d_6$): δ 11.7 (s, 1H), 7.03 (s, 1H), 4.30 (br d, 1H, J=11.0 Hz), 4.06 (dd, 1H, J=3.6, 11.2 Hz), 4.00-3.80 (m, 2H), 3.10-2.80 (m, 3H), 1.50-1.30 (m, 9H)

Step 2: tert-butyl 2-(2-(methoxymethoxy)phenyl)-6-oxo-5,6,6a,7,9,10-hexahydro-8H-pyrazino[1',2':4,5]pyrazino[2,3-c]pyridazine-8-carboxylate To a solution of tert-butyl 2-chloro-6-oxo-5,6,6a,7,9,10-hexahydro-8H-pyrazino[1',2':4,5]pyrazino[2,3-c]pyridazine-8-carboxylate (5.00 g, 14.7 mmol, 1.00 eq) and (2-(methoxymethoxy)phenyl)boronic acid (3.21 g, 17.6 mmol, 1.20 eq) in dioxane (20.0 mL) and H₂O (2.00 mL). Then K₂CO₃ (6.10 g, 44.5 mmol, 3.00 eq) and RuPhos Pd G3 (1.23 g, 1.47 mmol, 0.10 eq) was added into the mixture. The reaction mixture was stirred at 100° C. for 10 hrs. TLC (Ethyl acetate/Petroleum ether=1/0, R$_f$=0.48) showed the reaction was completed. The reaction mixture was added water (10 mL). The aqueous phase was extracted with EtOAc (10.0 mL×2). The combined organic layer was washed with brine (30.0 mL), dried over Na₂SO₄, concentrated in vacuum. The residue was purified by column chromatography (SiO₂, EtOAc/MeOH=80/1 to 0/1) to give the titled compound (2.50 g, 5.66 mmol, 38.4% yield) as a yellow solid.

Step 3: tert-butyl 2-(2-(methoxymethoxy)phenyl)-5,6,6a,7,9,10-hexahydro-8H-pyrazino[1',2':4,5]pyrazino[2,3-c]pyridazine-8-carboxylate

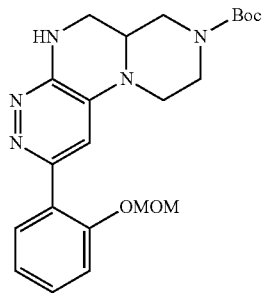

To a solution of tert-butyl 2-(2-(methoxymethoxy)phenyl)-6-oxo-5,6,6a,7,9,10-hexahydro-8H-pyrazino[1',2':4,5]pyrazino[2,3-c]pyridazine-8-carboxylate (1.50 g, 3.40 mmol, 1.00 eq) in THF (15.0 mL) was added BH₃-Me₂S (10.0 M, 1.70 mL, 5.00 eq) at 0° C. Then the mixture was stirred at 55° C. for 10 hrs. TLC (Dichloromethane/Methanol=10/1, R$_f$=0.48) showed the reaction was completed. The reaction mixture was quenched with MeOH (25.0 mL) and concentrated in vacuum to give a crude product. The crude product was triturated with Petroleum ether (10.0 mL) at 20° C. for 1 hr to give the titled compound (1.20 g, crude) as a gray solid.

Step 4: 2-(6,6a,7,8,9,10-hexahydro-5H-pyrazino[1',2':4,5]pyrazino[2,3-c]pyridazin-2-yl)phenol

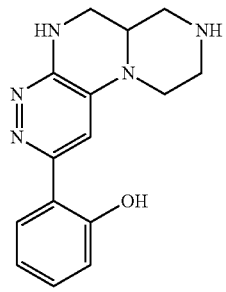 [SMILES: Oc1ccccc1-c1cc2c(nn1)NCC1CNCCN21]

To a solution of tert-butyl 2-(2-(methoxymethoxy)phenyl)-5,6,6a,7,9,10-hexahydro-8H-pyrazino[1',2':4,5]pyrazino[2,3-c]pyridazine-8-carboxylate (900 mg, 2.11 mmol, 1 eq) in EtOAc (2.00 mL) was added HCl/EtOAc (4 M, 1 mL). Then the mixture was stirred at 25° C. for 1 hr. TLC (Dichloromethane/Methanol=10/1, R$_f$=0.01) showed the reaction was completed. The reaction mixture was filtered and the filter cake was concentrated in vacuum without purification to give the titled compound (300 mg, crude, HCl) as a gray solid.

Step 5: 2-(8-(2-bromopyridin-4-yl)-6,6a,7,8,9,10-hexahydro-5H-pyrazino[1',2':4,5]pyrazino[2,3-c]pyridazin-2-yl)phenol

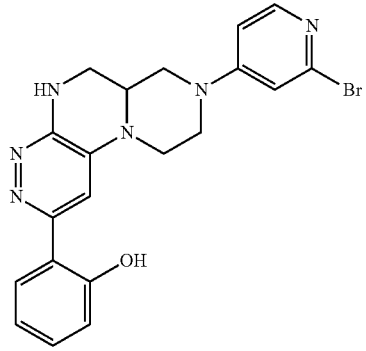 [SMILES: Oc1ccccc1-c1cc2c(nn1)NCC1CN(c3ccnc(Br)c3)CCN21]

To a solution of 2-(6,6a,7,8,9,10-hexahydro-5H-pyrazino[1',2':4,5]pyrazino[2,3-c]pyridazin-2-yl)phenol (1.05 g, 3.28 mmol, 1.00 eq, HCl) in DMSO (10.0 mL) was added DIEA (2.12 g, 16.4 mmol, 2.86 mL, 5.00 eq) and 2-bromo-4-fluoro-pyridine (577 mg, 3.28 mmol, 1.00 eq). Then the mixture was stirred at 60° C. for 5 hrs. The reaction mixture was filtered and the filtrate was collected. The residue was purified by prep-HPLC (column: Welch Xtimate® C18 250*70 mm*10 μm; mobile phase: [water(NH₄HCO₃)-ACN]; B %: 30%-60%, 20 min) to give the titled compound (300 mg, 682.89 μmol, 20.80% yield) as a yellow solid. ¹H NMR (400 MHz, DMSO-d₆): δ 14.7 (br s, 1H), 8.00-7.90 (m, 2H), 7.39 (d, 1H, J=3.1 Hz), 7.32 (s, 1H), 7.24-7.21 (m, 1H), 7.12 (s, 1H), 6.99 (dd, 1H, J=2.3, 6.1 Hz), 6.90-6.80 (m, 2H), 4.20-4.10 (m, 3H), 3.61 (td, 1H, J=3.6, 11.7 Hz), 3.41 (br d, 1H, J=2.9 Hz), 3.30-3.00 (m, 3H), 2.80-2.70 (m, 1H).

Step 6: (S)-2-(8-(2-(3-(Azepan-1-yl)prop-1-yn-1-yl)
pyridin-4-yl)-6,6a,7,8,9,10-hexahydro-5H-pyrazino
[1',2':4,5]pyrazino[2,3-c]pyridazin-2-yl)phenol and
(R)-2-(8-(2-(3-(Azepan-1-yl)prop-1-yn-1-yl)pyridin-
4-yl)-6,6a,7,8,9,10-hexahydro-5H-pyrazino[1',2':4,5]
pyrazino[2,3-c]pyridazin-2-yl)phenol

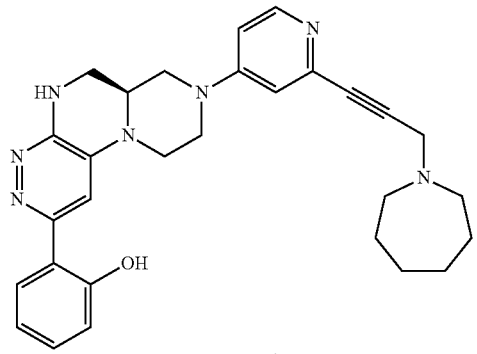

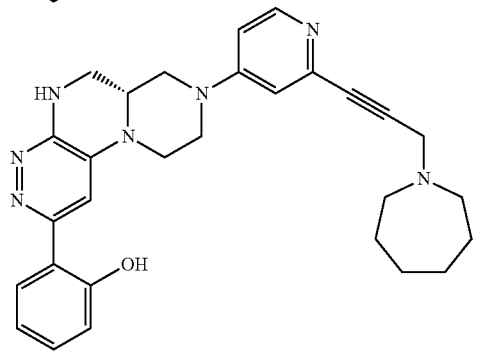

To a solution of 2-(8-(2-bromopyridin-4-yl)-6,6a,7,8,9,
10-hexahydro-5H-pyrazino[1',2':4,5]pyrazino[2,3-c]
pyridazin-2-yl)phenol (20.0 mg, 45.5 µmol, 1.00 eq) in
DMF (2.00 mL) was added TEA (13.8 mg, 136 µmol, 19.0
µL, 3.00 eq), CuI (433 µg, 2.28 µmol, 0.05 eq), PPh$_3$ (2.39
mg, 9.11 µmol, 0.20 eq), Pd(PPh$_3$)$_4$ (2.63 mg, 2.28 µmol,
0.05 eq) under N$_2$. Then 1-prop-2-ynylazepane (12.5 mg,
91.0 µmol, 2.00 eq) was added into the mixture under N$_2$.
The reaction mixture was stirred at 80° C. for 10 hrs. The
reaction mixture was filtered and the filtrate was concentrated in vacuum. The residue was purified by prep-HPLC
(column: Phenomenex luna C18 (250*70 mm*15 µm);
mobile phase: [water(HCl)-ACN]; B %: 1%-22%, 16 min)
to give the titled compounds (50.0 mg, 93.9 µmol, 41.3%
yield, HCl) as a yellow solid. The enantiomer mixture was
separated by prep-HPLC (column: ChiralPak IH, 250*30
mm, 10 µm; mobile phase: [0.1% NH$_3$H$_2$O EtOH]; B %:
55%-55%, 20 min) to give pure enantiomers. Peak 1 Compound 252: (10.8 mg, 21.7 µmol, 54.0% yield) as an
off-white solid. Peak 2 Compound 253: (4.61 mg, 9.30 µmol,
23.0% yield) as an off-white solid. $^1$H NMR (400 MHz,
DMSO-d$_6$): δ 14.7 (s, 1H), 8.14 (d, J=6.0 Hz, 1H), 7.94 (d,
J=7.6 Hz, 1H), 7.38 (d, J=3.2 Hz, 1H), 7.31 (s, 1H), 7.21 (t,
1H), 7.04 (s, 1H), 6.92 (d, J=6.0 Hz, 1H), 6.88-6.86 (m, 2H),
4.14 (q, J=11.6 Hz, 3H), 3.63-3.60 (m, 1H), 3.56 (s, 2H),
3.40-3.19 (m, 2H), 3.10-3.04 (m, 2H), 2.69-2.60 (m, 5H),
1.70-1.50 (m, 8H). LCMS (ESI): m/z 496.2 (M+H)$^+$.

Example 21 Compound 245

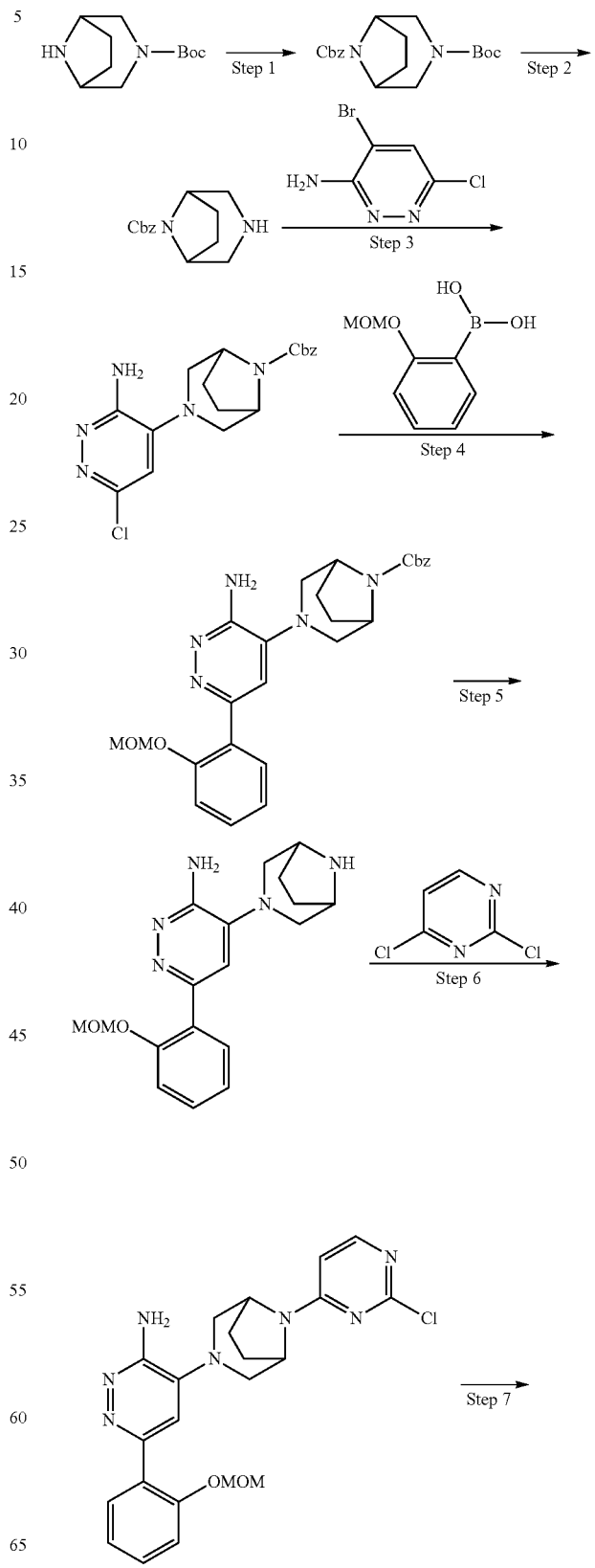

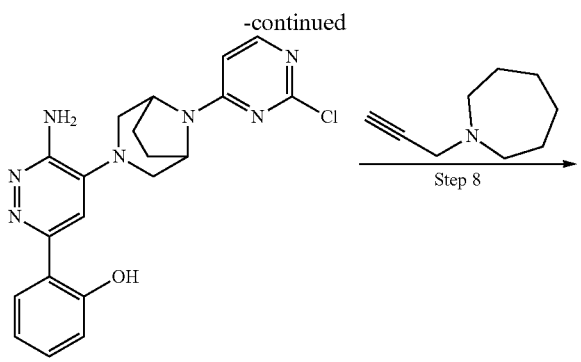

Step 8

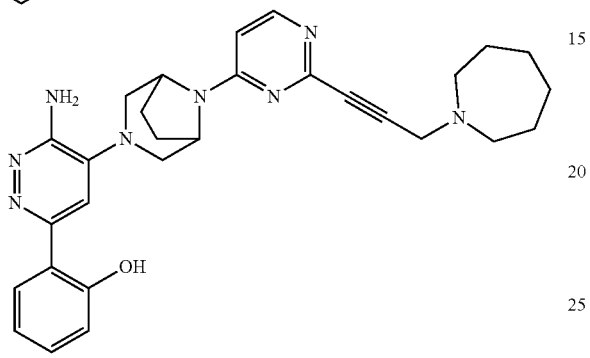

Step 1: 8-benzyl 3-(tert-butyl) 3,8-diazabicyclo[3.2.1]octane-3,8-dicarboxylate

A mixture of tert-butyl 3,8-diazabicyclo[3.2.1]octane-3-carboxylate (125 g, 589 mmol, 1.00 eq) in DCM (620 mL), TEA (179 g, 1.77 mol, 246 mL, 3.00 eq) and CbzCl (151 g, 883 mmol, 126 mL, 1.50 eq) was added, and then the mixture was stirred at 25° C. for 3 hrs under $N_2$ atmosphere. TLC (Petroleum ether:Ethyl acetate=3:1) showed new spots ($R_f$=0.37) were formed. The solution was washed with water 50.0 mL, extracted with EtOAc 150×3 mL, washed with brine 50.0 mL and concentrated under reduced pressure to give a residue. The residue was purified by column chromatography (Petroleum ether/Ethyl acetate=3:1) to afford the title compound (89.0 g, 257 mmol, 43.6% yield) as a white solid. $^1$H NMR (400 MHz, CDCl$_3$): δ 7.38-7.34 (m, 5H), 5.15 (s, 2H), 4.30 (s, 2H), 3.87-3.70 (m, 2H), 3.03 (d, J=28.8 Hz, 2H), 1.95 (s, 2H), 1.88 (d, J=16.8 Hz, 2H), 1.45 (s, 9H).

Step 2: benzyl 3,8-diazabicyclo[3.2.1]octane-8-carboxylate

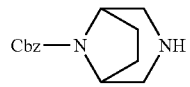 [SMILES: O=C(OCc1ccccc1)N1C2CCC1CNC2]

To a solution of 8-benzyl 3-(tert-butyl) 3,8-diazabicyclo[3.2.1]octane-3,8-dicarboxylate (89.0 g, 257 mmol, 1.00 eq) in EtOAc (150 mL) was added HC/EtOAc (4 M, 321 mL, 5.00 eq). The mixture was stirred at 25° C. for 3 hrs. The solution was concentrated under reduced pressure to remove most of the solvent and filtered to afford the title compound (59.0 g, 209 mmol, 81.2% yield) as a crude white solid. $^1$H NMR (400 MHz, CDCl$_3$): δ 7.39-7.32 (m, 5H), 5.15 (s, 2H), 4.44 (s, 2H), 3.20 (s, 4H), 2.32-2.27 (m, 2H), 2.16-2.00 (m, 2H).

Step 3: benzyl 3-(3-amino-6-chloropyridazin-4-yl)-3,8-diazabicyclo[3.2.1]octane-8-carboxylate

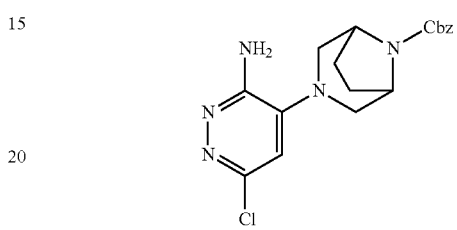

A mixture of benzyl 3,8-diazabicyclo[3.2.1]octane-8-carboxylate (59.0 g, 209 mmol, 1.00 eq) in DMSO (410 mL), 4-bromo-6-chloro-pyridazin-3-amine (45.7 g, 219 mmol, 1.05 eq), DIPEA (108 g, 835 mmol, 145 mL, 4.00 eq) was added, and then the mixture was stirred at 130° C. for 16 hrs under $N_2$ atmosphere. The solution was added water 100 mL, and combined with another crude reaction mixture of the same product, extracted with EtOAc 150×3 mL, and then washed with brine 20.0 mL, concentrated under reduced pressure to afford the title compound (200 g, crude) as a white solid. $^1$H NMR (400 MHz, CDCl$_3$): δ 7.39-7.27 (m, 5H), 6.70 (s, 1H), 5.17 (s, 2H), 5.10 (s, 2H), 4.46 (s, 2H), 3.25 (d, J=9.6 Hz, 2H), 2.89 (d, J=33.6 Hz, 2H), 2.08-2.05 (m, 2H), 1.95-1.91 (m, 2H).

Step 4: benzyl 3-(3-amino-6-(2-(methoxymethoxy)phenyl)pyridazin-4-yl)-3,8-diazabicyclo[3.2.1]octane-8-carboxylate

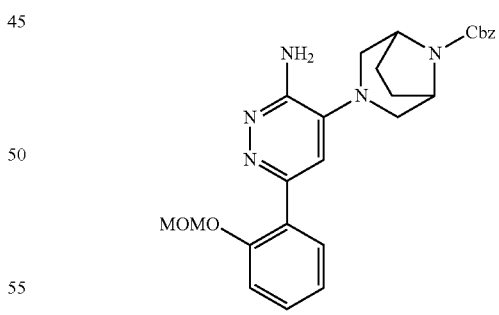

To a mixture of benzyl 3-(3-amino-6-chloropyridazin-4-yl)-3,8-diazabicyclo[3.2.1]octane-8-carboxylate (100 g, 268 mmol, 1.00 eq) in dioxane (800 mL) and H$_2$O (150 mL) was added (2-(methoxymethoxy)phenyl)boronic acid (73.0 g, 401 mmol, 1.50 eq), Pd(PPh$_3$)$_4$ (30.9 g, 26.8 mmol, 0.100 eq) and K$_2$CO$_3$ (73.9 g, 534 mmol, 2.00 eq), then the mixture was stirred at 100° C. for 2 hrs under $N_2$ atmosphere. The solution was added 100 mL water and combined with another crude reaction mixture of the same reaction. The mixture was extracted with EtOAc 200 mL×3, the organic was washed with brine 100 mL, dried over Na$_2$SO$_4$, concentrated under reduced pressure to give a residue. The residue was purified by column chromatography (Petroleum ether/Ethyl acetate=0:1) to afford the title compound (182 g, combined yield: 71.7%) as a yellow solid. $^1$H NMR (400 MHz, CDCl$_3$): δ 7.68 (d, J=1.2 Hz, 1H), 7.66-7.25 (m, 6H), 7.17 (d, J=6.0 Hz, 1H), 7.11-7.10 (m, 1H), 7.04 (s, 1H), 5.08 (s, 2H), 5.06 (s, 2H), 4.92 (s, 2H), 4.39 (s, 2H), 3.32 (s, 3H), 3.17 (d, J=10.0 Hz, 2H), 2.83 (d, J=46.8 Hz, 2H), 1.92-2.15 (m, 4H).

Step 5: 4-(3,8-diazabicyclo[3.2.1]octan-3-yl)-6-(2-(methoxymethoxy)phenyl)pyridazin-3-amine

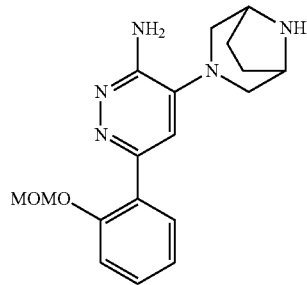

To a solution of benzyl 3-(3-amino-6-(2-(methoxymethoxy)phenyl)pyridazin-4-yl)-3,8-diazabicyclo[3.2.1]octane-8-carboxylate (182 g, 383 mmol, 1.00 eq) in MeOH (1.27 L) was added Pd(OH)$_2$/C (53.8 g, 38.3 mmol, 10.0% purity, 0.100 eq) under N$_2$ atmosphere. The suspension was degassed and purged with H$_2$ 3 times. The mixture was stirred under H$_2$ at 35° C. for 16 hrs. The solution was filtered and the filtrate was concentrated under reduced pressure to afford the title compound (100 g, crude) as a brown solid.

Step 6: 4-(8-(2-chloropyrimidin-4-yl)-3,8-diazabicyclo[3.2.1]octan-3-yl)-6-(2-(methoxymethoxy)phenyl)pyridazin-3-amine

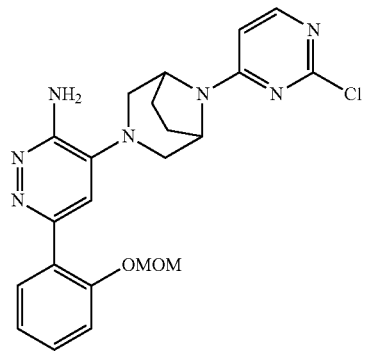

To a solution of 2,4-dichloropyrimidine (40.0 mg, 268.5 μmol, 1.0 eq) in EtOH (2 mL) was added 4-(3,8-diazabicyclo[3.2.1]octan-3-yl)-6-[2-(methoxymethoxy)phenyl]pyridazin-3-amine (100.8 mg, 295.3 μmol, 1.1 eq) and DIEA (93.53 uL, 537.0 μmol, 2.0 eq) at 25° C. The mixture was stirred at 25° C. for 2 hrs. TLC (DCM/MeOH=10/1, R$_f$=0.7) showed the reaction was completed. The reaction mixture was concentrated in vacuum to give a residue. The residue was purified by column chromatography (SiO$_2$, DCM/MeOH=100/1 to 10/1) to give the title compound (70 mg, 154.2 μmol, 57.4% yield) as a yellow solid. $^1$H NMR (400 MHz, DMSO-d$_6$): δ 8.08 (d, J=6.0 Hz, 1H), 7.58 (dd, J=7.6, 1.6 Hz, 1H), 7.38-7.31 (m, 1H), 7.20 (s, 1H), 7.16 (d, J=8.4 Hz, 1H), 7.07 (t, J=7.6 Hz, 1H), 6.82 (d, J=6.0 Hz, 1H), 5.76 (d, J=6.4 Hz, 2H), 5.16 (s, 2H), 4.96-4.45 (m, 2H), 3.31-3.28 (m, 2H), 3.27 (s, 3H), 2.91-2.72 (m, 2H), 2.21 (m, 2H), 1.96-1.94 (m, 2H).

Step 7: 2-(6-amino-5-(8-(2-chloropyrimidin-4-yl)-3,8-diazabicyclo[3.2.1]octan-3-yl)pyridazin-3-yl)phenol

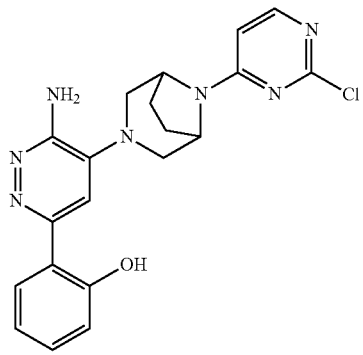 [SMILES: Nc1nnc(-c2ccccc2O)cc1N1CC2CCC(C1)N2c1ccnc(Cl)n1]

To a solution of 4-[8-(2-chloropyrimidin-4-yl)-3,8-diazabicyclo[3.2.1]octan-3-yl]-6-[2-(methoxymethoxy)phenyl]pyridazin-3-amine (70.0 mg, 154.2 μmol, 1.00 eq) in dioxane (5 mL) was added 4M HCl (0.4 mL, 1.6 mmol, 10 eq) in dioxane (5 mL). The reaction mixture was stirred at 25° C. for 16 hrs. TLC (DCM/MeOH=10/1, R$_f$=0.5) showed the reaction was completed. The mixture was concentrated in vacuum to give the titled compound (60 mg, 146.4 μmol, 94.9% yield) as a yellow solid. The crude product was directly used in the next step without further purification.

Step 8: 2-(6-amino-5-(8-(2-(3-(azepan-1-yl)prop-1-yn-1-yl)pyrimidin-4-yl)-3,8-diazabicyclo[3.2.1]octan-3-yl)pyridazin-3-yl)phenol

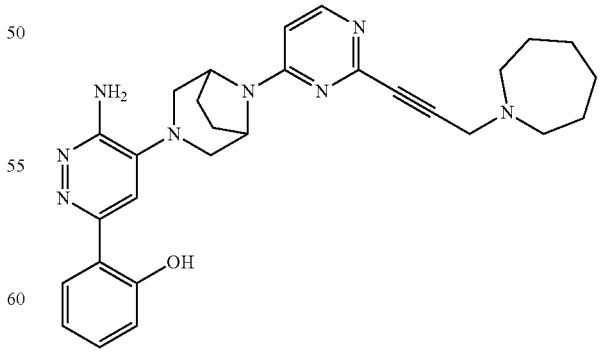

To a solution of 1-prop-2-ynylazepane (50.2 mg, 366.0 μmol, 5.00 eq) and bis(triphenylphosphine)palladium(ii)dichloride (5.1 mg, 7.3 μmol, 0.10 eq) in DMF (5 mL) was added PPh$_3$ (3.8 mg, 14.6 μmol, 0.20 eq), CuI (1.4 mg, 14.6

μmol, 0.10 eq), Et₃N (0.03 mL, 219.6 μmol, 3.00 eq) and 2-[6-amino-5-[8-(2-chloropyrimidin-4-yl)-3,8-diazabicyclo[3.2.1]octan-3-yl]pyridazin-3-yl]phenol (30.0 mg, 73.2 μmol, 1.00 eq). Then the reaction was stirred at 50° C. for 6 hrs. TLC (DCM/MeOH=10/1, R$_f$=0.3) showed the reaction was completed. The reaction mixture was filtered and the filtrate was collected. The residue was purified by prep-HPLC (column: WelchXtimate C18 150*30 mm*5 um; mobile phase: [water(FA)-ACN]) to give the titled compound (9.9 mg, 18.2 μmol, 24.9% yield) as a yellow solid. $^1$H NMR (400 MHz, CDCl₃): δ 8.22 (s, 1H), 7.55 (d, J=8.0 Hz, 1H), 7.29-7.26 (m, 2H) 7.03 (d, J=8.4 Hz, 1H), 6.88 (t, J=7.2 Hz, 1H), 6.41 (d, J=5.6 Hz, 1H), 4.90-4.70 (m, 4H), 3.72 (s, 2H), 3.37-3.41 (m, 2H), 3.17-3.00 (m, 2H), 2.95-2.77 (m, 4H), 2.26-2.00 (m, 4H), 1.75-1.63 (m, 8H). LCMS (ESI): m/z 511.1 (M+H)⁺.

Example 22 Compound 246

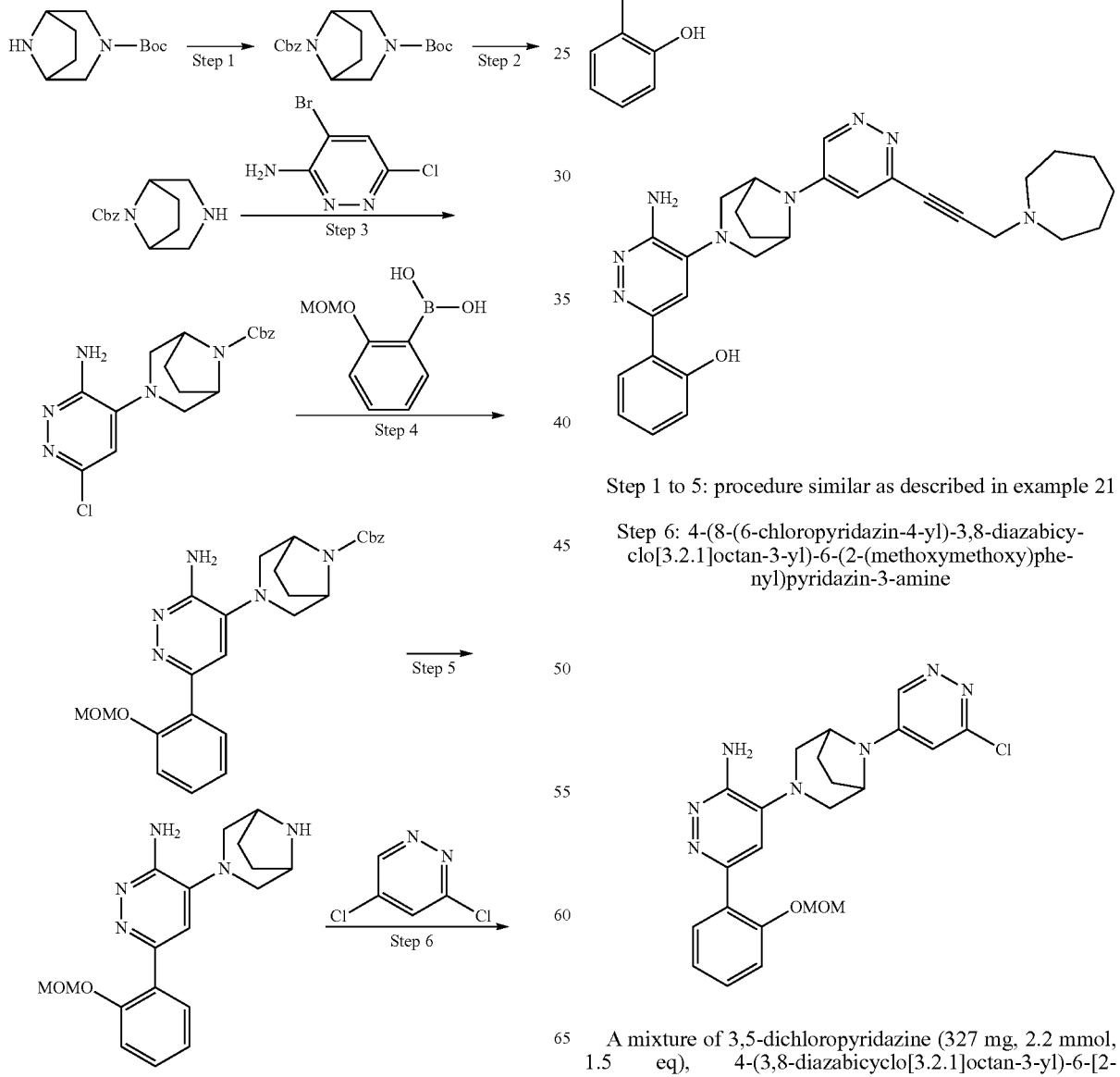

Step 1 to 5: procedure similar as described in example 21

Step 6: 4-(8-(6-chloropyridazin-4-yl)-3,8-diazabicyclo[3.2.1]octan-3-yl)-6-(2-(methoxymethoxy)phenyl)pyridazin-3-amine A mixture of 3,5-dichloropyridazine (327 mg, 2.2 mmol, 1.5 eq), 4-(3,8-diazabicyclo[3.2.1]octan-3-yl)-6-[2-(methoxymethoxy)phenyl]pyridazin-3-amine (500 mg, 1.46 mmol, 1 eq) and triethylamine (0.82 mL, 5.86 mmol, 5 eq) in Ethanol (10 mL) was degassed and purged with N₂ for 3 times. Then the mixture was stirred at 90° C. for 5 h. TLC (MeOH/DCM=1/10, R$_f$=0.5) showed the reaction was completed. The reaction mixture was concentrated to give crude product, which was purified by column chromatography (SiO₂, MeOH/DCM=0 to 3/100) to afford the title compound (350 mg, 0.77 mmol, 52.6% yield) as a yellow solid.

Step 7: 2-(6-amino-5-(8-(6-chloropyridazin-4-yl)-3,8-diazabicyclo[3.2.1]octan-3-yl)pyridazin-3-yl)phenol

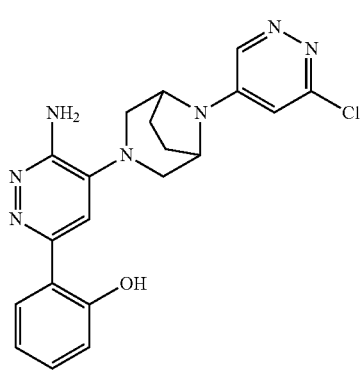 [SMILES: Nc1nnc(-c2ccccc2O)cc1N1CC2CCC(C1)N2c1cnnc(Cl)c1]

4-[8-(6-chloropyridazin-4-yl)-3,8-diazabicyclo[3.2.1]octan-3-yl]-6-[2-(methoxymethoxy)phenyl]pyridazin-3-amine (250.0 mg, 0.55 mmol, 1 eq) was dissolved in 4M HCl in 1,4-Dioxane (10.0 mL, 40 mmol, 72.6 eq) at 25° C. The reaction mixture was stirred at 25° C. for 16 hours. The reaction mixture was concentrated to give crude title compound (220 mg, 0.537 mmol, 97.5% yield) as a yellow solid. The crude product was directly used in the next step without further purification.

Step 8: 2-(6-amino-5-(8-(6-(3-(azepan-1-yl)prop-1-yn-1-yl)pyridazin-4-yl)-3,8-diazabicyclo[3.2.1]octan-3-yl)pyridazin-3-yl)phenol

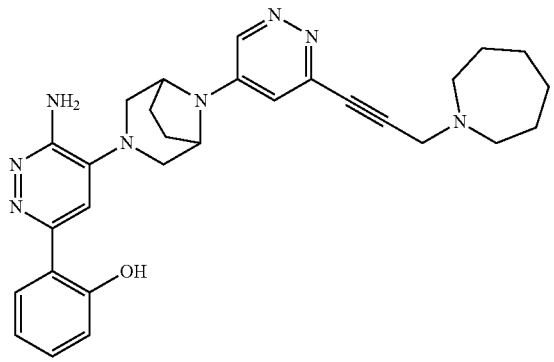 [SMILES: Nc1nnc(-c2ccccc2O)cc1N1CC2CCC(C1)N2c1cnnc(C#CCN2CCCCCC2)c1]

A solution of triethylamine (0.34 mL, 2.44 mmol, 10 eq), 2-[6-amino-5-[8-(6-chloropyridazin-4-yl)-3,8-diazabicyclo[3.2.1]octan-3-yl]pyridazin-3-yl]phenol (100.0 mg, 0.24 mmol, 1 eq), triphenylphosphine (12.8 mg, 0.05 mmol, 0.2 eq), copper(I) iodide (4.6 mg, 0.020 mmol, 0.1 eq), bis(triphenylphosphine)palladium(II)dichloride (17.1 mg, 0.020 mmol, 0.1 eq) and 1-prop-2-ynylazepane (167.4 mg, 1.22 mmol, 5 eq) in DMF (1.5 mL) was stirred at 80° C. for 16 hours. LCMS (5-95AB/1.5 min): R$_f$=0.630 min, [M+H]⁺ 511.1, showed 20.8% of desired product. The residue was purified by pre-HPLC (column: Welch Xtimate C18 (150*30 mm*5 um); mobile phase: [water(FA)-ACN]; B %: 3%-33%, 7 min) to give the title compound (9.3 mg, 0.018 mmol, 7.2% yield) as a yellow solid. ¹H NMR (400 MHz, DMSO-d₆): δ 8.90 (s, 1H), 7.89 (d, J=8.0 Hz, 1H), 7.54 (s, 1H), 7.22 (t, J=7.6 Hz, 1H), 7.08 (d, J=2.4 Hz, 1H), 6.93-6.80 (m, 2H), 6.02 (s, 2H), 4.72 (s, 2H), 3.62 (s, 2H), 3.25 (s, 2H), 3.02 (d, J=12.0 Hz, 2H), 2.70-2.66 (m, 4H), 2.23 (d, J=7.2 Hz, 2H), 2.02-1.93 (m, 2H), 1.65-1.52 (m, 8H). LCMS (ESI): m/z 511.1 (M+H)⁺.

Table 2 below shows the additional compounds prepared according to general synthetic procedure A, or B (Scheme 2), or C (Scheme 3). Table 2 gives a list of routes used to prepare each compound.

TABLE 2

| Compound No. | General Synthetic Procedure |
|---|---|
| 1 | A |
| 2 | See Example 1 |
| 3 | A |
| 4 | A |
| 5 | A |
| 6 | A |
| 7 | A |
| 8 | A |
| 9 | See Example 2 |
| 10 | A |
| 11 | A |
| 12 | A |
| 13 | A |
| 14 | A |
| 15 | A |
| 16 | A |
| 17 | A |
| 18 | A |
| 19 | See Example 3 |
| 20 | B |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | B |
| 33 | See Example 4 |
| 34 | A |
| 35 | A |
| 36 | A |
| 37 | C |
| 38 | C |
| 39 | C |
| 40 | C |
| 41 | C |
| 42 | C |
| 43 | C |
| 44 | C |
| 45 | See Example 5 |
| 46 | C |
| 47 | C |
| 48 | C |
| 49 | C |
| 50 | C |
| 51 | C |
| 52 | C |
| 53 | C |

TABLE 2-continued

| Compound No. | General Synthetic Procedure |
|---|---|
| 54 | C |
| 55 | C |
| 56 | C |
| 57 | C |
| 58 | See Example 6 |
| 59 | C |
| 60 | C |
| 61 | C |
| 62 | C |
| 63 | C |
| 64 | C |
| 65 | C |
| 66 | C |
| 67 | C |
| 68 | C |
| 69 | C |
| 70 | C |
| 71 | C |
| 72 | C |
| 73 | C |
| 74 | C |
| 75 | See Example 7 |
| 76 | C |
| 77 | C |
| 78 | C |
| 79 | C |
| 80 | C |
| 81 | C |
| 82 | C |
| 83 | C |
| 84 | C |
| 85 | C |
| 86 | C |
| 87 | C |
| 88 | C |
| 89 | C |
| 90 | C |
| 91 | C |
| 92 | C |
| 93 | C |
| 94 | C |
| 95 | C |
| 96 | C |
| 97 | C |
| 98 | C |
| 99 | C |
| 100 | C |
| 101 | C |
| 102 | C |
| 103 | C |
| 104 | C |
| 105 | See Example 8 |
| 106 | C |
| 107 | C |
| 108 | C |
| 109 | C |
| 110 | C |
| 111 | C |
| 112 | C |
| 113 | C |
| 114 | C |
| 115 | C |
| 116 | C |
| 117 | C |
| 118 | C |
| 119 | C |
| 120 | C |
| 121 | C |
| 122 | C |
| 123 | C |
| 124 | C |
| 125 | C |
| 126 | C |
| 127 | C |
| 128 | C |
| 129 | C |
| 130 | C |
| 131 | C |
| 132 | C |
| 133 | C |
| 134 | C |
| 135 | C |
| 136 | See Example 9 |
| 137 | C |
| 138 | C |
| 139 | C |
| 140 | C |
| 141 | C |
| 142 | C |
| 143 | C |
| 144 | C |
| 145 | C |
| 146 | C |
| 147 | C |
| 148 | C |
| 149 | C |
| 150 | C |
| 151 | C |
| 152 | C |
| 153 | C |
| 154 | C |
| 155 | C |
| 156 | C |
| 157 | C |
| 158 | C |
| 159 | C |
| 160 | C |
| 161 | C |
| 162 | See Example 10 |
| 163 | C |
| 164 | C |
| 165 | C |
| 166 | See Example 11 |
| 167 | C |
| 168 | C |
| 169 | C |
| 170 | C |
| 171 | C |
| 172 | C |
| 173 | C |
| 174 | C |
| 175 | C |
| 176 | C |
| 177 | C |
| 178 | C |
| 179 | C |
| 180 | C |
| 181 | C |
| 182 | A |
| 183 | C |
| 184 | C |
| 185 | C |
| 186 | C |
| 187 | C |
| 188 | C |
| 189 | C |
| 190 | C |
| 191 | C |
| 192 | C |
| 193 | C |
| 194 | C |
| 195 | C |
| 196 | C |
| 197 | C |
| 198 | C |
| 199 | C |
| 200 | C |
| 201 | C |
| 202 | C |
| 203 | C |
| 204 | C |
| 205 | C |
| 206 | C |
| 207 | C |

TABLE 2-continued

| Compound No. | General Synthetic Procedure |
|---|---|
| 208 | C |
| 209 | C |
| 210 | C |
| 211 | C |
| 212 | C |
| 213 | C |
| 214 | C |
| 215 | C |
| 216 | C |
| 217 | C |
| 218 | C |
| 219 | C |
| 220 | C |
| 221 | C |
| 222 | A |
| 223 | C |
| 224 | C |
| 225 | C |
| 226 | C |
| 227 | C |
| 228 | C |
| 229 | C |
| 230 | C |
| 231 | C |
| 232 | C |
| 233 | C |
| 234 | C |
| 235 | C |
| 236 | C |
| 237 | C |
| 238 | C |
| 239 | C |
| 240 | C |
| 241 | C |
| 242 | C |
| 243 | C |
| 244 | C |
| 245 | See Example 21 |
| 246 | See Example 22 |
| 247 | See Example 14 |
| 248 | See Example 15 |
| 249 | See Example 16 |
| 250 | See Example 17 |
| 251 | See Example 18 |
| 252 | See Example 19 |
| 253 | See Example 20 |

Table 3 below shows data relating to $^1$H NMR and LCMS characterization of the compounds disclosed herein. Note that, in Table 3: the "Compound Number" corresponds to that used in Table 1; "N/A" indicates that data are not available.

TABLE 3

| Compound Number | $^1$H NMR | LCMS (M + H, unless indicated otherwise) |
|---|---|---|
| 1 | N/A | 511.4 |
| 2 | $^1$H NMR (400 MHz, DMSO-d$_6$) δ 14.12 (s, 1H), 8.10 (d, J = 5.9 Hz, 1H), 7.91 (dd, J = 8.0, 1.6 Hz, 1H), 7.51 (s, 1H), 7.27-7.18 (m, 1H), 6.95 (d, J = 2.4 Hz, 1H), 6.90-6.82 (m, 2H), 6.80 (dd, J = 6.0, 2.5 Hz, 1H), 5.98 (s, 2H), 4.58 (t, J = 3.4 Hz, 2H), 3.64 (s, 2H), 3.26 (dd, J = 12.0, 2.3 Hz, 2H), 3.01 (d, J = 11.6 Hz, 2H), 2.62 (d, J = 6.0 Hz, 4H), 2.20 (q, J = 6.2, 5.7 Hz, 2H), 1.97 (dd, J = 8.0, 4.0 Hz, 2H), 1.79-1.68 (m, 4H). | 482.3 |
| 3 | $^1$H NMR (400 MHz, DMSO-d$_6$) δ 14.12 (s, 1H), 8.10 (d, J = 5.9 Hz, 1H), 7.91 (dd, J = 8.0, 1.7 Hz, 1H), 7.51 (s, 1H), 7.22 (ddd, J = 8.4, 7.1, 1.5 Hz, 1H), 6.94 (d, J = 2.4 Hz, 1H), 6.90-6.82 (m, 2H), 6.80 (dd, J = 6.0, 2.5 Hz, 1H), 5.98 (s, 2H), 4.58 (s, 2H), 4.43 (t, J = 5.4 Hz, 1H), 3.53 (s, 2H), 3.50 (q, J = 6.0 Hz, 2H), 3.27 (d, J = 11.9 Hz, 2H), 3.01 (d, J = 11.6 Hz, 2H), 2.55-2.50 (m, 2H), 2.29 (s, 3H), 2.19 (q, J = 6.1, 5.7 Hz, 2H), 1.97 (dd, J = 8.3, 4.0 Hz, 2H). | 486.2 |
| 4 | N/A | 473.2 |
| 5 | $^1$H NMR (400 MHz, DMSO-d$_6$) δ 14.13 (s, 1H), 8.09 (d, J = 5.9 Hz, 1H), 7.91 (dd, J = 8.1, 1.3 Hz, 1H), 7.51 (s, 1H), 7.25-7.20 (m, 1H), 6.94 (d, J = 2.2 Hz, 1H), 6.89-6.78 (m, 3H), 5.99 (s, 2H), 4.58 (s, 2H), 3.62 (s, 2H), 3.27 (br d, J = 11.1 Hz, 2H), 3.01 (br d, J = 11.5 Hz, 2H), 2.56 (q, J = 6.6 Hz, 4H), 2.23-2.16 (m, 2H), 2.00-1.93 (m, 2H), 1.0 (t, J = 7.2 Hz, 6H). | 484.3 |
| 6 | N/A | 454.3 |
| 7 | $^1$H NMR (400 MHz, DMSO-d$_6$) δ 14.12 (s, 1H), 8.11 (d, J = 6.0 Hz, 1H), 7.91 (dd, J = 8.0, 1.6 Hz, 1H), 7.51 (s, 1H), 7.26-7.18 (m, 1H), 6.98 (d, J = 2.4 Hz, 1H), 6.89-6.79 (m, 3H), 5.98 (s, 2H), 4.58 (s, 2H), 4.42 (dd, J = 8.2, 2.9 Hz, 1H), 3.78 (dt, J = 11.3, 3.4 Hz, 1H), 3.48 (ddd, J = 11.6, 6.9, 5.0 Hz, 1H), 3.26 (d, J = 11.9 Hz, 2H), 3.04-2.94 (m, 3H), 2.80-2.63 (m, 3H), 2.20 (q, J = 6.2, 5.8 Hz, 2H), 1.97 (dd, J = 8.1, 4.0 Hz, 2H). | 484.3 |
| 8 | N/A | 482.3 |
| 9 | $^1$H NMR (400 MHz, DMSO-d$_6$) δ 8.33 (d, J = 7.2 Hz, 1H), 7.49-7.61 (m, 3H), 7.19-7.45 (m, 3H), 6.94-7.16 (t, J = 7.2 Hz, 1H), 4.99 (s, 1H), 4.93 (s, 1H), 4.35 (s, 4H), 3.95 (s, 4H), 3.62 (s, 2H), 3.22 (s, 4H), 2.25 (d, J = 7.2 Hz, 2H), 2.02 (s, 2H). | 498.3 |

TABLE 3-continued

| Compound Number | ¹H NMR | LCMS (M + H, unless indicated otherwise) |
|---|---|---|
| 10 | 1H NMR (400 MHz, DMSO-d$_6$) δ 14.12 (s, 1H), 8.10 (d, J = 5.9 Hz, 1H), 7.91 (dd, J = 8.1, 1.7 Hz, 1H), 7.51 (s, 1H), 7.22 (ddd, J = 8.4, 7.1, 1.5 Hz, 1H), 6.98 (d, J = 2.5 Hz, 1H), 6.89-6.84 (m, 2H), 6.81 (dd, J = 6.0, 2.5 Hz, 1H), 5.98 (s, 2H), 4.58 (s, 2H), 4.42 (s, 2H), 3.38 (t, J = 5.5 Hz, 2H), 3.30-3.22 (m, 4H), 3.00 (d, J = 11.6 Hz, 2H), 2.93 (t, J = 5.5 Hz, 2H), 2.24-2.15 (m, 2H), 2.01-1.93 (m, 2H). | 511.3 |
| 11 | ¹H NMR (400 MHz, DMSO-d$_6$) δ 8.07 (d, J = 5.8 Hz, 1H), 7.91 (dd, J = 8.0, 1.6 Hz, 1H), 7.50 (s, 1H), 7.22 (ddd, J = 8.4, 7.1, 1.5 Hz, 1H), 6.91-6.80 (m, 3H), 6.77 (dd, J = 6.0, 2.5 Hz, 1H), 5.98 (s, 2H), 4.56 (s, 2H), 3.30-3.22 (m, 2H), 3.00 (d, J = 11.6 Hz, 2H), 2.62 (t, J = 7.0 Hz, 2H), 2.41 (t, J = 7.0 Hz, 2H), 2.24-2.15 (m, 2H), 1.96 (dd, J = 8.1, 4.1 Hz, 2H), 1.60-1.48 (m, 2H), 1.48-1.37 (m, 4H), 1.36-1.26 (m, 2H). | 498.3 |
| 12 | ¹H NMR (400 MHz, DMSO-d$_6$) δ 14.12 (s, 1H), 8.11 (d, J = 5.9 Hz, 1H), 7.91 (dd, J = 8.2, 1.6 Hz, 1H), 7.51 (s, 1H), 7.27-7.18 (m, 1H), 6.98 (d, J = 2.5 Hz, 1H), 6.90-6.78 (m, 3H), 5.98 (s, 2H), 4.58 (d, J = 4.4 Hz, 2H), 4.40 (s, 2H), 3.47-3.40 (m, 1H), 3.30-3.22 (m, 2H), 3.01 (d, J = 11.7 Hz, 2H), 2.72 (dt, J = 12.7, 4.1 Hz, 1H), 2.43-2.38 (m, 2H), 2.24-2.15 (m, 2H), 2.01-1.93 (m, 4H), 1.71-1.55 (m, 2H), 1.38-1.27 (m, 2H). | 512.3 |
| 13 | ¹H NMR (400 MHz, DMSO-d$_6$) δ 14.12 (s, 1H), 8.08 (d, J = 5.9 Hz, 1H), 7.91 (dd, J = 8.0, 1.6 Hz, 1H), 7.51 (s, 1H), 7.27-7.18 (m, 1H), 6.92 (d, J = 2.5 Hz, 1H), 6.90-6.80 (m, 2H), 6.77 (dd, J = 6.0, 2.5 Hz, 1H), 5.98 (s, 2H), 4.57 (d, J = 4.4 Hz, 2H), 3.26 (dd, J = 11.8, 2.3 Hz, 2H), 2.98 (dd, J = 15.5, 10.7 Hz, 3H), 2.71-2.52 (m, 2H), 2.43 (dd, J = 8.2, 6.4 Hz, 2H), 2.18 (t, J = 6.5 Hz, 2H), 2.01-1.93 (m, 2H), 1.81-1.70 (m, 2H), 1.50 (s, 1H), 1.38-1.21 (m, 2H), 1.16-1.04 (m, 1H). | 496.4 |
| 14 | ¹H NMR (400 MHz, DMSO-d$_6$) δ 14.11 (s, 1H), 8.08 (d, J = 5.9 Hz, 1H), 7.91 (dd, J = 8.0, 1.7 Hz, 1H), 7.51 (s, 1H), 7.26-7.18 (m, 1H), 6.93-6.81 (m, 3H), 6.77 (dd, J = 6.0, 2.5 Hz, 1H), 5.98 (s, 2H), 4.56 (s, 2H), 3.93 (dd, J = 7.5, 5.5 Hz, 1H), 3.26 (d, J = 12.4 Hz, 2H), 3.00 (d, J = 11.4 Hz, 2H), 2.95-2.87 (m, 1H), 2.83-2.72 (m, 1H), 2.24-2.16 (m, 2H), 2.09-1.89 (m, 4H), 1.84-1.60 (m, 2H). | 468.3 |
| 15 | ¹H NMR (400 MHz, DMSO-d$_6$) δ 14.10 (s, 1H), 8.10 (d, J = 5.9 Hz, 1H), 7.90 (dd, J = 8.1, 1.6 Hz, 1H), 7.48 (d, J = 13.4 Hz, 1H), 7.27-7.18 (m, 1H), 6.94 (d, J = 2.5 Hz, 1H), 6.89-6.77 (m, 3H), 5.99 (s, 2H), 4.57 (s, 2H), 3.61 (s, 2H), 3.27 (d, J = 11.7 Hz, 2H), 3.00 (d, J = 11.5 Hz, 2H), 2.87-2.72 (m, 1H), 2.63-2.52 (m, 1H), 2.30-2.10 (m, 3H), 2.06-1.93 (m, 2H), 1.84-1.72 (m, 1H), 1.66-1.55 (m, 1H). | 497.4 |
| 16 | ¹H NMR (400 MHz, DMSO-d$_6$) δ 14.11 (s, 1H), 8.08 (d, J = 5.8 Hz, 1H), 7.91 (dd, J = 8.1, 1.6 Hz, 1H), 7.50 (s, 1H), 7.27-7.18 (m, 1H), 6.94-6.81 (m, 3H), 6.78 (dd, J = 6.0, 2.5 Hz, 1H), 5.98 (s, 2H), 4.56 (s, 2H), 3.49-3.41 (m, 1H), 3.26 (d, J = 12.8 Hz, 2H), 3.00 (d, J = 11.5 Hz, 2H), 2.97-2.89 (m, 1H), 2.88-2.78 (m, 1H), 2.56-2.51 (m, 1H), 2.19 (t, J = 6.6 Hz, 2H), 2.00-1.85 (m, 3H), 1.84-1.60 (m, 2H), 1.53-1.40 (m, 1H), 1.05 (t, J = 7.0 Hz, 1H). | 482.3 |
| 17 | ¹H NMR (400 MHz, DMSO-d$_6$) δ 14.11 (s, 1H), 8.10 (d, J = 6.0 Hz, 1H), 7.90-7.86 (m, 1H), 7.49 (s, 1H), 7.21 (d, J = 8.4 Hz, 1H), 6.98-6.74 (m, 4H), 5.98 (s, 2H), 4.61-4.45 (m, 2H), 3.53-3.42 (m, 1H), 3.30-3.22 (m, 2H), 3.01 (d, J = 11.9 Hz, 2H), 2.43-2.30 (m, 1H), 2.18 (s, 2H), 2.00-1.94 (m, 4H). | 454.3 |
| 18 | ¹H NMR (400 MHz, DMSO-d$_6$) δ 13.95 (s, 1H), 8.18 (d, J = 6.8 Hz, 1H), 7.85 (d, J = 7.9 Hz, 1H), 7.54 (s, 1H), 7.29-7.21 (m, 0H), 7.08-7.01 (m, 1H), 6.96-6.81 (m, 3H), 6.13 (s, 2H), 4.80 (s, 2H), 3.79 (s, 2H), 3.54-3.47 (m, 4H), 3.17 (t, J = 5.2 Hz, 4H), 3.04 (d, J = 8.0 Hz, 6H), 2.30-2.21 (m, 2H), 2.05-1.93 (m, 2H). | 546.2 |
| 19 | 1H NMR (400 MHz, DMSO-d$_6$) δ 14.12 (s, 1H), 8.07 (d, J = 5.8 Hz, 1H), 7.91 (dd, J = 8.0, 1.7 Hz, 1H), 7.51 (s, 1H), 7.27-7.18 (m, 1H), 6.92-6.80 (m, 3H), 6.77 (dd, J = 6.0, 2.5 Hz, 1H), 5.98 (s, 2H), 4.57 (s, 2H), 3.26 (dd, J = 11.9, 2.3 Hz, 2H), 3.04-2.91 (m, 4H), 2.78-2.67 (m, 1H), 2.62 (ddd, J = 12.5, 9.8, 2.9 Hz, 2H), 2.24-2.13 (m, 2H), 2.00-1.92 (m, 2H), 1.82 (dq, J = 12.4, 3.9 Hz, 2H), 1.60-1.46 (m, 2H). | 482.3 |
| 20 | ¹H NMR (400 MHz, DMSO-d$_6$) δ 8.27 (s, 1H), 8.07 (d, J = 5.8 Hz, 1H), 7.89 (dd, J = 8.1, 1.7 Hz, 1H), 7.48 (s, 1H), 7.22 (ddd, J = 8.5, 7.1, 1.5 Hz, 1H), 6.91-6.80 (m, 2H), 6.71-6.63 (m, 2H), 5.98 (s, 2H), 4.53 (s, 2H), 3.28 (dd, J = 12.0, 2.4 Hz, 2H), 3.01 (d, J = 11.5 Hz, 2H), 2.78-2.69 (m, 2H), 2.57 (dd, J = 8.8, 6.6 Hz, 2H), 2.24-2.11 (m, 2H), 1.96 (dd, J = 8.2, 4.0 Hz, 2H), 1.64 (p, J = 7.4, 6.7 Hz, 2H), 1.50 (q, J = 7.3 Hz, 2H), 1.37-1.27 (m, 4H). | 543.4 (M + Na) |
| 21 | ¹H NMR (400 MHz, DMSO-d$_6$) δ 14.12 (s, 1H), 8.12 (d, J = 5.9 Hz, 1H), 8.09 (s, 1H), 7.91 (dd, J = 8.0, 1.7 Hz, 1H), 7.70 (s, 1H), 7.52 (s, 1H), 7.22 (ddd, J = 8.5, 7.2, 1.5 Hz, 1H), 7.01 (d, J = 2.4 Hz, 1H), 6.90-6.77 (m, 3H), 5.98 (s, 2H), 4.59 (s, 2H), 3.87 (s, 3H), 3.28 (d, J = 11.6 Hz, 2H), 3.03 (d, J = 11.6 Hz, 2H), 2.25-2.15 (m, 2H), 2.02-1.95 (m, 2H). | 479.3 |

TABLE 3-continued

| Compound Number | $^1$H NMR | LCMS (M + H, unless indicated otherwise) |
|---|---|---|
| 22 | $^1$H NMR (400 MHz, DMSO-d$_6$) δ 14.12 (s, 1H), 8.08 (d, J = 5.8 Hz, 1H), 7.91 (dd, J = 8.1, 1.6 Hz, 1H), 7.51 (s, 1H), 7.22 (ddd, J = 8.4, 7.1, 1.5 Hz, 1H), 6.91 (s, 1H), 6.89-6.81 (m, 2H), 6.78 (dd, J = 6.1, 2.5 Hz, 1H), 5.98 (s, 2H), 4.57 (s, 2H), 3.81 (dt, J = 11.5, 4.2 Hz, 2H), 3.44 (ddd, J = 11.8, 9.4, 2.7 Hz, 2H), 3.26 (d, J = 11.4 Hz, 2H), 3.00 (d, J = 11.6 Hz, 2H), 2.88 (tt, J = 9.1, 4.0 Hz, 1H), 2.19 (q, J = 6.2, 5.7 Hz, 2H), 2.00-1.93 (m, 2H), 1.88-1.79 (m, 2H), 1.60 (ddt, J = 13.9, 9.4, 4.7 Hz, 2H). | 483.2 |
| 23 | $^1$H NMR (400 MHz, DMSO-d$_6$) δ 14.12 (s, 1H), 8.09 (d, J = 5.9 Hz, 1H), 7.91 (dd, J = 8.1, 1.7 Hz, 1H), 7.51 (s, 1H), 7.27-7.18 (m, 1H), 6.91-6.81 (m, 3H), 6.78 (dd, J = 6.0, 2.5 Hz, 1H), 5.98 (s, 2H), 4.55 (s, 2H), 3.85 (q, J = 6.8 Hz, 1H), 3.26 (d, J = 12.4 Hz, 2H), 3.00 (d, J = 11.5 Hz, 2H), 2.19 (q, J = 6.1, 5.7 Hz, 2H), 2.01-1.91 (m, 2H), 1.31 (d, J = 6.7 Hz, 3H). | 442.2 |
| 24 | $^1$H NMR (400 MHz, DMSO-d$_6$) δ 14.10 (s, 1H), 8.10 (d, J = 5.9 Hz, 1H), 7.91 (dd, J = 7.8, 1.6 Hz, 1H), 7.50 (s, 1H), 7.27-7.18 (m, 1H), 6.93-6.77 (m, 3H), 5.98 (s, 2H), 4.56 (s, 2H), 3.54 (s, 2H), 3.26 (d, J = 11.6 Hz, 2H), 3.01 (d, J = 11.2 Hz, 2H), 2.25-2.15 (m, 2H), 2.01-1.94 (m, 2H). | 428.2 |
| 25 | $^1$H NMR (400 MHz, DMSO-d$_6$) δ 14.02 (s, 1H), 9.68 (s, 1H), 7.87 (d, J = 8.0 Hz, 1H), 7.53 (s, 1H), 7.23 (d, J = 7.7 Hz, 0H), 6.92-6.82 (m, 4H), 6.08 (s, 2H), 4.73 (s, 2H), 3.50 (s, 3H), 3.28-3.17 (m, 4H), 3.01 (d, J = 11.7 Hz, 2H), 2.27-2.21 (m, 2H), 2.01-1.97 (m, 4H). | 468.2 |
| 26 | $^1$H NMR (400 MHz, DMSO-d$_6$) δ 14.11 (s, 1H), 8.08 (d, J = 6.0 Hz, 1H), 7.91 (dd, J = 8.0, 1.6 Hz, 1H), 7.51 (s, 1H), 7.22 (ddd, J = 8.4, 7.1, 1.5 Hz, 1H), 6.92 (d, J = 2.5 Hz, 1H), 6.90-6.81 (m, 2H), 6.78 (dd, J = 6.0, 2.5 Hz, 1H), 5.98 (s, 2H), 4.90 (t, J = 5.5 Hz, 1H), 4.57 (t, J = 3.7 Hz, 2H), 3.58 (td, J = 6.8, 5.5 Hz, 2H), 3.26 (dd, J = 12.0, 2.4 Hz, 2H), 3.00 (d, J = 11.6 Hz, 2H), 2.55 (t, J = 6.8 Hz, 2H), 2.24-2.11 (m, 2H), 1.96 (dd, J = 8.3, 4.1 Hz, 2H). | 443.3 |
| 27 | $^1$H NMR (400 MHz, DMSO-d$_6$) δ 14.12 (s, 1H), 8.07 (d, J = 5.8 Hz, 1H), 7.91 (dd, J = 8.0, 1.7 Hz, 1H), 7.51 (s, 1H), 7.22 (ddd, J = 8.4, 7.1, 1.5 Hz, 1H), 6.90 (d, J = 2.5 Hz, 1H), 6.90-6.82 (m, 2H), 6.77 (dd, J = 6.0, 2.5 Hz, 1H), 5.97 (s, 2H), 4.57 (s, 2H), 4.42 (t, J = 5.2 Hz, 1H), 3.43 (q, J = 5.8 Hz, 2H), 3.26 (d, J = 10.7 Hz, 2H), 3.00 (d, J = 11.6 Hz, 2H), 2.46-2.38 (m, 2H), 2.24-2.13 (m, 2H), 2.00-1.93 (m, 2H), 1.63-1.52 (m, 4H). | 471.2 |
| 28 | N/A | 497.3 |
| 29 | $^1$H NMR (400 MHz, DMSO-d$_6$) δ 14.12 (s, 1H), 8.07 (d, J = 5.9 Hz, 1H), 7.90 (dd, J = 8.0, 1.6 Hz, 1H), 7.50 (s, 1H), 7.27-7.18 (m, 1H), 6.90-6.81 (m, 3H), 6.77 (dd, J = 6.0, 2.5 Hz, 1H), 5.98 (s, 2H), 4.55 (s, 2H), 3.26 (dd, J = 11.9, 2.3 Hz, 2H), 3.03-2.86 (m, 3H), 2.48-2.43 (m, 1H), 2.24-2.14 (m, 2H), 1.97 (dt, J = 22.0, 14.1 Hz, 6H), 1.46 (q, J = 12.4 Hz, 2H), 1.39-1.23 (m, 2H). | 496.3 |
| 30 | $^1$H NMR (400 MHz, DMSO-d$_6$) δ 14.12 (s, 1H), 8.08 (d, J = 5.9 Hz, 1H), 7.91 (dd, J = 8.1, 1.6 Hz, 1H), 7.50 (s, 1H), 7.27-7.18 (m, 1H), 6.93 (d, J = 2.4 Hz, 1H), 6.86 (dd, J = 8.3, 4.1 Hz, 2H), 6.77 (dd, J = 6.0, 2.5 Hz, 1H), 5.98 (s, 2H), 4.56 (s, 2H), 3.26 (d, J = 12.0 Hz, 2H), 3.00 (d, J = 11.5 Hz, 2H), 2.76 (s, 2H), 2.50-2.44 (m, 2H), 2.19 (q, J = 6.1 Hz, 2H), 1.96 (dd, J = 8.2, 4.1 Hz, 2H). | 442.2 |
| 31 | N/A | 511.4 |
| 32 | $^1$H NMR (400 MHz, DMSO-d$_6$) δ 14.12 (s, 1H), 8.07 (d, J = 5.8 Hz, 1H), 7.94-7.84 (m, 2H), 7.50 (s, 1H), 7.22 (ddd, J = 8.5, 7.1, 1.6 Hz, 1H), 6.90-6.79 (m, 2H), 6.70 (d, J = 2.4 Hz, 1H), 6.65 (dd, J = 5.8, 2.4 Hz, 1H), 5.97 (s, 2H), 4.53 (s, 2H), 3.27 (d, J = 11.4 Hz, 3H), 3.17-3.07 (m, 4H), 3.03 (d, J = 11.6 Hz, 2H), 2.58 (t, J = 7.5 Hz, 2H), 2.24-2.11 (m, 2H), 1.97 (dd, J = 8.0, 3.9 Hz, 2H), 1.79 (p, J = 7.2 Hz, 2H). | 489.3 |
| 33 | $^1$H NMR (400 MHz, DMSO-d$_6$) δ 8.06 (d, J = 5.8 Hz, 1H), 7.90 (dd, J = 8.1, 1.6 Hz, 1H), 7.49 (s, 1H), 7.22 (ddd, J = 8.6, 7.2, 1.6 Hz, 1H), 6.90-6.80 (m, 2H), 6.69 (s, 1H), 6.65 (dd, J = 5.8, 2.4 Hz, 1H), 5.97 (s, 2H), 4.53 (s, 2H), 3.36-3.23 (m, 2H), 3.02 (d, J = 11.5 Hz, 2H), 2.58 (t, J = 7.6 Hz, 3H), 2.24-2.15 (m, 2H), 2.01-1.91 (m, 2H), 1.72 (p, J = 7.2 Hz, 2H). | 432.3 |
| 34 | $^1$H NMR (400 MHz, DMSO-d$_6$) δ 14.14 (s, 1H), 8.08 (d, J = 5.8 Hz, 1H), 7.91 (dd, J = 8.0, 1.6 Hz, 1H), 7.51 (s, 1H), 7.27-7.18 (m, 1H), 6.94-6.80 (m, 3H), 6.77 (dd, J = 6.0, 2.5 Hz, 1H), 5.98 (s, 2H), 4.57 (s, 2H), 3.27 (d, J = 11.5 Hz, 2H), 3.07-2.96 (m, 3H), 2.91 (ddd, J = 10.8, 8.2, 5.3 Hz, 1H), 2.81 (dt, J = 10.8, 7.4 Hz, 1H), 2.59 (dd, J = 11.0, 6.3 Hz, 1H), 2.55-2.51 (m, 1H), 2.50-2.43 (m, 2H), 2.32-2.24 (m, 1H), 2.22-2.15 (m, 2H), 2.04-1.84 (m, 3H), 1.47 (ddd, J = 15.0, 12.8, 6.9 Hz, 1H). | 482.3 |
| 35 | N/A | 539.4 |
| 36 | N/A | 456.3 |
| 37 | N/A | 526.2 |
| 38 | N/A | 537.3 |

TABLE 3-continued

| Compound Number | ¹H NMR | LCMS (M + H, unless indicated otherwise) |
|---|---|---|
| 39 | N/A | 536.3 |
| 40 | N/A | 511.3 |
| 41 | N/A | 540.3 |
| 42 | N/A | 526.3 |
| 43 | N/A | 518.3 |
| 44 | N/A | 538.3 |
| 45 | ¹H NMR (400 MHz, DMSO-d₆) δ 14.13 (br s, 1H), 8.09 (d, J = 5.88 Hz, 1H), 7.88-7.94 (m, 1H), 7.51 (s, 1H), 7.19-7.26 (m, 1H), 6.94 (d, J = 2.25 Hz, 1H), 6.82-6.89 (m, 2H), 6.80 (dd, J = 2.38, 6.00 Hz, 1H), 5.98 (s, 2H), 4.58 (br s, 2H), 4.42 (t, J = 5.32 Hz, 1H), 3.46 (s, 2H), 3.27 (br s, 1H), 3.22-3.26 (m, 3H), 3.01 (br d, J = 11.51 Hz, 2H), 2.86 (br d, J = 11.26 Hz, 2H), 2.07-2.23 (m, 4H), 1.90-2.01 (m, 2H), 1.67 (br d, J = 11.01 Hz, 2H), 1.26-1.37 (m, 1H), 1.08-1.19 (m, 2H) | 526.4 |
| 46 | N/A | 512.3 |
| 47 | N/A | 525.3 |
| 48 | N/A | 526.3 |
| 49 | N/A | 538.3 |
| 50 | N/A | 512.3 |
| 51 | N/A | 560.3 |
| 52 | N/A | 498.3 |
| 53 | N/A | 534.3 |
| 54 | N/A | 523.3 |
| 55 | N/A | 526.3 |
| 56 | N/A | 531.3 |
| 57 | N/A | 512.2 |
| 58 | ¹H NMR (400 MHz, Methanol-d₄) δ 8.49 (br s, 1H), 8.11 (br d, J = 6.1 Hz, 1H), 7.75 (br d, J = 7.8 Hz, 1H), 7.51 (s, 1H), 7.25 (br t, J = 7.5 Hz, 1H), 7.10 (s, 1H), 6.98-6.83 (m, 3H), 4.70-4.57 (m, 2H), 3.94 (s, 2H), 3.41 (br d, J = 11.2 Hz, 2H), 3.19-3.04 (m, 6H), 2.37-2.07 (m, 4H), 1.85 (br s, 4H), 1.80-1.62 (m, 4H) | 510.2 |
| 59 | N/A | 526.3 |
| 60 | N/A | 536.3 |
| 61 | N/A | 510.3 |
| 62 | N/A | 512.3 |
| 63 | N/A | 522.2 |
| 64 | N/A | 526.3 |
| 65 | N/A | 512.3 |
| 66 | N/A | 538.4 |
| 67 | N/A | 537.3 |
| 68 | N/A | 494.3 |
| 69 | N/A | 524.3 |
| 70 | N/A | 512.3 |
| 71 | N/A | 512.3 |
| 72 | N/A | 534.3 |
| 73 | N/A | 524.3 |
| 74 | N/A | 510.3 |
| 75 | ¹H NMR (400 MHz, DMSO-d₆) δ 8.09 (d, J = 5.77 Hz, 1H), 7.88-7.94 (m, 1H), 7.51 (s, 1H), 7.18-7.26 (m, 1H), 6.94 (d, J = 2.26 Hz, 1H), 6.77-6.90 (m, 3H), 5.99 (s, 2H), 4.57 (br s, 2H), 3.50-3.59 (m, 2H), 3.27 (br s, 1H), 3.25 (br s, 1H), 3.00 (br d, J = 11.54 Hz, 2H), 2.80 (t, J = 7.28 Hz, 1H), 2.57-2.68 (m, 2H), 2.12-2.24 (m, 4H), 1.90-2.01 (m, 3H), 1.23-1.33 (m, 1H), 0.99 (d, J = 6.53 Hz, 3H) | 496.3 |
| 76 | N/A | 524.3 |
| 77 | N/A | 538.3 |
| 78 | N/A | 538.4 |
| 79 | N/A | 526.3 |
| 80 | N/A | 567.3 |
| 81 | N/A | 524.3 |
| 82 | N/A | 538.3 |
| 83 | N/A | 554.3 |
| 84 | N/A | 544.3 |
| 85 | N/A | 569.4 |
| 86 | N/A | 494.3 |
| 87 | N/A | 494.3 |
| 88 | N/A | 538.3 |
| 89 | ¹H NMR (400 MHz, DMSO-d₆) δ 14.13 (br s, 1H), 8.10 (d, J = 6.02 Hz, 1H), 7.89-7.95 (m, 2H), 7.52 (s, 1H), 7.19-7.25 (m, 1H), 6.97 (d, J = 2.01 Hz, 1H), 6.79-6.88 (m, 3H), 5.99 (s, 2H), 4.58 (br s, 2H), 3.73-3.85 (m, 2H), 3.47-3.63 (m, 3H), 3.27 (br d, J = 11.80 Hz, 3H), 3.12 (dd, J = 3.26, 10.04 Hz, 1H), 3.01 (br d, J = 12.30 Hz, 1H), 2.82 (br d, J = 11.54 Hz, 1H), 2.60 (d, J = 4.77 Hz, 4H), 2.20 (br d, J = 7.28 Hz, 2H), 1.93-2.01 (m, 2H) | 555.3 |
| 90 | N/A | 538.4 |
| 91 | N/A | 508.3 |
| 92 | N/A | 538.4 |

TABLE 3-continued

| Compound Number | ¹H NMR | LCMS (M + H, unless indicated otherwise) |
|---|---|---|
| 93 | N/A | 522.4 |
| 94 | N/A | 522.4 |
| 95 | N/A | 518.3 |
| 96 | N/A | 553.4 |
| 97 | N/A | 526.3 |
| 98 | N/A | 524.3 |
| 99 | N/A | 522.4 |
| 100 | N/A | 538.3 |
| 101 | N/A | 538.4 |
| 102 | N/A | 522.4 |
| 103 | N/A | 538.4 |
| 104 | N/A | 524.4 |
| 105 | ¹H NMR (400 MHz, DMSO-$d_6$) δ 14.07 (br s, 1H), 8.10 (d, J = 6.02 Hz, 1H), 7.88-7.95 (m, 1H), 7.51 (s, 1H), 7.18-7.25 (m, 1H), 6.96 (d, J = 2.26 Hz, 1H), 6.76-6.90 (m, 3H), 5.99 (s, 2H), 5.68 (br s, 1H), 4.58 (br s, 2H), 3.49-3.63 (m, 2H), 3.28 (br s, 1H), 3.25 (br s, 1H), 2.93-3.05 (m, 3H), 2.72-2.77 (m, 2H), 2.65-2.69 (m, 1H), 2.19 (br d, J = 7.28 Hz, 2H), 1.93-2.02 (m, 2H), 1.24-1.32 (m, 1H), 0.84 (t, J = 4.39 Hz, 1H), 0.69 (dd, J = 4.52, 8.78 Hz, 1H) | 510.3 |
| 106 | N/A | 522.4 |
| 107 | N/A | 533.3 |
| 108 | N/A | 537.4 |
| 109 | N/A | 524.3 |
| 110 | N/A | 538.4 |
| 111 | ¹H NMR (400 MHz, DMSO-$d_6$) δ 14.13 (br s, 1H), 8.09 (d, J = 6.02 Hz, 1H), 7.91 (d, J = 6.78 Hz, 1H), 7.51 (s, 1H), 7.18-7.26 (m, 1H), 6.94 (d, J = 2.01 Hz, 1H), 6.82-6.89 (m, 2H), 6.79 (dd, J = 2.38, 5.90 Hz, 1H), 5.99 (s, 2H), 4.57 (br s, 2H), 3.69-3.87 (m, 6H), 3.27 (br s, 1H), 3.24 (br s, 1H), 3.00 (br d, J = 11.54 Hz, 2H), 2.77 (br s, 2H), 2.28-2.36 (m, 1H), 2.19 (br d, J = 7.03 Hz, 2H), 1.91-2.04 (m, 4H), 1.41-1.59 (m, 3H) | 538.2 |
| 112 | N/A | 534.2 |
| 113 | N/A | 524.3 |
| 114 | N/A | 530.3 |
| 115 | N/A | 508.3 |
| 116 | ¹H NMR (400 MHz, DMSO-$d_6$) δ 14.11 (br s, 1H), 8.09 (d, J = 6.02 Hz, 1H), 7.91 (d, J = 6.78 Hz, 1H), 7.51 (s, 1H), 7.19-7.25 (m, 1H), 6.93 (d, J = 2.26 Hz, 1H), 6.78-6.89 (m, 3H), 5.99 (s, 2H), 4.57 (br s, 2H), 3.57 (d, J = 8.78 Hz, 4H), 3.26 (br d, J = 11.04 Hz, 2H), 3.01 (br d, J = 11.54 Hz, 2H), 2.84 (s, 2H), 2.20 (br d, J = 7.28 Hz, 2H), 1.81-2.03 (m, 3H), 1.58 (br s, 2H), 1.37-1.46 (m, 2H) | 524.3 |
| 117 | N/A | 524.3 |
| 118 | N/A | 524.3 |
| 119 | N/A | 526.4 |
| 120 | N/A | 521.3 |
| 121 | ¹H NMR (400 MHz, DMSO-$d_6$) δ 14.18 (br s, 1H), 8.09 (d, J = 5.77 Hz, 1H), 7.91 (d, J = 6.78 Hz, 1H), 7.51 (s, 1H), 7.18-7.26 (m, 1H), 6.94 (d, J = 2.26 Hz, 1H), 6.77-6.89 (m, 3H), 5.99 (s, 2H), 4.57 (br s, 2H), 3.60 (s, 2H), 3.51 (br t, J = 4.52 Hz, 2H), 3.35 (br s, 2H), 3.27 (br s, 1H), 3.25 (br s, 1H), 3.01 (br d, J = 11.54 Hz, 2H), 2.19 (br d, J = 7.03 Hz, 2H), 1.93-2.02 (m, 2H), 1.54-1.77 (m, 4H), 1.25-1.37 (m, 4H) | 538.4 |
| 122 | N/A | 539.4 |
| 123 | N/A | 520.2 |
| 124 | N/A | 524.3 |
| 125 | N/A | 522.4 |
| 126 | N/A | 524.4 |
| 127 | ¹H NMR (400 MHz, DMSO-$d_6$) δ 14.11 (br s, 1H), 8.09 (d, J = 5.60 Hz, 1H), 7.90 (d, J = 6.80 Hz, 1H), 7.51 (s, 1H), 7.22 (t, J = 6.8 Hz, 1H), 6.94 (d, J = 2.26 Hz, 1H), 6.78-6.89 (m, 3H), 5.99 (s, 2H), 4.57 (br s, 2H), 4.29 (s, 1H), 3.54 (s, 2H), 3.15-3.28 (m, 2H), 2.94-3.04 (m, 2H), 2.66 (t, J = 7.03 Hz, 2H), 2.19 (br d, J = 7.03 Hz, 2H), 1.92-2.01 (m, 2H), 1.65 (t, J = 7.03 Hz, 2H), 1.46-1.61 (m, 10H) | 536.4 |
| 128 | N/A | 512.4 |
| 129 | N/A | 522.4 |
| 130 | N/A | 524.3 |
| 131 | N/A | 514.3 |
| 132 | ¹H NMR (400 MHz, DMSO-$d_6$) δ 14.21 (s, 1H), 8.09 (d, J = 5.77 Hz, 1H), 7.91 (d, J = 6.78 Hz, 1H), 7.51 (s, 1H), 7.19-7.25 (m, 1H), 6.95 (d, J = 2.26 Hz, 1H), 6.78-6.89 (m, 3H), 5.99 (s, 2H), 4.57 (br s, 2H), 4.37 (s, 1H), 3.82 (d, J = 7.53 Hz, 1H), 3.53-3.64 (m, 3H), 3.52 (br d, J = 1.76 Hz, 1H), 3.27 (br s, 1H), 3.24 (br s, 1H), 3.00 (br d, J = 11.54 Hz, 1H), 2.80 (dd, J = 1.38, 9.91 Hz, 1H), 2.53-2.58 (m, 1H), 2.19 (br d, J = 7.28 Hz, 2H), 1.93-2.01 (m, 2H), 1.84 (br d, J = 9.79 Hz, 1H), 1.58 (br d, J = 9.79 Hz, 1H) | 510.3 |
| 133 | N/A | 500.3 |
| 134 | N/A | 526.3 |

TABLE 3-continued

| Compound Number | ¹H NMR | LCMS (M + H, unless indicated otherwise) |
|---|---|---|
| 135 | N/A | 496.3 |
| 136 | ¹H NMR (400 MHz, DMSO-$d_6$) δ 14.04 (br s, 1H), 8.10 (d, J = 5.88 Hz, 1H), 7.91 (d, J = 7.25 Hz, 1H), 7.51 (s, 1H), 7.22 (t, J = 7.25 Hz, 1H), 6.95 (d, J = 1.88 Hz, 1H), 6.77-6.89 (m, 3H), 5.99 (s, 2H), 4.57 (br s, 2H), 3.50 (s, 2H), 3.26 (br d, J = 11.2 Hz, 2H), 3.01 (br d, J = 11.51 Hz, 2H), 2.53 (m, 4H), 2.20 (br d, J = 7.13 Hz, 2H), 1.86-2.07 (m, 2H), 1.22-1.51 (m, 4H), 0.25 (s, 4H) | 522.4 |
| 137 | N/A | 524.4 |
| 138 | N/A | 510.4 |
| 139 | N/A | 521.3 |
| 140 | N/A | 538.3 |
| 141 | N/A | 508.3 |
| 142 | N/A | 584.3 |
| 143 | N/A | 544.3 |
| 144 | N/A | 556.3 |
| 145 | N/A | 538.3 |
| 146 | N/A | 523.3 |
| 147 | N/A | 553.4 |
| 148 | N/A | 551.3 |
| 149 | N/A | 520.3 |
| 150 | N/A | 508.4 |
| 151 | N/A | 530.3 |
| 152 | N/A | 507.3 |
| 153 | N/A | 522.3 |
| 154 | N/A | 524.4 |
| 155 | N/A | 522.4 |
| 156 | N/A | 537.4 |
| 157 | N/A | 538.3 |
| 158 | N/A | 532.4 |
| 159 | N/A | 538.3 |
| 160 | N/A | 540.4 |
| 161 | N/A | 510.3 |
| 162 | ¹H NMR (400 MHz, DMSO-$d_6$) δ 14.12 (br s, 1H), 8.10 (d, J = 5.88 Hz, 1H), 7.91 (d, J = 6.88 Hz, 1H), 7.51 (s, 1H), 7.19-7.25 (m, 1H), 6.95 (d, J = 2.13 Hz, 1H), 6.78-6.89 (m, 3H), 5.99 (s, 2H), 4.57 (br s, 2H), 3.81-3.88 (m, 1H), 3.42 (s, 2H), 3.26 (br d, J = 11.2 Hz, 2H), 3.01 (br d, J = 11.51 Hz, 2H), 2.92 (dd, J = 3.25, 7.63 Hz, 1H), 2.69-2.78 (m, 1H), 2.20 (br d, J = 7.13 Hz, 2H), 1.91-2.07 (m, 4H), 1.70-1.79 (m, 1H), 1.61-1.70 (m, 2H), 1.36-1.49 (m, 1H), 1.13-1.25 (m, 1H) | 508.4 |
| 163 | N/A | 539.4 |
| 164 | N/A | 523.3 |
| 165 | N/A | 537.4 |
| 166 | ¹H NMR (400 MHz, Methanol-$d_4$) δ 8.06 (d, J = 6.0 Hz, 1H), 7.73 (br d, J = 7.2 Hz, 1H), 7.48 (s, 1H), 7.23 (t, J = 7.6 Hz, 1H), 7.00 (d, J = 2.4 Hz, 1H), 6.89 (d, J = 7.6 Hz, 1H), 6.81 (dd, J = 6.0, 2.4 Hz, 1H), 4.52 (br s, 2H), 3.50 (s, 2H), 3.36 (br d, J = 10.0 Hz, 2H), 2.26-2.23 (m, 2H), 2.16-2.13 (m, 2H), 1.68-1.63 (m, 4H), 1.50-1.49 (m, 2H) | 496.2 |
| 167 | | 524.4 |
| 168 | | 484.3 |
| 169 | | 512.4 |
| 170 | | 512.5 |
| 171 | | 516.3 |
| 172 | | 482.4 |
| 173 | | 500.4 |
| 174 | | 498.4 |
| 175 | | 538.3 |
| 176 | | 526.2 |
| 177 | | 604.2 |
| 178 | | 524.2 |
| 179 | | 574.5 |
| 180 | | 496.5 |
| 181 | | 546.4 |
| 182 | ¹H NMR (400 MHz, Methanol-$d_4$) δ 8.11 (d, J = 7.6 Hz, 1H), 7.54-7.60 (m, 2H), 7.50 (d, J = 2.4 Hz, 1H), 7.41-7.47 (m, 1H), 7.15 (dd, J = 2.4, 7.2 Hz, 1H), 7.01-7.07 (m, 2H), 3.89 (d, J = 12.4 Hz, 2H), 3.62 (br s, 2H), 3.46 (t, J = 7.2 Hz, 3H), 3.16 (t, J = 7.0 Hz, 3H), 3.05 (br s, 2H), 2.17-2.36 (m, 5H), 1.95 (br s, 5H), 1.85 (br s, 1H), 1.55 (br s, 1H) | 510.3 |

TABLE 3-continued

| Compound Number | ¹H NMR | LCMS (M + H, unless indicated otherwise) |
|---|---|---|
| 183 | | 630.2 |
| 184 | | 482.3 |
| 185 | | 524.2 |
| 186 | ¹H NMR (400 MHz, DMSO-d₆) δ 14.07 (s, 1H), 8.11 (d, J = 5.8 Hz, 1H), 7.91 (dd, J = 8.1, 1.6 Hz, 1H), 7.51 (s, 1H), 7.28-7.18 (m, 1H), 6.97 (d, J = 2.4 Hz, 1H), 6.92-6.77 (m, 3H), 5.98 (s, 2H), 4.58 (s, 2H), 3.54-3.37 (m, 3H), 3.28 (d, J = 2.4 Hz, 1H), 3.25 (s, 7H), 3.21-3.06 (m, 1H), 3.02 (d, J = 11.6 Hz, 2H), 2.24-2.15 (m, 2H), 2.04-1.89 (m, 3H), 1.88-1.77 (m, 1H) | 512.4 |
| 187 | | 496.3 |
| 188 | | 553.2 |
| 189 | | 546.3 |
| 190 | ¹H NMR (400 MHz, DMSO-d₆) δ 14.10 (s, 1H), 8.09 (d, J = 5.9 Hz, 1H), 7.91 (dd, J = 8.0, 1.6 Hz, 1H), 7.51 (s, 1H), 7.27-7.18 (m, 1H), 6.93 (d, J = 2.4 Hz, 1H), 6.90-6.80 (m, 2H), 6.79 (dd, J = 6.0, 2.5 Hz, 1H), 5.98 (s, 2H), 4.57 (s, 2H), 3.67 (s, 1H), 3.55 (s, 2H), 3.26 (d, J = 11.8 Hz, 2H), 3.01 (d, J = 11.6 Hz, 2H), 2.82-2.72 (m, 2H), 2.66-2.52 (m, 2H), 2.24-2.15 (m, 2H), 2.01-1.93 (m, 2H), 1.85-1.60 (m, 3H), 1.39 (ddt, J = 14.3, 7.0, 3.7 Hz, 1H), 0.99-0.87 (m, 4H). | 540.3 |
| 191 | | 526.3 |
| 192 | | 524.3 |
| 193 | | 528.3 |
| 194 | | 528.2 |
| 195 | | 538.3 |
| 196 | | 540.5 |
| 197 | | 554.3 |
| 198 | | 538.3 |
| 199 | | 564.3 |
| 200 | ¹H NMR (400 MHz, Methanol-d₄) δ 8.07 (d, J = 6.0 Hz, 1H), 7.74 (d, J = 8.0 Hz, 1H), 7.49 (s, 1H), 7.23 (t, J = 7.6 Hz, 1H), 7.01 (d, J = 2.4, Hz, 1H), 6.92-6.84 (m, 2H), 6.82 (d, J = 4.0 Hz), 4.59 (br s, 2H), 3.66 (s, 2H), 3.37 (d, J = 10.4 Hz, 2H), 3.09 (d, J = 11.6 Hz, 2H), 2.90-2.78 (m, 4H), 2.28-2.24 (m, 1H), 2.17-2.08 (m, 2H), 1.86-1.63 (m, 5H), 1.55-1.42 (m, 1H), 1.35-1.26 (m, 2H), 0.95 (d, J = 6.4 Hz, 3H). | 524.4 |
| 201 | | 524.3 |
| 202 | 1H NMR (400 MHz, DMSO-d₆) δ 14.04 (s, 1H), 8.05 (d, J = 5.9 Hz, 1H), 7.90 (dd, J = 8.1, 1.6 Hz, 1H), 7.49 (s, 1H), 7.27-7.16 (m, 1H), 7.15-7.05 (m, 4H), 6.93-6.80 (m, 3H), 6.77 (dd, J = 6.0, 2.4 Hz, 1H), 5.97 (s, 2H), 4.54 (s, 2H), 3.64 (s, 2H), 3.24 (d, J = 11.9 Hz, 2H), 2.98 (d, J = 11.6 Hz, 2H), 2.88 (dd, J = 6.6, 3.6 Hz, 4H), 2.67 (t, J = 4.4 Hz, 4H), 2.23-2.13 (m, 2H), 1.95 (dd, J = 8.0, 3.9 Hz, 2H). | 558.5 |
| 203 | | 548.3 |
| 204 | | 588.3 |
| 205 | ¹H NMR (400 MHz, Methanol-d₄) δ 8.06 (d, J = 6.0 Hz, 1H), 7.74 (d, J = 7.6 Hz, 1H), 7.49 (s, 1H), 7.24 (t, J = 6.3 Hz, 1H), 7.00 (d, J = 2.4, Hz, 1H), 6.91-6.85 (m, 2H), 6.81 (d, J = 4.0 Hz), 4.62-4.46 (m, 2H), 3.58 (s, 2H), 3.36 (d, J = 11.6 Hz, 2H), 3.09 (d, J = 11.6 Hz, 2H), 2.79 (t, J = 5.4 Hz, 2H), 2.73 (t, J = 5.2 Hz, 2H), 2.27-2.24 (m, 2H), 2.17-2.11 (m, 2H), 1.68-1.58 (m, 4H), 1.52-1.45 (m, 2H), 0.94 (s, 6H). | 538.3 |
| 206 | | 585.3 |
| 207 | | 570.3 |
| 208 | | 572.3 |
| 209 | | 578.2 |
| 210 | | 570.3 |
| 211 | | 554.3 |
| 212 | | 560.4 |
| 213 | | 554.3 |
| 214 | | 540.3 |
| 215 | | 540.4 |
| 216 | | 540.4 |
| 217 | | 538.3 |
| 218 | | 536.3 |
| 219 | | 540.3 |
| 220 | | 534.2 |
| 221 | | 522.2 |
| 222 | ¹H NMR (400 MHz, Methanol-d₄) δ 8.11 (br s, 1H), 7.76 (d, J = 7.9 Hz, 1H), 7.51 (s, 1H), 7.25 (t, J = 7.3 Hz, 1H), 7.03 (s, 1H), 6.97-6.80 (m, 3H), 4.62 (s, 2H), 3.43-3.37 (m, 2H), 3.31-3.25 (m, 4H), 3.14-3.07 (m, 2H), 2.93 (t, J = 6.6 Hz, 2H), 2.30 (br d, J = 7.0 Hz, 2H), 2.25-2.11 (m, 2H), 1.91 (br s, 5H), 1.74 (br s, 5H) | 524.3 |
| 223 | | 504.4 |
| 224 | | 512.4 |
| 225 | | 526.4 |
| 226 | ¹H NMR (400 MHz, DMSO-d₆) δ 14.07 (s, 1H), 8.10 (d, J = 5.9 Hz, 1H), 7.90 (dd, J = 8.0, 1.6 Hz, 1H), 7.51 (s, 1H), 7.28-7.20 (m, 3H), | 560.4 |

TABLE 3-continued

| Compound Number | ¹H NMR | LCMS (M + H, unless indicated otherwise) |
|---|---|---|
| | 6.98-6.90 (m, 2H), 6.89-6.78 (m, 5H), 5.98 (s, 2H), 4.79 (p, J = 5.6 Hz, 1H), 4.56 (s, 2H), 3.76 (td, J = 6.1, 1.9 Hz, 2H), 3.56 (s, 2H), 3.30-3.21 (m, 4H), 3.01 (d, J = 11.6 Hz, 2H), 2.20 (q, J = 6.1, 5.6 Hz, 2H), 1.97 (dd, J = 8.1, 3.6 Hz, 2H) | |
| 227 | ¹H NMR (400 MHz, DMSO-d₆) δ 14.05 (br s, 1H), 8.13 (d, J = 6.0, 1H), 7.90 (dd, J = 1.1, 8.0 Hz, 1H), 7.51 (s, 1H), 7.22 (t, J = 6.8 Hz, 1H), 7.05-7.16 (m, 1H), 6.80-6.93 (m, 3H), 6.03 (s, 2H), 4.63 (br s, 2H), 3.98-4.21 (m, 2H), 3.58 (dd, J = 1.9, 7.2 Hz, 3H), 3.51-3.55 (m, 2H), 3.26-3.33 (m, 2H), 3.07 (s, 1H), 2.91-3.05 (m, 4H), 2.17-2.24 (m, 2H), 1.93-2.06 (m, 2H) | 546.3 |
| 228 | | 586.4 |
| 229 | | 553.5 |
| 230 | | 536.5 |
| 231 | | 546.4 |
| 232 | ¹H NMR (400 MHz, DMSO-d₆) δ 14.05 (br s, 1H), 8.15 (d, J = 6.3 Hz, 1H), 7.89 (dd, J = 1.2, 7.9 Hz, 1H), 7.52 (s, 1H), 7.18-7.29 (m, 1H), 7.09 (s, 1H), 6.78-6.99 (m, 3H), 6.05 (s, 2H), 4.67 (s, 2H), 3.45-3.60 (m, 4H), 3.35-3.38 (m, 3H), 3.30 (br s, 2H), 3.02 (d, J = 11.5 Hz, 2H), 2.23 (br d, J = 7.3 Hz, 2H), 1.93-2.03 (m, 2H) | 536.3 |
| 233 | | 494.4 |
| 234 | | 544.4 |
| 235 | | 508.4 |
| 236 | | 601.5 |
| 237 | | 569.4 |
| 238 | | 526.4 |
| 239 | ¹H NMR (400 MHz, DMSO-d₆) δ 14.13 (br s, 1H), 8.12 (d, J = 6.0 Hz, 1H), 7.90 (dd, J = 1.3, 8.0 Hz, 1H), 7.51 (s, 1H), 7.18-7.27 (m, 1H), 7.00 (s, 1H), 6.80-6.92 (m, 3H), 6.01 (s, 2H), 4.59 (s, 2H), 3.59-4.32 (m, 3H), 3.27 (d, J = 11.5 Hz, 3H), 3.15 (br s, 1H), 3.00 (d, J = 11.8 Hz, 3H), 2.21 (br d, J = 7.3 Hz, 2H), 1.93-2.05 (m, 2H), 1.71-1.92 (m, 3H), 1.47-1.59 (m, 1H), 1.39 (br s, 1H), 1.06-1.15 (m, 3H), 0.88 (d, J = 6.8 Hz, 3H) | 554.5 |
| 240 | | 540.4 |
| 241 | | 558.4 |
| 242 | | 526.4 |
| 243 | | 542.4 |
| 244 | | 540.4 |
| 245 | ¹H NMR (400 MHz, CDCl₃): δ 8.22 (s, 1H), 7.55 (d, J = 8.0 Hz, 1H), 7.29-7.26 (m, 2H) 7.03 (d, J = 8.4 Hz, 1H), 6.88 (t, J = 7.2 Hz, 1H), 6.41 (d, J = 5.6 Hz, 1H), 4.90-4.70 (m, 4H), 3.72 (s, 2H), 3.37-3.41 (m, 2H), 3.17-3.00 (m, 2H), 2.95-2.77 (m, 4H), 2.26-2.00 (m, 4H), 1.75-1.63 (m, 8H) | 511.1 |
| 246 | ¹H NMR (400 MHz, DMSO-d₆): δ 8.90 (s, 1H), 7.89 (d, J = 8.0 Hz, 1H), 7.54 (s, 1H), 7.22 (t, J = 7.6 Hz, 1H), 7.08 (d, J = 2.4 Hz, 1H), 6.93-6.80 (m, 2H), 6.02 (s, 2H), 4.72 (s, 2H), 3.62 (s, 2H), 3.25 (s, 2H), 3.02 (d, J = 12.0 Hz, 2H), 2.70-2.66 (m, 4H), 2.23 (d, J = 7.2 Hz, 2H), 2.02-1.93 (m, 2H), 1.65-1.52 (m, 8H) | 511.1 |
| 247 | ¹H NMR (400 MHz, DMSO-d₆): δ 8.45 (s, 1H), 8.16 (s, 1H), 7.92 (d, J = 8.0 Hz, 1H), 7.55 (s, 1H), 7.27-7.18 (m, 1H), 6.95 (s, 1H), 6.89-6.82 (m, 2H), 6.03 (s, 2H), 5.06-4.60 (m, 2H), 3.59 (s, 2H), 3.27-3.26 (m, 2H), 3.01-2.98 (m, 2H), 2.67-2.66 (m, 4H), 2.24-2.20 (m, 2H), 2.00-1.91 (m, 2H), 1.64-1.52 (m, 8H) | 511.1 |
| 248 | ¹H NMR (400 MHz, MeOD): δ 8.39 (s, 1H), 8.14 (d, J = 6.4 Hz, 1H), 7.72 (dd, J = 8.0, 1.2 Hz, 1H), 7.49 (s, 1H), 7.26-7.21 (m, 1H), 7.04 (d, J = 2.4 Hz, 1H), 6.90-6.80 (m, 3H), 6.75-6.69 (m, 1H), 4.70 (s, 2H), 3.92 (d, J = 6.8 Hz, 2H), 3.44 (d, J = 10.8 Hz, 2H), 3.30-3.29 (m, 4H), 3.11 (d, J = 11.6 Hz, 2H), 2.36-2.29 (m, 2H), 2.19-2.17 (m, 2H), 1.94-1.88 (m, 4H), 1.76-1.75 (m, 4H) | 512.1 |
| 249 | ¹H NMR (400 MHz, MeOD): δ 8.48-8.41 (m, 1H) 8.10-8.05 (m, 1H) 7.83-7.78 (m, 1H) 7.57 (s, 1H) 7.30-7.25 (m, 1H) 7.09-7.06 (m, 1H) 6.96 (s, 2H) 6.92-6.88 (m, 1H) 3.93 (s, 2H) 3.58-3.50 (m, 4H) 3.24-3.18 (m, 4H) 3.15-3.09 (m, 4H) 1.90-1.81 (m, 8H) 1.79-1.70 (m, 8H). LCMS (ESI) | 552.2 |
| 250 | ¹H NMR (CDCl₃, 400 MHz): δ 8.20-8.18 (d, 1H), 7.62-7.60 (d, 1H), 7.38 (s, 1H), 7.32-7.30 (m, 1H), 7.08-7.06 (d, 1H), 6.93-6.89 (t, 1H), 6.60 (s, 1H), 6.36-6.35 (m, 1H), 4.86 (s, 2H), 3.65 (s, 2H), 3.40-3.37 (t, 2H), 3.21 (s, 2H), 3.16-3.13 (m, 2H), 3.05-3.02 (m, 2H), 2.86-2.84 (m, 4H), 1.98-1.94 (t, 2H), 1.82-1.76 (m, 4H), 1.75-1.66 (m, 4H), 1.63-1.52 (m, 4H) | 538.4 |
| 251 | ¹H NMR (400 MHz, MeOD): δ 8.10-8.08 (d, 1H, J = 8.0 Hz), 7.73-7.71 (d, 1H, J = 8.0 Hz), 7.31-7.29 (t, 1H, J = 8.0 Hz), 6.96-6.92 (m, 3H), 6.66-6.65 (d, 1H, J = 4.0 Hz), 6.50-6.48 (m, 1H), 4.51 (s, 4H), 4.31 (s, 4H), 4.04 (s, 2H), 3.21-3.18 (m, 4H,), 1.86 (m, 4H), 1.74 (m, 4H) | 496.1 |
| 252 | ¹H NMR (400 MHz, DMSO-d₆): δ 14.7 (s, 1H), 8.14 (d, J = 6.0 Hz, 1H), 7.94 (d, J = 7.6 Hz, 1H), 7.38 (d, J = 3.2 Hz, 1H), 7.31 (s, 1H), 7.21 (t, 1H), 7.04 (s, 1H), 6.92 (d, J = 6.0 Hz, 1H), 6.88-6.86 (m, 2H), | 496.2 |

TABLE 3-continued

| Compound Number | $^1$H NMR | LCMS (M + H, unless indicated otherwise) |
|---|---|---|
|  | 4.14 (q, J = 11.6 Hz, 3H), 3.63-3.60 (m, 1H), 3.56 (s, 2H), 3.40-3.19 (m, 2H), 3.10-3.04 (m, 2H), 2.69-2.60 (m, 5H), 1.70-1.50 (m, 8H) |  |
| 253 | $^1$H NMR (400 MHz, DMSO-d$_6$): δ 14.7 (s, 1H), 8.14 (d, J = 6.0 Hz, 1H), 7.94 (d, J = 7.6 Hz, 1H), 7.38 (d, J = 3.2 Hz, 1H), 7.31 (s, 1H), 7.21 (t, 1H), 7.04 (s, 1H), 6.92 (d, J = 6.0 Hz, 1H), 6.88-6.86 (m, 2H), 4.14 (q, J = 11.6 Hz, 3H), 3.63-3.60 (m, 1H), 3.56 (s, 2H), 3.40-3.19 (m, 2H), 3.10-3.04 (m, 2H), 2.69-2.60 (m, 5H), 1.70-1.50 (m, 8H) | 496.2 |

Biological Assays

Example B-1: HiBIT Nanoluciferase Complementation Screen for BRM Degraders

To assess BRM degradation, compounds were screened for their effect of BRM levels using the HiBIT nanoluciferase complementation strategy developed at Promega. In brief, a HELA cell line that was genetically modified via CRISPR/CAS9 was used to fuse the HiBIT sequence at the 3' end of BRM (BRM-HiBIT KI Hela). BRM protein levels were then detected using the Nano-Glo HiBIT lytic detection reagent (Promega).

The screened compounds were plated into a white 384-well plate at 10 µM and 1 µM in 25 nL DMSO using an Echo dispenser (Labcyte). BRM-HiBIT KI Hela cells were seeded in the compound plate at 5000 cell per well at 25 µl in DMEM growth media (containing 10% FBS, 1% Glutamax (GIBCO cat #31053-028), 1× Penicillin-Streptomycin (ROCHE, cat #1107444001), 4.5 g/L D-Glucose, and no phenol red). After incubation with compounds for 18 hours at 37° C., cell viability was assessed by the addition of 5 µl Cell Titer-Fluor reagent (Promega). After 30 s of mixing on an orbital shaker, and 30 minutes incubation at 37° C., fluorescence was measured with an INFINITE F500 (Tecan) (380-400 nM excitation, 505 nM emission). Next, to assess BRM HiBIT levels, 30 µl of Nano-Glo HiBIT lytic detection reagent (Promega) containing 1:50 Nano-Glo HiBIT lytic substrate and 1:100 LgBIT protein per ml of lytic buffer was added. After shaking on an orbital shaker at 350 rpm for 10 minutes, luminescence was measured on the INFINITE F500 (Tecan). To assess compound effects, luminescence signal was normalized with the mean of wells treated with DMSO only set to 0% and the mean of wells containing no cells set to −100%. Data for compounds disclosed herein are shown in Table 4 below. Note that, in Table 4, the "Compound Number" corresponds to that used in Table 1.

TABLE 4

| Compound Number | Median HiBiT activity 1 µM | Median HiBiT activity 10 µM |
|---|---|---|
| 1 | −87.0122 | −81.2914 |
| 2 | −73.6048 | −28.0898 |
| 3 | −68.4262 | −39.6172 |
| 4 | −65.5436 | −51.5968 |
| 5 | −63.6385 | −31.0597 |
| 6 | −61.1458 | −67.7912 |
| 7 | −56.5569 | −25.5864 |
| 8 | −51.6794 | −23.8415 |
| 9 | −50.6553 | −33.5251 |
| 10 | −50.554 | −56.7556 |
| 11 | −46.2503 | −53.1423 |
| 12 | −45.7932 | −34.0604 |
| 13 | −44.9864 | −32.1865 |
| 14 | −42.9269 | −50.5501 |
| 15 | −41.5313 | −55.0083 |
| 16 | −38.7074 | −29.4258 |
| 17 | −37.0864 | −51.9890 |
| 18 | −37.0807 | −56.4043 |
| 19 | −36.9943 | −56.3342 |
| 20 | −33.3403 | −8.90957 |
| 21 | −32.7297 | −42.1813 |
| 22 | −30.6701 | −33.6373 |
| 23 | −29.3818 | −58.9213 |
| 24 | −27.1137 | −43.5174 |
| 25 | −26.7344 | −55.1975 |
| 26 | −25.9348 | −28.4202 |
| 27 | −23.7734 | −28.4819 |
| 28 | −23.3156 | −44.9026 |
| 29 | −22.4859 | −33.4085 |
| 30 | −18.8155 | −47.5549 |
| 31 | −16.7799 | −47.9900 |
| 32 | −16.4623 | −30.3732 |
| 33 | −14.8996 | −55.0132 |
| 34 | −7.21674 | −29.4355 |

Example B-2: Immunofluorescence Assay for BRM and BRG1 Degraders

SW1573 cells were seeded at 3000 cells/well in 384 well plates. The next day, compounds were added using an Echo dispenser. After 20 hours of incubation with compound, cells were fixed with 4% formaldehyde then permeabilized with 0.2% Triton X-100 and blocked with 10% FCS. Fixed and permeabilized cells were treated overnight at 4° C. with either BRM primary antibody (Cell signaling Cat #11966) or BRG primary antibody (Abcam, ab110641). Finally, cells were treated with fluorescently labeled secondary antibodies for 1 hr (Donkey anti-Rabbit IgG AF488, Life Technologies, A21206) and Hoechst nuclear stain (#H3569) was added for 30 minutes. Cells were washed with PBS in between each step and before imaging on an Opera Phenix microscope (Perkin Elmer). Harmony software (Perking Elmer) was used to quantify the mean nuclear signaling intensity of BRM or BRG signaling per cell in each well. Dose responses were determined from the concentration dependent response of mean nuclear signal intensity with data normalized to a known degrader control. Dose response curves were fit to a floating maximum to allow for calculation of the $D_{max}$.

Data for compounds disclosed herein are shown in Table 5 below. Note that, in Table 5, the "Compound Number" corresponds to that used in Table 1. In Table 5, for BRM and BRG1 IF degradation IC$_{50}$ (µM): A indicates <0.010 µM, B indicates 0.010-0.10 µM, and C indicates >0.10 µM; and for BRM and BRG1 IF degradation $S_{inf}$ % D indicates 0--30%, E indicates -30%--70%, F indicates -71%--120% and ND indicates the value was not determined.

TABLE 5

| Compound Number | BRM IF Degradation IC$_{50}$ (μM) | BRM IF Degradation S$_{inf}$ (%) | BRG1 IF Degradation IC$_{50}$ (μM) | BRG1 IF Degradation S$_{inf}$ (%) |
|---|---|---|---|---|
| 1 | B | F | C | F |
| 2 | A | E | A | E |
| 3 | B | E | B | E |
| 4 | B | E | B | D |
| 5 | A | E | A | E |
| 6 | B | E | C | D |
| 7 | A | E | C | ND |
| 8 | B | E | C | ND |
| 9 | B | E | A | D |
| 10 | B | E | C | ND |
| 11 | B | F | B | E |
| 12 | B | E | B | D |
| 13 | B | E | B | D |
| 14 | A | E | B | D |
| 15 | C | E | C | D |
| 16 | B | E | B | D |
| 17 | B | E | B | D |
| 18 | C | E | C | ND |
| 19 | B | E | C | E |
| 20 | B | F | B | F |
| 21 | C | ND | B | D |
| 22 | C | ND | C | D |
| 23 | A | E | B | E |
| 24 | B | E | C | ND |
| 25 | C | E | C | ND |
| 26 | C | ND | C | ND |
| 27 | C | D | C | ND |
| 28 | C | E | C | ND |
| 29 | C | ND | C | ND |
| 30 | C | E | C | D |
| 31 | C | ND | C | ND |
| 32 | B | E | B | D |
| 33 | C | E | C | E |
| 34 | C | ND | ND | ND |
| 35 | C | E | C | ND |
| 36 | B | E | B | E |
| 37 | B | E | A | E |
| 38 | B | E | C | ND |
| 39 | A | F | A | E |
| 40 | C | E | C | ND |
| 41 | B | E | B | E |
| 42 | B | E | B | E |
| 43 | B | E | A | D |
| 44 | A | E | B | E |
| 45 | B | E | B | E |
| 46 | A | E | B | E |
| 47 | C | E | C | D |
| 48 | B | E | B | D |
| 49 | A | F | A | E |
| 50 | B | E | C | E |
| 51 | C | E | C | E |
| 52 | B | E | B | E |
| 53 | B | E | B | D |
| 54 | C | F | C | E |
| 55 | B | E | B | E |
| 56 | B | E | C | D |
| 57 | B | E | C | ND |
| 58 | A | F | A | E |
| 59 | B | E | A | D |
| 60 | A | E | A | E |
| 61 | A | E | A | E |
| 62 | A | E | A | E |
| 63 | A | F | A | E |
| 64 | B | E | B | D |
| 65 | A | E | B | D |
| 66 | A | F | B | E |
| 67 | B | E | A | D |
| 68 | A | F | A | E |
| 69 | A | F | A | E |
| 70 | A | E | A | E |
| 71 | B | E | A | E |
| 72 | B | E | C | ND |
| 73 | C | E | C | ND |
| 74 | B | E | C | ND |
| 75 | A | E | A | E |
| 76 | A | E | A | D |
| 77 | B | E | C | ND |
| 78 | A | E | C | ND |
| 79 | B | E | C | ND |
| 80 | B | E | A | D |
| 81 | A | E | A | E |
| 82 | A | E | A | E |
| 83 | C | E | B | E |
| 84 | A | E | C | ND |
| 85 | C | E | C | ND |
| 86 | A | E | A | E |
| 87 | A | E | A | E |
| 88 | A | E | A | D |
| 89 | B | E | C | ND |
| 90 | B | E | B | D |
| 91 | A | E | A | E |
| 92 | A | F | A | E |
| 93 | A | E | C | ND |
| 94 | A | E | A | E |
| 95 | A | E | A | E |
| 96 | C | E | B | D |
| 97 | A | F | A | E |
| 98 | B | E | C | ND |
| 99 | A | E | A | E |
| 100 | A | E | A | E |
| 101 | B | E | C | ND |
| 102 | A | E | A | E |
| 103 | A | E | C | E |
| 104 | A | E | A | D |
| 105 | B | E | B | D |
| 106 | A | E | A | E |
| 107 | B | E | B | D |
| 108 | C | E | C | ND |
| 109 | A | E | A | E |
| 110 | A | E | C | ND |
| 111 | A | E | A | D |
| 112 | A | E | B | D |
| 113 | B | E | A | D |
| 114 | B | E | C | ND |
| 115 | A | E | A | E |
| 116 | B | E | A | D |
| 117 | B | E | B | D |
| 118 | B | E | A | E |
| 119 | C | E | C | ND |
| 120 | B | E | B | E |
| 121 | A | E | C | E |
| 122 | B | F | B | E |
| 123 | A | E | A | E |
| 124 | A | E | C | ND |
| 125 | A | E | A | E |
| 126 | A | E | A | D |
| 127 | A | E | A | E |
| 128 | B | F | A | E |
| 129 | A | E | A | E |
| 130 | A | E | B | E |
| 131 | A | E | A | D |
| 132 | A | E | A | E |
| 133 | A | E | A | D |
| 134 | B | E | B | E |
| 135 | A | E | A | E |
| 136 | A | E | A | E |
| 137 | A | E | A | E |
| 138 | B | E | A | E |
| 139 | A | E | B | D |
| 140 | A | F | A | E |
| 141 | A | E | A | E |
| 142 | B | E | B | E |
| 143 | A | E | A | E |
| 144 | C | E | B | D |
| 145 | A | E | A | D |
| 146 | C | E | C | E |
| 147 | C | E | C | E |

TABLE 5-continued

| Compound Number | BRM IF Degradation IC$_{50}$ (μM) | BRM IF Degradation S$_{inf}$ (%) | BRG1 IF Degradation IC$_{50}$ (μM) | BRG1 IF Degradation S$_{inf}$ (%) |
|---|---|---|---|---|
| 148 | B | E | C | E |
| 149 | B | E | B | D |
| 150 | A | F | A | E |
| 151 | A | E | A | D |
| 152 | A | E | A | E |
| 153 | A | E | A | D |
| 154 | A | F | A | E |
| 155 | A | E | A | E |
| 156 | C | E | C | E |
| 157 | B | E | B | E |
| 158 | A | F | A | E |
| 159 | A | E | A | E |
| 160 | B | E | B | D |
| 161 | A | E | B | E |
| 162 | A | F | A | E |
| 163 | B | E | C | E |
| 164 | B | E | C | D |
| 165 | C | E | C | ND |
| 166 | A | E | C | ND |
| 167 | A | F | A | F |
| 168 | B | F | B | E |
| 169 | A | E | B | E |
| 170 | B | E | C | E |
| 171 | C | E | C | ND |
| 172 | A | E | B | F |
| 173 | B | F | B | E |
| 174 | B | F | B | E |
| 175 | A | E | A | E |
| 176 | B | E | C | ND |
| 177 | B | E | B | E |
| 178 | B | F | A | E |
| 179 | B | F | B | E |
| 180 | A | E | A | E |
| 181 | B | F | B | E |
| 182 | C | F | ND | ND |
| 183 | C | E | C | ND |
| 184 | A | E | A | E |
| 185 | C | F | B | E |
| 186 | A | E | B | E |
| 187 | A | E | A | E |
| 188 | C | E | C | ND |
| 189 | A | F | A | E |
| 190 | A | F | A | E |
| 191 | A | F | A | F |
| 192 | A | F | A | F |
| 193 | A | F | A | F |
| 194 | A | F | A | E |
| 195 | A | F | A | E |
| 196 | A | F | A | F |
| 197 | A | F | A | E |
| 198 | A | E | ND | ND |
| 199 | A | F | B | E |
| 200 | A | F | A | F |
| 201 | A | F | A | E |
| 202 | B | E | B | E |
| 203 | B | E | C | ND |
| 204 | B | E | ND | ND |
| 205 | A | F | A | E |
| 206 | B | E | C | ND |
| 207 | B | E | C | F |
| 208 | A | E | A | E |
| 209 | A | F | A | E |
| 210 | C | E | C | ND |
| 211 | B | E | B | E |
| 212 | A | F | A | F |
| 213 | B | E | ND | ND |
| 214 | A | F | A | E |
| 215 | A | F | B | F |
| 216 | A | F | A | F |
| 217 | B | E | B | E |
| 218 | A | F | A | E |
| 219 | A | F | A | F |
| 220 | C | E | ND | ND |
| 221 | A | E | A | E |
| 222 | A | F | A | F |
| 223 | B | E | A | E |
| 224 | A | E | A | E |
| 225 | B | E | A | D |
| 226 | B | E | A | E |
| 227 | C | E | C | ND |
| 228 | A | E | A | D |
| 229 | B | F | B | E |
| 230 | B | E | B | E |
| 231 | A | E | A | E |
| 232 | B | E | A | E |
| 233 | A | E | A | E |
| 234 | B | E | B | F |
| 235 | B | F | A | E |
| 236 | C | F | B | D |
| 237 | B | E | B | E |
| 238 | B | E | A | E |
| 239 | A | E | A | E |
| 240 | B | F | B | E |
| 241 | B | E | A | D |
| 242 | A | F | A | E |
| 243 | B | F | A | E |
| 244 | B | E | A | E |
| 245 | A | F | A | E |
| 246 | B | F | A | F |
| 247 | A | F | A | F |
| 248 | A | E | ND | ND |
| 249 | A | E | C | ND |
| 250 | A | E | B | E |
| 251 | A | E | B | E |
| 252 | A | F | A | F |
| 253 | A | F | A | F |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A compound of formula (IV'),

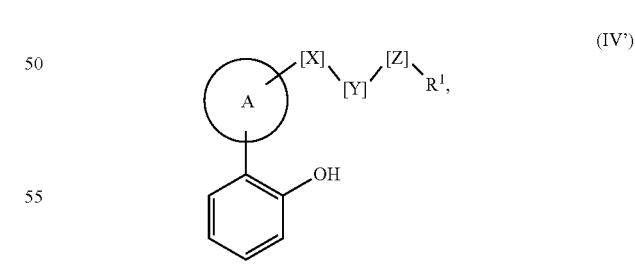

or a stereoisomer or tautomer thereof, or a pharmaceutically acceptable salt of any of the foregoing, wherein

is

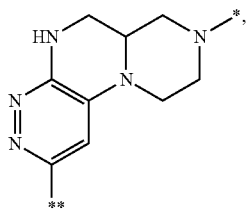

wherein * denotes the point of attachment to [Z] and ** denotes the point of attachment to the remainder of the molecule,

[X] is absent;
[Y] is absent;
[Z] is

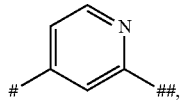

wherein ## denotes the attachment point to $R^1$, and # denotes the point of attachment to the remainder of the molecule;

$R^1$ is —C≡C—$R^a$, wherein $R^a$ is $C_{1-6}$alkyl substituted with one $R^b$, wherein $R^b$ is —N($R^j$)($R^k$), wherein the $R^j$ and $R^k$ of —N(R)($R^k$), together with the N atom to which they are attached, form a 4- to 12-membered heterocycle optionally substituted with at least one $R^c$; and each $R^c$ is independently —OH, —CN, halo, oxo, $C_{1-6}$alkyl, $C_{1-6}$alkoxy, —S(O)$_2$—($C_{1-6}$alkyl), $C_{3-10}$cycloalkyl, $C_{6-10}$aryl, 3-15 membered heterocyclyl, 5-20 membered heteroaryl, —O—($C_{6-10}$aryl), —C(O)-(3-15 membered heterocyclyl), —C(O)—$C_{1-6}$alkoxy, —C(O)—N($R^x$)($R^y$), or —N($R^x$)($R^y$), wherein the $C_{1-6}$alkyl of $R^c$ is optionally substituted with one or more —OH, —CN, halo, $C_{1-6}$alkoxy, or 3-15 membered heterocyclyl, the $C_{3-10}$cycloalkyl of $R^c$ is optionally substituted with one or more halo, the $C_{6-10}$aryl of $R^c$ is optionally substituted with one or more -CN, the 3-15 membered heterocyclyl of $R^c$ is optionally substituted with one or more $C_{1-6}$alkyl or —C(O)—$C_{1-6}$alkyl; and the $R^x$ and $R^y$ of —C(O)N($R^x$)($R^y$) and —N($R^x$)($R^y$) are, independently of each other and independently at each occurrence, H, —C(O)—(CH$_2$)$_p$—N($R^p$)($R^q$), —C(O)—$R^s$, 5-20 membered heterocycle, 5-20 membered heteroaryl, or $C_{1-6}$alkyl, wherein p is an integer from 1-6, $R^p$ and $R^q$ are, independently of each other and independently at each occurrence H, or $C_{1-6}$alkyl, $R^s$ is 5-20 membered heterocycle optionally substituted with one or more substituents selected from the group consisting of $C_{1-4}$alkyl, $C_{3-8}$cycloalkyl, and —C(O)—$C_{1-6}$alkyl, the $C_{1-6}$alkyl of $R^x$ or $R^y$ is optionally substituted with one or more —OH, 3-15 membered heterocyclyl, or —C(O)-(3-15 membered heterocyclyl), and the 5-20 membered heterocycle of $R^x$ or $R^y$ is optionally substituted with one or more oxo.

2. A compound selected from the group consisting of
N-[3-[4-[3-[3-amino-6-(2-hydroxyphenyl)pyridazin-4-yl]-3,8-diazabicyclo[3.2.1]octan-8-yl]-2-pyridyl]prop-2-ynyl]piperidine-4-carboxamide;
2-[6-amino-5-[8-[2-[3-[(1,1-dioxothiolan-3-yl)-methylamino]prop-1-ynyl]-4-pyridyl]-3,8-diazabicyclo[3.2.1]octan-3-yl]pyridazin-3-yl]phenol;
2-[6-amino-5-[8-[2-[3-[3-(hydroxymethyl)-3-phenyl-azetidin-1-yl]prop-1-ynyl]-4-pyridyl]-3,8-diazabicyclo[3.2.1]octan-3-yl]pyridazin-3-yl]phenol;
2-[6-amino-5-[8-[2-[3-(3-phenoxyazetidin-1-yl) prop-1-ynyl]-4-pyridyl]-3,8-diazabicyclo[3.2.1]octan-3-yl]pyridazin-3-yl]phenol;
2-[6-amino-5-[8-[2-[3-(3-methylsulfonylazetidin-1-yl) prop-1-ynyl]-4-pyridyl]-3,8-diazabicyclo[3.2.1]octan-3-yl]pyridazin-3-yl]phenol;
2-[6-amino-5-[8-[2-[3-(3-phenylazetidin-1-yl) prop-1-ynyl]-4-pyridyl]-3,8-diazabicyclo[3.2.1]octan-3-yl]pyridazin-3-yl]phenol;
2-[6-amino-5-[8-[2-[3-(7-methylsulfonyl-2,7-diazaspiro[3.4]octan-2-yl) prop-1-ynyl]-4-pyridyl]-3,8-diazabicyclo[3.2.1]octan-3-yl]pyridazin-3-yl]phenol;
4-[1-[3-[4-[3-[3-amino-6-(2-hydroxyphenyl)pyridazin-4-yl]-3,8-diazabicyclo[3.2.1]octan-8-yl]-2-pyridyl]prop-2-ynyl]azetidin-3-yl]benzonitrile;
2-[6-amino-5-[8-[2-[3-(azepan-1-yl) prop-1-ynyl]pyrimidin-4-yl]-3,8-diazabicyclo[3.2.1]octan-3-yl]pyridazin-3-yl]phenol;
2-[6-amino-5-[8-[6-[3-(azepan-1-yl) prop-1-ynyl]pyridazin-4-yl]-3,8-diazabicyclo[3.2.1]octan-3-yl]pyridazin-3-yl]phenol;
2-[6-amino-5-[8-[6-[3-(azepan-1-yl) prop-1-ynyl]pyrimidin-4-yl]-3,8-diazabicyclo[3.2.1]octan-3-yl]pyridazin-3-yl]phenol;
2-[6-amino-5-[8-[2-[(E)-3-(azepan-1-yl) prop-1-enyl]-4-pyridyl]-3,8-diazabicyclo[3.2.1]octan-3-yl]pyridazin-3-yl]phenol;
2-[6-amino-5-[9-[2-[3-(azepan-1-yl) prop-1-ynyl]-4-pyridyl]-3,9-diazaspiro[5.5]undecan-3-yl]pyridazin-3-yl]phenol;
2-[6-amino-5-[2-[2-[3-(azepan-1-yl) prop-1-ynyl]-4-pyridyl]-2,8-diazaspiro[4.5]decan-8-yl]pyridazin-3-yl]phenol;
2-[6-amino-5-[6-[2-[3-(azepan-1-yl) prop-1-ynyl]-4-pyridyl]-2,6-diazaspiro[3.3]heptan-2-yl]pyridazin-3-yl]phenol;
2-[(10S)-12-[2-[3-(azepan-1-yl) prop-1-ynyl]-4-pyridyl]-1,5,6,8,12-pentazatricyclo[8.4.0.02,7]tetradeca-2 (7),3,5-trien-4-yl]phenol; and
2-[(10R)-12-[2-[3-(azepan-1-yl) prop-1-ynyl]-4-pyridyl]-1,5,6,8,12-pentazatricyclo[8.4.0.02,7]tetradeca-2 (7),3,5-trien-4-yl]phenol, or a stereoisomer or tautomer thereof, or a pharmaceutically acceptable salt of any of the foregoing.

3. A pharmaceutical composition, comprising (i) a compound of claim 1, or a stereoisomer or tautomer thereof, or a pharmaceutically acceptable salt of any of the foregoing, and (ii) one or more pharmaceutically acceptable excipients.

4. The pharmaceutical composition of claim 3, further comprising an additional bioactive agent.

5. A method of inhibiting BRM in a cell, comprising exposing the cell to an effective amount of a compound of claim 1, or a stereoisomer or tautomer thereof, or a pharmaceutically acceptable salt of any of the foregoing.

6. A method of degrading BRM in a cell, comprising exposing the cell to an effective amount of a compound according to claim 1, or a stereoisomer or tautomer thereof, or a pharmaceutically acceptable salt of any of the foregoing.

7. A method of treating cancer in a human in need thereof, comprising administering to the human an effective amount of a compound of claim 1, or a stereoisomer or tautomer thereof, or a pharmaceutically acceptable salt of any of the foregoing, wherein the cancer is selected from the group consisting of melanoma, lung cancer, prostate cancer, esophageal cancer, colorectal cancer, and breast cancer.

8. The compound of claim 1, or a stereoisomer or tautomer thereof, or a pharmaceutically acceptable salt of any of the foregoing, wherein $R^b$ is a monocyclic 4- to 12-membered heterocycle.

9. The compound of claim 8, or a stereoisomer or tautomer thereof, or a pharmaceutically acceptable salt of any of the foregoing, wherein the monocyclic 4- to 12-membered heterocycle is selected from the group consisting of

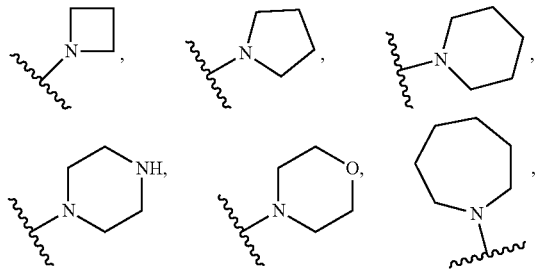

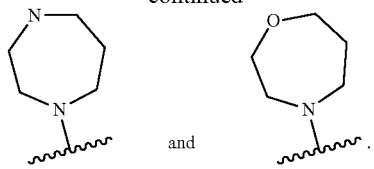

and

10. A pharmaceutical composition, comprising (i) a compound of claim 2, or a stereoisomer or tautomer thereof, or a pharmaceutically acceptable salt of any of the foregoing, and (ii) one or more pharmaceutically acceptable excipients.

11. The pharmaceutical composition of claim 10, further comprising an additional bioactive agent.

12. A method of inhibiting BRM in a cell, comprising exposing the cell to an effective amount of a compound of claim 2, or a stereoisomer or tautomer thereof, or a pharmaceutically acceptable salt of any of the foregoing.

13. A method of degrading BRM in a cell, comprising exposing the cell to an effective amount of a compound according to claim 2, or a stereoisomer or tautomer thereof, or a pharmaceutically acceptable salt of any of the foregoing.

14. A method of treating cancer in a human in need thereof, comprising administering to the human an effective amount of a compound of claim 2, or a stereoisomer or tautomer thereof, or a pharmaceutically acceptable salt of any of the foregoing, wherein the cancer is selected from the group consisting of melanoma, lung cancer, prostate cancer, esophageal cancer, colorectal cancer, and breast cancer.

* * * * *